United States Patent
Kim et al.

(10) Patent No.: US 10,913,730 B2
(45) Date of Patent: Feb. 9, 2021

(54) HETEROARYL COMPOUNDS AND THEIR USE AS MER INHIBITORS

(71) Applicant: Dong-A Socio Holdings Co., Ltd., Seoul (KR)

(72) Inventors: Jin Kwan Kim, Suwon-si (KR); Hadong Kim, Seoul (KR); Ki Moon Ryu, Yongin-si (KR); Seong Jin Park, Seoul (KR); Taeyoung Yoon, Seoul (KR); Mi Yeon Jang, Yongin-si (KR)

(73) Assignee: Dong-A Socio Holdings Co., Ltd., Seoul (KR)

(*) Notice: Subject to any disclaimer, the term of this patent is extended or adjusted under 35 U.S.C. 154(b) by 0 days.

(21) Appl. No.: 16/341,005

(22) PCT Filed: Oct. 9, 2017

(86) PCT No.: PCT/US2017/055793
§ 371 (c)(1),
(2) Date: Apr. 10, 2019

(87) PCT Pub. No.: WO2018/071343
PCT Pub. Date: Apr. 19, 2018

(65) Prior Publication Data
US 2019/0315716 A1    Oct. 17, 2019

Related U.S. Application Data

(60) Provisional application No. 62/406,015, filed on Oct. 10, 2016.

(51) Int. Cl.
| | | |
|---|---|---|
| *C07D 401/14* | (2006.01) | |
| *C07D 401/12* | (2006.01) | |
| *C07D 471/04* | (2006.01) | |

(52) U.S. Cl.
CPC ......... *C07D 401/14* (2013.01); *C07D 401/12* (2013.01); *C07D 471/04* (2013.01)

(58) Field of Classification Search
CPC ... C07D 401/14; C07D 471/04; C07D 401/12
See application file for complete search history.

(56) References Cited

U.S. PATENT DOCUMENTS

| | | |
|---|---|---|
| 2002/0151712 A1 | 10/2002 | Lin et al. |
| 2004/0180905 A1 | 9/2004 | Munchhof |
| 2013/0072679 A1 | 3/2013 | Aebi et al. |
| 2013/0209422 A1 | 8/2013 | Kang et al. |
| 2017/0066742 A1 | 3/2017 | Kim et al. |

FOREIGN PATENT DOCUMENTS

| | | | |
|---|---|---|---|
| WO | WO 01/19817 | * | 3/2001 |
| WO | 2003093297 A2 | | 11/2003 |
| WO | 2004054977 A1 | | 7/2004 |
| WO | 2004080982 A1 | | 9/2004 |
| WO | 2007011760 A2 | | 1/2007 |
| WO | 2008009122 A1 | | 1/2008 |
| WO | 2017039331 A1 | | 3/2017 |

OTHER PUBLICATIONS

Lemke. Cold Spring Harbor Perspectives in Biology, 2013, 5: a009076 (Year: 2013).*
Database Caplus Chemical Abstracts Service, Columbus, Ohio, US; Database Accession No. 1935:19785, Abstract of Gryszkiewicz-Trochimowski, E., Archiwum Chemji i Farmacji, (1934), 1, 65-71.
Database Caplus Chemical Abstracts Service, Columbus, Ohio, US; Database Accession No. 1949:13185, Abstract of Charonnat et al., Bulletin de la Societe Chimique de France, (1949), 1014-1017.
Database PubChem Compound [Online] XP002787138, Database accession No. 55069206, Compound 55069206, retrieved from NCBI (3 pages), Jan. 24, 2012 (Jan. 24, 2012).
Database PubChem Compound [Online] XP002787139, Database accession No. 60315064, Compound 60315064, retrieved from NCBI (3 pages), Oct. 18, 2012 (Oct. 18, 2012).
Database PubChem Compound [Online] XP002787140, Database accession No. 60315178, Compound 60315178, retrieved from NCBI (3 pages), Oct. 18, 2012 (Oct. 18, 2012).
Database PubChem Compound [Online] XP002787141, Database accession No. 62160816, Compound 62160816, retrieved from NCBI (3 pages), Oct. 22, 2012 (Oct. 22, 2012).
Database PubChem Compound [Online] XP002787142, Database accession No. 63279265, Compound 63279265, retrieved from NCBI (3 pages), Oct. 22, 2012 (Oct. 22, 2012).
Database PubChem Compound [Online] XP002787143, Database accession No. 64915258, Compound 64915258, retrieved from NCBI (3 pages), Oct. 23, 2012 (Oct. 23, 2012).
Huang et al., "Structural insights into the inhibited states of the Mer receptor tyrosine kinase," J. Struc. Biol., 2009, vol. 165, No. 2, pp. 88-96.
Liu et al., "Discovery of Novel Small Molecule Mer Kinase Inhibitors for the Treatment of Pediatric Acute Lymphoblastic Leukemia," ACS Med. Chem. Lett., 2012, vol. 3, pp. 129-134.
Liu et al., "UNC1062, a new and potent Mer inhibitor," Eur. J. Med. Chem., 2013, vol. 65, pp. 83-93.

(Continued)

*Primary Examiner* — Noble E Jarrell

(57) ABSTRACT

Compounds of formula (I) and a pharmaceutically acceptable salt thereof, wherein A, $R^1$, $R^2$, $R^3$, $R^4$, $R^5$, $R^6$, $R^7$, $R^{24}$, X, L, n and p are as defined in the specification, are useful for treating or preventing Mer tyrosine kinase receptor modulated disease or conditions. Also described are pharmaceutical compositions of compounds of formula (I), and methods for using such compounds and compositions.

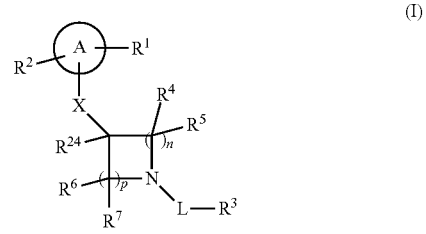

(I)

14 Claims, No Drawings

(56) References Cited

OTHER PUBLICATIONS

Rahmani et al., "6-Arylpyrazine-2-carboxamides: A New Core for Trypanosoma brucei Inhibitors," J. Med. Chem., 2015, vol. 58, No. 17, pp. 6753-6765.
Zhang et al., "Pseudo-Cyclization through Intramolecular Hydrogen Bond Enables Discovery of Pyridine Substituted Pyrimidines as New Mer Kinase Inhibitors," J. Med. Chem., 2013, vol. 56, No. 23, pp. 9683-9692.
Zhang et al., "UNC2025, a potent and orally bioavailable MER/FLT3 dual inhibitor," J. Med. Chem., 2014, vol. 57, No. 16, pp. 7031-7041.
International Search Report and Written Opinion for International Application No. PCT/KR2016/009743 dated Dec. 9, 2016, 17 pages.
International Search Report and Written Opinion for International Application No. PCT/US2017/055793 dated Dec. 1, 2017, 10 pages.

\* cited by examiner

HETEROARYL COMPOUNDS AND THEIR USE AS MER INHIBITORS

RELATED APPLICATIONS

This application is the 35 USC § 371 national stage of International Application No. PCT/US2017/055793, filed Oct. 9, 2017, the contents of which are hereby incorporated by reference in their entirety. International Application No. PCT/US2017/055793 claims priority to U.S. provisional application Ser. No. 62/406,015 filed Oct. 10, 2016. The disclosure of this priority application is incorporated herein in its entirety.

TECHNICAL FIELD

Compounds of formula (I) and methods for inhibiting Mer kinases are disclosed. Additionally, the present disclosure relates to compositions containing compounds of the present disclosure and methods for their use.

DESCRIPTION OF RELATED TECHNOLOGY

Receptor tyrosine kinases (RTKs) are enzymes that can phosphorylate specific tyrosine residues in target proteins, using ATP and share a highly conserved catalytic domain. The conservation makes it hard to develop a selective tyrosine kinase inhibitor (TKI). The TAM receptor family consists of Tyro3, Axl, and Mer, which play important roles in hemostasis and inflammation. Mer is, especially, a key regulator of macrophage activation and promotes apoptotic cell clearance. Moreover, Mer is abnormally expressed and activated in human cancers such as pituitary adenomas, mantle cell lymphomas, and T-cell acute lymphoblastic leukemia.

Since ATP-binding site is similar for all protein kinases, it is challenging to find an inhibitor that is specific for the Mer. Compound-52, a 2,6,9-trisubstituted purine that competitively binds to the ATP binding pocket, was actually the first molecule that was found to be successful in inhibiting Mer (J Struct Biol. 2009 February; 165(2): 88-96). This inhibitor has, however, limited potency and lack of selectivity. Lately, several compounds have been discovered mostly by modifying Compound-52 including UNC-569, UNC-1062, and UNC-2025 (ACS Med Chem Lett. 2012 Feb. 9; 3(2):129-134, Eur J Med Chem. 2013 July; 65:83-93, J Med Chem. 2014 Aug. 28; 57(16):7031-41). And quite recently, highly potent and selective Mer kinase inhibitors were disclosed based on aminopyridine or aminopyrimidine scaffolds (US20170066742, Ser. No. 15/253,773).

It is an object of the invention to provide reagents and methods of regulating a receptor tyrosine kinase Mer. This and other objects of the invention are provided by one or more of the embodiments described below.

SUMMARY

The present invention provides novel compounds capable of selectively inhibiting Mer kinase, which compounds are useful for the prevention and/or the treatment of cancer and other immune-related disease such as infection and sepsis. Highly potent and selective receptor tyrosine kinase Mer inhibitors based on several heteroaryl scaffolds, including aminopyridine and 7-azaindole are described. Such compounds have the following formula (I).

The present disclosure is directed to compounds having a structure of formula (I):

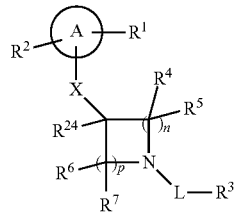

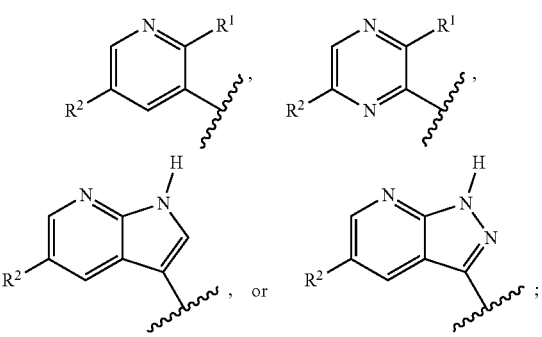

or a pharmaceutically acceptable salt thereof, wherein:
Ring A is

X is —C(=O)O—, —C(=O)N($R^8$)—, —C(=O)N($R^8$)CH$_2$—, —SO$_2$N($R^8$)—, —N($R^8$)—, —O—, or —S—;
n is 1 or 2;
p is 1, 2, or 3;
L is none, $C_{1-3}$ alkyl, $C_{2-3}$ alkenyl, $C_{1-3}$ alkyl-O—, $C_{1-3}$ alkyl-O—$C_{1-3}$alkyl, —C(=O)—, —C(=O)—C(=O)—, —C(=O)O—, —C(=O)N($R^8$)—, —C(=S)N($R^8$)—(CR$^{12}$R$^{13}$)$_m$—, —C(=S)—, —C(=S)O—, —SO$_2$—, —SO$_2$—(CH$_2$)$_m$—, —(CR$^{12}$R$^{13}$)$_m$—C(=O)(CR$^{12}$R$^{13}$)$_m$—, —C(=O)O(CR$^{12}$R$^{13}$)$_m$—, —C(=O)—CR$^1$=CR$^{13}$—, or —CHR$^{14}$;
$R^1$ is H, halogen, $C_{1-3}$ alkyl, —NH($R^8$), —OR$^8$ or —(CH$_2$)$_l$—NR$^{12}$R$^{13}$;
$R^2$ is —Br, —Cl, —CN, cycloalkenyl, $C_{2-6}$ alkenyl, aryl, biaryl, heteroaryl, heterobiaryl, heterocycle, $C_{1-2}$ alkylaryl, $C_{1-2}$ alkylheteroaryl, or $C_{1-2}$ alkylheterocycle, which aryl, biaryl, heteroaryl, heterobiaryl, or heterocycle may optionally be substituted with one or more $R^{18}$;
$R^3$ is halogen, cycloalkyl, cycloalkenyl, aryl, biaryl, heteroaryl, heterobiaryl, or heterocycle which cycloalkyl, cycloalkenyl, aryl, biaryl, heteroaryl, heterobiaryl, or heterocycle, may optionally be substituted with one or more $R^9$;
$R^4$, $R^5$, $R^6$, and $R^7$ are the same as or different from each other, and are each independently H, halogen, $C_{1-3}$ alkyl, —OR$^{21}$; —OCH$_2$R$^{21}$; —C(=O)NHR$^{21}$, —C(=O)OR$^{21}$, —C(=O)SR$^{21}$; —C(=O)S—SR$^{21}$, —CH$_2$OR$^{21}$, or —CH$_2$NHR$^{21}$;
$R^8$ is H, $C_{1-6}$ alkyl, $C_{1-3}$ alkylaryl, or $C_{1-3}$ alkylheteroaryl which $C_{1-6}$ alkyl, $C_{1-3}$ alkylaryl or $C_{1-3}$ alkylheteroaryl may optionally be substituted with one or more $R^9$;
when $R^1$ is —NH($R^8$)— and X is —C(=O)N($R^8$)—, the $R^8$ groups together may be —CH$_2$—, forming a ring with the nitrogen atoms to which they are attached;
$R^9$ is halogen, hydroxyl, —CN, —NO$_2$, —CHO, —COOH, —(C=O)H, $C_{1-6}$ alkyl, $C_{2-6}$ alkenyl, $C_{2-6}$ alkynyl, $C_{1-6}$ aminoalkyl, $C_{3-10}$ cycloalkyl, $C_{1-6}$ haloalkyl, $C_{1-4}$ hydroxyalkyl, $C_{1-6}$ alkoxy, cycloalkenyl, aryl, heterocycle, heteroaryl, —NR$^{10}$R$^{11}$, -J$^9$-NR$^{10}$R$^{11}$, -J$^9$-COOR$^8$, -J$^9$-alkyl, -J$^9$-C$_{3-10}$ cycloalkyl, -J$^9$-cycloalkenyl, -J$^9$-heterocycle, -J$^9$-heteroaryl, or -J$^9$-aryl, which alkyl, C$_{1-6}$ alkoxy, C$_{3-10}$ cycloalkyl, heterocycle, heteroaryl, aryl, -J$^9$-alkyl, -J$^9$-C$_{3-10}$ cycloalky, -J$^9$-heterocycle, -J$^9$-heteroaryl, or -J$^9$-aryl, may be substituted with one or more R$^{16}$;

R$^{10}$ and R$^{11}$ each independently is H, C$_{1-6}$ alkyl, C$_{3-10}$ cycloalkyl or SO$_2$R$^8$;

R$^{12}$ and R$^{13}$ each independently is H, C$_{1-6}$ alkyl, or C$_{3-10}$ cycloalkyl;

R$^{12}$ and R$^{13}$ together with the carbon atom to which they are attached may form a C$_{3-6}$ cycloalkyl;

R$^{14}$ is —C(=O)NHR$^{15}$, —C(=O)OR$^{15}$, —CH$_2$OR$^{15}$, or —CH$_2$NHR$^{15}$;

R$^{15}$ is H, or C$_{1-3}$ alkyl;

R$^{16}$ is halogen, hydroxyl, —CN, —CHO, —NR$^{10}$R$^{11}$, —NO$_2$, C$_{1-6}$ alkyl, (=O), C$_{3-10}$ cycloalkyl, C$_{1-4}$ hydroxyalkyl, C$_{1-6}$ alkoxy, C$_{2-6}$ alkenyl, aryl, heterocycle, -J$^{16}$-alkyl, -J$^{16}$-aryl, -J$^{16}$-heterocycle, —(CH$_2$)$_l$—NR$^{10}$R$^{11}$, —(CH$_2$)$_l$—COOR$^8$, or —(CH$_2$)$_l$—C(=O)—NR$^{10}$R$^{11}$, which -J$^{16}$-heterocycle may be substituted with one or more R$^{17}$;

R$^{17}$ is C$_{1-6}$ alkyl, C$_{1-4}$ hydroxyalkyl, or C$_{1-4}$ aminoalkyl;

R$^{18}$ is halogen, hydroxyl, —CN, —NO$_2$, —CHO, —COOH, —(C=O)H, C$_{1-6}$ alkyl, C$_{2-6}$ alkenyl, C$_{2-6}$ alkynyl, C$_{1-6}$ aminoalkyl, C$_{3-10}$ cycloalkyl, C$_{1-6}$ haloalkyl, C$_{1-4}$ hydroxyalkyl, C$_{1-6}$ alkoxy, cycloalkenyl, aryl, heterocycle, heteroaryl, —NR$^{10}$R$^{11}$, J$^{18}$-NR$^{10}$R$^{11}$, -J$^{18}$-COOR$^8$, -J$^{18}$-alkyl, -J$^{18}$-C$_{3-10}$ cycloalkyl, -J$^{18}$-cycloalkenyl, -J$^{18}$-heterocycle, -J$^{18}$-heteroaryl, or -J$^{18}$-aryl, which alkyl, C$_{1-6}$ alkoxy, C$_{3-10}$ cycloalkyl, heterocycle, heteroaryl, aryl, -J$^{18}$-alkyl, -J$^{18}$-C$_{3-10}$ cycloalky, -J$^{18}$-heterocycle, -J$^{18}$-heteroaryl, or -J$^{18}$-aryl, may be substituted with one or more R$^{19}$;

R$^{19}$ is halogen, hydroxyl, —CN, —CHO, —NR$^{10}$R$^{11}$, —NO$_2$, C$_{1-6}$ alkyl, (=O), C$_{3-10}$ cycloalkyl, C$_{1-4}$ hydroxyalkyl, C$_{1-6}$ alkoxy, C$_{2-6}$ alkenyl, aryl, heterocycle, -J$^{19}$-alkyl, -J$^{19}$-aryl, -J$^{19}$-heterocycle, —(CH$_2$)$_l$—NR$^{10}$R$^{11}$, —(CH$_2$)$_l$—COOR$^8$, or —(CH$_2$)$_l$—C(=O)—NR$^{10}$R$^{11}$, which -J$^{19}$ heterocycle may be substituted with one or more R$^{20}$;

R$^{20}$ is —NO$_2$, C$_{1-6}$ alkyl, C$_{1-4}$ hydroxyalkyl, or C$_{1-4}$ aminoalkyl;

R$^{21}$ is H, halogen, C$_{1-6}$ alkyl, cycloalkyl, cycloalkenyl, aryl, biaryl, heteroaryl, heterobiaryl, or heterocycle which cycloalkyl, cycloalkenyl, aryl, biaryl, heteroaryl, heterobiaryl, or heterocycle, may optionally be substituted with one or more R$^{22}$;

R$^{22}$ is halogen, hydroxyl, —CN, —NO$_2$, —CHO, —COOH, —(C=O)H, C$_{1-6}$ alkyl, C$_{2-6}$ alkenyl, C$_{2-6}$ alkynyl, C$_{1-6}$ aminoalkyl, C$_{3-10}$ cycloalkyl, C$_{1-6}$ haloalkyl, C$_{1-4}$ hydroxyalkyl, C$_{1-6}$ alkoxy, cycloalkenyl, aryl, heterocycle, heteroaryl, —NR$^{10}$R$^{11}$, -J$^{22}$-NR$^{10}$R$^{11}$, -J$^{22}$-COOR$^8$, -J$^{22}$ alkyl, -J$^{22}$-C$_{3-10}$ cycloalkyl, -J$^{22}$-cycloalkenyl, -J$^{22}$-heterocycle, -J$^{22}$-heteroaryl, or -J$^{22}$-aryl, which alkyl, C$_{1-6}$ alkoxy, C$_{3-10}$ cycloalkyl, heterocycle, heteroaryl, aryl, -J$^{22}$-alkyl, -J$^{22}$-C$_{3-10}$ cycloalkyl, -J$^{22}$-heterocycle, -J$^{22}$-heteroaryl, or -J$^{22}$-aryl, may be substituted with one or more R$^{23}$;

R$^{23}$ is C$_{1-6}$ alkyl;

R$^{24}$ is —CN, —(CH$_2$)$_l$—OR$^8$, —(CH$_2$)$_l$—N(R)$_2$, or C$_{1-3}$ alkyl;

J$^9$ is C$_{1-3}$ alkyl, C$_{1-3}$ alkyl-O—, C$_{2-6}$ alkenyl, C$_{2-6}$ alkynyl, C$_{3-10}$ cycloalkyl, —(CH$_2$)$_l$—C(=O)—(CH$_2$)$_m$—, —(CH$_2$)$_l$—CH=CH—C(=O)—(CH$_2$)$_m$—, —C(=O)O—, —(CH$_2$)$_l$—C(=O)NH—(CH$_2$)$_m$—, —(CH$_2$)$_l$—NHC(=O)—(CH$_2$)$_m$—, —(CR$^{10}$R$^{11}$)$_l$—NR—(CR$^{10}$R$^{11}$)$_m$—, —NH—C(=O)—CR$^{10}$R$^{11}$—NH—C(=O)—, —NHC(=O)—, —O—, —O(C=O)—, —S—, —S(=O)—, —SO$_2$—, or —NHSO$_2$—;

J$^{16}$ is C$_{1-3}$ alkyl, C$_{1-3}$ alkyl-O—, C$_{2-6}$ alkenyl, C$_{2-6}$ alkynyl, C$_{3-10}$ cycloalkyl, —(CH$_2$)$_l$—C(=O)—(CH$_2$)$_m$—, —(CH$_2$)$_l$—CH=CH—C(=O)—(CH$_2$)$_m$—, —C(=O)O—, —(CH$_2$)$_l$—C(=O)NH—(CH$_2$)$_m$—, —(CH$_2$)$_l$—NHC(=O)—(CH$_2$)$_m$—, —(CR$^{10}$R$^{11}$)$_l$—NR—(CR$^{10}$R$^{11}$)$_m$—, —NH—C(=O)—CR$^{10}$R$^{11}$—NH—C(=O)—, —NHC(=O)—, —O—, —O(C=O)—, —S—, —S(=O)—, or —SO$_2$—;

J$^{18}$ is C$_{1-3}$ alkyl, C$_{1-3}$ alkyl-O—, C$_{2-6}$ alkenyl, C$_{2-6}$ alkynyl, C$_{3-10}$ cycloalkyl, —(CH$_2$)$_l$—C(=O)—(CH$_2$)$_m$—, —(CH$_2$)$_l$—CH=CH—C(=O)—(CH$_2$)$_m$—, —C(=O)—, —C(=O)O—, —(CH$_2$)$_l$—C(=O)NH—(CH$_2$)$_m$—, —(CH$_2$)$_l$—NHC(=O)—(CH$_2$)$_m$—, —(CR$^{10}$R$^{11}$)$_l$—NR$^8$—(CR$^{10}$R$^{11}$)$_m$—, —NH—C(=O)—CR$^{10}$R$^{11}$—NH—C(=O)—, —NHC(=O)—, —O—, —O(C=O)—, —S—, —S(=O)—, —SO$_2$—, or —NHSO$_2$—;

J$^{19}$ is C$_{1-3}$ alkyl, C$_{1-3}$ alkyl-O—, C$_{2-6}$ alkenyl, C$_{2-6}$ alkynyl, C$_{3-10}$ cycloalkyl, —(CH$_2$)$_l$—C(=O)—(CH$_2$)$_m$—, —(CH$_2$)$_l$—CH=CH—C(=O)—(CH$_2$)$_m$—, —C(=O)O—, —(CH$_2$)$_l$—C(=O)NH—(CH$_2$)$_m$—, —(CH$_2$)$_l$—NHC(=O)—(CH$_2$)$_m$—, —(CR$^{10}$R$^{11}$)$_l$—NR—(CR$^{10}$R$^{11}$)$_m$—, —NH—C(=O)—CR$^{10}$R$^{11}$—NH—C(=O)—, —NHC(=O)—, —O—, —O(C=O)—, —S—, —S(=O)—, or —SO$_2$—;

J$^{22}$ is C$_{1-3}$ alkyl, C$_{1-3}$ alkyl-O—, or —O—; and l and m each independently is an integer of 0 to 3;

with the proviso that when Ring A is

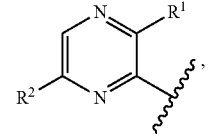

then R$^2$ is not

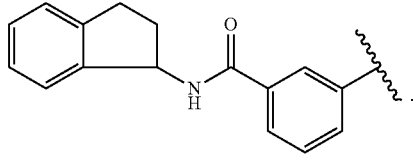 [SMILES: *c1cccc(C(=O)NC2CCc3ccccc32)c1]

Another aspect of the present disclosure relates to pharmaceutical compositions comprising compounds of the present disclosure or pharmaceutically acceptable salts thereof, and a pharmaceutical carrier.

Moreover, the compounds of the present disclosure or pharmaceutically acceptable salts thereof, useful in the pharmaceutical compositions and treatment methods disclosed herein, are pharmaceutically acceptable as prepared and used.

In embodiments, the present disclosure relates to a method of modulating the Mer tyrosine kinase receptor activity. This method is useful for the prevention and/or the treatment of cancer and other immune-related disease such as infection and sepsis. Accordingly, the compounds and compositions of the present disclosure are useful as a medicament for treating or preventing Mer tyrosine kinase receptor modulated disease or conditions.

These and other objects of the present disclosure are described in the following paragraphs. These objects should not be deemed to narrow the scope of the present disclosure.

DETAILED DESCRIPTION

Disclosed herein are compounds of formula (I), or a pharmaceutically acceptable salt thereof,

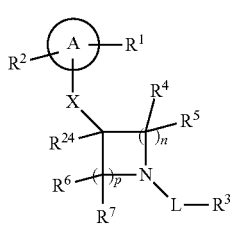

(I)

wherein A, $R^1$, $R^2$, $R^3$, $R^4$, $R^5$, $R^6$, $R^7$, $R^{24}$, X, L, n and p are defined above in the Summary and below in the Detailed Description. Further, compositions comprising such compounds and methods for treating conditions and disorders using such compounds and compositions are also described.

Compounds included herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

Definition of Terms

It is noted that, as used in this specification and the intended claims, the singular form "a," "an," and "the" include plural referents unless the context clearly dictates otherwise. Thus, for example, reference to "a compound" includes a single compound as well as one or more of the same or different compounds, reference to "optionally a pharmaceutically acceptable carrier" refers to a single optional pharmaceutically acceptable carrier as well as one or more pharmaceutically acceptable carriers, and the like.

As used in the specification and the appended claims, unless specified to the contrary, the following terms have the meaning indicated:

The term "alkenyl" as used herein, means a straight or branched hydrocarbon chain containing from 2 to 10 carbons and containing at least one carbon-carbon double bond. Representative examples of alkenyl include, but are not limited to buta-1,3-dienyl, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy" as used herein, means a $C_1$-$C_6$ alkyl group, as defined herein, appended to the parent molecular moiety through an oxygen atom. Representative, non-limiting examples of alkoxy include methoxy, ethoxy, propoxy, 2-propoxy, butoxy, tert-butoxy, pentyloxy, and hexyloxy.

The term "alkyl" as used herein, means a straight or branched, saturated hydrocarbon chain containing from 1 to 10 carbon atoms. The term "lower alkyl" or "$C_1$-$C_6$alkyl" means a straight or branched chain hydrocarbon containing from 1 to 6 carbon atoms. The term "$C_{1-3}$alkyl" or "$C_1$-$C_3$alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene" or "alkylenyl" denotes a divalent group derived from a straight or branched chain hydrocarbon containing from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "aminoalkyl" as used herein, means a $C_1$-$C_6$ alkyl group, as defined herein, which is substituted by a —$NH_2$ group substituent. Representative, non-limiting examples of alkoxy include aminomethyl, 1-aminoethyl, 2-aminoethyl, 1-aminopropyl, 2-aminopropyl, 3-aminopropyl.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present disclosure can be unsubstituted or substituted.

The term "biaryl" as used herein, means a group comprising two aryl groups joined by a single bond. The aryl group may be phenyl or a bicyclic aryl.

The term "carbonyl" as used herein means a —C(=O)— group.

The term "cyano" as used herein, means a —CN group.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group, or a bridged monocyclic ring system in which two non-adjacent carbon atoms of the monocyclic ring are linked by an alkylene bridge containing one, two, three, or four carbon atoms. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "cycloalkyl" or "cycloalkane" as used herein, means a monocyclic, a bicyclic, a tricyclic, or a spirocyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system. Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The spirocyclic cycloalkyl groups of the invention can be appended to the parent molecular moiety through any substitutable carbon atom of the groups. In a bridged cycloalkyl, the rings share at least two non-adjacent atoms. Examples of bridged cycloalkyls include, but are not limited to, bicyclo[1.1.1]pentanyl, bicyclo[2.2.2]octanyl, bicyclo[3.2.1]octanyl, bicyclo[3.1.1]heptyl, bicyclo[2.2.1]heptyl, bicyclo[3.2.2]nonyl, bicyclo[3.3.1]nonyl, bicyclo[4.2.1]nonyl, tricyclo[3.3.1.0$^{3,7}$]nonyl (octahydro-2,5-methanopentalenyl or noradamantyl), tricyclo[3.3.1.1$^{3,7}$]decyl (adamantyl), and tricyclo[4.3.1.1$^{3,8}$]undecyl (homoadamantyl). In a fused ring cycloalkyl, the rings share one common bond. Example of fused-ring cycloalkyl include, but not limited to, decalin (decahydronaphthyl).

The term "halo" or "halogen" as used herein, means Cl, Br, I, and F.

The term "haloalkyl" as used herein, means an alkyl group, as defined herein, in which one, two, three, four, five, six, seven or eight hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "heteroaryl" as used herein, means a monocyclic heteroaryl or a bicyclic heteroaryl. The monocyclic heteroaryl is a five- or six-membered hydrocarbon ring wherein at least one carbon ring atom is replaced by heteroatom independently selected from the group consisting of O, N, and S. The five-membered ring contains two double bonds. The five-membered ring may contain one heteroatom selected from O, N, or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the invention can be substituted or unsubstituted and are connected to the parent molecular moiety through any carbon atom or any nitrogen atom contained within the ring systems.

The term "heterobiaryl" as used herein, means a group comprising two heteroaryl groups joined by a single bond, or a group comprising one aryl and one heteroaryl group joined by a single bond. The aryl group may be phenyl or a bicyclic aryl. The heteroaryl group may be a monocyclic heteroaryl or a bicyclic heteroaryl The term "heterocycle" or "heterocyclic" or "heterocyclyl" as used herein, means a monocyclic heterocycle, a bicyclic heterocycle, a tricyclic heterocycle, or a spirocyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$] decane), oxa-adamantane (2-oxatricyclo[3.3.1.1$^{3,7}$]decane), and octahydro-1H-4,7-epiminoisoindole. The spirocyclic heterocycles are exemplified by a monocyclic heterocycle as defined herein wherein one carbon atom of the monocyclic heterocycle is bridged by two ends of an alkylene chain. In the spirocyclic heterocycle, one or more carbon atoms in the bridging alkylene chain may be replaced with a heteroatom. Examples of spirocyclic heterocycles include, but are not limited to, 4,7-diazaspiro[2.5]octane, 2-oxa-6-azaspiro[3.3]heptane, 2,6-diazaspiro[3.3]heptane, 2-oxa-5,8-diazaspiro[3.5]nonane, 2,7-diazaspiro[3.5]nonane, 1,4-dioxa-8-azaspiro[4.5]decane, 1,6-diazaspiro[3.3]heptane, 1-azaspiro[4.4]nonane, 7-azaspiro[3.5]nonane, 1,4-dioxa-7-azaspiro[4.4]nonane, 5,8-diazaspiro[3.5]nonane, 5,8-dioxa-2-azaspiro[3.4]octane, 2-oxa-6-azaspiro[3.4]octane, 6-oxa-1-azaspiro[3.3]heptane, 6-oxa-2-azaspiro[3.4]octane, 6-oxa-2-azaspiro[3.5]nonane, and 7-oxa-2-azaspiro[3.5]nonane. The monocyclic, bicyclic, tricyclic, and spirocyclic heterocycles are connected to the parent molecular moiety through any carbon atom or any nitrogen atom contained within the rings, and can be unsubstituted or substituted.

The term "heteroatom" as used herein, means a nitrogen, oxygen, and sulfur.

The term "hydroxyl" or "hydroxy" as used herein, means an —OH group.

The term "hydroxyalkyl" as used herein, means a $C_1$-$C_6$ alkyl group, as defined herein, which is substituted by an —OH group substituent. Representative, non-limiting examples of alkoxy include hydroxymethyl, 1-hydroxyethyl, 2-hydroxyethyl, 1-hydroxypropyl, 2-hydroxypropyl, and 3-hydroxypropyl.

The term "oxo" as used herein, means a =O group.

In some instances, the number of carbon atoms in a hydrocarbyl substituent (e.g., alkyl, alkenyl, alkynyl, or cycloalkyl) is indicated by the prefix "$C_x$-$C_y$" or "$C_{x-y}$", wherein x is the minimum and y is the maximum number of carbon atoms in the substituent. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms.

Where a group is a divalent group, the group may be attached in any order to the two groups to which it is attached. By way of example, when W and V are attached by the divalent group —CH$_2$O— this will be understood to include W—CH$_2$O—V and V—CH$_2$O—W.

As used herein, the term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

If a moiety is described as "substituted", a non-hydrogen radical is in the place of hydrogen radical of any substitutable atom of the moiety. Thus, for example, a substituted heterocycle moiety is a heterocycle moiety in which at least one non-hydrogen radical is in the place of a hydrogen radical on the heterocycle. It should be recognized that if there are more than one substitution on a moiety, each non-hydrogen radical may be identical or different (unless otherwise stated).

If a moiety is described as being "optionally substituted," the moiety may be either (1) not substituted or (2) substituted. If a moiety is described as being optionally substituted with up to a particular number of non-hydrogen radicals, that moiety may be either (1) not substituted; or (2) substituted by up to that particular number of non-hydrogen radicals or by up to the maximum number of substitutable positions on the moiety, whichever is less. Thus, for example, if a moiety is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

The terms "treat", "treating", and "treatment" refer to a method of alleviating or abrogating a disease and/or its attendant symptoms. In certain embodiments, "treat," "treating," and "treatment" refer to ameliorating at least one physical parameter, which may not be discernible by the subject. In yet another embodiment, "treat", "treating", and "treatment" refer to modulating the disease or disorder, either physically (for example, stabilization of a discernible symptom), physiologically (for example, stabilization of a physical parameter), or both. In a further embodiment, "treat", "treating", and "treatment" refer to slowing the progression of the disease or disorder.

The terms "prevent", "preventing", and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring or developing a disease or disorder.

The phrase "therapeutically effective amount" means an amount of a compound, or a pharmaceutically acceptable salt thereof, sufficient to prevent the development of or to alleviate to some extent one or more of the symptoms of the condition or disorder being treated when administered alone or in conjunction with another therapeutic agent or treatment in a particular subject or subject population. For example in a human or other mammal, a therapeutically effective amount can be determined experimentally in a laboratory or clinical setting, or may be the amount required by the guidelines of the United States Food and Drug Administration, or equivalent foreign agency, for the particular disease and subject being treated.

The term "subject" is defined herein to refer to animals such as mammals, including, but not limited to, primates (e.g., humans), cows, sheep, goats, pigs, horses, dogs, cats, rabbits, rats, mice and the like. In preferred embodiments, the subject is a human. The terms "human", "patient", and "subject" are used interchangeably herein.

Compounds

In one embodiment, compounds of the present disclosure are represented by formula (I) as described in the Summary.

In one embodiment, compounds of the present disclosure are represented by formula (II):

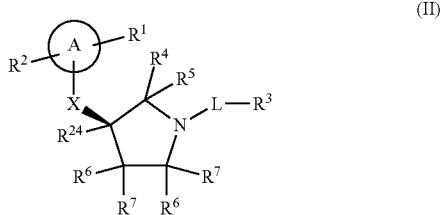

(II)

or a pharmaceutically acceptable salt thereof, wherein:
Ring A is

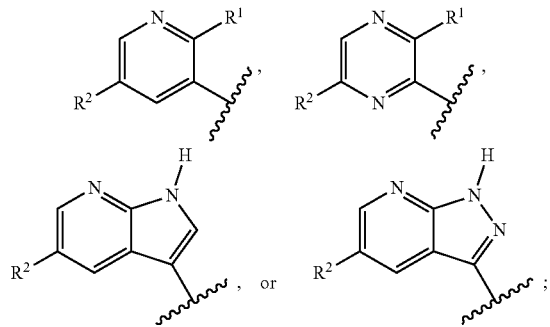

X is —C(=O)O—, —C(=O)N($R^8$)—, —C(=O)N($R^8$)$CH_2$—, —$SO_2$N($R^8$)—, —N($R^8$)—, —O—, or —S—;

L is none, $C_{1-3}$ alkyl, $C_{2-3}$ alkenyl, $C_{1-3}$ alkyl-O—, $C_{1-3}$ alkyl-O—$C_{1-3}$alkyl, —C(=O)—, —C(=O)—C(=O)—, —C(=O)O—, —C(=O)N($R^8$)—, —C(=S)N($R^8$)—($CR^{12}R^{13}$)$_m$—, —C(=S)—, —C(=S)O—, —$SO_2$—, —$SO_2$—($CH_2$)$_m$—, —($CR^{12}R^{13}$)$_m$—C(=O)—($CR^{12}R^{13}$)$_m$—, —C(=O)O($CR^{12}R^{13}$)$_m$—, —C(=O)—$CR^{12}$=$CR^{13}$—, or —$CHR^{14}$—;

$R^1$ is H, halogen, $C_{1-3}$ alkyl, —NH($R^8$)—, —$OR^8$ or —($CH_2$)$_l$—$NR^{12}R^{13}$;

$R^2$ is —Br, —Cl, —CN, cycloalkenyl, $C_{2-6}$ alkenyl, aryl, biaryl, heteroaryl, heterobiaryl, heterocycle, $C_{1-2}$ alkylaryl, $C_{1-2}$ alkylheteroaryl, or $C_{1-2}$ alkylheterocycle which aryl, biaryl, heteroaryl, heterobiaryl, or heterocycle may optionally be substituted with one or more $R^{18}$;

$R^3$ is halogen, cycloalkyl, cycloalkenyl, aryl, biaryl, heteroaryl, heterobiaryl, or heterocycle which cycloalkyl, cycloalkenyl, aryl, biaryl, heteroaryl, heterobiaryl, or heterocycle, may optionally be substituted with one or more $R^9$;

$R^4$, $R^5$, $R^6$, and $R^7$ are the same as or different from each other, and are each independently H, halogen, $C_{1-3}$ alkyl, —$OR^{21}$; —$OCH_2R^{21}$; —C(=O)$NHR^{21}$, —C(=)$OR^{21}$, —C(=O)$SR^{21}$; —C(=O)S—$SR^{21}$, —$CH_2OR^{21}$, or —$CH_2NHR^{21}$;

$R^8$ is H, $C_{1-6}$ alkyl, $C_{1-3}$ alkylaryl, or $C_{1-3}$ alkylheteroaryl which $C_{1-6}$ alkyl, $C_{1-3}$ alkylaryl or $C_{1-3}$ alkylheteroaryl may optionally be substituted with one or more $R^9$;

when $R^1$ is —NH($R^8$)— and X is —C(=O)N($R^8$)—, the $R^8$ groups together may be —$CH_2$—, forming a ring with the nitrogen atoms to which they are attached;

$R^9$ is halogen, hydroxyl, —CN, —$NO_2$, —CHO, —COOH, —(C=O)H, $C_{1-6}$ alkyl, $C_{2-6}$ alkenyl, $C_{2-6}$ alkynyl, $C_{1-6}$ aminoalkyl, $C_{3-10}$ cycloalkyl, $C_{1-6}$ haloalkyl, $C_{1-4}$ hydroxyalkyl, $C_{1-6}$ alkoxy, cycloalkenyl, aryl, heterocycle, heteroaryl, —$NR^{10}R^{11}$, -$J^9$-$NR^{10}R^{11}$, -$J^9$-$COOR^8$, -$J^9$-alkyl, -$J^9$-$C_{3-10}$ cycloalkyl, -$J^9$-cycloalkenyl, -$J^9$-heterocycle, -$J^9$-heteroaryl, or -$J^9$-aryl which alkyl, $C_{1-6}$ alkoxy, $C_{3-10}$ cycloalkyl, heterocycle, heteroaryl, aryl, -$J^9$-alkyl, -$J^9$-$C_{3-10}$ cycloalky, -$J^9$-heterocycle, -$J^9$-heteroaryl, or -$J^9$-aryl, may be substituted with one or more $R^{16}$;

$R^{10}$ and $R^{11}$ each independently is H, $C_{1-6}$ alkyl, $C_{3-10}$ cycloalkyl or $SO_2R^8$;

$R^{12}$ and $R^{13}$ each independently is H, $C_{1-6}$ alkyl, or $C_{3-10}$ cycloalkyl;

$R^{12}$ and $R^{13}$ together with the carbon atom to which they are attached may form a $C_{3-6}$ cycloalkyl;

$R^{14}$ is —C(=O)$NHR^{15}$, —C(=O)$OR^{15}$, —$CH_2OR^{15}$, or —$CH_2NHR^{15}$;

$R^{15}$ is H, or $C_{1-3}$ alkyl;

$R^{16}$ is halogen, hydroxyl, —CN, —CHO, —$NR^{10}R^{11}$, —$NO_2$, $C_{1-6}$ alkyl, (=O), $C_{3-10}$ cycloalkyl, $C_{1-4}$ hydroxyalkyl, $C_{1-6}$ alkoxy, $C_{2-6}$ alkenyl, aryl, heterocycle, -$J^{16}$-alkyl, -$J^{16}$-aryl, -$J^{16}$-heterocycle, —($CH_2$)$_l$—$NR^{10}R^{11}$, —($CH_2$)$_l$—$COOR^8$, or —($CH_2$)$_l$—C(=O)—$NR^{10}R^{11}$, which -$J^{16}$-heterocycle may be substituted with one or more $R^{17}$;

$R^{17}$ is $C_{1-6}$ alkyl, $C_{1-4}$ hydroxyalkyl, or $C_{1-4}$ aminoalkyl;

$R^{18}$ is halogen, hydroxyl, —CN, —$NO_2$, —CHO, —COOH, —(C=O)H, $C_{1-6}$ alkyl, $C_{2-6}$ alkenyl, $C_{2-6}$ alkynyl, $C_{1-6}$ aminoalkyl, $C_{3-10}$ cycloalkyl, $C_{1-6}$ haloalkyl, $C_{1-4}$ hydroxyalkyl, $C_{1-6}$ alkoxy, cycloalkenyl, aryl, heterocycle, heteroaryl, —$NR^{10}R^{11}$, $J^{18}$-$NR^{10}R^{11}$, -$J^{18}$-$COOR^8$, -$J^{18}$-alkyl, -$J^{18}$-$C_{3-10}$ cycloalkyl, -$J^{18}$-cycloalkenyl, -$J^{18}$-heterocycle, -$J^{18}$-heteroaryl, or -$J^{18}$-aryl which alkyl, $C_{1-6}$ alkoxy, $C_{3-10}$ cycloalkyl, heterocycle, heteroaryl, aryl, -$J^{18}$-alkyl, -$J^{18}$-$C_{3-10}$ cycloalkyl, -$J^{18}$-cycloalky, -$J^{18}$-heterocycle, -$J^{18}$-heteroaryl, or -$J^{18}$-aryl may be substituted with one or more $R^{19}$;

$R^{19}$ is halogen, hydroxyl, —CN, —CHO, —$NR^{10}R^{11}$, —$NO_2$, $C_{1-6}$ alkyl, (=O), $C_{3-10}$ cycloalkyl, $C_{1-4}$ hydroxyalkyl, $C_{1-6}$ alkoxy, $C_{2-6}$ alkenyl, aryl, heterocycle, -$J^{19}$-alkyl, -$J^{19}$-aryl, -$J^{19}$-heterocycle, —($CH_2$)$_l$—$NR^{10}R^{11}$, —($CH_2$)$_l$—$COOR^8$, or —($CH_2$)$_l$—C(=O)—$NR^{10}R^{11}$, which -$J^{19}$-heterocycle may be substituted with one or more $R^{20}$;

$R^{20}$ is $C_{1-6}$ alkyl, $C_{1-4}$ hydroxyalkyl, or $C_{1-4}$ aminoalkyl;

$R^{21}$ is H, halogen, $C_{1-6}$ alkyl, cycloalkyl, cycloalkenyl, aryl, biaryl, heteroaryl, heterobiaryl, or heterocycle which cycloalkyl, cycloalkenyl, aryl, biaryl, heteroaryl, heterobiaryl, or heterocycle, may optionally be substituted with one or more $R^{22}$;

$R^{22}$ is halogen, hydroxyl, —CN, —$NO_2$, —CHO, —COOH, —(C=O)H, $C_{1-6}$ alkyl, $C_{2-6}$ alkenyl, $C_{2-6}$ alkynyl, $C_{1-6}$ aminoalkyl, $C_{3-10}$ cycloalkyl, $C_{1-6}$ haloalkyl, $C_{1-4}$ hydroxyalkyl, $C_{1-6}$ alkoxy, cycloalkenyl, aryl, heterocycle, heteroaryl, —$NR^{10}R^{11}$, -$J^{22}$-$NR^{10}R^{11}$, -$J^{22}$-$COOR^8$, -$J^{22}$-alkyl, -$J^{22}$-$C_{3-10}$ cycloalkyl, -$J^{22}$-cycloalkenyl, -$J^{22}$-heterocycle, -$J^{22}$-heteroaryl, or -$J^{22}$-aryl, which alkyl, $C_{1-6}$ alkoxy, $C_{3-10}$ cycloalkyl, heterocycle, heteroaryl, aryl, -$J^{22}$-alkyl, -$J^{22}$-$C_{3-10}$ cycloalky, -$J^{22}$-heterocycle, -$J^{22}$-heteroaryl, or -$J^{22}$-aryl may be substituted with one or more $R^{23}$;

$R^{23}$ is $C_{1-6}$ alkyl;

$R^{24}$ is —CN, —($CH_2$)$_l$—$OR^8$, —($CH_2$)$_l$—N($R^8$)$_2$, or $C_{1-3}$ alkyl;

$J^9$ is $C_{1-3}$ alkyl, $C_{1-3}$ alkyl-O—, $C_{2-6}$ alkenyl, $C_{2-6}$ alkynyl, $C_{3-10}$ cycloalkyl, —($CH_2$)$_l$—C(=O)—($CH_2$)$_m$—, —($CH_2$)$_l$—CH=CH—C(=O)—($CH_2$)$_m$—, —C(=O)O—, —($CH_2$)$_l$—C(=O)NH—($CH_2$)$_m$—, —($CH_2$)$_l$—NHC(=O)—($CH_2$)$_m$—, —($CR^{10}R^{11}$)$_l$—$NR^8$—($CR^{10}R^{11}$)$_m$—, —NH—C(=O)—$CR^{10}R^{11}$—NH—C(=O)—, —NHC(=O)—, —O—, —O(C=O)—, —S—, —S(=O)—, —$SO_2$—, or —$NHSO_2$;

$J^{16}$ is $C_{1-3}$ alkyl, $C_{1-3}$ alkyl-O—, $C_{2-6}$ alkenyl, $C_{2-6}$ alkynyl, $C_{3-10}$ cycloalkyl, —(CH$_2$)$_l$—C(=O)—(CH$_2$)$_m$—, —(CH$_2$)$_l$—CH=CH—C(=O)—(CH$_2$)$_m$—, —C(=O)O—, —(CH$_2$)$_l$—C(=O)NH—(CH$_2$)$_m$—, —(CH$_2$)$_l$—NHC(=O)—(CH$_2$)$_m$—, —(CR$^{10}$R$^{11}$)$_l$—NR$^8$—(CR$^{10}$R$^{11}$)$_m$—, —NH—C(=O)—CR$^{10}$R$^{11}$—NH—C(=O)—, —NHC(=O)—, —O—, —O(C=O)—, —S—, —S(=O)—, or —SO$_2$—;

$J^{18}$ is $C_{1-3}$ alkyl, $C_{1-3}$ alkyl-O—, $C_{2-6}$ alkenyl, $C_{2-6}$ alkynyl, $C_{3-10}$ cycloalkyl, —(CH$_2$)$_l$—C(=O)—(CH$_2$)$_m$—, —(CH$_2$)$_l$—CH=CH—C(=O)—(CH$_2$)$_m$—, —C(=O)—, —C(=O)O—, —(CH$_2$)$_l$—C(=O)NH—(CH$_2$)$_m$—, —(CH$_2$)$_l$—NHC(=O)—(CH$_2$)$_m$—, —(CR$^{10}$R$^{11}$)$_l$—NR$^8$—(CR$^{10}$R$^{11}$)$_m$—, —NH—C(=O)—CR$^{10}$R$^{11}$—NH—C(=O)—, —NHC(=O)—, —O—, —O(C=O)—, —S—, —S(=O)—, —SO$_2$—, or —NHSO$_2$—;

$J^{19}$ is $C_{1-3}$ alkyl, $C_{1-3}$ alkyl-O—, $C_{2-6}$ alkenyl, $C_{2-6}$ alkynyl, $C_{3-10}$ cycloalkyl, —(CH$_2$)$_l$—C(=O)—(CH$_2$)$_m$—, —(CH$_2$)$_l$—CH=CH—C(=O)—(CH$_2$)$_m$—, —C(=O)O—, —(CH$_2$)$_l$—C(=O)NH—(CH$_2$)$_m$—, —(CH$_2$)$_l$—NHC(=O)—(CH$_2$)$_m$—, —(CR$^{10}$R$^{11}$)$_l$—NR$^8$—(CR$^{10}$R$^{11}$)$_m$—, —NH—C(=O)—CR$^{10}$R$^{11}$—NH—C(=O)—, —NHC(=O)—, —O—, —O(C=O)—, —S—, —S(=O)—, or —SO$_2$—;

$J^{22}$ is $C_{1-3}$ alkyl, $C_{1-3}$ alkyl-O—, or —O—; and l and m each independently is an integer of 0 to 3;

with the proviso that when Ring A is

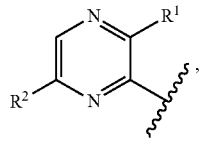

then $R^2$ is not

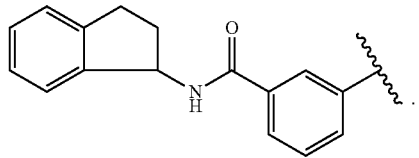 [SMILES: *c1cccc(C(=O)NC2CCc3ccccc32)c1]

In one embodiment, compounds of the present disclosure are represented by formula (III):

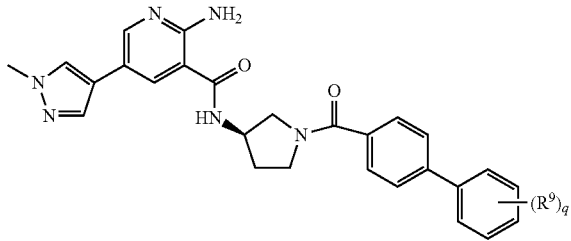

(III)

or a pharmaceutically acceptable salt thereof; wherein:
$R^9$ is F or Cl; and
q is 1, 2, or 3.

In another embodiment, the present disclosure relates to a heterocyclic compound represented by the following formula A, a stereoisomer thereof, an enantiomer thereof, or a pharmaceutically acceptable salt thereof:

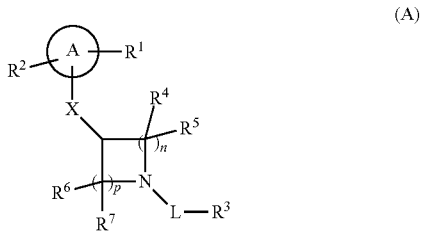

(A)

wherein

Ring A is a monocyclic or bicyclic ring selected from a 5 to 10-membered heteroaryl; wherein said heteroaryl contains from 0 to 3 ring heteroatoms independently selected from N, O, or S;

X is —C(=O)O—, —C(=O)N(R$^8$)—, —SO$_2$N(R$^8$)—, —N(R$^8$)—, —O—, or —S—;

n is 0, 1, 2, or 3;

p is 1, 2, or 3;

L is none, $C_{1-3}$ alkyl, $C_{2-3}$ alkenyl, $C_{1-3}$ alkyl-O—, $C_{1-3}$ alkyl-O—$C_{1-3}$alkyl, —C(=O)—, —C(=O)O—, —C(=O)N(R$^8$)—, C(=S)N(R$^8$)—, —C(=S)—, —C(=S)O—, —SO$_2$—(CH$_2$)$_m$—, —C(=O)—(CH$_2$)$_m$—, or —C(=O)—CH=CH—;

$R^1$ is H, halogen, $C_{1-3}$ alkyl, —NH(R$^8$)—, or —OR$^8$;

$R^2$ is H, halogen, —CN, $C_{1-3}$ alkyl, cycloalkenyl, $C_{2-6}$ alkenyl, aryl, biaryl, heteroaryl, heterobiaryl, heterocycle, $C_{1-2}$ alkylaryl, $C_{1-2}$ alkylheteroaryl, or $C_{1-2}$ alkylheterocycle which aryl, biaryl, heteroaryl, heterobiaryl, or heterocycle may optionally be substituted with one or more $R^9$;

$R^3$ is H, halogen, aryl, biaryl, heteroaryl, heterobiaryl, or heterocycle, which aryl, biaryl, heteroaryl, heterobiaryl or heterocycle may optionally be substituted with one or more $R^9$;

$R^4$ to $R^7$ are the same as or different from each other, and are each independently H, halogen, —C(=O)NHR$^3$, —C(=O)OR$^3$, —CH$_2$OR$^3$, or —CH$_2$NHR$^3$;

$R^8$ is H, $C_{1-6}$ alkyl, $C_{1-3}$ alkylaryl, or $C_{1-3}$ alkylheteroaryl which $C_{1-6}$ alkyl, $C_{1-3}$ alkylaryl or $C_{1-3}$ alkylheteroaryl may optionally be substituted with one or more $R^9$;

$R^9$ is halogen, hydroxyl, —CN, —NO$_2$, —COOH, —(C=O)H, $C_{1-6}$ alkyl, $C_{2-6}$ alkenyl, $C_{2-6}$ alkynyl, $C_{3-10}$ cycloalkyl, $C_{1-4}$ hydroxyalkyl, $C_{1-6}$ alkoxy, cycloalkenyl, aryl, heterocycle, heteroaryl, —NR$^{10}$R$^{11}$, -J-NR$^{10}$R$^{11}$, -J-COOR$^8$, -J-alkyl, -J-$C_{3-10}$ cycloalkyl, -J-heterocycle, -J-heteroaryl, or -J-aryl which alkyl, $C_{1-6}$ alkoxy, $C_{3-10}$ cycloalkyl, heterocycle, heteroaryl, or aryl may be substituted with halogen, hydroxyl, —CN, —NR$^{10}$R$^{11}$, $C_{1-6}$ alkyl, $C_{3-10}$ cycloalkyl, $C_{1-4}$ hydroxyalkyl, $C_{2-6}$ alkenyl, aryl, heterocycle, -J-alkyl, -J-aryl, -J-heterocycle, or —(CH$_2$)$_l$—C(=O)—NR$^{10}$R$^{11}$;

$R^{10}$ and $R^{11}$ each independently is H, $C_{1-6}$ alkyl, $C_{3-10}$ cycloalkyl or SO$_2$R$^8$;

J is $C_{1-3}$ alkyl, $C_{1-3}$ alkyl-O—, $C_{2-6}$ alkynyl, $C_{3-10}$ cycloalkyl, —(CH$_2$)$_l$—C(=O)—(CH$_2$)$_m$—, —C(=O)O—, —(CH$_2$)$_l$—C(=O)NH—(CH$_2$)$_m$—, —(CH$_2$)$_l$—NHC(=O)—(CH$_2$)$_m$—, —(CH$_2$)$_l$—NR$^8$—(CH$_2$)$_m$—, —NH—C(=O)—CR$^{10}$R$^{11}$—NH—C(=O)—, —NHC(=O)—, —O—, —O(C=O)—, —S—, —S(=O)—, or —SO$_2$—; and l and m each independently is an integer of 0 to 3.

Particular values of variable groups in compounds of formula (I), (II), or (III) are as follows. Such values can be used where appropriate with any of the other values, definitions, claims or embodiments defined hereinbefore or hereinafter.

In one embodiment of formula (I), $R^4$, $R^5$, and $R^{24}$ are H; n is 1; and A, X, $R^1$, $R^2$, $R^3$, $R^6$, $R^7$, $R^{24}$, L, and p are as defined for formula (I); with the proviso that when Ring A is

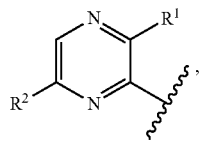

then $R^2$ is not

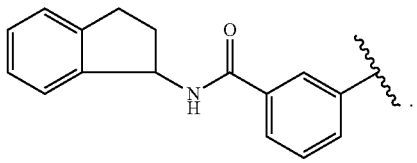 [SMILES: *c1cccc(C(=O)NC2CCc3ccccc32)c1]

In one embodiment of formula (I),
$R^4$, $R^5$, and $R^{24}$ are H;
n is 1;
$R^6$, and $R^7$ are the same as or different from each other, and are each independently H, halogen, —OR 21; —OCH$_2$R$^{21}$; —C(=O)NHR$^{21}$, —C(=O)OR$^{21}$, —C(=O)SR$^{21}$; —C(=O)S—SR$^{21}$, —CH$_2$OR$^{21}$ or —CH$_2$NHR$^{21}$;
$J^9$ is C$_{1-3}$ alkyl, C$_{1-3}$ alkyl-O—, C$_{2-6}$ alkenyl, C$_{2-6}$ alkynyl, C$_{3-10}$ cycloalkyl, —(CH$_2$)$_f$—C(=O)—(CH$_2$)$_m$—, —(CH$_2$)$_f$—CH=CH—C(=O)—(CH$_2$)$_m$—, —C(=O)O—, —(CH$_2$)$_f$—C(=O)NH—(CH$_2$)$_m$—, —(CH$_2$)$_f$—NHC(=O)—(CH$_2$)$_m$—, —(CH$_2$)$_f$—NR—(CR$^{10}$R$^{11}$)$_m$—, —NH—C(=O)—CR$^{10}$R$^{11}$NH—C(=O)—, —NHC(=O)—, —O—, —O(C=O)—, —S—, —S(=O)—, —SO$_2$—, or —NHSO$_2$—; and
A, X, $R^1$, $R^2$, $R^3$, L, and p are as defined for formula (I); with the proviso that when Ring A is

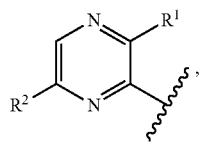

then R is not

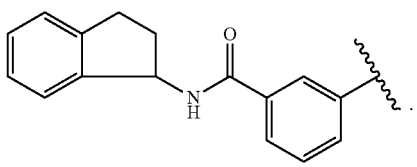 [SMILES: *c1cccc(C(=O)NC2CCc3ccccc32)c1]

In one embodiment of formula (II), $R^4$, $R^5$, and $R^{24}$ are H; and A, X, $R^1$, $R^2$, $R^3$, $R^6$, $R^7$, $R^{24}$, and L, are as defined for formula (I); with the proviso that when Ring A is

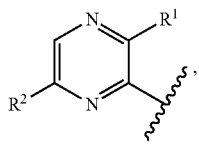

then $R^2$ is not

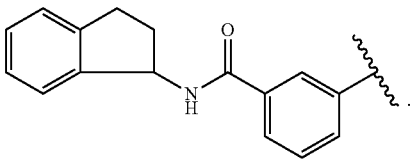 [SMILES: *c1cccc(C(=O)NC2CCc3ccccc32)c1]

In one embodiment of formula (II),
$R^4$, $R^5$, and $R^{24}$ are H;
$R^6$, and $R^7$ are the same as or different from each other, and are each independently H, halogen, —OR$^{21}$; —OCH$_2$R$^{21}$; —C(=O)NHR$^{21}$, —C(=O)OR$^{21}$, —C(=O)SR$^{21}$; —C(=O)S—SR$^{21}$, —CH$_2$OR$^{21}$, or —CH$_2$NHR$^{21}$;
$J^9$ is C$_{1-3}$ alkyl, C$_{1-3}$ alkyl-O—, C$_{2-6}$ alkenyl, C$_{2-6}$ alkynyl, C$_{3-10}$ cycloalkyl, —(CH$_2$)$_f$—C(=O)—(CH$_2$)$_m$—, j—(CH$_2$)$_f$—CH=CH—C(=O)—(CH$_2$)$_m$—, —C(=O)O—, —(CH$_2$)$_f$—C(=O)NH—(CH$_2$)$_m$—, —(CH$_2$)$_f$—NHC(=O)—(CH$_2$)$_m$—, —(CH$_2$)$_f$—NR—(CR$^{10}$R$^{11}$)$_m$—, —NH—C(=O)—CR$^{10}$R$^{11}$NH—C(=O)—, —NHC(=O)—, —O—, —O(C=O)—, —S—, —S(=O)—, —SO$_2$—, or —NHSO$_2$—; and
A, X, $R^1$, $R^2$, $R^3$, and L, are as defined for formula (I); with the proviso that when Ring A is

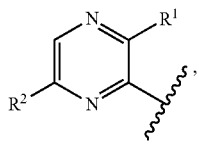

then $R^2$ is not

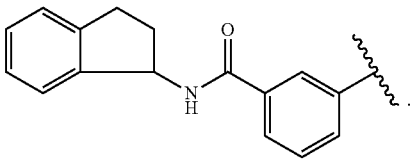 [SMILES: *c1cccc(C(=O)NC2CCc3ccccc32)c1]

In one embodiment of formula (II), A is

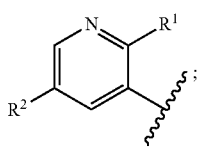

X is —C(=O)N(R$^8$)—; and
$R^1$, $R^2$, $R^3$, $R^4$, $R^5$, $R^6$, $R^7$, $R^{24}$, and L are as defined for formula (II).

In one embodiment of formula (II), A is

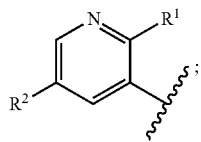

X is —C(=O)N(R⁸)—;
R¹ is —NH₂;
R² is —Br, —Cl, aryl, heteroaryl, or heterocycle, which aryl, heteroaryl, or heterocycle may optionally be substituted with one or more R¹; and
R³, R⁴, R⁵, R⁶, R⁷, R⁸, R²⁴ and L are as defined for formula (II).

In one embodiment of formula (II), A is

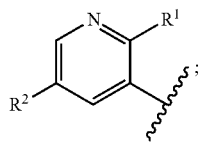

X is —C(=O)N(R⁸)—;
R¹ is —NH₂;
R² is

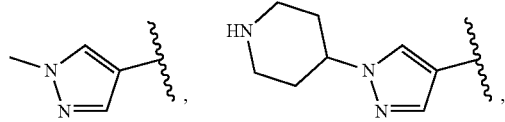

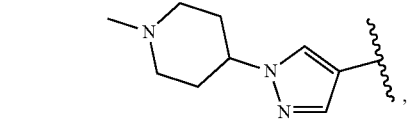

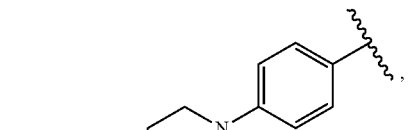

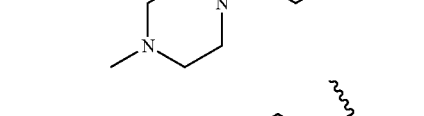

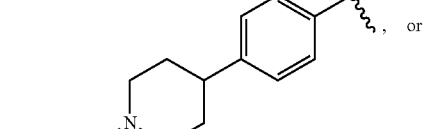, or

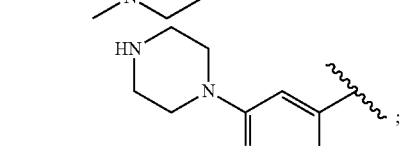

R³, R⁴, R⁵, R⁶, R⁷, R²⁴, and L are as defined for formula (II).

In one embodiment of formula (II), A is

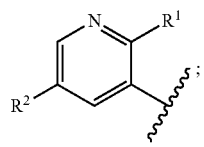

X is —C(=O)N(R⁸)—;
R¹ is —NH₂;
R² is

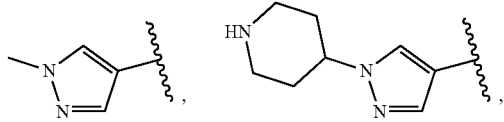

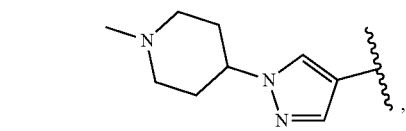

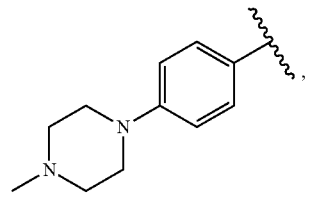

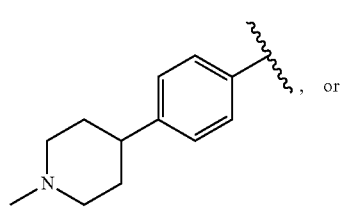, or

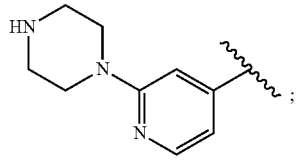

L is C₁₋₃ alkyl, C₁₋₃ alkyl-O—, —C(=O)—, —C(=O)O—, or —C(=O)N(R⁸)—; and
R³, R⁴, R⁵, R⁶, R⁷, and R²⁴, are as defined for formula (II).

In one embodiment of formula (II), A is

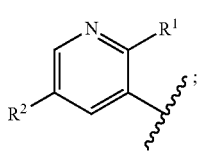

X is —C(=O)N(R$^8$)—;
R$^1$ is —NH$_2$;
R$^2$ is

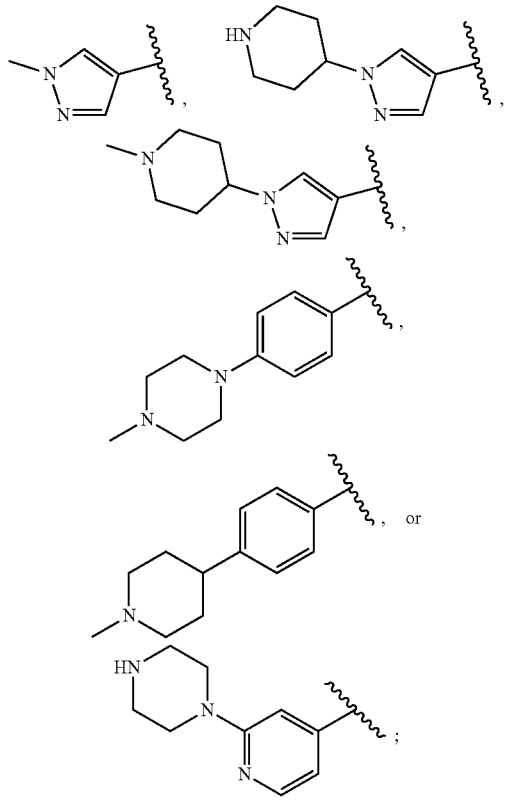

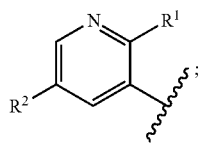;

L is C$_{1-3}$ alkyl, C$_{1-3}$ alkyl-O—, —C(=O)—, —C(=O)O—, or —C(=O)N(R$^8$)—;

R$^3$ is aryl, biaryl, or heterobiaryl, which aryl, biaryl, or heterobiaryl, may optionally be substituted with one or more R$^9$; and R$^4$, R$^5$, R$^6$, R$^7$, R$^9$, and R$^{24}$, are as defined for formula (II).

In one embodiment of formula (II), A is

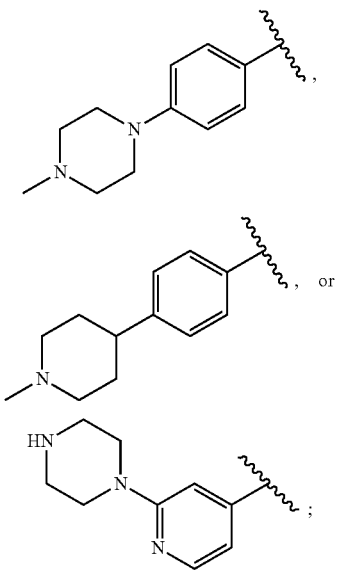

X is —C(=O)N(R$^8$)—;
R$^1$ is —NH$_2$;
R$^2$ is

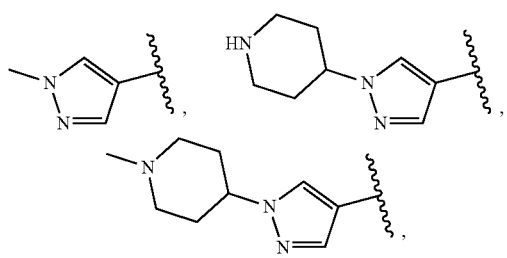

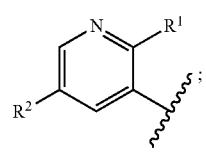;

L is C$_{1-3}$ alkyl, C$_{1-3}$ alkyl-O—, —C(=O)—, —C(=O)O—, or —C(=O)N(R$^8$)—;

R$^3$ is aryl, biaryl, or heterobiaryl, which aryl, biaryl, or heterobiaryl, may optionally be substituted with one or more R$^9$;

R$^9$ is halogen, C$_{1-6}$ alkyl, aryl, heterocycle, -J$^9$-heterocycle, or -J$^9$-aryl which alkyl, aryl, heterocycle, -J$^9$-heterocycle, or -J$^9$-aryl may be substituted with may be substituted with one or more R$^{16}$;

R$^{16}$ is —NR$^{10}$R$^{11}$, C$_{1-6}$ alkyl, C$_{1-4}$ hydroxyalkyl, or heterocycle; and R$^4$, R$^5$, R$^6$, R$^7$, R$^{10}$, R$^{11}$, R$^{24}$, and -J$^9$ are as defined for formula (II).

In one embodiment of formula (II), A is

-continued

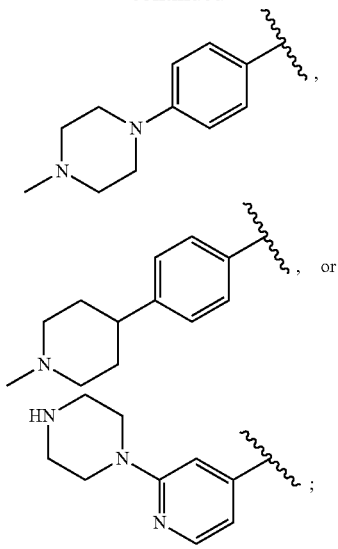

L is —C(=O)—;
R³ is biphenyl substituted with one, two, or three R⁹;
R⁹ is halogen; and
R⁴, R⁵, R⁶ and R⁷ are as defined for formula (II).
In one embodiment of formula (II), A is

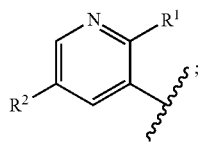

X is —C(=O)N(R⁸)—;
L is —C(=O)—;
R¹ is NH₂;
R² is phenyl, pyridyl, or pyrazole, which phenyl, pyridyl, or pyrazole may optionally be substituted with one or more R¹⁸;
R³ is biphenyl which may optionally be substituted with one or more R⁹;
R⁴, R⁵, R⁶, and R⁷ are each independently H;
R⁸ is H;
R⁹ is halogen, or -J⁹-aryl which -J⁹-aryl, may be substituted with one or more R¹⁶;
R¹⁶ is —(CH₂)ⱼ—NR¹⁰R¹¹;
R¹⁸ is C₁₋₆ alkyl, heterocycle, or -J¹⁸-heterocycle, which heterocycle, or -J¹⁸-heterocycle may be substituted with R¹⁹;
R¹⁹ is C₁₋₆ alkyl;
R²⁴ is H; and
J⁹ is —C(=O)NH—.
In one embodiment of formula (II), A is

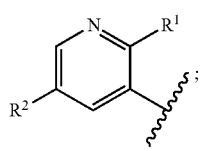

X is —C(=O)N(R⁸)—;
L is —C(=O)—;
R¹ is NH₂;
R² is

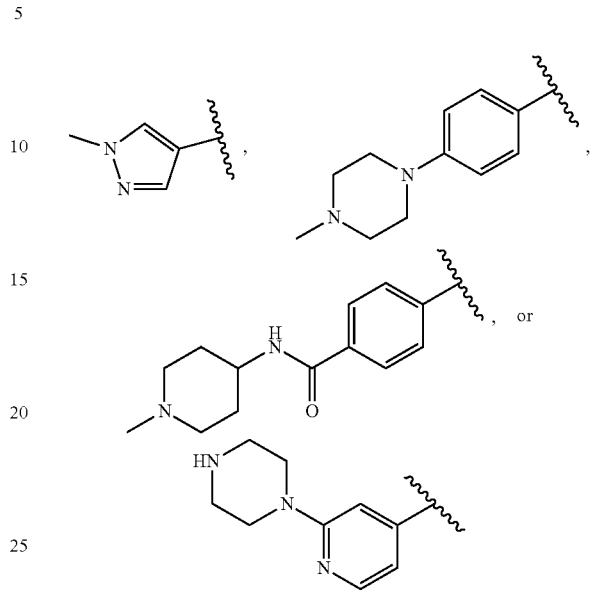

R³ is biphenyl which may optionally be substituted with one or more R⁹;
R⁴, R⁵, R⁶, and R⁷ are each independently H;
R⁸ is H;
R⁹ is halogen, or -J⁹-aryl which -J⁹-aryl, may be substituted with one or more R¹⁶;
R¹⁶ is —(CH₂)ⱼ—NR¹⁰R¹¹;
R¹⁸ is C₁₋₆ alkyl, heterocycle, or -J¹⁸-heterocycle, which heterocycle, or -J¹⁸-heterocycle may be substituted with R¹⁹;
R¹⁹ is C₁₋₆ alkyl;
R²⁴ is H; and
J⁹ is —C(=O)NH—.
In one embodiment of formula (II), A is

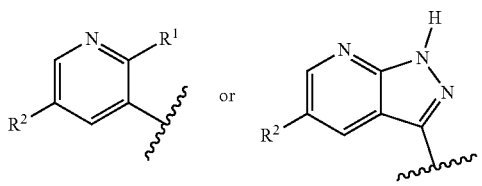

X is —C(=O)N(R⁸)— or —N(R⁸)—;
L is —C(=O)—, —C(=O)O—, —C(=O)N(R⁸)—;
R¹ is H or —NH₂;
R² is phenyl, pyridyl, or pyrazole which phenyl, pyridyl, or pyrazole may optionally be substituted with one or more R¹⁸;
R³ is phenyl or biphenyl which may optionally be substituted with one or more R⁹;
R⁴, R⁵, and R⁶, are each independently H;
R⁷ is H, halogen, —OR²¹; —C(=O)NHR²¹, —C(=O)OR²¹, or —CH₂OR²¹;
R⁸ is H, or C₁₋₆ alkyl;
R²¹ is H, C₁₋₆ alkyl, aryl, biaryl, or heterobiaryl, which aryl, biaryl, or heterobiaryl, may optionally be substituted with one or more R²²;

$R^{22}$ is halogen, $C_{1-6}$ alkyl, heterocycle, -$J^{22}$-$NR^{10}R^{11}$, -$J^{22}$-heterocycle, or -$J^{22}$-aryl, which alkyl, heterocycle, -$J^{22}$-heterocycle or -$J^{22}$-aryl, may be substituted with one or more $R^{23}$;

$R^{23}$ is $C_{1-6}$ alkyl;

$R^{24}$ is H; and $J^{22}$ is $C_{1-3}$ alkyl, $C_{1-3}$ alkyl-O—, or —O—.

In one embodiment of formula (II), A is

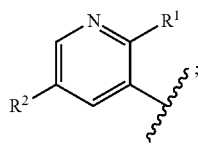

X is —C(=O)N($R^8$)—;
L is —C(=O)—;
$R^1$ is $NH_2$;
$R^2$ is

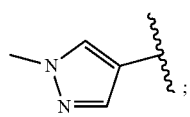

$R^3$ is biphenyl substituted with 1-3 $R^9$;
$R^4$, $R^5$, $R^6$ and $R^7$ are each independently H;
$R^8$ is H;
$R^9$ is halogen; and
$R^{24}$ is H.

In one embodiment of formula (II), Ring A is

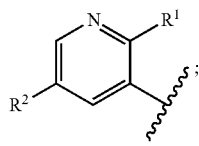

X is —C(=O)N($R^8$)—;
L is —C(=O)—;
$R^1$ is $NH_2$;
$R^2$ is

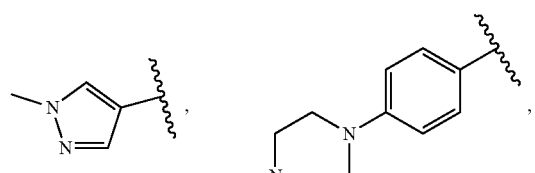

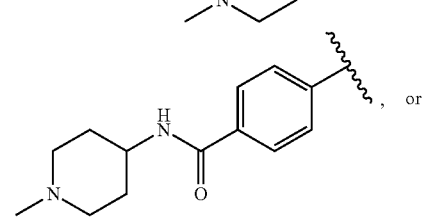

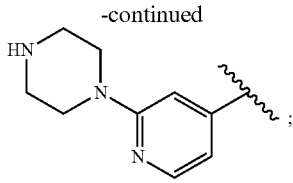

$R^3$ is biphenyl substituted with 1-3 $R^9$;
$R^4$, $R^5$, $R^6$ and $R^7$ are each independently H;
$R^8$ is H;
$R^9$ is halogen; and
$R^{24}$ is H.

In one embodiment of formula (II), A is

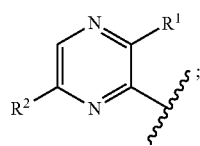

X is —C(=O)N($R^8$)—; and
$R^1$, $R^2$, $R^3$, $R^4$, $R^5$, $R^6$, $R^7$, $R^{24}$, and L are as defined for formula (II);

with the proviso that $R^2$ is not

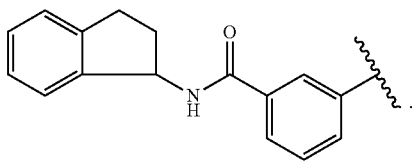 [SMILES: *c1cccc(C(=O)NC2CCc3ccccc32)c1]

In one embodiment of formula (II), A is

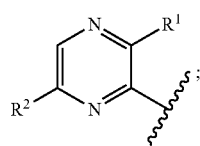

X is —C(=O)N($R^8$)—;
$R^1$ is —$NH_2$;
$R^2$ is —Br, —Cl, aryl, heteroaryl, or heterocycle, which aryl, heteroaryl, or heterocycle may optionally be substituted with one or more $R^{18}$;

with the proviso that $R^2$ is not

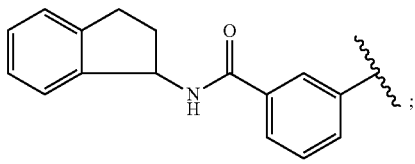 [SMILES: *c1cccc(C(=O)NC2CCc3ccccc32)c1]

and
$R^3$, $R^4$, $R^5$, $R^6$, $R^7$, $R^8$, $R^{24}$ and L are as defined for formula (II).

In one embodiment of formula (II), A is
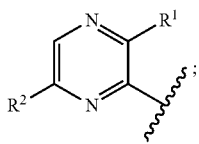
X is —C(=O)N(R⁸)—;
R¹ is —NH₂;
R² is
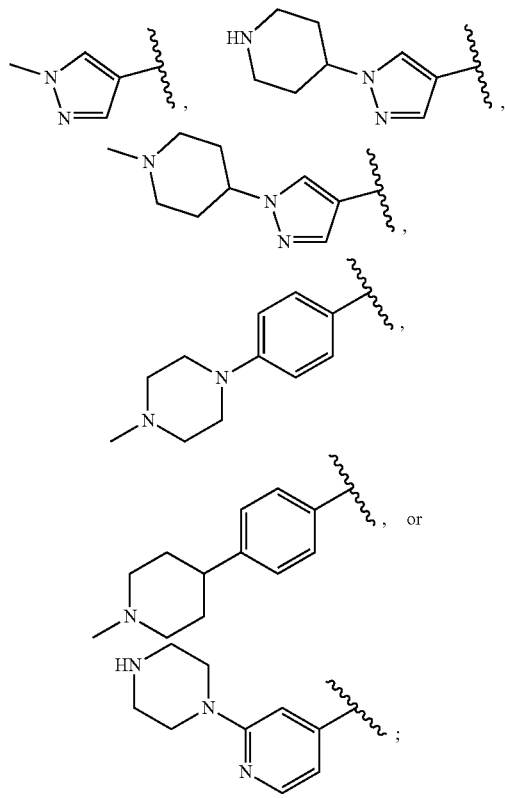
R³, R⁴, R⁵, R⁶, R⁷, R²⁴, and L are as defined for formula (II).
In one embodiment of formula (II), A is
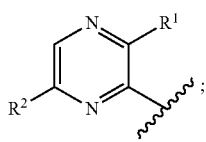
X is —C(=O)N(R⁸)—;
R¹ is —NH₂;
R² is
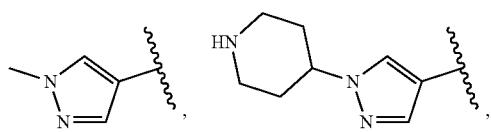
-continued
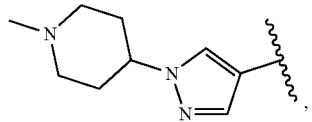
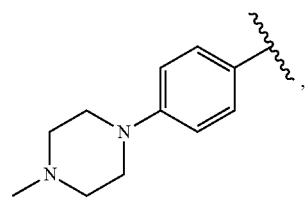
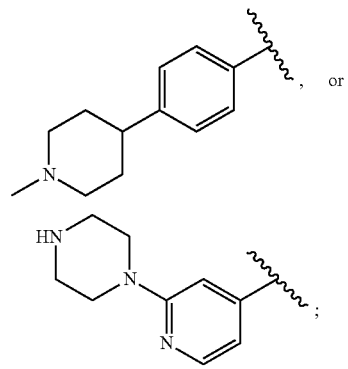
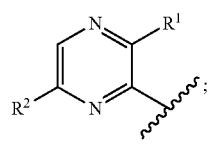
L is C₁₋₃ alkyl, C₁₋₃ alkyl-O—, —C(=O)—, —C(=O)O—, or —C(=O)N(R⁸)—; and
R³, R⁴, R⁵, R⁶, R⁷, and R²⁴, are as defined for formula (II).
In one embodiment of formula (II), A is
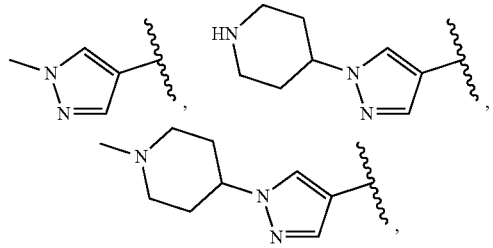
X is —C(=O)N(R⁸)—;
R¹ is —NH₂;
R² is
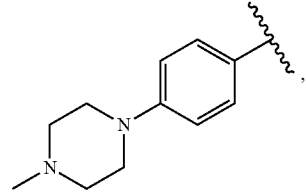

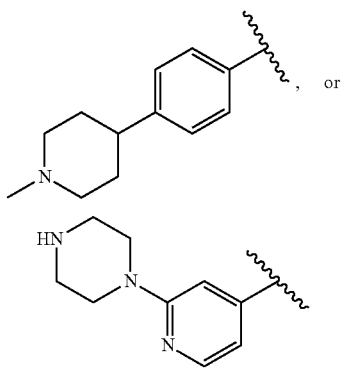

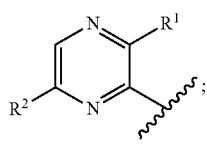

L is $C_{1-3}$ alkyl, $C_{1-3}$ alkyl-O—, —C(=O)—, —C(=O)O—, or —C(=O)N(R$^8$)—;

R$^3$ is aryl, biaryl, or heterobiaryl, which aryl, biaryl, or heterobiaryl, may optionally be substituted with one or more R$^9$; and R$^4$, R$^5$, R$^6$, R$^7$, R$^9$, and R$^{24}$, are as defined for formula (II).

In one embodiment of formula (II), A is

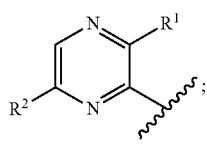

X is —C(=O)N(R$^8$)—;
R$^1$ is —NH$_2$;
R$^2$ is

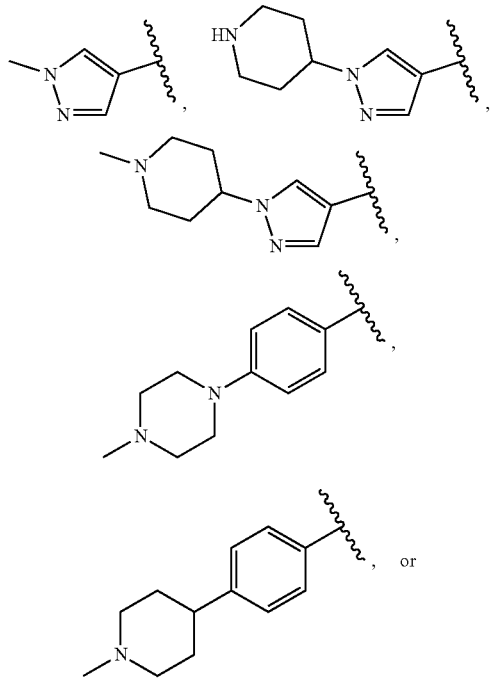

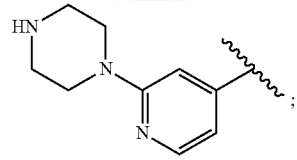

L is $C_{1-3}$ alkyl, $C_{1-3}$ alkyl-O—, —C(=O)—, —C(=O)O—, or —C(=O)N(R$^8$)—;

R$^3$ is aryl, biaryl, or heterobiaryl, which aryl, biaryl, or heterobiaryl, may optionally be substituted with one or more R$^9$;

R$^9$ is halogen, $C_{1-6}$ alkyl, aryl, heterocycle, -J$^9$-heterocycle, or -J$^9$-aryl which alkyl, aryl, heterocycle, -J$^9$-heterocycle, or -J$^9$-aryl may be substituted with may be substituted with one or more R$^{16}$;

R$^{16}$ is —NR$^{10}$R$^{11}$, $C_{1-6}$ alkyl, $C_{1-4}$ hydroxyalkyl, or heterocycle; and R$^4$, R$^5$, R$^6$, R$^7$, R$^{10}$, R$^{11}$, R$^{24}$, and -J$^9$ are as defined for formula (II).

In one embodiment of formula (II), A is

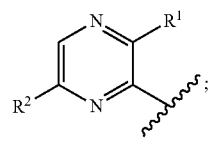

X is —C(=O)N(R$^8$)—;
R$^1$ is —NH$_2$;
R$^2$ is

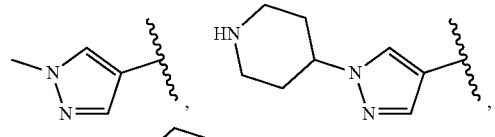

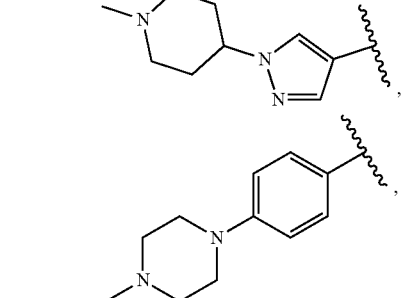

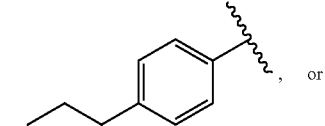

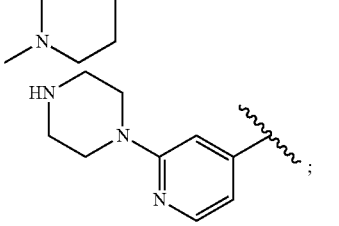

L is —C(=O)—;
R³ is biphenyl substituted with one, two, or three R⁹;
R⁹ is halogen; and
R⁴, R⁵, R⁶, R⁷, and R²⁴ are as defined for formula (II).
In one embodiment of formula (II), A is

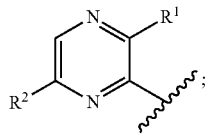

X is —C(=O)N(R⁸)—;
L is —C(=O)—;
R¹ is NH₂;
R² is phenyl, pyridyl, or pyrazole, which phenyl, pyridyl, or pyrazole may optionally be substituted with one or more R¹⁸; with the proviso that R² is not

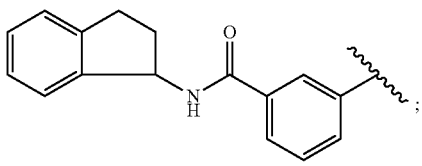 [SMILES: *c1cccc(C(=O)NC2CCc3ccccc32)c1]

R³ is biphenyl which may optionally be substituted with one or more R⁹;
R⁴, R⁵, R⁶, and R⁷ are each independently H;
R⁸ is H;
R⁹ is halogen, or -J⁹-aryl which -J⁹-aryl, may be substituted with one or more R¹⁶;
R¹⁶ is —(CH₂)$_f$—NR¹⁰R¹¹;
R¹⁸ is C₁₋₆ alkyl, heterocycle, or -J¹⁸-heterocycle, which heterocycle, or -J¹⁸-heterocycle may be substituted with R¹⁹;
R¹⁹ is C₁₋₆ alkyl;
R²⁴ is H; and
J⁹ is —C(=O)NH—.
In one embodiment of formula (II), A is

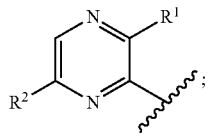

X is —C(=O)N(R⁸)—;
L is —C(=O)—;
R¹ is NH₂;
R² is

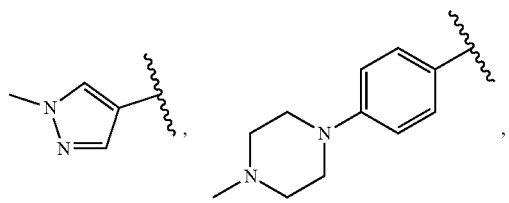

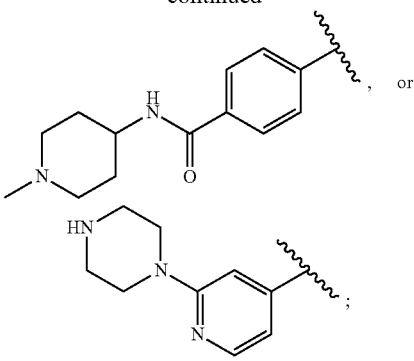

R³ is biphenyl which may optionally be substituted with one or more R⁹;
R⁴, R⁵, R⁶, and R⁷ are each independently H;
R⁸ is H;
R⁹ is halogen, or -J⁹-aryl which -J⁹-aryl, may be substituted with one or more R¹⁶;
R¹⁶ is —(CH₂)$_f$—NR¹⁰R¹¹;
R¹⁸ is C₁₋₆ alkyl, heterocycle, or -J¹⁸-heterocycle, which heterocycle, or -J¹⁸-heterocycle may be substituted with R¹⁹;
R¹⁹ is C₁₋₆ alkyl;
R²⁴ is H; and
J⁹ is —C(=O)NH—.
In one embodiment of formula (II), A is

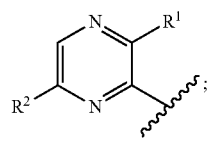

X is —C(=O)N(R⁸)—;
L is —C(=O)—;
R¹ is NH₂;
R² is

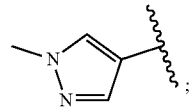 [SMILES: *c1cnn(C)c1]

R³ is biphenyl substituted with 1-3 R⁹;
R⁴, R⁵, R⁶ and R⁷ are each independently H;
R⁸ is H;
R⁹ is halogen; and
R²⁴ is H.
In one embodiment of formula (II), Ring A is

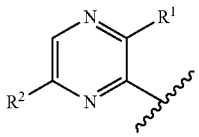

X is —C(=O)N(R⁸)—;
L is —C(=O)—;

$R^1$ is $NH_2$;
$R^2$ is

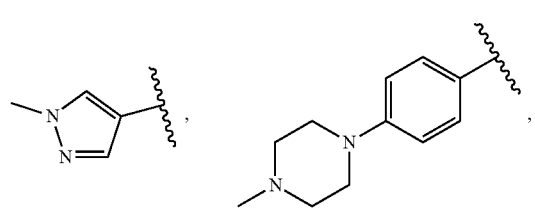,

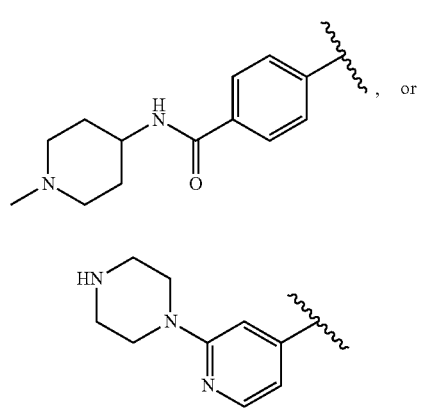

$R^3$ is biphenyl substituted with 1-3 $R^9$;
$R^4$, $R^5$, $R^6$ and $R^7$ are each independently H;
$R^8$ is H;
$R^9$ is halogen; and
$R^{24}$ is H.

In one embodiment of formula (II), A is

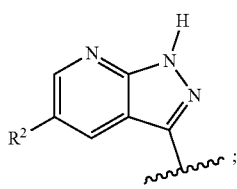;

and

A, $R^1$, $R^2$, $R^3$, $R^4$, $R^5$, $R^6$, $R^7$, $R^{24}$, X, and L are as defined for formula (II).

In one embodiment of formula (II), A is

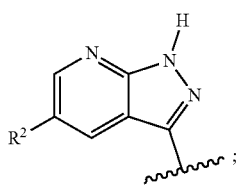;

X is —N($R^8$)—;
L is —C(=O)—;

$R^1$ is H;
$R^2$ is

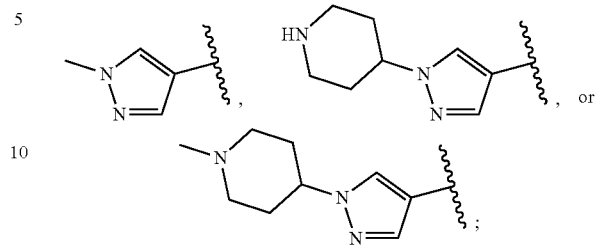;

$R^3$ is phenyl or biphenyl each of which may optionally be substituted with one or more $R^9$;
$R^4$, $R^5$, $R^6$, and $R^7$ are each independently H;
$R^8$ is H;
$R^9$ is halogen, $C_{1-6}$ alkyl, heterocycle, -$J^9$-heterocycle, or -$J^9$-aryl which alkyl, heterocycle, or aryl, may be substituted with one or more $R^{16}$;
$R^{10}$ and $R^1$ each independently is H, or $C_{1-6}$ alkyl;
$J^9$ is $C_{1-3}$ alkyl, or —O—;
$R^{16}$ is $C_{1-6}$ alkyl, or —(CH$_2$)$_l$—NR$^{10}$R$^{11}$;
$R^{24}$ is H; and
l and m each independently is an integer of 0 to 3.

In one embodiment of formula (III), q is 1; and $R^9$ is F.
In one embodiment of formula (III), q is 1; and $R^9$ is Cl.
In one embodiment of formula (III), q is 2; and both $R^9$ are F.
In one embodiment of formula (III), q is 2; and both $R^9$ are Cl.
In one embodiment of formula (III), q is 2; and one $R^9$ is F; and the other $R^9$ is Cl.

Particular values of variable groups in compounds of formula (I, II or III) are as follows. Such values can be used where appropriate with any of the other values, definitions, claims or embodiments defined hereinbefore or hereinafter.

In one embodiment, in a compound or pharmaceutically acceptable salt of formula (I or II), A is

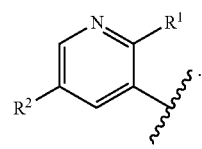.

In one embodiment, in a compound or pharmaceutically acceptable salt of formula (I or II), A is

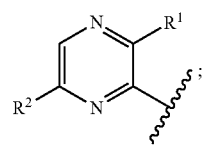;

with the proviso that $R^2$ is not

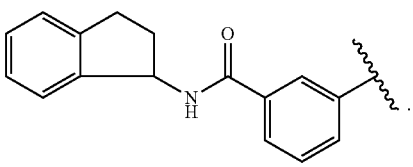 [SMILES: *c1cccc(C(=O)NC2CCc3ccccc32)c1].

In one embodiment, in a compound or pharmaceutically acceptable salt of formula (I or II), A is

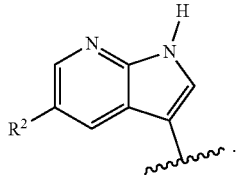

In one embodiment, in a compound or pharmaceutically acceptable salt of formula (I or II), A is

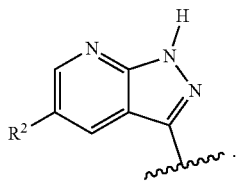

In one embodiment, in a compound or pharmaceutically acceptable salt of formula (I or II), $R^1$ is H, —NH($R^8$), or —(CH$_2$)$_f$—NR$^{12}$R$^{13}$; where $R^8$, $R^{12}$, and $R^{13}$ are as defined for formula (I or II).

In one embodiment, in a compound or pharmaceutically acceptable salt of formula (I or II), $R^1$ is NH$_2$.

In one embodiment, in a compound or pharmaceutically acceptable salt of formula (I or II), $R^2$ is phenyl, pyridyl, or pyrazole, which phenyl, pyridyl, or pyrazole may optionally be substituted with one or more $R^{18}$; where $R^{18}$ is as defined for formula (I or II).

In one embodiment, in a compound or pharmaceutically acceptable salt of formula (I or II), $R^2$ is —Br, aryl, heteroaryl, heterocycle, which aryl, heteroaryl, or heterocycle may optionally be substituted with one or more $R^{18}$; where $R^{18}$ is as defined for formula (I or II).

In one embodiment, in a compound or pharmaceutically acceptable salt of formula (I or II), $R^2$ is

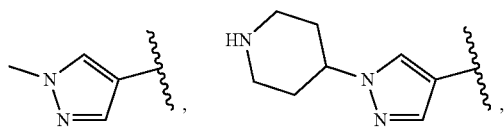

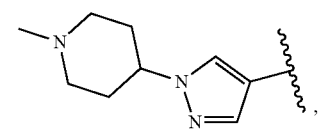

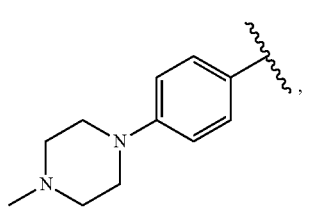

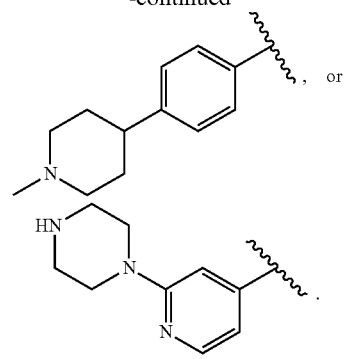

In one embodiment, in a compound or pharmaceutically acceptable salt of formula (I or II), $R^2$ is

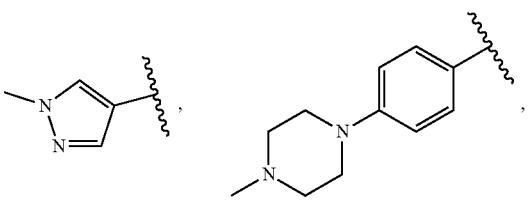

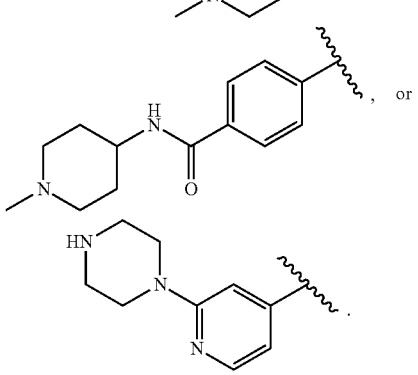

In one embodiment, in a compound or pharmaceutically acceptable salt of formula (I or II), $R^2$ is

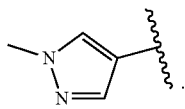

In one embodiment, in a compound or pharmaceutically acceptable salt of formula (I or II), $R^2$ is

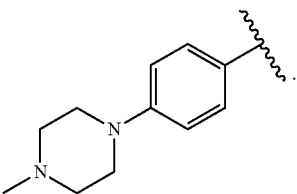 [SMILES: *c1ccc(N2CCN(C)CC2)cc1]

In one embodiment, in a compound or pharmaceutically acceptable salt of formula (I or II), $R^2$ is

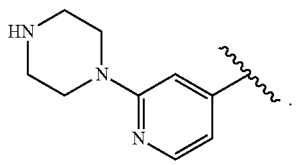 [SMILES: *c1ccnc(N2CCNCC2)c1]

In one embodiment, in a compound or pharmaceutically acceptable salt of formula (I or II), $R^3$ is aryl, biaryl, or heterobiaryl, which aryl, biaryl, or heterobiaryl, may optionally be substituted with one or more $R^9$; where $R^9$ is as defined for formula (I or II).

In one embodiment, in a compound or pharmaceutically acceptable salt of formula (I or II), $R^3$ is phenyl, naphthyl, biphenyl, phenyl-pyridine, phenyl-pyrazole, or phenyl-thiophene, which phenyl, naphthyl, biphenyl, phenyl-pyridine, phenyl-pyrazole, or phenyl-thiophene, may optionally be substituted with one or more $R^9$; where $R^9$ is as defined for formula (I or II).

In one embodiment, in a compound or pharmaceutically acceptable salt of formula (I or II), $R^3$ is biphenyl which may optionally be substituted with one or more $R^9$; where $R^9$ is as defined for formula (I or II).

In one embodiment, in a compound or pharmaceutically acceptable salt of formula (I or II), $R^3$ is biphenyl substituted with one or more halogen.

In one embodiment, in a compound or pharmaceutically acceptable salt of formula (I or II), $R^3$ is biphenyl substituted with one or more $R^9$; where $R^9$ is —F or —Cl.

In one embodiment, in a compound or pharmaceutically acceptable salt of formula (I or II), $R^4$ is H and $R^5$ is H.

In one embodiment, in a compound or pharmaceutically acceptable salt of formula (I or II), $R^4$, $R^5$, $R^6$, and $R^7$, are each independently H.

In one embodiment, in a compound or pharmaceutically acceptable salt of formula (I or II), $R^6$ is H and $R^7$ is H.

In one embodiment, in a compound or pharmaceutically acceptable salt of formula (I or II), $R^6$ is H and $R^7$ is H, halogen, —$OR^{21}$; —$OCH_2R^{21}$; —$C(=O)NHR^{21}$, —$C(=O)OR^{21}$, —$C(=O)SR^{21}$; —$C(=O)S$—$SR^{21}$, —$CH_2OR^{21}$, or —$CH_2NHR^{21}$; where $R^{21}$ is as defined in formula (I or II).

In one embodiment, in a compound or pharmaceutically acceptable salt of formula (I or II), $R^6$ is H and $R^7$ is H, halogen, —$OR^{21}$; —$OCH_2R^{21}$; —$C(=O)NHR^{21}$, —$C(=O)OR^{21}$, —$C(=O)SR^{21}$; —$C(=O)S$—$SR^{21}$, or —$CH_2OR^{21}$; where $R^{21}$ is as defined in formula (I or II).

In one embodiment, in a compound or pharmaceutically acceptable salt of formula (I or II), $R^8$ is H or $C_{1-6}$ alkyl.

In one embodiment, in a compound or pharmaceutically acceptable salt of formula (I or II), $R^8$ is H.

In one embodiment, in a compound or pharmaceutically acceptable salt of formula (I or II), $R^9$ is halogen, hydroxyl, —CN, —$NO_2$, —CHO, —COOH, $C_{1-6}$ alkyl, $C_{2-6}$ alkenyl, $C_{1-6}$ aminoalkyl, $C_{3-10}$ cycloalkyl, $C_{1-6}$ haloalkyl, $C_{1-4}$ hydroxyalkyl, $C_{1-6}$ alkoxy, cycloalkenyl, aryl, heterocycle, heteroaryl, —$NR^{10}R^{11}$, $J^9$-$NR^{10}R^{11}$, -$J^9$-$COOR^8$, -$J^9$-alkyl, -$J^9$-$C_{3-10}$ cycloalkyl, -$J^9$-cycloalkenyl, -$J^9$-heterocycle, -$J^9$-heteroaryl, or -$J^9$-aryl, which alkyl, $C_{1-6}$ alkoxy, $C_{3-10}$ cycloalkyl, heterocycle, heteroaryl, aryl, -$J^9$-alkyl, -$J^9$-$C_{3-10}$ cycloalky, -$J^9$-heterocycle, -$J^9$-heteroaryl, or -$J^9$-aryl, may be substituted with one or more $R^{16}$; where $R^{10}$, $R^1$, $R^{16}$ and $J^9$ are as defined in formula (I or II).

In one embodiment, in a compound or pharmaceutically acceptable salt of formula (I or II), $R^9$ is halogen, $C_{1-6}$ alkyl, aryl, heterocycle, -$J^9$-heterocycle, or -$J^9$-aryl which alkyl, aryl, heterocycle, -$J^9$-heterocycle, or -$J^9$-aryl, may be substituted with may substituted with one or more $R^{16}$; where $R^{16}$ and $J^9$ are as defined in formula (I or II).

In one embodiment, in a compound or pharmaceutically acceptable salt of formula (I or II), $R^9$ is halogen, $C_{1-6}$ alkyl, aryl, heterocycle, -$J^9$-heterocycle, or -$J^9$-aryl which alkyl, aryl, heterocycle, -$J^9$-heterocycle, or -$J^9$-aryl, may be substituted with may substituted with one or more $R^{16}$; and $R^{16}$ is —$NR^{10}R^{11}$, $C_{1-6}$ alkyl, $C_{1-4}$ hydroxyalkyl, or heterocycle; where $R^{10}$, $R^{11}$, and $J^9$ are as defined in formula (I or II).

In one embodiment, in a compound or pharmaceutically acceptable salt of formula (I or II), $R^9$ is halogen, or -$J^9$-aryl which -$J^9$-aryl may substituted with one or more $R^{16}$; $R^{16}$ is —$(CH_2)_t$—$NR^{10}R^{11}$; $J^9$ is —C(=O)NH; where $R^{10}$ and $R^{11}$ are as defined in formula (I or II).

In one embodiment, in a compound or pharmaceutically acceptable salt of formula (I or II), $R^9$ is halogen.

In one embodiment, in a compound or pharmaceutically acceptable salt of formula (I or II), $R^9$ is F or Cl.

In one embodiment, in a compound or pharmaceutically acceptable salt of formula (I or II), $R^{10}$ and $R^{11}$ is H.

In one embodiment, in a compound or pharmaceutically acceptable salt of formula (I or II), $R^{10}$ is H and $R^{11}$ is $C_{1-6}$ alkyl.

In one embodiment, in a compound or pharmaceutically acceptable salt of formula (I or II), $R^{12}$ and $R^{13}$ is H.

In one embodiment, in a compound or pharmaceutically acceptable salt of formula (I or II), $R^{12}$ is H and $R^{13}$ is $C_{1-6}$ alkyl.

In one embodiment, in a compound or pharmaceutically acceptable salt of formula (I or II), $R^{14}$ is —C(=O)$NHR^{15}$, —C(=O)$OR^{15}$, —$CH_2OR^{15}$; and $R^{15}$ is H, or $C_{1-3}$ alkyl.

In one embodiment, in a compound or pharmaceutically acceptable salt of formula (I or II), $R^{14}$ is —C(=O)$NHR^{15}$, —C(=O)$OR^{15}$, —$CH_2OR^{15}$; and $R^{15}$ is $C_{1-3}$ alkyl.

In one embodiment, in a compound or pharmaceutically acceptable salt of formula (I or II), $R^{16}$ is halogen, hydroxyl, —CN, —CHO, —$NR^{10}R^{11}$, —$NO_2$, $C_{1-6}$ alkyl, (=O), $C_{1-4}$ hydroxyalkyl, $C_{1-6}$ alkoxy, heterocycle, -$J^{16}$-alkyl, -$J^{16}$-heterocycle, —$(CH_2)_t$—$NR^{10}R^{11}$, —$(CH_2)_t$—$COOR^8$, or —$(CH_2)_t$—C(=O)—$NR^{10}R^{11}$; where $R^{10}$, $R^{11}$, and $J^9$ are as defined in formula (I or II).

In one embodiment, in a compound or pharmaceutically acceptable salt of formula (I or II), $R^{16}$ is —$NR^{10}R^{11}$, $C_{1-6}$ alkyl, $C_{1-4}$ hydroxyalkyl, or heterocycle; where $R^{10}$ and $R^{11}$ are as defined in formula (I or II).

In one embodiment, in a compound or pharmaceutically acceptable salt of formula (I or II), $R^{16}$ is $R^{16}$ is $C_{1-6}$ alkyl, or —$(CH_2)_t$—$NR^{10}R^{11}$; where $R^{10}$, $R^{11}$, and 1 are as defined in formula (I or II).

In one embodiment, in a compound or pharmaceutically acceptable salt of formula (I or II), $R^{16}$ is —$(CH_2)_t$—$NR^{10}R^{11}$; where $R^{10}$, $R^{11}$, and 1 are as defined in formula (I or II).

In one embodiment, in a compound or pharmaceutically acceptable salt of formula (I or II), $R^{17}$ is $C_{1-6}$ alkyl or $C_{1-4}$ hydroxyalkyl.

In one embodiment, in a compound or pharmaceutically acceptable salt of formula (I or II), $R^{18}$ is halogen, hydroxyl, —CN, —CHO, —COOH, $C_{1-6}$ alkyl, $C_{1-4}$ hydroxyalkyl, $C_{1-6}$ alkoxy, heterocycle, $NR^{10}R^{11}$, -$J^{18}$-$NR^{10}R^{11}$, -$J^{18}$-alkyl, -$J^{18}$-$C_{3-10}$ cycloalkyl, -$J^{18}$-heterocycle, which alkyl, $C_{1-6}$ alkoxy, heterocycle, -$J^{18}$-alkyl, -$J^{18}$-$C_{3-10}$ cycloalky, or -$J^{18}$-heterocycle, may substituted with one or more $R^{19}$; where $R^{19}$ is as defined in formula (I or II).

In one embodiment, in a compound or pharmaceutically acceptable salt of formula (I or II), $R^{18}$ is $C_{1-6}$ alkyl, heterocycle, or $-J^{18}$-heterocycle, which heterocycle, or $-J^{18}$-heterocycle may be substituted with $R^{19}$; where $R^{19}$ is as defined in formula (I or II).

In one embodiment, in a compound or pharmaceutically acceptable salt of formula (I or II), $R^{19}$ is hydroxyl, $C_{1-6}$ alkyl, $C_{1-4}$ hydroxyalkyl, $C_{1-6}$ alkoxy, $-J^{19}$-alkyl, $-J^{19}$-aryl, $-J^{19}$-heterocycle, which $-J^{19}$-heterocycle may be substituted with one or more $R^{20}$; where $J^{19}$ and $R^{20}$ are as defined in formula (I or II).

In one embodiment, in a compound or pharmaceutically acceptable salt of formula (I or II), $R^{19}$ is $C_{1-6}$ alkyl.

In one embodiment, in a compound or pharmaceutically acceptable salt of formula (I or II), $R^{20}$ is $-NO_2$, or $C_{1-6}$ alkyl.

In one embodiment, in a compound or pharmaceutically acceptable salt of formula (I or II), $R^{20}$ is $C_{1-6}$ alkyl.

In one embodiment, in a compound or pharmaceutically acceptable salt of formula (I or II), $R^{21}$ is H, $C_{1-6}$ alkyl, aryl, biaryl, or heterobiaryl, which aryl, biaryl, or heterobiaryl, may optionally be substituted with one or more $R^{22}$; where $R^{22}$ is as defined in formula (I or II).

In one embodiment, in a compound or pharmaceutically acceptable salt of formula (I or II), $R^{22}$ is halogen, $C_{1-6}$ alkyl, heterocycle, $-J^{22}-NR^{10}R^{11}$, $-J^{22}$-heterocycle, or $-J^{22}$-aryl, which alkyl, heterocycle, $-J^{22}$-heterocycle, or $-J^{22}$-aryl may substituted with one or more $R^{23}$; where $R^{23}$ is as defined in formula (I or II).

In one embodiment, in a compound or pharmaceutically acceptable salt of formula (I or II), $R^{23}$ is $C_{1-6}$ alkyl.

In one embodiment, in a compound or pharmaceutically acceptable salt of formula (I or II), $R^{24}$ is $-(CH_2)_l-OR^8$.

In one embodiment, in a compound or pharmaceutically acceptable salt of formula (I or II), $R^{24}$ is H.

In one embodiment, in a compound or pharmaceutically acceptable salt of formula (I or II), $J^9$ is $C_{1-3}$ alkyl, $C_{1-3}$ alkyl-O—, $C_{2-6}$ alkenyl, $C_{2-6}$ alkynyl, $-(CH_2)_l-C(=O)-(CH_2)_m-$, $-(CH_2)_l-CH=CH-C(=O)-(CH_2)_m-$, $-C(=O)O-$, $-(CH_2)_l-C(=O)NH-(CH_2)_m-$, $-(CR^{10}R^{11})_l-NR-(CR^{10}R^{11})_m-$, $-NHC(=O)-$, $-O-$, $-S-$, or $-SO_2-$; where $R^8$, $R^{10}$, $R^{11}$, l and m are as defined in formula (I or II).

In one embodiment, in a compound or pharmaceutically acceptable salt of formula (I or II), $J^9$ is $-C(=O)NH-$.

In one embodiment, in a compound or pharmaceutically acceptable salt of formula (I or II), $J^9$ is $C_{1-3}$ alkyl or —O—.

In one embodiment, in a compound or pharmaceutically acceptable salt of formula (I or II), $J^{16}$ is $C_{1-3}$ alkyl, $C_{1-3}$ alkyl-O—, $C_{2-6}$ alkenyl, $C_{2-6}$ alkynyl, $-(CH_2)_l-C(=O)-(CH_2)_m-$, $-(CH_2)_l-CH=CH-C(=O)-(CH_2)_m-$, $-C(=O)O-$, $-(CH_2)_l-C(=O)NH-(CH_2)_m-$, $-(CR^{10}R^{11})_l-NR-(CR^{10}R^{11})_m-$, $-NHC(=O)-$, $-O-$, $-S-$, or $-SO_2-$; where $R^8$, $R^{10}$, $R^{11}$, l and m are as defined in formula (I or II).

In one embodiment, in a compound or pharmaceutically acceptable salt of formula (I or II), $J^{18}$ is $C_{1-3}$ alkyl, $-C(=O)-$, $-(CH_2)_l-C(=O)NH-(CH_2)_m-$, $-(CR^{10}R^{11})_l-NR^8-(CR^{10}R^{11})_m-$, $-NHC(=O)-$, $-SO_2-$, or $-NHSO_2-$.

In one embodiment, in a compound or pharmaceutically acceptable salt of formula (I or II), $J^{19}$ is $C_{1-3}$ alkyl, $-C(=O)O-$, or $-SO_2-$.

In one embodiment, in a compound or pharmaceutically acceptable salt of formula (I or II), $J^{22}$ is $C_{1-3}$ alkyl, $C_{1-3}$ alkyl-O—, or —O—.

In one embodiment, in a compound or pharmaceutically acceptable salt of formula (I or II), X is $-C(=O)N(R^8)-$, $-C(=O)N(R^8)CH_2-$, or $-N(R^8)-$.

In one embodiment, in a compound or pharmaceutically acceptable salt of formula (I or II), X is $-C(=O)N(R^8)-$.

In one embodiment, in a compound or pharmaceutically acceptable salt of formula (I or II), X is $-N(R^8)-$.

In one embodiment, in a compound or pharmaceutically acceptable salt of formula (I or II), L is none, $C_{1-3}$ alkyl, $C_{2-3}$ alkenyl, $C_{1-3}$ alkyl-O—, $C_{1-3}$ alkyl-O—$C_{1-3}$alkyl, $-C(=O)-$, $-C(=O)-C(=O)-$, $-C(=O)O-$, $-C(=O)N(R^8)-$, $-C(=S)N(R^8)-(CR^{12}R^{13})_m-$, $-SO_2-$, $-SO_2-(CH_2)_m-$, $-(CR^{12}R^{13})_m-C(=O)-(CR^{13})_m-$, $-C(=O)O(CR^{12}R^{13})_m-$, $-C(=O)CR^{12}=CR^{13}-$, or $-CHR^{14}-$; where $R^{12}$, $R^{13}$, $R^{14}$, l and m are as defined in formula (I or II).

In one embodiment, in a compound or pharmaceutically acceptable salt of formula (I or II), L is $C_{1-3}$ alkyl, $C_{1-3}$ alkyl-O—, $-C(=O)-$, $-C(=O)O-$, or $-C(=O)N(R^8)-$; where $R^8$ is as defined in formula (I or II).

In one embodiment, in a compound or pharmaceutically acceptable salt of formula (I or II), L is $-C(=O)-$, $-C(=O)O-$, $-C(=O)N(R^8)-$.

In one embodiment, in a compound or pharmaceutically acceptable salt of formula (I or II), L is $-C(=O)-$.

In one embodiment, in a compound or pharmaceutically acceptable salt of formula (I), n is 1.

In one embodiment, in a compound or pharmaceutically acceptable salt of formula (I), n is 2.

In one embodiment, in a compound or pharmaceutically acceptable salt of formula (I), n is 1; and p is 1.

In one embodiment, in a compound or pharmaceutically acceptable salt of formula (I), n is 1; and p is 2.

In one embodiment, in a compound or pharmaceutically acceptable salt of formula (I), n is 1; and p is 3.

In one embodiment, in a compound or pharmaceutically acceptable salt of formula (I), p is 1.

In one embodiment, in a compound or pharmaceutically acceptable salt of formula (I), p is 2.

In one embodiment, in a compound or pharmaceutically acceptable salt of formula (I), p is 3.

Specific embodiments contemplated as part of the present disclosure also include, but are not limited to, compounds or pharmaceutically acceptable salts of formula (I), as defined, for example:

(R)-2-amino-5-(1-methyl-1H-pyrazol-4-yl)-N-(1-(phenylcarbamoyl)pyrrolidin-3-yl)nicotinamide;

(R)-2-amino-N-(1-((3-fluorophenyl)carbamoyl)pyrrolidin-3-yl)-5-(1-methyl-1H-pyrazol-4-yl)nicotinamide;

(R)-2-amino-N-(1-((3,4-difluorophenyl)carbamoyl)pyrrolidin-3-yl)-5-(1-methyl-1H-pyrazol-4-yl)nicotinamide;

(R)-2-amino-N-(1-((3,5-dimethylphenyl)carbamoyl)pyrrolidin-3-yl)-5-(1-methyl-1H-pyrazol-4-yl)nicotinamide;

(R)-2-amino-N-(1-((3,5-bis(trifluoromethyl)phenyl)carbamoyl)pyrrolidin-3-yl)-5-(1-methyl-1H-pyrazol-4-yl)nicotinamide;

(R)-2-amino-5-(1-methyl-1H-pyrazol-4-yl)-N-(1-((4-(trifluoromethyl)phenyl)carbamoyl)pyrrolidin-3-yl)nicotinamide;

(R)-2-amino-N-(1-((4-cyanophenyl)carbamoyl)pyrrolidin-3-yl)-5-(1-methyl-1H-pyrazol-4-yl)nicotinamide;

(R)-2-amino-N-(1-((3,5-dichlorophenyl)carbamoyl)pyrrolidin-3-yl)-5-(4-(morpholine-4-carbonyl)phenyl)nicotinamide;

(R)-2-amino-N-(1-((3,5-dichlorophenyl)carbamoyl)pyrrolidin-3-yl)-5-(4-(hydroxymethyl)phenyl)nicotinamide;

(R)-2-amino-N-(1-((3,5-dichlorophenyl)carbamoyl)pyrrolidin-3-yl)-5-(1-(1-methylpiperidin-4-yl)-1H-pyrazol-4-yl)nicotinamide;
(R)-2-amino-N-(1-((1-methyl-1H-pyrazol-3-yl)carbamoyl)pyrrolidin-3-yl)-5-(1-methyl-1H-pyrazol-4-yl)nicotinamide;
(R)-2-amino-5-(1-methyl-1H-pyrazol-4-yl)-N-(1-(pyridin-3-ylcarbamoyl)pyrrolidin-3-yl)nicotinamide;
(R)-2-amino-N-(1-((3-chlorophenyl)carbamoyl)pyrrolidin-3-yl)-5-(1-methyl-1H-pyrazol-4-yl)nicotinamide;
(R)-2-amino-N-(1-((2,3-dichlorophenyl)carbamoyl)pyrrolidin-3-yl)-5-(1-methyl-1H-pyrazol-4-yl)nicotinamide;
(R)-2-amino-N-(1-((3-isopropoxyphenyl)carbamoyl)pyrrolidin-3-yl)-5-(1-methyl-1H-pyrazol-4-yl)nicotinamide;
(R)-2-amino-5-(1-methyl-1H-pyrazol-4-yl)-N-(1-((3-phenoxyphenyl)carbamoyl)pyrrolidin-3-yl)nicotinamide;
(R)-2-amino-5-(1-methyl-1H-pyrazol-4-yl)-N-(1-((2-phenoxyphenyl)carbamoyl)pyrrolidin-3-yl)nicotinamide;
(R)-2-amino-N-(1-((3-ethylphenyl)carbamoyl)pyrrolidin-3-yl)-5-(1-methyl-1H-pyrazol-4-yl)nicotinamide;
(R)-2-amino-N-(1-((2-ethylphenyl)carbamoyl)pyrrolidin-3-yl)-5-(1-methyl-1H-pyrazol-4-yl)nicotinamide;
(R)-2-amino-N-(1-((2-chlorophenyl)carbamoyl)pyrrolidin-3-yl)-5-(1-methyl-1H-pyrazol-4-yl)nicotinamide;
(R)—N-(1-((3,5-dichlorophenyl)carbamoyl)pyrrolidin-3-yl)-5-(1-methyl-1H-pyrazol-4-yl)nicotinamide;
(R)—N-(1-([1,1'-biphenyl]-3-ylcarbamoyl)pyrrolidin-3-yl)-2-amino-5-(1-methyl-1H-pyrazol-4-yl)nicotinamide;
(R)-2-amino-N-(1-((3-bromophenyl)carbamoyl)pyrrolidin-3-yl)-5-(1-methyl-1H-pyrazol-4-yl)nicotinamide;
(R)-2-amino-N-(1-((4-bromophenyl)carbamoyl)pyrrolidin-3-yl)-5-(1-methyl-1H-pyrazol-4-yl)nicotinamide;
(R)-2-amino-5-(1-methyl-1H-pyrazol-4-yl)-N-(1-((3-(morpholinomethyl)phenyl)carbamoyl)pyrrolidin-3-yl)nicotinamide;
(S)-2-amino-5-(1-methyl-1H-pyrazol-4-yl)-N-(1-(phenylcarbamoyl)pyrrolidin-3-yl)nicotinamide;
(R)-2-amino-N-(1-(5-amino-1,2,3,4-tetrahydroisoquinoline-2-carbonyl)pyrrolidin-3-yl)-5-(1-methyl-1H-pyrazol-4-yl)nicotinamide;
(R)-2-amino-N-(1-(8-bromo-1,2,3,4-tetrahydroisoquinoline-2-carbonyl)pyrrolidin-3-yl)-5-(1-methyl-1H-pyrazol-4-yl)nicotinamide;
(R)-2-amino-N-(1-(cyclohexylcarbamoyl)pyrrolidin-3-yl)-5-(1-methyl-1H-pyrazol-4-yl)nicotinamide;
2-amino-N—((R)-1-(((1R,2S)-2-hydroxycyclohexyl)carbamoyl)pyrrolidin-3-yl)-5-(1-methyl-1H-pyrazol-4-yl)nicotinamide;
2-amino-N—((R)-1-(((1R,2R)-2-hydroxycyclohexyl)carbamoyl)pyrrolidin-3-yl)-5-(1-methyl-1H-pyrazol-4-yl)nicotinamide;
(R)-2-amino-5-(1-methyl-1H-pyrazol-4-yl)-N-(1-((2,4,6-trichlorophenyl)carbamoyl)pyrrolidin-3-yl)nicotinamide;
(R)-2-amino-N-(1-((3,5-dichlorophenyl)carbamoyl)pyrrolidin-3-yl)-5-(1-methyl-1H-pyrazol-4-yl)nicotinamide;
(R)-2-amino-5-(1-methyl-1H-pyrazol-4-yl)-N-(1-((3,4,5-trimethoxyphenyl)carbamoyl)pyrrolidin-3-yl)nicotinamide;
(R)—N-(1-([1,1'-biphenyl]-2-ylcarbamoyl)pyrrolidin-3-yl)-2-amino-5-(1-methyl-1H-pyrazol-4-yl)nicotinamide;
(R)—N-(1-([1,1'-biphenyl]-3-ylcarbamoyl)pyrrolidin-3-yl)-2-amino-5-(4-((4-methylpiperazin-1-yl)methyl)phenyl)nicotinamide;
(R)—N-(1-([1,1'-biphenyl]-3-ylcarbamoyl)pyrrolidin-3-yl)-2-amino-5-(4-(morpholinomethyl)phenyl)nicotinamide;
(R)—N-(1-([1,1'-biphenyl]-3-ylcarbamoyl)pyrrolidin-3-yl)-2-amino-5-(4-((4-hydroxypiperidin-1-yl)methyl)phenyl)nicotinamide;
2-amino-N—((R)-1-(((1S,2S)-2-(benzyloxy)cyclopentyl)carbamoyl)pyrrolidin-3-yl)-5-(1-methyl-1H-pyrazol-4-yl)nicotinamide;
2-amino-N-((3R)-1-((3-(benzyloxy)cyclopentyl)carbamoyl)pyrrolidin-3-yl)-5-(1-methyl-1H-pyrazol-4-yl)nicotinamide;
(R)-2-amino-N-(1-((4-fluorophenyl)carbamothioyl)pyrrolidin-3-yl)-5-(1-methyl-1H-pyrazol-4-yl)nicotinamide;
(R)-2-amino-N-(1-(benzylcarbamothioyl)pyrrolidin-3-yl)-5-(1-methyl-1H-pyrazol-4-yl)nicotinamide;
(R)-2-amino-N-(1-((3,4-dichlorophenyl)carbamothioyl)pyrrolidin-3-yl)-5-(1-methyl-1H-pyrazol-4-yl)nicotinamide;
(R)-2-amino-N-(1-((4-methoxyphenyl)carbamothioyl)pyrrolidin-3-yl)-5-(1-methyl-1H-pyrazol-4-yl)nicotinamide;
(R)-2-amino-N-(1-((4-bromophenyl)carbamothioyl)pyrrolidin-3-yl)-5-(1-methyl-1H-pyrazol-4-yl)nicotinamide;
(R)-2-amino-5-(1-methyl-1H-pyrazol-4-yl)-N-(1-((4-nitrophenyl)carbamothioyl)pyrrolidin-3-yl)nicotinamide;
(R)-2-amino-N-(1-((4-(dimethylamino)phenyl)carbamothioyl)pyrrolidin-3-yl)-5-(1-methyl-1H-pyrazol-4-yl)nicotinamide;
(R)-2-amino-5-(1-methyl-1H-pyrazol-4-yl)-N-(1-((4-morpholinophenyl)carbamothioyl)pyrrolidin-3-yl)nicotinamide;
(R)-2-amino-N-(1-((3,5-dichlorophenyl)carbamothioyl)pyrrolidin-3-yl)-5-(1-methyl-1H-pyrazol-4-yl)nicotinamide;
(R)—N-(1-([1,1'-biphenyl]-3-ylcarbamothioyl)pyrrolidin-3-yl)-2-amino-5-(1-methyl-1H-pyrazol-4-yl)nicotinamide;
(R)-2-amino-N-(1-((3-bromophenyl)carbamothioyl)pyrrolidin-3-yl)-5-(1-methyl-1H-pyrazol-4-yl)nicotinamide;
3-bromophenyl (R)-3-(2-amino-5-(1-methyl-1H-pyrazol-4-yl)nicotinamido)pyrrolidine-1-carboxylate;
phenyl (R)-3-(2-amino-5-(1-methyl-1H-pyrazol-4-yl)nicotinamido)pyrrolidine-1-carboxylate;
3-(piperidine-1-carbonyl)phenyl (R)-3-(2-amino-5-(1-methyl-1H-pyrazol-4-yl)nicotinamido)pyrrolidine-1-carboxylate;
5,6,7,8-tetrahydronaphthalen-2-yl (R)-3-(2-amino-5-(1-methyl-1H-pyrazol-4-yl)nicotinamido)pyrrolidine-1-carboxylate;
3-isopropyl-5-methylphenyl (R)-3-(2-amino-5-(1-methyl-1H-pyrazol-4-yl)nicotinamido)pyrrolidine-1-carboxylate;
2-(benzyloxy)phenyl (R)-3-(2-amino-5-(1-methyl-1H-pyrazol-4-yl)nicotinamido)pyrrolidine-1-carboxylate;
3-(benzyloxy)phenyl (R)-3-(2-amino-5-(1-methyl-1H-pyrazol-4-yl)nicotinamido)pyrrolidine-1-carboxylate;
2,3-dichlorophenyl (R)-3-(2-amino-5-(1-methyl-1H-pyrazol-4-yl)nicotinamido)pyrrolidine-1-carboxylate;
2,5-dichlorophenyl (R)-3-(2-amino-5-(1-methyl-1H-pyrazol-4-yl)nicotinamido)pyrrolidine-1-carboxylate;
2-cyanophenyl (R)-3-(2-amino-5-(1-methyl-1H-pyrazol-4-yl)nicotinamido)pyrrolidine-1-carboxylate;
4-bromo-2-methoxyphenyl (R)-3-(2-amino-5-(1-methyl-1H-pyrazol-4-yl)nicotinamido)pyrrolidine-1-carboxylate;
3-(methoxycarbonyl)phenyl (R)-3-(2-amino-5-(1-methyl-1H-pyrazol-4-yl)nicotinamido)pyrrolidine-1-carboxylate;
5-methoxy-2-(methoxycarbonyl)phenyl (R)-3-(2-amino-5-(1-methyl-1H-pyrazol-4-yl)nicotinamido)pyrrolidine-1-carboxylate;
cyclohexyl (R)-3-(2-amino-5-(1-methyl-1H-pyrazol-4-yl)nicotinamido)pyrrolidine-1-carboxylate;
6-bromonaphthalen-2-yl (R)-3-(2-amino-5-(1-methyl-1H-pyrazol-4-yl)nicotinamido)pyrrolidine-1-carboxylate;

naphthalen-1-yl (R)-3-(2-amino-5-(1-methyl-1H-pyrazol-4-yl)nicotinamido)pyrrolidine-1-carboxylate;
1-aminonaphthalen-2-yl (R)-3-(2-amino-5-(1-methyl-1H-pyrazol-4-yl)nicotinamido)pyrrolidine-1-carboxylate;
2-aminophenyl (R)-3-(2-amino-5-(1-methyl-1H-pyrazol-4-yl)nicotinamido)pyrrolidine-1-carboxylate;
2-(hydroxymethyl)phenyl (R)-3-(2-amino-5-(1-methyl-1H-pyrazol-4-yl)nicotinamido)pyrrolidine-1-carboxylate;
quinolin-6-yl (R)-3-(2-amino-5-(1-methyl-1H-pyrazol-4-yl)nicotinamido)pyrrolidine-1-carboxylate;
quinolin-8-yl (R)-3-(2-amino-5-(1-methyl-1H-pyrazol-4-yl)nicotinamido)pyrrolidine-1-carboxylate;
3-(ethylamino)-4-methylphenyl (R)-3-(2-amino-5-(1-methyl-1H-pyrazol-4-yl)nicotinamido)pyrrolidine-1-carboxylate;
4-chloro-2-cyclohexylphenyl (R)-3-(2-amino-5-(1-methyl-1H-pyrazol-4-yl)nicotinamido)pyrrolidine-1-carboxylate;
3-acetamidophenyl (R)-3-(2-amino-5-(1-methyl-1H-pyrazol-4-yl)nicotinamido)pyrrolidine-1-carboxylate;
4-(methylsulfonyl)phenyl (R)-3-(2-amino-5-(1-methyl-1H-pyrazol-4-yl)nicotinamido)pyrrolidine-1-carboxylate;
2-((dimethylamino)methyl)phenyl (R)-3-(2-amino-5-(1-methyl-1H-pyrazol-4-yl)nicotinamido)pyrrolidine-1-carboxylate;
3,5-dimethylcyclohexyl (3R)-3-(2-amino-5-(1-methyl-1H-pyrazol-4-yl)nicotinamido)pyrrolidine-1-carboxylate;
benzyl (R)-3-(2-amino-5-(1-methyl-1H-pyrazol-4-yl)nicotinamido)pyrrolidine-1-carboxylate;
[1,1'-biphenyl]-3-yl (R)-3-(2-amino-5-(4-(hydroxymethyl)phenyl)nicotinamido)pyrrolidine-1-carboxylate;
[1,1'-biphenyl]-3-yl (R)-3-(2-amino-5-(4-((4-methylpiperazin-1-yl)methyl)phenyl)nicotinamido)pyrrolidine-1-carboxylate;
[1,1'-biphenyl]-3-yl (R)-3-(2-amino-5-(4-(morpholine-4-carbonyl)phenyl)nicotinamido)pyrrolidine-1-carboxylate;
[1,1'-biphenyl]-3-yl (R)-3-(2-amino-5-(3,4-difluorophenyl)nicotinamido)pyrrolidine-1-carboxylate;
[1,1'-biphenyl]-3-yl (R)-3-(2-amino-5-bromonicotinamido)pyrrolidine-1-carboxylate;
4-chloro-3-methylphenyl (R)-3-(2-amino-5-(1-methyl-1H-pyrazol-4-yl)nicotinamido)pyrrolidine-1-carboxylate;
3-cyanophenyl (R)-3-(2-amino-5-(1-methyl-1H-pyrazol-4-yl)nicotinamido)pyrrolidine-1-carboxylate;
3,4-dichlorophenyl (R)-3-(2-amino-5-(1-methyl-1H-pyrazol-4-yl)nicotinamido)pyrrolidine-1-carboxylate;
4-amino-3-chlorophenyl (R)-3-(2-amino-5-(1-methyl-1H-pyrazol-4-yl)nicotinamido)pyrrolidine-1-carboxylate;
3,5-difluorophenyl (R)-3-(2-amino-5-(1-methyl-1H-pyrazol-4-yl)nicotinamido)pyrrolidine-1-carboxylate;
3,5-dimethylphenyl (R)-3-(2-amino-5-(1-methyl-1H-pyrazol-4-yl)nicotinamido)pyrrolidine-1-carboxylate;
2-(methoxycarbonyl)phenyl (R)-3-(2-amino-5-(1-methyl-1H-pyrazol-4-yl)nicotinamido)pyrrolidine-1-carboxylate;
4-ethylphenyl (R)-3-(2-amino-5-(1-methyl-1H-pyrazol-4-yl)nicotinamido)pyrrolidine-1-carboxylate;
3,4-dimethylphenyl (R)-3-(2-amino-5-(1-methyl-1H-pyrazol-4-yl)nicotinamido)pyrrolidine-1-carboxylate;
7-hydroxynaphthalen-2-yl (R)-3-(2-amino-5-(1-methyl-1H-pyrazol-4-yl)nicotinamido)pyrrolidine-1-carboxylate;
[1,1'-biphenyl]-3-yl (R)-3-(2-amino-5-(1-(1-methylpiperidin-4-yl)-1H-pyrazol-4-yl)nicotinamido)pyrrolidine-1-carboxylate;
3-hydroxynaphthalen-2-yl (R)-3-(2-amino-5-(1-methyl-1H-pyrazol-4-yl)nicotinamido)pyrrolidine-1-carboxylate;
2-hydroxyphenyl (R)-3-(2-amino-5-(1-methyl-1H-pyrazol-4-yl)nicotinamido)pyrrolidine-1-carboxylate;
2-amino-4-chlorophenyl (R)-3-(2-amino-5-(1-methyl-1H-pyrazol-4-yl)nicotinamido)pyrrolidine-1-carboxylate;
2-amino-5-nitrophenyl (R)-3-(2-amino-5-(1-methyl-1H-pyrazol-4-yl)nicotinamido)pyrrolidine-1-carboxylate;
3-hydroxyphenyl (R)-3-(2-amino-5-(1-methyl-1H-pyrazol-4-yl)nicotinamido)pyrrolidine-1-carboxylate;
4-phenoxyphenyl (R)-3-(2-amino-5-(1-methyl-1H-pyrazol-4-yl)nicotinamido)pyrrolidine-1-carboxylate;
naphthalen-2-yl (R)-3-(2-amino-5-(1-methyl-1H-pyrazol-4-yl)nicotinamido)pyrrolidine-1-carboxylate;
6-hydroxynaphthalen-2-yl (R)-3-(2-amino-5-(1-methyl-1H-pyrazol-4-yl)nicotinamido)pyrrolidine-1-carboxylate;
(1R,2S,4S)-bicyclo[2.2.1]heptan-2-yl (R)-3-(2-amino-5-(1-methyl-1H-pyrazol-4-yl)nicotinamido)pyrrolidine-1-carboxylate;
cyclopentyl (R)-3-(2-amino-5-(1-methyl-1H-pyrazol-4-yl)nicotinamido)pyrrolidine-1-carboxylate;
cycloheptyl (R)-3-(2-amino-5-(1-methyl-1H-pyrazol-4-yl)nicotinamido)pyrrolidine-1-carboxylate;
(1R,2S)-2-methylcyclohexyl (R)-3-(2-amino-5-(1-methyl-1H-pyrazol-4-yl)nicotinamido)pyrrolidine-1-carboxylate;
(1S,2S,4R)-bicyclo[2.2.1]heptan-2-yl (R)-3-(2-amino-5-(1-methyl-1H-pyrazol-4-yl)nicotinamido)pyrrolidine-1-carboxylate;
3-phenoxyphenyl (R)-3-(2-amino-5-(1-methyl-1H-pyrazol-4-yl)nicotinamido)pyrrolidine-1-carboxylate;
4-(4-nitrophenoxy)phenyl (R)-3-(2-amino-5-(1-methyl-1H-pyrazol-4-yl)nicotinamido)pyrrolidine-1-carboxylate;
4-(4-aminophenoxy)phenyl (R)-3-(2-amino-5-(1-methyl-1H-pyrazol-4-yl)nicotinamido)pyrrolidine-1-carboxylate;
4-(4-((4-methylpiperazin-1-yl)methyl)phenoxy)phenyl (R)-3-(2-amino-5-(1-methyl-1H-pyrazol-4-yl)nicotinamido)pyrrolidine-1-carboxylate;
4-(4-(hydroxymethyl)phenoxy)phenyl (R)-3-(2-amino-5-(1-methyl-1H-pyrazol-4-yl)nicotinamido)pyrrolidine-1-carboxylate;
4-(4-((dimethylamino)methyl)phenoxy)phenyl (R)-3-(2-amino-5-(1-methyl-1H-pyrazol-4-yl)nicotinamido)pyrrolidine-1-carboxylate;
3,5-dichlorophenyl (R)-3-(2-amino-5-(1-methyl-1H-pyrazol-4-yl)nicotinamido)pyrrolidine-1-carboxylate;
[1,1'-biphenyl]-3-yl (R)-3-(2-amino-5-(1-methyl-1H-pyrazol-4-yl)nicotinamido)pyrrolidine-1-carboxylate;
phenyl (R)-3-(2-amino-5-(4-((4-methylpiperazin-1-yl)methyl)phenyl)nicotinamido)pyrrolidine-1-carboxylate;
phenyl (R)-3-(2-amino-5-(1-(1-methylpiperidin-4-yl)-1H-pyrazol-4-yl)nicotinamido)pyrrolidine-1-carboxylate;
(1S,2S)-2-(benzyloxy)cyclopentyl (R)-3-(2-amino-5-(1-methyl-1H-pyrazol-4-yl)nicotinamido)pyrrolidine-1-carboxylate;
3-phenylcyclopentyl (3R)-3-(2-amino-5-(1-methyl-1H-pyrazol-4-yl)nicotinamido)pyrrolidine-1-carboxylate;
1-benzylpiperidin-3-yl (3R)-3-(2-amino-5-(1-methyl-1H-pyrazol-4-yl)nicotinamido)pyrrolidine-1-carboxylate;
1-(4-formylphenyl)piperidin-3-yl (3R)-3-(2-amino-5-(1-methyl-1H-pyrazol-4-yl)nicotinamido)pyrrolidine-1-carboxylate;
1-(4-((4-methylpiperazin-1-yl)methyl)phenyl)piperidin-3-yl (3R)-3-(2-amino-5-(1-methyl-1H-pyrazol-4-yl)nicotinamido)pyrrolidine-1-carboxylate;
4-phenylcyclohexyl (R)-3-(2-amino-5-(1-methyl-1H-pyrazol-4-yl)nicotinamido)pyrrolidine-1-carboxylate;
1-phenylpyrrolidin-3-yl (3R)-3-(2-amino-5-(1-methyl-1H-pyrazol-4-yl)nicotinamido)pyrrolidine-1-carboxylate;
(R)-1-phenylpyrrolidin-3-yl (R)-3-(2-amino-5-(1-methyl-1H-pyrazol-4-yl)nicotinamido)pyrrolidine-1-carboxylate;

(S)-1-phenylpyrrolidin-3-yl (R)-3-(2-amino-5-(1-methyl-1H-pyrazol-4-yl)nicotinamido)pyrrolidine-1-carboxylate;

3-phenylcyclohexyl (3R)-3-(2-amino-5-(1-methyl-1H-pyrazol-4-yl)nicotinamido)pyrrolidine-1-carboxylate;

[1,1'-biphenyl]-3-yl (R)-3-(2-amino-N-methyl-5-(1-methyl-1H-pyrazol-4-yl)nicotinamido)pyrrolidine-1-carboxylate;

(R)-2-amino-N-(1-benzylpyrrolidin-3-yl)-N-methyl-5-(1-methyl-1H-pyrazol-4-yl)nicotinamide;

(R)-2-amino-N-(1-(2-chlorobenzyl)pyrrolidin-3-yl)-N-methyl-5-(1-methyl-1H-pyrazol-4-yl)nicotinamide;

(R)—N-(1-(1H-benzo[d]imidazol-2-yl)pyrrolidin-3-yl)-2-amino-5-(1-methyl-1H-pyrazol-4-yl)nicotinamide;

(R)-2-amino-5-(1-methyl-1H-pyrazol-4-yl)-N-(1-(p-tolyl)pyrrolidin-3-yl)nicotinamide;

(R)-2-amino-5-(1-methyl-1H-pyrazol-4-yl)-N-(1-(pyridin-2-yl)pyrrolidin-3-yl)nicotinamide;

(R)-2-amino-N-(1-(5-ethylpyrimidin-2-yl)pyrrolidin-3-yl)-5-(1-methyl-1H-pyrazol-4-yl)nicotinamide;

(R)-2-amino-5-(1-methyl-1H-pyrazol-4-yl)-N-(1-(quinazolin-2-yl)pyrrolidin-3-yl)nicotinamide;

(R)-2-amino-5-(1-methyl-1H-pyrazol-4-yl)-N-(1-(5-nitrothiazol-2-yl)pyrrolidin-3-yl)nicotinamide;

ethyl (R)-2-(3-(2-amino-5-(1-methyl-1H-pyrazol-4-yl)nicotinamido)pyrrolidin-1-yl)thiazole-4-carboxylate;

(R)-2-amino-N-(1-(benzylsulfonyl)pyrrolidin-3-yl)-5-(1-methyl-1H-pyrazol-4-yl)nicotinamide;

(R)-2-amino-5-(1-methyl-1H-pyrazol-4-yl)-N-(1-(phenylsulfonyl)pyrrolidin-3-yl)nicotinamide;

(R)-2-amino-N-(1-((2,4-dichlorophenyl)sulfonyl)pyrrolidin-3-yl)-5-(1-methyl-1H-pyrazol-4-yl)nicotinamide;

(R)-2-amino-N-(1-((3-chloropropyl)sulfonyl)pyrrolidin-3-yl)-5-(1-methyl-1H-pyrazol-4-yl)nicotinamide;

2-amino-5-(1-methyl-1H-pyrazol-4-yl)-N-((3S,5S)-1-(methylsulfonyl)-5-(phenoxymethyl)pyrrolidin-3-yl)nicotinamide;

2-amino-5-(1-methyl-1H-pyrazol-4-yl)-N-((3S,5S)-1-methyl-5-(phenoxymethyl)pyrrolidin-3-yl)nicotinamide;

(R)-2-amino-N-(1-((3,5-dichlorophenyl)carbamoyl)pyrrolidin-3-yl)-5-(1-(piperidin-4-yl)-1H-pyrazol-4-yl)nicotinamide;

[1,1'-biphenyl]-3-yl (R)-3-(2-amino-5-(1-(piperidin-4-yl)-1H-pyrazol-4-yl)nicotinamido)pyrrolidine-1-carboxylate;

2-amino-N-((3R)-1-(1-(2-chlorophenyl)ethyl)pyrrolidin-3-yl)-5-(1-(piperidin-4-yl)-1H-pyrazol-4-yl)nicotinamide;

2-amino-N-((3R)-1-(1-(3-chlorophenyl)ethyl)pyrrolidin-3-yl)-5-(1-(piperidin-4-yl)-1H-pyrazol-4-yl)nicotinamide;

2-amino-N-((3R)-1-(1-(3,4-dichlorophenyl)ethyl)pyrrolidin-3-yl)-5-(1-(piperidin-4-yl)-1H-pyrazol-4-yl)nicotinamide;

(R)-2-amino-N-(1-benzylpyrrolidin-3-yl)-5-(1-(piperidin-4-yl)-1H-pyrazol-4-yl)nicotinamide;

2-amino-N-(1-benzylpyrrolidin-3-yl)-5-(1-(piperidin-4-yl)-1H-pyrazol-4-yl)nicotinamide;

(R)-2-amino-N-(1-(4-fluorobenzyl)pyrrolidin-3-yl)-5-(1-(piperidin-4-yl)-1H-pyrazol-4-yl)nicotinamide;

(R)-2-amino-N-(1-(3-methoxybenzyl)pyrrolidin-3-yl)-5-(1-(piperidin-4-yl)-1H-pyrazol-4-yl)nicotinamide;

(R)-2-amino-N-(1-(2-chlorobenzyl)pyrrolidin-3-yl)-5-(1-(piperidin-4-yl)-1H-pyrazol-4-yl)nicotinamide;

(R)-2-amino-N-(1-(4-nitrobenzyl)pyrrolidin-3-yl)-5-(1-(piperidin-4-yl)-1H-pyrazol-4-yl)nicotinamide;

(R)-2-amino-5-(1-(piperidin-4-yl)-1H-pyrazol-4-yl)-N-(1-(2,4,5-trifluorobenzyl)pyrrolidin-3-yl)nicotinamide;

(R)-2-amino-N-(1-(3-chloro-4-fluorobenzyl)pyrrolidin-3-yl)-5-(1-(piperidin-4-yl)-1H-pyrazol-4-yl)nicotinamide;

(R)-2-amino-N-(1-(2,6-dichlorobenzyl)pyrrolidin-3-yl)-5-(1-(piperidin-4-yl)-1H-pyrazol-4-yl)nicotinamide;

(R)-2-amino-N-(1-(3,4-difluorobenzyl)pyrrolidin-3-yl)-5-(1-(piperidin-4-yl)-1H-pyrazol-4-yl)nicotinamide;

(R)-2-amino-N-(1-(3,4-dichlorobenzyl)pyrrolidin-3-yl)-5-(1-(piperidin-4-yl)-1H-pyrazol-4-yl)nicotinamide;

(R)-2-amino-5-(1-(piperidin-4-yl)-1H-pyrazol-4-yl)-N-(1-(2,3,6-trifluorobenzyl)pyrrolidin-3-yl)nicotinamide;

(R)-2-amino-N-(1-((2,4-dimethylthiazol-5-yl)methyl)pyrrolidin-3-yl)-5-(1-(piperidin-4-yl)-1H-pyrazol-4-yl)nicotinamide;

(R)-2-amino-N-(1-(2,3-dichlorobenzyl)pyrrolidin-3-yl)-5-(1-(piperidin-4-yl)-1H-pyrazol-4-yl)nicotinamide;

(R)-2-amino-N-(1-(2,4-dichlorobenzyl)pyrrolidin-3-yl)-5-(1-(piperidin-4-yl)-1H-pyrazol-4-yl)nicotinamide;

(R)-2-amino-N-(1-(2,5-dimethylbenzyl)pyrrolidin-3-yl)-5-(1-(piperidin-4-yl)-1H-pyrazol-4-yl)nicotinamide;

(R)-2-amino-N-(1-(2-methoxybenzyl)pyrrolidin-3-yl)-5-(1-(piperidin-4-yl)-1H-pyrazol-4-yl)nicotinamide;

(R)-2-amino-5-(1-(piperidin-4-yl)-1H-pyrazol-4-yl)-N-(1-(2-(trifluoromethyl)benzyl)pyrrolidin-3-yl)nicotinamide;

2-amino-N-((3R)-1-(cyclohex-3-en-1-ylmethyl)pyrrolidin-3-yl)-5-(1-(piperidin-4-yl)-1H-pyrazol-4-yl)nicotinamide;

2-amino-N—((R)-1-(((1R,5S)-6,6-dimethylbicyclo[3.1.1]hept-2-en-2-yl)methyl)pyrrolidin-3-yl)-5-(1-(piperidin-4-yl)-1H-pyrazol-4-yl)nicotinamide;

2-amino-5-(1-methyl-1H-pyrazol-4-yl)-N-((3R,5S)-5-(phenylcarbamoyl)pyrrolidin-3-yl)nicotinamide;

2-amino-5-(1-methyl-1H-pyrazol-4-yl)-N-((3R,5S)-5-((4'-((4-methylpiperazin-1-yl)methyl)-[1,1'-biphenyl]-3-yl)carbamoyl)pyrrolidin-3-yl)nicotinamide;

2-amino-5-(1-methyl-1H-pyrazol-4-yl)-N-((3S,5S)-5-(phenylcarbamoyl)pyrrolidin-3-yl)nicotinamide;

2-amino-5-(1-methyl-1H-pyrazol-4-yl)-N-((3S,5S)-5-((4'-((4-methylpiperazin-1-yl)methyl)-[1,1'-biphenyl]-3-yl)carbamoyl)pyrrolidin-3-yl)nicotinamide;

phenyl (2S,4S)-4-(2-amino-5-(1-methyl-1H-pyrazol-4-yl)nicotinamido)pyrrolidine-2-carboxylate;

2-amino-5-(1-methyl-1H-pyrazol-4-yl)-N-((3S,5S)-5-(phenoxymethyl)pyrrolidin-3-yl)nicotinamide;

2-amino-5-(1-methyl-1H-pyrazol-4-yl)-N-((3S,5R)-5-(phenoxymethyl)pyrrolidin-3-yl)nicotinamide;

2-amino-5-(1-methyl-1H-pyrazol-4-yl)-N-((3R,5S)-5-(phenoxymethyl)pyrrolidin-3-yl)nicotinamide;

2-amino-5-(1-methyl-1H-pyrazol-4-yl)-N-((3S,5S)-5-(((3'-((4-methylpiperazin-1-yl)methyl)-[1,1'-biphenyl]-3-yl)oxy)methyl)pyrrolidin-3-yl)nicotinamide;

2-amino-5-(1-methyl-1H-pyrazol-4-yl)-N-((3S,5S)-5-(((4'-((4-methylpiperazin-1-yl)methyl)-[1,1'-biphenyl]-3-yl)oxy)methyl)pyrrolidin-3-yl)nicotinamide;

2-amino-5-(1-methyl-1H-pyrazol-4-yl)-N-((3S,5S)-5-(((3'-((4-methylpiperazin-1-yl)methyl)-[1,1'-biphenyl]-4-yl)oxy)methyl)pyrrolidin-3-yl)nicotinamide;

2-amino-5-(1-methyl-1H-pyrazol-4-yl)-N-((3S,5S)-5-(((4'-((4-methylpiperazin-1-yl)methyl)-[1,1'-biphenyl]-4-yl)oxy)methyl)pyrrolidin-3-yl)nicotinamide;

2-amino-5-(1-methyl-1H-pyrazol-4-yl)-N-((3R,5R)-5-(phenoxymethyl)pyrrolidin-3-yl)nicotinamide;

2-amino-N-((3S,5S)-5-((2-(sec-butyl)phenoxy)methyl)pyrrolidin-3-yl)-5-(1-methyl-1H-pyrazol-4-yl)nicotinamide;

2-amino-N-((3S,5S)-5-((2,6-dimethylphenoxy)methyl)pyrrolidin-3-yl)-5-(1-methyl-1H-pyrazol-4-yl)nicotinamide;

2-amino-N-((3S,5S)-5-((2,3-dichlorophenoxy)methyl)pyrrolidin-3-yl)-5-(1-methyl-1H-pyrazol-4-yl)nicotinamide;

2-amino-N-((3S,5S)-5-((2,4-dichlorophenoxy)methyl)pyrrolidin-3-yl)-5-(1-methyl-1H-pyrazol-4-yl)nicotinamide;

2-amino-N-((3S,5S)-5-((4-chloro-2-methylphenoxy)methyl)pyrrolidin-3-yl)-5-(1-methyl-1H-pyrazol-4-yl)nicotinamide;
2-amino-N-((3S,5S)-5-((4-(tert-butyl)phenoxy)methyl)pyrrolidin-3-yl)-5-(1-methyl-1H-pyrazol-4-yl)nicotinamide;
2-amino-5-(1-methyl-1H-pyrazol-4-yl)-N-((3S,5S)-5-((4-phenoxyphenoxy)methyl)pyrrolidin-3-yl)nicotinamide;
2-amino-N-((3S,5S)-5-((4-benzylphenoxy)methyl)pyrrolidin-3-yl)-5-(1-methyl-1H-pyrazol-4-yl)nicotinamide;
N-((3S,5S)-5-(([1,1'-biphenyl]-2-yloxy)methyl)pyrrolidin-3-yl)-2-amino-5-(1-methyl-1H-pyrazol-4-yl)nicotinamide;
N-((3S,5S)-5-(([1,1'-biphenyl]-4-yloxy)methyl)pyrrolidin-3-yl)-2-amino-5-(1-methyl-1H-pyrazol-4-yl)nicotinamide;
2-amino-N-((3S,5S)-5-((4-(benzyloxy)phenoxy)methyl)pyrrolidin-3-yl)-5-(1-methyl-1H-pyrazol-4-yl)nicotinamide;
2-amino-N-((3S,5S)-5-((4-((dimethylamino)methyl)phenoxy)methyl)pyrrolidin-3-yl)-5-(1-methyl-1H-pyrazol-4-yl)nicotinamide;
2-amino-5-(1-methyl-1H-pyrazol-4-yl)-N-((3S,5S)-5-((4-(2-(piperazin-1-yl)pyridin-4-yl)phenoxy)methyl)pyrrolidin-3-yl)nicotinamide;
2-amino-N-((3S,5S)-5-((4-(1-(2-(dimethylamino)ethyl)-1H-pyrazol-4-yl)phenoxy)methyl)pyrrolidin-3-yl)-5-(1-methyl-1H-pyrazol-4-yl)nicotinamide;
2-amino-5-(1-methyl-1H-pyrazol-4-yl)-N-((3S,5S)-5-((4-(2-phenylpropan-2-yl)phenoxy)methyl)pyrrolidin-3-yl)nicotinamide;
N-((3S,5S)-5-(([1,1'-biphenyl]-3-yloxy)methyl)pyrrolidin-3-yl)-2-amino-5-(1-methyl-1H-pyrazol-4-yl)nicotinamide;
2-amino-N-((3S,5S)-5-(((2,6-dimethyl-[1,1'-biphenyl]-4-yl)oxy)methyl)pyrrolidin-3-yl)-5-(1-methyl-1H-pyrazol-4-yl)nicotinamide;
2-amino-N-((3S,5S)-5-((3,4-dimethylphenoxy)methyl)pyrrolidin-3-yl)-5-(1-methyl-1H-pyrazol-4-yl)nicotinamide;
2-amino-N-((3S,5S)-5-((3,5-dimethylphenoxy)methyl)pyrrolidin-3-yl)-5-(1-methyl-1H-pyrazol-4-yl)nicotinamide;
2-amino-N-((3S,5S)-5-((2-chlorophenoxy)methyl)pyrrolidin-3-yl)-5-(1-methyl-1H-pyrazol-4-yl)nicotinamide;
2-amino-5-(1-methyl-1H-pyrazol-4-yl)-N-((3S,5S)-5-((4-((4-methylpiperazin-1-yl)methyl)phenoxy)methyl)pyrrolidin-3-yl)nicotinamide;
(R)-2-amino-N-(1-benzylpyrrolidin-3-yl)-5-(1-methyl-1H-pyrazol-4-yl)nicotinamide;
2-amino-N-(1-benzylpyrrolidin-3-yl)-5-(1-methyl-1H-pyrazol-4-yl)nicotinamide;
(S)-2-amino-N-(1-benzylpyrrolidin-3-yl)-5-(1-methyl-1H-pyrazol-4-yl)nicotinamide;
(R)-2-amino-N-(1-(2-chlorobenzyl)pyrrolidin-3-yl)-5-(1-methyl-1H-pyrazol-4-yl)nicotinamide;
(R)-2-amino-N-(1-(3-methoxybenzyl)pyrrolidin-3-yl)-5-(1-methyl-1H-pyrazol-4-yl)nicotinamide;
(R)-2-amino-N-(1-(4-chlorobenzyl)pyrrolidin-3-yl)-5-(1-methyl-1H-pyrazol-4-yl)nicotinamide;
(R)-2-amino-N-(1-(4-ethylbenzyl)pyrrolidin-3-yl)-5-(1-methyl-1H-pyrazol-4-yl)nicotinamide;
(R)-2-amino-N-(1-(4-isopropylbenzyl)pyrrolidin-3-yl)-5-(1-methyl-1H-pyrazol-4-yl)nicotinamide;
(R)-2-amino-N-(1-(3,4-dichlorobenzyl)pyrrolidin-3-yl)-5-(1-methyl-1H-pyrazol-4-yl)nicotinamide;
(R)-2-amino-N-(1-(3,4-dimethylbenzyl)pyrrolidin-3-yl)-5-(1-methyl-1H-pyrazol-4-yl)nicotinamide;
(R)-2-amino-5-(1-methyl-1H-pyrazol-4-yl)-N-(1-(2-oxo-2-phenylethyl)pyrrolidin-3-yl)nicotinamide;
(R)-2-amino-N-(1-(3,5-dimethoxybenzyl)pyrrolidin-3-yl)-5-(1-methyl-1H-pyrazol-4-yl)nicotinamide;
(R)-2-amino-N-(1-(2,3-dimethoxybenzyl)pyrrolidin-3-yl)-5-(1-methyl-1H-pyrazol-4-yl)nicotinamide;
(R)-2-amino-N-(1-(2,5-dimethoxybenzyl)pyrrolidin-3-yl)-5-(1-methyl-1H-pyrazol-4-yl)nicotinamide;
(R)-2-amino-N-(1-(2-hydroxy-5-methoxybenzyl)pyrrolidin-3-yl)-5-(1-methyl-1H-pyrazol-4-yl)nicotinamide;
(R)-2-amino-N-(1-(2,4-dimethoxybenzyl)pyrrolidin-3-yl)-5-(1-methyl-1H-pyrazol-4-yl)nicotinamide;
(R)-2-amino-5-(1-methyl-1H-pyrazol-4-yl)-N-(1-(3-phenoxybenzyl)pyrrolidin-3-yl)nicotinamide;
(R)-2-amino-N-(1-(3-(benzyloxy)benzyl)pyrrolidin-3-yl)-5-(1-methyl-1H-pyrazol-4-yl)nicotinamide;
(R)-2-amino-N-(1-(3,5-dichloro-2-hydroxybenzyl)pyrrolidin-3-yl)-5-(1-methyl-1H-pyrazol-4-yl)nicotinamide;
(R)-2-amino-N-(1-(3,5-dichlorobenzyl)pyrrolidin-3-yl)-5-(1-methyl-1H-pyrazol-4-yl)nicotinamide;
(R)—N-(1-([1,1'-biphenyl]-2-ylmethyl)pyrrolidin-3-yl)-2-amino-5-(1-methyl-1H-pyrazol-4-yl)nicotinamide;
(R)—N-(1-([1,1'-biphenyl]-4-ylmethyl)pyrrolidin-3-yl)-2-amino-5-(1-methyl-1H-pyrazol-4-yl)nicotinamide;
(R)-2-amino-5-(1-methyl-1H-pyrazol-4-yl)-N-(1-(3-phenylpropyl)pyrrolidin-3-yl)nicotinamide;
(R)-2-amino-N-(1-cinnamylpyrrolidin-3-yl)-5-(1-methyl-1H-pyrazol-4-yl)nicotinamide;
(R)-2-amino-N-(1-(2-(benzyloxy)ethyl)pyrrolidin-3-yl)-5-(1-methyl-1H-pyrazol-4-yl)nicotinamide;
(R)-2-amino-5-(1-methyl-1H-pyrazol-4-yl)-N-(1-phenethylpyrrolidin-3-yl)nicotinamide;
(R)-2-amino-N-(1-(3-bromobenzyl)pyrrolidin-3-yl)-5-(1-methyl-1H-pyrazol-4-yl)nicotinamide;
(R)-2-amino-N-(1-(2-bromobenzyl)pyrrolidin-3-yl)-5-(1-methyl-1H-pyrazol-4-yl)nicotinamide;
(R)-2-amino-N-(1-(3-bromo-4-fluorobenzyl)pyrrolidin-3-yl)-5-(1-methyl-1H-pyrazol-4-yl)nicotinamide;
(R)-2-amino-N-(1-(3-bromophenethyl)pyrrolidin-3-yl)-5-(1-methyl-1H-pyrazol-4-yl)nicotinamide;
(R)-2-amino-N-(1-(4-chlorobenzyl)pyrrolidin-3-yl)-5-(4-(morpholine-4-carbonyl)phenyl)nicotinamide;
(R)-2-amino-N-(1-(4-chlorobenzyl)pyrrolidin-3-yl)-5-(4-((4-methylpiperazin-1-yl)methyl)phenyl)nicotinamide;
(R)-2-amino-N-(1-(4-chlorobenzyl)pyrrolidin-3-yl)-5-(4-(hydroxymethyl)phenyl)nicotinamide;
(R)-2-amino-N-(1-(4-chlorobenzyl)pyrrolidin-3-yl)-5-(4-cyanophenyl)nicotinamide;
(R)-2-amino-N-(1-(4-chlorobenzyl)pyrrolidin-3-yl)-5-(quinolin-3-yl)nicotinamide;
(R)-5-(1-(1-acetylpiperidin-4-yl)-1H-pyrazol-4-yl)-2-amino-N-(1-benzylpyrrolidin-3-yl)nicotinamide;
(R)-2-amino-N-(1-benzylpyrrolidin-3-yl)-5-(1-(1-(methylsulfonyl)piperidin-4-yl)-1H-pyrazol-4-yl)nicotinamide;
(R)-2-amino-N-(1-benzylpyrrolidin-3-yl)-5-(1-(1-((3,4,5-trimethoxyphenyl)carbamoyl)piperidin-4-yl)-1H-pyrazol-4-yl)nicotinamide;
(R)-2-amino-N-(1-((3'-(hydroxymethyl)-[1,1'-biphenyl]-3-yl)methyl)pyrrolidin-3-yl)-5-(1-methyl-1H-pyrazol-4-yl)nicotinamide;
(R)-2-amino-N-(1-((4'-(hydroxymethyl)-[1,1'-biphenyl]-3-yl)methyl)pyrrolidin-3-yl)-5-(1-methyl-1H-pyrazol-4-yl)nicotinamide;
(R)-2-amino-5-(1-methyl-1H-pyrazol-4-yl)-N-(1-((3'-((4-methylpiperazin-1-yl)methyl)-[1,1'-biphenyl]-3-yl)methyl)pyrrolidin-3-yl)nicotinamide;
(R)-2-amino-5-(1-methyl-1H-pyrazol-4-yl)-N-(1-((4'-((4-methylpiperazin-1-yl)methyl)-[1,1'-biphenyl]-3-yl)methyl)pyrrolidin-3-yl)nicotinamide;

(R)-2-amino-N-(1-((3'-(hydroxymethyl)-[1,1'-biphenyl]-2-yl)methyl)pyrrolidin-3-yl)-5-(1-methyl-1H-pyrazol-4-yl)nicotinamide;
(R)-2-amino-N-(1-((4'-(hydroxymethyl)-[1,1'-biphenyl]-2-yl)methyl)pyrrolidin-3-yl)-5-(1-methyl-1H-pyrazol-4-yl)nicotinamide;
(R)-2-amino-N-(1-((6-fluoro-[1,1'-biphenyl]-3-yl)methyl)pyrrolidin-3-yl)-5-(1-methyl-1H-pyrazol-4-yl)nicotinamide;
(R)-2-amino-N-(1-((6-fluoro-3'-(hydroxymethyl)-[1,1'-biphenyl]-3-yl)methyl)pyrrolidin-3-yl)-5-(1-methyl-1H-pyrazol-4-yl)nicotinamide;
(R)-2-amino-N-(1-((6-fluoro-3'-((4-methylpiperazin-1-yl)methyl)-[1,1'-biphenyl]-3-yl)methyl)pyrrolidin-3-yl)-5-(1-methyl-1H-pyrazol-4-yl)nicotinamide;
(R)-2-amino-N-(1-(4-fluoro-3-(1,2,3,6-tetrahydropyridin-4-yl)benzyl)pyrrolidin-3-yl)-5-(1-methyl-1H-pyrazol-4-yl)nicotinamide;
(R)-2-amino-5-(1-methyl-1H-pyrazol-4-yl)-N-(1-(2-(4'-((4-methylpiperazin-1-yl)methyl)-[1,1'-biphenyl]-3-yl)ethyl)pyrrolidin-3-yl)nicotinamide;
(R)-2-amino-N-(1-((3'-(aminomethyl)-[1,1'-biphenyl]-3-yl)carbamoyl)pyrrolidin-3-yl)-5-(1-methyl-1H-pyrazol-4-yl)nicotinamide;
(R)-2-amino-N-(1-((4'-(aminomethyl)-[1,1'-biphenyl]-3-yl)carbamoyl)pyrrolidin-3-yl)-5-(1-methyl-1H-pyrazol-4-yl)nicotinamide;
(R)—N-(1-([1,1'-biphenyl]-3-ylcarbamoyl)pyrrolidin-3-yl)-2-amino-5-(4-(hydroxymethyl)phenyl)nicotinamide;
(R)-2-amino-N-(1-((3'-amino-[1,1'-biphenyl]-3-yl)carbamoyl)pyrrolidin-3-yl)-5-(1-methyl-1H-pyrazol-4-yl)nicotinamide;
(R)-2-amino-N-(1-((4'-amino-[1,1'-biphenyl]-3-yl)carbamoyl)pyrrolidin-3-yl)-5-(1-methyl-1H-pyrazol-4-yl)nicotinamide;
(R)-2-amino-N-(1-((4'-(hydroxymethyl)-[1,1'-biphenyl]-3-yl)carbamoyl)pyrrolidin-3-yl)-5-(1-methyl-1H-pyrazol-4-yl)nicotinamide;
(R)-2-amino-5-(1-methyl-1H-pyrazol-4-yl)-N-(1-((3-(1-(piperidin-4-yl)-1H-pyrazol-4-yl)phenyl)carbamoyl)pyrrolidin-3-yl)nicotinamide;
(R)-2-amino-5-(1-methyl-1H-pyrazol-4-yl)-N-(1-((3-(6-(piperazin-1-yl)pyridin-3-yl)phenyl)carbamoyl)pyrrolidin-3-yl)nicotinamide;
(R)-2-amino-5-(1-methyl-1H-pyrazol-4-yl)-N-(1-((4'-(methylamino)-[1,1'-biphenyl]-3-yl)carbamoyl)pyrrolidin-3-yl)nicotinamide;
(R)-2-amino-N-(1-((4'-(dimethylamino)-[1,1'-biphenyl]-3-yl)carbamoyl)pyrrolidin-3-yl)-5-(1-methyl-1H-pyrazol-4-yl)nicotinamide;
(R)-2-amino-N-(1-((3'-(hydroxymethyl)-[1,1'-biphenyl]-3-yl)carbamoyl)pyrrolidin-3-yl)-5-(1-methyl-1H-pyrazol-4-yl)nicotinamide;
(R)-2-amino-N-(1-((3'-((dimethylamino)methyl)-[1,1'-biphenyl]-3-yl)carbamoyl)pyrrolidin-3-yl)-5-(1-methyl-1H-pyrazol-4-yl)nicotinamide;
(R)-2-amino-N-(1-((4'-((dimethylamino)methyl)-[1,1'-biphenyl]-3-yl)carbamoyl)pyrrolidin-3-yl)-5-(1-methyl-1H-pyrazol-4-yl)nicotinamide;
(R)-2-amino-5-(1-methyl-1H-pyrazol-4-yl)-N-(1-((3'-((4-methylpiperazin-1-yl)methyl)-[1,1'-biphenyl]-3-yl)carbamoyl)pyrrolidin-3-yl)nicotinamide;
(R)-2-amino-5-(1-methyl-1H-pyrazol-4-yl)-N-(1-((4'-((4-methylpiperazin-1-yl)methyl)-[1,1'-biphenyl]-3-yl)carbamoyl)pyrrolidin-3-yl)nicotinamide;
(R)-2-amino-N-(1-((3'-(aminomethyl)-[1,1'-biphenyl]-4-yl)carbamoyl)pyrrolidin-3-yl)-5-(1-methyl-1H-pyrazol-4-yl)nicotinamide;
(R)-2-amino-N-(1-((4'-(aminomethyl)-[1,1'-biphenyl]-4-yl)carbamoyl)pyrrolidin-3-yl)-5-(1-methyl-1H-pyrazol-4-yl)nicotinamide;
(R)—N-(1-([1,1'-biphenyl]-4-ylcarbamoyl)pyrrolidin-3-yl)-2-amino-5-(1-methyl-1H-pyrazol-4-yl)nicotinamide;
(R)-2-amino-5-(1-methyl-1H-pyrazol-4-yl)-N-(1-((3'-((4-methylpiperazin-1-yl)methyl)-[1,1'-biphenyl]-4-yl)carbamoyl)pyrrolidin-3-yl)nicotinamide;
(R)-2-amino-5-(1-methyl-1H-pyrazol-4-yl)-N-(1-((4'-((4-methylpiperazin-1-yl)methyl)-[1,1'-biphenyl]-4-yl)carbamoyl)pyrrolidin-3-yl)nicotinamide;
(R)-2-amino-5-(1-methyl-1H-pyrazol-4-yl)-N-(1-((4'-((4-methylpiperazin-1-yl)methyl)-[1,1'-biphenyl]-3-yl)carbamothioyl)pyrrolidin-3-yl)nicotinamide;
4'-((4-methylpiperazin-1-yl)methyl)-[1,1'-biphenyl]-3-yl (R)-3-(2-amino-5-(1-methyl-1H-pyrazol-4-yl)nicotinamido)pyrrolidine-1-carboxylate;
(R)-3-(3'-((3-(2-amino-5-(1-methyl-1H-pyrazol-4-yl)nicotinamido)pyrrolidine-1-carbonyl)oxy)-[1,1'-biphenyl]-4-yl)propanoic acid;
3'-((2-cyanoethyl)carbamoyl)-[1,1'-biphenyl]-3-yl (R)-3-(2-amino-5-(1-methyl-1H-pyrazol-4-yl)nicotinamido)pyrrolidine-1-carboxylate;
(R)-3'-((3-(2-amino-5-(1-methyl-1H-pyrazol-4-yl)nicotinamido)pyrrolidine-1-carbonyl)oxy)-[1,1'-biphenyl]-4-carboxylic acid;
4'-hydroxy-[1,1'-biphenyl]-3-yl (R)-3-(2-amino-5-(1-methyl-1H-pyrazol-4-yl)nicotinamido)pyrrolidine-1-carboxylate;
4'-(hydroxymethyl)-[1,1'-biphenyl]-3-yl (R)-3-(2-amino-5-(1-methyl-1H-pyrazol-4-yl)nicotinamido)pyrrolidine-1-carboxylate;
4'-formyl-[1,1'-biphenyl]-3-yl (R)-3-(2-amino-5-(1-methyl-1H-pyrazol-4-yl)nicotinamido)pyrrolidine-1-carboxylate;
3'-formyl-[1,1'-biphenyl]-3-yl (R)-3-(2-amino-5-(1-methyl-1H-pyrazol-4-yl)nicotinamido)pyrrolidine-1-carboxylate;
3-(1-benzyl-1H-pyrazol-4-yl)phenyl (R)-3-(2-amino-5-(1-methyl-1H-pyrazol-4-yl)nicotinamido)pyrrolidine-1-carboxylate;
3-(1-(2-hydroxyethyl)-1H-pyrazol-4-yl)phenyl (R)-3-(2-amino-5-(1-methyl-1H-pyrazol-4-yl)nicotinamido)pyrrolidine-1-carboxylate;
3-(1-(piperidin-4-yl)-1H-pyrazol-4-yl)phenyl (R)-3-(2-amino-5-(1-methyl-1H-pyrazol-4-yl)nicotinamido)pyrrolidine-1-carboxylate;
3-(1-(2-(pyrrolidin-1-yl)ethyl)-1H-pyrazol-4-yl)phenyl (R)-3-(2-amino-5-(1-methyl-1H-pyrazol-4-yl)nicotinamido)pyrrolidine-1-carboxylate;
3-(1-(2-morpholinoethyl)-1H-pyrazol-4-yl)phenyl (R)-3-(2-amino-5-(1-methyl-1H-pyrazol-4-yl)nicotinamido)pyrrolidine-1-carboxylate;
3-(1-(2-(4-methylpiperazin-1-yl)ethyl)-1H-pyrazol-4-yl)phenyl (R)-3-(2-amino-5-(1-methyl-1H-pyrazol-4-yl)nicotinamido)pyrrolidine-1-carboxylate;
3-(isoquinolin-4-yl)phenyl (R)-3-(2-amino-5-(1-methyl-1H-pyrazol-4-yl)nicotinamido)pyrrolidine-1-carboxylate;
3-(2-(4-methylpiperazin-1-yl)pyridin-4-yl)phenyl (R)-3-(2-amino-5-(1-methyl-1H-pyrazol-4-yl)nicotinamido)pyrrolidine-1-carboxylate;
5-chloro-4'-(hydroxymethyl)-[1,1'-biphenyl]-3-yl (R)-3-(2-amino-5-(1-methyl-1H-pyrazol-4-yl)nicotinamido)pyrrolidine-1-carboxylate;

5-chloro-4'-((4-methylpiperazin-1-yl)methyl)-[1,1'-biphenyl]-3-yl (R)-3-(2-amino-5-(1-methyl-1H-pyrazol-4-yl)nicotinamido)pyrrolidine-1-carboxylate;

6-(4-((4-methylpiperazin-1-yl)methyl)phenyl)naphthalen-2-yl (R)-3-(2-amino-5-(1-methyl-1H-pyrazol-4-yl)nicotinamido)pyrrolidine-1-carboxylate;

7-(piperidin-4-yloxy)naphthalen-2-yl (R)-3-(2-amino-5-(1-methyl-1H-pyrazol-4-yl)nicotinamido)pyrrolidine-1-carboxylate;

7-(3-(dimethylamino)propoxy)naphthalen-2-yl (R)-3-(2-amino-5-(1-methyl-1H-pyrazol-4-yl)nicotinamido)pyrrolidine-1-carboxylate;

7-(2-(dimethylamino)ethoxy)naphthalen-2-yl (R)-3-(2-amino-5-(1-methyl-1H-pyrazol-4-yl)nicotinamido)pyrrolidine-1-carboxylate;

7-((1-methylpiperidin-4-yl)oxy)naphthalen-2-yl (R)-3-(2-amino-5-(1-methyl-1H-pyrazol-4-yl)nicotinamido)pyrrolidine-1-carboxylate;

7-(piperidin-4-ylmethoxy)naphthalen-2-yl (R)-3-(2-amino-5-(1-methyl-1H-pyrazol-4-yl)nicotinamido)pyrrolidine-1-carboxylate;

7-(2-hydroxyethoxy)naphthalen-2-yl (R)-3-(2-amino-5-(1-methyl-1H-pyrazol-4-yl)nicotinamido)pyrrolidine-1-carboxylate;

6-(2-(dimethylamino)ethoxy)naphthalen-2-yl (R)-3-(2-amino-5-(1-methyl-1H-pyrazol-4-yl)nicotinamido)pyrrolidine-1-carboxylate;

6-(3-(dimethylamino)propoxy)naphthalen-2-yl (R)-3-(2-amino-5-(1-methyl-1H-pyrazol-4-yl)nicotinamido)pyrrolidine-1-carboxylate;

6-(piperidin-4-yloxy)naphthalen-2-yl (R)-3-(2-amino-5-(1-methyl-1H-pyrazol-4-yl)nicotinamido)pyrrolidine-1-carboxylate;

6-(piperidin-4-ylmethoxy)naphthalen-2-yl (R)-3-(2-amino-5-(1-methyl-1H-pyrazol-4-yl)nicotinamido)pyrrolidine-1-carboxylate;

3-(piperidin-4-ylmethoxy)phenyl (R)-3-(2-amino-5-(1-methyl-1H-pyrazol-4-yl)nicotinamido)pyrrolidine-1-carboxylate;

3-(((1R,4R)-4-aminocyclohexyl)methoxy)phenyl (R)-3-(2-amino-5-(1-methyl-1H-pyrazol-4-yl)nicotinamido)pyrrolidine-1-carboxylate;

4'-((azetidin-3-ylamino)methyl)-[1,1'-biphenyl]-3-yl (R)-3-(2-amino-5-(1-methyl-1H-pyrazol-4-yl)nicotinamido)pyrrolidine-1-carboxylate;

4'-(((2-aminoethyl)amino)methyl)-[1,1'-biphenyl]-3-yl (R)-3-(2-amino-5-(1-methyl-1H-pyrazol-4-yl)nicotinamido)pyrrolidine-1-carboxylate;

4'-(((2-(dimethylamino)ethyl)amino)methyl)-[1,1'-biphenyl]-3-yl (R)-3-(2-amino-5-(1-methyl-1H-pyrazol-4-yl)nicotinamido)pyrrolidine-1-carboxylate;

4'-(((azetidin-3-ylmethyl)amino)methyl)-[1,1'-biphenyl]-3-yl (R)-3-(2-amino-5-(1-methyl-1H-pyrazol-4-yl)nicotinamido)pyrrolidine-1-carboxylate;

4'-((((R)-1-methylpyrrolidin-3-yl)amino)methyl)-[1,1'-biphenyl]-3-yl (R)-3-(2-amino-5-(1-methyl-1H-pyrazol-4-yl)nicotinamido)pyrrolidine-1-carboxylate;

4'-((3-(dimethylamino)pyrrolidin-1-yl)methyl)-[1,1'-biphenyl]-3-yl (3R)-3-(2-amino-5-(1-methyl-1H-pyrazol-4-yl)nicotinamido)pyrrolidine-1-carboxylate;

4'-((((S)-pyrrolidin-2-yl)methyl)amino)methyl)-[1,1'-biphenyl]-3-yl (R)-3-(2-amino-5-(1-methyl-1H-pyrazol-4-yl)nicotinamido)pyrrolidine-1-carboxylate;

4'-((((R)-pyrrolidin-3-yl)amino)methyl)-[1,1'-biphenyl]-3-yl (R)-3-(2-amino-5-(1-methyl-1H-pyrazol-4-yl)nicotinamido)pyrrolidine-1-carboxylate;

4'-(((((R)-1-ethylpyrrolidin-2-yl)methyl)amino)methyl)-[1,1'-biphenyl]-3-yl (R)-3-(2-amino-5-(1-methyl-1H-pyrazol-4-yl)nicotinamido)pyrrolidine-1-carboxylate;

4'-((((S)-piperidin-3-yl)amino)methyl)-[1,1'-biphenyl]-3-yl (R)-3-(2-amino-5-(1-methyl-1H-pyrazol-4-yl)nicotinamido)pyrrolidine-1-carboxylate;

4'-(((R)-3-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-((4-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-(((1-methylpiperidin-4-yl)amino)methyl)-[1,1'-biphenyl]-3-yl (R)-3-(2-amino-5-(1-methyl-1H-pyrazol-4-yl)nicotinamido)pyrrolidine-1-carboxylate;

4'-((3-hydroxypiperidin-1-yl)methyl)-[1,1'-biphenyl]-3-yl (3R)-3-(2-amino-5-(1-methyl-1H-pyrazol-4-yl)nicotinamido)pyrrolidine-1-carboxylate;

4'-((3-(hydroxymethyl)piperidin-1-yl)methyl)-[1,1'-biphenyl]-3-yl (3R)-3-(2-amino-5-(1-methyl-1H-pyrazol-4-yl)nicotinamido)pyrrolidine-1-carboxylate;

4'-((4-(hydroxymethyl)piperidin-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-(((3aR,6aR)-1-methylhexahydropyrrolo[3,4-b]pyrrol-5(1H)-yl)methyl)-[1,1'-biphenyl]-3-yl (R)-3-(2-amino-5-(1-methyl-1H-pyrazol-4-yl)nicotinamido)pyrrolidine-1-carboxylate;

4'-((1,4-diazepan-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-(((R)-2-(hydroxymethyl)pyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-(((S)-2-carbamoylpyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate;

(R)-((3'-((3-(2-amino-5-(1-methyl-1H-pyrazol-4-yl)nicotinamido)pyrrolidine-1-carbonyl)oxy)-[1,1'-biphenyl]-4-yl)methyl)glycine;

4'-((((R)-1-hydroxypropan-2-yl)amino)methyl)-[1,1'-biphenyl]-3-yl (R)-3-(2-amino-5-(1-methyl-1H-pyrazol-4-yl)nicotinamido)pyrrolidine-1-carboxylate;

4'-(((3-hydroxypropyl)amino)methyl)-[1,1'-biphenyl]-3-yl (R)-3-(2-amino-5-(1-methyl-1H-pyrazol-4-yl)nicotinamido)pyrrolidine-1-carboxylate;

1-((3'-(((R)-3-(2-amino-5-(1-methyl-1H-pyrazol-4-yl)nicotinamido)pyrrolidine-1-carbonyl)oxy)-[1,1'-biphenyl]-4-yl)methyl)pyrrolidine-3-carboxylic acid;

4'-(((R)-3-aminopyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-(((S)-3-aminopyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-(((S)-3-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-(pyrrolidin-1-ylmethyl)-[1,1'-biphenyl]-3-yl (R)-3-(2-amino-5-(1-methyl-1H-pyrazol-4-yl)nicotinamido)pyrrolidine-1-carboxylate;

4'-(piperidin-1-ylmethyl)-[1,1'-biphenyl]-3-yl (R)-3-(2-amino-5-(1-methyl-1H-pyrazol-4-yl)nicotinamido)pyrrolidine-1-carboxylate;

4'-(morpholinomethyl)-[1,1'-biphenyl]-3-yl (R)-3-(2-amino-5-(1-methyl-1H-pyrazol-4-yl)nicotinamido)pyrrolidine-1-carboxylate;

3'-(((R)-3-aminopyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate;

3'-(((S)-3-aminopyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate;

3'-(((R)-3-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate;

3'-(((S)-3-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate;

3'-((4-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate;

3'-((1,4-diazepan-1-yl)methyl)-[1,1'-biphenyl]-3-yl (R)-3-(2-amino-5-(1-methyl-1H-pyrazol-4-yl)nicotinamido)pyrrolidine-1-carboxylate;

(R)-2-amino-N-(1-(4-bromobenzoyl)pyrrolidin-3-yl)-5-(1-methyl-1H-pyrazol-4-yl)nicotinamide;

(R)—N-(1-([1,1'-biphenyl]-4-carbonyl)pyrrolidin-3-yl)-2-amino-5-(1-methyl-1H-pyrazol-4-yl)nicotinamide;

(S)—N-(1-([1,1'-biphenyl]-3-carbonyl)pyrrolidin-3-yl)-2-amino-5-(1-methyl-1H-pyrazol-4-yl)nicotinamide;

(S)—N-(1-([1,1'-biphenyl]-4-carbonyl)pyrrolidin-3-yl)-2-amino-5-(1-methyl-1H-pyrazol-4-yl)nicotinamide;

(R)-2-amino-N-(1-(2'-(hydroxymethyl)-[1,1'-biphenyl]-4-carbonyl)pyrrolidin-3-yl)-5-(1-methyl-1H-pyrazol-4-yl)nicotinamide;

(R)-2-amino-N-(1-(2'-isopropyl-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(2'-phenoxy-[1,1'-biphenyl]-4-carbonyl)pyrrolidin-3-yl)nicotinamide;

(R)—N-(1-([1,1':2',1''-terphenyl]-4-carbonyl)pyrrolidin-3-yl)-2-amino-5-(1-methyl-1H-pyrazol-4-yl)nicotinamide;

(R)-2-amino-N-(1-(2'-ethyl-[1,1'-biphenyl]-4-carbonyl)pyrrolidin-3-yl)-5-(1-methyl-1H-pyrazol-4-yl)nicotinamide;

(R)-2-amino-N-(1-(2'-methoxy-[1,1'-biphenyl]-4-carbonyl)pyrrolidin-3-yl)-5-(1-methyl-1H-pyrazol-4-yl)nicotinamide;

(R)-2-amino-N-(1-(2'-formyl-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(pyridin-3-yl)benzoyl)pyrrolidin-3-yl)nicotinamide;

(R)-2-amino-N-(1-(4-(6-fluoropyridin-3-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(thiophen-3-yl)benzoyl)pyrrolidin-3-yl)nicotinamide;

(R)-2-amino-N-(1-(2'-chloro-[1,1'-biphenyl]-4-carbonyl)pyrrolidin-3-yl)-5-(1-methyl-1H-pyrazol-4-yl)nicotinamide;

(R)-2-amino-N-(1-(3'-chloro-[1,1'-biphenyl]-4-carbonyl)pyrrolidin-3-yl)-5-(1-methyl-1H-pyrazol-4-yl)nicotinamide;

(R)-2-amino-N-(1-(2',4'-dichloro-[1,1'-biphenyl]-4-carbonyl)pyrrolidin-3-yl)-5-(1-methyl-1H-pyrazol-4-yl)nicotinamide;

(R)-2-amino-N-(1-(3',4'-dichloro-[1,1'-biphenyl]-4-carbonyl)pyrrolidin-3-yl)-5-(1-methyl-1H-pyrazol-4-yl)nicotinamide;

(R)-2-amino-N-(1-(3',5'-dichloro-[1,1'-biphenyl]-4-carbonyl)pyrrolidin-3-yl)-5-(1-methyl-1H-pyrazol-4-yl)nicotinamide;

(R)-2-amino-N-(1-(2',6'-difluoro-[1,1'-biphenyl]-4-carbonyl)pyrrolidin-3-yl)-5-(1-methyl-1H-pyrazol-4-yl)nicotinamide;

(R)-2-amino-N-(1-(2',4'-difluoro-[1,1'-biphenyl]-4-carbonyl)pyrrolidin-3-yl)-5-(l-methyl-1H-pyrazol-4-yl)nicotinamide;

(R)-2-amino-N-(1-(2'-chloro-4'-fluoro-[1,1'-biphenyl]-4-carbonyl)pyrrolidin-3-yl)-5-(1-methyl-1H-pyrazol-4-yl)nicotinamide;

(R)-2-amino-N-(1-(2',5'-dichloro-[1,1'-biphenyl]-4-carbonyl)pyrrolidin-3-yl)-5-(1-methyl-1H-pyrazol-4-yl)nicotinamide;

(R)-2-amino-N-(1-(2',6'-dichloro-[1,1'-biphenyl]-4-carbonyl)pyrrolidin-3-yl)-5-(1-methyl-1H-pyrazol-4-yl)nicotinamide;

(R)-2-amino-N-(1-(2',3'-dichloro-[1,1'-biphenyl]-4-carbonyl)pyrrolidin-3-yl)-5-(1-methyl-1H-pyrazol-4-yl)nicotinamide;

(R)-2-amino-N-(1-(2'-fluoro-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-(trifluoromethyl)-[1,1'-biphenyl]-4-carbonyl)pyrrolidin-3-yl)nicotinamide;

(R)-2-amino-N-(1-(4'-(benzyloxy)-[1,1'-biphenyl]-4-carbonyl)pyrrolidin-3-yl)-5-(1-methyl-1H-pyrazol-4-yl)nicotinamide;

(R)-2-amino-N-(1-(2'-bromo-[1,1'-biphenyl]-4-carbonyl)pyrrolidin-3-yl)-5-(1-methyl-1H-pyrazol-4-yl)nicotinamide;

(R)-2-amino-N-(1-(2',4'-bis(trifluoromethyl)-[1,1'-biphenyl]-4-carbonyl)pyrrolidin-3-yl)-5-(1-methyl-1H-pyrazol-4-yl)nicotinamide;

(R)-2-amino-N-(1-(2'-hydroxy-[1,1'-biphenyl]-4-carbonyl)pyrrolidin-3-yl)-5-(1-methyl-1H-pyrazol-4-yl)nicotinamide;

(R)-2-amino-N-(1-(3'-amino-2'-methyl-[1,1'-biphenyl]-4-carbonyl)pyrrolidin-3-yl)-5-(1-methyl-1H-pyrazol-4-yl)nicotinamide;

(R)-2-amino-N-(1-(4'-chloro-[1,1'-biphenyl]-4-carbonyl)pyrrolidin-3-yl)-5-(1-methyl-1H-pyrazol-4-yl)nicotinamide;

(R)-2-amino-N-(1-(4'-(tert-butyl)-[1,1'-biphenyl]-4-carbonyl)pyrrolidin-3-yl)-5-(1-methyl-1H-pyrazol-4-yl)nicotinamide;

(R)-2-amino-N-(1-(4'-(dimethylamino)-[1,1'-biphenyl]-4-carbonyl)pyrrolidin-3-yl)-5-(1-methyl-1H-pyrazol-4-yl)nicotinamide;

(R)-2-amino-N-(1-(4'-hydroxy-[1,1'-biphenyl]-4-carbonyl)pyrrolidin-3-yl)-5-(1-methyl-1H-pyrazol-4-yl)nicotinamide;

(R)-2-amino-N-(1-(4'-formyl-[1,1'-biphenyl]-4-carbonyl)pyrrolidin-3-yl)-5-(1-methyl-1H-pyrazol-4-yl)nicotinamide;

(R)-2-amino-N-(1-(3'-formyl-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-(4-methylpiperazin-1-yl)-[11'-biphenyl]-4-carbonyl)pyrrolidin-3-yl)nicotinamide;

(R)-2-amino-5-(1-methyl-1H-pyrazol-4-yl)-N-(1-(4'-(2-(piperazin-1-yl)propan-2-yl)-[1,1'-biphenyl]-4-carbonyl)pyrrolidin-3-yl)nicotinamide;

(R)-2-amino-5-(1-methyl-1H-pyrazol-4-yl)-N-(1-(4'-((4-methylpiperazin-1-yl)methyl)-[1,1'-biphenyl]-4-carbonyl)pyrrolidin-3-yl)nicotinamide;

(R)-2-amino-5-(1-methyl-1H-pyrazol-4-yl)-N-(1-(4'-(2-(4-methylpiperazin-1-yl)propan-2-yl)-[1,1'-biphenyl]-4-carbonyl)pyrrolidin-3-yl)nicotinamide;
(R)-2-amino-N-(1-(4'-(2-(4-(2-hydroxyethyl)piperazin-1-yl)propan-2-yl)-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(3'-((4-methylpiperazin-1-yl)methyl)-[1,1'-biphenyl]-4-carbonyl)pyrrolidin-3-yl)nicotinamide;
(R)-2-amino-N-(1-(3'-((4-(2-hydroxyethyl)piperazin-1-yl)methyl)-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(4'-((4-methylpiperazin-1-yl)methyl)-[1,1'-biphenyl]-3-carbonyl)pyrrolidin-3-yl)nicotinamide;
(R)-2-amino-5-(1-methyl-1H-pyrazol-4-yl)-N-(1-(3-methyl-4'-((4-methylpiperazin-1-yl)methyl)-[1,1'-biphenyl]-4-carbonyl)pyrrolidin-3-yl)nicotinamide;
(R)-2-amino-5-(1-methyl-1H-pyrazol-4-yl)-N-(1-(2-methyl-4'-((4-methylpiperazin-1-yl)methyl)-[1,1'-biphenyl]-4-carbonyl)pyrrolidin-3-yl)nicotinamide;
(R)-2-amino-N-(1-(3-amino-[1,1'-biphenyl]-4-carbonyl)pyrrolidin-3-yl)-5-(1-methyl-1H-pyrazol-4-yl)nicotinamide;
(R)-2-amino-N-(1-(2-chloro-[1,1'-biphenyl]-4-carbonyl)pyrrolidin-3-yl)-5-(1-methyl-1H-pyrazol-4-yl)nicotinamide;
(R)-2-amino-N-(1-(5-(2-chlorophenyl)picolinoyl)pyrrolidin-3-yl)-5-(1-methyl-1H-pyrazol-4-yl)nicotinamide;
(R)-2-amino-5-(1-methyl-1H-pyrazol-4-yl)-N-(1-(5-phenylpicolinoyl)pyrrolidin-3-yl)nicotinamide;
(R)-2-amino-N-(1-(6-(2-chlorophenyl)nicotinoyl)pyrrolidin-3-yl)-5-(1-methyl-1H-pyrazol-4-yl)nicotinamide;
(R)-2-amino-5-(1-methyl-1H-pyrazol-4-yl)-N-(1-(6-phenylnicotinoyl)pyrrolidin-3-yl)nicotinamide;
(R)-2-amino-5-(1-methyl-1H-pyrazol-4-yl)-N-(1-(2-methyl-[1,1'-biphenyl]-4-carbonyl)pyrrolidin-3-yl)nicotinamide;
(R)-2-amino-N-(1-(4-iodobenzoyl)pyrrolidin-3-yl)-5-(1-methyl-1H-pyrazol-4-yl)nicotinamide;
(R)-2-amino-N-(1-(benzofuran-2-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(3-methylbenzofuran-2-carbonyl)pyrrolidin-3-yl)nicotinamide;
(R)-2-amino-N-(1-(5-chlorobenzofuran-2-carbonyl)pyrrolidin-3-yl)-5-(1-methyl-1H-pyrazol-4-yl)nicotinamide;
2-amino-N-((3R)-1-(5-chloro-2,3-dihydrobenzofuran-2-carbonyl)pyrrolidin-3-yl)-5-(1-methyl-1H-pyrazol-4-yl)nicotinamide;
(R)—N-(1-(2-naphthoyl)pyrrolidin-3-yl)-2-amino-5-(1-methyl-1H-pyrazol-4-yl)nicotinamide;
(R)-2-amino-N-(1-(benzo[b]thiophene-2-carbonyl)pyrrolidin-3-yl)-5-(1-methyl-1H-pyrazol-4-yl)nicotinamide;
(R)-2-amino-N-(1-(4,5-dibromothiophene-2-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(5-methylthiophene-2-carbonyl)pyrrolidin-3-yl)nicotinamide;
(R)-2-amino-5-(1-methyl-1H-pyrazol-4-yl)-N-(1-(4-methylthiophene-2-carbonyl)pyrrolidin-3-yl)nicotinamide;
(R)-2-amino-N-(1-(4-(benzyloxy)benzoyl)pyrrolidin-3-yl)-5-(1-methyl-1H-pyrazol-4-yl)nicotinamide;
2-amino-N-((3R)-1-(4-(cyclohex-2-en-1-yloxy)benzoyl)pyrrolidin-3-yl)-5-(1-methyl-1H-pyrazol-4-yl)nicotinamide;
(R)-2-amino-5-(1-methyl-1H-pyrazol-4-yl)-N-(1-(3-phenoxybenzoyl)pyrrolidin-3-yl)nicotinamide;
(R)-2-amino-N-(1-(4-(2-bromoethyl)benzoyl)pyrrolidin-3-yl)-5-(1-methyl-1H-pyrazol-4-yl)nicotinamide;
(R)-2-amino-N-(1-(4-(tert-butyl)benzoyl)pyrrolidin-3-yl)-5-(1-methyl-1H-pyrazol-4-yl)nicotinamide;
(R)-2-amino-N-(1-(3,4-dimethylbenzoyl)pyrrolidin-3-yl)-5-(1-methyl-1H-pyrazol-4-yl)nicotinamide;
(R)-2-amino-5-(1-methyl-1H-pyrazol-4-yl)-N-(1-(4-(4-methylpiperazin-1-yl)benzoyl)pyrrolidin-3-yl)nicotinamide;
(R)-2-amino-5-(1-methyl-1H-pyrazol-4-yl)-N-(1-(4-vinylbenzoyl)pyrrolidin-3-yl)nicotinamide;
(R)-2-amino-N-(1-(4-isopropylbenzoyl)pyrrolidin-3-yl)-5-(1-methyl-1H-pyrazol-4-yl)nicotinamide;
(R)-2-amino-N-(1-(4-cyanobenzoyl)pyrrolidin-3-yl)-5-(1-methyl-1H-pyrazol-4-yl)nicotinamide;
(R)-2-amino-5-(1-methyl-1H-pyrazol-4-yl)-N-(1-(4-(methylthio)benzoyl)pyrrolidin-3-yl)nicotinamide;
(R)-2-amino-N-(1-(2-(3-bromophenyl)acetyl)pyrrolidin-3-yl)-5-(1-methyl-1H-pyrazol-4-yl)nicotinamide;
(R)—N-(1-(2-([1,1'-biphenyl]-4-yl)acetyl)pyrrolidin-3-yl)-2-amino-5-(1-methyl-1H-pyrazol-4-yl)nicotinamide;
(R)—N-(1-(2-([1,1'-biphenyl]-3-yl)acetyl)pyrrolidin-3-yl)-2-amino-5-(1-methyl-1H-pyrazol-4-yl)nicotinamide;
(R)-2-amino-N-(1-cinnamoylpyrrolidin-3-yl)-5-(1-methyl-1H-pyrazol-4-yl)nicotinamide;
(R,E)-2-amino-N-(1-(3-(benzo[d][1,3]dioxol-5-yl)acryloyl)pyrrolidin-3-yl)-5-(1-methyl-1H-pyrazol-4-yl)nicotinamide;
(R,E)-2-amino-5-(1-methyl-1H-pyrazol-4-yl)-N-(1-(2-methyl-3-phenylacryloyl)pyrrolidin-3-yl)nicotinamide;
(R,E)-2-amino-N-(1-(3-(4-bromophenyl)acryloyl)pyrrolidin-3-yl)-5-(1-methyl-1H-pyrazol-4-yl)nicotinamide;
(R,E)-2-amino-N-(1-(3-(3-bromophenyl)acryloyl)pyrrolidin-3-yl)-5-(1-methyl-1H-pyrazol-4-yl)nicotinamide;
(R,E)-2-amino-5-(1-methyl-1H-pyrazol-4-yl)-N-(1-(3-(4-((4-methylpiperazin-1-yl)methyl)phenyl)acryloyl)pyrrolidin-3-yl)nicotinamide;
(R,E)-2-amino-N-(1-(3-(4-((4-(2-hydroxyethyl)piperazin-1-yl)methyl)phenyl)acryloyl)pyrrolidin-3-yl)-5-(1-methyl-1H-pyrazol-4-yl)nicotinamide;
(R,E)-2-amino-5-(1-methyl-1H-pyrazol-4-yl)-N-(1-(3-(4'-((4-methylpiperazin-1-yl)methyl)-[1,1'-biphenyl]-3-yl)acryloyl)pyrrolidin-3-yl)nicotinamide;
(R,E)-2-amino-5-(1-methyl-1H-pyrazol-4-yl)-N-(1-(3-(4'-((4-methylpiperazin-1-yl)methyl)-[1,1'-biphenyl]-4-yl)acryloyl)pyrrolidin-3-yl)nicotinamide;
(R)-2-amino-5-(1-methyl-1H-pyrazol-4-yl)-N-(1-(2-phenylacetyl)pyrrolidin-3-yl)nicotinamide;
(R)-2-amino-N-(1-(2-(3-chlorophenyl)acetyl)pyrrolidin-3-yl)-5-(1-methyl-1H-pyrazol-4-yl)nicotinamide;
(R)-2-amino-N-(1-(2-(2-fluorophenyl)acetyl)pyrrolidin-3-yl)-5-(1-methyl-1H-pyrazol-4-yl)nicotinamide;
(R)-2-amino-N-(1-(2-(2-methoxyphenyl)acetyl)pyrrolidin-3-yl)-5-(1-methyl-1H-pyrazol-4-yl)nicotinamide;
(R)-2-amino-5-(1-methyl-1H-pyrazol-4-yl)-N-(1-(2-methyl-2-phenylpropanoyl)pyrrolidin-3-yl)nicotinamide;
(R)-2-amino-N-(1-benzoylpyrrolidin-3-yl)-5-(1-methyl-1H-pyrazol-4-yl)nicotinamide;
(R)-2-amino-N-(1-(4-fluoro-2-methylbenzoyl)pyrrolidin-3-yl)-5-(1-methyl-1H-pyrazol-4-yl)nicotinamide;
(R)-2-amino-N-(1-(5-bromo-2-chlorobenzoyl)pyrrolidin-3-yl)-5-(1-methyl-1H-pyrazol-4-yl)nicotinamide;
(R)-2-amino-N-(1-(3,5-dichlorobenzoyl)pyrrolidin-3-yl)-5-(1-methyl-1H-pyrazol-4-yl)nicotinamide;
2-amino-5-(1-methyl-1H-pyrazol-4-yl)-N—((R)-1-(trans-2-phenylcyclopropane-1-carbonyl)pyrrolidin-3-yl)nicotinamide;

(R)-2-amino-5-(1-methyl-1H-pyrazol-4-yl)-N-(1-(5-(4-((4-methylpiperazin-1-yl)methyl)phenyl)-1-naphthoyl)pyrrolidin-3-yl)nicotinamide;

2-amino-N—((R)-1-(5-(4-(((R)-2-(hydroxymethyl)pyrrolidin-1-yl)methyl)phenyl)-1-naphthoyl)pyrrolidin-3-yl)-5-(1-methyl-1H-pyrazol-4-yl)nicotinamide;

2-amino-5-(1-methyl-1H-pyrazol-4-yl)-N-((3R)-1-(5-(4-(((1-(1-methylpiperidin-4-yl)ethyl)amino)methyl)phenyl)-1-naphthoyl)pyrrolidin-3-yl)nicotinamide;

(R)-2-amino-5-(1-methyl-1H-pyrazol-4-yl)-N-(1-(3-(4-((4-methylpiperazin-1-yl)methyl)phenoxy)benzoyl)pyrrolidin-3-yl)nicotinamide;

2-amino-N—((R)-1-(3-(4-(((R)-2-(hydroxymethyl)pyrrolidin-1-yl)methyl)phenoxy)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(4-((4-methylpiperazin-1-yl)methyl)phenoxy)benzoyl)pyrrolidin-3-yl)nicotinamide;

2-amino-N—((R)-1-(4-(4-(((R)-2-(hydroxymethyl)pyrrolidin-1-yl)methyl)phenoxy)benzoyl)pyrrolidin-3-yl)-5-(1-methyl-1H-pyrazol-4-yl)nicotinamide;

(R)—N-(1-([1,1'-biphenyl]-3-carbonyl)pyrrolidin-3-yl)-2-amino-5-(1-methyl-1H-pyrazol-4-yl)nicotinamide;

(R)-2-amino-5-(1-methyl-1H-pyrazol-4-yl)-N-(1-(3-(1-(piperidin-4-yl)-1H-pyrazol-4-yl)benzoyl)pyrrolidin-3-yl)nicotinamide;

(R)-2-amino-5-(1-methyl-1H-pyrazol-4-yl)-N-(1-(3'-(2-(4-methylpiperazin-1-yl)-2-oxoethyl)-[1,1'-biphenyl]-3-carbonyl)pyrrolidin-3-yl)nicotinamide;

(R)-2-amino-5-(1-methyl-1H-pyrazol-4-yl)-N-(1-(3'-(2-(4-methylpiperazin-1-yl)ethyl)-[1,1'-biphenyl]-3-carbonyl)pyrrolidin-3-yl)nicotinamide;

(R)-2-amino-5-(1-methyl-1H-pyrazol-4-yl)-N-(1-(4'-(2-(4-methylpiperazin-1-yl)-2-oxoethyl)-[1,1'-biphenyl]-3-carbonyl)pyrrolidin-3-yl)nicotinamide;

(R)-2-amino-5-(1-methyl-1H-pyrazol-4-yl)-N-(1-(4'-(2-(4-methylpiperazin-1-yl)ethyl)-[1,1'-biphenyl]-3-carbonyl)pyrrolidin-3-yl)nicotinamide;

(R)-3'-(3-(2-amino-5-(1-methyl-1H-pyrazol-4-yl)nicotinamido)pyrrolidine-1-carbonyl)-[1,1'-biphenyl]-3-carboxylic acid;

(R)-2-amino-N-(1-(3'-amino-[1,1'-biphenyl]-3-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(2-phenyl-5-(trifluoromethyl)oxazole-4-carbonyl)pyrrolidin-3-yl)nicotinamide;

(R)—N-(1-(3'-((1H-pyrazol-1-yl)methyl)-[1,1'-biphenyl]-3-carbonyl)pyrrolidin-3-yl)-2-amino-5-(1-methyl-1H-pyrazol-4-yl)nicotinamide;

(R)—N-(1-(3'-((1H-imidazol-1-yl)methyl)-[1,1'-biphenyl]-3-carbonyl)pyrrolidin-3-yl)-2-amino-5-(1-methyl-1H-pyrazol-4-yl)nicotinamide;

(R)-2-amino-5-(1-methyl-1H-pyrazol-4-yl)-N-(1-(3'-(morpholinomethyl)-[1,1'-biphenyl]-3-carbonyl)pyrrolidin-3-yl)nicotinamide;

2-amino-N—((R)-1-(3'-(((R)-2-(hydroxymethyl)pyrrolidin-1-yl)methyl)-[1,1'-biphenyl]-3-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(3'-(thiomorpholine-4-carbonyl)-[1,1'-biphenyl]-3-carbonyl)pyrrolidin-3-yl)nicotinamide;

(R)-2-amino-5-(1-methyl-1H-pyrazol-4-yl)-N-(1-(3'-(piperazine-1-carbonyl)-[1,1'-biphenyl]-3-carbonyl)pyrrolidin-3-yl)nicotinamide;

(R)-2-amino-5-(1-methyl-1H-pyrazol-4-yl)-N-(1-(4'-(piperazine-1-carbonyl)-[1,1'-biphenyl]-3-carbonyl)pyrrolidin-3-yl)nicotinamide;

(R)-2-amino-5-(1-methyl-1H-pyrazol-4-yl)-N-(1-(3'-(piperazine-1-carbonyl)-[1,1'-biphenyl]-4-carbonyl)pyrrolidin-3-yl)nicotinamide;

(R)-2-amino-5-(1-methyl-1H-pyrazol-4-yl)-N-(1-(4'-(piperazine-1-carbonyl)-[1,1'-biphenyl]-4-carbonyl)pyrrolidin-3-yl)nicotinamide;

(R)-2-amino-N-(1-(3-(furan-3-yl)benzoyl)pyrrolidin-3-yl)-5-(1-methyl-1H-pyrazol-4-yl)nicotinamide;

(R)-2-amino-N-(1-(3-(1,3-dimethyl-1H-pyrazol-4-yl)benzoyl)pyrrolidin-3-yl)-5-(1-methyl-1H-pyrazol-4-yl)nicotinamide;

(R)-2-amino-N-(1-(3-(1-cyclopentyl-1H-pyrazol-4-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(3-(1-(phenylsulfonyl)-1H-pyrazol-4-yl)benzoyl)pyrrolidin-3-yl)nicotinamide;

(R)-2-amino-5-(1-methyl-1H-pyrazol-4-yl)-N-(1-(3-(pyridin-3-yl)benzoyl)pyrrolidin-3-yl)nicotinamide;

(R)-2-amino-5-(1-methyl-1H-pyrazol-4-yl)-N-(1-(3-(pyridin-4-yl)benzoyl)pyrrolidin-3-yl)nicotinamide;

(R)-2-amino-N-(1-(3-(benzo[b]thiophen-2-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(2',3',4',5'-tetrahydro-[1,1'-biphenyl]-3-carbonyl)pyrrolidin-3-yl)nicotinamide;

(R)-2-amino-5-(1-methyl-1H-pyrazol-4-yl)-N-(1-(3'-(4-methylpiperazin-1-yl)-[1,1'-biphenyl]-3-carbonyl)pyrrolidin-3-yl)nicotinamide;

(R)-2-amino-5-(1-methyl-1H-pyrazol-4-yl)-N-(1-(3'-(piperidin-1-yl)-1'-b[1,1'-biphenyl]-3-carbonyl)pyrrolidin-3-yl)nicotinamide;

(R)-2-amino-N-(1-(2'-chloro-[1,1'-biphenyl]-3-carbonyl)pyrrolidin-3-yl)-5-(1-methyl-1H-pyrazol-4-yl)nicotinamide;

(R)-2-amino-N-(1-(3'-chloro-[1,1'-biphenyl]-3-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(3-(2-(piperazin-1-yl)pyridin-4-yl)benzoyl)pyrrolidin-3-yl)nicotinamide;

(R)-2-amino-5-(1-methyl-1H-pyrazol-4-yl)-N-(1-(3'-(methylsulfonamido)-[1,1'-biphenyl]-3-carbonyl)pyrrolidin-3-yl)nicotinamide;

(R)-2-amino-5-(1-methyl-1H-pyrazol-4-yl)-N-(1-(6-methyl-[1,1'-biphenyl]-3-carbonyl)pyrrolidin-3-yl)nicotinamide;

(R)-2-amino-N-(1-(2'-chloro-6-methyl-[1,1'-biphenyl]-3-carbonyl)pyrrolidin-3-yl)-5-(1-methyl-1H-pyrazol-4-yl)nicotinamide;

(R)-2-amino-N-(1-(3'-chloro-6-methyl-[1,1'-biphenyl]-3-carbonyl)pyrrolidin-3-yl)-5-(1-methyl-1H-pyrazol-4-yl)nicotinamide;

(R)-2-amino-N-(1-(2-amino-5-methyl-[1,1'-biphenyl]-3-carbonyl)pyrrolidin-3-yl)-5-(1-methyl-1H-pyrazol-4-yl)nicotinamide;

(R)-2-amino-N-(1-(4-amino-[1,1'-biphenyl]-3-carbonyl)pyrrolidin-3-yl)-5-(1-methyl-1H-pyrazol-4-yl)nicotinamide;

(R)-2-amino-N-(1-(4-(furan-3-yl)benzoyl)pyrrolidin-3-yl)-5-(1-methyl-1H-pyrazol-4-yl)nicotinamide;

(R)-2-amino-N-(1-(4-(1,3-dimethyl-1H-pyrazol-4-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(pyridin-4-yl)benzoyl)pyrrolidin-3-yl)nicotinamide;
(R)-2-amino-N-(1-(4-(benzo[b]thiophen-2-yl)benzoyl)pyrrolidin-3-yl)-5-(1-methyl-1H-pyrazol-4-yl)nicotinamide;
(R)-2-amino-5-(1-methyl-1H-pyrazol-4-yl)-N-(1-(4-(2-(piperazin-1-yl)pyridin-4-yl)benzoyl)pyrrolidin-3-yl)nicotinamide;
(R)-2-amino-5-(1-methyl-1H-pyrazol-4-yl)-N-(1-(4'-morpholino-[1,1'-biphenyl]-4-carbonyl)pyrrolidin-3-yl)nicotinamide;
(R)-2-amino-5-(1-methyl-1H-pyrazol-4-yl)-N-(1-(4'-(morpholine-4-carbonyl)-[1,1'-biphenyl]-4-carbonyl)pyrrolidin-3-yl)nicotinamide;
(R)-2-amino-5-(1-methyl-1H-pyrazol-4-yl)-N-(1-(2',3',4',5'-tetrahydro-[1,1'-biphenyl]-4-carbonyl)pyrrolidin-3-yl)nicotinamide;
(R)-2-amino-N-(1-(3-(2,3-dioxoindolin-6-yl)benzoyl)pyrrolidin-3-yl)-5-(1-methyl-1H-pyrazol-4-yl)nicotinamide;
(R)-2-amino-N-(1-(2,3-dihydro-1H-indene-2-carbonyl)pyrrolidin-3-yl)-5-(1-methyl-1H-pyrazol-4-yl)nicotinamide;
(R)-2-amino-N-(1-(3-methyl-1H-indene-2-carbonyl)pyrrolidin-3-yl)-5-(1-methyl-1H-pyrazol-4-yl)nicotinamide;
(R)-2-amino-N-(1-(5-chlorobenzo[d]oxazole-2-carbonyl)pyrrolidin-3-yl)-5-(1-methyl-1H-pyrazol-4-yl)nicotinamide;
(R)-2-amino-N-(1-(1-methyl-1H-indazole-3-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(5-methyl-3-phenylisoxazole-4-carbonyl)pyrrolidin-3-yl)nicotinamide;
(R)-2-amino-N-(1-(dibenzo[b,d]furan-4-carbonyl)pyrrolidin-3-yl)-5-(1-methyl-1H-pyrazol-4-yl)nicotinamide;
(R)—N-(1-(1H-indole-5-carbonyl)pyrrolidin-3-yl)-2-amino-5-(1-methyl-1H-pyrazol-4-yl)nicotinamide;
(R)-2-amino-5-(1-methyl-1H-pyrazol-4-yl)-N-(1-(1,2,3,4-tetrahydrocyclopenta[b]indole-7-carbonyl)pyrrolidin-3-yl)nicotinamide;
(R)—N-(1-(1H-indole-4-carbonyl)pyrrolidin-3-yl)-2-amino-5-(1-methyl-1H-pyrazol-4-yl)nicotinamide;
(R)-2-amino-N-(1-(4'-(4-aminophenoxy)-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(4-(1-methyl-1H-pyrazol-4-yl)benzoyl)pyrrolidin-3-yl)nicotinamide;
(R)-2-amino-5-(1-methyl-1H-pyrazol-4-yl)-N-(1-(4-(1,3,5-trimethyl-1H-pyrazol-4-yl)benzoyl)pyrrolidin-3-yl)nicotinamide;
(R)-2-amino-N-(1-(4-(1-cyclopentyl-1H-pyrazol-4-yl)benzoyl)pyrrolidin-3-yl)-5-(1-methyl-1H-pyrazol-4-yl)nicotinamide;
(R)-2-amino-5-(1-methyl-1H-pyrazol-4-yl)-N-(1-(4-(1-(tetrahydro-2H-pyran-4-yl)-1H-pyrazol-4-yl)benzoyl)pyrrolidin-3-yl)nicotinamide;
(R)-2-amino-5-(1-methyl-1H-pyrazol-4-yl)-N-(1-(4-(1-(piperidin-4-yl)-1H-pyrazol-4-yl)benzoyl)pyrrolidin-3-yl)nicotinamide;
tert-butyl (R)-4-(4-(4-(3-(2-amino-5-(1-methyl-1H-pyrazol-4-yl)nicotinamido)pyrrolidine-1-carbonyl)phenyl)-1H-pyrazol-1-yl)piperidine-1-carboxylate;
(R)-2-amino-5-(1-methyl-1H-pyrazol-4-yl)-N-(1-(5-phenylbenzofuran-2-carbonyl)pyrrolidin-3-yl)nicotinamide;
(R)—N-(1-(1-acetyl-1H-indole-5-carbonyl)pyrrolidin-3-yl)-2-amino-5-(1-methyl-1H-pyrazol-4-yl)nicotinamide;
(R)—N-(1-(1-acetyl-1H-indole-4-carbonyl)pyrrolidin-3-yl)-2-amino-5-(1-methyl-1H-pyrazol-4-yl)nicotinamide;
(R)-2-amino-N-(1-(3-hydroxybenzoyl)pyrrolidin-3-yl)-5-(1-methyl-1H-pyrazol-4-yl)nicotinamide;
(R)-2-amino-5-(1-methyl-1H-pyrazol-4-yl)-N-(1-(1-phenyl-3-(trifluoromethyl)-1H-pyrazole-4-carbonyl)pyrrolidin-3-yl)nicotinamide;
(R)-2-amino-N-(1-(4-(1,5-dimethyl-1H-pyrazol-4-yl)benzoyl)pyrrolidin-3-yl)-5-(1-methyl-1H-pyrazol-4-yl)nicotinamide;
(R)-2-amino-N-(1-(4-(3,5-dimethyl-1H-pyrazol-4-yl)benzoyl)pyrrolidin-3-yl)-5-(1-methyl-1H-pyrazol-4-yl)nicotinamide;
(R)-2-amino-N-(1-(4-(3,5-dimethyl-1-phenyl-1H-pyrazol-4-yl)benzoyl)pyrrolidin-3-yl)-5-(1-methyl-1H-pyrazol-4-yl)nicotinamide;
(R)-2-amino-N-(1-(4-(1-(4-aminophenyl)-3,5-dimethyl-1H-pyrazol-4-yl)benzoyl)pyrrolidin-3-yl)-5-(1-methyl-1H-pyrazol-4-yl)nicotinamide;
(R)-2-amino-N-(1-(4-(1,3-dimethyl-5-(trifluoromethyl)-1H-pyrazol-4-yl)benzoyl)pyrrolidin-3-yl)-5-(1-methyl-1H-pyrazol-4-yl)nicotinamide;
(R)-2-amino-N-(1-(4-(4-bromo-3,5-dimethylthiophen-2-yl)benzoyl)pyrrolidin-3-yl)-5-(1-methyl-1H-pyrazol-4-yl)nicotinamide;
(R)-2-amino-5-(1-methyl-1H-pyrazol-4-yl)-N-(1-(4-(4-methylthiophen-3-yl)benzoyl)pyrrolidin-3-yl)nicotinamide;
(R)-2-amino-N-(1-(4-(3-methoxythiophen-2-yl)benzoyl)pyrrolidin-3-yl)-5-(1-methyl-1H-pyrazol-4-yl)nicotinamide;
(R)-2-amino-5-(1-methyl-1H-pyrazol-4-yl)-N-(1-(4-(4-methylthiophen-2-yl)benzoyl)pyrrolidin-3-yl)nicotinamide;
(R)-2-amino-5-(1-methyl-1H-pyrazol-4-yl)-N-(1-(4-(5-methylthiophen-2-yl)benzoyl)pyrrolidin-3-yl)nicotinamide;
(R)-2-amino-5-(1-methyl-1H-pyrazol-4-yl)-N-(1-(4'-phenoxy-[1,1'-biphenyl]-4-carbonyl)pyrrolidin-3-yl)nicotinamide;
(R)-2-amino-N-(1-(4'-(4-methoxyphenoxy)-[1,1'-biphenyl]-4-carbonyl)pyrrolidin-3-yl)-5-(1-methyl-1H-pyrazol-4-yl)nicotinamide;
(R)-2-amino-N-(1-(4'-(4-(dimethylamino)phenoxy)-[1,1'-biphenyl]-4-carbonyl)pyrrolidin-3-yl)-5-(1-methyl-1H-pyrazol-4-yl)nicotinamide;
(R)-2-amino-N-(1-(4'-(3-aminophenoxy)-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(4'-(piperidin-4-yloxy)-[1,1'-biphenyl]-4-carbonyl)pyrrolidin-3-yl)nicotinamide;
2-amino-5-(1-methyl-1H-pyrazol-4-yl)-N-((3R)-1-(4'-(pyrrolidin-3-yloxy)-[1,1'-biphenyl]-4-carbonyl)pyrrolidin-3-yl)nicotinamide;
(R)-2-amino-N-(1-(4'-(4-aminophenoxy)-2'-fluoro-[1,1'-biphenyl]-4-carbonyl)pyrrolidin-3-yl)-5-(1-methyl-1H-pyrazol-4-yl)nicotinamide;
(R)-2-amino-N-(1-(4-(5-chlorothiophen-2-yl)benzoyl)pyrrolidin-3-yl)-5-(1-methyl-1H-pyrazol-4-yl)nicotinamide;
(R)-2-amino-N-(1-(3-hydroxy-4-(5-methylthiophen-2-yl)benzoyl)pyrrolidin-3-yl)-5-(1-methyl-1H-pyrazol-4-yl)nicotinamide;
(R)-2-amino-5-(1-methyl-1H-pyrazol-4-yl)-N-(1-(3-methyl-4-(5-methylthiophen-2-yl)benzoyl)pyrrolidin-3-yl)nicotinamide;
(R)-2-amino-N-(1-(4-(5-cyanothiophen-2-yl)benzoyl)pyrrolidin-3-yl)-5-(1-methyl-1H-pyrazol-4-yl)nicotinamide;

(R)—N-(1-(4-(5-acetylthiophen-2-yl)benzoyl)pyrrolidin-3-yl)-2-amino-5-(1-methyl-1H-pyrazol-4-yl)nicotinamide;

(R)-2-amino-N-(1-(4-(3,5-dimethylisoxazol-4-yl)benzoyl)pyrrolidin-3-yl)-5-(1-methyl-1H-pyrazol-4-yl)nicotinamide;

(R)-2-amino-N-(1-(4-(3-amino-5-methylisoxazol-4-yl)benzoyl)pyrrolidin-3-yl)-5-(1-methyl-1H-pyrazol-4-yl)nicotinamide;

2-amino-5-(1-methyl-1H-pyrazol-4-yl)-N—((R)-1-(4'-(((S)-pyrrolidin-3-yl)oxy)-[1,1'-biphenyl]-4-carbonyl)pyrrolidin-3-yl)nicotinamide;

2-amino-N-((3R)-1-(4-(5-(1-hydroxyethyl)thiophen-2-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(5-methylthiazol-2-yl)benzoyl)pyrrolidin-3-yl)nicotinamide;

(R)-2-amino-5-(1-methyl-1H-pyrazol-4-yl)-N-(1-(4-(4-methylthiazol-2-yl)benzoyl)pyrrolidin-3-yl)nicotinamide;

(R)—N-(1-(1H-benzo[d]imidazole-2-carbonyl)pyrrolidin-3-yl)-2-amino-5-(1-methyl-1H-pyrazol-4-yl)nicotinamide;

(R)-2-amino-5-(1-methyl-1H-pyrazol-4-yl)-N-(1-(2-oxo-2-phenylacetyl)pyrrolidin-3-yl)nicotinamide;

(R)-2-amino-N-(1-(4'-((4-aminopiperidin-1-yl)methyl)-[1,1'-biphenyl]-4-carbonyl)pyrrolidin-3-yl)-5-(1-methyl-1H-pyrazol-4-yl)nicotinamide;

2-amino-N-((3R)-1-(4'-((methyl((1-methylpiperidin-3-yl)methyl)amino)methyl)-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-(((1-methylpiperidin-4-yl)amino)methyl)-[1,1'-biphenyl]-4-carbonyl)pyrrolidin-3-yl)nicotinamide;

(R)-2-amino-5-(1-methyl-1H-pyrazol-4-yl)-N-(1-(4'-(piperidin-4-ylmethoxy)-[11'-biphenyl]-4-carbonyl)pyrrolidin-3-yl)nicotinamide;

(R)-2-amino-N-(1-(4'-(3-(dimethylamino)propoxy)-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-((1-methylpiperidin-4-yl)methoxy)-[1,1'-biphenyl]-4-carbonyl)pyrrolidin-3-yl)nicotinamide;

(R)-2-amino-N-(1-(4-(4-hydroxybut-1-yn-1-yl)benzoyl)pyrrolidin-3-yl)-5-(1-methyl-1H-pyrazol-4-yl)nicotinamide;

(R)-2-amino-N-(1-(4-(5-hydroxypent-1-yn-1-yl)benzoyl)pyrrolidin-3-yl)-5-(1-methyl-1H-pyrazol-4-yl)nicotinamide;

(R)—N-(1-([1,1'-biphenyl]-4-carbonyl)pyrrolidin-3-yl)-2-amino-5-(4-methoxyphenyl)nicotinamide;

(R)—N-(1-([1,1'-biphenyl]-4-carbonyl)pyrrolidin-3-yl)-2-amino-5-(4-(4-methylpiperazin-1-yl)phenyl)nicotinamide;

(R)—N-(1-([1,1'-biphenyl]-4-carbonyl)pyrrolidin-3-yl)-2-amino-5-(4-morpholinophenyl)nicotinamide;

(R)—N-(1-([1,1'-biphenyl]-4-carbonyl)pyrrolidin-3-yl)-6-amino-[3,3'-bipyridine]-5-carboxamide;

(R)—N-(1-([1,1'-biphenyl]-4-carbonyl)pyrrolidin-3-yl)-6-amino-6'-morpholino-[3,3'-bipyridine]-5-carboxamide;

(R)—N-(1-([1,1'-biphenyl]-4-carbonyl)pyrrolidin-3-yl)-6-amino-6'-fluoro-[3,3'-bipyridine]-5-carboxamide;

tert-butyl (R)-4-(4-(5-(((1-([1,1'-biphenyl]-4-carbonyl)pyrrolidin-3-yl)carbamoyl)-6-aminopyridin-3-yl)-1H-pyrazol-1-yl)piperidine-1-carboxylate;

(R)—N-(1-([1,1'-biphenyl]-4-carbonyl)pyrrolidin-3-yl)-2-amino-5-(1-(piperidin-4-yl)-1H-pyrazol-4-yl)nicotinamide;

(R)—N-(1-([1,1'-biphenyl]-4-carbonyl)pyrrolidin-3-yl)-2-amino-5-(1-(1-methylpiperidin-4-yl)-1H-pyrazol-4-yl)nicotinamide;

(R)—N-(1-([1,1'-biphenyl]-4-carbonyl)pyrrolidin-3-yl)-2-amino-5-(4-(2-(piperazin-1-yl)propan-2-yl)phenyl)nicotinamide;

(R)—N-(1-([1,1'-biphenyl]-4-carbonyl)pyrrolidin-3-yl)-2-amino-5-(4-(2-(4-(2-hydroxyethyl)piperazin-1-yl)propan-2-yl)phenyl)nicotinamide;

(R)—N-(1-([1,1'-biphenyl]-4-carbonyl)pyrrolidin-3-yl)-2-amino-5-(4-((4-methylpiperazin-1-yl)methyl)phenyl)nicotinamide;

(R)—N-(1-([1,1'-biphenyl]-4-carbonyl)pyrrolidin-3-yl)-2-amino-5-(4-(hydroxymethyl)phenyl)nicotinamide;

(R)—N-(1-([1,1'-biphenyl]-4-carbonyl)pyrrolidin-3-yl)-2-amino-5-(4-(morpholinomethyl)phenyl)nicotinamide;

(R)-2-amino-N-(1-(2'-chloro-[1,1'-biphenyl]-4-carbonyl)pyrrolidin-3-yl)-5-(4-(4-methylpiperazin-1-yl)phenyl)nicotinamide;

(R)-2-amino-N-(1-(2'-chloro-[1,1'-biphenyl]-4-carbonyl)pyrrolidin-3-yl)-5-(4-morpholinophenyl)nicotinamide;

(R)-2-amino-N-(1-(2'-chloro-[1,1'-biphenyl]-4-carbonyl)pyrrolidin-3-yl)-5-(4-((4-methylpiperazin-1-yl)methyl)phenyl)nicotinamide;

(R)-2-amino-N-(1-(2'-chloro-[1,1'-biphenyl]-4-carbonyl)pyrrolidin-3-yl)-5-(1-(2-methoxyethyl)-1H-pyrazol-4-yl)nicotinamide;

(R)-2-amino-5-(4-(azetidin-1-ylsulfonyl)phenyl)-N-(1-(2'-chloro-[1,1'-biphenyl]-4-carbonyl)pyrrolidin-3-yl)nicotinamide;

(R)-2-amino-N-(1-(2'-chloro-[1,1'-biphenyl]-4-carbonyl)pyrrolidin-3-yl)-5-(4-sulfamoylphenyl)nicotinamide;

(R)-2-amino-N-(1-(2'-chloro-[1,1'-biphenyl]-4-carbonyl)pyrrolidin-3-yl)-5-(4-(methylsulfonamido)phenyl)nicotinamide;

(R)-2-amino-5-(1-(tert-butyl)-1H-pyrazol-4-yl)-N-(1-(2'-chloro-[1,1'-biphenyl]-4-carbonyl)pyrrolidin-3-yl)nicotinamide;

(R)-4-(6-amino-5-((1-(2'-chloro-[1,1'-biphenyl]-4-carbonyl)pyrrolidin-3-yl)carbamoyl)pyridin-3-yl)benzoic acid;

(R)-2-amino-5-bromo-N-(1-(2'-chloro-4'-fluoro-[1,1'-biphenyl]-4-carbonyl)pyrrolidin-3-yl)nicotinamide;

(R)-6-amino-N-(1-(2'-chloro-4'-fluoro-[1,1'-biphenyl]-4-carbonyl)pyrrolidin-3-yl)-2'-(piperazin-1-yl)-[3,4'-bipyridine]-5-carboxamide;

(R)-6'-acetamido-6-amino-N-(1-(2'-chloro-4'-fluoro-[1,1'-biphenyl]-4-carbonyl)pyrrolidin-3-yl)-[3,3'-bipyridine]-5-carboxamide;

(R)-5',6-diamino-N-(1-(2'-chloro-4'-fluoro-[1,1'-biphenyl]-4-carbonyl)pyrrolidin-3-yl)-[3,3'-bipyridine]-5-carboxamide;

(R)-6-amino-N-(1-(2'-chloro-4'-fluoro-[1,1'-biphenyl]-4-carbonyl)pyrrolidin-3-yl)-6'-morpholino-[3,3'-bipyridine]-5-carboxamide;

(R)-2-amino-N-(1-(2'-chloro-4'-fluoro-[1,1'-biphenyl]-4-carbonyl)pyrrolidin-3-yl)-5-(4-(4-methylpiperazin-1-yl)phenyl)nicotinamide;

(R)-2-amino-N-(1-(2'-chloro-4'-fluoro-[1,1'-biphenyl]-4-carbonyl)pyrrolidin-3-yl)-5-(1-(pyridin-3-ylmethyl)-1H-pyrazol-4-yl)nicotinamide;

(R)-6'-amino-5'-((1-(2'-chloro-4'-fluoro-[1,1'-biphenyl]-4-carbonyl)pyrrolidin-3-yl)carbamoyl)-[3,3'-bipyridine]-5-carboxylic acid;

(R)-2-amino-N-(1-(2'-chloro-[1,1'-biphenyl]-4-carbonyl)
pyrrolidin-3-yl)-5-(4-(4-methylpiperazine-1-carbonyl)
phenyl)nicotinamide;
(R)-2-amino-N-(1-(2'-chloro-[1,1'-biphenyl]-4-carbonyl)
pyrrolidin-3-yl)-5-(4-(4-(2-hydroxyethyl)piperazine-1-
carbonyl)phenyl)nicotinamide;
(R)-2-amino-N-(1-(2'-chloro-[1,1'-biphenyl]-4-carbonyl)
pyrrolidin-3-yl)-5-(4-(morpholine-4-carbonyl)phenyl)
nicotinamide;
(R)-2-amino-N-(1-(2'-chloro-[1,1'-biphenyl]-4-carbonyl)
pyrrolidin-3-yl)-5-(4-((1-methylpiperidin-4-yl)carbam-
oyl)phenyl)nicotinamide;
(R)-2-amino-N-(1-(2'-chloro-[1,1'-biphenyl]-4-carbonyl)
pyrrolidin-3-yl)-5-(4-((4-methylcyclohexyl)carbamoyl)
phenyl)nicotinamide;
(R)-2-amino-N-(1-(2'-chloro-[1,1'-biphenyl]-4-carbonyl)
pyrrolidin-3-yl)-5-(4-((tetrahydro-2H-pyran-4-yl)car-
bamoyl)phenyl)nicotinamide;
2-amino-N—((R)-1-(2'-chloro-[1,1'-biphenyl]-4-carbonyl)
pyrrolidin-3-yl)-5-(4-(((1-methylpyrrolidin-3-yl)methyl)
carbamoyl)phenyl)nicotinamide;
(R)-2-amino-N-(1-(2'-chloro-[1,1'-biphenyl]-4-carbonyl)
pyrrolidin-3-yl)-5-(4-((3-(2-oxopyrrolidin-1-yl)propyl)
carbamoyl)phenyl)nicotinamide;
3-(1-phenylpyrrolidin-3-yl)-6-(1-(piperidin-4-yl)-1H-pyra-
zol-4-yl)-2,3-dihydropyrido[2,3-d]pyrimidin-4(1H)-one;
(R)-3-(1-phenylpyrrolidin-3-yl)-6-(1-(piperidin-4-yl)-1H-
pyrazol-4-yl)-2,3-dihydropyrido[2,3-d]pyrimidin-4(1H)-
one;
(R)—N-(1-benzylpyrrolidin-3-yl)-5-(1-(piperidin-4-yl)-1H-
pyrazol-4-yl)-1H-pyrazolo[3,4-b]pyridin-3-amine;
(R)-(3-((5-(1-methyl-1H-pyrazol-4-yl)-1H-pyrazolo[3,4-b]
pyridin-3-yl)amino)pyrrolidin-1-yl)(4-(5-methylthi-
ophen-2-yl)phenyl)methanone;
(R)-[1,1'-biphenyl]-4-yl(3-((5-(1-methyl-1H-pyrazol-4-yl)-
1H-pyrazolo[3,4-b]pyridin-3-yl)amino)pyrrolidin-1-yl)
methanone;
(R)-(2'-chloro-[1,1'-biphenyl]-4-yl)(3-((5-(1-methyl-1H-
pyrazol-4-yl)-1H-pyrazolo[3,4-b]pyridin-3-yl)amino)
pyrrolidin-1-yl)methanone;
(R)-(4-bromophenyl)(3-((5-(1-methyl-1H-pyrazol-4-yl)-
1H-pyrazolo[3,4-b]pyridin-3-yl)amino)pyrrolidin-1-yl)
methanone;
(R)-(3-((5-(1-methyl-1H-pyrazol-4-yl)-1H-pyrazolo[3,4-b]
pyridin-3-yl)amino)pyrrolidin-1-yl)(4'-phenoxy-[1,1'-bi-
phenyl]-4-yl)methanone;
(R)-(4'-(4-aminophenoxy)-[1,1'-biphenyl]-4-yl)(3-((5-(1-
methyl-1H-pyrazol-4-yl)-1H-pyrazolo[3,4-b]pyridin-3-
yl)amino)pyrrolidin-1-yl)methanone;
SS-methyl (2S,4R)-4-(2-amino-5-(1-methyl-1H-pyrazol-4-
yl)nicotinamido)-1-benzylpyrrolidine-2-carbo(dithioper-
oxoate);
SS-methyl (2S,4R)-4-(2-amino-5-(1-methyl-1H-pyrazol-4-
yl)nicotinamido)-1-(2-chlorobenzyl)pyrrolidine-2-carbo
(dithioperoxoate);
(R)-2-amino-N-(1-benzylpyrrolidin-3-yl)-N-methyl-5-(1-
methyl-1H-pyrazol-4-yl)nicotinamide;
(R)-2-amino-N-(1-(2-chlorobenzyl)pyrrolidin-3-yl)-N-
methyl-5-(1-methyl-1H-pyrazol-4-yl)nicotinamide;
(R)-2-amino-N-(1-(methyl(phenyl)carbamoyl)pyrrolidin-3-
yl)-5-(1-methyl-1H-pyrazol-4-yl)nicotinamide;
(S)-1-(3-((4-methylpiperazin-1-yl)methyl)phenyl)pyrroli-
din-3-yl (R)-3-(2-amino-5-(1-methyl-1H-pyrazol-4-yl)
nicotinamido)pyrrolidine-1-carboxylate;
2-amino-N-((3R)-1-(2-(methylamino)-2-oxo-1-phenyl-
ethyl)pyrrolidin-3-yl)-5-(1-(piperidin-4-yl)-1H-pyrazol-
4-yl)nicotinamide;

methyl 2-((R)-3-(2-amino-5-(1-(piperidin-4-yl)-1H-pyra-
zol-4-yl)nicotinamido)pyrrolidin-1-yl)-2-phenylacetate;
2-amino-N-((3R)-1-(2-hydroxy-1-phenylethyl)pyrrolidin-3-
yl)-5-(1-(piperidin-4-yl)-1H-pyrazol-4-yl)nicotinamide;
(R)-2-amino-5-(1-(piperidin-4-yl)-1H-pyrazol-4-yl)-N-(1-
(pyridin-3-ylmethyl)pyrrolidin-3-yl)nicotinamide;
(R)-2-amino-N-(1-((2-chloropyridin-4-yl)methyl)pyrroli-
din-3-yl)-5-(1-(piperidin-4-yl)-1H-pyrazol-4-yl)nicotina-
mide;
(R)-2-amino-N-(1-(2-chlorobenzyl)pyrrolidin-3-yl)-5-(1-
isobutyl-1H-pyrazol-4-yl)nicotinamide;
(R)-2-amino-N-(1-((6-fluoro-4'-((4-methylpiperazin-1-yl)
methyl)-[1,1'-biphenyl]-3-yl)methyl)pyrrolidin-3-yl)-5-
(1-methyl-1H-pyrazol-4-yl)nicotinamide;
(R)-2-amino-N-(1-(4'-(4-(aminomethyl)phenoxy)-[1,1'-bi-
phenyl]-4-carbonyl)pyrrolidin-3-yl)-5-(1-methyl-1H-
pyrazol-4-yl)nicotinamide;
(R)-2-amino-N-(1-(4'-(4-(hydroxymethyl)phenoxy)-[1,1'-
biphenyl]-4-carbonyl)pyrrolidin-3-yl)-5-(1-methyl-1H-
pyrazol-4-yl)nicotinamide;
(R)-2-amino-N-(1-(4'-(4-((dimethylamino)methyl)phe-
noxy)-[1,1'-biphenyl]-4-carbonyl)pyrrolidin-3-yl)-5-(1-
methyl-1H-pyrazol-4-yl)nicotinamide;
(R)-2-amino-N-(1-(4'-(4-(aminomethyl)phenoxy)-2'-
chloro-[1,1'-biphenyl]-4-carbonyl)pyrrolidin-3-yl)-5-(1-
methyl-1H-pyrazol-4-yl)nicotinamide;
(R)-2-amino-N-(1-(2'-chloro-4'-(4-((dimethylamino)
methyl)phenoxy)-[1,1'-biphenyl]-4-carbonyl)pyrrolidin-
3-yl)-5-(1-methyl-1H-pyrazol-4-yl)nicotinamide;
(R)-2-amino-N-(1-(2'-chloro-4'-(4-(hydroxymethyl)phe-
noxy)-[1,1'-biphenyl]-4-carbonyl)pyrrolidin-3-yl)-5-(1-
methyl-1H-pyrazol-4-yl)nicotinamide;
(R)-2-amino-5-(1-methyl-1H-pyrazol-4-yl)-N-(1-(4-((4-
methylpiperazin-1-yl)methyl)benzoyl)pyrrolidin-3-yl)
nicotinamide;
(R)-2-amino-N-(1-(4-((4-(2-hydroxyethyl)piperazin-1-yl)
methyl)benzoyl)pyrrolidin-3-yl)-5-(1-methyl-1H-pyra-
zol-4-yl)nicotinamide;
2-amino-N—((R)-1-(2'-chloro-4'-fluoro-[1,1'-biphenyl]-4-
carbonyl)pyrrolidin-3-yl)-5-(2-(((1 r,4R)-4-hydroxycy-
clohexyl)amino)methyl)phenyl)nicotinamide;
(R)-2-amino-5-(1-methyl-1H-pyrazol-4-yl)-N-(1-(4'-((1-
methylpiperidin-4-yl)methyl)-[1,1'-biphenyl]-4-carbo-
nyl)pyrrolidin-3-yl)nicotinamide;
(R)-2-amino-N-(1-(6-(methyl(1-methylpiperidin-4-yl)
amino)-2-naphthoyl)pyrrolidin-3-yl)-5-(1-methyl-1H-
pyrazol-4-yl)nicotinamide;
(R)-2-amino-N-(1-(6-((1-isopropylpiperidin-4-yl)(methyl)
amino)-2-naphthoyl)pyrrolidin-3-yl)-5-(1-methyl-1H-
pyrazol-4-yl)nicotinamide;
(R)-2-amino-5-(1-methyl-1H-pyrazol-4-yl)-N-(1-(2'-
methyl-[1,1'-biphenyl]-4-carbonyl)pyrrolidin-3-yl)nicoti-
namide;
(R)-2-amino-N-(1-(5'-chloro-2'-methyl-[1,1'-biphenyl]-4-
carbonyl)pyrrolidin-3-yl)-5-(1-methyl-1H-pyrazol-4-yl)
nicotinamide;
(R)-2-amino-N-(1-(3',5'-dimethyl-[1,1'-biphenyl]-4-carbo-
nyl)pyrrolidin-3-yl)-5-(1-methyl-1H-pyrazol-4-yl)nicoti-
namide;
(R)-2-amino-N-(1-(3',4'-dimethyl-[1,1'-biphenyl]-4-carbo-
nyl)pyrrolidin-3-yl)-5-(1-methyl-1H-pyrazol-4-yl)nicoti-
namide;
(R)-2-amino-N-(1-(4'-fluoro-2'-(trifluoromethyl)-[1,1'-bi-
phenyl]-4-carbonyl)pyrrolidin-3-yl)-5-(1-methyl-1H-
pyrazol-4-yl)nicotinamide;

(R)-2-amino-5-(1-methyl-1H-pyrazol-4-yl)-N-(1-(3-(trifluoromethyl)-[1,1'-biphenyl]-4-carbonyl)pyrrolidin-3-yl)nicotinamide;

(R)-2-amino-N-(1-(4'-chloro-2'-methyl-[1,1'-biphenyl]-4-carbonyl)pyrrolidin-3-yl)-5-(1-methyl-1H-pyrazol-4-yl)nicotinamide;

(R)-2-amino-N-(1-(4'-fluoro-3'-methyl-[1,1'-biphenyl]-4-carbonyl)pyrrolidin-3-yl)-5-(1-methyl-1H-pyrazol-4-yl)nicotinamide;

(R)—N-(1-(4-(1H-indol-5-yl)benzoyl)pyrrolidin-3-yl)-2-amino-5-(1-methyl-1H-pyrazol-4-yl)nicotinamide;

(R)-2-amino-N-(1-(4-(indolin-5-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(3'-methyl-[1,1'-biphenyl]-4-carbonyl)pyrrolidin-3-yl)nicotinamide;

(R)-2-amino-N-(1-(3'-ethyl-[1,1'-biphenyl]-4-carbonyl)pyrrolidin-3-yl)-5-(1-methyl-1H-pyrazol-4-yl)nicotinamide;

(R)-2-amino-N-(1-(3'-isopropyl-[1,1'-biphenyl]-4-carbonyl)pyrrolidin-3-yl)-5-(1-methyl-1H-pyrazol-4-yl)nicotinamide;

(R)-2-amino-N-(1-(3',4'-dimethoxy-[1,1'-biphenyl]-4-carbonyl)pyrrolidin-3-yl)-5-(1-methyl-1H-pyrazol-4-yl)nicotinamide;

(R)-2-amino-N-(1-(4'-(azetidin-1-ylsulfonyl)-[1,1'-biphenyl]-4-carbonyl)pyrrolidin-3-yl)-5-(1-methyl-1H-pyrazol-4-yl)nicotinamide;

(R)-2-amino-N-(1-(4'-chloro-3'-fluoro-[1,1'-biphenyl]-4-carbonyl)pyrrolidin-3-yl)-5-(1-methyl-1H-pyrazol-4-yl)nicotinamide;

(R)-2-amino-N-(1-(4'-amino-[1,1'-biphenyl]-4-carbonyl)pyrrolidin-3-yl)-5-(1-methyl-1H-pyrazol-4-yl)nicotinamide;

(R)-2-amino-N-(1-(3'-chloro-5'-fluoro-[1,1'-biphenyl]-4-carbonyl)pyrrolidin-3-yl)-5-(1-methyl-1H-pyrazol-4-yl)nicotinamide;

(R)-2-amino-N-(1-(3',5'-dichloro-4'-fluoro-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-(methylthio)-[1,1'-biphenyl]-4-carbonyl)pyrrolidin-3-yl)nicotinamide;

(R)-2-amino-N-(1-(4'-(ethylthio)-[1,1'-biphenyl]-4-carbonyl)pyrrolidin-3-yl)-5-(1-methyl-1H-pyrazol-4-yl)nicotinamide;

(R)-2-amino-N-(1-(2'-chloro-5'-fluoro-[1,1'-biphenyl]-4-carbonyl)pyrrolidin-3-yl)-5-(1-methyl-1H-pyrazol-4-yl)nicotinamide;

(R)-2-amino-N-(1-(3,5-dihydroxy-2-naphthoyl)pyrrolidin-3-yl)-5-(1-methyl-1H-pyrazol-4-yl)nicotinamide;

(R)-2-amino-N-(1-(5-bromo-1-naphthoyl)pyrrolidin-3-yl)-5-(1-methyl-1H-pyrazol-4-yl)nicotinamide;

N-(1-([1,1'-biphenyl]-4-carbonyl)-3-(hydroxymethyl)pyrrolidin-3-yl)-2-amino-5-(1-methyl-1H-pyrazol-4-yl)nicotinamide;

N-(1-([1,1'-biphenyl]-3-carbonyl)-3-(hydroxymethyl)pyrrolidin-3-yl)-2-amino-5-(1-methyl-1H-pyrazol-4-yl)nicotinamide;

(R)-2-amino-N-(1-(2'-chloro-3'-fluoro-[1,1'-biphenyl]-4-carbonyl)pyrrolidin-3-yl)-5-(1-methyl-1H-pyrazol-4-yl)nicotinamide;

N-((3S,4S)-1-([1,1'-biphenyl]-4-carbonyl)-4-((3-ethyl-4-methylbenzyl)oxy)pyrrolidin-3-yl)-2-amino-5-(1-methyl-1H-pyrazol-4-yl)nicotinamide;

N-((3S,4S)-1-([1,1'-biphenyl]-3-carbonyl)-4-((3-ethyl-4-methylbenzyl)oxy)pyrrolidin-3-yl)-2-amino-5-(1-methyl-1H-pyrazol-4-yl)nicotinamide;

(R)-2-amino-N-(1-(4'-(cyanomethyl)-[1,1'-biphenyl]-4-carbonyl)pyrrolidin-3-yl)-5-(1-methyl-1H-pyrazol-4-yl)nicotinamide;

(R,E)-3-(4'-(3-(2-amino-5-(1-methyl-1H-pyrazol-4-yl)nicotinamido)pyrrolidine-1-carbonyl)-[1,1'-biphenyl]-4-yl)acrylic acid;

(R)-3-(4'-(3-(2-amino-5-(1-methyl-1H-pyrazol-4-yl)nicotinamido)pyrrolidine-1-carbonyl)-[1,1'-biphenyl]-4-yl)propanoic acid;

(R)-2-amino-5-(1-methyl-1H-pyrazol-4-yl)-N-(1-(4'-(4-oxopiperidine-1-carbonyl)-[1,1'-biphenyl]-4-carbonyl)pyrrolidin-3-yl)nicotinamide;

(R)-2-amino-N-(1-(4'-carbamoyl-3'-fluoro-[1,1'-biphenyl]-4-carbonyl)pyrrolidin-3-yl)-5-(1-methyl-1H-pyrazol-4-yl)nicotinamide;

(R,E)-2-amino-5-(1-methyl-1H-pyrazol-4-yl)-N-(1-(4-(3-oxobut-1-en-1-yl)benzoyl)pyrrolidin-3-yl)nicotinamide;

2-amino-N-((3S,4R)-1-(2'-chloro-4'-fluoro-[1,1'-biphenyl]-4-carbonyl)-4-fluoropyrrolidin-3-yl)-5-(1-methyl-1H-pyrazol-4-yl)nicotinamide;

methyl (2R,4R)-1-([1,1'-biphenyl]-4-carbonyl)-4-(2-amino-5-(1-methyl-1H-pyrazol-4-yl)nicotinamido)pyrrolidine-2-carboxylate;

methyl (2R,4R)-1-([1,1'-biphenyl]-3-carbonyl)-4-(2-amino-5-(1-methyl-1H-pyrazol-4-yl)nicotinamido)pyrrolidine-2-carboxylate;

methyl (2S,4S)-1-([1,1'-biphenyl]-4-carbonyl)-4-(2-amino-5-(1-methyl-1H-pyrazol-4-yl)nicotinamido)pyrrolidine-2-carboxylate;

methyl (2S,4S)-1-([1,1'-biphenyl]-3-carbonyl)-4-(2-amino-5-(1-methyl-1H-pyrazol-4-yl)nicotinamido)pyrrolidine-2-carboxylate;

ethyl 1-([1,1'-biphenyl]-4-carbonyl)-4-(2-amino-5-(1-methyl-1H-pyrazol-4-yl)nicotinamido)pyrrolidine-3-carboxylate;

ethyl 1-([1,1'-biphenyl]-3-carbonyl)-4-(2-amino-5-(1-methyl-1H-pyrazol-4-yl)nicotinamido)pyrrolidine-3-carboxylate;

methyl (2R,4R)-4-(2-amino-5-(1-methyl-1H-pyrazol-4-yl)nicotinamido)-1-(2'-chloro-4'-fluoro-[1,1'-biphenyl]-4-carbonyl)pyrrolidine-2-carboxylate;

ethyl 4-(2-amino-5-(1-methyl-1H-pyrazol-4-yl)nicotinamido)-1-(2'-chloro-4'-fluoro-[1,1'-biphenyl]-4-carbonyl)pyrrolidine-3-carboxylate;

(R)-2-amino-N-(1-(2'-chloro-5'-fluoro-3-methyl-[1,1'-biphenyl]-4-carbonyl)pyrrolidin-3-yl)-5-(1-methyl-1H-pyrazol-4-yl)nicotinamide;

(R)-2-amino-N-(1-(2'-chloro-5'-fluoro-2-methyl-[1,1'-biphenyl]-4-carbonyl)pyrrolidin-3-yl)-5-(1-methyl-1H-pyrazol-4-yl)nicotinamide;

(R)-2-amino-N-(1-(2',3-dichloro-5'-fluoro-[1,1'-biphenyl]-4-carbonyl)pyrrolidin-3-yl)-5-(1-methyl-1H-pyrazol-4-yl)nicotinamide;

(R)-2-amino-N-(1-(2',3-dichloro-4'-fluoro-[1,1'-biphenyl]-4-carbonyl)pyrrolidin-3-yl)-5-(1-methyl-1H-pyrazol-4-yl)nicotinamide;

(R)-2-amino-N-(1-(1-methyl-1H-indole-2-carbonyl)pyrrolidin-3-yl)-5-(1-methyl-1H-pyrazol-4-yl)nicotinamide;

(R)-2-amino-N-(1-(5-fluoro-1H-indole-2-carbonyl)pyrrolidin-3-yl)-5-(1-methyl-1H-pyrazol-4-yl)nicotinamide;

(R)—N-(1-(1H-indole-2-carbonyl)pyrrolidin-3-yl)-2-amino-5-(1-methyl-1H-pyrazol-4-yl)nicotinamide;

(R)-2-amino-N-(1-(2,3-dimethyl-1H-indole-6-carbonyl)pyrrolidin-3-yl)-5-(1-methyl-1H-pyrazol-4-yl)nicotinamide;

(R)—N-(1-(1,8-naphthyridine-2-carbonyl)pyrrolidin-3-yl)-2-amino-5-(1-methyl-1H-pyrazol-4-yl)nicotinamide;

(R)—N-(1-(1,6-naphthyridine-2-carbonyl)pyrrolidin-3-yl)-2-amino-5-(1-methyl-1H-pyrazol-4-yl)nicotinamide;

(R)-2-amino-N-(1-(1-ethyl-1H-indole-2-carbonyl)pyrrolidin-3-yl)-5-(1-methyl-1H-pyrazol-4-yl)nicotinamide;

(R)-2-amino-N-(1-(1-benzyl-1H-indole-2-carbonyl)pyrrolidin-3-yl)-5-(1-methyl-1H-pyrazol-4-yl)nicotinamide;

(R)-2-amino-N-(1-(7-chloro-1-methyl-4-(trifluoromethyl)-1H-indole-2-carbonyl)pyrrolidin-3-yl)-5-(1-methyl-1H-pyrazol-4-yl)nicotinamide;

(R)-2-amino-N-(1-(7-chloro-4-(trifluoromethyl)-1H-indole-2-carbonyl)pyrrolidin-3-yl)-5-(1-methyl-1H-pyrazol-4-yl)nicotinamide;

2-amino-5-(1-methyl-1H-pyrazol-4-yl)-N—((R)-1-((1S, 2S)-2-phenylcyclopropane-1-carbonyl)pyrrolidin-3-yl)nicotinamide;

(R)-2-amino-N-(1-(6-hydroxy-2-naphthoyl)pyrrolidin-3-yl)-5-(1-methyl-1H-pyrazol-4-yl)nicotinamide;

(R)-2-amino-N-(1-(3-(4-fluorophenyl)-2,4-dioxo-1,2,3,4-tetrahydropyrimidine-5-carbonyl)pyrrolidin-3-yl)-5-(1-methyl-1H-pyrazol-4-yl)nicotinamide;

(R)-2-amino-N-(1-(5-bromobenzo[b]thiophene-2-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(1-(piperidin-4-ylmethyl)-1H-indole-5-carbonyl)pyrrolidin-3-yl)nicotinamide;

(R)—N-(1-(1H-indole-3-carbonyl)pyrrolidin-3-yl)-2-amino-5-(1-methyl-1H-pyrazol-4-yl)nicotinamide;

(R)-2-amino-5-(1-methyl-1H-pyrazol-4-yl)-N-(1-(4'-(morpholinomethyl)-[1,1'-biphenyl]-4-carbonyl)pyrrolidin-3-yl)nicotinamide;

(R)-2-amino-5-(1-methyl-1H-pyrazol-4-yl)-N-(1-(3'-(1-methyl-1H-tetrazol-5-yl)-[1,1'-biphenyl]-4-carbonyl)pyrrolidin-3-yl)nicotinamide;

(R)—N-(1-(3'-(1H-tetrazol-5-yl)-[1,1'-biphenyl]-4-carbonyl)pyrrolidin-3-yl)-2-amino-5-(1-methyl-1H-pyrazol-4-yl)nicotinamide;

(R)-2-amino-N-(1-(3'-(5-methyl-1,2,4-oxadiazol-3-yl)-[1,1'-biphenyl]-4-carbonyl)pyrrolidin-3-yl)-5-(1-methyl-1H-pyrazol-4-yl)nicotinamide;

(R)-2-amino-N-(1-(2'-chloro-4'-fluoro-2-methyl-[1,1'-biphenyl]-4-carbonyl)pyrrolidin-3-yl)-5-(1-methyl-1H-pyrazol-4-yl)nicotinamide;

(R)-2-amino-N-(1-(2-chloro-4-fluorobenzoyl)pyrrolidin-3-yl)-5-(1-methyl-1H-pyrazol-4-yl)nicotinamide;

(R)-2-amino-5-(1-methyl-1H-pyrazol-4-yl)-N-(1-(3-(1-(phenylsulfonyl)-1H-pyrazol-4-yl)benzoyl)pyrrolidin-3-yl)nicotinamide;

(R)-2-amino-N-(1-(4-(2-chlorophenoxy)benzoyl)pyrrolidin-3-yl)-5-(1-methyl-1H-pyrazol-4-yl)nicotinamide;

(R)-2-amino-N-(1-(4-(2-chloro-4-fluorophenoxy)benzoyl)pyrrolidin-3-yl)-5-(1-methyl-1H-pyrazol-4-yl)nicotinamide;

(R)-2-amino-N-(1-(6-(benzyl(1-methylpiperidin-4-yl)amino)-2-naphthoyl)pyrrolidin-3-yl)-5-(1-methyl-1H-pyrazol-4-yl)nicotinamide;

(R)-2-amino-N-(1-(6-(ethyl(1,2,2,6,6-pentamethylpiperidin-4-yl)amino)-2-naphthoyl)pyrrolidin-3-yl)-5-(1-methyl-1H-pyrazol-4-yl)nicotinamide;

(R)-2-amino-5-(1-methyl-1H-pyrazol-4-yl)-N-(1-(6-((1,2,2,6,6-pentamethylpiperidin-4-yl)amino)-2-naphthoyl)pyrrolidin-3-yl)nicotinamide;

(R)-2-amino-N-(1-(6-(ethyl(1-methylpiperidin-4-yl)amino)-2-naphthoyl)pyrrolidin-3-yl)-5-(1-methyl-1H-pyrazol-4-yl)nicotinamide;

(R)-2-amino-N-(1-(4'-hydroxy-3',5'-dimethyl-[1,1'-biphenyl]-4-carbonyl)pyrrolidin-3-yl)-5-(1-methyl-1H-pyrazol-4-yl)nicotinamide;

(R)-2-amino-N-(1-(4'-methoxy-3',5'-dimethyl-[1,1'-biphenyl]-4-carbonyl)pyrrolidin-3-yl)-5-(1-methyl-1H-pyrazol-4-yl)nicotinamide;

(R)-2-amino-N-(1-(4'-cyano-[1,1'-biphenyl]-4-carbonyl)pyrrolidin-3-yl)-5-(1-methyl-1H-pyrazol-4-yl)nicotinamide;

(R)-2-amino-N-(1-(3'-(aminomethyl)-[1,1'-biphenyl]-4-carbonyl)pyrrolidin-3-yl)-5-(1-methyl-1H-pyrazol-4-yl)nicotinamide;

(R)-2-amino-N-(1-(3-amino-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-((4-methylpiperazin-1-yl)methyl)-[1,1'-biphenyl]-3-carbonyl)pyrrolidin-3-yl)nicotinamide;

(R,E)-N-(1-(3-([1,1'-biphenyl]-4-yl)acryloyl)pyrrolidin-3-yl)-2-amino-5-(1-methyl-1H-pyrazol-4-yl)nicotinamide;

(R)-2-amino-5-(1-methyl-1H-pyrazol-4-yl)-N-(1-(4-phenoxybenzoyl)pyrrolidin-3-yl)nicotinamide;

2-amino-N-((3S,4S)-1-(4-bromobenzoyl)-4-hydroxypyrrolidin-3-yl)-5-(1-methyl-1H-pyrazol-4-yl)nicotinamide;

(R)-2-amino-N-(1-(3-bromobenzoyl)pyrrolidin-3-yl)-5-(1-methyl-1H-pyrazol-4-yl)nicotinamide;

(S)—N-((1-([1,1'-biphenyl]-4-carbonyl)pyrrolidin-2-yl)methyl)-2-amino-5-(1-methyl-1H-pyrazol-4-yl)nicotinamide;

(S)—N-((1-([1,1'-biphenyl]-3-carbonyl)pyrrolidin-2-yl)methyl)-2-amino-5-(1-methyl-1H-pyrazol-4-yl)nicotinamide;

(R)—N-((1-([1,1'-biphenyl]-4-carbonyl)pyrrolidin-2-yl)methyl)-2-amino-5-(1-methyl-1H-pyrazol-4-yl)nicotinamide;

(R)—N-((1-([1,1'-biphenyl]-3-carbonyl)pyrrolidin-2-yl)methyl)-2-amino-5-(1-methyl-1H-pyrazol-4-yl)nicotinamide;

(S)—N-((1-([1,1'-biphenyl]-4-carbonyl)pyrrolidin-3-yl)methyl)-2-amino-5-(1-methyl-1H-pyrazol-4-yl)nicotinamide;

(S)—N-((1-([1,1'-biphenyl]-3-carbonyl)pyrrolidin-3-yl)methyl)-2-amino-5-(1-methyl-1H-pyrazol-4-yl)nicotinamide;

(R)—N-((1-([1,1'-biphenyl]-4-carbonyl)pyrrolidin-3-yl)methyl)-2-amino-5-(1-methyl-1H-pyrazol-4-yl)nicotinamide;

(R)—N-((1-([1,1'-biphenyl]-3-carbonyl)pyrrolidin-3-yl)methyl)-2-amino-5-(1-methyl-1H-pyrazol-4-yl)nicotinamide;

N-((3S,4S)-1-([1,1'-biphenyl]-4-carbonyl)-4-hydroxypyrrolidin-3-yl)-2-amino-5-(1-methyl-1H-pyrazol-4-yl)nicotinamide;

N-((3R,4S)-1-([1,1'-biphenyl]-4-carbonyl)-4-hydroxypyrrolidin-3-yl)-2-amino-5-(1-methyl-1H-pyrazol-4-yl)nicotinamide;

(R)—N-(1-([1,1'-biphenyl]-4-carbonyl)pyrrolidin-3-yl)-3-amino-6-(1-methyl-1H-pyrazol-4-yl)pyrazine-2-carboxamide;

(R)-3-amino-N-(1-(2'-chloro-4'-fluoro-[1,1'-biphenyl]-4-carbonyl)pyrrolidin-3-yl)-6-(1-methyl-1H-pyrazol-4-yl)pyrazine-2-carboxamide;

2-amino-5-(1-methyl-1H-pyrazol-4-yl)-N-((3R)-1-(3'-(pyrrolidin-3-yloxy)-[1,1'-biphenyl]-4-carbonyl)pyrrolidin-3-yl)nicotinamide;

(R)-2-amino-N-(1-(4'-(hydroxymethyl)-[1,1'-biphenyl]-4-carbonyl)pyrrolidin-3-yl)-5-(1-methyl-1H-pyrazol-4-yl)nicotinamide;

(R)-2-amino-N-(1-(3'-(hydroxymethyl)-[1,1'-biphenyl]-4-carbonyl)pyrrolidin-3-yl)-5-(1-methyl-1H-pyrazol-4-yl)nicotinamide;

(R)-2-amino-N-(1-(4-(6-hydroxypyridin-3-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(naphthalen-2-yl)benzoyl)pyrrolidin-3-yl)nicotinamide;

(R)—N-(1-(4-(1H-indol-6-yl)benzoyl)pyrrolidin-3-yl)-2-amino-5-(1-methyl-1H-pyrazol-4-yl)nicotinamide;

(R)-2-amino-5-(1-methyl-1H-pyrazol-4-yl)-N-(1-(4-(4-methyl-3,4-dihydro-2H-benzo[b][1,4]oxazin-7-yl)benzoyl)pyrrolidin-3-yl)nicotinamide;

(R)-2-amino-5-(1-methyl-1H-pyrazol-4-yl)-N-(1-(4-(1,2,3,6-tetrahydropyridin-4-yl)benzoyl)pyrrolidin-3-yl)nicotinamide;

(R)-2-amino-N-(1-(4-(1-methyl-1,2,3,6-tetrahydropyridin-4-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-(1,2,3,6-tetrahydropyridin-4-yl)-[1,1'-biphenyl]-4-carbonyl)pyrrolidin-3-yl)nicotinamide;

(R)-2-amino-N-(1-(4-(1-methyl-1H-indol-5-yl)benzoyl)pyrrolidin-3-yl)-5-(1-methyl-1H-pyrazol-4-yl)nicotinamide;

(R)-2-amino-N-(1-(4-(1-methyl-1H-indazol-5-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(1-(2-(pyrrolidin-1-yl)ethyl)-1H-pyrazol-4-yl)benzoyl)pyrrolidin-3-yl)nicotinamide;

(R)—N-(1-(4-(1H-indazol-5-yl)benzoyl)pyrrolidin-3-yl)-2-amino-5-(1-methyl-1H-pyrazol-4-yl)nicotinamide;

(R)—N-(1-(4-(1H-indazol-6-yl)benzoyl)pyrrolidin-3-yl)-2-amino-5-(1-methyl-1H-pyrazol-4-yl)nicotinamide;

(R)-2-amino-5-(1-methyl-1H-pyrazol-4-yl)-N-(1-(6-(piperidin-4-ylmethoxy)-2-naphthoyl)pyrrolidin-3-yl)nicotinamide;

((R)-2-amino-N-(1-(6-(2-(dimethylamino)ethoxy)-2-naphthoyl)pyrrolidin-3-yl)-5-(1-methyl-1H-pyrazol-4-yl)nicotinamide;

2-amino-5-(1-methyl-1H-pyrazol-4-yl)-N-((3R)-1-(6-((1-methylpyrrolidin-3-yl)methoxy)-2-naphthoyl)pyrrolidin-3-yl)nicotinamide;

2-amino-5-(1-methyl-1H-pyrazol-4-yl)-N-((3R)-1-(6-(2-(1-methylpyrrolidin-2-yl)ethoxy)-2-naphthoyl)pyrrolidin-3-yl)nicotinamide;

(R)-2-amino-5-(1-methyl-1H-pyrazol-4-yl)-N-(1-(6-(2-(pyrrolidin-1-yl)ethoxy)-2-naphthoyl)pyrrolidin-3-yl)nicotinamide;

(R)-2-amino-N-(1-(6-(3-(dimethylamino)propoxy)-2-naphthoyl)pyrrolidin-3-yl)-5-(1-methyl-1H-pyrazol-4-yl)nicotinamide;

(R)-2-amino-5-(1-methyl-1H-pyrazol-4-yl)-N-(1-(6-((1-methylpiperidin-4-yl)methoxy)-2-naphthoyl)pyrrolidin-3-yl)nicotinamide;

(R)-2-amino-N-(1-(6-(piperidin-4-yloxy)-2-naphthoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-((4-nitrobenzyl)oxy)benzoyl)pyrrolidin-3-yl)nicotinamide;

(R)-2-amino-5-(1-methyl-1H-pyrazol-4-yl)-N-(1-(4-((3-nitrobenzyl)oxy)benzoyl)pyrrolidin-3-yl)nicotinamide;

(R)-2-amino-N-(1-(2'-chloro-4'-fluoro-[1,1'-biphenyl]-4-carbonyl)pyrrolidin-3-yl)-5-(2-(piperidin-4-ylmethoxy)phenyl)nicotinamide;

2-amino-N—((R)-1-(2'-chloro-4'-fluoro-[1,1'-biphenyl]-4-carbonyl)pyrrolidin-3-yl)-5-(2-((1-methylpyrrolidin-3-yl)methoxy)phenyl)nicotinamide;

2-amino-N—((R)-1-(2'-chloro-4'-fluoro-[1,1'-biphenyl]-4-carbonyl)pyrrolidin-3-yl)-5-(2-(2-(1-methylpyrrolidin-2-yl)ethoxy)phenyl)nicotinamide;

(R)-6-amino-N-(1-(2'-chloro-4'-fluoro-[1,1'-biphenyl]-4-carbonyl)pyrrolidin-3-yl)-6'-fluoro-[3,3'-bipyridine]-5-carboxamide;

(R)-2-amino-N-(1-(2'-chloro-4'-fluoro-[1,1'-biphenyl]-4-carbonyl)pyrrolidin-3-yl)-5-phenylnicotinamide;

(R)-2-amino-5-(2-carbamoylphenyl)-N-(1-(2'-chloro-4'-fluoro-[1,1'-biphenyl]-4-carbonyl)pyrrolidin-3-yl)nicotinamide;

(R)-2-(6-amino-5-((1-(2'-chloro-4'-fluoro-[1,1'-biphenyl]-4-carbonyl)pyrrolidin-3-yl)carbamoyl)pyridin-3-yl)benzoic acid;

(R)-2-amino-N-(1-(2'-chloro-4'-fluoro-[1,1'-biphenyl]-4-carbonyl)pyrrolidin-3-yl)-5-(2-hydroxyphenyl)nicotinamide;

(R)-3-amino-6-(2-aminophenyl)-N-(1-(2'-chloro-4'-fluoro-[1,1'-biphenyl]-4-carbonyl)pyrrolidin-3-yl)pyrazine-2-carboxamide;

(R)-6-amino-N-(1-(2'-chloro-4'-fluoro-[1,1'-biphenyl]-4-carbonyl)pyrrolidin-3-yl)-2'-(4-methylpiperazin-1-yl)-[3,4'-bipyridine]-5-carboxamide;

(R)-2-amino-N-(1-(2'-chloro-4'-fluoro-[1,1'-biphenyl]-4-carbonyl)pyrrolidin-3-yl)-5-(3-chloro-4-(morpholine-4-carbonyl)phenyl)nicotinamide;

(R)-2-amino-N-(1-(2'-chloro-4'-fluoro-[1,1'-biphenyl]-4-carbonyl)pyrrolidin-3-yl)-5-(4-morpholinophenyl)nicotinamide;

(R)—N-(1-([1,1'-biphenyl]-4-carbonyl)pyrrolidin-3-yl)-2-amino-5-(4-(2-(4-((2-nitrophenyl)sulfonyl)piperazin-1-yl)propan-2-yl)phenyl)nicotinamide;

2-amino-N—((R)-1-(2'-chloro-4'-fluoro-[1,1'-biphenyl]-4-carbonyl)pyrrolidin-3-yl)-5-(2-(((1 r,4R)-4-hydroxycyclohexyl)carbamoyl)phenyl)nicotinamide;

(R)-2-amino-5-(1-methyl-1H-pyrazol-4-yl)-N-(1-(6-(4-methylpiperazine-1-carbonyl)-2-naphthoyl)pyrrolidin-3-yl)nicotinamide;

(R)-2-amino-N-(1-(6-(4-(2-hydroxyethyl)piperazine-1-carbonyl)-2-naphthoyl)pyrrolidin-3-yl)-5-(1-methyl-1H-pyrazol-4-yl)nicotinamide;

(R)-2-amino-N-(1-(4'-(4-(dimethylcarbamoyl)phenoxy)-[1,1'-biphenyl]-4-carbonyl)pyrrolidin-3-yl)-5-(1-methyl-1H-pyrazol-4-yl)nicotinamide;

(R)-2-amino-N-(1-(4'-(4-carbamoylphenoxy)-[1,1'-biphenyl]-4-carbonyl)pyrrolidin-3-yl)-5-(1-methyl-1H-pyrazol-4-yl)nicotinamide;

(R,E)-2-amino-N-(1-(4'-(3-(dimethylamino)-3-oxoprop-1-en-1-yl)-[1,1'-biphenyl]-4-carbonyl)pyrrolidin-3-yl)-5-(1-methyl-1H-pyrazol-4-yl)nicotinamide;

(R)-(3-((5-(1-methyl-1H-pyrazol-4-yl)-1H-pyrazolo[3,4-b]pyridin-3-yl)amino)pyrrolidin-1-yl)(4-(1,2,3,4-tetrahydroquinolin-6-yl)phenyl)methanone;

(R)-(3-((5-(1-methyl-1H-pyrazol-4-yl)-1H-pyrazolo[3,4-b]pyridin-3-yl)amino)pyrrolidin-1-yl)(4-phenoxyphenyl)methanone;

(R)-(3-((5-(1-methyl-1H-pyrazol-4-yl)-1H-pyrazolo[3,4-b]pyridin-3-yl)amino)pyrrolidin-1-yl)(4'-(piperidin-4-yloxy)-[1,1'-biphenyl]-4-yl)methanone;

(R)-(3-((5-(1-methyl-1H-pyrazol-4-yl)-1H-pyrazolo[3,4-b]pyridin-3-yl)amino)pyrrolidin-1-yl)(4'-(morpholinomethyl)-[1,1'-biphenyl]-4-yl)methanone;

(R)-3-((5-(1-methyl-1H-pyrazol-4-yl)-1H-pyrazolo[3,4-b]pyridin-3-yl)amino)pyrrolidin-1-yl)(4'-((4-methylpiperazin-1-yl)methyl)-[1,1'-biphenyl]-4-yl)methanone;

(R)-2-amino-N-(1-(4'-((2-chloropyridin-4-yl)oxy)-[1,1'-biphenyl]-4-carbonyl)pyrrolidin-3-yl)-5-(1-methyl-1H-pyrazol-4-yl)nicotinamide;

(R)-2-amino-N-(1-(4'-(4-aminophenoxy)-2'-chloro-[1,1'-biphenyl]-4-carbonyl)pyrrolidin-3-yl)-5-(1-methyl-1H-pyrazol-4-yl)nicotinamide;

(R)-2-amino-N-(1-(4'-(3-aminophenoxy)-2'-chloro-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-(pyridin-4-yloxy)-[1,1'-biphenyl]-4-carbonyl)pyrrolidin-3-yl)nicotinamide;

(R)—N-(1-(4'-((1H-indol-5-yl)amino)-[1,1'-biphenyl]-4-carbonyl)pyrrolidin-3-yl)-2-amino-5-(1-methyl-1H-pyrazol-4-yl)nicotinamide;

(R)-2-amino-N-(1-(4'-(4-hydroxyphenoxy)-[1,1'-biphenyl]-4-carbonyl)pyrrolidin-3-yl)-5-(1-methyl-1H-pyrazol-4-yl)nicotinamide;

(R)-2-amino-N-(1-(4'-(2-aminopropan-2-yl)-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-(pyridin-3-yloxy)-[1,1'-biphenyl]-4-carbonyl)pyrrolidin-3-yl)nicotinamide;

(R)-2-amino-N-(1-(4'-(methyl(4-nitrophenyl)amino)-[1,1'-biphenyl]-4-carbonyl)pyrrolidin-3-yl)-5-(1-methyl-1H-pyrazol-4-yl)nicotinamide;

(R)-2-amino-N-(1-(4'-((2-fluoro-4-nitrophenyl)(methyl)amino)-[1,1'-biphenyl]-4-carbonyl)pyrrolidin-3-yl)-5-(1-methyl-1H-pyrazol-4-yl)nicotinamide;

(R)-2-amino-N-(1-(4'-(methyl(2-methyl-4-nitrophenyl)amino)-[1,1'-biphenyl]-4-carbonyl)pyrrolidin-3-yl)-5-(1-methyl-1H-pyrazol-4-yl)nicotinamide;

(R)-2-amino-N-(1-(4'-((2-chloro-4-nitrophenyl)(methyl)amino)-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-(piperidin-4-ylmethyl)-[1,1'-biphenyl]-4-carbonyl)pyrrolidin-3-yl)nicotinamide;

(R)-2-amino-N-(1-(3'-chloro-4'-(4-hydroxyphenoxy)-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-((1-methylpiperidin-4-yl)oxy)-[1,1'-biphenyl]-4-carbonyl)pyrrolidin-3-yl)nicotinamide;

(R)-2-amino-N-(1-(4'-((4-aminocyclohexyl)oxy)-[1,1'-biphenyl]-4-carbonyl)pyrrolidin-3-yl)-5-(1-methyl-1H-pyrazol-4-yl)nicotinamide;

(R)-2-amino-N-(1-(4'-(4-formylphenoxy)-[1,1'-biphenyl]-4-carbonyl)pyrrolidin-3-yl)-5-(1-methyl-1H-pyrazol-4-yl)nicotinamide;

(R)-4-((4'-(3-(2-amino-5-(1-methyl-1H-pyrazol-4-yl)nicotinamido)pyrrolidine-1-carbonyl)-[1,1'-biphenyl]-4-yl)oxy)benzoic acid;

(R)-2-amino-N-(1-(4'-((6-aminopyridin-3-yl)oxy)-[1,1'-biphenyl]-4-carbonyl)pyrrolidin-3-yl)-5-(1-methyl-1H-pyrazol-4-yl)nicotinamide;

(R)—N-(1-(4'-((2H-tetrazol-5-yl)oxy)-[1,1'-biphenyl]-4-carbonyl)pyrrolidin-3-yl)-2-amino-5-(1-methyl-1H-pyrazol-4-yl)nicotinamide;

(R)-2-amino-N-(1-(4'-((4-aminophenyl)amino)-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(6-(piperidin-4-ylamino)-2-naphthoyl)pyrrolidin-3-yl)nicotinamide;

(R)-2-amino-N-(1-(6-((1-(2-hydroxyethyl)piperidin-4-yl)amino)-2-naphthoyl)pyrrolidin-3-yl)-5-(1-methyl-1H-pyrazol-4-yl)nicotinamide;

(R)-2-amino-N-(1-(6-(methyl(piperidin-4-yl)amino)-2-naphthoyl)pyrrolidin-3-yl)-5-(1-methyl-1H-pyrazol-4-yl)nicotinamide;

(R)-2-amino-N-(1-(4'-((1-(2-hydroxyethyl)piperidin-4-yl)methyl)-[1,1'-biphenyl]-4-carbonyl)pyrrolidin-3-yl)-5-(1-methyl-1H-pyrazol-4-yl)nicotinamide;

(R)-2-amino-N-(1-(6-((1-(2-hydroxyethyl)piperidin-4-yl)(methyl)amino)-2-naphthoyl)pyrrolidin-3-yl)-5-(1-methyl-1H-pyrazol-4-yl)nicotinamide;

(R)-2-amino-N-(1-(6-((1-(2-hydroxyethyl)piperidin-4-yl)oxy)-2-naphthoyl)pyrrolidin-3-yl)-5-(1-methyl-1H-pyrazol-4-yl)nicotinamide;

2-amino-5-(1-methyl-1H-pyrazol-4-yl)-N-((3R)-1-(4-((E)-3-(4-methylpiperazin-1-yl)but-1-en-1-yl)benzoyl)pyrrolidin-3-yl)nicotinamide;

2-amino-N-((3R)-1-(4-((E)-3-(4-(2-hydroxyethyl)piperazin-1-yl)but-1-en-1-yl)benzoyl)pyrrolidin-3-yl)-5-(1-methyl-1H-pyrazol-4-yl)nicotinamide;

(R,E)-2-amino-5-(1-methyl-1H-pyrazol-4-yl)-N-(1-(4-(2-(pyridin-4-yl)vinyl)benzoyl)pyrrolidin-3-yl)nicotinamide;

(R,E)-2-amino-5-(1-methyl-1H-pyrazol-4-yl)-N-(1-(4-(2-(pyridin-2-yl)vinyl)benzoyl)pyrrolidin-3-yl)nicotinamide;

(R,E)-2-amino-5-(1-methyl-1H-pyrazol-4-yl)-N-(1-(4-(2-phenylprop-1-en-1-yl)benzoyl)pyrrolidin-3-yl)nicotinamide;

(R,E)-2-amino-5-(1-methyl-1H-pyrazol-4-yl)-N-(1-(4-(2-(piperidin-4-yl)vinyl)benzoyl)pyrrolidin-3-yl)nicotinamide;

methyl (R,E)-3-(4-(3-(2-amino-5-(1-methyl-1H-pyrazol-4-yl)nicotinamido)pyrrolidine-1-carbonyl)phenyl)acrylate;

(R)-2-amino-5-(1-methyl-1H-pyrazol-4-yl)-N-(1-(4-(3-nitrophenoxy)benzoyl)pyrrolidin-3-yl)nicotinamide;

(R)-2-amino-N-(1-(4-(3-aminophenoxy)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(4-nitrophenoxy)benzoyl)pyrrolidin-3-yl)nicotinamide;

(R)-2-amino-N-(1-(4-(4-aminophenoxy)benzoyl)pyrrolidin-3-yl)-5-(1-methyl-1H-pyrazol-4-yl)nicotinamide;

(R)-2-amino-N-(1-(6-(4-aminophenoxy)-2-naphthoyl)pyrrolidin-3-yl)-5-(1-methyl-1H-pyrazol-4-yl)nicotinamide;

(R)-2-amino-N-(1-(4'-((2-chloro-4-nitrophenyl)(methyl)amino)-[1,1'-biphenyl]-4-carbonyl)pyrrolidin-3-yl)-5-(1-methyl-1H-pyrazol-4-yl)nicotinamide;

(R)-2-amino-N-(1-(4'-((4-amino-2-fluorophenyl)(methyl)amino)-[1,1'-biphenyl]-4-carbonyl)pyrrolidin-3-yl)-5-(1-methyl-1H-pyrazol-4-yl)nicotinamide;

(R)-2-amino-N-(1-(4'-((4-amino-2-methylphenyl)(methyl)amino)-[1,1'-biphenyl]-4-carbonyl)pyrrolidin-3-yl)-5-(1-methyl-1H-pyrazol-4-yl)nicotinamide;

(R)-2-amino-N-(1-(4'-((4-amino-2-chlorophenyl)(methyl)amino)-[1,1'-biphenyl]-4-carbonyl)pyrrolidin-3-yl)-5-(1-methyl-1H-pyrazol-4-yl)nicotinamide;

(R)-2-amino-N-(1-(4-((3-aminobenzyl)oxy)benzoyl)pyrrolidin-3-yl)-5-(1-methyl-1H-pyrazol-4-yl)nicotinamide;

(2R,4R)-4-(2-amino-5-(1-methyl-1H-pyrazol-4-yl)nicotinamido)-1-(2'-chloro-4'-fluoro-[1,1'-biphenyl]-4-carbonyl)pyrrolidine-2-carboxylic acid;

(R)-2-amino-N-(1-(4-hydroxybenzoyl)pyrrolidin-3-yl)-5-(1-methyl-1H-pyrazol-4-yl)nicotinamide;

(R)-2-amino-N-(1-(4-formylbenzoyl)pyrrolidin-3-yl)-5-(1-methyl-1H-pyrazol-4-yl)nicotinamide;
methyl (R)-6-(3-(2-amino-5-(1-methyl-1H-pyrazol-4-yl)nicotinamido)pyrrolidine-1-carbonyl)-2-naphthoate;
(R)-6-(3-(2-amino-5-(1-methyl-1H-pyrazol-4-yl)nicotinamido)pyrrolidine-1-carbonyl)-2-naphthoic acid;
(R)-2-amino-N-(1-(2'-chloro-4'-(4-formylphenoxy)-[1,1'-biphenyl]-4-carbonyl)pyrrolidin-3-yl)-5-(1-methyl-1H-pyrazol-4-yl)nicotinamide;
(R)-2-amino-N-(1-(2'-chloro-4'-fluoro-[1,1'-biphenyl]-4-carbonyl)pyrrolidin-3-yl)-5-(2-formylphenyl)nicotinamide;
3-bromo-5-chlorophenyl (R)-3-(2-amino-5-(1-methyl-1H-pyrazol-4-yl)nicotinamido)pyrrolidine-1-carboxylate;
tert-butyl (R)-4-(4-(3-(2-amino-5-(1-methyl-1H-pyrazol-4-yl)nicotinamido)pyrrolidine-1-carbonyl)phenyl)-3,6-dihydropyridine-1 (2H)-carboxylate;
(R)—N-(1-(4'-(3-(dimethylamino)propoxy)-[1,1'-biphenyl]-4-carbonyl)pyrrolidin-3-yl)-2-((3-(dimethylamino)propyl)amino)-5-(1-methyl-1H-pyrazol-4-yl)nicotinamide;
(R)-2-amino-N-(1-(2,4'-dimethyl-[1,1'-biphenyl]-4-carbonyl)pyrrolidin-3-yl)-5-(1-methyl-1H-pyrazol-4-yl)nicotinamide;
(R)-2-amino-N-(1-(4'-(ethylthio)-2-methyl-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(3-methyl-4-(4-methylthiophen-2-yl)benzoyl)pyrrolidin-3-yl)nicotinamide;
(R)—N-(1-(4-(1H-indol-6-yl)-3-methylbenzoyl)pyrrolidin-3-yl)pyridin-3-yl)-2-amino-5-(1-methyl-1H-pyrazol-4-yl)nicotinamide;
(R)—N-(1-(4-(1H-indol-5-yl)-3-methylbenzoyl)pyrrolidin-3-yl)-2-amino-5-(1-methyl-1H-pyrazol-4-yl)nicotinamide;
(R)-2-amino-5-(1-methyl-1H-pyrazol-4-yl)-N-(1-(3-methyl-4-(1-methyl-1H-indol-5-yl)benzoyl)pyrrolidin-3-yl)nicotinamide;
(R)-2-amino-N-(1-(2',4'-difluoro-2-methyl-[1,1'-biphenyl]-4-carbonyl)pyrrolidin-3-yl)-5-(1-methyl-1H-pyrazol-4-yl)nicotinamide;
(R)-2-amino-N-(1-(2',3'-difluoro-2-methyl-[1,1'-biphenyl]-4-carbonyl)pyrrolidin-3-yl)-5-(1-methyl-1H-pyrazol-4-yl)nicotinamide;
(R)-2-amino-N-(1-(2'-chloro-3'-fluoro-2-methyl-[1,1'-biphenyl]-4-carbonyl)pyrrolidin-3-yl)-5-(1-methyl-1H-pyrazol-4-yl)nicotinamide;
(R)-2-amino-N-(1-(2',3'-dichloro-2-methyl-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(2,3',5'-trimethyl-[1,1'-biphenyl]-4-carbonyl)pyrrolidin-3-yl)nicotinamide;
(R)-2-amino-5-(1-methyl-1H-pyrazol-4-yl)-N-(1-(2,3',4'-trimethyl-[1,1'-biphenyl]-4-carbonyl)pyrrolidin-3-yl)nicotinamide; and
(R)-2-amino-N-(1-(2,3'-dimethyl-[1,1'-biphenyl]-4-carbonyl)pyrrolidin-3-yl)-5-(1-methyl-1H-pyrazol-4-yl)nicotinamide.

Compound names are assigned by using CHEMDRAW® ULTRA v. 12.0.2.1076 or CHEMDRAW® PROFESSIONAL v. 15.0.0.106.

Compounds of the present disclosure may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The present disclosure contemplates various stereoisomers and mixtures thereof and these are specifically included within the scope of this disclosure. Stereoisomers include enantiomers and diastereomers, and mixtures of enantiomers or diastereomers. Individual stereoisomers of compounds of the present disclosure may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Fumrniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the present disclosure may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the present disclosure may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the present disclosure may possess tautomeric forms, as well as geometric isomers, and that these also constitute an aspect of the present disclosure.

The present disclosure includes all pharmaceutically acceptable isotopically-labelled compounds of formula (I) wherein one or more atoms are replaced by atoms having the same atomic number, but an atomic mass or mass number different from the atomic mass or mass number which predominates in nature. Examples of isotopes suitable for inclusion in the compounds of the disclosure include isotopes of hydrogen, such as $^{2}$H and $^{3}$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S. Certain isotopically-labelled compounds of formula (I), for example, those incorporating a radioactive isotope, are useful in drug and/or substrate tissue distribution studies. The radioactive isotopes tritium, i.e. $^{3}$H, and carbon-14, i.e. $^{14}$C, are particularly useful for this purpose in view of their ease of incorporation and ready means of detection. Substitution with heavier isotopes such as deuterium, i.e. $^{2}$H, may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining substrate receptor occupancy. Isotopically-labeled compounds of formula (I) can generally be prepared by conventional techniques known to those skilled in the art or by processes analogous to those described in the accompanying Examples using an appropriate isotopically-labeled reagents in place of the non-labeled reagent previously employed.

The compounds of this disclosure can be prepared by a variety of synthetic procedures. Representative procedures are shown in, but are not limited to, Schemes 1 and 2.

One general approach to the compounds of this invention is illustrated in general Scheme 1.

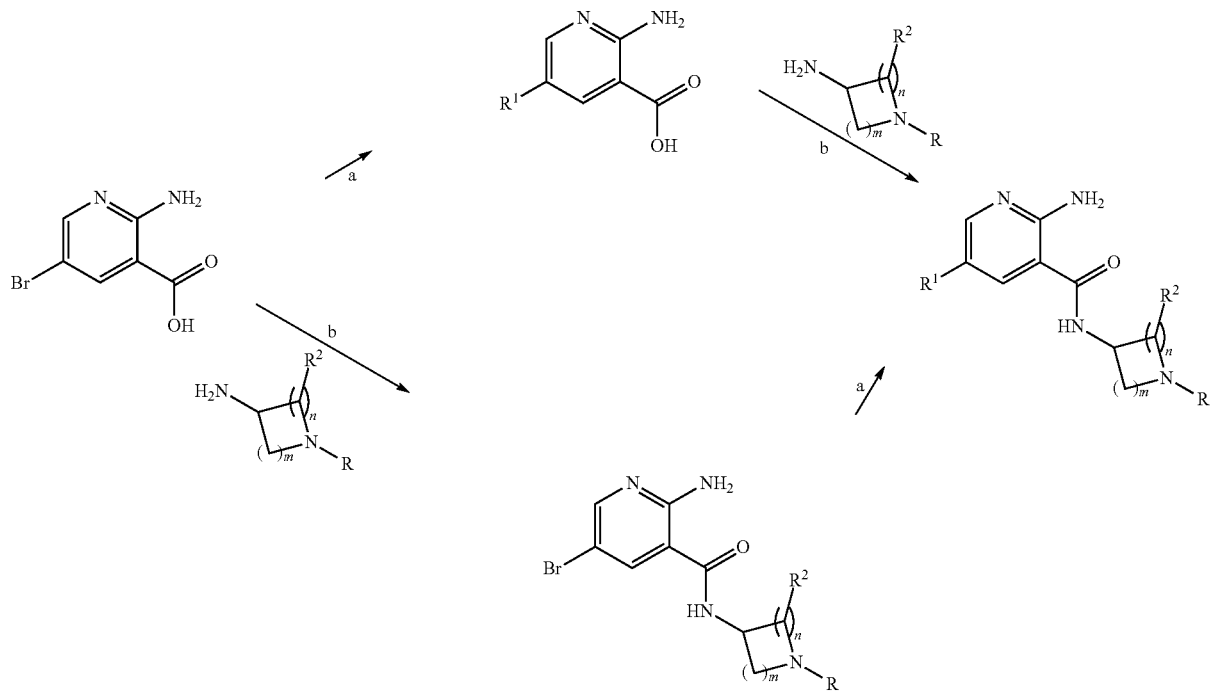

a) R¹-B(OH)₂ or its pinacol ester, Pd(PPh₃)₄, K₂CO₃, Dioxane/H₂O(3/1), heat; b) HATU, triethylamine, N,N-dimethylformamide Thus, the formula drawings within this specification can represent only one of the possible tautomeric, geometric, or stereoisomeric forms. It is to be understood that the present disclosure encompasses any tautomeric, geometric, or stereoisomeric form, and mixtures thereof, and is not to be limited merely to any one tautomeric, geometric, or stereoisomeric form utilized within the formula drawings.

Present compounds may be used in the form of pharmaceutically acceptable salts. The phrase "pharmaceutically acceptable salt" means those salts which are, within the scope of sound medical judgment, suitable for use in contact with the tissues of humans and lower animals without undue toxicity, irritation, allergic response and the like and are commensurate with a reasonable benefit/risk ratio.

Pharmaceutically acceptable salts have been described in S. M. Berge et al. J. Pharmaceutical Sciences, 1977, 66: 1-19.

Compounds of the present disclosure may contain either a basic or an acidic functionality, or both, and can be converted to a pharmaceutically acceptable salt, when desired, by using a suitable acid or base. The salts may be prepared in situ during the final isolation and purification of the compounds of the present disclosure.

General Synthesis

The compounds of the present disclosure can be better understood in connection with the following synthetic schemes and methods which illustrate a means by which the compounds can be prepared.

Another general approach to the compounds of this invention is illustrated in general Scheme 2.

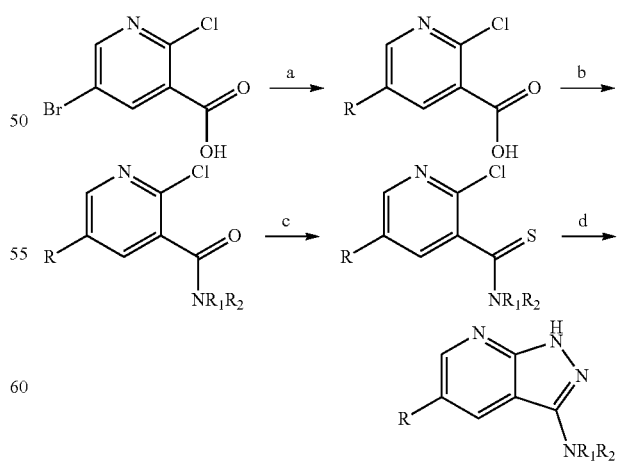

a) R-B(OH)₂ or its pinacol ester, Pd(PPh₃)₄, aq. K₂CO₃, Dioxane/H₂O(3/1), heat; b) amine, HATU, triethylamine, N,N-dimethylformamide; c) Lawesson's reagent, tetrahydrofuran, heat; d) N₂H₄, dimethyl sulfoxide, heat.

The compounds and intermediates of the present disclosure may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furnrniss, Hannaford, Smith, and Tatchell, pub. Longman Scientific & Technical, Essex CM20 2JE, England.

Many of the compounds of the present disclosure have at least one basic nitrogen whereby the compound can be treated with an acid to form a desired salt. For example, a compound may be reacted with an acid at or above room temperature to provide the desired salt, which is deposited, and collected by filtration after cooling.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the present disclosure. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis (4$^{th}$ ed.), John Wiley & Sons, NY (2006), which is incorporated herein by reference in its entirety. Synthesis of the compounds of the present disclosure can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the present disclosure is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the present disclosure is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the present disclosure as it is defined in the appended claims. All alternatives, modifications, and equivalents of the synthetic methods and specific examples are included within the scope of the claims.

Pharmaceutical Compositions

This disclosure also provides for pharmaceutical compositions comprising a therapeutically effective amount of a compound disclosed herein, or a pharmaceutically acceptable salt thereof together with a pharmaceutically acceptable carrier.

The term "pharmaceutically acceptable carrier" as used herein, means a non-toxic, inert solid, semi-solid or liquid filler, diluent, encapsulating material or formulation auxiliary of any type.

The pharmaceutical composition may be a unit dosage form. In such form the preparation is subdivided into unit doses containing appropriate quantities of the active component.

The dose to be administered to a subject may be determined by the efficacy of the particular compound employed and the condition of the subject, as well as the body weight or surface area of the subject to be treated. The size of the dose also will be determined by the existence, nature, and extent of any adverse side-effects that accompany the administration of a particular compound in a particular subject. In determining the effective amount of the compound to be administered in the treatment or prophylaxis of the disorder being treated, the physician can evaluate factors such as the circulating plasma levels of the compound, compound toxicities, and/or the progression of the disease, etc.

Methods of Use

Novel heterocyclic compounds according to the present invention, a stereoisomer thereof, an enantiomer thereof, or a pharmaceutically acceptable salt thereof exhibit the effect of effectively inhibiting Mer kinase.

Novel heterocyclic compounds according to the present invention, a stereoisomer thereof, an enantiomer thereof, or a pharmaceutically acceptable salt can be used for the prevention or treatment of cancer or immune-related disease.

The compounds described herein, or pharmaceutically acceptable salts thereof, and pharmaceutical compositions comprising a compound described herein, or a pharmaceutically acceptable salt thereof, may be administered to a subject suffering from a disorder or condition associated with Mer kinase kinase expression/over-expression or up-regulation and with activating genetic and epigenetic alterations. The term "administering" refers to the method of contacting a compound with a subject.

A "Mer kinase-mediated disorder or condition" is characterized by the participation of Mer kinase in the inception, manifestation of one or more symptoms or disease markers, maintenance, severity, or progression or resistance to therapeutic intervention of a disorder or condition. Accordingly, in embodiments, the present disclosure provides a method for treating cancer. The method comprises the step of administering to a subject in need thereof a therapeutically effective amount of a compound disclosed herein with or without a pharmaceutically acceptable carrier.

In embodiments, the present disclosure provides compounds of the disclosure, or pharmaceutical compositions comprising a compound of the disclosure, for use in medicine. In embodiments, the present disclosure provides compounds of the disclosure, or pharmaceutical compositions comprising a compound of the disclosure, for use in the treatment of diseases or disorders as described herein above.

One embodiment is directed to the use of a compound disclosed herein or a pharmaceutically acceptable salt thereof in the preparation of a medicament. The medicament optionally can comprise at least one additional therapeutic agent. In some embodiments the medicament is for use in the treatment of diseases and disorders as described herein above.

This disclosure is also directed to the use of a compound disclosed herein or a pharmaceutically acceptable salt thereof in the manufacture of a medicament for the treatment of the diseases and disorders as described herein above. The medicament optionally can comprise at least one additional therapeutic agent.

The compounds disclosed herein may be administered as the sole active agent or may be co-administered with other therapeutic agents, including other compounds that demonstrate the same or a similar therapeutic activity and that are determined to be safe and efficacious for such combined administration. The term "co-administered" means the administration of two or more different therapeutic agents or treatments (e.g., radiation treatment) that are administered to a subject in a single pharmaceutical composition or in separate pharmaceutical compositions. Thus co-administration involves administration at the same time of a single pharmaceutical composition comprising two or more different therapeutic agents or administration of two or more different compositions to the same subject at the same or different times.

The compounds of the present disclosure may be co-administered with a therapeutically effective amount of at least one additional therapeutic agent to treat cancer.

Further benefits of Applicants' disclosure will be apparent to one skilled in the art from reading this patent application.

The following Examples may be used for illustrative purposes and should not be deemed to narrow the scope of the present disclosure.

EXAMPLES

General

Embodiments of the present invention are described in the following examples, which are meant to illustrate and not limit the scope of this invention. Common abbreviations well known to those with ordinary skills in the synthetic art used throughout.

Abbreviations: atm for atmospheres of gas pressure; BINAP for 2,2'-Bis(diphenylphosphino)-1,1'-binaphthyl; CDI for N,N'-carbonyldiimidazole; DCE for 1,2-dichloroethane; DCM for dichloromethane; DIAD for diisopropyl azodicarboxylate; DMAP for 4-dimethylamino pyridine; DMF for N,N-dimethylformamide; DMAP for dimethylamino pyridine; DMFDMA for N,N-Dimethylformamide dimethyl acetal, DMSO for dimethyl sulfoxide; DPT for di-2-pyridyl thionocarbonate; EA or EtOAc for ethyl acetate; ESI for electrospray ionization; HATU for 1-[bis (dimethylamino)methylene]-1H-1,2,3-triazolo[4,5-b]pyridinium 3-oxid hexafluorophosphate; HPLC for high performance liquid chromatography; KOtBu for potassium tert-butoxide; Lawesson's reagent for 2,4-bis(4-methoxyphenyl)-2,4-dithioxo-1,3,2,4-dithiadiphosphetane; MeOH for methanol; MS for mass spectrum; NMR for nuclear magnetic resonance; psi for pounds per square inch; rt for room temperature; TEA for triethylamine; TFA for trifluoroacetic acid; and THF for tetrahydrofuran.

Flash column chromatography means silica gel chromatography unless specified otherwise, which was performed on Teledyne Combiflash-RF200 System. $^1$H NMR spectra (6, ppm) are recorded on 400 MHz or 600 MHz instrument. Mass spectroscopy data for a positive ionization method are provided. Preparative HPLC was performed on Agilent technologies G1361A, using a Agilent ZORBAX SB-C18 (21.2×150 mm; 5 m) stationary phase, with 0.1% aqueous TFA/acetonitrile gradients as the mobile phase (typically 10-100% acetonitrile over 10 min) with a flow rate of 20 mL/min.

Reagents and solvents may be obtained from commercial sources such as Seno International (Seoul, Korea) which may source compounds from various manufacturers including WuXi AppTec, J&H Chemical, Chemlin, Angene International, or Leap Labchem. Other reagents and intermediates were prepared according to general methods disclosed herein as detailed in Table 1.

TABLE 1

Reagent and Intermediate Preparations

| Reference | Name | General method | MS (ESI, m/z): [M + H]$^+$ |
|---|---|---|---|
| I-1 | 2-amino-5-(1-methyl-1H-pyrazol-4-yl)nicotinic acid | A | 219.1 |
| I-2 | 2-amino-5-(1-(1-(tert-butoxycarbonyl)piperidin-4-yl)-1H-pyrazol-4-yl)nicotinic acid | B | 388.1 |
| I-3 | (R)-2-amino-5-(1-methyl-1H-pyrazol-4-yl)-N-(pyrrolidin-3-yl)nicotinamide | C | 287.1 |
| I-4 | (R)-N-(1-([1,1'-biphenyl]-4-carbonyl)pyrrolidin-3-yl)-2-amino-5-bromonicotinamide | J | 465.1/467.1 |
| I-5 | tert-butyl 4-(4-(6-amino-5-((1-phenylpyrrolidin-3-yl)carbamoyl)pyridin-3-yl)-1H-pyrazol-1-yl)piperidine-1-carboxylate | L | 444.24 |
| I-6 | (R)-2-amino-5-(1-methyl-1H-pyrazol-4-yl)-N-(1-(4-(4,4,5,5-tetramethyl-1,3,2-dioxaborolan-2-yl)benzoyl)pyrrolidin-3-yl)nicotinamide | U | 517.3 |

TABLE 1-continued

Reagent and Intermediate Preparations

| Reference | Name | General method | MS (ESI, m/z): [M + H]+ |
|---|---|---|---|
| I-7 | (E)-4-(4-((R)-3-(2-amino-5-(1-methyl-1H-pyrazol-4-yl)nicotinamido)pyrrolidine-1-carbonyl)phenyl)but-3-en-2-yl acetate | W | 503.2 |
| I-8 | (R)-3-amino-N-(3-fluorophenyl)pyrrolidine-1-carboxamide | O | 224.1 |
| I-9 | (R)-3-amino-N-(3,4-difluorophenyl)pyrrolidine-1-carboxamide | O | 242.1 |
| I-10 | (R)-3-amino-N-(3,5-dimethylphenyl)pyrrolidine-1-carboxamide | O | 234.2 |
| I-11 | (R)-3-amino-N-(3,5-bis(trifluoromethyl)phenyl)pyrrolidine-1-carboxamide | O | 342.1 |
| I-12 | (R)-3-amino-N-(4-(trifluoromethyl)phenyl)pyrrolidine-1-carboxamide | O | 274.1 |
| I-13 | (R)-3-amino-N-(4-cyanophenyl)pyrrolidine-1-carboxamide | O | 231.1 |
| I-14 | (R)-3-amino-N-isopropylpyrrolidine-1-carboxamide | P | 172.1 |
| I-15 | (R)-3-amino-N-(3,5-dichlorophenyl)pyrrolidine-1-carboxamide | O | 274.0 |
| I-16 | (R)-3-amino-N-(1-methyl-1H-pyrazol-3-yl)pyrrolidine-1-carboxamide | O | 210.1 |
| I-17 | (R)-3-amino-N-(pyridin-3-yl)pyrrolidine-1-carboxamide | O | 207.1 |
| I-18 | (R)-3-amino-N-(3-chlorophenyl)pyrrolidine-1-carboxamide | O | 240.1 |
| I-19 | (R)-3-amino-N-(2,3-dichlorophenyl)pyrrolidine-1-carboxamide | O | 274.0 |
| I-20 | (R)-3-amino-N-(3-isopropoxyphenyl)pyrrolidine-1-carboxamide | O | 264.2 |
| I-21 | (R)-3-amino-N-(3-phenoxyphenyl)pyrrolidine-1-carboxamide | O | 298.1 |
| I-22 | (R)-3-amino-N-(2-phenoxyphenyl)pyrrolidine-1-carboxamide | O | 298.1 |
| I-23 | (R)-3-amino-N-(3-ethylphenyl)pyrrolidine-1-carboxamide | O | 234.1 |
| I-24 | (R)-3-amino-N-(2-ethylphenyl)pyrrolidine-1-carboxamide | O | 234.1 |
| I-25 | (R)-3-amino-N-(2-chlorophenyl)pyrrolidine-1-carboxamide | O | 240.1 |
| I-26 | (R)-3-amino-N-(3-bromophenyl)pyrrolidine-1-carboxamide | O | 284.1/286.1 |
| I-27 | (R)-3-amino-N-(4-bromophenyl)pyrrolidine-1-carboxamide | O | 284.1/286.1 |
| I-28 | (R)-3-amino-N-(3-(morpholinomethyl)phenyl)pyrrolidine-1-carboxamide | O | 305.2 |
| I-29 | (S)-3-amino-N-phenylpyrrolidine-1-carboxamide | O | 206.1 |
| I-30 | (R)-(5-amino-3,4-dihydroisoquinolin-2(1H)-yl)(3-aminopyrrolidin-1-yl)methanone | O | 261.1 |
| I-31 | (R)-(3-aminopyrrolidin-1-yl)(8-bromo-3,4-dihydroisoquinolin-2(1H)-yl)methanone | O | 324.1/346.1 |
| I-32 | (R)-3-amino-N-cyclohexylpyrrolidine-1-carboxamide | O | 212.1 |
| I-33 | (R)-3-amino-N-((1R,2S)-2-hydroxycyclohexyl)pyrrolidine-1-carboxamide | O | 228.1 |
| I-34 | (R)-3-amino-N-((1R,2R)-2-hydroxycyclohexyl)pyrrolidine-1-carboxamide | O | 228.1 |
| I-35 | (R)-3-amino-N-(2,4,6-trichlorophenyl)pyrrolidine-1-carboxamide | O | 308.0 |
| I-36 | (R)-3-amino-N-(3,4,5-trimethoxyphenyl)pyrrolidine-1-carboxamide | O | 296.1 |
| I-37 | (R)-N-([1,1'-biphenyl]-2-yl)-3-aminopyrrolidine-1-carboxamide | O | 282.1 |
| I-38 | (R)-3-amino-N-((1S,2S)-2-(benzyloxy)cyclopentyl)pyrrolidine-1-carboxamide | O | 304.2 |
| I-39 | (3R)-3-amino-N-(3-(benzyloxy)cyclopentyl)pyrrolidine-1-carboxamide | O | 304.2 |
| I-40 | (R)-3-amino-N-(4-fluorophenyl)pyrrolidine-1-carbothioamide | R | 240.1 |

TABLE 1-continued

Reagent and Intermediate Preparations

| Reference | Name | General method | MS (ESI, m/z): [M + H]+ |
|---|---|---|---|
| I-41 | (R)-3-amino-N-benzylpyrrolidine-1-carbothioamide | R | 236.1 |
| I-42 | (R)-3-amino-N-(3,4-dichlorophenyl)pyrrolidine-1-carbothioamide | R | 290.0 |
| I-43 | (R)-3-amino-N-(4-methoxyphenyl)pyrrolidine-1-carbothioamide | R | 252.1 |
| I-44 | (R)-3-amino-N-(4-bromophenyl)pyrrolidine-1-carbothioamide | R | 300.0/302.0 |
| I-45 | (R)-3-amino-N-(4-nitrophenyl)pyrrolidine-1-carbothioamide | R | 267.1 |
| I-46 | (R)-3-amino-N-(4-(dimethylamino)phenyl)pyrrolidine-1-carbothioamide | R | 265.1 |
| I-47 | (R)-3-amino-N-(4-morpholinophenyl)pyrrolidine-1-carbothioamide | R | 307.1 |
| I-48 | (R)-3-amino-N-(3,5-dichlorophenyl)pyrrolidine-1-carbothioamide | R | 290.0 |
| I-49 | (R)-3-amino-N-(3-bromophenyl)pyrrolidine-1-carbothioamide | R | 300.0/302.0 |
| I-50 | 3-(piperidine-1-carbonyl)phenyl (R)-3-aminopyrrolidine-1-carboxylate | Q | 318.1 |
| I-51 | 5,6,7,8-tetrahydronaphthalen-2-yl (R)-3-aminopyrrolidine-1-carboxylate | Q | 261.1 |
| I-52 | 3-isopropyl-5-methylphenyl (R)-3-aminopyrrolidine-1-carboxylate | Q | 262.2 |
| I-53 | 2-(benzyloxy)phenyl (R)-3-aminopyrrolidine-1-carboxylate | Q | 313.1 |
| I-54 | 3-(benzyloxy)phenyl (R)-3-aminopyrrolidine-1-carboxylate | Q | 313.1 |
| I-55 | 2,3-dichlorophenyl (R)-3-aminopyrrolidine-1-carboxylate | Q | 275.0 |
| I-56 | 2,5-dichlorophenyl (R)-3-aminopyrrolidine-1-carboxylate | Q | 275.0 |
| I-57 | 2-cyanophenyl (R)-3-aminopyrrolidine-1-carboxylate | Q | 232.1 |
| I-58 | 4-bromo-2-methoxyphenyl (R)-3-aminopyrrolidine-1-carboxylate | Q | 315.0/317.0 |
| I-59 | 4-(methoxycarbonyl)phenyl (R)-3-aminopyrrolidine-1-carboxylate | Q | 265.1 |
| I-60 | 5-methoxy-2-(methoxycarbonyl)phenyl (R)-3-aminopyrrolidine-1-carboxylate | Q | 295.1 |
| I-61 | cyclohexyl (R)-3-aminopyrrolidine-1-carboxylate | Q | 213.1 |
| I-62 | 6-bromonaphthalen-2-yl (R)-3-aminopyrrolidine-1-carboxylate | Q | 335.0/337.0 |
| I-63 | naphthalen-1-yl (R)-3-aminopyrrolidine-1-carboxylate | Q | 257.1 |
| I-64 | 1-aminonaphthalen-2-yl (R)-3-aminopyrrolidine-1-carboxylate | Q | 272.1 |
| I-65 | 2-aminophenyl (R)-3-aminopyrrolidine-1-carboxylate | Q | 222.1 |
| I-66 | 2-(hydroxymethyl)phenyl (R)-3-aminopyrrolidine-1-carboxylate | Q | 237.1 |
| I-67 | quinolin-6-yl (R)-3-aminopyrrolidine-1-carboxylate | Q | 258.1 |
| I-68 | quinolin-8-yl (R)-3-aminopyrrolidine-1-carboxylate | Q | 258.1 |
| I-69 | 3-(ethylamino)-4-methylphenyl (R)-3-aminopyrrolidine-1-carboxylate | Q | 264.1 |
| I-70 | 4-chloro-2-cyclohexylphenyl (R)-3-aminopyrrolidine-1-carboxylate | Q | 323.1 |
| I-71 | 3-acetamidophenyl (R)-3-aminopyrrolidine-1-carboxylate | Q | 264.1 |
| I-72 | 4-(methylsulfonyl)phenyl (R)-3-aminopyrrolidine-1-carboxylate | Q | 285.1 |
| I-73 | 2-((dimethylamino)methyl)phenyl (R)-3-aminopyrrolidine-1-carboxylate | Q | 264.1 |
| I-74 | 3,5-dimethylcyclohexyl (3R)-3-aminopyrrolidine-1-carboxylate | Q | 241.2 |
| I-75 | benzyl (R)-3-aminopyrrolidine-1-carboxylate | Q | 221.1 |
| I-76 | [1,1'-biphenyl]-3-yl (R)-3-aminopyrrolidine-1-carboxylate | Q | 283.1 |
| I-77 | 4-chloro-3-methylphenyl (R)-3-aminopyrrolidine-1-carboxylate | Q | 255.1 |

TABLE 1-continued

Reagent and Intermediate Preparations

| Reference | Name | General method | MS (ESI, m/z): [M + H]+ |
|---|---|---|---|
| I-78 | 3-cyanophenyl (R)-3-aminopyrrolidine-1-carboxylate | Q | 232.1 |
| I-79 | 3,4-dichlorophenyl (R)-3-aminopyrrolidine-1-carboxylate | Q | 275.0 |
| I-80 | 4-amino-3-chlorophenyl (R)-3-aminopyrrolidine-1-carboxylate | Q | 256.1 |
| I-81 | 3,5-difluorophenyl (R)-3-aminopyrrolidine-1-carboxylate | Q | 243.1 |
| I-82 | 3,5-dimethylphenyl (R)-3-aminopyrrolidine-1-carboxylate | Q | 235.1 |
| I-83 | 2-(methoxycarbonyl)phenyl (R)-3-aminopyrrolidine-1-carboxylate | Q | 265.1 |
| I-84 | 4-ethylphenyl (R)-3-aminopyrrolidine-1-carboxylate | Q | 235.1 |
| I-85 | 3,4-dimethylphenyl (R)-3-aminopyrrolidine-1-carboxylate | Q | 235.1 |
| I-86 | 7-hydroxynaphthalen-2-yl (R)-3-aminopyrrolidine-1-carboxylate | Q | 273.1 |
| I-87 | 3-hydroxynaphthalen-2-yl (R)-3-aminopyrrolidine-1-carboxylate | Q | 273.1 |
| I-88 | 2-hydroxyphenyl (R)-3-aminopyrrolidine-1-carboxylate | Q | 223.1 |
| I-89 | 2-amino-4-chlorophenyl (R)-3-aminopyrrolidine-1-carboxylate | Q | 256.0 |
| I-90 | 2-amino-5-nitrophenyl (R)-3-aminopyrrolidine-1-carboxylate | Q | 267.1 |
| I-91 | 3-hydroxyphenyl (R)-3-aminopyrrolidine-1-carboxylate | Q | 223.1 |
| I-92 | 4-bromo-2-chlorophenyl (R)-3-aminopyrrolidine-1-carboxylate | Q | 318.9/320.9 |
| I-93 | [1,1'-biphenyl]-3-yl (R)-3-(methylamino)pyrrolidine-1-carboxylate | Q | 297.1 |
| I-94 | 3,5-dichlorophenyl (R)-3-aminopyrrolidine-1-carboxylate | Q | 275.0 |
| I-95 | 4-phenoxyphenyl (R)-3-aminopyrrolidine-1-carboxylate | Q | 299.1 |
| I-96 | naphthalen-2-yl (R)-3-aminopyrrolidine-1-carboxylate | Q | 257.1 |
| I-97 | 6-hydroxynaphthalen-2-yl (R)-3-aminopyrrolidine-1-carboxylate | Q | 273.1 |
| I-98 | (1R,2S,4S)-bicyclo[2.2.1]heptan-2-yl (R)-3-aminopyrrolidine-1-carboxylate | Q | 225.1 |
| I-99 | cyclopentyl (R)-3-aminopyrrolidine-1-carboxylate | Q | 199.1 |
| I-100 | cycloheptyl (R)-3-aminopyrrolidine-1-carboxylate | Q | 227.1 |
| I-101 | (1R,2S)-2-methylcyclohexyl (R)-3-aminopyrrolidine-1-carboxylate | Q | 227.1 |
| I-102 | (1S,2S,4R)-bicyclo[2.2.1]heptan-2-yl (R)-3-aminopyrrolidine-1-carboxylate | Q | 225.1 |
| I-103 | 3-phenoxyphenyl (R)-3-aminopyrrolidine-1-carboxylate | Q | 299.1 |
| I-104 | 4-(4-nitrophenoxy)phenyl (R)-3-aminopyrrolidine-1-carboxylate | Q | 344.1 |
| I-105 | 4-(4-aminophenoxy)phenyl (R)-3-aminopyrrolidine-1-carboxylate | Q | 314.1 |
| I-106 | 4-(4-((4-methylpiperazin-1-yl)methyl)phenoxy)phenyl (R)-3-aminopyrrolidine-1-carboxylate | Q | 411.2 |
| I-107 | 4-(4-(hydroxymethyl)phenoxy)phenyl (R)-3-aminopyrrolidine-1-carboxylate | Q | 329.1 |
| I-108 | 4-(4-((dimethylamino)methyl)phenoxy)phenyl (R)-3-aminopyrrolidine-1-carboxylate | Q | 356.2 |
| I-109 | 3-bromophenyl (R)-3-aminopyrrolidine-1-carboxylate | O | 285.0/287.0 |
| I-110 | phenyl (R)-3-aminopyrrolidine-1-carboxylate | O | 207.1 |
| I-111 | 3-bromo-5-chlorophenyl (R)-3-aminopyrrolidine-1-carboxylate | O | 319.0/321.0 |
| I-112 | (1S,2S)-2-(benzyloxy)cyclopentyl (R)-3-aminopyrrolidine-1-carboxylate | O | 305.2 |
| I-113 | 3-phenylcyclopentyl (3R)-3-aminopyrrolidine-1-carboxylate | O | 275.1 |
| I-114 | 1-benzylpiperidin-3-yl (3R)-3-aminopyrrolidine-1-carboxylate | O | 304.2 |
| I-115 | 1-(4-formylphenyl)piperidin-3-yl (3R)-3-aminopyrrolidine-1-carboxylate | O | 318.2 |

TABLE 1-continued

Reagent and Intermediate Preparations

| Reference | Name | General method | MS (ESI, m/z): [M + H]+ |
|---|---|---|---|
| I-116 | 4-phenylcyclohexyl (R)-3-aminopyrrolidine-1-carboxylate | O | 289.2 |
| I-117 | 1-phenylpyrrolidin-3-yl (3R)-3-aminopyrrolidine-1-carboxylate | O | 276.1 |
| I-118 | (R)-1-phenylpyrrolidin-3-yl (R)-3-aminopyrrolidine-1-carboxylate | O | 276.1 |
| I-119 | (S)-1-phenylpyrrolidin-3-yl (R)-3-aminopyrrolidine-1-carboxylate | O | 276.1 |
| I-120 | 3-phenylcyclohexyl (3R)-3-aminopyrrolidine-1-carboxylate | O | 289.2 |
| I-121 | (R)-1-(1H-benzoimidazol-2-yl)pyrrolidin-3-amine | S | 203.1 |
| I-122 | (R)-1-(p-tolyl)pyrrolidin-3-amine | S | 177.1 |
| I-123 | (R)-1-(pyridin-2-yl)pyrrolidin-3-amine | S | 164.1 |
| I-124 | (R)-1-(5-ethylpyrimidin-2-yl)pyrrolidin-3-amine | S | 193.1 |
| I-125 | (R)-1-(quinazolin-2-yl)pyrrolidin-3-amine | S | 215.1 |
| I-126 | (R)-1-(5-nitrothiazol-2-yl)pyrrolidin-3-amine | S | 215.0 |
| I-127 | ethyl (R)-2-(3-aminopyrrolidin-1-yl)thiazole-4-carboxylate | S | 242.1 |
| I-128 | (R)-1-([1,1'-biphenyl]-4-yl)pyrrolidin-3-amine | S | 239.1 |
| I-129 | (R)-1-([1,1'-biphenyl]-3-yl)pyrrolidin-3-amine | S | 239.1 |
| I-130 | (R)-1-benzylpyrrolidin-3-amine | T | 177.1 |
| I-131 | 1-benzylpyrrolidin-3-amine | T | 177.1 |
| I-132 | (R)-1-(4-fluorobenzyl)pyrrolidin-3-amine | T | 195.1 |
| I-133 | (R)-1-(3-methoxybenzyl)pyrrolidin-3-amine | T | 207.1 |
| I-134 | (R)-1-(2-chlorobenzyl)pyrrolidin-3-amine | T | 211.1 |
| I-135 | (R)-1-(4-nitrobenzyl)pyrrolidin-3-amine | T | 222.1 |
| I-136 | (R)-1-(2,4,5-trifluorobenzyl)pyrrolidin-3-amine | T | 231.1 |
| I-137 | (R)-1-(3-chloro-4-fluorobenzyl)pyrrolidin-3-amine | T | 229.0 |
| I-138 | (R)-1-(2,6-dichlorobenzyl)pyrrolidin-3-amine | T | 245.0 |
| I-139 | (R)-1-(3,4-difluorobenzyl)pyrrolidin-3-amine | T | 213.1 |
| I-140 | (R)-1-(3,4-dichlorobenzyl)pyrrolidin-3-amine | T | 25.0 |
| I-141 | (R)-1-(2,3,6-trifluorobenzyl)pyrrolidin-3-amine | T | 231.1 |
| I-142 | (R)-1-((2,4-dimethylthiazol-5-yl)methyl)pyrrolidin-3-amine | T | 212.1 |
| I-143 | (R)-1-(2,3-dichlorobenzyl)pyrrolidin-3-amine | T | 245.0 |
| I-144 | (R)-1-(2,4-dichlorobenzyl)pyrrolidin-3-amine | T | 245.0 |
| I-145 | (R)-1-(2,5-di methylbenzyl)pyrrolidin-3-amine | T | 205.1 |
| I-146 | (R)-1-(2-methoxybenzyl)pyrrolidin-3-amine | T | 207.1 |
| I-147 | (R)-1-(2-(trifluoromethyl)benzyl)pyrrolidin-3-amine | T | 245.1 |
| I-148 | (3R)-1-(cyclohex-3-en-1-ylmethyl)pyrrolidin-3-amine | T | 181.1 |
| I-149 | (R)-1-(((1R,5S)-6,6-dimethylbicyclo[3.1.1]hept-2-en-2-yl)methyl)pyrrolidin-3-amine | T | 221.2 |
| I-150 | (3R)-1-(1-(2-chlorophenyl)ethyl)pyrrolidin-3-amine | T | 225.1 |
| I-151 | (3R)-1-(1-(3-chlorophenyl)ethyl)pyrrolidin-3-amine | T | 225.1 |
| I-152 | (3R)-1-(1-(3,4-dichlorophenyl)ethyl)pyrrolidin-3-amine | T | 259.0 |
| I-153 | (R)-1-(benzylsulfonyl)pyrrolidin-3-amine | AF | 241.1 |
| I-154 | (R)-1-(phenylsulfonyl)pyrrolidin-3-amine | AF | 227.1 |
| I-155 | (R)-1-((2,4-dichlorophenyl)sulfonyl)pyrrolidin-3-amine | AF | 295.0 |
| I-156 | (R)-1-((3-chloropropyl)sulfonyl)pyrrolidin-3-amine | AF | 227.0 |
| I-157 | (R)-1-benzyl-N-methylpyrrolidin-3-amine | T | 191.1 |
| I-158 | (R)-1-(2-chlorobenzyl)-N-methylpyrrolidin-3-amine | T | 225.1 |
| I-159 | SS-methyl (2S,4R)-4-amino-1-benzylpyrrolidine-2-carbo(dithioperoxoate) | T | 283.1 |
| I-160 | SS-methyl (2S,4R)-4-amino-1-(2-chlorobenzyl)pyrrolidine-2-carbo(dithioperoxoate) | T | 317.0 |
| I-161 | (S)-1-(3-((4-methylpiperazin-1-yl)methyl)phenyl)pyrrolidin-3-yl (R)-3-aminopyrrolidine-1-carboxylate | Q | 388.2 |
| I-162 | (R)-3-amino-N-methyl-N-phenylpyrrolidine-1-carboxamide | O | 220.1 |
| I-163 | (R)-1-(pyridin-3-ylmethyl)pyrrolidin-3-amine | T | 178.1 |
| I-164 | (R)-1-((2-chloropyridin-4-yl)methyl)pyrrolidin-3-amine | T | 212.1 |
| I-165 | tert-butyl (3S,4S)-3-amino-4-((3-ethyl-4-methylbenzyl)oxy)pyrrolidine-1-carboxylate | AE | 335.2 |

TABLE 1-continued

Reagent and Intermediate Preparations

| Reference | Name | General method | MS (ESI, m/z): [M + H]+ |
|---|---|---|---|
| I-166 | tert-butyl 3-(3-(4,4,5,5-tetramethyl-1,3,2-dioxaborolan-2-yl)phenoxy)pyrrolidine-1-carboxylate | AD | 390.2 |
| I-167 | (R)-[1,1'-biphenyl]-4-yl(3-aminopyrrolidin-1-yl)methanone | AF | 267.1 |
| I-168 | (R)-(3-aminopyrrolidin-1-yl)(2'-chloro-[1,1'-biphenyl]-4-yl)methanone | AF | 301.1 |
| I-169 | (R)-(3-aminopyrrolidin-1-yl)(2'-chloro-4'-fluoro-[1,1'-biphenyl]-4-yl)methanone | AF | 319.1 |
| I-170 | tert-butyl (3R,4S)-3-amino-4-((benzyloxy)methyl)pyrrolidine-1-carboxylate | AE | 307.2 |
| I-171 | tert-butyl (3S,4S)-3-amino-4-(benzyloxy)pyrrolidine-1-carboxylate | AE | 293.2 |
| I-172 | tert-butyl (3R,4R)-3-amino-4-((3-ethyl-4-methylbenzyl)oxy)pyrrolidine-1-carboxylate, | AE | 335.2 |
| I-173 | 4-(4-bromo-3-chlorophenoxy)aniline | AC | 298.0/300.0 |
| I-174 | 4-bromo-N-methyl-N-(4-nitrophenyl)aniline | AB | 307.0/309.0 |
| I-175 | N-(4-bromophenyl)-2-fluoro-N-methyl-4-nitroaniline | AB | 325.0/327.0 |
| I-176 | N-(4-bromophenyl)-N,2-dimethyl-4-nitroaniline | AB | 321.0/323.0 |
| I-177 | N-(4-bromophenyl)-2-chloro-N-methyl-4-nitroaniline | AB | 341.0/343.0 |
| I-178 | 4-(4-bromo-2-chlorophenoxy)phenol | AC | 298.9/300.9 |
| I-179 | 5-(4-bromophenoxy)pyridin-2-amine | AA | 265.0/267.0 |
| I-180 | 5-(4-bromophenoxy)-2H-tetrazole | AC | 240.9/242.9 |
| I-181 | $N^1$-(4-bromophenyl)benzene-1,4-diamine | AB | 263.0/265.0 |
| I-182 | 4-(4-bromo-3-chlorophenoxy)benzaldehyde | AA | 310.9/312.9 |

In the general methods disclosed herein, boronic acids may be substituted for boronic acid pinacol esters and boronic acid pinacol esters may be substituted for boronic acids as known to one skilled in the art.

General Method A

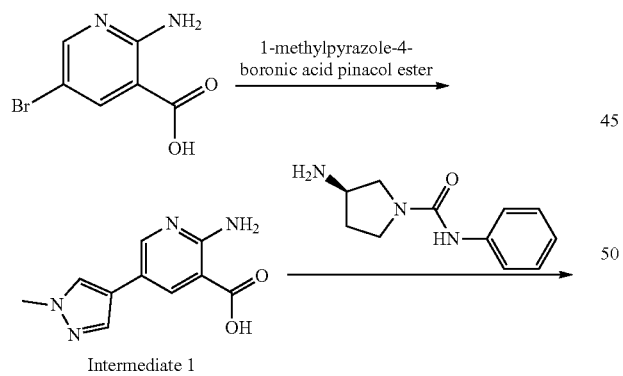

Intermediate 1

To a mixture of 2-amino-5-bromonicotinic acid (23 g, 100 mmol) and 1-methylpyrazole-4-boronic acid pinacol ester (27 g, 130 mmol) in 400 mL of 1,4-dioxane/water (3/1) was added $K_2CO_3$ (27.6 g, 200 mmol) followed by Pd(PPh$_3$)$_4$ (8.1 g, 7 mmol). The reaction mixture was heated at 100° C. for 3 h, cooled to room temperature, and partitioned between water and ethyl acetate. Water layer was separated and adjusted to pH value around 5. The precipitate was collected by filtration and triturated in mixture of methanol and water. The precipitate was filtered. The wet cake was dried to afford 17.5 g of the title compound. The crude product was used for the next step without further purification. $^1$H NMR (600 MHz, DIMETHYL SULFOXIDE-d$_6$) δ ppm 3.82 (s, 3H), 5.73 (s, 2H), 7.77 (s, 1H), 8.05 (s, 1H), 8.13 (d, J=2.4 Hz, 1H), 8.42 (d, J=2.4 Hz, 1H); MS (ESI, m/z): 219.1 [M+H]$^+$ Example 001

(R)-2-amino-5-(1-methyl-1H-pyrazol-4-yl)-N-(1-(phenylcarbamoyl)pyrrolidin-3-yl)nicotinamide To a mixture of intermediate 1 (20 mg, 0.09 mmol) and triethylamine (0.038 mL, 0.28 mmol) in 0.5 mL of N,N-dimethylformamide was added 1-[bis(dimethylamino)methylene]-1H-1,2,3-triazolo[4,5-b]pyridinium 3-oxid hexafluorophosphate (35 mg, 0.09 mmol) followed (R)-3-amino-N-phenylpyrrolidine-1-carboxamide (19 mg, 0.09 mmol). The mixture was stirred at room temperature for 1 h and then saturated sodium bicarbonate solution was added. The mixture was extracted with ethyl acetate, washed with brine, dried over MgSO$_4$, and concentrated in vacuo. The crude residue was purified by preparative HPLC to afford 10 mg of the title compound. MS (ESI, m/z): 406.1 [M+H]$^+$

Example 002

(R)-2-amino-N-(1-((3-fluorophenyl)carbamoyl)pyrrolidin-3-yl)-5-(1-methyl-1H-pyrazol-4-yl)nicotinamide Using (R)-3-amino-N-(3-fluorophenyl)pyrrolidine-1-carboxamide, the title compound was obtained as described in general method A. MS (ESI, m/z): 424.2 [M+H]$^+$

Example 003

(R)-2-amino-N-(1-((3,4-difluorophenyl)carbamoyl)pyrrolidin-3-yl)-5-(1-methyl-1H-pyrazol-4-yl)nicotinamide Using (R)-3-amino-N-(3,4-difluorophenyl)pyrrolidine-1-carboxamide, the title compound was obtained as described in general method A. MS (ESI, m/z): 442.2 [M+H]$^+$

Example 004

(R)-2-amino-N-(1-((3,5-dimethylphenyl)carbamoyl)pyrrolidin-3-yl)-5-(1-methyl-1H-pyrazol-4-yl)nicotinamide Using (R)-3-amino-N-(3,5-dimethylphenyl)pyrrolidine-1-carboxamide, the title compound was obtained as described in general method A. MS (ESI, m/z): 434.2 [M+H]$^+$

Example 005

(R)-2-amino-N-(1-((3,5-bis(trifluoromethyl)phenyl)carbamoyl)pyrrolidin-3-yl)-5-(1-methyl-1H-pyrazol-4-yl)nicotinamide Using (R)-3-amino-N-(3,5-di(trifluoromethyl)phenyl)pyrrolidine-1-carboxamide, the title compound was obtained as described in general method A. MS (ESI, m/z): 542.2 [M+H]$^+$

Example 006

(R)-2-amino-5-(1-methyl-1H-pyrazol-4-yl)-N-(1-((4-(trifluoromethyl)phenyl)carbamoyl)pyrrolidin-3-yl)nicotinamide Using (R)-3-amino-N-(4-trifluoromethylphenyl)pyrrolidine-1-carboxamide, the title compound was obtained as described in general method A. MS (ESI, m/z): 474.2 [M+H]$^+$

Example 007

(R)-2-amino-N-(1-((4-cyanophenyl)carbamoyl)pyrrolidin-3-yl)-5-(1-methyl-1H-pyrazol-4-yl)nicotinamide Using (R)-3-amino-N-(4-cyanophenyl)pyrrolidine-1-carboxamide, the title compound was obtained as described in general method A. MS (ESI, m/z): 430.2 [M+H]$^+$

Example 008

(R)-2-amino-N-(1-(isopropylcarbamoyl)pyrrolidin-3-yl)-5-(1-methyl-1H-pyrazol-4-yl)nicotinamide Using (R)-3-amino-N-isopropylpyrrolidine-1-carboxamide, the title compound was obtained as described in general method A. MS (ESI, m/z): 372.2 [M+H]$^+$

Example 009

(R)-2-amino-N-(1-((3,5-dichlorophenyl)carbamoyl)pyrrolidin-3-yl)-5-(4-(morpholine-4-carbonyl)phenyl)nicotinamide Using (4-(morpholine-4-carbonyl)phenyl)boronic acid and (R)-3-amino-N-(3,5-dichlorophenyl)pyrrolidine-1-carboxamide, the title compound was obtained as described in general method A. MS (ESI, m/z): 583.2 [M+H]$^+$

Example 010

(R)-2-amino-N-(1-((3,5-dichlorophenyl)carbamoyl)pyrrolidin-3-yl)-5-(4-(hydroxymethyl)phenyl)nicotinamide Using (4-hydroxymethylphenyl)boronic acid and (R)-3-amino-N-(3,5-dichlorophenyl)pyrrolidine-1-carboxamide, the title compound was obtained as described in general method A. MS (ESI, m/z): 500.2 [M+H]$^+$

Example 011

(R)-2-amino-N-(1-((3,5-dichlorophenyl)carbamoyl)pyrrolidin-3-yl)-5-(1-(1-methylpiperidin-4-yl)-1H-pyrazol-4-yl)nicotinamide Using (1-(1-methylpiperidin-4-yl)-1H-pyrazol-4-yl)boronic acid pinacol ester and (R)-3-amino-N-(3,5-dichlorophenyl)pyrrolidine-1-carboxamide, the title compound was obtained as described in general method A. MS (ESI, m/z): 557.2 [M+H]$^+$

Example 012

(R)-2-amino-N-(1-((1-methyl-1H-pyrazol-3-yl)carbamoyl)pyrrolidin-3-yl)-5-(1-methyl-1H-pyrazol-4-yl)nicotinamide Using (R)-3-amino-N-(1-methyl-1H-pyrazol-3-yl)pyrrolidine-1-carboxamide, the title compound was obtained as described in general method A. MS (ESI, m/z): 410.2 [M+H]$^+$

Example 013

(R)-2-amino-5-(1-methyl-1H-pyrazol-4-yl)-N-(1-(pyridin-3-ylcarbamoyl)pyrrolidin-3-yl)nicotinamide Using (R)-3-amino-N-(pyridin-3-yl)pyrrolidine-1-carboxamide, the title compound was obtained as described in general method A. MS (ESI, m/z): 407.2 [M+H]$^+$

Example 014

(R)-2-amino-N-(1-((3-chlorophenyl)carbamoyl)pyrrolidin-3-yl)-5-(1-methyl-1H-pyrazol-4-yl)nicotinamide Using (R)-3-amino-N-(3-chlorophenyl)pyrrolidine-1-carboxamide, the title compound was obtained as described in general method A. MS (ESI, m/z): 440.2 [M+H]$^+$

Example 015

(R)-2-amino-N-(1-((2,3-dichlorophenyl)carbamoyl)pyrrolidin-3-yl)-5-(1-methyl-1H-pyrazol-4-yl)nicotinamide Using (R)-3-amino-N-(2,3-dichlorophenyl)pyrrolidine-1-carboxamide, the title compound was obtained as described in general method A. MS (ESI, m/z): 474.2 [M+H]$^+$

Example 016

(R)-2-amino-N-(1-((3-isopropoxyphenyl)carbamoyl)pyrrolidin-3-yl)-5-(1-methyl-1H-pyrazol-4-yl)nicotinamide Using (R)-3-amino-N-(3-isopropoxyphenyl)pyrrolidine-1-carboxamide, the title compound was obtained as described in general method A. MS (ESI, m/z): 464.2 [M+H]$^+$

Example 017

(R)-2-amino-5-(1-methyl-1H-pyrazol-4-yl)-N-(1-((3-phenoxyphenyl)carbamoyl)pyrrolidin-3-yl)nicotinamide Using (R)-3-amino-N-(3-phenoxyphenyl)pyrrolidine-1-carboxamide, the title compound was obtained as described in general method A. MS (ESI, m/z): 498.2 [M+H]$^+$

Example 018

(R)-2-amino-5-(1-methyl-1H-pyrazol-4-yl)-N-(1-((2-phenoxyphenyl)carbamoyl)pyrrolidin-3-yl)nicotinamide Using (R)-3-amino-N-(2-phenoxyphenyl)pyrrolidine-1-carboxamide, the title compound was obtained as described in general method A. MS (ESI, m/z): 498.2 [M+H]$^+$

Example 019

(R)-2-amino-N-(1-((3-ethylphenyl)carbamoyl)pyrrolidin-3-yl)-5-(1-methyl-1H-pyrazol-4-yl)nicotinamide Using (R)-3-amino-N-(3-ethylphenyl)pyrrolidine-1-carboxamide, the title compound was obtained as described in general method A. MS (ESI, m/z): 434.2 [M+H]$^+$

Example 020

(R)-2-amino-N-(1-((2-ethylphenyl)carbamoyl)pyrrolidin-3-yl)-5-(1-methyl-1H-pyrazol-4-yl)nicotinamide Using (R)-3-amino-N-(2-ethylphenyl)pyrrolidine-1-carboxamide, the title compound was obtained as described in general method A. MS (ESI, m/z): 434.2 [M+H]$^+$

Example 021

(R)-2-amino-N-(1-((2-chlorophenyl)carbamoyl)pyrrolidin-3-yl)-5-(1-methyl-1H-pyrazol-4-yl)nicotinamide Using (R)-3-amino-N-(2-chlorophenyl)pyrrolidine-1-carboxamide, the title compound was obtained as described in general method A. MS (ESI, m/z): 440.2 [M+H]$^+$

Example 022

(R)—N-(1-((3,5-dichlorophenyl)carbamoyl)pyrrolidin-3-yl)-5-(1-methyl-1H-pyrazol-4-yl)nicotinamide Using (R)-3-amino-N-(3,5-dichlorophenyl)pyrrolidine-1-carboxamide, the title compound was obtained as described in general method A. MS (ESI, m/z): 459.2 [M+H]$^+$

Example 023

(R)—N-(1-([1,1'-biphenyl]-3-ylcarbamoyl)pyrrolidin-3-yl)-2-amino-5-(1-methyl-1H-pyrazol-4-yl)nicotinamide Using (R)-3-amino-N-(3-biphenyl)pyrrolidine-1-carboxamide, the title compound was obtained as described in general method A. MS (ESI, m/z): 482.2 [M+H]$^+$

Example 024

(R)-2-amino-N-(1-((3-bromophenyl)carbamoyl)pyrrolidin-3-yl)-5-(1-methyl-1H-pyrazol-4-yl)nicotinamide Using (R)-3-amino-N-(3-bromophenyl)pyrrolidine-1-carboxamide, the title compound was obtained as described in general method A. MS (ESI, m/z): 484.2 [M+H]$^+$

Example 025

(R)-2-amino-N-(1-((4-bromophenyl)carbamoyl)pyrrolidin-3-yl)-5-(1-methyl-1H-pyrazol-4-yl)nicotinamide Using (R)-3-amino-N-(4-bromophenyl)pyrrolidine-1-carboxamide, the title compound was obtained as described in general method A. MS (ESI, m/z): 484.2 [M+H]$^+$

Example 026

(R)-2-amino-5-(1-methyl-1H-pyrazol-4-yl)-N-(1-((3-(morpholinomethyl)phenyl)carbamoyl)pyrrolidin-3-yl)nicotinamide Using (R)-3-amino-N-(3-(morpholinomethyl)phenyl)pyrrolidine-1-carboxamide, the title compound was obtained as described in general method A. MS (ESI, m/z): 505.2 [M+H]$^+$

Example 027

(S)-2-amino-5-(1-methyl-1H-pyrazol-4-yl)-N-(1-(phenylcarbamoyl)pyrrolidin-3-yl)nicotinamide Using (S)-3-amino-N-phenylpyrrolidine-1-carboxamide, the title compound was obtained as described in general method A. MS (ESI, m/z): 406.2 [M+H]$^+$

Example 028

(R)-2-amino-N-(1-(5-amino-1,2,3,4-tetrahydroisoquinoline-2-carbonyl)pyrrolidin-3-yl)-5-(1-methyl-1H-pyrazol-4-yl)nicotinamide Using (R)-(5-amino-3,4-dihydroisoquinolin-2(1H)-yl)(3-aminopyrrolidin-1-yl)methanone, the title compound was obtained as described in general method A. MS (ESI, m/z): 461.2 [M+H]$^+$

Example 029

(R)-2-amino-N-(1-(8-bromo-1,2,3,4-tetrahydroisoquinoline-2-carbonyl)pyrrolidin-3-yl)-5-(1-methyl-1H-pyrazol-4-yl)nicotinamide Using (R)-(3-aminopyrrolidin-1-yl)(8-bromo-3,4-dihydroisoquinolin-2(1H)-yl)methanone, the title compound was obtained as described in general method A. MS (ESI, m/z): 524.2 [M+H]$^+$

Example 030

(R)-2-amino-N-(1-(cyclohexylcarbamoyl)pyrrolidin-3-yl)-5-(1-methyl-1H-pyrazol-4-yl)nicotinamide Using (R)-3-amino-N-cyclohexylpyrrolidine-1-carboxamide, the title compound was obtained as described in general method A. MS (ESI, m/z): 412.2 [M+H]$^+$

Example 031

2-amino-N—((R)-1-(((1R,2S)-2-hydroxycyclohexyl)carbamoyl)pyrrolidin-3-yl)-5-(1-methyl-1H-pyrazol-4-yl)nicotinamide Using (R)-3-amino-N-((1R,2S)-2-hydroxycyclohexyl)pyrrolidine-1-carboxamide, the title compound was obtained as described in general method A. MS (ESI, m/z): 428.2 [M+H]$^+$

Example 032

2-amino-N—((R)-1-(((1R,2R)-2-hydroxycyclohexyl)carbamoyl)pyrrolidin-3-yl)-5-(1-methyl-1H-pyrazol-4-yl)nicotinamide Using (R)-3-amino-N-((1R,2R)-2-hydroxycyclohexyl)pyrrolidine-1-carboxamide, the title compound was obtained as described in general method A. MS (ESI, m/z): 428.2 [M+H]$^+$

Example 033

(R)-2-amino-5-(1-methyl-1H-pyrazol-4-yl)-N-(1-((2,4,6-trichlorophenyl)carbamoyl)pyrrolidin-3-yl)nicotinamide Using (R)-3-amino-N-(2,4,6-trichlorophenyl)pyrrolidine-1-carboxamide, the title compound was obtained as described in general method A. MS (ESI, m/z): 508.07 [M+H]$^+$

Example 034

(R)-2-amino-N-(1-((3,5-dichlorophenyl)carbamoyl)pyrrolidin-3-yl)-5-(1-methyl-1H-pyrazol-4-yl)nicotinamide Using (R)-3-amino-N-(3,5-dichlorophenyl)pyrrolidine-1-carboxamide, the title compound was obtained as described in general method A. MS (ESI, m/z): 474.11 [M+H]$^+$

Example 035

(R)-2-amino-5-(1-methyl-1H-pyrazol-4-yl)-N-(1-((3,4,5-trimethoxyphenyl)carbamoyl)pyrrolidin-3-yl)nicotinamide Using (R)-3-amino-N-(3,4,5-trimethoxyphenyl)pyrrolidine-1-carboxamide, the title compound was obtained as described in general method A. MS (ESI, m/z): 496.22 [M+H]$^+$

Example 036

(R)—N-(1-([1,1'-biphenyl]-2-ylcarbamoyl)pyrrolidin-3-yl)-2-amino-5-(1-methyl-1H-pyrazol-4-yl)nicotinamide Using (R)—N-([1,1'-biphenyl]-2-yl)-3-aminopyrrolidine-1-carboxamide, the title compound was obtained as described in general method A. MS (ESI, m/z): 482.22 [M+H]$^+$

Example 037

(R)—N-(1-([1,1'-biphenyl]-3-ylcarbamoyl)pyrrolidin-3-yl)-2-amino-5-(4-((4-methylpiperazin-1-yl)methyl)phenyl)nicotinamide Using (4-((4-methylpiperazin-1-yl)methyl)phenyl)boronic acid and (R)—N-([1,1'-biphenyl]-3-yl)-3-aminopyrrolidine-1-carboxamide, the title compound was obtained as described in general method A. MS (ESI, m/z): 590.2 [M+H]$^+$

Example 038

(R)—N-(1-([1,1'-biphenyl]-3-ylcarbamoyl)pyrrolidin-3-yl)-2-amino-5-(4-(morpholinomethyl)phenyl)nicotinamide Using (4-(morpholinomethyl)phenyl)boronic acid and (R)—N-([1,1'-biphenyl]-3-yl)-3-aminopyrrolidine-1-carboxamide, the title compound was obtained as described in general method A. MS (ESI, m/z): 577.2 [M+H]$^+$

Example 039

(R)—N-(1-([1,1'-biphenyl]-3-ylcarbamoyl)pyrrolidin-3-yl)-2-amino-5-(4-((4-hydroxypiperidin-1-yl)methyl)phenyl)nicotinamide Using (4-((4-hydroxypiperidin-1-yl)methyl)phenyl)boronic acid and (R)—N-([1,1'-biphenyl]-3-yl)-3-aminopyrrolidine-1-carboxamide, the title compound was obtained as described in general method A. MS (ESI, m/z): 591.2 [M+H]$^+$

Example 040

2-amino-N—((R)-1-(((1S,2S)-2-(benzyloxy)cyclopentyl)carbamoyl)pyrrolidin-3-yl)-5-(1-methyl-1H-pyrazol-4-yl)nicotinamide Using (R)-3-amino-N-((1 S,2S)-2-(benzyloxy)cyclopentyl)pyrrolidine-1-carboxamide, the title compound was obtained as described in general method A. MS (ESI, m/z): 504.26 [M+H]$^+$

Example 041

2-amino-N-((3R)-1-((3-(benzyloxy)cyclopentyl)carbamoyl)pyrrolidin-3-yl)-5-(1-methyl-1H-pyrazol-4-yl)nicotinamide Using (3R)-3-amino-N-(3-(benzyloxy)cyclopentyl)pyrrolidine-1-carboxamide, the title compound was obtained as described in general method A. MS (ESI, m/z): 504.26 [M+H]$^+$

Example 042

(R)-2-amino-N-(1-((4-fluorophenyl)carbamothioyl)pyrrolidin-3-yl)-5-(1-methyl-1H-pyrazol-4-yl)nicotinamide Using (R)-3-amino-N-(4-fluorophenyl)pyrrolidine-1-carbothioamide, the title compound was obtained as described in general method A. MS (ESI, m/z): 440.2 [M+H]$^+$

Example 043

(R)-2-amino-N-(1-(benzylcarbamothioyl)pyrrolidin-3-yl)-5-(1-methyl-1H-pyrazol-4-yl)nicotinamide Using (R)-3-amino-N-benzylpyrrolidine-1-carbothioamide, the title compound was obtained as described in general method A. MS (ESI, m/z): 436.2 [M+H]$^+$

Example 044

(R)-2-amino-N-(1-((3,4-dichlorophenyl)carbamothioyl)pyrrolidin-3-yl)-5-(1-methyl-1H-pyrazol-4-yl)nicotinamide Using (R)-3-amino-N-(3,4-dichlorophenyl)pyrrolidine-1-carbothioamide, the title compound was obtained as described in general method A. MS (ESI, m/z): 490.2 [M+H]$^+$

Example 045

(R)-2-amino-N-(1-((4-methoxyphenyl)carbamothioyl)pyrrolidin-3-yl)-5-(1-methyl-1H-pyrazol-4-yl)nicotinamide Using (R)-3-amino-N-(4-methoxyphenyl)pyrrolidine-1-carbothioamide, the title compound was obtained as described in general method A. MS (ESI, m/z): 452.2 [M+H]$^+$

Example 046

(R)-2-amino-N-(1-((4-bromophenyl)carbamothioyl)pyrrolidin-3-yl)-5-(1-methyl-1H-pyrazol-4-yl)nicotinamide Using (R)-3-amino-N-(4-bromophenyl)pyrrolidine-1-carbothioamide, the title compound was obtained as described in general method A. MS (ESI, m/z): 500.2 [M+H]$^+$

Example 047

(R)-2-amino-5-(1-methyl-1H-pyrazol-4-yl)-N-(1-((4-nitrophenyl)carbamothioyl)pyrrolidin-3-yl)nicotinamide Using (R)-3-amino-N-(4-nitorphenyl)pyrrolidine-1-carbothioamide, the title compound was obtained as described in general method A. MS (ESI, m/z): 467.2 [M+H]$^+$

Example 048

(R)-2-amino-N-(1-((4-(dimethylamino)phenyl)carbamothioyl)pyrrolidin-3-yl)-5-(1-methyl-1H-pyrazol-4-yl)nicotinamide Using (R)-3-amino-N-(4-dimethylaminophenyl)pyrrolidine-1-carbothioamide, the title compound was obtained as described in general method A. MS (ESI, m/z): 465.2 [M+H]$^+$

Example 049

(R)-2-amino-5-(1-methyl-1H-pyrazol-4-yl)-N-(1-((4-morpholinophenyl)carbamothioyl)pyrrolidin-3-yl)nicotinamide Using (R)-3-amino-N-(4-(1-morpholino)phenyl)pyrrolidine-1-carbothioamide, the title compound was obtained as described in general method A. MS (ESI, m/z): 507.2 [M+H]$^+$

Example 050

(R)-2-amino-N-(1-((3,5-dichlorophenyl)carbamothioyl)pyrrolidin-3-yl)-5-(1-methyl-1H-pyrazol-4-yl)nicotinamide Using (R)-3-amino-N-(3,5-dichlorohenyl)pyrrolidine-1-carbothioamide, the title compound was obtained as described in general method A. MS (ESI, m/z): 490.2 [M+H]$^+$

Example 051

(R)—N-(1-([1,1'-biphenyl]-3-ylcarbamothioyl)pyrrolidin-3-yl)-2-amino-5-(1-methyl-1H-pyrazol-4-yl)nicotinamide Using (R)-3-amino-N-(3-biphenyl)pyrrolidine-1-carbothioamide, the title compound was obtained as described in general method A. MS (ESI, m/z): 498.2 [M+H]$^+$

Example 052

(R)-2-amino-N-(1-((3-bromophenyl)carbamothioyl)pyrrolidin-3-yl)-5-(1-methyl-1H-pyrazol-4-yl)nicotinamide Using (R)-3-amino-N-(3-bromophenyl)pyrrolidine-1-carbothioamide, the title compound was obtained as described in general method A. MS (ESI, m/z): 500.2 [M+H]$^+$

Example 053

3-bromophenyl (R)-3-(2-amino-5-(1-methyl-1H-pyrazol-4-yl)nicotinamido)pyrrolidine-1-carboxylate Using 3-bromophenyl (R)-3-aminopyrrolidine-1-carboxylate, the title compound was obtained as described in general method A. MS (ESI, m/z): 485.2/487.2 [M+H]$^+$

Example 054 phenyl (R)-3-(2-amino-5-(1-methyl-1H-pyrazol-4-yl)nicotinamido)pyrrolidine-1-carboxylate Using phenyl (R)-3-aminopyrrolidine-1-carboxylate, the title compound was obtained as described in general method A. MS (ESI, m/z): 407.2 [M+H]$^+$

Example 055

3-(piperidine-1-carbonyl)phenyl (R)-3-(2-amino-5-(1-methyl-1H-pyrazol-4-yl)nicotinamido)pyrrolidine-1-carboxylate Using 3-(piperidine-1-carbonyl)phenyl (R)-3-aminopyrrolidine-1-carboxylate, the title compound was obtained as described in general method A. MS (ESI, m/z): 518.2 [M+H]$^+$

Example 056

5,6,7,8-tetrahydronaphthalen-2-yl (R)-3-(2-amino-5-(1-methyl-1H-pyrazol-4-yl)nicotinamido)pyrrolidine-1-carboxylate Using 5,6,7,8-tetrahydronaphthalen-2-yl (R)-3-aminopyrrolidine-1-carboxylate, the title compound was obtained as described in general method A. MS (ESI, m/z): 461.2 [M+H]$^+$

Example 057

3-isopropyl-5-methylphenyl (R)-3-(2-amino-5-(1-methyl-1H-pyrazol-4-yl)nicotinamido)pyrrolidine-1-carboxylate Using 3-isopropyl-5-methylphenyl (R)-3-aminopyrrolidine-1-carboxylate, the title compound was obtained as described in general method A. MS (ESI, m/z): 463.2 [M+H]$^+$

Example 058

2-(benzyloxy)phenyl (R)-3-(2-amino-5-(1-methyl-1H-pyrazol-4-yl)nicotinamido)pyrrolidine-1-carboxylate Using 2-benzyloxyphenyl (R)-3-aminopyrrolidine-1-carboxylate, the title compound was obtained as described in general method A. MS (ESI, m/z): 513.2 [M+H]$^+$

Example 059

3-(benzyloxy)phenyl (R)-3-(2-amino-5-(1-methyl-1H-pyrazol-4-yl)nicotinamido)pyrrolidine-1-carboxylate Using 3-benzyloxyphenyl (R)-3-aminopyrrolidine-1-carboxylate, the title compound was obtained as described in general method A. MS (ESI, m/z): 513.2 [M+H]$^+$

Example 060

2,3-dichlorophenyl (R)-3-(2-amino-5-(1-methyl-1H-pyrazol-4-yl)nicotinamido)pyrrolidine-1-carboxylate Using 2,3-dichlorophenyl (R)-3-aminopyrrolidine-1-carboxylate, the title compound was obtained as described in general method A. MS (ESI, m/z): 475.2 [M+H]$^+$

Example 061

2,5-dichlorophenyl (R)-3-(2-amino-5-(1-methyl-1H-pyrazol-4-yl)nicotinamido)pyrrolidine-1-carboxylate Using 2,5-dichlorophenyl (R)-3-aminopyrrolidine-1-carboxylate, the title compound was obtained as described in general method A. MS (ESI, m/z): 475.2 [M+H]$^+$

Example 062

2-cyanophenyl (R)-3-(2-amino-5-(1-methyl-1H-pyrazol-4-yl)nicotinamido)pyrrolidine-1-carboxylate Using 2-cyanophenyl (R)-3-aminopyrrolidine-1-carboxylate, the title compound was obtained as described in general method A. MS (ESI, m/z): 432.2 [M+H]$^+$

Example 063

4-bromo-2-methoxyphenyl (R)-3-(2-amino-5-(1-methyl-1H-pyrazol-4-yl)nicotinamido)pyrrolidine-1-carboxylate Using 4-bromo-2-methoxyphenyl (R)-3-aminopyrrolidine-1-carboxylate, the title compound was obtained as described in general method A. MS (ESI, m/z): 515.2 [M+H]$^+$

Example 064

3-(methoxycarbonyl)phenyl (R)-3-(2-amino-5-(1-methyl-1H-pyrazol-4-yl)nicotinamido)pyrrolidine-1-carboxylate Using 3-(methoxycarbonyl)phenyl (R)-3-aminopyrrolidine-1-carboxylate, the title compound was obtained as described in general method A. MS (ESI, m/z): 465.2 [M+H]$^+$

Example 065

5-methoxy-2-(methoxycarbonyl)phenyl (R)-3-(2-amino-5-(1-methyl-1H-pyrazol-4-yl)nicotinamido)pyrrolidine-1-carboxylate Using 5-methoxy-2-(methoxycarbonyl)phenyl (R)-3-aminopyrrolidine-1-carboxylate, the title compound was obtained as described in general method A. MS (ESI, m/z): 495.2 [M+H]$^+$

Example 066 cyclohexyl (R)-3-(2-amino-5-(1-methyl-1H-pyrazol-4-yl)nicotinamido)pyrrolidine-1-carboxylate Using cyclohexyl (R)-3-aminopyrrolidine-1-carboxylate, the title compound was obtained as described in general method A. MS (ESI, m/z): 413.2 [M+H]$^+$

Example 067

6-bromonaphthalen-2-yl (R)-3-(2-amino-5-(1-methyl-1H-pyrazol-4-yl)nicotinamido)pyrrolidine-1-carboxylate Using 6-bromonaphthalen-2-yl (R)-3-aminopyrrolidine-1-carboxylate, the title compound was obtained as described in general method A. MS (ESI, m/z): 535.2 [M+H]$^+$

Example 068 naphthalen-1-yl (R)-3-(2-amino-5-(1-methyl-1H-pyrazol-4-yl)nicotinamido)pyrrolidine-1-carboxylate Using naphthalen-1-yl (R)-3-aminopyrrolidine-1-carboxylate, the title compound was obtained as described in general method A. MS (ESI, m/z): 457.2 [M+H]$^+$

Example 069

1-aminonaphthalen-2-yl (R)-3-(2-amino-5-(1-methyl-1H-pyrazol-4-yl)nicotinamido)pyrrolidine-1-carboxylate Using 1-aminonaphthalen-2-yl (R)-3-aminopyrrolidine-1-carboxylate, the title compound was obtained as described in general method A. MS (ESI, m/z): 472.2 [M+H]$^+$

Example 070

2-aminophenyl (R)-3-(2-amino-5-(1-methyl-1H-pyrazol-4-yl)nicotinamido)pyrrolidine-1-carboxylate Using 2-aminophenyl (R)-3-aminopyrrolidine-1-carboxylate, the title compound was obtained as described in general method A. MS (ESI, m/z): 422.2 [M+H]$^+$

Example 071

2-(hydroxymethyl)phenyl (R)-3-(2-amino-5-(1-methyl-1H-pyrazol-4-yl)nicotinamido)pyrrolidine-1-carboxylate Using 2-hydroxymethylphenyl (R)-3-aminopyrrolidine-1-carboxylate, the title compound was obtained as described in general method A. MS (ESI, m/z): 437.2 [M+H]$^+$

Example 072 quinolin-6-yl (R)-3-(2-amino-5-(1-methyl-1H-pyrazol-4-yl)nicotinamido)pyrrolidine-1-carboxylate Using quinolin-6-yl (R)-3-aminopyrrolidine-1-carboxylate, the title compound was obtained as described in general method A. MS (ESI, m/z): 458.2 [M+H]$^+$

Example 073 quinolin-8-yl (R)-3-(2-amino-5-(1-methyl-1H-pyrazol-4-yl)nicotinamido)pyrrolidine-1-carboxylate Using quinolin-8-yl (R)-3-aminopyrrolidine-1-carboxylate, the title compound was obtained as described in general method A. MS (ESI, m/z): 458.2 [M+H]$^+$

Example 074

3-(ethylamino)-4-methylphenyl (R)-3-(2-amino-5-(1-methyl-1H-pyrazol-4-yl)nicotinamido)pyrrolidine-1-carboxylate Using 3-(ethylamino)-4-methylphenyl (R)-3-aminopyrrolidine-1-carboxylate, the title compound was obtained as described in general method A. MS (ESI, m/z): 464.2 [M+H]$^+$

Example 075

4-chloro-2-cyclohexylphenyl (R)-3-(2-amino-5-(1-methyl-1H-pyrazol-4-yl)nicotinamido)pyrrolidine-1-carboxylate Using 4-chloro-2-cyclohexylphenyl (R)-3-aminopyrrolidine-1-carboxylate, the title compound was obtained as described in general method A. MS (ESI, m/z): 523.2 [M+H]$^+$

Example 076

3-acetamidophenyl (R)-3-(2-amino-5-(1-methyl-1H-pyrazol-4-yl)nicotinamido)pyrrolidine-1-carboxylate Using 3-acetamidophenyl (R)-3-aminopyrrolidine-1-carboxylate, the title compound was obtained as described in general method A. MS (ESI, m/z): 464.2 [M+H]$^+$

Example 077

4-(methylsulfonyl)phenyl (R)-3-(2-amino-5-(1-methyl-1H-pyrazol-4-yl)nicotinamido)pyrrolidine-1-carboxylate Using 4-(methylsulfonyl)phenyl (R)-3-aminopyrrolidine-1-carboxylate, the title compound was obtained as described in general method A. MS (ESI, m/z): 485.2 [M+H]$^+$

Example 078

2-((dimethylamino)methyl)phenyl (R)-3-(2-amino-5-(1-methyl-1H-pyrazol-4-yl)nicotinamido)pyrrolidine-1-carboxylate Using 2-(N,N-dimethylaminomethyl)phenyl (R)-3-aminopyrrolidine-1-carboxylate, the title compound was obtained as described in general method A. MS (ESI, m/z): 464.2 [M+H]$^+$

Example 079

3,5-dimethylcyclohexyl (3R)-3-(2-amino-5-(1-methyl-1H-pyrazol-4-yl)nicotinamido)pyrrolidine-1-carboxylate Using 3,5-dimethylcyclohexyl (3R)-3-aminopyrrolidine-1-carboxylate, the title compound was obtained as described in general method A. MS (ESI, m/z): 441.2 [M+H]$^+$

Example 080 benzyl (R)-3-(2-amino-5-(1-methyl-1H-pyrazol-4-yl)nicotinamido)pyrrolidine-1-carboxylate Using benzyl (R)-3-aminopyrrolidine-1-carboxylate, the title compound was obtained as described in general method A. MS (ESI, m/z): 421.2 [M+H]$^+$

Example 081

[1,1'-biphenyl]-3-yl (R)-3-(2-amino-5-(4-(hydroxymethyl)phenyl)nicotinamido)pyrrolidine-1-carboxylate Using 4-hydroxymethylphenylboronic acid and [1,1'-biphenyl]-3-yl (R)-3-aminopyrrolidine-1-carboxylate, the title compound was obtained as described in general method A. MS (ESI, m/z): 509.2 [M+H]$^+$

Example 082

[1,1'-biphenyl]-3-yl (R)-3-(2-amino-5-(4-((4-methylpiperazin-1-yl)methyl)phenyl)nicotinamido)pyrrolidine-1-carboxylate Using (4-((4-methylpiperazin-1-yl)methyl)phenyl)boronic acid pinacol ester and [1,1'-biphenyl]-3-yl (R)-3-aminopyrrolidine-1-carboxylate, the title compound was obtained as described in general method A. MS (ESI, m/z): 591.2 [M+H]$^+$

Example 083

[1,1'-biphenyl]-3-yl (R)-3-(2-amino-5-(4-(morpholine-4-carbonyl)phenyl)nicotinamido)pyrrolidine-1-carboxylate Using (4-(morpholine-4-carbonyl)phenyl)boronic acid and [1,1'-biphenyl]-3-yl (R)-3-aminopyrrolidine-1-carboxylate, the title compound was obtained as described in general method A. MS (ESI, m/z): 592.2 [M+H]$^+$

Example 084

[1,1'-biphenyl]-3-yl (R)-3-(2-amino-5-(3,4-difluorophenyl)nicotinamido)pyrrolidine-1-carboxylate Using 3,4-difluorophenylboronic acid and [1,1'-biphenyl]-3-yl (R)-3-aminopyrrolidine-1-carboxylate, the title compound was obtained as described in general method A. MS (ESI, m/z): 515.2 [M+H]$^+$

Example 085

[1,1'-biphenyl]-3-yl (R)-3-(2-amino-5-bromonicotinamido)pyrrolidine-1-carboxylate Using 2-amino-5-bromonicotinic acid and [1,1'-biphenyl]-3-yl (R)-3-aminopyrrolidine-1-carboxylate, the title compound was obtained as described in general method A. MS (ESI, m/z): 481.2 [M+H]$^+$

Example 086

4-chloro-3-methylphenyl (R)-3-(2-amino-5-(1-methyl-1H-pyrazol-4-yl)nicotinamido)pyrrolidine-1-carboxylate Using 4-chloro-3-methylphenyl (R)-3-aminopyrrolidine-1-carboxylate, the title compound was obtained as described in general method A. MS (ESI, m/z): 455.2 [M+H]$^+$

Example 087

3-cyanophenyl (R)-3-(2-amino-5-(1-methyl-1H-pyrazol-4-yl)nicotinamido)pyrrolidine-1-carboxylate Using 3-cyanophenyl (R)-3-aminopyrrolidine-1-carboxylate, the title compound was obtained as described in general method A. MS (ESI, m/z): 432.2 [M+H]$^+$

Example 088

3,4-dichlorophenyl (R)-3-(2-amino-5-(1-methyl-1H-pyrazol-4-yl)nicotinamido)pyrrolidine-1-carboxylate Using 3,4-dichlorophenyl (R)-3-aminopyrrolidine-1-carboxylate, the title compound was obtained as described in general method A. MS (ESI, m/z): 475.2 [M+H]$^+$

Example 089

4-amino-3-chlorophenyl (R)-3-(2-amino-5-(1-methyl-1H-pyrazol-4-yl)nicotinamido)pyrrolidine-1-carboxylate Using 4-amino-3-chlorophenyl (R)-3-aminopyrrolidine-1-carboxylate, the title compound was obtained as described in general method A. MS (ESI, m/z): 456.2 [M+H]$^+$

Example 090

3,5-difluorophenyl (R)-3-(2-amino-5-(1-methyl-1H-pyrazol-4-yl)nicotinamido)pyrrolidine-1-carboxylate Using 3,5-difluorophenyl (R)-3-aminopyrrolidine-1-carboxylate, the title compound was obtained as described in general method A. MS (ESI, m/z): 443.2 [M+H]$^+$

Example 091

3,5-dimethylphenyl (R)-3-(2-amino-5-(1-methyl-1H-pyrazol-4-yl)nicotinamido)pyrrolidine-1-carboxylate Using 3,5-dimethylphenyl (R)-3-aminopyrrolidine-1-carboxylate, the title compound was obtained as described in general method A. MS (ESI, m/z): 435.2 [M+H]$^+$

Example 092

2-(methoxycarbonyl)phenyl (R)-3-(2-amino-5-(1-methyl-1H-pyrazol-4-yl)nicotinamido)pyrrolidine-1-carboxylate Using 2-(methoxycarbonyl)phenyl (R)-3-aminopyrrolidine-1-carboxylate, the title compound was obtained as described in general method A. MS (ESI, m/z): 465.2 [M+H]$^+$

Example 093

4-ethylphenyl (R)-3-(2-amino-5-(1-methyl-1H-pyrazol-4-yl)nicotinamido)pyrrolidine-1-carboxylate Using 4-ethylphenyl (R)-3-aminopyrrolidine-1-carboxylate, the title compound was obtained as described in general method A. MS (ESI, m/z): 435.2 [M+H]$^+$

Example 094

3,4-dimethylphenyl (R)-3-(2-amino-5-(1-methyl-1H-pyrazol-4-yl)nicotinamido)pyrrolidine-1-carboxylate Using 3,4-dimethylphenyl (R)-3-aminopyrrolidine-1-carboxylate, the title compound was obtained as described in general method A. MS (ESI, m/z): 435.2 [M+H]$^+$

Example 095

7-hydroxynaphthalen-2-yl (R)-3-(2-amino-5-(1-methyl-1H-pyrazol-4-yl)nicotinamido)pyrrolidine-1-carboxylate Using 7-hydroxynaphthalen-2-yl (R)-3-aminopyrrolidine-1-carboxylate, the title compound was obtained as described in general method A. MS (ESI, m/z): 473.2 [M+H]$^+$

Example 096

[1,1'-biphenyl]-3-yl (R)-3-(2-amino-5-(1-(1-methylpiperidin-4-yl)-1H-pyrazol-4-yl)nicotinamido)pyrrolidine-1-carboxylate Using (1-(1-methylpiperidin-4-yl)-1H-pyrazol-4-yl)boronic acid pinacol ester and [1,1'-biphenyl]-3-yl (R)-3-aminopyrrolidine-1-carboxylate, the title compound was obtained as described in general method A. MS (ESI, m/z): 566.2 [M+H]$^+$

Example 097

3-hydroxynaphthalen-2-yl (R)-3-(2-amino-5-(1-methyl-1H-pyrazol-4-yl)nicotinamido)pyrrolidine-1-carboxylate Using 3-hydroxynaphthalen-2-yl (R)-3-aminopyrrolidine-1-carboxylate, the title compound was obtained as described in general method A. MS (ESI, m/z): 473.2 [M+H]$^+$

Example 098

2-hydroxyphenyl (R)-3-(2-amino-5-(1-methyl-1H-pyrazol-4-yl)nicotinamido)pyrrolidine-1-carboxylate Using 2-hydroxyphenyl (R)-3-aminopyrrolidine-1-carboxylate, the title compound was obtained as described in general method A. MS (ESI, m/z): 423.2 [M+H]$^+$

Example 099

2-amino-4-chlorophenyl (R)-3-(2-amino-5-(1-methyl-1H-pyrazol-4-yl)nicotinamido)pyrrolidine-1-carboxylate Using 2-amino-4-chlorophenyl (R)-3-aminopyrrolidine-1-carboxylate, the title compound was obtained as described in general method A. MS (ESI, m/z): 456.2 [M+H]$^+$

Example 100

2-amino-5-nitrophenyl (R)-3-(2-amino-5-(1-methyl-1H-pyrazol-4-yl)nicotinamido)pyrrolidine-1-carboxylate Using 2-amino-5-nitrophenyl (R)-3-aminopyrrolidine-1-carboxylate, the title compound was obtained as described in general method A. MS (ESI, m/z): 467.2 [M+H]$^+$

Example 101

3-hydroxyphenyl (R)-3-(2-amino-5-(1-methyl-1H-pyrazol-4-yl)nicotinamido)pyrrolidine-1-carboxylate Using 3-hydroxyphenyl (R)-3-aminopyrrolidine-1-carboxylate, the title compound was obtained as described in general method A. MS (ESI, m/z): 423.2 [M+H]$^+$

Example 102

4-phenoxyphenyl (R)-3-(2-amino-5-(1-methyl-1H-pyrazol-4-yl)nicotinamido)pyrrolidine-1-carboxylate Using 4-phenoxyphenyl (R)-3-aminopyrrolidine-1-carboxylate, the title compound was obtained as described in general method A. MS (ESI, m/z): 499.2 [M+H]$^+$

Example 103 naphthalen-2-yl (R)-3-(2-amino-5-(1-methyl-1H-pyrazol-4-yl)nicotinamido)pyrrolidine-1-carboxylate Using naphthalen-2-yl (R)-3-aminopyrrolidine-1-carboxylate, the title compound was obtained as described in general method A. MS (ESI, m/z): 457.2 [M+H]$^+$

Example 104

6-hydroxynaphthalen-2-yl (R)-3-(2-amino-5-(1-methyl-1H-pyrazol-4-yl)nicotinamido)pyrrolidine-1-carboxylate Using 6-hydroxynaphthalen-2-yl (R)-3-aminopyrrolidine-1-carboxylate, the title compound was obtained as described in general method A. MS (ESI, m/z): 473.2 [M+H]$^+$

Example 105

(1R,2S,4S)-bicyclo[2.2.1]heptan-2-yl (R)-3-(2-amino-5-(1-methyl-1H-pyrazol-4-yl)nicotinamido)pyrrolidine-1-carboxylate Using (1R,2S,4S)-bicyclo[2.2.1]heptan-2-yl (R)-3-aminopyrrolidine-1-carboxylate, the title compound was obtained as described in general method A. MS (ESI, m/z): 425.2 [M+H]$^+$

Example 106 cyclopentyl (R)-3-(2-amino-5-(1-methyl-1H-pyrazol-4-yl)nicotinamido)pyrrolidine-1-carboxylate Using cyclopentyl (R)-3-aminopyrrolidine-1-carboxylate, the title compound was obtained as described in general method A. MS (ESI, m/z): 399.2 [M+H]$^+$

Example 107 cycloheptyl (R)-3-(2-amino-5-(1-methyl-1H-pyrazol-4-yl)nicotinamido)pyrrolidine-1-carboxylate Using cycloheptyl (R)-3-aminopyrrolidine-1-carboxylate, the title compound was obtained as described in general method A. MS (ESI, m/z): 427.2 [M+H]$^+$

Example 108

(1R,2S)-2-methylcyclohexyl (R)-3-(2-amino-5-(1-methyl-1H-pyrazol-4-yl)nicotinamido)pyrrolidine-1-carboxylate Using (1R,2S)-2-methylcyclohexyl (R)-3-aminopyrrolidine-1-carboxylate, the title compound was obtained as described in general method A. MS (ESI, m/z): 427.2 [M+H]$^+$

Example 109

(1S,2S,4R)-bicyclo[2.2.1]heptan-2-yl (R)-3-(2-amino-5-(1-methyl-1H-pyrazol-4-yl)nicotinamido)pyrrolidine-1-carboxylate Using (1S,2S,4R)-bicyclo[2.2.1]heptan-2-yl (R)-3-aminopyrrolidine-1-carboxylate, the title compound was obtained as described in general method A. MS (ESI, m/z): 425.2 [M+H]$^+$

Example 110

3-phenoxyphenyl (R)-3-(2-amino-5-(1-methyl-1H-pyrazol-4-yl)nicotinamido)pyrrolidine-1-carboxylate Using 3-phenoxyphenyl (R)-3-aminopyrrolidine-1-carboxylate, the title compound was obtained as described in general method A. MS (ESI, m/z): 499.2 [M+H]$^+$

Example 111

4-(4-nitrophenoxy)phenyl (R)-3-(2-amino-5-(1-methyl-1H-pyrazol-4-yl)nicotinamido)pyrrolidine-1-carboxylate Using 4-(4-nitrophenoxy)phenyl (R)-3-aminopyrrolidine-1-carboxylate, the title compound was obtained as described in general method A. MS (ESI, m/z): 544.2 [M+H]$^+$

Example 112

4-(4-aminophenoxy)phenyl (R)-3-(2-amino-5-(1-methyl-1H-pyrazol-4-yl)nicotinamido)pyrrolidine-1-carboxylate Using 4-(4-aminophenoxy)phenyl (R)-3-aminopyrrolidine-1-carboxylate, the title compound was obtained as described in general method A. MS (ESI, m/z): 514.2 [M+H]$^+$

Example 113

4-(4-((4-methylpiperazin-1-yl)methyl)phenoxy)phenyl (R)-3-(2-amino-5-(1-methyl-1H-pyrazol-4-yl)nicotinamido)pyrrolidine-1-carboxylate Using 4-(4-((4-methylpiperazin-1-yl)methyl)phenoxy)phenyl (R)-3-aminopyrrolidine-1-carboxylate, the title compound was obtained as described in general method A. MS (ESI, m/z): 611.2 [M+H]$^+$

Example 114

4-(4-(hydroxymethyl)phenoxy)phenyl (R)-3-(2-amino-5-(1-methyl-1H-pyrazol-4-yl)nicotinamido)pyrrolidine-1-carboxylate Using 4-(4-(hydroxymethyl)phenoxy)phenyl (R)-3-aminopyrrolidine-1-carboxylate, the title compound was obtained as described in general method A. MS (ESI, m/z): 529.2 [M+H]$^+$

Example 115

4-(4-((dimethylamino)methyl)phenoxy)phenyl (R)-3-(2-amino-5-(1-methyl-1H-pyrazol-4-yl)nicotinamido)pyrrolidine-1-carboxylate Using 4-(4-(N,N-dimethylaminomethyl)phenoxy)phenyl (R)-3-aminopyrrolidine-1-carboxylate, the title compound was obtained as described in general method A. MS (ESI, m/z): 556.2 [M+H]$^+$

Example 116

3,5-dichlorophenyl (R)-3-(2-amino-5-(1-methyl-1H-pyrazol-4-yl)nicotinamido)pyrrolidine-1-carboxylate Using 3,5-dichlorophenyl (R)-3-aminopyrrolidine-1-carboxylate, the title compound was obtained as described in general method A. MS (ESI, m/z): 475.10 [M+H]$^+$

Example 117

[1,1'-biphenyl]-3-yl (R)-3-(2-amino-5-(1-methyl-1H-pyrazol-4-yl)nicotinamido)pyrrolidine-1-carboxylate Using [1,1'-biphenyl]-3-yl (R)-3-aminopyrrolidine-1-carboxylate, the title compound was obtained as described in general method A. MS (ESI, m/z): 483.21 [M+H]$^+$

Example 118 phenyl (R)-3-(2-amino-5-(4-((4-methylpiperazin-1-yl)methyl)phenyl)nicotinamido)pyrrolidine-1-carboxylate Using (4-((4-methylpiperazin-1-yl)methyl)phenyl)boronic acid pinacol ester and phenyl (R)-3-aminopyrrolidine-1-carboxylate, the title compound was obtained as described in general method A. MS (ESI, m/z): 515.27 [M+H]$^+$

Example 119 phenyl (R)-3-(2-amino-5-(1-(1-methylpiperidin-4-yl)-1H-pyrazol-4-yl)nicotinamido)pyrrolidine-1-carboxylate Using (1-(1-methylpiperidin-4-yl)-1H-pyrazol-4-yl)boronic acid pinacol ester and phenyl (R)-3-aminopyrrolidine-1-carboxylate, the title compound was obtained as described in general method A. MS (ESI, m/z): 490.25 [M+H]$^+$

Example 120

(1S,2S)-2-(benzyloxy)cyclopentyl (R)-3-(2-amino-5-(1-methyl-1H-pyrazol-4-yl)nicotinamido)pyrrolidine-1-carboxylate Using (1S,2S)-2-(benzyloxy)cyclopentyl (R)-3-aminopyrrolidine-1-carboxylate, the title compound was obtained as described in general method A. MS (ESI, m/z): 505.25 [M+H]$^+$

Example 121

3-phenylcyclopentyl (3R)-3-(2-amino-5-(1-methyl-1H-pyrazol-4-yl)nicotinamido)pyrrolidine-1-carboxylate Using 3-phenylcyclopentyl (3R)-3-aminopyrrolidine-1-carboxylate, the title compound was obtained as described in general method A. MS (ESI, m/z): 475.24 [M+H]$^+$

Example 122

1-benzylpiperidin-3-yl (3R)-3-(2-amino-5-(1-methyl-1H-pyrazol-4-yl)nicotinamido)pyrrolidine-1-carboxylate Using 1-benzylpiperidin-3-yl (3R)-3-aminopyrrolidine-1-carboxylate, the title compound was obtained as described in general method A. MS (ESI, m/z): 504.26 [M+H]$^+$

Example 123

1-(4-formylphenyl)piperidin-3-yl (3R)-3-(2-amino-5-(1-methyl-1H-pyrazol-4-yl)nicotinamido)pyrrolidine-1-carboxylate Using 1-(4-formylphenyl)piperidin-3-yl (3R)-3-aminopyrrolidine-1-carboxylate, the title compound was obtained as described in general method A. MS (ESI, m/z): 518.24 [M+H]$^+$

Example 124

1-(4-((4-methylpiperazin-1-yl)methyl)phenyl)piperidin-3-yl (3R)-3-(2-amino-5-(1-methyl-1H-pyrazol-4-yl)nicotinamido)pyrrolidine-1-carboxylate Using 1-(4-((4-methylpiperazin-1-yl)methyl)phenyl)piperidin-3-yl (3R)-3-aminopyrrolidine-1-carboxylate, the title compound was obtained as described in general method A. MS (ESI, m/z): 602.35 [M+H]$^+$

Example 125

4-phenylcyclohexyl (R)-3-(2-amino-5-(1-methyl-1H-pyrazol-4-yl)nicotinamido)pyrrolidine-1-carboxylate Using 4-phenylcyclohexyl (R)-3-aminopyrrolidine-1-carboxylate, the title compound was obtained as described in general method A. MS (ESI, m/z): 489.25 [M+H]$^+$

Example 126

1-phenylpyrrolidin-3-yl (3R)-3-(2-amino-5-(1-methyl-1H-pyrazol-4-yl)nicotinamido)pyrrolidine-1-carboxylate Using 1-phenylpyrrolidin-3-yl (3R)-3-aminopyrrolidine-1-carboxylate, the title compound was obtained as described in general method A. MS (ESI, m/z): 476.23 [M+H]$^+$

Example 127

(R)-1-phenylpyrrolidin-3-yl (R)-3-(2-amino-5-(1-methyl-1H-pyrazol-4-yl)nicotinamido)pyrrolidine-1-carboxylate Using (R)-1-phenylpyrrolidin-3-yl (R)-3-aminopyrrolidine-1-carboxylate, the title compound was obtained as described in general method A. MS (ESI, m/z): 476.23 [M+H]$^+$

Example 128

(S)-1-phenylpyrrolidin-3-yl (R)-3-(2-amino-5-(1-methyl-1H-pyrazol-4-yl)nicotinamido)pyrrolidine-1-carboxylate Using (S)-1-phenylpyrrolidin-3-yl (R)-3-aminopyrrolidine-1-carboxylate, the title compound was obtained as described in general method A. MS (ESI, m/z): 476.23 [M+H]$^+$

Example 129

3-phenylcyclohexyl (3R)-3-(2-amino-5-(1-methyl-1H-pyrazol-4-yl)nicotinamido)pyrrolidine-1-carboxylate Using 3-phenylcyclohexyl (3R)-3-aminopyrrolidine-1-carboxylate, the title compound was obtained as described in general method A. MS (ESI, m/z): 489.25 [M+H]$^+$

Example 130

[1,1'-biphenyl]-3-yl (R)-3-(2-amino-N-methyl-5-(1-methyl-1H-pyrazol-4-yl)nicotinamido)pyrrolidine-1-carboxylate Using [1,1'-biphenyl]-3-yl (R)-3-(methylamino)pyrrolidine-1-carboxylate, the title compound was obtained as described in general method A. MS (ESI, m/z): 497.25 [M+H]$^+$

Example 131

(R)-2-amino-N-(1-benzylpyrrolidin-3-yl)-N-methyl-5-(1-methyl-1H-pyrazol-4-yl)nicotinamide Using (R)-1-benzyl-N-methylpyrrolidin-3-amine, the title compound was obtained as described in general method A. MS (ESI, m/z): 391.22 [M+H]$^+$

Example 132

(R)-2-amino-N-(1-(2-chlorobenzyl)pyrrolidin-3-yl)-N-methyl-5-(1-methyl-1H-pyrazol-4-yl)nicotinamide Using (R)-1-(2-chlorobenzyl)-N-methylpyrrolidin-3-amine, the title compound was obtained as described in general method A. MS (ESI, m/z): 425.18 [M+H]$^+$

Example 133

(R)—N-(1-(1H-benzo[d]imidazol-2-yl)pyrrolidin-3-yl)-2-amino-5-(1-methyl-1H-pyrazol-4-yl)nicotinamide Using (R)-1-(1H-benzo[d]imidazol-2-yl)pyrrolidin-3-amine, the title compound was obtained as described in general method A. MS (ESI, m/z): 403.2 [M+H]$^+$

Example 134

(R)-2-amino-5-(1-methyl-1H-pyrazol-4-yl)-N-(1-(p-tolyl)pyrrolidin-3-yl)nicotinamide Using (R)-1-(p-tolyl)pyrrolidin-3-amine, the title compound was obtained as described in general method A. MS (ESI, m/z): 377.2 [M+H]$^+$

Example 135

(R)-2-amino-5-(1-methyl-1H-pyrazol-4-yl)-N-(1-(pyridin-2-yl)pyrrolidin-3-yl)nicotinamide Using (R)-1-(pyridin-2-yl)pyrrolidin-3-amine, the title compound was obtained as described in general method A. MS (ESI, m/z): 364.2 [M+H]$^+$

Example 136

(R)-2-amino-N-(1-(5-ethylpyrimidin-2-yl)pyrrolidin-3-yl)-5-(1-methyl-1H-pyrazol-4-yl)nicotinamide Using (R)-1-(5-ethylpyrimidin-2-yl)pyrrolidin-3-amine, the title compound was obtained as described in general method A. MS (ESI, m/z): 393.2 [M+H]$^+$

Example 137

(R)-2-amino-5-(1-methyl-1H-pyrazol-4-yl)-N-(1-(quinazolin-2-yl)pyrrolidin-3-yl)nicotinamide Using (R)-1-(quinazolin-2-yl)pyrrolidin-3-amine, the title compound was obtained as described in general method A. MS (ESI, m/z): 415.2 [M+H]$^+$

Example 138

(R)-2-amino-5-(1-methyl-1H-pyrazol-4-yl)-N-(1-(5-nitrothiazol-2-yl)pyrrolidin-3-yl)nicotinamide Using (R)-1-(5-nitrothiazol-2-yl)pyrrolidin-3-amine, the title compound was obtained as described in general method A. MS (ESI, m/z): 415.2 [M+H]$^+$

Example 139 ethyl (R)-2-(3-(2-amino-5-(1-methyl-1H-pyrazol-4-yl)nicotinamido)pyrrolidin-1-yl)thiazole-4-carboxylate Using ethyl (R)-2-(3-aminopyrrolidin-1-yl)thiazole-4-carboxylate, the title compound was obtained as described in general method A. MS (ESI, m/z): 442.2 [M+H]$^+$

Example 140

(R)-2-amino-N-(1-(benzylsulfonyl)pyrrolidin-3-yl)-5-(1-methyl-1H-pyrazol-4-yl)nicotinamide Using (R)-1-(benzylsulfonyl)pyrrolidin-3-amine, the title compound was obtained as described in general method A. MS (ESI, m/z): 441.16 [M+H]$^+$

Example 141

(R)-2-amino-5-(1-methyl-1H-pyrazol-4-yl)-N-(1-(phenylsulfonyl)pyrrolidin-3-yl)nicotinamide Using (R)-1-(phenylsulfonyl)pyrrolidin-3-amine, the title compound was obtained as described in general method A. MS (ESI, m/z): 427.15 [M+H]$^+$

Example 142

(R)-2-amino-N-(1-((2,4-dichlorophenyl)sulfonyl)pyrrolidin-3-yl)-5-(1-methyl-1H-pyrazol-4-yl)nicotinamide Using (R)-1-((2,4-dichlorophenyl)sulfonyl)pyrrolidin-3-amine, the title compound was obtained as described in general method A. MS (ESI, m/z): 495.07 [M+H]$^+$

Example 143

(R)-2-amino-N-(1-((3-chloropropyl)sulfonyl)pyrrolidin-3-yl)-5-(1-methyl-1H-pyrazol-4-yl)nicotinamide Using (R)-1-((3-chloropropyl)sulfonyl)pyrrolidin-3-amine, the title compound was obtained as described in general method A. MS (ESI, m/z): 427.07 [M+H]$^+$

Example 144

2-amino-5-(1-methyl-1H-pyrazol-4-yl)-N-((3S,5S)-1-(methylsulfonyl)-5-(phenoxymethyl)pyrrolidin-3-yl)nicotinamide Using (3S,5S)-1-(methylsulfonyl)-5-(phenoxymethyl)pyrrolidin-3-amine, the title compound was obtained as described in general method A. MS (ESI, m/z): 471.17 [M+H]$^+$

Example 145

2-amino-5-(1-methyl-1H-pyrazol-4-yl)-N-((3S,5S)-1-methyl-5-(phenoxymethyl)pyrrolidin-3-yl)nicotinamide Using (3S,5S)-1-methyl-5-(phenoxymethyl)pyrrolidin-3-amine, the title compound was obtained as described in general method A. MS (ESI, m/z): 407.21 [M+H]$^+$

Example 256

(R)—N-(1-([1,1'-biphenyl]-3-ylcarbamoyl)pyrrolidin-3-yl)-2-amino-5-(4-(hydroxymethyl)phenyl)nicotinamide Using 4-hydroxymethylphenylboronic acid and (R)—N-([1,1'-biphenyl]-3-yl)-3-aminopyrrolidine-1-carboxamide, the title compound was obtained as described in general method A. MS (ESI, m/z): 508.2 [M+H]$^+$

Example 621

SS-methyl (2S,4R)-4-(2-amino-5-(1-methyl-1H-pyrazol-4-yl)nicotinamido)-1-benzylpyrrolidine-2-carbo(dithioperoxoate)

Using SS-methyl (2S,4R)-4-amino-1-benzylpyrrolidine-2-carbo(dithioperoxoate) (BB Library), the title compound was obtained as described in general method A. MS (ESI, m/z): 483.2 [M+H]$^+$

Example 622

SS-methyl (2S,4R)-4-(2-amino-5-(1-methyl-1H-pyrazol-4-yl)nicotinamido)-1-(2-chlorobenzyl)pyrrolidine-2-carbo(dithioperoxoate)

Using SS-methyl (2S,4R)-4-amino-1-(2-chlorobenzyl)pyrrolidine-2-carbo(dithioperoxoate) (BB Library), the title compound was obtained as described in general method A. MS (ESI, m/z): 517.1 [M+H]$^+$

Example 623

(R)-2-amino-N-(1-benzylpyrrolidin-3-yl)-N-methyl-5-(1-methyl-1H-pyrazol-4-yl)nicotinamide Using (R)-1-benzyl-N-methylpyrrolidin-3-amine, the title compound was obtained as described in general method A. MS (ESI, m/z): 391.2 [M+H]$^+$

Example 624

(R)-2-amino-N-(1-(2-chlorobenzyl)pyrrolidin-3-yl)-N-methyl-5-(1-methyl-1H-pyrazol-4-yl)nicotinamide Using (R)-1-(2-chlorobenzyl)-N-methylpyrrolidin-3-amine, the title compound was obtained as described in general method A. MS (ESI, m/z): 425.2 [M+H]$^+$

Example 625

(R)-2-amino-N-(1-(methyl(phenyl)carbamoyl)pyrrolidin-3-yl)-5-(1-methyl-1H-pyrazol-4-yl)nicotinamide Using (R)-3-amino-N-methyl-N-phenylpyrrolidine-1-carboxamide, the title compound was obtained as described in general method A. MS (ESI, m/z): 420.2 [M+H]$^+$

Example 626

(S)-1-(3-((4-methylpiperazin-1-yl)methyl)phenyl)pyrrolidin-3-yl (R)-3-(2-amino-5-(1-methyl-1H-pyrazol-4-yl)nicotinamido)pyrrolidine-1-carboxylate Using (S)-1-(3-((4-methylpiperazin-1-yl)methyl)phenyl)pyrrolidin-3-yl (R)-3-aminopyrrolidine-1-carboxylate, the title compound was obtained as described in general method A. MS (ESI, m/z): 588.3 [M+H]$^+$

Example 846

3-bromo-5-chlorophenyl (R)-3-(2-amino-5-(1-methyl-1H-pyrazol-4-yl)nicotinamido)pyrrolidine-1-carboxylate Using 3-bromo-5-chlorophenyl (R)-3-aminopyrrolidine-1-carboxylate, the title compound was obtained as described in general method A. MS (ESI, m/z): 519.0 [M+H]$^+$

General Method B

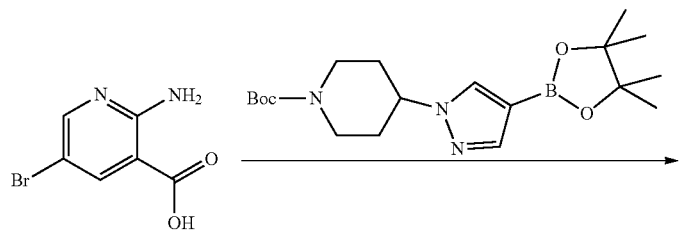

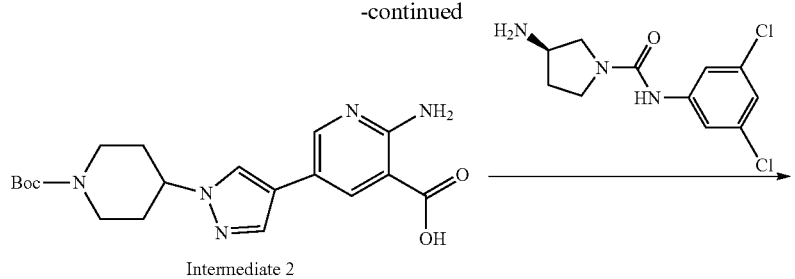

Example 146

Intermediate 2

To a mixture of 2-amino-5-bromonicotinic acid (1 g, 4.61 mmol) and (1-(1-(tert-butoxycarbonyl)piperidin-4-yl)-1H-pyrazol-4-yl)boronic acid pinacol ester (2.6 g, 6.91 mmol) in 25 mL of 1,4-dioxane/water (3/1) was added $K_2CO_3$ (1.9 g, 13.8 mmol) followed by $Pd(PPh_3)_4$ (0.26 g, 0.23 mmol). The reaction mixture was heated at 100° C. for 3 h, cooled to room temperature, and partitioned between water and ethyl acetate. Water layer was separated and adjusted to pH value around 5. The precipitate was collected by filtration and triturated in mixture of methanol and water. The precipitate was filtered. The wet cake was dried to afford 1.5 g of the title compound. The crude product was used for the next step without further purification. MS (ESI, m/z): 388.1 $[M+H]^+$

Example 146

(R)-2-amino-N-(1-((3,5-dichlorophenyl)carbamoyl)pyrrolidin-3-yl)-5-(1-(piperidin-4-yl)-1H-pyrazol-4-yl)nicotinamide To a mixture of Intermediate 2 (20 mg, 0.05 mmol) and triethylamine (0.022 mL, 0.15 mmol) in 0.5 mL of N,N-dimethylformamide was added 1-[bis(dimethylamino)methylene]-1H-1,2,3-triazolo[4,5-b]pyridinium 3-oxid hexafluorophosphate (20 mg, 0.05 mmol) followed (R)-3-amino-N-3,5-dichlorophenylpyrrolidine-1-carboxamide (14 mg, 0.05 mmol). The mixture was stirred at room temperature for 1 h and then saturated sodium bicarbonate solution was added. The mixture was extracted with ethyl acetate, washed with brine, dried over $MgSO_4$, and concentrated in vacuo. The crude residue was dissolved in 0.5 mL of dichloromethane/trifluoroacetic acid (4/1) and stirred at room temperature for 3 h. After concentration in vacuo, the crude residue was purified by preparative HPLC to afford 10 mg of the title compound. MS (ESI, m/z): 543.2 $[M+H]^+$

Example 147

[1,1'-biphenyl]-3-yl (R)-3-(2-amino-5-(1-(piperidin-4-yl)-1H-pyrazol-4-yl)nicotinamido)pyrrolidine-1-carboxylate Using [1,1'-biphenyl]-3-yl (R)-3-aminopyrrolidine-1-carboxylate, the title compound was obtained as described in general method B. MS (ESI, m/z): 552.2 $[M+H]^+$

Example 148

2-amino-N-((3R)-1-(1-(2-chlorophenyl)ethyl)pyrrolidin-3-yl)-5-(1-(piperidin-4-yl)-1H-pyrazol-4-yl)nicotinamide Using (3R)-1-(1-(2-chlorophenyl)ethyl)pyrrolidin-3-amine, the title compound was obtained as described in general method B. MS (ESI, m/z): 494.24 $[M+H]^+$

Example 149

2-amino-N-((3R)-1-(1-(3-chlorophenyl)ethyl)pyrrolidin-3-yl)-5-(1-(piperidin-4-yl)-1H-pyrazol-4-yl)nicotinamide Using (3R)-1-(1-(3-chlorophenyl)ethyl)pyrrolidin-3-amine, the title compound was obtained as described in general method B. MS (ESI, m/z): 494.24 $[M+H]^+$

Example 150

2-amino-N-((3R)-1-(1-(3,4-dichlorophenyl)ethyl)pyrrolidin-3-yl)-5-(1-(piperidin-4-yl)-1H-pyrazol-4-yl)nicotinamide Using (3R)-1-(1-(3,4-dichlorophenyl)ethyl)pyrrolidin-3-amine, the title compound was obtained as described in general method B. MS (ESI, m/z): 528.20 $[M+H]^+$

Example 151

(R)-2-amino-N-(1-benzylpyrrolidin-3-yl)-5-(1-(piperidin-4-yl)-1H-pyrazol-4-yl)nicotinamide Using (R)-1-benzylpyrrolidin-3-amine, the title compound was obtained as described in general method B. MS (ESI, m/z): 446.26 [M+H]$^+$

Example 152

2-amino-N-(1-benzylpyrrolidin-3-yl)-5-(1-(piperidin-4-yl)-1H-pyrazol-4-yl)nicotinamide Using 1-benzylpyrrolidin-3-amine, the title compound was obtained as described in general method B. MS (ESI, m/z): 446.26 [M+H]$^+$

Example 153

(R)-2-amino-N-(1-(4-fluorobenzyl)pyrrolidin-3-yl)-5-(1-(piperidin-4-yl)-1H-pyrazol-4-yl)nicotinamide Using (R)-1-(4-fluorobenzyl)pyrrolidin-3-amine, the title compound was obtained as described in general method B. MS (ESI, m/z): 464.25 [M+H]$^+$

Example 154

(R)-2-amino-N-(1-(3-methoxybenzyl)pyrrolidin-3-yl)-5-(1-(piperidin-4-yl)-1H-pyrazol-4-yl)nicotinamide Using (R)-1-(3-methoxybenzyl)pyrrolidin-3-amine, the title compound was obtained as described in general method B. MS (ESI, m/z): 476.27 [M+H]$^+$

Example 155

(R)-2-amino-N-(1-(2-chlorobenzyl)pyrrolidin-3-yl)-5-(1-(piperidin-4-yl)-1H-pyrazol-4-yl)nicotinamide Using (R)-1-(2-chlorobenzyl)pyrrolidin-3-amine, the title compound was obtained as described in general method B. MS (ESI, m/z): 480.22 [M+H]$^+$

Example 156

(R)-2-amino-N-(1-(4-nitrobenzyl)pyrrolidin-3-yl)-5-(1-(piperidin-4-yl)-1H-pyrazol-4-yl)nicotinamide Using (R)-1-(4-nitrobenzyl)pyrrolidin-3-amine, the title compound was obtained as described in general method B. MS (ESI, m/z): 491.24 [M+H]$^+$

Example 157

(R)-2-amino-5-(1-(piperidin-4-yl)-1H-pyrazol-4-yl)-N-(1-(2,4,5-trifluorobenzyl)pyrrolidin-3-yl)nicotinamide Using (R)-1-(2,4,5-trifluorobenzyl)pyrrolidin-3-amine, the title compound was obtained as described in general method B. MS (ESI, m/z): 500.23 [M+H]$^+$

Example 158

(R)-2-amino-N-(1-(3-chloro-4-fluorobenzyl)pyrrolidin-3-yl)-5-(1-(piperidin-4-yl)-1H-pyrazol-4-yl)nicotinamide Using (R)-1-(3-chloro-4-fluorobenzyl)pyrrolidin-3-amine, the title compound was obtained as described in general method B. MS (ESI, m/z): 498.21 [M+H]$^+$

Example 159

(R)-2-amino-N-(1-(2,6-dichlorobenzyl)pyrrolidin-3-yl)-5-(1-(piperidin-4-yl)-1H-pyrazol-4-yl)nicotinamide Using (R)-1-(2,6-dichlorobenzyl)pyrrolidin-3-amine, the title compound was obtained as described in general method B. MS (ESI, m/z): 514.18 [M+H]$^+$

Example 160

(R)-2-amino-N-(1-(3,4-difluorobenzyl)pyrrolidin-3-yl)-5-(1-(piperidin-4-yl)-1H-pyrazol-4-yl)nicotinamide Using (R)-1-(3,4-difluorobenzyl)pyrrolidin-3-amine, the title compound was obtained as described in general method B. MS (ESI, m/z): 482.24 [M+H]$^+$

Example 161

(R)-2-amino-N-(1-(3,4-dichlorobenzyl)pyrrolidin-3-yl)-5-(1-(piperidin-4-yl)-1H-pyrazol-4-yl)nicotinamide Using (R)-1-(3,4-dichlorobenzyl)pyrrolidin-3-amine, the title compound was obtained as described in general method B. MS (ESI, m/z): 514.18 [M+H]$^+$

Example 162

(R)-2-amino-5-(1-(piperidin-4-yl)-1H-pyrazol-4-yl)-N-(1-(2,3,6-trifluorobenzyl)pyrrolidin-3-yl)nicotinamide Using (R)-1-(2,3,6-trifluorobenzyl)pyrrolidin-3-amine, the title compound was obtained as described in general method B. MS (ESI, m/z): 500.23 [M+H]$^+$

Example 163

(R)-2-amino-N-(1-((2,4-dimethylthiazol-5-yl)methyl)pyrrolidin-3-yl)-5-(1-(piperidin-4-yl)-1H-pyrazol-4-yl)nicotinamide Using (R)-1-((2,4-dimethylthiazol-5-yl)methyl)pyrrolidin-3-amine, the title compound was obtained as described in general method B. MS (ESI, m/z): 481.24 [M+H]$^+$

Example 164

(R)-2-amino-N-(1-(2,3-dichlorobenzyl)pyrrolidin-3-yl)-5-(1-(piperidin-4-yl)-1H-pyrazol-4-yl)nicotinamide Using (R)-1-(2,3-dichlorobenzyl)pyrrolidin-3-amine, the title compound was obtained as described in general method B. MS (ESI, m/z): 514.18 [M+H]$^+$

Example 165

(R)-2-amino-N-(1-(2,4-dichlorobenzyl)pyrrolidin-3-yl)-5-(1-(piperidin-4-yl)-1H-pyrazol-4-yl)nicotinamide Using (R)-1-(2,4-dichlorobenzyl)pyrrolidin-3-amine, the title compound was obtained as described in general method B. MS (ESI, m/z): 514.18 [M+H]+

Example 166

(R)-2-amino-N-(1-(2,5-dimethylbenzyl)pyrrolidin-3-yl)-5-(1-(piperidin-4-yl)-1H-pyrazol-4-yl)nicotinamide Using (R)-1-(2,5-dimethylbenzyl)pyrrolidin-3-amine, the title compound was obtained as described in general method B. MS (ESI, m/z): 474.29 [M+H]+

Example 167

(R)-2-amino-N-(1-(2-methoxybenzyl)pyrrolidin-3-yl)-5-(1-(piperidin-4-yl)-1H-pyrazol-4-yl)nicotinamide Using (R)-1-(2-methoxybenzyl)pyrrolidin-3-amine, the title compound was obtained as described in general method B. MS (ESI, m/z): 476.27 [M+H]+

Example 168

(R)-2-amino-5-(1-(piperidin-4-yl)-1H-pyrazol-4-yl)-N-(1-(2-(trifluoromethyl)benzyl)pyrrolidin-3-yl)nicotinamide Using (R)-1-(2-trifluoromethylbenzyl)pyrrolidin-3-amine, the title compound was obtained as described in general method B. MS (ESI, m/z): 514.25 [M+H]+

Example 169

2-amino-N-((3R)-1-(cyclohex-3-en-1-ylmethyl)pyrrolidin-3-yl)-5-(1-(piperidin-4-yl)-1H-pyrazol-4-yl)nicotinamide Using (3R)-1-(cyclohex-3-en-1-ylmethyl)pyrrolidin-3-amine, the title compound was obtained as described in general method B. MS (ESI, m/z): 450.29 [M+H]+

Example 170

2-amino-N—((R)-1-(((1R,5S)-6,6-dimethylbicyclo[3.1.1]hept-2-en-2-yl)methyl)pyrrolidin-3-yl)-5-(1-(piperidin-4-yl)-1H-pyrazol-4-yl)nicotinamide Using (R)-1-(((1R,5S)-6,6-dimethylbicyclo[3.1.1]hept-2-en-2-yl)methyl)pyrrolidin-3-amine, the title compound was obtained as described in general method B. MS (ESI, m/z): 490.32 [M+H]+

Example 171

2-amino-5-(1-methyl-1H-pyrazol-4-yl)-N-((3R,5S)-5-(phenylcarbamoyl)pyrrolidin-3-yl)nicotinamide Using 1-methylpyrazole-4-boronic acid pinacol ester and (2S,4R)-4-amino-1-boc-N-phenylpyrrolidine-2-carboxamide, the title compound was obtained as described in general method B. MS (ESI, m/z): 406.19 [M+H]+

Example 172

2-amino-5-(1-methyl-1H-pyrazol-4-yl)-N-((3R,5S)-5-((4'-((4-methylpiperazin-1-yl)methyl)-[1,1'-biphenyl]-3-yl)carbamoyl)pyrrolidin-3-yl)nicotinamide Using 1-methylpyrazole-4-boronic acid pinacol ester and (2S,4R)-4-amino-1-boc-N-(4'-((4-methylpiperazin-1-yl)methyl)-[1,1'-biphenyl]-3-yl)pyrrolidine-2-carboxamide, the title compound was obtained as described in general method B. MS (ESI, m/z): 594.32 [M+H]+

Example 173

2-amino-5-(1-methyl-1H-pyrazol-4-yl)-N-((3S,5S)-5-(phenylcarbamoyl)pyrrolidin-3-yl)nicotinamide Using 1-methylpyrazole-4-boronic acid pinacol ester and (2S,4S)-4-amino-1-boc-N-phenylpyrrolidine-2-carboxamide and trifluoroacetic acid, the title compound was obtained as described in general method B. MS (ESI, m/z): 406.19 [M+H]+

Example 174

2-amino-5-(1-methyl-1H-pyrazol-4-yl)-N-((3S,5S)-5-((4'-((4-methylpiperazin-1-yl)methyl)-[1,1'-biphenyl]-3-yl)carbamoyl)pyrrolidin-3-yl)nicotinamide Using 1-methylpyrazole-4-boronic acid pinacol ester and (2S,4S)-4-amino-1-boc-N-(4'-((4-methylpiperazin-1-yl)methyl)-[1,1'-biphenyl]-3-yl)pyrrolidine-2-carboxamide, the title compound was obtained as described in general method B. MS (ESI, m/z): 594.32 [M+H]+

Example 175 phenyl (2S,4S)-4-(2-amino-5-(1-methyl-1H-pyrazol-4-yl)nicotinamido)pyrrolidine-2-carboxylate Using 1-methylpyrazole-4-boronic acid pinacol ester and phenyl (2S,4S)-4-amino-1-boc-pyrrolidine-2-carboxylate, the title compound was obtained as described in general method B. MS (ESI, m/z): 407.18 [M+H]+

Example 176

2-amino-5-(1-methyl-1H-pyrazol-4-yl)-N-((3S,5S)-5-(phenoxymethyl)pyrrolidin-3-yl)nicotinamide Using 1-methylpyrazole-4-boronic acid pinacol ester and (3S,5S)-1-boc-5-(phenoxymethyl)pyrrolidin-3-amine, the title compound was obtained as described in general method B. MS (ESI, m/z): 393.20 [M+H]+

Example 177

2-amino-5-(1-methyl-1H-pyrazol-4-yl)-N-((3S,5R)-5-(phenoxymethyl)pyrrolidin-3-yl)nicotinamide Using 1-methylpyrazole-4-boronic acid pinacol ester and (3S,5R)-1-boc-5-(phenoxymethyl)pyrrolidin-3-amine, the title compound was obtained as described in general method B. MS (ESI, m/z): 393.20 [M+H]+

Example 178

2-amino-5-(1-methyl-1H-pyrazol-4-yl)-N-((3R,5S)-5-(phenoxymethyl)pyrrolidin-3-yl)nicotinamide Using 1-methylpyrazole-4-boronic acid pinacol ester and (3R,5S)-1-boc-5-(phenoxymethyl)pyrrolidin-3-amine, the title compound was obtained as described in general method B. MS (ESI, m/z): 393.20 [M+H]+

Example 179

2-amino-5-(1-methyl-1H-pyrazol-4-yl)-N-((3S,5S)-5-(((3'-((4-methylpiperazin-1-yl)methyl)-[1,1'-biphenyl]-3-yl)oxy)methyl)pyrrolidin-3-yl)nicotinamide Using 1-methylpyrazole-4-boronic acid pinacol ester and (3S,5S)-1-boc-5-(((3'-((4-methylpiperazin-1-yl)methyl)-[1,1'-biphenyl]-3-yl)oxy)methyl)pyrrolidin-3-amine, the title compound was obtained as described in general method B. MS (ESI, m/z): 581.33 [M+H]+

Example 180

2-amino-5-(1-methyl-1H-pyrazol-4-yl)-N-((3S,5S)-5-(((4'-((4-methylpiperazin-1-yl)methyl)-[1,1'-biphenyl]-3-yl)oxy)methyl)pyrrolidin-3-yl)nicotinamide Using 1-methylpyrazole-4-boronic acid pinacol ester and (3S,5S)-1-boc-5-(((4'-((4-methylpiperazin-1-yl)methyl)-[1,1'-biphenyl]-3-yl)oxy)methyl)pyrrolidin-3-amine, the title compound was obtained as described in general method B. MS (ESI, m/z): 581.33 [M+H]+

Example 181

2-amino-5-(1-methyl-1H-pyrazol-4-yl)-N-((3S,5S)-5-(((3'-((4-methylpiperazin-1-yl)methyl)-[1,1'-biphenyl]-4-yl)oxy)methyl)pyrrolidin-3-yl)nicotinamide Using 1-methylpyrazole-4-boronic acid pinacol ester and (3S,5S)-1-boc-5-(((3'-((4-methylpiperazin-1-yl)methyl)-[1,1'-biphenyl]-4-yl)oxy)methyl)pyrrolidin-3-amine, the title compound was obtained as described in general method B. MS (ESI, m/z): 581.33 [M+H]+

Example 182

2-amino-5-(1-methyl-1H-pyrazol-4-yl)-N-((3S,5S)-5-(((4'-((4-methylpiperazin-1-yl)methyl)-[1,1'-biphenyl]-4-yl)oxy)methyl)pyrrolidin-3-yl)nicotinamide Using 1-methylpyrazole-4-boronic acid pinacol ester and (3S,5S)-1-boc-5-(((4'-((4-methylpiperazin-1-yl)methyl)-[1,1'-biphenyl]-4-yl)oxy)methyl)pyrrolidin-3-amine, the title compound was obtained as described in general method B. MS (ESI, m/z): 581.33 [M+H]+

Example 183

2-amino-5-(1-methyl-1H-pyrazol-4-yl)-N-((3R,5R)-5-(phenoxymethyl)pyrrolidin-3-yl)nicotinamide Using 1-methylpyrazole-4-boronic acid pinacol ester and (3R,5R)-1-boc-5-(phenoxymethyl)pyrrolidin-3-amine, the title compound was obtained as described in general method B. MS (ESI, m/z): 393.20 [M+H]+

Example 184

2-amino-N-((3S,5S)-5-((2-(sec-butyl)phenoxy)methyl)pyrrolidin-3-yl)-5-(1-methyl-1H-pyrazol-4-yl)nicotinamide Using 1-methylpyrazole-4-boronic acid pinacol ester and (3S,5S)-1-boc-5-((2-(sec-butyl)phenoxy)methyl)pyrrolidin-3-amine, the title compound was obtained as described in general method B. MS (ESI, m/z): 449.26 [M+H]+

Example 185

2-amino-N-((3S,5S)-5-((2,6-dimethylphenoxy)methyl)pyrrolidin-3-yl)-5-(1-methyl-1H-pyrazol-4-yl)nicotinamide Using 1-methylpyrazole-4-boronic acid pinacol ester and (3S,5S)-1-boc-5-((2,6-dimethylphenoxy)methyl)pyrrolidin-3-amine, the title compound was obtained as described in general method B. MS (ESI, m/z): 421.23 [M+H]+

Example 186

2-amino-N-((3S,5S)-5-((2,3-dichlorophenoxy)methyl)pyrrolidin-3-yl)-5-(1-methyl-1H-pyrazol-4-yl)nicotinamide Using 1-methylpyrazole-4-boronic acid pinacol ester and (3S,5S)-1-boc-5-((2,3-dichlorophenoxy)methyl)pyrrolidin-3-amine, the title compound was obtained as described in general method B. MS (ESI, m/z): 461.12 [M+H]+

Example 187

2-amino-N-((3S,5S)-5-((2,4-dichlorophenoxy)methyl)pyrrolidin-3-yl)-5-(1-methyl-1H-pyrazol-4-yl)nicotinamide Using 1-methylpyrazole-4-boronic acid pinacol ester and (3S,5S)-1-boc-5-((2,4-dichlorophenoxy)methyl)pyrrolidin-3-amine, the title compound was obtained as described in general method B. MS (ESI, m/z): 461.12 [M+H]+

Example 188

2-amino-N-((3S,5S)-5-((4-chloro-2-methylphenoxy)methyl)pyrrolidin-3-yl)-5-(1-methyl-1H-pyrazol-4-yl)nicotinamide Using 1-methylpyrazole-4-boronic acid pinacol ester and (3S,5S)-1-boc-5-((4-chloro-2-methylphenoxy)methyl)pyrrolidin-3-amine, the title compound was obtained as described in general method B. MS (ESI, m/z): 441.17 [M+H]+

Example 189

2-amino-N-((3S,5S)-5-((4-(tert-butyl)phenoxy)methyl)pyrrolidin-3-yl)-5-(1-methyl-1H-pyrazol-4-yl)nicotinamide Using 1-methylpyrazole-4-boronic acid pinacol ester and (3S,5S)-1-boc-5-((4-(tert-butyl)phenoxy)methyl)pyrrolidin- 3-amine, the title compound was obtained as described in general method B. MS (ESI, m/z): 449.26 [M+H]⁺

Example 190

2-amino-5-(1-methyl-1H-pyrazol-4-yl)-N-((3S,5S)-5-((4-phenoxyphenoxy)methyl)pyrrolidin-3-yl)nicotinamide Using 1-methylpyrazole-4-boronic acid pinacol ester and (3S,5S)-1-boc-5-((4-phenoxyphenoxy)methyl)pyrrolidin-3-amine, the title compound was obtained as described in general method B. MS (ESI, m/z): 485.22 [M+H]⁺

Example 191

2-amino-N-((3S,5S)-5-((4-benzylphenoxy)methyl)pyrrolidin-3-yl)-5-(1-methyl-1H-pyrazol-4-yl)nicotinamide Using (1-methylpyrazole-4-boronic acid pinacol ester and (3S,5S)-1-boc-5-((4-benzylphenoxy)methyl)pyrrolidin-3-amine, the title compound was obtained as described in general method B. MS (ESI, m/z): 483.24 [M+H]⁺

Example 192

N-((3S,5S)-5-(([1,1'-biphenyl]-2-yloxy)methyl)pyrrolidin-3-yl)-2-amino-5-(1-methyl-1H-pyrazol-4-yl)nicotinamide Using 1-methylpyrazole-4-boronic acid pinacol ester and (3S,5S)-1-boc-5-(([1,1'-biphenyl]-2-yloxy)methyl)pyrrolidin-3-amine, the title compound was obtained as described in general method B. MS (ESI, m/z): 469.23 [M+H]⁺

Example 193

N-((3S,5S)-5-(([1,1'-biphenyl]-4-yloxy)methyl)pyrrolidin-3-yl)-2-amino-5-(1-methyl-1H-pyrazol-4-yl)nicotinamide Using 1-methylpyrazole-4-boronic acid pinacol ester and (3S,5S)-1-boc-5-(([1,1'-biphenyl]-4-yloxy)methyl)pyrrolidin-3-amine, the title compound was obtained as described in general method B. MS (ESI, m/z): 469.23 [M+H]⁺

Example 194

2-amino-N-((3S,5S)-5-((4-(benzyloxy)phenoxy)methyl)pyrrolidin-3-yl)-5-(1-methyl-1H-pyrazol-4-yl)nicotinamide Using 1-methylpyrazole-4-boronic acid pinacol ester and (3S,5S)-1-boc-5-((4-(benzyloxy)phenoxy)methyl)pyrrolidin-3-amine, the title compound was obtained as described in general method B. MS (ESI, m/z): 499.24 [M+H]⁺

Example 195

2-amino-N-((3S,5S)-5-((4-((dimethylamino)methyl)phenoxy)methyl)pyrrolidin-3-yl)-5-(1-methyl-1H-pyrazol-4-yl)nicotinamide Using 1-methylpyrazole-4-boronic acid pinacol ester and (3S,5S)-1-boc-5-((4-((dimethylamino)methyl)phenoxy)methyl)pyrrolidin-3-amine, the title compound was obtained as described in general method B. MS (ESI, m/z): 450.25 [M+H]⁺

Example 196

2-amino-5-(1-methyl-1H-pyrazol-4-yl)-N-((3S,5S)-5-((4-(2-(piperazin-1-yl)pyridin-4-yl)phenoxy)methyl)pyrrolidin-3-yl)nicotinamide Using 1-methylpyrazole-4-boronic acid pinacol ester and tert-butyl 4-(4-(4-(((2S,4S)-4-amino-1-boc-pyrrolidin-2-yl)methoxy)phenyl)pyridin-2-yl)piperazine-1-carboxylate, the title compound was obtained as described in general method B. MS (ESI, m/z): 554.29 [M+H]⁺

Example 197

2-amino-N-((3S,5S)-5-((4-(1-(2-(dimethylamino)ethyl)-1H-pyrazol-4-yl)phenoxy)methyl)pyrrolidin-3-yl)-5-(1-methyl-1H-pyrazol-4-yl)nicotinamide Using 1-methylpyrazole-4-boronic acid pinacol ester and (3S,5S)-1-boc-5-((4-(1-(2-(dimethylamino)ethyl)-1H-pyrazol-4-yl)phenoxy)methyl)pyrrolidin-3-amine, the title compound was obtained as described in general method B. MS (ESI, m/z): 530.29 [M+H]⁺

Example 198

2-amino-5-(1-methyl-1H-pyrazol-4-yl)-N-((3S,5S)-5-((4-(2-phenylpropan-2-yl)phenoxy)methyl)pyrrolidin-3-yl)nicotinamide Using 1-methylpyrazole-4-boronic acid pinacol ester and (3S,5S)-1-boc-5-((4-(2-phenylpropan-2-yl)phenoxy)methyl)pyrrolidin-3-amine, the title compound was obtained as described in general method B. MS (ESI, m/z): 511.27 [M+H]⁺

Example 199

N-((3S,5S)-5-(([1,1'-biphenyl]-3-yloxy)methyl)pyrrolidin-3-yl)-2-amino-5-(1-methyl-1H-pyrazol-4-yl)nicotinamide Using 1-methylpyrazole-4-boronic acid pinacol ester and (3S,5S)-1-boc-5-(([1,1'-biphenyl]-3-yloxy)methyl)pyrrolidin-3-amine, the title compound was obtained as described in general method B. MS (ESI, m/z): 469.23 [M+H]⁺

Example 200

2-amino-N-((3S,5S)-5-(((2,6-dimethyl-[1,1'-biphenyl]-4-yl)oxy)methyl)pyrrolidin-3-yl)-5-(1-methyl-1H-pyrazol-4-yl)nicotinamide Using 1-methylpyrazole-4-boronic acid pinacol ester and (3S,5S)-1-boc-5-(((2,6-dimethyl-[1,1'-biphenyl]-4-yl)oxy)methyl)pyrrolidin-3-amine, the title compound was obtained as described in general method B. MS (ESI, m/z): 497.26 [M+H]⁺

Example 201

2-amino-N-((3S,5S)-5-((3,4-dimethylphenoxy)methyl)pyrrolidin-3-yl)-5-(1-methyl-1H-pyrazol-4-yl)nicotinamide Using 1-methylpyrazole-4-boronic acid pinacol ester and (3S,5S)-1-boc-5-((3,4-dimethylphenoxy)methyl)pyrrolidin-3-amine, the title compound was obtained as described in general method B. MS (ESI, m/z): 421.2 [M+H]$^+$

Example 202

2-amino-N-((3S,5S)-5-((3,5-dimethylphenoxy)methyl)pyrrolidin-3-yl)-5-(1-methyl-1H-pyrazol-4-yl)nicotinamide Using 1-methylpyrazole-4-boronic acid pinacol ester and (3S,5S)-1-boc-5-((3,5-dimethylphenoxy)methyl)pyrrolidin-3-amine, the title compound was obtained as described in general method B. MS (ESI, m/z): 421.2 [M+H]$^+$

Example 203

2-amino-N-((3S,5S)-5-((2-chlorophenoxy)methyl)pyrrolidin-3-yl)-5-(1-methyl-1H-pyrazol-4-yl)nicotinamide Using 1-methylpyrazole-4-boronic acid pinacol ester and (3S,5S)-1-boc-5-((2-chlorophenoxy)methyl)pyrrolidin-3-amine, the title compound was obtained as described in general method B. MS (ESI, m/z): 428.2 [M+H]$^+$

Example 204

2-amino-5-(1-methyl-1H-pyrazol-4-yl)-N-((3S,5S)-5-((4-((4-methylpiperazin-1-yl)methyl)phenoxy)methyl)pyrrolidin-3-yl)nicotinamide Using 1-methylpyrazole-4-boronic acid pinacol ester and (3S,5S)-1-boc-5-((4-((4-methylpiperazin-1-yl)methyl)phenoxy)methyl)pyrrolidin-3-amine, the title compound was obtained as described in general method B. MS (ESI, m/z): 505.3 [M+H]$^+$

Example 627

2-amino-N-((3R)-1-(2-(methylamino)-2-oxo-1-phenylethyl)pyrrolidin-3-yl)-5-(1-(piperidin-4-yl)-1H-pyrazol-4-yl)nicotinamide Using 2-((R)-3-aminopyrrolidin-1-yl)-N-methyl-2-phenylacetamide, the title compound was obtained as described in general method B. MS (ESI, m/z): 503.3 [M+H]$^+$

Example 628 methyl 2-((R)-3-(2-amino-5-(1-(piperidin-4-yl)-1H-pyrazol-4-yl)nicotinamido)pyrrolidin-1-yl)-2-phenylacetate Using methyl 2-((R)-3-aminopyrrolidin-1-yl)-2-phenylacetate, the title compound was obtained as described in general method B. MS (ESI, m/z): 504.3 [M+H]$^+$

Example 629

2-amino-N-((3R)-1-(2-hydroxy-1-phenylethyl)pyrrolidin-3-yl)-5-(1-(piperidin-4-yl)-1H-pyrazol-4-yl)nicotinamide Using 2-((R)-3-aminopyrrolidin-1-yl)-2-phenylethan-1-ol, the title compound was obtained as described in general method B. MS (ESI, m/z): 476.3 [M+H]$^+$

Example 630

(R)-2-amino-5-(1-(piperidin-4-yl)-1H-pyrazol-4-yl)-N-(1-(pyridin-3-ylmethyl)pyrrolidin-3-yl)nicotinamide Using (R)-1-(pyridin-3-ylmethyl)pyrrolidin-3-amine, the title compound was obtained as described in general method B. MS (ESI, m/z): 447.2 [M+H]$^+$

Example 631

(R)-2-amino-N-(1-((2-chloropyridin-4-yl)methyl)pyrrolidin-3-yl)-5-(1-(piperidin-4-yl)-1H-pyrazol-4-yl)nicotinamide Using (R)-1-((2-chloropyridin-4-yl)methyl)pyrrolidin-3-amine, the title compound was obtained as described in general method B. MS (ESI, m/z): 481.2 [M+H]$^+$

General Method C

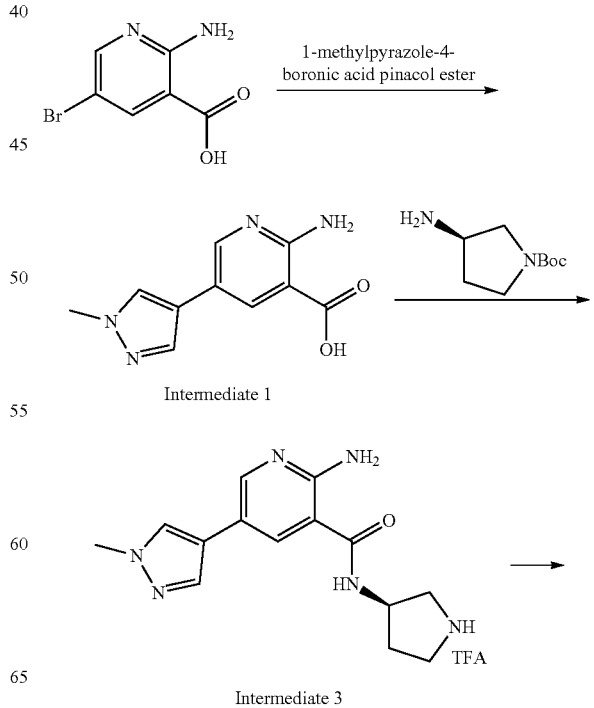

Intermediate 1

Intermediate 3

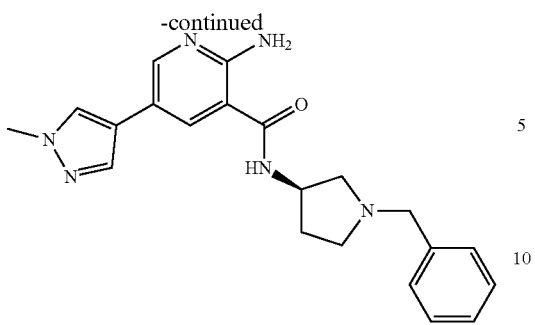

Example 205

Intermediate 1

To a mixture of 2-amino-5-bromonicotinic acid (23 g, 100 mmol) and 1-methylpyrazole-4-boronic acid pinacol ester (27 g, 130 mmol) in 400 mL of 1,4-dioxane/water (3/1) was added $K_2CO_3$ (27.6 g, 200 mmol) followed by $Pd(PPh_3)_4$ (8.1 g, 7 mmol). The reaction mixture was heated at 100° C. for 3 h, cooled to room temperature, and partitioned between water and ethyl acetate. Water layer was separated and adjusted to pH value around 5. The precipitate was collected by filtration and triturated in mixture of methanol and water. The precipitate was filtered. The wet cake was dried to afford 17.5 g of the title compound. The crude product was used for the next step without further purification. $^1$H NMR (600 MHz, DIMETHYL SULFOXIDE-$d_6$) δ ppm 3.82 (s, 3H), 5.73 (s, 2H), 7.77 (s, 1H), 8.05 (s, 1H), 8.13 (d, J=2.4 Hz, 1H), 8.42 (d, J=2.4 Hz, 1H); MS (ESI, m/z): 219.1 [M+H]$^+$

Intermediate 3

To a mixture of Intermediate 1 (1.0 g, 4.58 mmol) and triethylamine (0.958 mL, 6.87 mmol) in 12 mL of N,N-dimethylformamide was added 1-[bis(dimethylamino)methylene]-1H-1,2,3-triazolo[4,5-b]pyridinium 3-oxid hexafluorophosphate (1.7 g, 4.58 mmol) followed by tert-butyl (R)-3-aminopyrrolidine-1-carboxylate (0.853 g, 4.58 mmol). The mixture was stirred at room temperature for 1 h and then saturated sodium bicarbonate solution was added. The mixture was extracted with ethyl acetate, washed with brine, dried over $MgSO_4$, and concentrated in vacuo. The crude product was purified through silicagel column chromatography (5% methanol/$CH_2Cl_2$) to give off-white solid. To a mixture of product in dichloromethane (12 mL) was added trifluoroacetic acid (3 mL) and stirred at room temperature for overnight. After removing volatiles, the crude product was diluted with diethylether and the precipitate was collected by filtration and dried to afford 1.3 g of the title compound. $^1$H NMR (600 MHz, DIMETHYL SULFOXIDE-$d_6$) δ ppm 2.01 (br d, J=5.87 Hz, 1H) 2.20 (dd, J=13.50, 7.63 Hz, 1H) 3.14-3.19 (m, 1H) 3.26 (br d, J=6.46 Hz, 1H) 3.35 (br dd, J=7.04, 4.70 Hz, 1H) 3.43 (br dd, J=11.74, 5.28 Hz, 1H) 4.47 (br d, J=5.87 Hz, 1H) 7.83 (s, 1H) 8.07 (s, 1H) 8.29 (d, J=1.76 Hz, 1H) 8.36 (d, J=2.35 Hz, 1H); MS (ESI, m/z): 287.1 [M+H]$^+$

Example 205

(R)-2-amino-N-(1-benzylpyrrolidin-3-yl)-5-(1-methyl-1H-pyrazol-4-yl)nicotinamide To a mixture of Intermediate 3 (20 mg, 0.05 mmol) in 0.4 mL of dichloroethane was added benzaldehyde (0.011 mL, 0.10 mmol) followed by NaBH(OAc)$_3$ (33 mg, 0.16 mmol). The mixture was stirred at room temperature for 4 h and then water was added. The mixture was extracted with ethyl acetate, washed with brine, dried over $MgSO_4$, and concentrated in vacuo. The crude residue was purified by preparative HPLC to afford 10 mg of the title compound. MS (ESI, m/z): 377.20 [M+H]$^+$

Example 206

2-amino-N-(1-benzylpyrrolidin-3-yl)-5-(1-methyl-1H-pyrazol-4-yl)nicotinamide

Using tert-butyl 3-aminopyrrolidine-1-carboxylate, the title compound was obtained as described in general method C. MS (ESI, m/z): 377.20 [M+H]$^+$

Example 207

(S)-2-amino-N-(1-benzylpyrrolidin-3-yl)-5-(1-methyl-1H-pyrazol-4-yl)nicotinamide Using tert-butyl (S)-3-aminopyrrolidine-1-carboxylate, the title compound was obtained as described in general method C. MS (ESI, m/z): 377.20 [M+H]$^+$

Example 208

(R)-2-amino-N-(1-(2-chlorobenzyl)pyrrolidin-3-yl)-5-(1-methyl-1H-pyrazol-4-yl)nicotinamide Using 2-chlorobenzaldehyde, the title compound was obtained as described in general method C. MS (ESI, m/z): 411.2 [M+H]$^+$

Example 209

(R)-2-amino-N-(1-(3-methoxybenzyl)pyrrolidin-3-yl)-5-(1-methyl-1H-pyrazol-4-yl)nicotinamide Using 3-methoxybenzaldehyde, the title compound was obtained as described in general method C. MS (ESI, m/z): 407.2 [M+H]$^+$

Example 210

(R)-2-amino-N-(1-(4-chlorobenzyl)pyrrolidin-3-yl)-5-(1-methyl-1H-pyrazol-4-yl)nicotinamide Using 4-chlorobenzaldehyde, the title compound was obtained as described in general method C. MS (ESI, m/z): 411.2 [M+H]$^+$

Example 211

(R)-2-amino-N-(1-(4-ethylbenzyl)pyrrolidin-3-yl)-5-(1-methyl-1H-pyrazol-4-yl)nicotinamide Using 4-ethylbenzaldehyde, the title compound was obtained as described in general method C. MS (ESI, m/z): 405.2 [M+H]$^+$

Example 212

(R)-2-amino-N-(1-(4-isopropylbenzyl)pyrrolidin-3-yl)-5-(1-methyl-1H-pyrazol-4-yl)nicotinamide Using 4-isopropylbenzaldehyde, the title compound was obtained as described in general method C. MS (ESI, m/z): 419.2 [M+H]$^+$

Example 213

(R)-2-amino-N-(1-(3,4-dichlorobenzyl)pyrrolidin-3-yl)-5-(1-methyl-1H-pyrazol-4-yl)nicotinamide Using 3,4-dichlorobenzaldehyde, the title compound was obtained as described in general method C. MS (ESI, m/z): 445.2 [M+H]$^+$

Example 214

(R)-2-amino-N-(1-(3,4-dimethylbenzyl)pyrrolidin-3-yl)-5-(1-methyl-1H-pyrazol-4-yl)nicotinamide Using 3,4-dimethylbenzaldehyde, the title compound was obtained as described in general method C. MS (ESI, m/z): 405.2 [M+H]$^+$

Example 215

(R)-2-amino-5-(1-methyl-1H-pyrazol-4-yl)-N-(1-(2-oxo-2-phenylethyl)pyrrolidin-3-yl)nicotinamide Using 2-oxo-2-phenylacetaldehyde, the title compound was obtained as described in general method C. MS (ESI, m/z): 405.2 [M+H]$^+$

Example 216

(R)-2-amino-N-(1-(3,5-dimethoxybenzyl)pyrrolidin-3-yl)-5-(1-methyl-1H-pyrazol-4-yl)nicotinamide Using 3,5-dimethoxybenzaldehyde, the title compound was obtained as described in general method C. MS (ESI, m/z): 437.2 [M+H]$^+$

Example 217

(R)-2-amino-N-(1-(2,3-dimethoxybenzyl)pyrrolidin-3-yl)-5-(1-methyl-1H-pyrazol-4-yl)nicotinamide Using 2,3-dimethoxybenzaldehyde, the title compound was obtained as described in general method C. MS (ESI, m/z): 437.2 [M+H]$^+$

Example 218

(R)-2-amino-N-(1-(2,5-dimethoxybenzyl)pyrrolidin-3-yl)-5-(1-methyl-1H-pyrazol-4-yl)nicotinamide Using 2,5-dimethoxybenzaldehyde, the title compound was obtained as described in general method C. MS (ESI, m/z): 437.2 [M+H]$^+$

Example 219

(R)-2-amino-N-(1-(2-hydroxy-5-methoxybenzyl)pyrrolidin-3-yl)-5-(1-methyl-1H-pyrazol-4-yl)nicotinamide Using 2-hydroxy-5-methylbenzaldehyde, the title compound was obtained as described in general method C. MS (ESI, m/z): 423.2 [M+H]$^+$

Example 220

(R)-2-amino-N-(1-(2,4-dimethoxybenzyl)pyrrolidin-3-yl)-5-(1-methyl-1H-pyrazol-4-yl)nicotinamide Using 2,4-dimethoxybenzaldehyde, the title compound was obtained as described in general method C. MS (ESI, m/z): 437.2 [M+H]$^+$

Example 221

(R)-2-amino-5-(1-methyl-1H-pyrazol-4-yl)-N-(1-(3-phenoxybenzyl)pyrrolidin-3-yl)nicotinamide Using 3-phenoxybenzaldehyde, the title compound was obtained as described in general method C. MS (ESI, m/z): 469.2 [M+H]$^+$

Example 222

(R)-2-amino-N-(1-(3-(benzyloxy)benzyl)pyrrolidin-3-yl)-5-(1-methyl-1H-pyrazol-4-yl)nicotinamide Using 3-benzyloxybenzaldehyde, the title compound was obtained as described in general method C. MS (ESI, m/z): 483.2 [M+H]$^+$

Example 223

(R)-2-amino-N-(1-(3,5-dichloro-2-hydroxybenzyl)pyrrolidin-3-yl)-5-(1-methyl-1H-pyrazol-4-yl)nicotinamide Using 3,5-dichloro-2-hydroxybenzaldehyde, the title compound was obtained as described in general method C. MS (ESI, m/z): 461.2 [M+H]$^+$

Example 224

(R)-2-amino-N-(1-(3,5-dichlorobenzyl)pyrrolidin-3-yl)-5-(1-methyl-1H-pyrazol-4-yl)nicotinamide Using 3,5-dichlorobenzaldehyde, the title compound was obtained as described in general method C. MS (ESI, m/z): 445.2 [M+H]$^+$

Example 225

(R)—N-(1-([1,1'-biphenyl]-2-ylmethyl)pyrrolidin-3-yl)-2-amino-5-(1-methyl-1H-pyrazol-4-yl)nicotinamide Using [1,1'-biphenyl]-2-carbaldehyde, the title compound was obtained as described in general method C. MS (ESI, m/z): 453.2 [M+H]$^+$

Example 226

(R)—N-(1-([1,1'-biphenyl]-4-ylmethyl)pyrrolidin-3-yl)-2-amino-5-(1-methyl-1H-pyrazol-4-yl)nicotinamide Using [1,1'-biphenyl]-4-carbaldehyde, the title compound was obtained as described in general method C. MS (ESI, m/z): 453.2 [M+H]$^+$

Example 227

(R)-2-amino-5-(1-methyl-1H-pyrazol-4-yl)-N-(1-(3-phenylpropyl)pyrrolidin-3-yl)nicotinamide Using 3-phenylpropanal, the title compound was obtained as described in general method C. MS (ESI, m/z): 405.23 [M+H]$^+$

Example 228

(R)-2-amino-N-(1-cinnamylpyrrolidin-3-yl)-5-(1-methyl-1H-pyrazol-4-yl)nicotinamide Using cinnamaldehyde, the title compound was obtained as described in general method C. MS (ESI, m/z): 403.22 [M+H]$^+$

Example 229

(R)-2-amino-N-(1-(2-(benzyloxy)ethyl)pyrrolidin-3-yl)-5-(1-methyl-1H-pyrazol-4-yl)nicotinamide Using 2-(benzyloxy)acetaldehyde, the title compound was obtained as described in general method C. MS (ESI, m/z): 421.23 [M+H]$^+$

Example 230

(R)-2-amino-5-(1-methyl-1H-pyrazol-4-yl)-N-(1-phenethylpyrrolidin-3-yl)nicotinamide Using phenylacetaldehyde, the title compound was obtained as described in general method C. MS (ESI, m/z): 391.23 [M+H]$^+$

Example 231

(R)-2-amino-N-(1-(3-bromobenzyl)pyrrolidin-3-yl)-5-(1-methyl-1H-pyrazol-4-yl)nicotinamide Using 3-bromobenzaldehyde, the title compound was obtained as described in general method C. MS (ESI, m/z): 455.2/457.2 [M+H]$^+$

Example 232

(R)-2-amino-N-(1-(2-bromobenzyl)pyrrolidin-3-yl)-5-(1-methyl-1H-pyrazol-4-yl)nicotinamide Using 2-bromobenzaldehyde, the title compound was obtained as described in general method C. MS (ESI, m/z): 455.2/457.2 [M+H]$^+$

Example 233

(R)-2-amino-N-(1-(3-bromo-4-fluorobenzyl)pyrrolidin-3-yl)-5-(1-methyl-1H-pyrazol-4-yl)nicotinamide Using 3-bromo-4-fluorobenzaldehyde, the title compound was obtained as described in general method C. MS (ESI, m/z): 473.2/475.2[M+H]$^+$

Example 234

(R)-2-amino-N-(1-(3-bromophenethyl)pyrrolidin-3-yl)-5-(1-methyl-1H-pyrazol-4-yl)nicotinamide Using 2-(3-bromophenyl)acetaldehyde, the title compound was obtained as described in general method C. MS (ESI, m/z): 469.2/471.2 [M+H]$^+$

Example 235

(R)-2-amino-N-(1-(4-chlorobenzyl)pyrrolidin-3-yl)-5-(4-(morpholine-4-carbonyl)phenyl)nicotinamide Using (4-(morpholine-4-carbonyl)phenyl)boronic acid and 4-chlorobenzaldehyde, the title compound was obtained as described in general method C. MS (ESI, m/z): 520.2 [M+H]$^+$

Example 236

(R)-2-amino-N-(1-(4-chlorobenzyl)pyrrolidin-3-yl)-5-(4-((4-methylpiperazin-1-yl)methyl)phenyl)nicotinamide Using (4-((4-methylpiperazin-1-yl)methyl)phenyl)boronic acid, pinacol ester and 4-chlorobenzaldehyde, the title compound was obtained as described in general method C. MS (ESI, m/z): 519 [M+H]$^+$

Example 237

(R)-2-amino-N-(1-(4-chlorobenzyl)pyrrolidin-3-yl)-5-(4-(hydroxymethyl)phenyl)nicotinamide Using (4-hydroxymethyl)phenylboronic acid and 4-chlorobenzaldehyde, the title compound was obtained as described in general method C. MS (ESI, m/z): 437.2 [M+H]$^+$

Example 238

(R)-2-amino-N-(1-(4-chlorobenzyl)pyrrolidin-3-yl)-5-(4-cyanophenyl)nicotinamide

Using 4-cyanophenylboronic acid and 4-chlorobenzaldehyde, the title compound was obtained as described in general method C. MS (ESI, m/z): 432.2 [M+H]$^+$

Example 239

(R)-2-amino-N-(1-(4-chlorobenzyl)pyrrolidin-3-yl)-5-(quinolin-3-yl)nicotinamide

Using quinolin-3-ylboronic acid and 4-chlorobenzaldehyde, the title compound was obtained as described in general method C. MS (ESI, m/z): 458.2 [M+H]$^+$

Example 240

(R)-5-(1-(1-acetylpiperidin-4-yl)-1H-pyrazol-4-yl)-2-amino-N-(1-benzylpyrrolidin-3-yl)nicotinamide Using 1-(1-acetyl-4-piperidyl)pyrazole-4-boronic acid pinacol ester, the title compound was obtained as described in general method C. MS (ESI, m/z): 488.27 [M+H]$^+$

Example 241

(R)-2-amino-N-(1-benzylpyrrolidin-3-yl)-5-(1-(1-(methylsulfonyl)piperidin-4-yl)-1H-pyrazol-4-yl)nicotinamide Using 1-(1-methylsulfonyl-4-piperidyl)pyrazole-4-boronic acid pinacol ester, the title compound was obtained as described in general method C. MS (ESI, m/z): 524.24 [M+H]$^+$

Example 242

(R)-2-amino-N-(1-benzylpyrrolidin-3-yl)-5-(1-(1-((3,4,5-trimethoxyphenyl)carbamoyl)piperidin-4-yl)-1H-pyrazol-4-yl)nicotinamide Using (1-(1-((3,4,5-trimethoxyphenyl)carbamoyl)piperidin-4-yl)-1H-pyrazol-4-yl)boronic acid pinacol ester, the title compound was obtained as described in general method C. MS (ESI, m/z): 655.33 [M+H]$^+$

Example 632

(R)-2-amino-N-(1-(2-chlorobenzyl)pyrrolidin-3-yl)-5-(1-isobutyl-1H-pyrazol-4-yl)nicotinamide Using 1-isobutyl-4-(4,4,5,5-tetramethyl-1,3,2-dioxaborolan-2-yl)-1H-pyrazole and (R)-1-(2-chlorobenzyl)pyrrolidin-3-amine, the title compound was obtained as described in general method C. MS (ESI, m/z): 453.2 [M+H]$^+$

General Method D

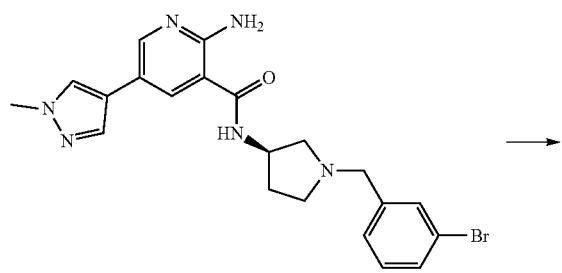

Example 231

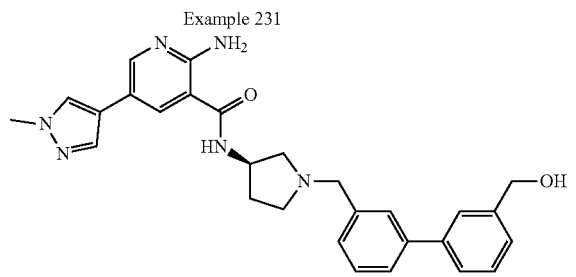

Example 243

Example 243

(R)-2-amino-N-(1-((3'-(hydroxymethyl)-[1,1'-biphenyl]-3-yl)methyl)pyrrolidin-3-yl)-5-(1-methyl-1H-pyrazol-4-yl)nicotinamide To a mixture of Example 231 (20 mg, 0.04 mmol) and (3-hydroxymethyl)phenylboronic acid (10 mg, 0.07 mmol) in 0.4 mL of 1,4-dioxane/water (3/1) was added K$_2$CO$_3$ (18 mg, 0.13 mmol) followed by Pd(PPh$_3$)$_4$ (3 mg, 0.002 mmol). The reaction mixture was heated at 100° C. for 3 h, cooled to room temperature, the mixture was extracted with ethyl acetate, washed with brine, dried over MgSO$_4$, and concentrated in vacuo. The crude residue was purified by preparative HPLC to afford 10 mg of the title compound. MS (ESI, m/z): 483.2 [M+H]$^+$

Example 244

(R)-2-amino-N-(1-((4'-(hydroxymethyl)-[1,1'-biphenyl]-3-yl)methyl)pyrrolidin-3-yl)-5-(1-methyl-1H-pyrazol-4-yl)nicotinamide Using (4-hydroxymethyl)phenylboronic acid, the title compound was obtained as described in general method D. MS (ESI, m/z): 483.2 [M+H]$^+$

Example 245

(R)-2-amino-5-(1-methyl-1H-pyrazol-4-yl)-N-(1-((3'-((4-methylpiperazin-1-yl)methyl)-[1,1'-biphenyl]-3-yl)methyl)pyrrolidin-3-yl)nicotinamide Using (3-((4-methylpiperazin-1-yl)methyl)phenyl)boronic acid pinacol ester, the title compound was obtained as described in general method D. MS (ESI, m/z): 565.2 [M+H]$^+$

Example 246

(R)-2-amino-5-(1-methyl-1H-pyrazol-4-yl)-N-(1-((4'-((4-methylpiperazin-1-yl)methyl)-[1,1'-biphenyl]-3-yl)methyl)pyrrolidin-3-yl)nicotinamide Using (4-((4-methylpiperazin-1-yl)methyl)phenyl)boronic acid pinacol ester, the title compound was obtained as described in general method D. MS (ESI, m/z): 565.2 [M+H]$^+$

Example 247

(R)-2-amino-N-(1-((3'-(hydroxymethyl)-[1,1'-biphenyl]-2-yl)methyl)pyrrolidin-3-yl)-5-(1-methyl-1H-pyrazol-4-yl)nicotinamide Using Example 232, the title compound was obtained as described in general method D. MS (ESI, m/z): 483.2 [M+H]$^+$

Example 248

(R)-2-amino-N-(1-((4'-(hydroxymethyl)-[1,1'-biphenyl]-2-yl)methyl)pyrrolidin-3-yl)-5-(1-methyl-1H-pyrazol-4-yl)nicotinamide Using Example 232 and (4-hydroxymethyl)phenylboronic acid, the title compound was obtained as described in general method D. MS (ESI, m/z): 483.2 [M+H]$^+$

Example 249

(R)-2-amino-N-(1-((6-fluoro-[1,1'-biphenyl]-3-yl)
methyl)pyrrolidin-3-yl)-5-(1-methyl-1H-pyrazol-4-
yl)nicotinamide Using Example 233 and phenylboronic acid, the title compound was obtained as described in general method D. MS (ESI, m/z): 471.2 [M+H]⁺

Example 250

(R)-2-amino-N-(1-((6-fluoro-3'-(hydroxymethyl)-[1,
1'-biphenyl]-3-yl)methyl)pyrrolidin-3-yl)-5-(1-
methyl-1H-pyrazol-4-yl)nicotinamide Using Example 233, the title compound was obtained as described in general method D. MS (ESI, m/z): 501.2 [M+H]⁺

Example 251

(R)-2-amino-N-(1-((6-fluoro-3'-((4-methylpiperazin-
1-yl)methyl)-[1,1'-biphenyl]-3-yl)methyl)pyrrolidin-
3-yl)-5-(1-methyl-1H-pyrazol-4-yl)nicotinamide Using Example 233 and (3-((4-methylpiperazin-1-yl)methyl)phenyl)boronic acid pinacol ester, the title compound was obtained as described in general method D. MS (ESI, m/z): 583.2 [M+H]⁺

Example 252

(R)-2-amino-N-(1-(4-fluoro-3-(1,2,3,6-tetrahydro-
pyridin-4-yl)benzyl)pyrrolidin-3-yl)-5-(1-methyl-
1H-pyrazol-4-yl)nicotinamide Using Example 233 and (1,2,3,6-tetrahydropyridin-4-yl)boronic acid, the title compound was obtained as described in general method D. MS (ESI, m/z): 476.2 [M+H]⁺

Example 253

(R)-2-amino-5-(1-methyl-1H-pyrazol-4-yl)-N-(1-(2-
(4'-((4-methylpiperazin-1-yl)methyl)-[1,1'-biphenyl]-
3-yl)ethyl)pyrrolidin-3-yl)nicotinamide Using Example 234 and (4-((4-methylpiperazin-1-yl)methyl)phenyl)boronic acid pinacol ester, the title compound was obtained as described in general method D. MS (ESI, m/z): 579.2 [M+H]⁺

Example 254

(R)-2-amino-N-(1-((3'-(aminomethyl)-[1,1'-biphe-
nyl]-3-yl)carbamoyl)pyrrolidin-3-yl)-5-(1-methyl-
1H-pyrazol-4-yl)nicotinamide Using Example 024 and (3-(aminomethyl)phenyl)boronic acid, the title compound was obtained as described in general method D. MS (ESI, m/z): 511.2 [M+H]⁺

Example 255

(R)-2-amino-N-(1-((4-((4'-(aminomethyl)-[1,1'-bi-
phenyl]-3-yl)carbamoyl)pyrrolidin-3-yl)-5-(1-
methyl-1H-pyrazol-4-yl)nicotinamide Using Example 024 and (4-(aminomethyl)phenyl)boronic acid, the title compound was obtained as described in general method D. MS (ESI, m/z): 511.2 [M+H]⁺

Example 257

(R)-2-amino-N-(1-((3'-amino-[1,1'-biphenyl]-3-yl)
carbamoyl)pyrrolidin-3-yl)-5-(1-methyl-1H-pyrazol-
4-yl)nicotinamide Using Example 024 and 3-aminophenylboronic acid, the title compound was obtained as described in general method D. MS (ESI, m/z): 497.2 [M+H]⁺

Example 258

(R)-2-amino-N-(1-((4'-amino-[1,1'-biphenyl]-3-yl)
carbamoyl)pyrrolidin-3-yl)-5-(1-methyl-1H-pyrazol-
4-yl)nicotinamide Using Example 024 and 4-aminophenylboronic acid, the title compound was obtained as described in general method D. MS (ESI, m/z): 497.2 [M+H]⁺

Example 259

(R)-2-amino-N-(1-((4'-(hydroxymethyl)-[1,1'-biphe-
nyl]-3-yl)carbamoyl)pyrrolidin-3-yl)-5-(1-methyl-
1H-pyrazol-4-yl)nicotinamide Using Example 024 and 4-hydroxymethylphenylboronic acid, the title compound was obtained as described in general method D. MS (ESI, m/z): 512.2 [M+H]⁺

Example 260

(R)-2-amino-5-(1-methyl-1H-pyrazol-4-yl)-N-(1-((3-
(1-(piperidin-4-yl)-1H-pyrazol-4-yl)phenyl)carbam-
oyl)pyrrolidin-3-yl)nicotinamide Using Example 024 and (1-(piperidin-4-yl)-1H-pyrazol-4-yl)boronic acid pinacol ester, the title compound was obtained as described in general method D. MS (ESI, m/z): 555.2 [M+H]⁺

Example 261

(R)-2-amino-5-(1-methyl-1H-pyrazol-4-yl)-N-(1-((3-
(6-(piperazin-1-yl)pyridin-3-yl)phenyl)carbamoyl)
pyrrolidin-3-yl)nicotinamide Using Example 024 and (6-(piperazin-1-yl)pyridin-3-yl)boronic acid pinacol ester, the title compound was obtained as described in general method D. MS (ESI, m/z): 567.2 [M+H]⁺

Example 262

(R)-2-amino-5-(1-methyl-1H-pyrazol-4-yl)-N-(1-((4'-(methylamino)-[1,1'-biphenyl]-3-yl)carbamoyl)pyrrolidin-3-yl)nicotinamide Using Example 024 and 4-(N-methylamino)phenylboronic acid pinacol ester, the title compound was obtained as described in general method D. MS (ESI, m/z): 511.2 [M+H]$^+$

Example 263

(R)-2-amino-N-(1-((4'-(dimethylamino)-[1,1'-biphenyl]-3-yl)carbamoyl)pyrrolidin-3-yl)-5-(1-methyl-1H-pyrazol-4-yl)nicotinamide Using Example 024 and 4-(N,N-dimethylamino)phenylboronic acid pinacol ester, the title compound was obtained as described in general method D. MS (ESI, m/z): 583.2 [M+H]$^+$

Example 264

(R)-2-amino-N-(1-((3'-(hydroxymethyl)-[1,1'-biphenyl]-3-yl)carbamoyl)pyrrolidin-3-yl)-5-(1-methyl-1H-pyrazol-4-yl)nicotinamide Using Example 024 and 3-hydroxy methylphenylboronic acid, the title compound was obtained as described in general method D. MS (ESI, m/z): 512.2 [M+H]$^+$

Example 265

(R)-2-amino-N-(1-((3'-((dimethylamino)methyl)-[1,1'-biphenyl]-3-yl)carbamoyl)pyrrolidin-3-yl)-5-(1-methyl-1H-pyrazol-4-yl)nicotinamide Using Example 024 and (3-(N,N-dimethylaminomethyl)phenyl)boronic acid, the title compound was obtained as described in general method D. MS (ESI, m/z): 539.2 [M+H]$^+$

Example 266

(R)-2-amino-N-(1-((4'-((dimethylamino)methyl)-[1,1'-biphenyl]-3-yl)carbamoyl)pyrrolidin-3-yl)-5-(1-methyl-1H-pyrazol-4-yl)nicotinamide Using Example 024 and (4-(N,N-dimethylaminomethyl)phenyl)boronic acid, the title compound was obtained as described in general method D. MS (ESI, m/z): 539.2 [M+H]$^+$

Example 267

(R)-2-amino-5-(1-methyl-1H-pyrazol-4-yl)-N-(1-((3'-((4-methylpiperazin-1-yl)methyl)-[1,1'-biphenyl]-3-yl)carbamoyl)pyrrolidin-3-yl)nicotinamide Using Example 024 and (3-((4-methylpiperazin-1-yl)methyl)phenyl)boronic acid pinacol ester, the title compound was obtained as described in general method D. MS (ESI, m/z): 594.32 [M+H]$^+$

Example 268

(R)-2-amino-5-(1-methyl-1H-pyrazol-4-yl)-N-(1-((4'-((4-methylpiperazin-1-yl)methyl)-[1,1'-biphenyl]-3-yl)carbamoyl)pyrrolidin-3-yl)nicotinamide Using Example 024 and (4-((4-methylpiperazin-1-yl)methyl)phenyl)boronic acid pinacol ester, the title compound was obtained as described in general method D. MS (ESI, m/z): 594.32 [M+H]$^+$

Example 269

(R)-2-amino-N-(1-((3-((3'-(aminomethyl)-[1,1'-biphenyl]-4-yl)carbamoyl)pyrrolidin-3-yl)-5-(1-methyl-1H-pyrazol-4-yl)nicotinamide Using Example 025 and (3-(aminomethyl)phenyl)boronic acid, the title compound was obtained as described in general method D. MS (ESI, m/z): 511.2 [M+H]$^+$

Example 270

(R)-2-amino-N-(1-((4-((4'-(aminomethyl)-[1,1'-biphenyl]-4-yl)carbamoyl)pyrrolidin-3-yl)-5-(1-methyl-1H-pyrazol-4-yl)nicotinamide Using Example 025 and (4-(aminomethyl)phenyl)boronic acid, the title compound was obtained as described in general method D. MS (ESI, m/z): 511.2 [M+H]$^+$

Example 271

(R)—N-(1-([1,1'-biphenyl]-4-ylcarbamoyl)pyrrolidin-3-yl)-2-amino-5-(1-methyl-1H-pyrazol-4-yl)nicotinamide Using Example 025 and phenylboronic acid, the title compound was obtained as described in general method D. MS (ESI, m/z): 482.2 [M+H]$^+$

Example 272

(R)-2-amino-5-(1-methyl-1H-pyrazol-4-yl)-N-(1-((3'-((4-methylpiperazin-1-yl)methyl)-[1,1'-biphenyl]-4-yl)carbamoyl)pyrrolidin-3-yl)nicotinamide Using Example 025 and (3-((4-methylpiperazin-1-yl)methyl)phenyl)boronic acid pinacol ester, the title compound was obtained as described in general method D. MS (ESI, m/z): 594.32 [M+H]$^+$

Example 273

(R)-2-amino-5-(1-methyl-1H-pyrazol-4-yl)-N-(1-((4'-((4-methylpiperazin-1-yl)methyl)-[1,1'-biphenyl]-4-yl)carbamoyl)pyrrolidin-3-yl)nicotinamide Using Example 025 and (4-((4-methylpiperazin-1-yl)methyl)phenyl)boronic acid pinacol ester, the title compound was obtained as described in general method D. MS (ESI, m/z): 594.32 [M+H]$^+$

Example 274

(R)-2-amino-5-(1-methyl-1H-pyrazol-4-yl)-N-(1-((4'-((4-methylpiperazin-1-yl)methyl)-[1,1'-biphenyl]-3-yl)carbamothioyl)pyrrolidin-3-yl)nicotinamide Using Example 052 and (4-((4-methylpiperazin-1-yl)methyl)phenyl)boronic acid pinacol ester, the title compound was obtained as described in general method D. MS (ESI, m/z): 610.2 [M+H]$^+$

Example 275

4'-((4-methylpiperazin-1-yl)methyl)-[1,1'-biphenyl]-3-yl (R)-3-(2-amino-5-(1-methyl-1H-pyrazol-4-yl)nicotinamido)pyrrolidine-1-carboxylate Using Example 053 and (4-((4-methylpiperazin-1-yl)methyl)phenyl)boronic acid pinacol ester, the title compound was obtained as described in general method D. MS (ESI, m/z): 595.31 [M+H]$^+$

Example 276

(R)-3-(3'-((3-(2-amino-5-(1-methyl-1H-pyrazol-4-yl)nicotinamido)pyrrolidine-1-carbonyl)oxy)-[1,1'-biphenyl]-4-yl)propanoic acid Using Example 053 and 3-(4-boronophenyl)propanoic acid, the title compound was obtained as described in general method D. MS (ESI, m/z): 555.23 [M+H]$^+$

Example 277

3'-((2-cyanoethyl)carbamoyl)-[1,1'-biphenyl]-3-yl (R)-3-(2-amino-5-(1-methyl-1H-pyrazol-4-yl)nicotinamido)pyrrolidine-1-carboxylate Using Example 053 and (3-((2-cyanoethyl)carbamoyl)phenyl)boronic acid, the title compound was obtained as described in general method D. MS (ESI, m/z): 579.24 [M+H]$^+$

Example 278

(R)-3'-((3-(2-amino-5-(1-methyl-1H-pyrazol-4-yl)nicotinamido)pyrrolidine-1-carbonyl)oxy)-[1,1'-biphenyl]-4-carboxylic acid Using Example 053 and 4-carboxyphenylboronic acid, the title compound was obtained as described in general method D. MS (ESI, m/z): 527.20 [M+H]$^+$

Example 279

4'-hydroxy-[1,1'-biphenyl]-3-yl (R)-3-(2-amino-5-(1-methyl-1H-pyrazol-4-yl)nicotinamido)pyrrolidine-1-carboxylate Using Example 053 and 4-hydroxyphenylboronic acid, the title compound was obtained as described in general method D. MS (ESI, m/z): 499.20 [M+H]$^+$

Example 280

4'-(hydroxymethyl)-[1,1'-biphenyl]-3-yl (R)-3-(2-amino-5-(1-methyl-1H-pyrazol-4-yl)nicotinamido)pyrrolidine-1-carboxylate Using Example 053 and 4-hydroxymethylphenylboronic acid, the title compound was obtained as described in general method D. MS (ESI, m/z): 513.22 [M+H]$^+$

Example 281

4'-formyl-[1,1'-biphenyl]-3-yl (R)-3-(2-amino-5-(1-methyl-1H-pyrazol-4-yl)nicotinamido)pyrrolidine-1-carboxylate Using Example 053 and 4-formylphenylboronic acid, the title compound was obtained as described in general method D. MS (ESI, m/z): 511.20 [M+H]$^+$

Example 282

3'-formyl-[1,1'-biphenyl]-3-yl (R)-3-(2-amino-5-(1-methyl-1H-pyrazol-4-yl)nicotinamido)pyrrolidine-1-carboxylate Using Example 053 and 4-formylphenylboronic acid, the title compound was obtained as described in general method D. MS (ESI, m/z): 511.20 [M+H]$^+$

Example 283

3-(1-benzyl-1H-pyrazol-4-yl)phenyl (R)-3-(2-amino-5-(1-methyl-1H-pyrazol-4-yl)nicotinamido)pyrrolidine-1-carboxylate Using Example 053 and (1-benzyl-1H-pyrazol-4-yl)boronic acid pinacol ester, the title compound was obtained as described in general method D. MS (ESI, m/z): 563.24 [M+H]$^+$

Example 284

3-(1-(2-hydroxyethyl)-1H-pyrazol-4-yl)phenyl (R)-3-(2-amino-5-(1-methyl-1H-pyrazol-4-yl)nicotinamido)pyrrolidine-1-carboxylate Using Example 053 and (1-(2-hydroxyethyl)-1H-pyrazol-4-yl)boronic acid pinacol ester, the title compound was obtained as described in general method D. MS (ESI, m/z): 517.22 [M+H]$^+$

Example 285

3-(1-(piperidin-4-yl)-1H-pyrazol-4-yl)phenyl (R)-3-(2-amino-5-(1-methyl-1H-pyrazol-4-yl)nicotinamido)pyrrolidine-1-carboxylate Using Example 053 and (1-(4-piperidinyl)-1H-pyrazol-4-yl)boronic acid pinacol ester, the title compound was obtained as described in general method D. MS (ESI, m/z): 556.27 [M+H]$^+$

Example 286

3-(1-(2-(pyrrolidin-1-yl)ethyl)-1H-pyrazol-4-yl)phenyl (R)-3-(2-amino-5-(1-methyl-1H-pyrazol-4-yl)nicotinamido)pyrrolidine-1-carboxylate Using Example 053 and (1-(2-(pyrrolidin-1-yl)ethyl)-1H-pyrazol-4-yl)boronic acid pinacol ester, the title compound was obtained as described in general method D. MS (ESI, m/z): 570.29 [M+H]$^+$

Example 287

3-(1-(2-morpholinoethyl)-1H-pyrazol-4-yl)phenyl (R)-3-(2-amino-5-(1-methyl-1H-pyrazol-4-yl)nicotinamido)pyrrolidine-1-carboxylate Using Example 053 and (1-(2-morpholinoethyl)-1H-pyrazol-4-yl)boronic acid pinacol ester, the title compound was obtained as described in general method D. MS (ESI, m/z): 586.28 [M+H]$^+$

Example 288

3-(1-(2-(4-methylpiperazin-1-yl)ethyl)-1H-pyrazol-4-yl)phenyl (R)-3-(2-amino-5-(1-methyl-1H-pyrazol-4-yl)nicotinamido)pyrrolidine-1-carboxylate Using Example 053 and (1-(2-(4-methylpiperazin-1-yl)ethyl)-1H-pyrazol-4-yl)boronic acid pinacol ester, the title compound was obtained as described in general method D. MS (ESI, m/z): 599.31 [M+H]$^+$

Example 289

3-(isoquinolin-4-yl)phenyl (R)-3-(2-amino-5-(1-methyl-1H-pyrazol-4-yl)nicotinamido)pyrrolidine-1-carboxylate Using Example 053 and isoquinolin-4-ylboronic acid, the title compound was obtained as described in general method D. MS (ESI, m/z): 534.22 [M+H]$^+$

Example 290

3-(2-(4-methylpiperazin-1-yl)pyridin-4-yl)phenyl (R)-3-(2-amino-5-(1-methyl-1H-pyrazol-4-yl)nicotinamido)pyrrolidine-1-carboxylate Using Example 053 and (2-(4-methylpiperazin-1-yl)pyridin-4-yl)boronic acid pinacol ester, the title compound was obtained as described in general method D. MS (ESI, m/z): 582.29 [M+H]$^+$

Example 291

5-chloro-4'-(hydroxymethyl)-[1,1'-biphenyl]-3-yl (R)-3-(2-amino-5-(1-methyl-1H-pyrazol-4-yl)nicotinamido)pyrrolidine-1-carboxylate Using Example 846 and 4-hydroxymethylphenylboronic acid, the title compound was obtained as described in general method D. MS (ESI, m/z): 547.18 [M+H]$^+$

Example 292

5-chloro-4'-((4-methylpiperazin-1-yl)methyl)-[1,1'-biphenyl]-3-yl (R)-3-(2-amino-5-(1-methyl-1H-pyrazol-4-yl)nicotinamido)pyrrolidine-1-carboxylate Using Example 846 and (4-((4-methylpiperazin-1-yl)methyl)phenyl)boronic acid pinacol ester, the title compound was obtained as described in general method D. MS (ESI, m/z): 629.27 [M+H]$^+$

Example 293

6-(4-((4-methylpiperazin-1-yl)methyl)phenyl)naphthalen-2-yl (R)-3-(2-amino-5-(1-methyl-1H-pyrazol-4-yl)nicotinamido)pyrrolidine-1-carboxylate Using Example 067 and (4-((4-methylpiperazin-1-yl)methyl)phenyl)boronic acid pinacol ester, the title compound was obtained as described in general method D. MS (ESI, m/z): 645.2 [M+H]$^+$

Example 633

(R)-2-amino-N-(1-((6-fluoro-4'-((4-methylpiperazin-1-yl)methyl)-[1,1'-biphenyl]-3-yl)methyl)pyrrolidin-3-yl)-5-(1-methyl-1H-pyrazol-4-yl)nicotinamide Using Example 233 and 1-methyl-4-(4-(4,4,5,5-tetramethyl-1,3,2-dioxaborolan-2-yl)benzyl)piperazine, the title compound was obtained as described in general method D. MS (ESI, m/z): 583.3 [M+H]$^+$

General Method E

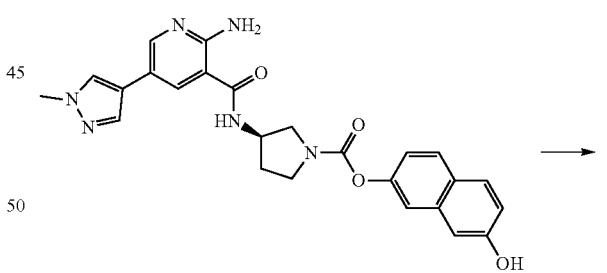

Example 095

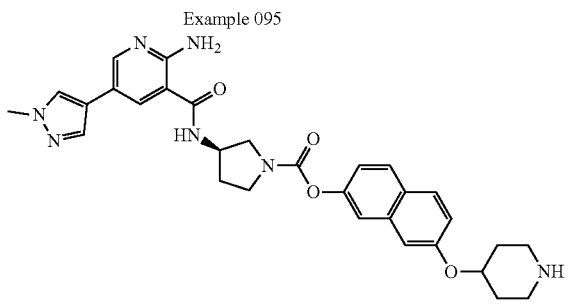

Example 294

Example 294

7-(piperidin-4-yloxy)naphthalen-2-yl (R)-3-(2-amino-5-(1-methyl-1H-pyrazol-4-yl)nicotinamido)pyrrolidine-1-carboxylate A mixture of Example 095 (20 mg, 0.04 mmol), tert-butyl 4-bromopiperidine-1-carboxylate (17 µL, 0.08 mmol) and $K_2CO_3$ (29 mg, 0.21 mmol) in N,N-dimethylformamide (0.5 mL) was heated at 60° C. for 12 h, cooled to room temperature, and extracted with ethyl acetate, dried over anhydrous $MgSO_4$ and concentrated under vacuum. The crude residue was dissolved in 0.5 mL of dichloromethane/trifluoroacetic acid (4/1) and stirred at room temperature for 3 h. After concentration in vacuo, the crude residue was purified by preparative HPLC to afford 10 mg of the title compound. MS (ESI, m/z): 556.2 $[M+H]^+$

Example 295

7-(3-(dimethylamino)propoxy)naphthalen-2-yl (R)-3-(2-amino-5-(1-methyl-1H-pyrazol-4-yl)nicotinamido)pyrrolidine-1-carboxylate Using 3-(N,N-dimethylamino)propyl chloride hydrochloride, the title compound was obtained as described in general method E. MS (ESI, m/z): 558.2 $[M+H]^+$

Example 296

7-(2-(dimethylamino)ethoxy)naphthalen-2-yl (R)-3-(2-amino-5-(1-methyl-1H-pyrazol-4-yl)nicotinamido)pyrrolidine-1-carboxylate Using 2-dimethylaminoethyl chloride hydrochloride, the title compound was obtained as described in general method E. MS (ESI, m/z): 544.2 $[M+H]^+$

Example 297

7-((1-methylpiperidin-4-yl)oxy)naphthalen-2-yl (R)-3-(2-amino-5-(1-methyl-1H-pyrazol-4-yl)nicotinamido)pyrrolidine-1-carboxylate Using 4-bromo-1-methylpiperidine, the title compound was obtained as described in general method E. MS (ESI, m/z): 570.2 $[M+H]^+$

Example 298

7-(piperidin-4-ylmethoxy)naphthalen-2-yl (R)-3-(2-amino-5-(1-methyl-1H-pyrazol-4-yl)nicotinamido)pyrrolidine-1-carboxylate Using tert-butyl 4-(bromomethyl)piperidine-1-carboxylate, the title compound was obtained as described in general method E. MS (ESI, m/z): 570.2 $[M+H]^+$

Example 299

7-(2-hydroxyethoxy)naphthalen-2-yl (R)-3-(2-amino-5-(1-methyl-1H-pyrazol-4-yl)nicotinamido)pyrrolidine-1-carboxylate Using 2-bromoethanol, the title compound was obtained as described in general method E. MS (ESI, m/z): 517.2 $[M+H]^+$

Example 300

6-(2-(dimethylamino)ethoxy)naphthalen-2-yl (R)-3-(2-amino-5-(1-methyl-1H-pyrazol-4-yl)nicotinamido)pyrrolidine-1-carboxylate Using Example 104, the title compound was obtained as described in general method E. MS (ESI, m/z): 544.2 $[M+H]^+$

Example 301

6-(3-(dimethylamino)propoxy)naphthalen-2-yl (R)-3-(2-amino-5-(1-methyl-1H-pyrazol-4-yl)nicotinamido)pyrrolidine-1-carboxylate Using Example 104 and 3-(N,N-dimethylamino)propyl chloride hydrochloride, the title compound was obtained as described in general method E. MS (ESI, m/z): 558.2 $[M+H]^+$

Example 302

6-(piperidin-4-yloxy)naphthalen-2-yl (R)-3-(2-amino-5-(1-methyl-1H-pyrazol-4-yl)nicotinamido)pyrrolidine-1-carboxylate Using Example 104 and tert-butyl 4-bromopiperidine-1-carboxylate, the title compound was obtained as described in general method E. MS (ESI, m/z): 556.2 $[M+H]^+$

Example 303

6-(piperidin-4-ylmethoxy)naphthalen-2-yl (R)-3-(2-amino-5-(1-methyl-1H-pyrazol-4-yl)nicotinamido)pyrrolidine-1-carboxylate Using Example 104 and tert-butyl 4-(bromomethyl)piperidine-1-carboxylate, the title compound was obtained as described in general method E. MS (ESI, m/z): 570.2 $[M+H]^+$

Example 304

3-(piperidin-4-ylmethoxy)phenyl (R)-3-(2-amino-5-(1-methyl-1H-pyrazol-4-yl)nicotinamido)pyrrolidine-1-carboxylate Using Example 101 and tert-butyl 4-(bromomethyl)piperidine-1-carboxylate, the title compound was obtained as described in general method E. MS (ESI, m/z): 520.2 $[M+H]^+$

Example 305

3-(((1R,4R)-4-aminocyclohexyl)methoxy)phenyl (R)-3-(2-amino-5-(1-methyl-1H-pyrazol-4-yl)nicotinamido)pyrrolidine-1-carboxylate Using Example 101 and tert-butyl ((1R,4R-4-(chloromethyl)cyclohexyl)carbamate, the title compound was obtained as described in general method E. MS (ESI, m/z): 570.2 $[M+H]^+$ General Method F

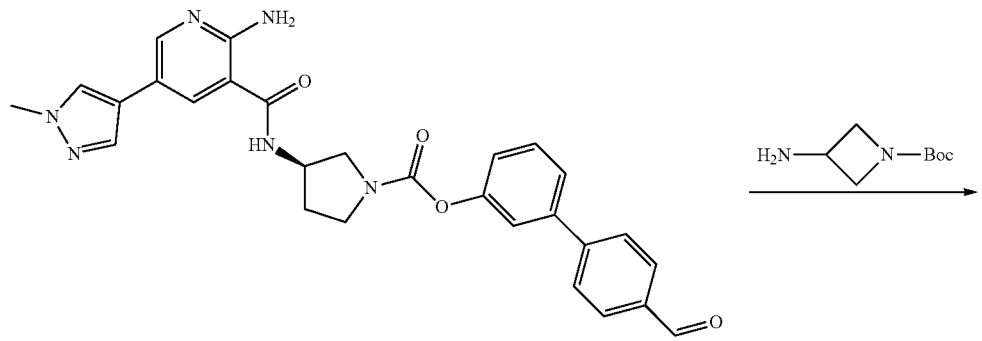

Example 281

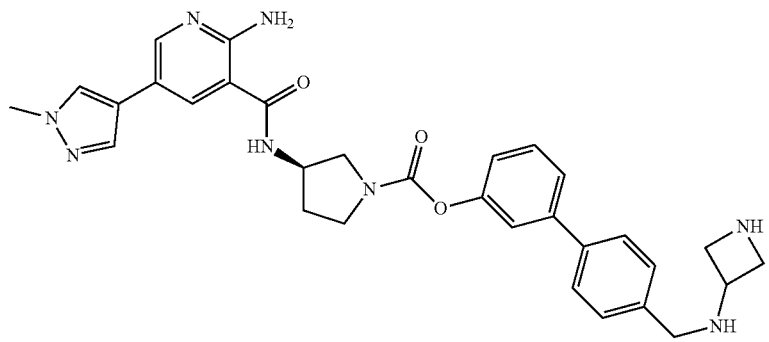

Example 306

Example 306

4'-((azetidin-3-ylamino)methyl)-[1,1'-biphenyl]-3-yl (R)-3-(2-amino-5-(1-methyl-1H-pyrazol-4-yl)nicotinamido)pyrrolidine-1-carboxylate To a mixture of Example 281 (20 mg, 0.04 mmol) in 0.4 mL of dichloroethane was added tert-butyl 3-aminoazetidine-1-carboxylate (13 mg, 0.08 mmol) followed by NaBH(OAc)$_3$ (25 mg, 0.12 mmol). The mixture was stirred at 80° C. for 4 h and then water was added. The mixture was extracted with ethyl acetate, washed with brine, dried over MgSO$_4$, and concentrated in vacuo. The crude residue was dissolved in 0.5 mL of dichloromethane/trifluoroacetic acid (4/1) and stirred at room temperature for 3 h. After concentration in vacuo, the crude residue was purified by preparative HPLC to afford 10 mg of the title compound. MS (ESI, m/z): 567.28 [M+H]$^+$

Example 307

4'-(((2-aminoethyl)amino)methyl)-[1,1'-biphenyl]-3-yl (R)-3-(2-amino-5-(1-methyl-1H-pyrazol-4-yl)nicotinamido)pyrrolidine-1-carboxylate Using 2-aminoethylamine, the title compound was obtained as described in general method F. MS (ESI, m/z): 555.28 [M+H]$^+$

Example 308

4'-(((2-(dimethylamino)ethyl)amino)methyl)-[1,1'-biphenyl]-3-yl (R)-3-(2-amino-5-(1-methyl-1H-pyrazol-4-yl)nicotinamido)pyrrolidine-1-carboxylate Using 2-dimethylaminoethylamine, the title compound was obtained as described in general method F. MS (ESI, m/z): 583.31 [M+H]$^+$

Example 309

4'-(((azetidin-3-ylmethyl)amino)methyl)-[1,1'-biphenyl]-3-yl (R)-3-(2-amino-5-(1-methyl-1H-pyrazol-4-yl)nicotinamido)pyrrolidine-1-carboxylate Using tert-butyl 3-(aminomethyl)azetidine-1-carboxylate, the title compound was obtained as described in general method F. MS (ESI, m/z): 581.29 [M+H]$^+$

Example 310

4'-((((R)-1-methylpyrrolidin-3-yl)amino)methyl)-[1,1'-biphenyl]-3-yl (R)-3-(2-amino-5-(1-methyl-1H-pyrazol-4-yl)nicotinamido)pyrrolidine-1-carboxylate Using (R)-1-methylpyrrolidin-3-amine, the title compound was obtained as described in general method F. MS (ESI, m/z): 595.31 [M+H]$^+$

Example 311

4'-((3-(dimethylamino)pyrrolidin-1-yl)methyl)-[1,1'-biphenyl]-3-yl (3R)-3-(2-amino-5-(1-methyl-1H-pyrazol-4-yl)nicotinamido)pyrrolidine-1-carboxylate Using 3-dimethylaminopyrrolidine, the title compound was obtained as described in general method F. MS (ESI, m/z): 609.32 [M+H]$^+$

Example 312

4'-(((((S)-pyrrolidin-2-yl)methyl)amino)methyl)-[1,1'-biphenyl]-3-yl (R)-3-(2-amino-5-(1-methyl-1H-pyrazol-4-yl)nicotinamido)pyrrolidine-1-carboxylate Using tert-butyl (S)-2-(aminomethyl)pyrrolidine-1-carboxylate, the title compound was obtained as described in general method F. MS (ESI, m/z): 595.31 [M+H]$^+$

Example 313

4'-((((R)-pyrrolidin-3-yl)amino)methyl)-[1,1'-biphenyl]-3-yl (R)-3-(2-amino-5-(1-methyl-1H-pyrazol-4-yl)nicotinamido)pyrrolidine-1-carboxylate Using tert-butyl (R)-3-aminopyrrolidine-1-carboxylate, the title compound was obtained as described in general method F. MS (ESI, m/z): 581.29 [M+H]$^+$

Example 314

4'-(((((R)-1-ethylpyrrolidin-2-yl)methyl)amino)methyl)-[1,1'-biphenyl]-3-yl (R)-3-(2-amino-5-(1-methyl-1H-pyrazol-4-yl)nicotinamido)pyrrolidine-1-carboxylate Using (R)-(1-ethylpyrrolidin-2-yl)methanamine, the title compound was obtained as described in general method F. MS (ESI, m/z): 623.34 [M+H]$^+$

Example 315

4'-((((S)-piperidin-3-yl)amino)methyl)-[1,1'-biphenyl]-3-yl (R)-3-(2-amino-5-(1-methyl-1H-pyrazol-4-yl)nicotinamido)pyrrolidine-1-carboxylate Using tert-butyl (S)-3-aminopiperidine-1-carboxylate, the title compound was obtained as described in general method F. MS (ESI, m/z): 595.31 [M+H]$^+$

Example 316

4'-(((R)-3-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate Using tert-butyl (R)-piperidin-3-ylcarbamate, the title compound was obtained as described in general method F. MS (ESI, m/z): 595.31 [M+H]$^+$

Example 317

4'-((4-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate Using tert-butyl piperidin-4-ylcarbamate, the title compound was obtained as described in general method F. MS (ESI, m/z): 595.31 [M+H]$^+$

Example 318

4'-(((1-methylpiperidin-4-yl)amino)methyl)-[1,1'-biphenyl]-3-yl (R)-3-(2-amino-5-(1-methyl-1H-pyrazol-4-yl)nicotinamido)pyrrolidine-1-carboxylate Using 1-methylpiperidin-4-amine, the title compound was obtained as described in general method F. MS (ESI, m/z): 609.32 [M+H]$^+$

Example 319

4'-((3-hydroxypiperidin-1-yl)methyl)-[1,1'-biphenyl]-3-yl (3R)-3-(2-amino-5-(1-methyl-1H-pyrazol-4-yl)nicotinamido)pyrrolidine-1-carboxylate Using 3-hydroxypiperidine, the title compound was obtained as described in general method F. MS (ESI, m/z): 596.29 [M+H]$^+$

Example 320

4'-((3-(hydroxymethyl)piperidin-1-yl)methyl)-[1,1'-biphenyl]-3-yl (3R)-3-(2-amino-5-(1-methyl-1H-pyrazol-4-yl)nicotinamido)pyrrolidine-1-carboxylate Using 3-hydroxymethylpiperidine, the title compound was obtained as described in general method F. MS (ESI, m/z): 610.31 [M+H]$^+$

Example 321

4'-((4-(hydroxymethyl)piperidin-1-yl)methyl)-[1,1'-biphenyl]-3-yl (R)-3-(2-amino-5-(1-methyl-1H-pyrazol-4-yl)nicotinamido)pyrrolidine-1-carboxylate Using 4-hydroxymethylpiperidine, the title compound was obtained as described in general method F. MS (ESI, m/z): 610.31 [M+H]$^+$

Example 322

4'-(((3aR,6aR)-1-methylhexahydropyrrolo[3,4-b]pyrrol-5(1H)-yl)methyl)-[1,1'-biphenyl]-3-yl (R)-3-(2-amino-5-(1-methyl-1H-pyrazol-4-yl)nicotinamido)pyrrolidine-1-carboxylate Using (3aR,6aR)-1-methyloctahydropyrrolo[3,4-b]pyrrole, the title compound was obtained as described in general method F. MS (ESI, m/z): 621.32 [M+H]$^+$

Example 323

4'-((1,4-diazepan-1-yl)methyl)-[1,1'-biphenyl]-3-yl (R)-3-(2-amino-5-(1-methyl-1H-pyrazol-4-yl)nicotinamido)pyrrolidine-1-carboxylate Using tert-butyl 1,4-diazepane-1-carboxylate, the title compound was obtained as described in general method F. MS (ESI, m/z): 595.31 [M+H]$^+$

Example 324

4'-(((R)-2-(hydroxymethyl)pyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate Using (R)-2-hydroxymethylpyrrolidine, the title compound was obtained as described in general method F. MS (ESI, m/z): 596.29 [M+H]$^+$

Example 325

4'-(((S)-2-carbamoylpyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate Using (S)-2-carbamoylpyrrolidine, the title compound was obtained as described in general method F. MS (ESI, m/z): 609.29 [M+H]$^+$

Example 326

(R)-((3'-((3-(2-amino-5-(1-methyl-1H-pyrazol-4-yl)nicotinamido)pyrrolidine-1-carbonyl)oxy)-[1,1'-biphenyl]-4-yl)methyl)glycine Using glycine, the title compound was obtained as described in general method F. MS (ESI, m/z): 570.24 [M+H]$^+$

Example 327

4'-((((R)-1-hydroxypropan-2-yl)amino)methyl)-[1,1'-biphenyl]-3-yl (R)-3-(2-amino-5-(1-methyl-1H-pyrazol-4-yl)nicotinamido)pyrrolidine-1-carboxylate Using (R)-2-aminopropan-1-ol, the title compound was obtained as described in general method F. MS (ESI, m/z): 570.24 [M+H]$^+$

Example 328

4'-(((3-hydroxypropyl)amino)methyl)-[1,1'-biphenyl]-3-yl (R)-3-(2-amino-5-(1-methyl-1H-pyrazol-4-yl)nicotinamido)pyrrolidine-1-carboxylate Using 3-aminopropan-1-ol, the title compound was obtained as described in general method F. MS (ESI, m/z): 570.24 [M+H]$^+$

Example 329

1-((3'-(((R)-3-(2-amino-5-(1-methyl-1H-pyrazol-4-yl)nicotinamido)pyrrolidine-1-carbonyl)oxy)-[1,1'-biphenyl]-4-yl)methyl)pyrrolidine-3-carboxylic acid Using pyrrolidine-3-carboxylic acid, the title compound was obtained as described in general method F. MS (ESI, m/z): 610.27 [M+H]$^+$

Example 330

4'-(((R)-3-aminopyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate Using tert-butyl (R)-pyrrolidin-3-ylcarbamate, the title compound was obtained as described in general method F. MS (ESI, m/z): 581.29 [M+H]$^+$

Example 331

4'-(((S)-3-aminopyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate Using tert-butyl (S)-pyrrolidin-3-ylcarbamate, the title compound was obtained as described in general method F. MS (ESI, m/z): 581.29 [M+H]$^+$

Example 332

4'-(((S)-3-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate Using tert-butyl (S)-piperidin-3-ylcarbamate, the title compound was obtained as described in general method F. MS (ESI, m/z): 595.31 [M+H]$^+$

Example 333

4'-(pyrrolidin-1-ylmethyl)-[1,1'-biphenyl]-3-yl (R)-3-(2-amino-5-(1-methyl-1H-pyrazol-4-yl)nicotinamido)pyrrolidine-1-carboxylate Using pyrrolidine, the title compound was obtained as described in general method F. MS (ESI, m/z): 566.28 [M+H]$^+$

Example 334

4'-(piperidin-1-ylmethyl)-[1,1'-biphenyl]-3-yl (R)-3-(2-amino-5-(1-methyl-1H-pyrazol-4-yl)nicotinamido)pyrrolidine-1-carboxylate Using piperidine, the title compound was obtained as described in general method F. MS (ESI, m/z): 580.30 [M+H]$^+$

Example 335

4'-(morpholinomethyl)-[1,1'-biphenyl]-3-yl (R)-3-(2-amino-5-(1-methyl-1H-pyrazol-4-yl)nicotinamido)pyrrolidine-1-carboxylate Using morpholine, the title compound was obtained as described in general method F. MS (ESI, m/z): 582.28 [M+H]$^+$

Example 336

3'-(((R)-3-aminopyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate Using Example 282, tert-butyl (R)-pyrrolidin-3-ylcarbamate, the title compound was obtained as described in general method F. MS (ESI, m/z): 581.29 [M+H]$^+$

Example 337

3'-(((S)-3-aminopyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate Using Example 282, tert-butyl (S)-pyrrolidin-3-ylcarbamate, the title compound was obtained as described in general method F. MS (ESI, m/z): 581.29 [M+H]$^+$

Example 338

3'-(((R)-3-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate Using Example 282, tert-butyl (R)-piperidin-3-ylcarbamate, the title compound was obtained as described in general method F. MS (ESI, m/z): 595.31 [M+H]$^+$

Example 339

3'-(((S)-3-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate Using Example 282, tert-butyl (S)-piperidin-3-ylcarbamate, the title compound was obtained as described in general method F. MS (ESI, m/z): 595.31 [M+H]$^+$

Example 340

3'-((4-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate Using Example 282, tert-butyl piperidin-4-ylcarbamate, the title compound was obtained as described in general method F. MS (ESI, m/z): 595.31 [M+H]$^+$

Example 341

3'-((1,4-diazepan-1-yl)methyl)-[1,1'-biphenyl]-3-yl (R)-3-(2-amino-5-(1-methyl-1H-pyrazol-4-yl)nicotinamido)pyrrolidine-1-carboxylate Using Example 282, tert-butyl 1,4-diazepane-1-carboxylate, the title compound was obtained as described in general method F. MS (ESI, m/z): 595.31 [M+H]$^+$

Example 634

(R)-2-amino-N-(1-(4'-(4-(aminomethyl)phenoxy)-[1,1'-biphenyl]-4-carbonyl)pyrrolidin-3-yl)-5-(1-methyl-1H-pyrazol-4-yl)nicotinamide Using Example 811 and ammonia, the title compound was obtained as described in general method F. $^1$H NMR (600 MHz, METHANOL-d$_4$) δ ppm 2.08-2.24 (m, 1H) 2.28-2.44 (m, 1H) 3.57 (br dd, J=11.15, 5.28 Hz, 0.5H) 3.65-3.73 (m, 1H) 3.73-3.81 (m, 1H) 3.81-3.89 (m, 0.5H) 3.93 (d, J=4.70 Hz, 3H) 3.95-4.04 (m, 1H) 4.09 (s, 2H) 4.51-4.59 (m, 0.5H) 4.66-4.73 (m, 0.5H) 7.05-7.19 (m, 4H) 7.46 (dd, J=8.80, 1.76 Hz, 1H) 7.60-7.78 (m, 7H) 7.89 (d, J=18.19 Hz, 1H) 8.05 (d, J=15.85 Hz, 1H) 8.23 (dd, J=18.78, 2.35 Hz, 1H) 8.61-8.74 (m, 1H); MS (ESI, m/z): 588.3 [M+H]$^+$

Example 635

(R)-2-amino-N-(1-(4'-(4-(hydroxymethyl)phenoxy)-[1,1'-biphenyl]-4-carbonyl)pyrrolidin-3-yl)-5-(1-methyl-1H-pyrazol-4-yl)nicotinamide It was isolated as a side product of Example 634. $^1$H NMR (600 MHz, METHANOL-d$_4$) δ ppm 2.07-2.23 (m, 1H) 2.26-2.45 (m, 1H) 3.56 (br dd, J=11.15, 5.28 Hz, 1H) 3.67 (br d, J=9.98 Hz, 1H) 3.71-3.79 (m, 1H) 3.81-3.89 (m, 1H) 3.93 (d, J=5.28 Hz, 2H) 3.94-4.03 (m, 1H) 4.52-4.56 (m, 1H) 4.58 (s, 1H) 4.65-4.71 (m, 1H) 5.65-5.65 (m, 1H) 6.97-7.17 (m, 3H) 7.31-7.40 (m, 1H) 7.41-7.55 (m, 2H) 7.56-7.72 (m, 6H) 7.89 (d, J=19.37 Hz, 1H) 8.03 (d, J=18.19 Hz, 1H) 8.18-8.25 (m, 1H) 8.60-8.74 (m, 1H); MS (ESI, m/z): 589.3 [M+H]$^+$

Example 636

(R)-2-amino-N-(1-(4'-(4-((dimethylamino)methyl)phenoxy)-[1,1'-biphenyl]-4-carbonyl)pyrrolidin-3-yl)-5-(1-methyl-1H-pyrazol-4-yl)nicotinamide Using Example 811 and dimethylamine, the title compound was obtained as described in general method F. $^1$H NMR (600 MHz, METHANOL-d$_4$) δ ppm 2.11-2.26 (m, 1H) 2.30-2.46 (m, 1H) 2.88 (s, 6H) 3.60 (br dd, J=11.15, 5.28 Hz, 0.5H) 3.66-3.74 (m, 1H) 3.75-3.84 (m, 1H) 3.86-3.92 (m, 0.5H) 3.96 (d, J=5.28 Hz, 3H) 3.98-4.06 (m, 1H) 4.31 (s, 2H) 4.55-4.60 (m, 0.5H) 4.69-4.75 (m, 0.5H) 7.10-7.20 (m, 4H) 7.52 (br d, J=8.22 Hz, 2H) 7.64-7.79 (m, 6H) 7.92 (d, J=17.61 Hz, 1H) 8.07 (d, J=15.85 Hz, 1H) 8.26 (br d, J=18.78 Hz, 1H) 8.65-8.76 (m, 1H); MS (ESI, m/z): 616.3 [M+H]$^+$

Example 637

(R)-2-amino-N-(1-(4'-(4-(aminomethyl)phenoxy)-2'-chloro-[1,1'-biphenyl]-4-carbonyl)pyrrolidin-3-yl)-5-(1-methyl-1H-pyrazol-4-yl)nicotinamide Using Example 844 and ammonia, the title compound was obtained as described in general method F. MS (ESI, m/z): 622.2 [M+H]$^+$

Example 638

(R)-2-amino-N-(1-(2'-chloro-4'-(4-((dimethylamino)methyl)phenoxy)-[1,1'-biphenyl]-4-carbonyl)pyrrolidin-3-yl)-5-(1-methyl-1H-pyrazol-4-yl)nicotinamide Using Example 844 and dimethylamine, the title compound was obtained as described in general method F. $^1$H NMR (600 MHz, METHANOL-d$_4$) δ ppm 2.09-2.25 (m, 1H) 2.29-2.45 (m, 1H) 2.86-2.90 (s, 6H) 3.59 (dd, J=11.15, 5.28 Hz, 0.5H) 3.70 (br dd, J=12.62, 4.99 Hz, 1H) 3.74-3.82 (m, 1H) 3.84-3.91 (m, 0.5H) 3.94 (d, J=4.11 Hz, 3H) 3.96-4.06 (m, 1H) 4.30-4.34 (s, 2H) 4.55-4.61 (m, 0.5H)

4.65-4.74 (m, 0.5H) 7.08 (ddd, J=8.07, 5.43, 2.35 Hz, 1H) 7.16-7.22 (m, 3H) 7.40-7.45 (m, 1H) 7.50-7.57 (m, 4H) 7.65 (dd, J=13.50, 8.22 Hz, 2H) 7.90 (d, J=17.02 Hz, 1H) 8.06 (d, J=15.26 Hz, 1H) 8.25 (dd, J=18.49, 2.05 Hz, 1H) 8.63-8.73 (m, 1H); MS (ESI, m/z): 650.3 [M+H]$^+$ Example 639

(R)-2-amino-N-(1-(2'-chloro-4'-(4-(hydroxymethyl)phenoxy)-[1,1'-biphenyl]-4-carbonyl)pyrrolidin-3-yl)-5-(1-methyl-1H-pyrazol-4-yl)nicotinamide It was isolated as a side product of Example 637. $^1$H NMR (600 MHz, METHANOL-d$_4$) δ ppm 2.10-2.24 (m, 1H) 2.30-2.45 (m, 1H) 3.58 (br dd, J=11.15, 5.28 Hz, 0.5H) 3.70 (br dd, J=12.33, 4.70 Hz, 1H) 3.78 (br dd, J=12.33, 6.46 Hz, 1H) 3.87 (br s, 0.5H) 3.95 (d, J=4.70 Hz, 3H) 3.97-4.05 (m, 1H) 4.54-4.60 (m, 0.5H) 4.62 (s, 2H) 4.67-4.76 (m, 0.5H) 7.00 (ddd, J=8.22, 5.28, 2.35 Hz, 1H) 7.04-7.10 (m, 2H) 7.10-7.23 (m, 1H) 7.33-7.40 (m, 1H) 7.42 (br d, J=6.46 Hz, 2H) 7.50-7.55 (m, 2H) 7.64 (br dd, J=13.50, 8.22 Hz, 2H) 7.91 (d, J=17.61 Hz, 1H) 8.06 (d, J=16.43 Hz, 1H) 8.25 (dd, J=19.37, 1.76 Hz, 1H) 8.63-8.76 (m, 1H); MS (ESI, m/z): 623.2 [M+H]$^+$ Example 640

(R)-2-amino-5-(1-methyl-1H-pyrazol-4-yl)-N-(1-(4-((4-methylpiperazin-1-yl)methyl)benzoyl)pyrrolidin-3-yl)nicotinamide Using Example 841 and 1-methylpiperazine, the title compound was obtained as described in general method F. $^1$H NMR (600 MHz, METHANOL-d$_4$) δ ppm 2.05-2.22 (m, 1H) 2.25-2.42 (m, 1H) 2.91 (d, J=4.11 Hz, 3H) 3.20 (br s, 4H) 3.40 (br s, 4H) 3.49 (br dd, J=11.15, 5.28 Hz, 0.5H) 3.58-3.76 (m, 2H) 3.79-3.86 (m, 0.5H) 3.88-3.92 (m, 0.5H) 3.94 (d, J=2.93 Hz, 3H) 3.96-4.04 (m, 2.5H) 4.51-4.56 (m, 0.5H) 4.65-4.72 (m, 0.5H) 7.50-7.56 (m, 2H) 7.56-7.63 (m, 2H) 7.90 (d, J=16.43 Hz, 1H) 8.05 (d, J=12.91 Hz, 1H) 8.24 (dd, J=13.50, 2.35 Hz, 1H) 8.61-8.76 (m, 1H); MS (ESI, m/z): 503.3 [M+H]$^+$ Example 641

(R)-2-amino-N-(1-(4-((4-(2-hydroxyethyl)piperazin-1-yl)methyl)benzoyl)pyrrolidin-3-yl)-5-(1-methyl-1H-pyrazol-4-yl)nicotinamide Using Example 841 and 2-(piperazin-1-yl)ethan-1-ol, the title compound was obtained as described in general method F. $^1$H NMR (600 MHz, METHANOL-d$_4$) δ ppm 2.06-2.22 (m, 1H) 2.25-2.45 (m, 1H) 3.20 (br s, 4H) 3.28-3.31 (m, 2H) 3.41-3.57 (m, 4.5H) 3.58-3.78 (m, 2H) 3.82-3.92 (m, 3H) 3.94 (d, J=2.93 Hz, 3H) 4.00 (dd, J=12.91, 7.04 Hz, 0.5H) 4.09 (d, J=11.15 Hz, 2H) 4.50-4.57 (m, 0.5H) 4.66-4.72 (m, 0.5H) 7.50-7.57 (m, 2H) 7.57-7.65 (m, 1H) 7.89 (d, J=15.85 Hz, 1H) 8.05 (d, J=13.50 Hz, 1H) 8.24 (dd, J=13.21, 2.05 Hz, 1H) 8.62-8.75 (m, 1H); MS (ESI, m/z): 533.3 [M+H]$^+$ Example 642

2-amino-N—((R)-1-(2'-chloro-4'-fluoro-[1,1'-biphenyl]-4-carbonyl)pyrrolidin-3-yl)-5-(2-((((1 r,4R)-4-hydroxycyclohexyl)amino)methyl)phenyl)nicotinamide Using Example 845 and (1r,4r)-4-aminocyclohexan-1-ol, the title compound was obtained as described in general method F. $^1$H NMR (600 MHz, METHANOL-d$_4$) δ ppm 1.22-1.33 (m, 2H) 1.42 (br dd, J=12.33, 9.98 Hz, 2H) 1.51-1.63 (m, 1H) 1.98-2.02 (m, 1H) 2.03-2.11 (m, 2H) 2.14-2.21 (m, 1H) 2.26-2.40 (m, 1H) 3.01-3.11 (m, 1H) 3.62-3.68 (m, 1.5H) 3.70-3.76 (m, 1H) 3.79 (br t, J=7.34 Hz, 1H) 3.92-4.01 (m, 1H) 4.23 (d, J=17.61 Hz, 2H) 4.25 (d, J=17.61 Hz, 1H) 4.53-4.59 (m, 0.5H) 4.67-4.73 (m, 0.5H) 7.17 (td, J=8.36, 2.64 Hz, 1H) 7.34 (d, J=8.65 Hz, 1H) 7.38-7.47 (m, 2H) 7.47-7.51 (m, 2H) 7.53-7.63 (m, 4H) 7.64-7.69 (m, 1H) 8.05-8.13 (m, 1H) 8.36-8.48 (m, 1H); MS (ESI, m/z): 642.3 [M+H]$^+$ Example 643

(R)-2-amino-5-(1-methyl-1H-pyrazol-4-yl)-N-(1-(4'-((1-methylpiperidin-4-yl)methyl)-[1,1'-biphenyl]-4-carbonyl)pyrrolidin-3-yl)nicotinamide Using Example 807 and formaldehyde, the title compound was obtained as described in general method F. MS (ESI, m/z): 578.3 [M+H]$^+$ Example 644

(R)-2-amino-N-(1-(6-(methyl(1-methylpiperidin-4-yl)amino)-2-naphthoyl)pyrrolidin-3-yl)-5-(1-methyl-1H-pyrazol-4-yl)nicotinamide Using Example 818 and formaldehyde, the title compound was obtained as described in general method F. $^1$H NMR (600 MHz, METHANOL-d$_4$) δ ppm 2.03 (br d, J=11.15 Hz, 2H) 2.06-2.15 (m, 2H) 2.06-2.22 (m, 1H) 2.26-2.44 (m, 1H) 2.89 (s, 3H) 2.97 (br d, J=8.80 Hz, 3H) 3.14-3.26 (m, 2H) 3.51 (br d, J=11.15 Hz, 0.5H) 3.57-3.65 (m, 2H) 3.65-3.83 (m, 2H) 3.85-3.90 (m, 0.5H) 3.93 (d, J=7.04 Hz, 3H) 3.96-4.06 (m, 1H) 4.15-4.24 (m, 1H) 4.49-4.55 (m, 0.5H) 4.65-4.73 (m, 0.5H) 7.24 (br d, J=14.09 Hz, 1H) 7.42 (br t, J=9.68 Hz, 1H) 7.48-7.59 (m, 1H) 7.72-7.79 (m, 1H) 7.83 (br dd, J=16.43, 8.80 Hz, 1H) 7.86-7.91 (m, 1H) 7.91-7.97 (m, 1H) 7.99-8.08 (m, 1H) 8.16-8.28 (m, 1H) 8.59-8.73 (m, 1H); MS (ESI, m/z): 567.3 [M+H]$^+$ Example 645

(R)-2-amino-N-(1-(6-((1-isopropylpiperidin-4-yl)(methyl)amino)-2-naphthoyl)pyrrolidin-3-yl)-5-(1-methyl-1H-pyrazol-4-yl)nicotinamide Using Example 818 and acetone, the title compound was obtained as described in general method F. $^1$H NMR (600 MHz, METHANOL-d$_4$) δ ppm 1.38 (br s, 6H) 2.02-2.10 (m, 2H) 2.10-2.26 (m, 3H) 2.27-2.45 (m, 1H) 2.97 (br s, 3H) 3.21-3.28 (m, 2H) 3.55 (br d, J=11.15 Hz, 2H) 3.62 (br d, J=11.15 Hz, 0.5H) 3.68-3.92 (m, 3.5H) 3.94 (br s, 3H) 4.02 (br s, 1H) 4.24 (br s, 1H) 4.54 (br s, 0.5H) 4.71 (br s, 0.5H) 7.22 (br d, J=7.63 Hz, 1H) 7.42 (br s, 1H) 7.54 (br s, 1H) 7.75 (br s, 1H) 7.82 (br t, J=9.32 Hz, 1H) 7.87-7.93 (m, 1H) 7.95 (br d, J=17.02 Hz, 1H) 8.02-8.13 (m, 1H) 8.19-8.29 (m, 1H) 8.61-8.75 (m, 1H); MS (ESI, m/z): 595.3 [M+H]$^+$ General Method G

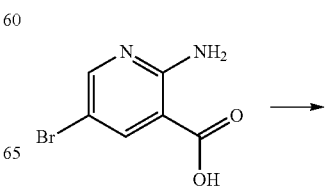

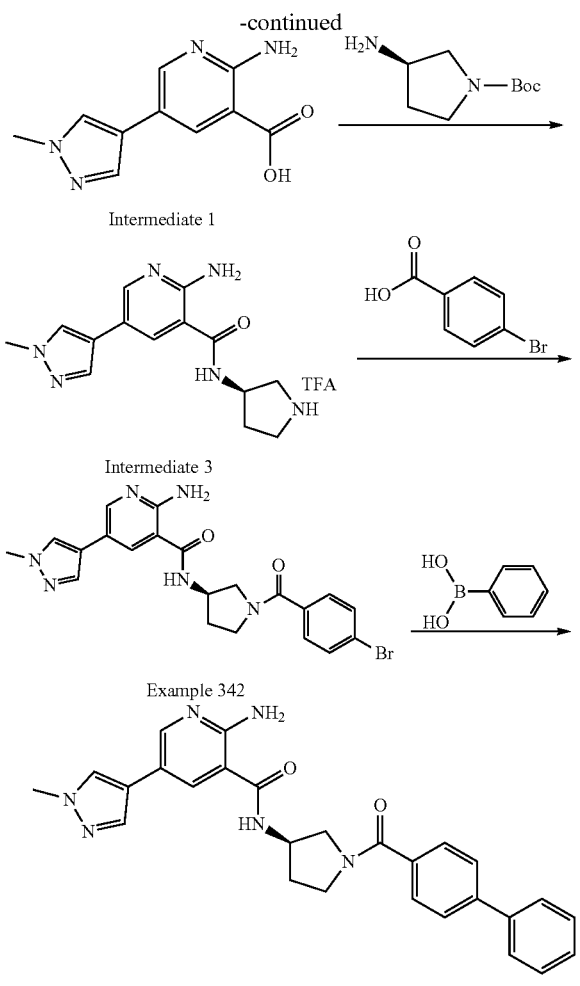

Intermediate 1

Intermediate 3

Example 342

Example 343

Intermediate 1

To a mixture of 2-amino-5-bromonicotinic acid (4.48 g, 20.6 mmol) and 1-methylpyrazole-4-boronic acid pinacol ester (5.5 g, 26.8 mmol) in 100 mL of 1,4-dioxane/water (3/1) was added $K_2CO_3$ (8.5 g, 61.9 mmol) followed by Pd(PPh$_3$)$_4$ (1.19 g, 1.03 mmol). The reaction mixture was heated at 100° C. for 3 h, cooled to room temperature, and partitioned between water and ethyl acetate. Water layer was separated and adjusted to pH value between 4 and 5. The precipitate was collected by filtration and dried to afford 4.1 g of the title compound. The crude product was used for the next step without further purification. $^1$H NMR (600 MHz, DIMETHYL SULFOXIDE-d$_6$) δ ppm 3.82 (s, 3H), 5.73 (s, 2H), 7.77 (s, 1H), 8.05 (s, 1H), 8.13 (d, J=2.4 Hz, 1H), 8.42 (d, J=2.4 Hz, 1H); MS (ESI, m/z): 219.1 [M+H]$^+$ Intermediate 3

To a mixture of intermediate 1 (1.0 g, 4.58 mmol) and triethylamine (0.958 mL, 6.87 mmol) in 12 mL of N,N-dimethylformamide was added 1-[bis(dimethylamino)methylene]-1H-1,2,3-triazolo[4,5-b]pyridinium 3-oxid hexafluorophosphate (1.7 g, 4.58 mmol) followed by tert-butyl (R)-3-aminopyrrolidine-1-carboxylate (0.853 g, 4.58 mmol). The mixture was stirred at room temperature for 1 h and then saturated sodium bicarbonate solution was added. The mixture was extracted with ethyl acetate, washed with brine, dried over MgSO$_4$, and concentrated in vacuo. The crude product was purified through silica gel column chromatography (5% methanol/CH$_2$Cl$_2$) to give off-white solid. To a mixture of product in dichloromethane (12 mL) was added trifluoroacetic acid (3 mL) and stirred at room temperature for overnight. After removing volatiles, the crude product was diluted with diethylether and the precipitate was collected by filtration and dried to afford 1.3 g of the title compound. $^1$H NMR (600 MHz, DIMETHYL SULFOXIDE-d$_6$) δ ppm 2.01 (br d, J=5.87 Hz, 1H) 2.20 (dd, J=13.50, 7.63 Hz, 1H) 3.14-3.19 (m, 1H) 3.26 (br d, J=6.46 Hz, 1H) 3.35 (br dd, J=7.04, 4.70 Hz, 1H) 3.43 (br dd, J=11.74, 5.28 Hz, 1H) 4.47 (br d, J=5.87 Hz, 1H) 7.83 (s, 1H) 8.07 (s, 1H) 8.29 (d, J=1.76 Hz, 1H) 8.36 (d, J=2.35 Hz, 1H); MS (ESI, m/z): 287.1 [M+H]$^+$ Example 342

(R)-2-amino-N-(1-(4-bromobenzoyl)pyrrolidin-3-yl)-5-(1-methyl-1H-pyrazol-4-yl)nicotinamide To a mixture of 4-bromobenzoic acid (0.262 g, 1.3 mmol) and triethylamine (0.545 mL, 3.91 mmol) in 3 mL of N,N-dimethylformamide was added 1-[bis(dimethylamino)methylene]-1H-1,2,3-triazolo[4,5-b]pyridinium 3-oxid hexafluorophosphate (0.496 g, 1.3 mmol) followed by Intermediate 3 (0.5 g, 1.3 mmol). The mixture was stirred at room temperature for 1 h and then saturated sodium bicarbonate solution was added. The mixture was extracted with ethyl acetate, washed with brine, dried over MgSO$_4$, and concentrated in vacuo. The crude product was purified through silicagel column chromatography (5% methanol/CH$_2$Cl$_2$) to give 0.5 g off-white solid. $^1$H NMR (400 MHz, METHANOL-d$_4$) δ ppm 2.06-2.21 (m, 1H) 2.26-2.42 (m, 1H) 3.49 (br dd, J=10.76, 4.89 Hz, 0.5H) 3.58-3.77 (m, 1.5H) 3.77-4.03 (m, 1H) 3.95 (d, J=1.96 Hz, 3H) 4.51-4.58 (m, 0.5H) 4.65-4.71 (m, 0.5H) 7.49 (t, J=8.02 Hz, 2H) 7.60-7.69 (m, 2H) 7.91 (d, J=10.17 Hz, 1H) 8.05 (d, J=9.78 Hz, 1H) 8.25 (dd, J=10.56, 1.96 Hz, 1H) 8.59-8.73 (m, 1H); MS (ESI, m/z): 469.1/471.1 [M+H]$^+$ Example 343

(R)—N-(1-([1,1'-biphenyl]-4-carbonyl)pyrrolidin-3-yl)-2-amino-5-(1-methyl-1H-pyrazol-4-yl)nicotinamide To a mixture of Example 342 (15 mg, 0.03 mmol) and phenylboronic acid (5 mg, 0.04 mmol) in 0.4 mL of 1,4-dioxane/water (3/1) was added $K_2CO_3$ (13 mg, 0.1 mmol) followed by Pd(PPh$_3$)$_4$ (2 mg, 0.001 mmol). The reaction mixture was heated at 100° C. for 3 h, cooled to room temperature, and extracted with ethyl acetate, dried over anhydrous MgSO$_4$ and concentrated under vacuum. The crude residue was purified by preparative HPLC to afford 10 mg of the title compound. $^1$H NMR (400 MHz, METHANOL-d$_4$) δ ppm 2.08-2.23 (m, 1H) 2.27-2.46 (m, 1H) 3.57 (br dd, J=11.15, 5.28 Hz, 0.5H) 3.69 (br dd, J=12.52, 5.09 Hz, 1H) 3.73-3.81 (m, 1H) 3.81-3.90 (m, 0.5H) 3.94 (d, J=3.52 Hz, 3H) 3.96-4.07 (m, 1H) 4.50-4.63 (m, 0.5H) 4.63-4.76 (m, 0.5H) 7.32-7.41 (m, 1H) 7.45 (td, J=7.53, 3.33 Hz, 2H) 7.54-7.67 (m, 4H) 7.67-7.76 (m, 2H) 7.90 (d, J=12.52 Hz, 1H) 8.04 (d, J=11.74 Hz, 1H) 8.23 (dd, J=13.89, 2.15 Hz, 1H) 8.63 (br d, J=1.96 Hz, 1H); MS (ESI, m/z): 467.2 [M+H]$^+$

Example 344

N-(1-([1,1'-biphenyl]-4-carbonyl)azetidin-3-yl)-2-amino-5-(1-methyl-1H-pyrazol-4-yl)nicotinamide Using tert-butyl 3-aminoazetidine-1-carboxylate, the title compound was obtained as described for the Example 343. $^1$H NMR (600 MHz, METHANOL-d$_4$) δ ppm 3.93 (s, 3H) 4.25 (br dd, J=10.56, 5.28 Hz, 1H) 4.43 (br dd, J=9.10, 4.99 Hz, 1H) 4.53-4.60 (m, 1H) 4.80 (br t, J=8.80 Hz, 1H) 4.83-4.86 (m, 1H) 7.36-7.39 (m, 1H) 7.44-7.48 (m, 2H) 7.63-7.67 (m, 2H) 7.72-7.78 (m, 4H) 7.89 (s, 1H) 8.03 (s, 1H) 8.26 (d, J=2.35 Hz, 1H) 8.67 (d, J=2.35 Hz, 1H); MS (ESI, m/z): 453.2 [M+H]$^+$

Example 345

(S)—N-(1-([1,1'-biphenyl]-3-carbonyl)pyrrolidin-3-yl)-2-amino-5-(1-methyl-1H-pyrazol-4-yl)nicotinamide Using (S)-3-aminopyrrolidine-1-carboxylate and 3-bromobenzoic acid, the title compound was obtained as described for the Example 343. $^1$H NMR (400 MHz, METHANOL-d$_4$) δ ppm 2.06-2.24 (m, 1H) 2.25-2.46 (m, 1H) 3.56 (dd, J=11.35, 5.09 Hz, 0.5H) 3.64-3.81 (m, 2H) 3.85-3.91 (m, 0.5H) 3.93 (d, J=4.30 Hz, 3H) 3.94-4.05 (m, 1H) 4.51-4.59 (m, 0.5H) 4.65-4.73 (m, 0.5H) 7.33-7.39 (m, 1H) 7.39-7.46 (m, 2H) 7.46-7.51 (m, 1H) 7.51-7.56 (m, 1H) 7.56-7.61 (m, 1H) 7.61-7.66 (m, 1H) 7.70-7.77 (m, 1H) 7.78 (s, 1H) 7.88 (d, J=18.78 Hz, 1H) 8.02 (d, J=18.39 Hz, 1H) 8.18-8.26 (m, 1H) 8.58-8.71 (m, 1H); MS (ESI, m/z): 467.2 [M+H]$^+$

Example 346

(S)—N-(1-([1,1'-biphenyl]-4-carbonyl)pyrrolidin-3-yl)-2-amino-5-(1-methyl-1H-pyrazol-4-yl)nicotinamide Using (R)-3-aminopyrrolidine-1-carboxylate, the title compound was obtained as described for the Example 343. $^1$H NMR (400 MHz, METHANOL-d$_4$) δ ppm 2.07-2.23 (m, 1H) 2.28-2.46 (m, 1H) 3.54-3.60 (m, 0.5H) 3.64-3.72 (m, 1H) 3.72-3.81 (m, 1H) 3.84 (br d, J=7.04 Hz, 0.5H) 3.95 (d, J=3.91 Hz, 3H) 3.96-4.06 (m, 1H) 4.55 (br d, J=5.48 Hz, 0.5H) 4.72 (br d, J=5.48 Hz, 0.5H) 7.32-7.41 (m, 1H) 7.41-7.50 (m, 2H) 7.61-7.69 (m, 4H) 7.69-7.77 (m, 2H) 7.91 (d, J=12.13 Hz, 1H) 8.05 (d, J=11.74 Hz, 1H) 8.25 (dd, J=13.30, 1.96 Hz, 1H) 8.60-8.73 (n, 1H); MS (ESI, m/z): 467.2 [M+H]$^+$

Example 347

(R)—N-(1-([1,1'-biphenyl]-4-carbonyl)piperidin-3-yl)-2-amino-5-(1-methyl-1H-pyrazol-4-yl)nicotinamide Using tert-butyl (R)-3-aminopiperidine-1-carboxylate, the title compound was obtained as described for the Example 343. $^1$H NMR (600 MHz, METHANOL-d$_4$) δ ppm 1.55-1.88 (m, 2H) 1.93-2.05 (m, 1H) 2.11-2.20 (m, 1H) 3.09-3.28 (m, 2H) 3.70 (brs, 0.5H) 3.89-3.99 (m, 3.5H) 4.00-4.18 (m, 1H) 4.33 (br s, 0.5H) 4.52 (br s, 0.5H) 7.37 (br d, J=5.87 Hz, 1H) 7.45 (br s, 2H) 7.52 (d, J=8.22 Hz, 2H) 7.63 (br s, 2H) 7.70 (br d, J=18.78 Hz, 2H) 7.87 (br d, J=18.78 Hz, 1H) 8.01 (br d, J=9.39 Hz, 1H) 8.22 (br d, J=11.74 Hz, 1H) 8.46-8.56 (m, 1H); MS (ESI, m/z): 481.2 [M+H]$^+$

Example 348

(S)—N-(1-([1,1'-biphenyl]-4-carbonyl)piperidin-3-yl)-2-amino-5-(1-methyl-1H-pyrazol-4-yl)nicotinamide Using tert-butyl (S)-3-aminopiperidine-1-carboxylate, the title compound was obtained as described for the Example 343. $^1$H NMR (600 MHz, METHANOL-d$_4$) δ ppm 1.55-1.87 (m, 2H) 1.91-2.06 (m, 1H) 2.11-2.20 (m, 1H) 3.09-3.27 (m, 2H) 3.70 (br s, 0.5H) 3.86-3.99 (m, 3.5H) 4.00-4.18 (m, 1H) 4.33 (br s, 0.5H) 4.50 (br s, 0.5H) 7.36 (br s, 1H) 7.45 (br s, 2H) 7.49-7.55 (m, 2H) 7.63 (br s, 2H) 7.70 (br d, J=17.61 Hz, 2H) 7.87 (br d, J=18.19 Hz, 1H) 8.01 (br d, J=12.33 Hz, 1H) 8.22 (br d, J=11.74 Hz, 1H) 8.46-8.58 (m, 1H); MS (ESI, m/z): 481.2 [M+H]$^+$

Example 349

(R)-2-amino-N-(1-(2'-(hydroxymethyl)-[1,1'-biphenyl]-4-carbonyl)pyrrolidin-3-yl)-5-(1-methyl-1H-pyrazol-4-yl)nicotinamide Using (2-hydroxymethylphenyl)boronic acid, the title compound was obtained as described for the Example 343. MS (ESI, m/z): 497.2 [M+H]$^+$

Example 350

(R)-2-amino-N-(1-(2'-isopropyl-[1,1'-biphenyl]-4-carbonyl)pyrrolidin-3-yl)-5-(1-methyl-1H-pyrazol-4-yl)nicotinamide Using (2-isopropylphenyl)boronic acid, the title compound was obtained as described for the Example 343. $^1$H NMR (400 MHz, CHLOROFORM-d) δ ppm 1.10 (br d, J=6.65 Hz, 6H) 1.93-2.22 (m, 1H) 2.35 (br s, 1H) 2.86 (br s, 1H) 3.65-3.85 (m, 2H) 3.90-3.95 (m, 3H) 3.97 (br s, 1H) 4.10 (br s, 1H) 4.79 (br s, 1H) 6.98-7.08 (m, 1H) 7.19 (br s, 1H) 7.37 (br s, 2H) 7.50 (br d, J=7.83 Hz, 1H) 7.66 (br s, 1H) 7.76 (br s, 1H) 8.12 (br s, 1H) 8.46 (br s, 1H) 8.62 (br d, J=10.17 Hz, 1H) 8.80 (br s, 1H) 8.96 (br s, 1H); MS (ESI, m/z): 509.3 [M+H]$^+$

Example 351

(R)-2-amino-5-(1-methyl-1H-pyrazol-4-yl)-N-(1-(2'-phenoxy-[1,1'-biphenyl]-4-carbonyl)pyrrolidin-3-yl)nicotinamide Using (2-phenoxyphenyl)boronic acid, the title compound was obtained as described for the Example 343. MS (ESI, m/z): 559.3 [M+H]$^+$

Example 352

(R)—N-(1-([1,1':2',1''-1,1-terphenyl]-4-carbonyl)pyrrolidin-3-yl)-2-amino-5-(1-methyl-1H-pyrazol-4-yl)nicotinamide Using (2-biphenyl)boronic acid, the title compound was obtained as described for the Example 343. MS (ESI, m/z): 543.2 [M+H]$^+$

Example 353

(R)-2-amino-N-(1-(2'-ethyl-[1,1'-biphenyl]-4-carbonyl)pyrrolidin-3-yl)-5-(1-methyl-1H-pyrazol-4-yl)nicotinamide Using (2-ethylphenyl)boronic acid, the title compound was obtained as described for the Example 343. $^1$H NMR (400 MHz, CHLOROFORM-d) δ ppm 1.01 (t, J=7.43 Hz, 3H) 1.97-2.17 (m, 1H) 2.30-2.45 (m, 1H) 2.48 (q, J=7.43 Hz, 2H) 3.63-3.86 (m, 2H) 3.91 (s, 3H) 3.97 (br s, 1H) 4.13 (br s, 1H) 4.79 (br s, 1H) 6.98-7.11 (m, 1H) 7.20 (br s, 2H) 7.27-7.36 (m, 2H) 7.49 (br d, J=7.04 Hz, 1H) 7.62 (br d, J=11.74 Hz, 1H) 7.66-7.77 (m, 1H) 8.04 (br d, J=19.95 Hz, 1H) 8.62 (br s, 1H) 8.73 (br s, 1H) 8.82 (br s, 1H); MS (ESI, m/z): 495.2 [M+H]$^+$

Example 354

(R)-2-amino-N-(1-(2'-methoxy-[1,1'-biphenyl]-4-carbonyl)pyrrolidin-3-yl)-5-(1-methyl-1H-pyrazol-4-yl)nicotinamide Using (2-methoxylphenyl)boronic acid, the title compound was obtained as described for the Example 343. MS (ESI, m/z): 497.2 [M+H]$^+$

Example 355

(R)-2-amino-N-(1-(2'-formyl-[1,1'-biphenyl]-4-carbonyl)pyrrolidin-3-yl)-5-(1-methyl-1H-pyrazol-4-yl)nicotinamide Using (2-formylphenyl)boronic acid, the title compound was obtained as described for the Example 343. MS (ESI, m/z): 495.2 [M+H]$^+$

Example 356

(R)-2-amino-5-(1-methyl-1H-pyrazol-4-yl)-N-(1-(4-(pyridin-3-yl)benzoyl)pyrrolidin-3-yl)nicotinamide Using 3-pyridineboronic acid, the title compound was obtained as described for the Example 343. $^1$H NMR (400 MHz, METHANOL-d$_4$) δ ppm 2.10-2.26 (m, 1H) 2.28-2.45 (m, 1H) 3.53-3.67 (m, 1H) 3.68-3.82 (m, 2H) 3.87 (br d, J=5.87 Hz, 0.5H) 3.94 (d, J=3.13 Hz, 3H) 4.00-4.07 (m, 0.5H) 4.52-4.59 (m, 0.5H) 4.68-4.74 (m, 0.5H) 7.74-7.81 (m, 1H) 7.86-7.95 (m, 2H) 7.97 (dd, J=7.43, 5.48 Hz, 2H) 8.06 (d, J=10.17 Hz, 1H) 8.10-8.16 (m, 1H) 8.25 (dd, J=11.15, 2.15 Hz, 1H) 8.65-8.71 (m, 1H) 8.85 (dd, J=5.48, 1.17 Hz, 2H) 9.18 (d, J=1.57 Hz, 1H); MS (ESI, m/z): 468.2 [M+H]$^+$

Example 357

(R)-2-amino-N-(1-(4-(6-fluoropyridin-3-yl)benzoyl)pyrrolidin-3-yl)-5-(1-methyl-1H-pyrazol-4-yl)nicotinamide Using 2-fluoropyridine-5-boronic acid, the title compound was obtained as described for the Example 343. $^1$H NMR (400 MHz, METHANOL-d$_4$) δ ppm 2.07-2.24 (m, 1H) 2.25-2.46 (m, 1H) 3.55 (br dd, J=11.15, 5.28 Hz, 0.5H) 3.63-3.80 (m, 2H) 3.80-3.91 (m, 0.5H) 3.95 (d, J=2.74 Hz, 3H) 3.97-4.06 (m, 1H) 4.51-4.59 (m, 0.5H) 4.66-4.74 (m, 0.5H) 7.18 (br d, J=8.22 Hz, 1H) 7.48 (br t, J=8.22 Hz, 0.5H) 7.56-7.66 (m, 0.5H) 7.66-7.79 (m, 3H) 7.91 (d, J=12.13 Hz, 1H) 8.06 (br d, J=11.35 Hz, 1H) 8.24 (br d, J=10.56 Hz, 2H) 8.49 (br s, 1H) 8.62-8.74 (m, 1H); MS (ESI, m/z): 486.2 [M+H]$^+$

Example 358

(R)-2-amino-5-(1-methyl-1H-pyrazol-4-yl)-N-(1-(4-(thiophen-3-yl)benzoyl)pyrrolidin-3-yl)nicotinamide Using 3-thiopheneboronic acid, the title compound was obtained as described for the Example 343. $^1$H NMR (400 MHz, METHANOL-d$_4$) δ ppm 2.04-2.19 (m, 1H) 2.23-2.40 (m, 1H) 3.57-3.67 (m, 1H) 3.67-3.90 (m, 2H) 3.91 (d, J=3.91 Hz, 3H) 3.94-4.02 (m, 1H) 4.51 (br dd, J=11.74, 5.87 Hz, 0.5H) 4.59-4.76 (m, 0.5H) 7.44-7.49 (m, 1H) 7.51-7.60 (m, 2H) 7.68-7.75 (m, 2H) 7.84-7.90 (m, 1H) 8.01 (br d, J=12.13 Hz, 1H) 8.16-8.20 (m, 1H) 8.20-8.23 (m, 1H) 8.60 (br d, J=1.96 Hz, 1H) 8.64-8.70 (m, 1H); MS (ESI, m/z): 473.2 [M+H]$^+$

Example 359

(R)-2-amino-N-(1-(2'-chloro-[1,1'-biphenyl]-4-carbonyl)pyrrolidin-3-yl)-5-(1-methyl-1H-pyrazol-4-yl)nicotinamide Using 2-chlorobenzeneboronic acid, the title compound was obtained as described for the Example 343. $^1$H NMR (400 MHz, METHANOL-d$_4$) δ ppm 2.07-2.25 (m, 1H) 2.27-2.46 (m, 1H) 3.58 (br dd, J=11.35, 5.09 Hz, 0.5H) 3.66-3.82 (m, 2H) 3.82-3.91 (m, 0.5H) 3.94 (d, J=2.74 Hz, 3H) 3.95-4.05 (m, 1H) 4.54-4.61 (m, 0.5H) 4.67-4.75 (m, 0.5H) 7.33-7.43 (m, 3H) 7.46-7.58 (m, 3H) 7.60-7.69 (m, 2H) 7.90 (d, J=11.35 Hz, 1H) 8.05 (d, J=10.56 Hz, 1H) 8.24 (dd, J=12.91, 1.96 Hz, 1H) 8.62-8.75 (m, 1H); MS (ESI, m/z): 501.2 [M+H]$^+$

Example 360

(R)-2-amino-N-(1-(3'-chloro-[1,1'-biphenyl]-4-carbonyl)pyrrolidin-3-yl)-5-(1-methyl-1H-pyrazol-4-yl)nicotinamide Using 3-chlorobenzeneboronic acid, the title compound was obtained as described for the Example 343. $^1$H NMR (400 MHz, METHANOL-d$_4$) δ ppm 2.06-2.24 (m, 1H) 2.25-2.46 (m, 1H) 3.52-3.61 (m, 0.5H) 3.64-3.81 (m, 2H) 3.81-3.90 (m, 0.5H) 3.94 (d, J=3.91 Hz, 3H) 3.95-4.07 (m, 1H) 4.51-4.58 (m, 0.5H) 4.66-4.73 (m, 0.5H) 7.34-7.41 (m, 1H) 7.44 (td, J=7.83, 3.91 Hz, 1H) 7.58 (br t, J=6.46 Hz, 1H) 7.61-7.68 (m, 3H) 7.68-7.75 (m, 2H) 7.90 (d, J=12.91 Hz, 1H) 8.04 (d, J=12.13 Hz, 1H) 8.23 (dd, J=14.09, 1.96 Hz, 1H) 8.61-8.73 (m, 1H); MS (ESI, m/z): 501.2 [M+H]$^+$

Example 361

(R)-2-amino-N-(1-(2',4'-dichloro-[1,1'-biphenyl]-4-carbonyl)pyrrolidin-3-yl)-5-(1-methyl-1H-pyrazol-4-yl)nicotinamide Using 2,4-dichlorobenzeneboronic acid, the title compound was obtained as described for the Example 343. $^1$H NMR (400 MHz, METHANOL-d$_4$) δ ppm 2.07-2.24 (m, 1H) 2.27-2.46 (m, 1H) 3.57 (br dd, J=11.15, 5.28 Hz, 0.5H) 3.65-3.81 (m, 2H) 3.81-3.90 (m, 0.5H) 3.94 (d, J=2.35 Hz, 3H) 3.96-4.06 (m, 1H) 4.53-4.61 (m, 0.5H) 4.64-4.74 (m, 0.5H) 7.34-7.46 (m, 2H) 7.52 (dd, J=7.83, 5.87 Hz, 2H) 7.58 (br s, 1H) 7.61-7.70 (m, 2H) 7.90 (d, J=11.35 Hz, 1H) 8.05 (d, J=10.56 Hz, 1H) 8.24 (dd, J=12.52, 1.96 Hz, 1H) 8.63-8.74 (m, 1H); MS (ESI, m/z): 536.2 [M+H]$^+$ Example 362

(R)-2-amino-N-(1-(3',4'-dichloro-[1,1'-biphenyl]-4-carbonyl)pyrrolidin-3-yl)-5-(1-methyl-1H-pyrazol-4-yl)nicotinamide Using 3,4-dichlorobenzeneboronic acid, the title compound was obtained as described for the Example 343. $^1$H NMR (400 MHz, METHANOL-d$_4$) δ ppm 2.07-2.24 (m, 1H) 2.25-2.45 (m, 1H) 3.55 (br dd, J=11.15, 5.28 Hz, 0.5H) 3.63-3.80 (m, 2H) 3.86 (br d, J=7.43 Hz, 0.5H) 3.94 (d, J=3.91 Hz, 3H) 4.00 (td, J=12.13, 6.65 Hz, 1H) 4.50-4.58 (m, 0.5H) 4.65-4.72 (m, 0.5H) 7.59 (br d, J=3.91 Hz, 2H) 7.62-7.69 (m, 2H) 7.69-7.75 (m, 2H) 7.82 (br d, J=5.87 Hz, 1H) 7.90 (d, J=12.91 Hz, 1H) 8.05 (d, J=12.13 Hz, 1H) 8.23 (dd, J=13.69, 1.96 Hz, 1H) 8.61-8.72 (m, 1H); MS (ESI, m/z): 536.2 [M+H]$^+$ Example 363

(R)-2-amino-N-(1-(3',5'-dichloro-[1,1'-biphenyl]-4-carbonyl)pyrrolidin-3-yl)-5-(1-methyl-1H-pyrazol-4-yl)nicotinamide Using 3,5-dichlorobenzeneboronic acid, the title compound was obtained as described for the Example 343. $^1$H NMR (400 MHz, METHANOL-d$_4$) δ ppm 2.06-2.24 (m, 1H) 2.25-2.45 (m, 1H) 3.55 (br dd, J=10.96, 5.09 Hz, 0.5H) 3.62-3.80 (m, 2H) 3.81-3.91 (m, 0.5H) 3.94 (d, J=3.91 Hz, 3H) 3.96-4.06 (m, 1H) 4.50-4.59 (m, 0.5H) 4.63-4.74 (m, 0.5H) 7.45 (br s, 1H) 7.58-7.75 (m, 6H) 7.90 (d, J=12.52 Hz, 1H) 8.05 (d, J=11.74 Hz, 1H) 8.23 (dd, J=13.30, 1.96 Hz, 1H) 8.61-8.72 (m, 1H); MS (ESI, m/z): 536.2 [M+H]$^+$ Example 364

(R)-2-amino-N-(1-(2',6'-difluoro-[1,1'-biphenyl]-4-carbonyl)pyrrolidin-3-yl)-5-(1-methyl-1H-pyrazol-4-yl)nicotinamide Using 2,6-difluorobenzeneboronic acid, the title compound was obtained as described for the Example 343. $^1$H NMR (400 MHz, METHANOL-d$_4$) δ ppm 2.09-2.24 (m, 1H) 2.29-2.46 (m, 1H) 3.57 (br dd, J=11.15, 5.28 Hz, 0.5H) 3.64-3.82 (m, 2H) 3.86 (br dd, J=13.30, 6.65 Hz, 0.5H) 3.95 (d, J=2.74 Hz, 3H) 3.96-4.06 (m, 1H) 4.55-4.62 (m, 0.5H) 4.68-4.74 (m, 0.5H) 7.05-7.16 (m, 2H) 7.37-7.50 (m, 1H) 7.52-7.60 (m, 2H) 7.64-7.72 (m, 2H) 7.91 (d, J=11.35 Hz, 1H) 8.06 (d, J=10.56 Hz, 1H) 8.24 (dd, J=13.30, 1.96 Hz, 1H) 8.63-8.74 (m, 1H); MS (ESI, m/z): 503.2 [M+H]$^+$ Example 365

(R)-2-amino-N-(1-(2',4'-difluoro-[1,1'-biphenyl]-4-carbonyl)pyrrolidin-3-yl)-5-(1-methyl-1H-pyrazol-4-yl)nicotinamide Using 2,4-difluorobenzeneboronic acid, the title compound was obtained as described for the Example 343. $^1$H NMR (400 MHz, METHANOL-d$_4$) δ ppm 2.08-2.25 (m, 1H) 2.26-2.46 (m, 1H) 3.56 (dd, J=11.15, 5.28 Hz, 0.5H) 3.65-3.81 (m, 2H) 3.85 (br t, J=7.24 Hz, 0.5H) 3.94 (d, J=3.13 Hz, 3H) 3.96-4.05 (m, 1H) 4.57 (br t, J=5.67 Hz, 0.5H) 4.67-4.74 (m, 0.5H) 7.05-7.13 (m, 2H) 7.51-7.58 (m, 1H) 7.58-7.72 (m, 4H) 7.90 (d, J=11.74 Hz, 1H) 8.05 (d, J=10.96 Hz, 1H) 8.24 (dd, J=13.30, 1.96 Hz, 1H) 8.63-8.75 (m, 1H); MS (ESI, m/z): 503.2 [M+H]$^+$ Example 366

(R)-2-amino-N-(1-(2'-chloro-4'-fluoro-[1,1'-biphenyl]-4-carbonyl)pyrrolidin-3-yl)-5-(1-methyl-1H-pyrazol-4-yl)nicotinamide Using 2-chloro-4-fluorobenzeneboronic acid, the title compound was obtained as described for the Example 343. $^1$H NMR (600 MHz, METHANOL-d$_4$) δ ppm 2.08-2.24 (m, 1H) 2.28-2.45 (m, 1H) 3.56 (dd, J=11.15, 5.28 Hz, 0.5H) 3.65-3.72 (m, 1H) 3.72-3.81 (m, 1H) 3.86 (dt, J=12.03, 7.48 Hz, 0.5H) 3.93 (d, J=4.11 Hz, 3H) 3.95-4.03 (m, 1H) 4.53-4.60 (m, 0.5H) 4.66-4.73 (m, 0.5H) 7.13-7.20 (m, 1H) 7.31-7.36 (m, 1H) 7.40 (dt, J=8.80, 6.46 Hz, 1H) 7.50 (t, J=8.22 Hz, 2H) 7.63 (dd, J=12.91, 8.22 Hz, 2H) 7.89 (d, J=16.43 Hz, 1H) 8.04 (d, J=15.26 Hz, 1H) 8.23 (dd, J=18.19, 1.76 Hz, 1H) 8.62-8.72 (m, 1H); MS (ESI, m/z): 519.2 [M+H]$^+$ Example 367

(R)-2-amino-N-(1-(2',5'-dichloro-[1,1'-biphenyl]-4-carbonyl)pyrrolidin-3-yl)-5-(1-methyl-1H-pyrazol-4-yl)nicotinamide Using 2,5-dichlorobenzeneboronic acid, the title compound was obtained as described for the Example 343. $^1$H NMR (600 MHz, METHANOL-d$_4$) δ ppm 2.07-2.25 (m, 1H) 2.29-2.45 (m, 1H) 3.56 (dd, J=11.15, 5.28 Hz, 0.5H) 3.65-3.72 (m, 1H) 3.73-3.81 (m, 1H) 3.83-3.90 (m, 0.5H) 3.93 (d, J=4.70 Hz, 3H) 3.95-4.04 (m, 1H) 4.54-4.60 (m, 0.5H) 4.67-4.73 (m, 0.5H) 7.33-7.43 (m, 2H) 7.46-7.56 (m, 3H) 7.65 (dd, J=12.91, 8.22 Hz, 2H) 7.89 (d, J=16.43 Hz, 1H) 8.04 (d, J=15.85 Hz, 1H) 8.23 (dd, J=18.19, 2.35 Hz, 1H) 8.61-8.74 (m, 1H); MS (ESI, m/z): 536.2 [M+H]$^+$ Example 368

(R)-2-amino-N-(1-(2',6'-dichloro-[1,1'-biphenyl]-4-carbonyl)pyrrolidin-3-yl)-5-(1-methyl-1H-pyrazol-4-yl)nicotinamide Using 2,6-dichlorobenzeneboronic acid, the title compound was obtained as described for the Example 343. MS (ESI, m/z): 536.2 [M+H]$^+$ Example 369

(R)-2-amino-N-(1-(2',3'-dichloro-[1,1'-biphenyl]-4-carbonyl)pyrrolidin-3-yl)-5-(1-methyl-1H-pyrazol-4-yl)nicotinamide Using 2,3-dichlorobenzeneboronic acid, the title compound was obtained as described for the Example 343. $^1$H NMR (600 MHz, METHANOL-d$_4$) δ ppm 2.08-2.22 (m, 1H) 2.29-2.46 (m, 1H) 3.56 (dd, J=11.15, 5.28 Hz, 0.5H) 3.67-3.73 (m, 1H) 3.77 (dt, J=11.30, 6.97 Hz, 1H) 3.83-3.89 (m, 1H) 3.94 (d, J=4.11 Hz, 3H) 3.96-4.04 (m, 1H) 4.55-4.59 (m, 0.5H) 4.68-4.72 (m, 0.5H) 7.30-7.34 (m, 1H) 7.37 (td, J=7.78, 4.40 Hz, 1H) 7.49-7.53 (m, 2H) 7.57 (ddd, J=7.92, 3.23, 1.76 Hz, 1H) 7.62-7.69 (m, 2H) 7.90 (d, J=16.43 Hz, 1H) 8.05 (d, J=15.26 Hz, 1H) 8.24 (dd, J=17.61, 2.35 Hz, 1H) 8.62-8.74 (m, 1H); MS (ESI, m/z): 536.2 [M+H]+

Example 370

(R)-2-amino-N-(1-(2'-fluoro-[1,1'-biphenyl]-4-carbonyl)pyrrolidin-3-yl)-5-(1-methyl-1H-pyrazol-4-yl)nicotinamide Using 2-fluorobenzeneboronic acid, the title compound was obtained as described for the Example 343. $^1$H NMR (600 MHz, METHANOL-$d_4$) δ ppm 2.08-2.22 (m, 1H) 2.28-2.46 (m, 1H) 3.56 (dd, J=11.15, 5.28 Hz, 0.5H) 3.66-3.73 (m, 1H) 3.73-3.82 (m, 1H) 3.82-3.90 (m, 0.5H) 3.94 (d, J=5.28 Hz, 3H) 3.95-4.04 (m, 1H) 4.52-4.59 (m, 0.5H) 4.67-4.74 (m, 0.5H) 7.15-7.24 (m, 1H) 7.24-7.29 (m, 1H) 7.34-7.45 (m, 1H) 7.45-7.57 (m, 1H) 7.64 (s, 2H) 7.66 (s, 2H) 7.88 (s, 1H) 7.91 (s, 1H) 8.03 (s, 1H) 8.06 (s, 1H) 8.20-8.27 (m, 1H) 8.71 (d, J=2.35 Hz, 1H) 8.63 (d, J=1.76 Hz, 1H); MS (ESI, m/z): 485.2 [M+H]+

Example 371

(R)-2-amino-5-(1-methyl-1H-pyrazol-4-yl)-N-(1-(4'-(trifluoromethyl)-[1,1'-biphenyl]-4-carbonyl)pyrrolidin-3-yl)nicotinamide Using 4-trifluoromethylbenzeneboronic acid, the title compound was obtained as described for the Example 343. $^1$H NMR (600 MHz, METHANOL-$d_4$) δ ppm 2.08-2.24 (m, 1H) 2.28-2.45 (m, 1H) 3.55 (dd, J=11.15, 5.28 Hz, 0.5H) 3.63-3.72 (m, 1H) 3.72-3.81 (m, 1H) 3.81-3.90 (m, 0.5H) 3.93 (d, J=4.50 Hz, 3H) 3.94-4.05 (m, 1H) 4.50-4.62 (m, 0.5H) 4.63-4.79 (m, 0.5H) 7.65-7.72 (m, 2H) 7.74-7.80 (m, 4H) 7.82-7.87 (m, 2H) 7.89 (d, J=18.78 Hz, 1H) 8.06 (s, 1H) 8.19-8.28 (m, 1H) 8.60-8.73 (m, 1H); MS (ESI, m/z): 535.2 [M+H]+

Example 372

(R)-2-amino-N-(1-(4'-(benzyloxy)-[1,1'-biphenyl]-4-carbonyl)pyrrolidin-3-yl)-5-(1-methyl-1H-pyrazol-4-yl)nicotinamide Using 4-phenoxylbenzeneboronic acid, the title compound was obtained as described for the Example 343. $^1$H NMR (600 MHz, METHANOL-$d_4$) δ ppm 2.05-2.22 (m, 1H) 2.24-2.42 (m, 1H) 3.56 (dd, J=11.15, 5.28 Hz, 0.5H) 3.63-3.71 (m, 1H) 3.71-3.79 (m, 1H) 3.80-3.89 (m, 0.5H) 3.93 (d, J=5.87 Hz, 3H) 3.94-4.02 (m, 1H) 4.48-4.57 (m, 0.5H) 4.64-4.72 (m, 0.5H) 5.11 (d, J=4.11 Hz, 2H) 7.07 (dd, J=8.51, 6.16 Hz, 2H) 7.26-7.33 (m, 1H) 7.36 (td, J=7.63, 1.76 Hz, 2H) 7.43 (dd, J=7.92, 2.05 Hz, 2H) 7.53-7.62 (m, 4H) 7.62-7.68 (m, 2H) 7.89 (d, J=19.96 Hz, 1H) 8.03 (d, J=19.37 Hz, 1H) 8.18-8.25 (m, 1H) 8.54-8.72 (m, 1H); MS (ESI, m/z): 573.2 [M+H]+

Example 373

(R)-2-amino-N-(1-(2'-bromo-[1,1'-biphenyl]-4-carbonyl)pyrrolidin-3-yl)-5-(1-methyl-1H-pyrazol-4-yl)nicotinamide Using 2-bromobenzeneboronic acid, the title compound was obtained as described for the Example 343. MS (ESI, m/z): 545.2/547.2 [M+H]+

Example 374

(R)-2-amino-N-(1-(2',4'-bis(trifluoromethyl)-[1,1'-biphenyl]-4-carbonyl)pyrrolidin-3-yl)-5-(1-methyl-1H-pyrazol-4-yl)nicotinamide Using 2,4-di(trifluoromethyl)benzeneboronic acid, the title compound was obtained as described for the Example 343. $^1$H NMR (600 MHz, METHANOL-$d_4$) δ ppm 2.09-2.22 (m, 1H) 2.30-2.44 (m, 1H) 3.56 (br dd, J=11.15, 5.28 Hz, 0.5H) 3.66-3.72 (m, 1H) 3.72-3.80 (m, 1H) 3.82-3.90 (m, 0.5H) 3.94 (d, J=2.93 Hz, 3H) 3.95-4.04 (m, 1H) 4.55-4.61 (m, 0.5H) 4.68-4.74 (m, 0.5H) 7.46 (t, J=7.92 Hz, 2H) 7.62 (t, J=7.04 Hz, 1H) 7.64-7.70 (m, 2H) 7.90 (d, J=16.43 Hz, 1H) 7.99-8.02 (m, 1H) 8.04 (d, J=14.09 Hz, 1H) 8.07 (br d, J=2.35 Hz, 1H) 8.24 (dd, J=16.14, 2.05 Hz, 1H) 8.61-8.71 (m, 1H); MS (ESI, m/z): 603.2 [M+H]+

Example 375

(R)-2-amino-N-(1-(2'-hydroxy-[1,1'-biphenyl]-4-carbonyl)pyrrolidin-3-yl)-5-(1-methyl-1H-pyrazol-4-yl)nicotinamide Using 2-hydroxy benzeneboronic acid, the title compound was obtained as described for the Example 343. $^1$H NMR (400 MHz, METHANOL-$d_4$) δ ppm 2.07-2.24 (m, 1H) 2.26-2.47 (m, 1H) 3.59 (dd, J=10.96, 5.09 Hz, 0.5H) 3.65-3.82 (m, 2H) 3.82-3.90 (m, 0.5H) 3.94 (d, J=3.52 Hz, 3H) 3.96-4.04 (m, 1H) 4.48-4.62 (m, 0.5H) 4.63-4.74 (m, 0.5H) 6.73-6.81 (m, 0.5H) 6.84-6.92 (m, 1.5H) 7.11-7.22 (m, 1H) 7.27 (br dd, J=7.24, 3.72 Hz, 1H) 7.55-7.63 (m, 2H) 7.63-7.72 (m, 2H) 7.90 (d, J=12.52 Hz, 1H) 8.05 (d, J=11.74 Hz, 1H) 8.23 (dd, J=14.28, 2.15 Hz, 1H) 8.62-8.76 (m, 1H); MS (ESI, m/z): 483.2 [M+H]+

Example 376

(R)-2-amino-N-(1-(3'-amino-2'-methyl-[1,1'-biphenyl]-4-carbonyl)pyrrolidin-3-yl)-5-(1-methyl-1H-pyrazol-4-yl)nicotinamide Using 3-amino-2-methylbenzeneboronic acid, the title compound was obtained as described for the Example 343. $^1$H NMR (400 MHz, METHANOL-$d_4$) δ ppm 2.11-2.23 (m, 1H) 2.26 (d, J=3.13 Hz, 3H) 2.29-2.46 (m, 1H) 3.54-3.62 (m, 0.5H) 3.66-3.74 (m, 1H) 3.74-3.83 (m, 1H) 3.83-3.91 (m, 0.5H) 3.94 (d, J=2.35 Hz, 3H) 3.96-4.08 (m, 1H) 4.54-4.62 (m, 0.5H) 4.67-4.75 (m, 0.5H) 7.33-7.38 (m, 1H) 7.38-7.47 (m, 4H) 7.68 (t, J=8.41 Hz, 2H) 7.91 (d, J=10.17 Hz, 1H) 8.06 (d, J=8.61 Hz, 1H) 8.25 (dd, J=10.37, 2.15 Hz, 1H) 8.64-8.75 (m, 1H); MS (ESI, m/z): 496.2 [M+H]+

Example 377

(R)-2-amino-N-(1-(4'-chloro-[1,1'-biphenyl]-4-carbonyl)pyrrolidin-3-yl)-5-(1-methyl-1H-pyrazol-4-yl)nicotinamide Using 4-chlorobenzeneboronic acid, the title compound was obtained as described for the Example 343. $^1$H NMR (400 MHz, METHANOL-$d_4$) δ ppm 2.07-2.25 (m, 1H) 2.26-2.46 (m, 1H) 3.56 (br dd, J=11.15, 4.89 Hz, 0.5H) 3.69 (td, J=8.61, 4.30 Hz, 1H) 3.73-3.81 (m, 1H) 3.81-3.90 (m, 0.5H) 3.95 (d, J=3.91 Hz, 3H) 3.97-4.05 (m, 1H) 4.50-4.60 (m, 0.5H) 4.65-4.75 (m, 0.5H) 7.47 (dd, J=8.61, 2.74 Hz, 2H) 7.61-7.69 (m, 4H) 7.69-7.78 (m, 2H) 7.91 (d, J=12.52

Hz, 1H) 8.05 (d, J=11.35 Hz, 1H) 8.24 (dd, J=13.30, 1.96 Hz, 1H) 8.60-8.73 (m, 1H); MS (ESI, m/z): 501.2 [M+H]$^+$

Example 378

(R)-2-amino-N-(1-(4'-(tert-butyl)-[1,1'-biphenyl]-4-carbonyl)pyrrolidin-3-yl)-5-(1-methyl-1H-pyrazol-4-yl)nicotinamide Using 4-tert-butylbenzeneboronic acid, the title compound was obtained as described for the Example 343. $^1$H NMR (400 MHz, METHANOL-d$_4$) δ ppm 1.35 (d, J=2.35 Hz, 9H) 2.07-2.25 (m, 1H) 2.27-2.44 (m, 1H) 3.57 (br dd, J=11.15, 4.89 Hz, 0.5H) 3.69 (dt, J=12.81, 4.94 Hz, 1H) 3.73-3.82 (m, 1H) 3.82-3.90 (m, 0.5H) 3.94 (d, J=3.91 Hz, 3H) 3.97-4.04 (m, 1H) 4.49-4.59 (m, 0.5H) 4.67-4.76 (m, 0.5H) 7.46-7.54 (m, 2H) 7.56-7.62 (m, 2H) 7.62-7.67 (m, 2H) 7.67-7.74 (m, 2H) 7.91 (d, J=12.91 Hz, 1H) 8.06 (d, J=12.13 Hz, 1H) 8.24 (dd, J=14.28, 2.15 Hz, 1H) 8.63-8.74 (m, 1H); MS (ESI, m/z): 523.2 [M+H]$^+$

Example 379

(R)-2-amino-N-(1-(4'-(dimethylamino)-[1,1'-biphenyl]-4-carbonyl)pyrrolidin-3-yl)-5-(1-methyl-1H-pyrazol-4-yl)nicotinamide Using 4-dimethylaminobenzeneboronic acid, the title compound was obtained as described for the Example 343. MS (ESI, m/z): 510.2 [M+H]$^+$

Example 380

(R)-2-amino-N-(1-(4'-hydroxy-[1,1'-biphenyl]-4-carbonyl)pyrrolidin-3-yl)-5-(1-methyl-1H-pyrazol-4-yl)nicotinamide Using 4-hydroxy benzeneboronic acid, the title compound was obtained as described for the Example 343. $^1$H NMR (400 MHz, METHANOL-d$_4$) δ ppm 2.07-2.24 (m, 1H) 2.27-2.44 (m, 1H) 3.57 (br dd, J=11.54, 4.89 Hz, 0.5H) 3.64-3.72 (m, 1H) 3.77 (br t, J=6.85 Hz, 1H) 3.84 (br t, J=7.04 Hz, 0.5H) 3.95 (d, J=3.91 Hz, 3H) 3.96-4.04 (m, 1H) 4.51-4.61 (m, 0.5H) 4.66-4.73 (m, 0.5H) 6.87 (dd, J=8.61, 3.13 Hz, 2H) 7.50 (dd, J=8.61, 4.30 Hz, 2H) 7.56-7.70 (m, 4H) 7.91 (d, J=12.52 Hz, 1H) 8.05 (d, J=12.13 Hz, 1H) 8.24 (dd, J=13.89, 2.15 Hz, 1H) 8.63-8.73 (m, 1H); MS (ESI, m/z): 483.2 [M+H]$^+$

Example 381

(R)-2-amino-N-(1-(4'-formyl-[1,1'-biphenyl]-4-carbonyl)pyrrolidin-3-yl)-5-(1-methyl-1H-pyrazol-4-yl)nicotinamide Using 4-formylbenzeneboronic acid, the title compound was obtained as described for the Example 343. MS (ESI, m/z): 495.2 [M+H]$^+$

Example 382

(R)-2-amino-N-(1-(3'-formyl-[1,1'-biphenyl]-4-carbonyl)pyrrolidin-3-yl)-5-(1-methyl-1H-pyrazol-4-yl)nicotinamide Using 3-formylbenzeneboronic acid, the title compound was obtained as described for the Example 343. MS (ESI, m/z): 495.2 [M+H]$^+$

Example 383

(R)-2-amino-5-(1-methyl-1H-pyrazol-4-yl)-N-(1-(4'-(4-methylpiperazin-1-yl)-[1,1'-biphenyl]-4-carbonyl)pyrrolidin-3-yl)nicotinamide Using (4-(4-methylpiperazin-1-yl)phenyl)boronic acid, the title compound was obtained as described for the Example 343. MS (ESI, m/z): 565.2 [M+H]$^+$

Example 384

(R)-2-amino-5-(1-methyl-1H-pyrazol-4-yl)-N-(1-(4'-(2-(piperazin-1-yl)propan-2-yl)-[1,1'-biphenyl]-4-carbonyl)pyrrolidin-3-yl)nicotinamide Using 1-(4-(4,4,5,5-tetramethyl-1,3,2-dioxaborolan-2-yl)benzyl)piperazine, the title compound was obtained as described for the Example 343. MS (ESI, m/z): 593.2 [M+H]$^+$

Example 385

(R)-2-amino-5-(1-methyl-1H-pyrazol-4-yl)-N-(1-(4'-((4-methylpiperazin-1-yl)methyl)-[1,1'-biphenyl]-4-carbonyl)pyrrolidin-3-yl)nicotinamide Using 1-methyl-4-(4-(4,4,5,5-tetramethyl-1,3,2-dioxaborolan-2-yl)benzyl)piperazine, the title compound was obtained as described for the Example 343. $^1$H NMR (400 MHz, METHANOL-d$_4$) δ ppm 2.08-2.26 (m, 1H) 2.28-2.49 (m, 1H) 2.93 (s, 3H) 3.13-3.26 (m, 4H) 3.46 (br s, 4H) 3.54-3.61 (m, 0.5H) 3.63-3.81 (m, 2H) 3.86 (br dd, J=13.89, 6.46 Hz, 0.5H) 3.95 (d, J=3.52 Hz, 3H) 3.97-4.06 (m, 1H) 4.08-4.16 (m, 2H) 4.52-4.60 (m, 0.5H) 4.68-4.74 (m, 0.5H) 7.56 (dd, J=8.22, 2.35 Hz, 2H) 7.62-7.70 (m, 2H) 7.70-7.83 (m, 4H) 7.91 (d, J=12.13 Hz, 1H) 8.06 (d, J=10.96 Hz, 1H) 8.25 (dd, J=12.72, 2.15 Hz, 1H) 8.64-8.75 (m, 1H); MS (ESI, m/z): 579.2 [M+H]$^+$

Example 386

(R)-2-amino-5-(1-methyl-1H-pyrazol-4-yl)-N-(1-(4'-(2-(4-methylpiperazin-1-yl)propan-2-yl)-[1,1'-biphenyl]-4-carbonyl)pyrrolidin-3-yl)nicotinamide Using 1-methyl-4-(2-(4-(4,4,5,5-tetramethyl-1,3,2-dioxaborolan-2-yl)phenyl)propan-2-yl)piperazine, the title compound was obtained as described for the Example 343. MS (ESI, m/z): 607.2 [M+H]$^+$

Example 387

(R)-2-amino-N-(1-(4'-(2-(4-(2-hydroxyethyl)piperazin-1-yl)propan-2-yl)-[1,1'-biphenyl]-4-carbonyl)pyrrolidin-3-yl)-5-(1-methyl-1H-pyrazol-4-yl)nicotinamide Using 2-(4-(2-(4-(4,4,5,5-tetramethyl-1,3,2-dioxaborolan-2-yl)phenyl)propan-2-yl)piperazin-1-yl)ethan-1-ol, the title compound was obtained as described for the Example 343. MS (ESI, m/z): 607.2 [M+H]$^+$

Example 388

(R)-2-amino-5-(1-methyl-1H-pyrazol-4-yl)-N-(1-(3'-((4-methylpiperazin-1-yl)methyl)-[1,1'-biphenyl]-4-carbonyl)pyrrolidin-3-yl)nicotinamide Using 1-methyl-4-(3-(4,4,5,5-tetramethyl-1,3,2-dioxaborolan-2-yl)benzyl)piperazine, the title compound was obtained as described for the Example 343. MS (ESI, m/z): 579.2 [M+H]$^+$

Example 389

(R)-2-amino-N-(1-(3'-((4-(2-hydroxyethyl)piperazin-1-yl)methyl)-[1,1'-biphenyl]-4-carbonyl)pyrrolidin-3-yl)-5-(1-methyl-1H-pyrazol-4-yl)nicotinamide Using 2-(4-(3-(4,4,5,5-tetramethyl-1,3,2-dioxaborolan-2-yl)benzyl)piperazin-1-yl)ethan-1-ol, the title compound was obtained as described for the Example 343. MS (ESI, m/z): 609.2 [M+H]$^+$

Example 390

(R)-2-amino-5-(1-methyl-1H-pyrazol-4-yl)-N-(1-(4'-((4-methylpiperazin-1-yl)methyl)-[1,1'-biphenyl]-3-carbonyl)pyrrolidin-3-yl)nicotinamide Using 3-bromobenzoic acid and 1-methyl-4-(4-(4,4,5,5-tetramethyl-1,3,2-dioxaborolan-2-yl)benzyl)piperazine, the title compound was obtained as described for the Example 343. MS (ESI, m/z): 579.2 [M+H]$^+$

Example 391

(R)-2-amino-5-(1-methyl-1H-pyrazol-4-yl)-N-(1-(3-methyl-4'-((4-methylpiperazin-1-yl)methyl)-[1,1'-biphenyl]-4-carbonyl)pyrrolidin-3-yl)nicotinamide Using 4-bromo-2-methylbenzoic acid and 1-methyl-4-(4-(4,4,5,5-tetramethyl-1,3,2-dioxaborolan-2-yl)benzyl)piperazine, the title compound was obtained as described for the Example 343. $^1$H NMR (400 MHz, METHANOL-d$_4$) δ ppm 2.07-2.22 (m, 1H) 2.26-2.51 (m, 1H) 2.90 (d, J=1.57 Hz, 3H) 3.12 (br s, 4H) 3.33-3.46 (m, 4H) 3.48 (br dd, J=6.85, 4.11 Hz, 0.5H) 3.62-3.70 (m, 1H) 3.70-3.82 (m, 1H) 3.87 (br s, 0.5H) 3.95 (d, J=5.09 Hz, 3H) 4.01 (d, J=2.74 Hz, 2H) 4.07 (dd, J=12.72, 7.24 Hz, 1H) 4.48-4.58 (m, 0.5H) 4.65-4.73 (m, 0.5H) 7.30-7.38 (m, 1H) 7.45-7.61 (m, 4H) 7.68 (dd, J=8.22, 5.48 Hz, 2H) 7.86-7.93 (m, 1H) 8.05 (br d, J=9.78 Hz, 1H) 8.24 (dd, J=9.59, 2.15 Hz, 1H) 8.61-8.71 (m, 1H); MS (ESI, m/z): 593.2 [M+H]$^+$

Example 392

(R)-2-amino-5-(1-methyl-1H-pyrazol-4-yl)-N-(1-(2-methyl-4'-((4-methylpiperazin-1-yl)methyl)-[1,1'-biphenyl]-4-carbonyl)pyrrolidin-3-yl)nicotinamide Using 4-bromo-3-methylbenzoic acid and 1-methyl-4-(4-(4,4,5,5-tetramethyl-1,3,2-dioxaborolan-2-yl)benzyl)piperazine, the title compound was obtained as described for the Example 343. MS (ESI, m/z): 593.2 [M+H]$^+$

Example 393

(R)-2-amino-N-(1-(3-amino-[1,1'-biphenyl]-4-carbonyl)pyrrolidin-3-yl)-5-(1-methyl-1H-pyrazol-4-yl)nicotinamide Using 2-amino-4-bromobenzoic acid, the title compound was obtained as described for the Example 343. $^1$H NMR (400 MHz, METHANOL-d$_4$) δ ppm 2.18 (br d, J=11.35 Hz, 1H) 2.26-2.47 (m, 1H) 3.59 (br s, 0.5H) 3.63-3.74 (m, 1H) 3.78 (br s, 1H) 3.86 (br d, J=7.43 Hz, 0.5H) 3.94 (s, 3H) 3.97-4.10 (m, 1H) 4.56 (br s, 0.5H) 4.70 (br s, 0.5H) 7.28-7.42 (m, 3H) 7.45 (br t, J=7.63 Hz, 2H) 7.52 (br d, J=12.91 Hz, 1H) 7.62 (br d, J=7.04 Hz, 2H) 7.90 (br d, J=7.04 Hz, 1H) 8.05 (br d, J=8.22 Hz, 1H) 8.24 (br d, J=7.83 Hz, 1H) 8.64-8.76 (m, 1H); MS (ESI, m/z): 482.2 [M+H]$^+$

Example 394

(R)-2-amino-N-(1-(2-chloro-[1,1'-biphenyl]-4-carbonyl)pyrrolidin-3-yl)-5-(1-methyl-H-pyrazol-4-yl)nicotinamide Using 4-bromo-3-chlorobenzoic acid, the title compound was obtained as described for the Example 343. $^1$H NMR (400 MHz, CHLOROFORM-d) δ ppm 2.04 (br dd, J=12.52, 5.48 Hz, 0.5H) 2.28 (br d, J=6.65 Hz, 0.5H) 2.32-2.54 (m, 1H) 3.60 (br d, J=11.74 Hz, 0.5H) 3.65-3.77 (m, 1H) 3.77-3.89 (m, 1H) 3.93 (s, 3H) 3.95 (br d, J=6.65 Hz, 1H) 4.31 (br d, J=9.78 Hz, 0.5H) 4.79 (br d, J=16.43 Hz, 1H) 7.13 (br d, J=8.61 Hz, 1H) 7.30-7.45 (m, 4H) 7.58-7.68 (m, 1H) 7.68-7.80 (m, 1H) 7.99-8.17 (m, 1H) 8.52 (s, 1H) 8.67 (br d, J=6.26 Hz, 1H) 8.72-8.83 (m, 1H) 8.88 (br s, 1H); MS (ESI, m/z): 482.2 [M+H]$^+$

Example 395

(R)-2-amino-N-(1-(5-(2-chlorophenyl)picolinoyl)pyrrolidin-3-yl)-5-(1-methyl-1H-pyrazol-4-yl)nicotinamide Using 5-bromopicolinic acid and 2-chlorobenzeneboronic acid, the title compound was obtained as described for the Example 343. $^1$H NMR (400 MHz, METHANOL-d$_4$) δ ppm 2.14-2.23 (m, 1H) 2.31-2.43 (m, 1H) 3.79 (d, J=4.30 Hz, 0.5H) 3.80-3.92 (m, 2H) 3.94 (d, J=2.35 Hz, 3H) 4.04 (dd, J=12.52, 7.04 Hz, 1H) 4.18 (dd, J=12.13, 6.26 Hz, 0.5H) 4.60-4.73 (m, 1H) 7.41-7.49 (m, 3H) 7.55-7.60 (m, 1H) 7.88-7.94 (m, 2H) 8.03-8.09 (m, 2H) 8.24 (dd, J=9.00, 2.35 Hz, 1H) 8.67 (d, J=1.96 Hz, 1H) 8.70 (d, J=1.96 Hz, 0.5H) 8.73 (d, J=2.35 Hz, 0.5H); MS (ESI, m/z): 502.2 [M+H]$^+$

Example 396

(R)-2-amino-5-(1-methyl-1H-pyrazol-4-yl)-N-(1-(5-phenylpicolinoyl)pyrrolidin-3-yl)nicotinamide Using 5-bromopicolinic acid, the title compound was obtained as described for the Example 343. $^1$H NMR (400 MHz, METHANOL-d$_4$) δ ppm 2.12-2.22 (m, 1H) 2.36 (td, J=12.13, 6.26 Hz, 1H) 3.78 (d, J=4.30 Hz, 0.5H) 3.79-3.92 (m, 2H) 3.94 (d, J=3.91 Hz, 3H) 3.97-4.08 (m, 1H) 4.17 (dd, J=11.93, 6.06 Hz, 0.5H) 4.59-4.72 (m, 1H) 7.42-7.48 (m, 1H) 7.48-7.56 (m, 2H) 7.67-7.76 (m, 2H) 7.87-7.93 (m, 2H)

8.05 (d, J=11.35 Hz, 1H) 8.20 (ddd, J=8.41, 6.46, 2.35 Hz, 1H) 8.24 (dd, J=9.59, 2.15 Hz, 1H) 8.65-8.75 (m, 1H) 8.88 (dd, J=8.22, 1.96 Hz, 1H); MS (ESI, m/z): 468.2 [M+H]+

Example 397

(R)-2-amino-N-(1-(6-(2-chlorophenyl)nicotinoyl)pyrrolidin-3-yl)-5-(1-methyl-1H-pyrazol-4-yl)nicotinamide Using 6-bromonicotinic acid and 2-chlorobenzeneboronic acid, the title compound was obtained as described for the Example 343. $^1$H NMR (400 MHz, METHANOL-$d_4$) δ ppm 2.09-2.29 (m, 1H) 2.29-2.48 (m, 1H) 3.61 (br dd, J=10.96, 5.09 Hz, 0.5H) 3.70-3.86 (m, 2H) 3.86-3.93 (m, 0.5H) 3.95 (d, J=3.13 Hz, 3H) 3.98-4.10 (m, 1H) 4.57-4.76 (m, 1H) 7.43-7.51 (m, 2H) 7.53-7.62 (m, 2H) 7.80 (dd, J=8.02, 4.11 Hz, 1H) 7.91 (d, J=11.35 Hz, 1H) 8.06 (d, J=10.56 Hz, 1H) 8.11-8.20 (m, 1H) 8.25 (dd, J=11.93, 2.15 Hz, 1H) 8.63-8.74 (m, 1H) 8.85 (dd, J=6.85, 1.76 Hz, 1H); MS (ESI, m/z): 502.2 [M+H]+

Example 398

(R)-2-amino-5-(1-methyl-1H-pyrazol-4-yl)-N-(1-(6-phenylnicotinoyl)pyrrolidin-3-yl)nicotinamide Using 6-bromonicitinic acid, the title compound was obtained as described for the Example 343. $^1$H NMR (400 MHz, METHANOL-$d_4$) δ ppm 2.18 (dt, J=14.38, 7.09 Hz, 1H) 2.31-2.47 (m, 1H) 3.61 (br dd, J=10.76, 4.89 Hz, 0.5H) 3.67-3.86 (m, 2H) 3.86-3.92 (m, 0.5H) 3.95 (d, J=4.30 Hz, 3H) 3.98-4.10 (m, 1H) 4.55-4.64 (m, 0.5H) 4.72 (br d, J=5.48 Hz, 0.5H) 7.47-7.60 (m, 3H) 7.91 (d, J=12.91 Hz, 1H) 7.96-8.09 (m, 4H) 8.12 (td, J=8.31, 2.15 Hz, 1H) 8.24 (dd, J=14.09, 1.96 Hz, 1H) 8.62-8.77 (m, 1H) 8.84 (dd, J=8.41, 1.76 Hz, 1H); MS (ESI, m/z): 468.2 [M+H]+

Example 399

(R)-2-amino-5-(1-methyl-1H-pyrazol-4-yl)-N-(1-(2-methyl-[1,1'-biphenyl]-4-carbonyl)pyrrolidin-3-yl)nicotinamide Using 4-bromo-3-methylbenzoic acid, the title compound was obtained as described for the Example 343. MS (ESI, m/z): 481.2 [M+H]+

Example 400

(R)-2-amino-N-(1-(4-iodobenzoyl)pyrrolidin-3-yl)-5-(1-methyl-1H-pyrazol-4-yl)nicotinamide Using 4-iodobenzoic acid, the title compound was obtained as described for the Example 342. $^1$H NMR (400 MHz, METHANOL-$d_4$) δ ppm 2.05-2.22 (m, 1H) 2.24-2.44 (m, 1H) 3.45-3.52 (m, 0.5H) 3.57-3.78 (m, 2H) 3.78-3.85 (m, 0.5H) 3.87-4.04 (m, 1H) 3.95 (d, J=1.96 Hz, 3H) 4.50-4.60 (m, 0.5H) 4.64-4.72 (m, 0.5H) 7.33 (t, J=8.41 Hz, 2H) 7.79-7.88 (m, 2H) 7.90 (d, J=10.17 Hz, 1H) 8.05 (d, J=9.39 Hz, 1H) 8.25 (dd, J=10.37, 2.15 Hz, 1H) 8.60-8.71 (m, 1H); MS (ESI, m/z): 517.2 [M+H]+

Example 401

(R)-2-amino-N-(1-(benzofuran-2-carbonyl)pyrrolidin-3-yl)-5-(1-methyl-1H-pyrazol-4-yl)nicotinamide Using benzofuran-2-carboxylic acid, the title compound was obtained as described for the Example 342. $^1$H NMR (400 MHz, METHANOL-$d_4$) δ ppm 2.15-2.31 (m, 1H) 2.33-2.50 (m, 1H) 3.76-3.82 (m, 1H) 3.88-3.92 (m, 3H) 3.95-4.12 (m, 1H) 4.12-4.25 (m, 1H) 4.37 (br dd, J=11.74, 6.26 Hz, 1H) 4.63-4.77 (m, 1H) 7.27-7.35 (m, 1H) 7.41-7.48 (m, 1H) 7.48-7.53 (m, 1H) 7.53-7.59 (m, 1H) 7.67-7.73 (m, 1H) 7.86 (d, J=6.26 Hz, 1H) 8.00 (d, J=7.43 Hz, 1H) 8.21 (dd, J=5.48, 1.96 Hz, 1H) 8.68 (dd, J=9.78, 1.96 Hz, 1H); MS (ESI, m/z): 431.2 [M+H]+

Example 402

(R)-2-amino-5-(1-methyl-1H-pyrazol-4-yl)-N-(1-(3-methylbenzofuran-2-carbonyl)pyrrolidin-3-yl)nicotinamide Using 3-methylbenzofuran-2-carboxylic acid, the title compound was obtained as described for the Example 342. $^1$H NMR (400 MHz, METHANOL-$d_4$) δ ppm 2.09-2.26 (m, 1H) 2.36 (dt, J=16.82, 6.65 Hz, 1H) 2.52 (d, J=2.74 Hz, 3H) 3.70-3.81 (m, 1H) 3.85 (br t, J=7.63 Hz, 0.5H) 3.92 (s, 3H) 3.94-4.02 (m, 1H) 4.04-4.23 (m, 1H) 4.31 (br dd, J=11.93, 6.46 Hz, 0.5H) 4.61-4.71 (m, 1H) 7.27-7.37 (m, 1H) 7.37-7.47 (m, 1H) 7.47-7.53 (m, 1H) 7.63-7.71 (m, 1H) 7.88 (d, J=6.26 Hz, 1H) 8.02 (d, J=6.26 Hz, 1H) 8.18-8.27 (m, 1H) 8.66 (dd, J=14.87, 1.96 Hz, 1H); MS (ESI, m/z): 445.2 [M+H]+

Example 403

(R)-2-amino-N-(1-(5-chlorobenzofuran-2-carbonyl)pyrrolidin-3-yl)-5-(1-methyl-1H-pyrazol-4-yl)nicotinamide Using 5-chlorobenzofuran-2-carboxylic acid, the title compound was obtained as described for the Example 342. $^1$H NMR (400 MHz, METHANOL-$d_4$) δ ppm 2.14-2.31 (m, 1H) 2.31-2.50 (m, 1H) 3.74-3.90 (m, 1.5H) 3.92 (s, 3H) 3.96-4.11 (m, 1H) 4.18 (br dd, J=16.04, 7.43 Hz, 1H) 4.37 (br dd, J=11.93, 6.06 Hz, 0.5H) 4.64-4.77 (m, 1H) 7.40-7.47 (m, 1H) 7.50 (d, J=5.87 Hz, 1H) 7.58 (dd, J=9.00, 2.35 Hz, 2H) 7.76 (t, J=2.74 Hz, 1H) 7.88 (d, J=5.09 Hz, 1H) 8.02 (d, J=5.48 Hz, 1H) 8.24 (dd, J=3.91, 2.35 Hz, 1H) 8.65 (dd, J=10.76, 2.15 Hz, 1H); MS (ESI, m/z): 465.2 [M+H]+

Example 404

2-amino-N-((3R)-1-(5-chloro-2,3-dihydrobenzofuran-2-carbonyl)pyrrolidin-3-yl)-5-(1-methyl-1H-pyrazol-4-yl)nicotinamide Using 5-chloro-2,3-dihydrobenzofuran-2-carboxylic acid, the title compound was obtained as described for the Example 342. MS (ESI, m/z): 467.2 [M+H]+

Example 405

(R)—N-(1-(2-naphthoyl)pyrrolidin-3-yl)-2-amino-5-(1-methyl-1H-pyrazol-4-yl)nicotinamide Using 2-naphthoic acid, the title compound was obtained as described for the Example 342. MS (ESI, m/z): 441.2 [M+H]+

Example 406

(R)-2-amino-N-(1-(benzo[b]thiophene-2-carbonyl) pyrrolidin-3-yl)-5-(1-methyl-1H-pyrazol-4-yl)nicotinamide Using benzo[b]thiophene-2-carboxylic acid, the title compound was obtained as described for the Example 342. MS (ESI, m/z): 447.2 [M+H]$^+$

Example 407

(R)-2-amino-N-(1-(4,5-dibromothiophene-2-carbonyl)pyrrolidin-3-yl)-5-(1-methyl-1H-pyrazol-4-yl) nicotinamide Using 4,5-dibromothiophene-2-carboxylic acid, the title compound was obtained as described for the Example 342. $^1$H NMR (400 MHz, METHANOL-d$_4$) δ ppm 2.10-2.47 (m, 2H) 3.63-3.89 (m, 2H) 3.93 (s, 3H) 3.94-4.03 (m, 1.5H) 4.16-4.26 (m, 0.5H) 4.60-4.77 (m, 1H) 7.50 (br d, J=14.48 Hz, 1H) 7.88 (s, 1H) 8.03 (s, 1H) 8.24 (s, 1H) 8.67 (br d, J=7.83 Hz, 1H); MS (ESI, m/z): 553.0/555.1/557.1 [M+H]$^+$

Example 408

(R)-2-amino-5-(1-methyl-1H-pyrazol-4-yl)-N-(1-(5-methylthiophene-2-carbonyl)pyrrolidin-3-yl)nicotinamide Using 5-methylthiophene-2-carboxylic acid, the title compound was obtained as described for the Example 342. $^1$H NMR (400 MHz, METHANOL-d$_4$) δ ppm 2.11-2.28 (m, 1H) 2.29-2.42 (m, 1H) 2.49 (s, 3H) 3.70 (br d, J=13.69 Hz, 1H) 3.76-3.89 (m, 1H) 3.92 (s, 3H) 3.95-4.07 (m, 1.5H) 4.21 (br s, 0.5H) 4.65 (br s, 1H) 6.79 (d, J=2.74 Hz, 1H) 7.49 (d, J=3.91 Hz, 1H) 7.88 (s, 1H) 8.03 (s, 1H) 8.22 (s, 1H) 8.68 (br d, J=7.04 Hz, 1H); MS (ESI, m/z): 411.1 [M+H]$^+$

Example 409

(R)-2-amino-5-(1-methyl-1H-pyrazol-4-yl)-N-(1-(4-methylthiophene-2-carbonyl)pyrrolidin-3-yl)nicotinamide Using 4-methylthiophene-2-carboxylic acid, the title compound was obtained as described for the Example 342. $^1$H NMR (400 MHz, METHANOL-d$_4$) δ ppm 2.15 (br d, J=5.48 Hz, 1H) 2.26 (s, 3H) 2.29-2.44 (m, 1H) 3.68-3.78 (m, 1H) 3.78-3.88 (m, 1H) 3.92 (s, 3H) 3.93-4.08 (m, 1.5H) 4.18-4.26 (m, 0.5H) 4.66 (br s, 1H) 7.23 (s, 1H) 7.50 (s, 1H) 7.88 (s, 1H) 8.03 (s, 1H) 8.23 (s, 1H) 8.68 (br d, J=11.74 Hz, 1H); MS (ESI, m/z): 411.1 [M+H]$^+$

Example 410

(R)-2-amino-N-(1-(4-(benzyloxy)benzoyl)pyrrolidin-3-yl)-5-(1-methyl-1H-pyrazol-4-yl)nicotinamide Using 4-benzyloxybenzoic acid, the title compound was obtained as described for the Example 342. $^1$H NMR (400 MHz, METHANOL-d$_4$) δ ppm 2.05-2.21 (m, 1H) 2.23-2.44 (m, 1H) 3.56 (br dd, J=11.35, 5.09 Hz, 0.5H) 3.62-3.87 (m, 2.5H) 3.94 (s, 3H) 3.95-4.03 (m, 1H) 4.48-4.60 (m, 0.5H) 4.62-4.72 (m, 0.5H) 5.13 (d, J=3.52 Hz, 2H) 7.06 (dd, J=8.22, 5.48 Hz, 2H) 7.28-7.33 (m, 1H) 7.37 (br t, J=7.43 Hz, 2H) 7.40-7.47 (m, 2H) 7.54 (br t, J=9.59 Hz, 2H) 7.90 (d, J=10.17 Hz, 1H) 8.05 (d, J=9.39 Hz, 1H) 8.24 (dd, J=10.96, 1.96 Hz, 1H) 8.61-8.73 (m, 1H); MS (ESI, m/z): 497.1 [M+H]$^+$

Example 411

2-amino-N-((3R)-1-(4-(cyclohex-2-en-1-yloxy)benzoyl)pyrrolidin-3-yl)-5-(1-methyl-1H-pyrazol-4-yl) nicotinamide Using 4-(cyclohex-2-en-1-yloxy)benzoic acid, the title compound was obtained as described for the Example 342. MS (ESI, m/z): 487.1 [M+H]$^+$

Example 412

(R)-2-amino-5-(1-methyl-1H-pyrazol-4-yl)-N-(1-(3-phenoxybenzoyl)pyrrolidin-3-yl)nicotinamide Using 3-phenoxybenzoic acid, the title compound was obtained as described for the Example 342. $^1$H NMR (400 MHz, METHANOL-d$_4$) δ ppm 2.06-2.21 (m, 1H) 2.22-2.42 (m, 1H) 3.48 (dd, J=11.15, 4.89 Hz, 0.5H) 3.57-3.74 (m, 2H) 3.83 (br s, 0.5H) 3.84-3.92 (m, 0.5H) 3.94 (s, 3H) 3.95-4.01 (m, 0.5H) 4.50-4.60 (m, 0.5H) 4.60-4.71 (m, 0.5H) 6.97-7.05 (m, 2H) 7.05-7.18 (m, 3H) 7.27 (dd, J=12.72, 7.63 Hz, 1H) 7.31-7.40 (m, 2H) 7.40-7.48 (m, 1H) 7.90 (d, J=7.83 Hz, 1H) 8.05 (d, J=7.43 Hz, 1H) 8.24 (dd, J=6.85, 2.15 Hz, 1H) 8.60-8.71 (m, 1H); MS (ESI, m/z): 483.1 [M+H]$^+$

Example 413

(R)-2-amino-N-(1-(4-(2-bromoethyl)benzoyl)pyrrolidin-3-yl)-5-(1-methyl-1H-pyrazol-4-yl)nicotinamide Using 4-(2-bromoethyl)benzoic acid, the title compound was obtained as described for the Example 342. $^1$H NMR (400 MHz, METHANOL-d$_4$) δ ppm 2.15-2.21 (m, 1H) 2.26-2.43 (m, 1H) 3.21 (br s, 2H) 3.46-3.55 (m, 0.5H) 3.66 (br s, 2H) 3.69-3.88 (m, 2.5H) 3.82 (br s, 3H) 3.97-4.05 (m, 1H) 4.52 (br d, J=18.39 Hz, 0.5H) 4.68 (br s, 0.5H) 6.79 (dd, J=17.61, 10.96 Hz, 2H) 7.33-7.44 (m, 2H) 7.90 (br d, J=10.17 Hz, 1H) 8.05 (br d, J=10.17 Hz, 1H) 8.24 (br d, J=11.35 Hz, 1H) 8.69 (s, 1H); MS (ESI, m/z): 497.1/499.2 [M+H]$^+$

Example 414

(R)-2-amino-N-(1-(4-(tert-butyl)benzoyl)pyrrolidin-3-yl)-5-(1-methyl-1H-pyrazol-4-yl)nicotinamide Using 4-tert-butylbenzoic acid, the title compound was obtained as described for the Example 342. $^1$H NMR (400 MHz, METHANOL-d$_4$) δ ppm 1.33 (d, J=3.52 Hz, 9H) 2.03-2.22 (m, 1H) 2.22-2.44 (m, 1H) 3.48-3.58 (m, 0.5H) 3.66 (br dd, J=12.72, 4.89 Hz, 1H) 3.69-3.79 (m, 1H) 3.79-3.87 (m, 0.5H) 3.94 (s, 3H) 3.96-4.03 (m, 1H) 4.46-4.57 (m, 0.5H) 4.63-4.73 (m, 0.5H) 7.50 (br d, J=8.61 Hz, 4H) 7.90 (br d, J=11.35 Hz, 1H) 8.05 (d, J=10.17 Hz, 1H) 8.24 (br d, J=12.91 Hz, 1H) 8.61-8.74 (m, 1H); MS (ESI, m/z): 447.1 [M+H]$^+$

Example 415

(R)-2-amino-N-(1-(3,4-dimethylbenzoyl)pyrrolidin-3-yl)-5-(1-methyl-1H-pyrazol-4-yl)nicotinamide Using 3,4-dimethylbenzoic acid, the title compound was obtained as described for the Example 342. $^1$H NMR (400

MHz, METHANOL-d$_4$) δ ppm 2.04-2.20 (m, 1H) 2.26-2.61 (m, 7H) 3.51 (br dd, J=11.54, 5.28 Hz, 0.5H) 3.58-3.68 (m, 1H) 3.68-3.77 (m, 1H) 3.81-3.86 (m, 0.5H) 3.86-4.04 (m, 1H) 3.94 (s, 3H) 4.47-4.57 (m, 0.5H) 4.63-4.72 (m, 0.5H) 7.17-7.36 (m, 3H) 7.90 (d, J=11.74 Hz, 1H) 8.05 (d, J=10.96 Hz, 1H) 8.23 (dd, J=13.89, 1.76 Hz, 1H) 8.60-8.75 (m, 1H); MS (ESI, m/z): 419.1 [M+H]$^+$ Example 416

(R)-2-amino-5-(1-methyl-1H-pyrazol-4-yl)-N-(1-(4-(4-methylpiperazin-1-yl)benzoyl)pyrrolidin-3-yl) nicotinamide Using 4-(4-methylpiperazin-1-yl)benzoic acid, the title compound was obtained as described for the Example 342. $^1$H NMR (400 MHz, METHANOL-d$_4$) δ ppm 2.04-2.22 (m, 1H) 2.22-2.45 (m, 1H) 2.96 (s, 3H) 3.05-3.18 (m, 2H) 3.18-3.27 (m, 2H) 3.55-3.86 (m, 5H) 3.94 (s, 3H) 3.99 (br d, J=14.48 Hz, 2H) 4.51 (br d, J=5.09 Hz, 0.5H) 4.67 (br s, 0.5H) 6.96-7.10 (m, 2H) 7.54 (br t, J=9.59 Hz, 2H) 7.90 (br d, J=9.00 Hz, 1H) 8.05 (br d, J=7.04 Hz, 1H) 8.24 (br d, J=7.43 Hz, 1H) 8.62-8.75 (m, 1H); MS (ESI, m/z): 489.1 [M+H]$^+$ Example 417

(R)-2-amino-5-(1-methyl-1H-pyrazol-4-yl)-N-(1-(4-vinylbenzoyl)pyrrolidin-3-yl)nicotinamide Using 4-vinylbenzoic acid, the title compound was obtained as described for the Example 342. $^1$H NMR (400 MHz, METHANOL-d$_4$) δ ppm 2.04-2.21 (m, 1H) 2.26-2.46 (m, 1H) 3.45-3.59 (m, 0.5H) 3.59-3.69 (m, 1H) 3.69-3.78 (m, 1H) 3.82 (br s, 0.5H) 3.95 (d, J=2.35 Hz, 3H) 4.01 (br d, J=12.91 Hz, 1H) 4.54 (br s, 0.5H) 4.69 (br s, 0.5H) 5.34 (br d, J=10.56 Hz, 1H) 5.84-5.95 (m, 1H) 6.70-6.85 (m, 1H) 7.53 (d, J=7.04 Hz, 4H) 7.91 (br d, J=11.35 Hz, 1H) 8.05 (br d, J=10.17 Hz, 1H) 8.24 (br d, J=12.13 Hz, 1H) 8.61-8.73 (m, 1H); MS (ESI, m/z): 417.1 [M+H]$^+$ Example 418

(R)-2-amino-N-(1-(4-isopropylbenzoyl)pyrrolidin-3-yl)-5-(1-methyl-1H-pyrazol-4-yl)nicotinamide Using 4-isopropylbenzoic acid, the title compound was obtained as described for the Example 342. $^1$H NMR (400 MHz, METHANOL-d$_4$) δ ppm 1.26 (dd, J=7.04, 3.13 Hz, 6H) 1.99-2.23 (m, 1H) 2.23-2.49 (m, 1H) 2.90-3.00 (m, 1H) 3.49-3.58 (m, 0.5H) 3.65 (br dd, J=12.72, 5.28 Hz, 1H) 3.69-3.78 (m, 1H) 3.78-3.87 (m, 0.5H) 3.88-4.02 (m, 1H) 3.95 (d, J=1.96 Hz, 3H) 4.49-4.60 (m, 0.5H) 4.61-4.77 (m, 0.5H) 7.30-7.37 (m, 2H) 7.46-7.55 (m, 2H) 7.90 (d, J=10.96 Hz, 1H) 8.05 (d, J=9.78 Hz, 1H) 8.19-8.29 (m, 1H) 8.61-8.74 (m, 1H); MS (ESI, m/z): 433.1 [M+H]$^+$ Example 419

(R)-2-amino-N-(1-(4-cyanobenzoyl)pyrrolidin-3-yl)-5-(1-methyl-1H-pyrazol-4-yl)nicotinamide Using 4-cyanobenzoic acid, the title compound was obtained as described for the Example 342. $^1$H NMR (400 MHz, METHANOL-d$_4$) δ ppm 2.06-2.23 (m, 1H) 2.25-2.48 (m, 1H) 3.42-3.49 (m, 0.5H) 3.55-3.62 (m, 0.5H) 3.62-3.70 (m, 1H) 3.70-3.79 (m, 0.5H) 3.80-3.91 (m, 1H) 3.94 (d, J=1.96 Hz, 3H) 3.96-4.05 (m, 0.5H) 4.52-4.62 (m, 0.5H) 4.63-4.74 (m, 0.5H) 7.68-7.75 (m, 2H) 7.84 (dd, J=8.22, 5.09 Hz, 2H) 7.90 (d, J=10.56 Hz, 1H) 8.05 (d, J=9.39 Hz, 1H) 8.24 (dd, J=10.37, 2.15 Hz, 1H) 8.62-8.78 (m, 1H); MS (ESI, m/z): 416.1 [M+H]$^+$ Example 420

(R)-2-amino-5-(1-methyl-1H-pyrazol-4-yl)-N-(1-(4-(methylthio)benzoyl)pyrrolidin-3-yl)nicotinamide Using 4-(methylthio)benzoic acid, the title compound was obtained as described for the Example 342. MS (ESI, m/z): 437.1 [M+H]$^+$ Example 421

(R)-2-amino-N-(1-(2-(3-bromophenyl)acetyl)pyrrolidin-3-yl)-5-(1-methyl-1H-pyrazol-4-yl)nicotinamide Using 2-(3-bromophenyl)acetic acid, the title compound was obtained as described for the Example 342. MS (ESI, m/z): 483.1/485.1 [M+H]$^+$ Example 422

(R)—N-(1-(2-([1,1'-biphenyl]-4-yl)acetyl)pyrrolidin-3-yl)-2-amino-5-(1-methyl-1H-pyrazol-4-yl)nicotinamide Using 2-([1,1'-biphenyl]-4-yl)acetic acid, the title compound was obtained as described for the Example 342. $^1$H NMR (600 MHz, METHANOL-d$_4$) δ ppm 2.01-2.20 (m, 1H) 2.23-2.39 (m, 1H) 3.51-3.60 (m, 1H) 3.66-3.87 (m, 3H) 3.91 (s, 2H) 3.93 (s, 3H) 4.51 (br t, J=4.11 Hz, 0.5H) 4.53-4.59 (m, 0.5H) 7.29-7.42 (m, 5H) 7.43-7.47 (m, 2H) 7.52-7.58 (m, 2H) 7.81 (s, 0.5H) 7.87 (s, 0.5H) 7.94 (s, 0.5H) 8.00 (d, J=2.35 Hz, 0.5H) 8.01 (s, 0.5H) 8.21 (d, J=1.76 Hz, 0.5H) 8.39 (d, J=1.76 Hz, 0.5H) 8.62 (d, J=1.76 Hz, 0.5H); MS (ESI, m/z): 481.1 [M+H]$^+$ Example 423

(R)—N-(1-(2-([1,1'-biphenyl]-3-yl)acetyl)pyrrolidin-3-yl)-2-amino-5-(1-methyl-1H-pyrazol-4-yl)nicotinamide Using 2-([1,1'-biphenyl]-3-yl)acetic acid, the title compound was obtained as described for the Example 342. MS (ESI, m/z): 481.1 [M+H]$^+$ Example 424

(R)-2-amino-N-(1-cinnamoylpyrrolidin-3-yl)-5-(1-methyl-1H-pyrazol-4-yl)nicotinamide Using cinnamic acid, the title compound was obtained as described for the Example 342. MS (ESI, m/z): 417.1 [M+H]$^+$ Example 425

(R,E)-2-amino-N-(1-(3-(benzo[d][1,3]dioxol-5-yl)acryloyl)pyrrolidin-3-yl)-5-(1-methyl-1H-pyrazol-4-yl)nicotinamide Using (E)-3-(benzo[d][1,3]dioxol-5-yl)acrylic acid, the title compound was obtained as described for the Example 342. MS (ESI, m/z): 461.1 [M+H]$^+$

Example 426

(R,E)-2-amino-5-(1-methyl-1H-pyrazol-4-yl)-N-(1-(2-methyl-3-phenylacryloyl)pyrrolidin-3-yl)nicotinamide Using (E)-2-methyl-3-phenylacrylic acid, the title compound was obtained as described for the Example 342. MS (ESI, m/z): 431.1 [M+H]$^+$

Example 427

(R,E)-2-amino-N-(1-(3-(4-bromophenyl)acryloyl)pyrrolidin-3-yl)-5-(1-methyl-1H-pyrazol-4-yl)nicotinamide Using (E)-3-(4-bromophenyl)acrylic acid, the title compound was obtained as described for the Example 342. MS (ESI, m/z): 495.1/497.2 [M+H]$^+$

Example 428

(R,E)-2-amino-N-(1-(3-(3-bromophenyl)acryloyl)pyrrolidin-3-yl)-5-(1-methyl-1H-pyrazol-4-yl)nicotinamide Using (E)-3-(3-bromophenyl)acrylic acid, the title compound was obtained as described for the Example 342. MS (ESI, m/z): 495.1/497.2 [M+H]$^+$

Example 429

(R,E)-2-amino-5-(1-methyl-1H-pyrazol-4-yl)-N-(1-(3-(4-((4-methylpiperazin-1-yl)methyl)phenyl)acryloyl)pyrrolidin-3-yl)nicotinamide Using (E)-3-(4-((4-methylpiperazin-1-yl)methyl)phenyl)acrylic acid, the title compound was obtained as described for the Example 342. MS (ESI, m/z): 529.1 [M+H]$^+$

Example 430

(R,E)-2-amino-N-(1-(3-(4-((4-(2-hydroxyethyl)piperazin-1-yl)methyl)phenyl)acryloyl)pyrrolidin-3-yl)-5-(1-methyl-1H-pyrazol-4-yl)nicotinamide Using (E)-3-(4-((4-(2-hydroxyethyl)piperazin-1-yl)methyl)phenyl)acrylic acid, the title compound was obtained as described for the Example 342. MS (ESI, m/z): 559.1 [M+H]$^+$

Example 431

(R,E)-2-amino-5-(1-methyl-1H-pyrazol-4-yl)-N-(1-(3-(4'-((4-methylpiperazin-1-yl)methyl)-[1,1'-biphenyl]-3-yl)acryloyl)pyrrolidin-3-yl)nicotinamide Using (E)-3-(3-bromophenyl)acrylic acid and 1-methyl-4-(4-(4,4,5,5-tetramethyl-1,3,2-dioxaborolan-2-yl)benzyl)piperazine, the title compound was obtained for the Example 343. MS (ESI, m/z): 605.1 [M+H]$^+$

Example 432

(R,E)-2-amino-5-(1-methyl-1H-pyrazol-4-yl)-N-(1-(3-(4'-((4-methylpiperazin-1-yl)methyl)-[1,1'-biphenyl]-4-yl)acryloyl)pyrrolidin-3-yl)nicotinamide Using (E)-3-(4-bromophenyl)acrylic acid and 1-methyl-4-(4-(4,4,5,5-tetramethyl-1,3,2-dioxaborolan-2-yl)benzyl)piperazine, the title compound was obtained as described for the Example 343. MS (ESI, m/z): 605.1 [M+H]$^+$

Example 433

(R)-2-amino-5-(1-methyl-1H-pyrazol-4-yl)-N-(1-(2-phenylacetyl)pyrrolidin-3-yl)nicotinamide Using 2-phenylacetic acid, the title compound was obtained as described for the Example 342. MS (ESI, m/z): 405.20 [M+H]$^+$

Example 434

(R)-2-amino-N-(1-(2-(3-chlorophenyl)acetyl)pyrrolidin-3-yl)-5-(1-methyl-1H-pyrazol-4-yl)nicotinamide Using 2-(3-chlorophenyl)acetic acid, the title compound was obtained as described for the Example 342. MS (ESI, m/z): 439.16 [M+H]$^+$

Example 435

(R)-2-amino-N-(1-(2-(2-fluorophenyl)acetyl)pyrrolidin-3-yl)-5-(1-methyl-1H-pyrazol-4-yl)nicotinamide Using 2-(2-fluorophenyl)acetic acid, the title compound was obtained as described for the Example 342. MS (ESI, m/z): 423.19 [M+H]$^+$

Example 436

(R)-2-amino-N-(1-(2-(2-methoxyphenyl)acetyl)pyrrolidin-3-yl)-5-(1-methyl-1H-pyrazol-4-yl)nicotinamide Using 2-(2-methoxyphenyl)acetic acid, the title compound was obtained as described for the Example 342. MS (ESI, m/z): 435.21 [M+H]$^+$

Example 437

(R)-2-amino-5-(1-methyl-1H-pyrazol-4-yl)-N-(1-(2-methyl-2-phenylpropanoyl)pyrrolidin-3-yl)nicotinamide Using 2-methyl-2-phenylpropanoic acid, the title compound was obtained as described for the Example 342. MS (ESI, m/z): 433.23 [M+H]$^+$

Example 438

(R)-2-amino-N-(1-benzoylpyrrolidin-3-yl)-5-(1-methyl-1H-pyrazol-4-yl)nicotinamide Using benzoic acid, the title compound was obtained as described for the Example 342. MS (ESI, m/z): 391.18 [M+H]$^+$

Example 439

(R)-2-amino-N-(1-(4-fluoro-2-methylbenzoyl)pyrrolidin-3-yl)-5-(1-methyl-1H-pyrazol-4-yl)nicotinamide Using 4-fluoro-2-methylbenzoic acid, the title compound was obtained as described for the Example 342. MS (ESI, m/z): 423.19 [M+H]$^+$

Example 440

(R)-2-amino-N-(1-(5-bromo-2-chlorobenzoyl)pyrrolidin-3-yl)-5-(1-methyl-1H-pyrazol-4-yl)nicotinamide Using 5-bromo-2-chlorobenzoic acid, the title compound was obtained as described for the Example 342. MS (ESI, m/z): 503.05 [M+H]$^+$

Example 441

(R)-2-amino-N-(1-(3,5-dichlorobenzoyl)pyrrolidin-3-yl)-5-(1-methyl-1H-pyrazol-4-yl)nicotinamide Using 3,5-dichlorobenzoic acid, the title compound was obtained as described for the Example 342. MS (ESI, m/z): 459.10 [M+H]$^+$

Example 442

2-amino-5-(1-methyl-1H-pyrazol-4-yl)-N—((R)-1-(trans-2-phenylcyclopropane-1-carbonyl)pyrrolidin-3-yl)nicotinamide Using trans-2-phenylcyclopropane-1-carboxylic acid, the title compound was obtained as described for the Example 342. MS (ESI, m/z): 431.21 [M+H]$^+$

Example 443

(R)-2-amino-5-(1-methyl-1H-pyrazol-4-yl)-N-(1-(5-(4-((4-methylpiperazin-1-yl)methyl)phenyl)-1-naphthoyl)pyrrolidin-3-yl)nicotinamide Using 5-(4-((4-methylpiperazin-1-yl)methyl)phenyl)-1-naphthoic acid the title compound was obtained as described for the Example 342. MS (ESI, m/z): 629.33 [M+H]$^+$

Example 444

2-amino-N—((R)-1-(5-(4-(((R)-2-(hydroxymethyl)pyrrolidin-1-yl)methyl)phenyl)-1-naphthoyl)pyrrolidin-3-yl)-5-(1-methyl-1H-pyrazol-4-yl)nicotinamide Using (R)-5-(4-((2-(hydroxymethyl)pyrrolidin-1-yl)methyl)phenyl)-1-naphthoic acid, the title compound was obtained as described for the Example 342. MS (ESI, m/z): 630.31 [M+H]$^+$

Example 445

2-amino-5-(1-methyl-1H-pyrazol-4-yl)-N-((3R)-1-(5-(4-(((1-(1-methylpiperidin-4-yl)ethyl)amino)methyl)phenyl)-1-naphthoyl)pyrrolidin-3-yl)nicotinamide Using 5-(4-(((1-(1-methylpiperidin-4-yl)ethyl)amino)methyl)phenyl)-1-naphthoic acid, the title compound was obtained as described for the Example 342. MS (ESI, m/z): 671.37 [M+H]$^+$

Example 446

(R)-2-amino-5-(1-methyl-1H-pyrazol-4-yl)-N-(1-(3-(4-((4-methylpiperazin-1-yl)methyl)phenoxy)benzoyl)pyrrolidin-3-yl)nicotinamide Using 3-(4-((4-methylpiperazin-1-yl)methyl)phenoxy)benzoic acid, the title compound was obtained as described for the Example 342. MS (ESI, m/z): 595.31 [M+H]$^+$

Example 447

2-amino-N—((R)-1-(3-(4-(((R)-2-(hydroxymethyl)pyrrolidin-1-yl)methyl)phenoxy)benzoyl)pyrrolidin-3-yl)-5-(1-methyl-1H-pyrazol-4-yl)nicotinamide Using (R)-3-(4-((2-(hydroxymethyl)pyrrolidin-1-yl)methyl)phenoxy)benzoic acid, the title compound was obtained as described for the Example 342. MS (ESI, m/z): 596.29 [M+H]$^+$

Example 448

(R)-2-amino-5-(1-methyl-1H-pyrazol-4-yl)-N-(1-(4-(4-((4-methylpiperazin-1-yl)methyl)phenoxy)benzoyl)pyrrolidin-3-yl)nicotinamide Using 4-(4-((4-methylpiperazin-1-yl)methyl)phenoxy)benzoic acid, the title compound was obtained as described for the Example 342. MS (ESI, m/z): 595.31 [M+H]$^+$

Example 449

2-amino-N—((R)-1-(4-(4-(((R)-2-(hydroxymethyl)pyrrolidin-1-yl)methyl)phenoxy)benzoyl)pyrrolidin-3-yl)-5-(1-methyl-1H-pyrazol-4-yl)nicotinamide Using (R)-4-(4-((2-(hydroxymethyl)pyrrolidin-1-yl)methyl)phenoxy)benzoic acid, the title compound was obtained as described for the Example 342. MS (ESI, m/z): 596.29 [M+H]$^+$

Example 450

(R)—N-(1-([1,1'-biphenyl]-3-carbonyl)pyrrolidin-3-yl)-2-amino-5-(1-methyl-1H-pyrazol-4-yl)nicotinamide Using [1,1'-biphenyl]-3-carboxylic acid, the title compound was obtained as described for the Example 342. MS (ESI, m/z): 467.21 [M+H]$^+$

Example 451

(R)-2-amino-5-(1-methyl-1H-pyrazol-4-yl)-N-(1-(3-(1-(piperidin-4-yl)-1H-pyrazol-4-yl)benzoyl)pyrrolidin-3-yl)nicotinamide Using 3-(1-(1-(tert-butoxycarbonyl)piperidin-4-yl)-1H-pyrazol-4-yl)benzoic acid, the title compound was obtained as described for the Example 342. MS (ESI, m/z): 540.28 [M+H]$^+$

Example 452

(R)-2-amino-5-(1-methyl-1H-pyrazol-4-yl)-N-(1-(3'-(2-(4-methylpiperazin-1-yl)-2-oxoethyl)-[1,1'-biphenyl]-3-carbonyl)pyrrolidin-3-yl)nicotinamide Using 3'-(2-(4-methylpiperazin-1-yl)-2-oxoethyl)-[1,1'-biphenyl]-3-carboxylic acid, the title compound was obtained as described for the Example 342. MS (ESI, m/z): 607.31 [M+H]$^+$

Example 453

(R)-2-amino-5-(1-methyl-1H-pyrazol-4-yl)-N-(1-(3'-(2-(4-methylpiperazin-1-yl)ethyl)-[1,1'-biphenyl]-3-carbonyl)pyrrolidin-3-yl)nicotinamide Using 3'-(2-(4-methylpiperazin-1-yl)ethyl)-[1,1'-biphenyl]-3-carboxylic acid, the title compound was obtained as described for the Example 342. MS (ESI, m/z): 593.33 [M+H]$^+$

Example 454

(R)-2-amino-5-(1-methyl-1H-pyrazol-4-yl)-N-(1-(4'-(2-(4-methylpiperazin-1-yl)-2-oxoethyl)-[1,1'-biphenyl]-3-carbonyl)pyrrolidin-3-yl)nicotinamide Using 4'-(2-(4-methylpiperazin-1-yl)-2-oxoethyl)-[1,1'-biphenyl]-3-carboxylic acid, the title compound was obtained as described for the Example 342. MS (ESI, m/z): 607.31 [M+H]$^+$

Example 455

(R)-2-amino-5-(1-methyl-1H-pyrazol-4-yl)-N-(1-(4'-(2-(4-methylpiperazin-1-yl)ethyl)-[1,1'-biphenyl]-3-carbonyl)pyrrolidin-3-yl)nicotinamide Using 4'-(2-(4-methylpiperazin-1-yl)ethyl)-[1,1'-biphenyl]-3-carboxylic acid, the title compound was obtained as described for the Example 342. MS (ESI, m/z): 593.33 [M+H]$^+$

Example 456

(R)-3'-(3-(2-amino-5-(1-methyl-1H-pyrazol-4-yl)nicotinamido)pyrrolidine-1-carbonyl)-[1,1'-biphenyl]-3-carboxylic acid Using [1,1'-biphenyl]-3,3'-dicarboxylic acid, the title compound was obtained as described for the Example 342. MS (ESI, m/z): 511.20 [M+H]$^+$

Example 457

(R)-2-amino-N-(1-(3'-amino-[1,1'-biphenyl]-3-carbonyl)pyrrolidin-3-yl)-5-(1-methyl-1H-pyrazol-4-yl)nicotinamide Using 3'-amino-[1,1'-biphenyl]-3-carboxylic acid, the title compound was obtained as described for the Example 342. MS (ESI, m/z): 482.22 [M+H]$^+$

Example 458

(R)-2-amino-5-(1-methyl-1H-pyrazol-4-yl)-N-(1-(2-phenyl-5-(trifluoromethyl)oxazole-4-carbonyl)pyrrolidin-3-yl)nicotinamide Using 2-phenyl-5-(trifluoromethyl)oxazole-4-carboxylic acid, the title compound was obtained as described for the Example 342. MS (ESI, m/z): 526.17 [M+H]$^+$

Example 459

(R)—N-(1-(3'-((1H-pyrazol-1-yl)methyl)-[1,1'-biphenyl]-3-carbonyl)pyrrolidin-3-yl)-2-amino-5-(1-methyl-1H-pyrazol-4-yl)nicotinamide Using 3'-((1H-pyrazol-1-yl)methyl)-[1,1'-biphenyl]-3-carboxylic acid, the title compound was obtained as described for the Example 342. MS (ESI, m/z): 547.25 [M+H]$^+$

Example 460

(R)—N-(1-(3'-((1H-imidazol-1-yl)methyl)-[1,1'-biphenyl]-3-carbonyl)pyrrolidin-3-yl)-2-amino-5-(1-methyl-1H-pyrazol-4-yl)nicotinamide Using 3'-((1H-imidazol-1-yl)methyl)-[1,1'-biphenyl]-3-carboxylic acid, the title compound was obtained as described for the Example 342. MS (ESI, m/z): 547.25 [M+H]$^+$

Example 461

(R)-2-amino-5-(1-methyl-1H-pyrazol-4-yl)-N-(1-(3'-(morpholinomethyl)-[1,1'-biphenyl]-3-carbonyl)pyrrolidin-3-yl)nicotinamide Using 3'-(morpholinomethyl)-[1,1'-biphenyl]-3-carboxylic acid, the title compound was obtained as described for the Example 342. MS (ESI, m/z): 566.28 [M+H]$^+$

Example 462

2-amino-N—((R)-1-(3'-(((R)-2-(hydroxymethyl)pyrrolidin-1-yl)methyl)-[1,1'-biphenyl]-3-carbonyl)pyrrolidin-3-yl)-5-(1-methyl-1H-pyrazol-4-yl)nicotinamide Using (R)-3'-((2-(hydroxymethyl)pyrrolidin-1-yl)methyl)-[1,1'-biphenyl]-3-carboxylic acid, the title compound was obtained as described for the Example 342. MS (ESI, m/z): 580.30 [M+H]$^+$

Example 463

(R)-2-amino-5-(1-methyl-1H-pyrazol-4-yl)-N-(1-(3'-(thiomorpholine-4-carbonyl)-[1,1'-biphenyl]-3-carbonyl)pyrrolidin-3-yl)nicotinamide Using 3'-(thiomorpholine-4-carbonyl)-[1,1'-biphenyl]-3-carboxylic acid, the title compound was obtained as described for the Example 342. MS (ESI, m/z): 596.24 [M+H]$^+$

Example 464

(R)-2-amino-5-(1-methyl-1H-pyrazol-4-yl)-N-(1-(3'-(piperazine-1-carbonyl)-[1,1'-biphenyl]-3-carbonyl)pyrrolidin-3-yl)nicotinamide Using 3'-(4-(tert-butoxycarbonyl)piperazine-1-carbonyl)-[1,1'-biphenyl]-3-carboxylic acid, the title compound was obtained as described for the Example 342. MS (ESI, m/z): 579.28 [M+H]$^+$

Example 465

(R)-2-amino-5-(1-methyl-1H-pyrazol-4-yl)-N-(1-(4'-(piperazine-1-carbonyl)-[1,1'-biphenyl]-3-carbonyl)pyrrolidin-3-yl)nicotinamide Using 4'-(4-(tert-butoxycarbonyl)piperazine-1-carbonyl)-[1,1'-biphenyl]-3-carboxylic acid, the title compound was obtained as described for the Example 342. MS (ESI, m/z): 579.28 [M+H]$^+$

Example 466

(R)-2-amino-5-(1-methyl-1H-pyrazol-4-yl)-N-(1-(3'-(piperazine-1-carbonyl)-[1,1'-biphenyl]-4-carbonyl)pyrrolidin-3-yl)nicotinamide Using 3'-(4-(tert-butoxycarbonyl)piperazine-1-carbonyl)-[1,1'-biphenyl]-4-carboxylic acid, the title compound was obtained as described for the Example 342. MS (ESI, m/z): 579.28 [M+H]$^+$

Example 467

(R)-2-amino-5-(1-methyl-1H-pyrazol-4-yl)-N-(1-(4'-(piperazine-1-carbonyl)-[1,1'-biphenyl]-4-carbonyl)pyrrolidin-3-yl)nicotinamide Using 4'-(4-(tert-butoxycarbonyl)piperazine-1-carbonyl)-[1,1'-biphenyl]-4-carboxylic acid, the title compound was obtained as described for the Example 342. MS (ESI, m/z): 579.28 [M+H]$^+$

Example 468

(R)-2-amino-N-(1-(3-(furan-3-yl)benzoyl)pyrrolidin-3-yl)-5-(1-methyl-1H-pyrazol-4-yl)nicotinamide Using 3-(furan-3-yl)benzoic acid, the title compound was obtained as described for the Example 342. MS (ESI, m/z): 457.19 [M+H]$^+$

Example 469

(R)-2-amino-N-(1-(3-(1,3-dimethyl-1H-pyrazol-4-yl)benzoyl)pyrrolidin-3-yl)-5-(1-methyl-H-pyrazol-4-yl)nicotinamide Using 3-(1,3-dimethyl-1H-pyrazol-4-yl)benzoic acid, the title compound was obtained as described for the Example 342. MS (ESI, m/z): 485.23 [M+H]$^+$

Example 470

(R)-2-amino-N-(1-(3-(1-cyclopentyl-1H-pyrazol-4-yl)benzoyl)pyrrolidin-3-yl)-5-(1-methyl-1H-pyrazol-4-yl)nicotinamide Using 3-(1-cyclopentyl-1H-pyrazol-4-yl)benzoic acid, the title compound was obtained as described for the Example 342. MS (ESI, m/z): 525.26 [M+H]$^+$

Example 471

(R)-2-amino-5-(1-methyl-1H-pyrazol-4-yl)-N-(1-(3-(1-(phenylsulfonyl)-1H-pyrazol-4-yl)benzoyl)pyrrolidin-3-yl)nicotinamide Using 3-(1-(phenylsulfonyl)-1H-pyrazol-4-yl)benzoic acid, the title compound was obtained as described for the Example 342. MS (ESI, m/z): 597.20 [M+H]$^+$

Example 472

(R)-2-amino-5-(1-methyl-1H-pyrazol-4-yl)-N-(1-(3-(pyridin-3-yl)benzoyl)pyrrolidin-3-yl)nicotinamide Using 3-(pyridin-3-yl)benzoic acid, the title compound was obtained as described for the Example 342. MS (ESI, m/z): 468.21 [M+H]$^+$

Example 473

(R)-2-amino-5-(1-methyl-1H-pyrazol-4-yl)-N-(1-(3-(pyridin-4-yl)benzoyl)pyrrolidin-3-yl)nicotinamide Using 3-(pyridin-4-yl)benzoic acid, the title compound was obtained as described for the Example 342. MS (ESI, m/z): 468.21 [M+H]$^+$

Example 474

(R)-2-amino-N-(1-(3-(benzo[b]thiophen-2-yl)benzoyl)pyrrolidin-3-yl)-5-(1-methyl-1H-pyrazol-4-yl)nicotinamide Using 3-(benzo[b]thiophen-2-yl)benzoic acid, the title compound was obtained as described for the Example 342. MS (ESI, m/z): 523.18 [M+H]$^+$

Example 475

(R)-2-amino-5-(1-methyl-1H-pyrazol-4-yl)-N-(1-(2',3',4',5'-tetrahydro-[1,1'-biphenyl]-3-carbonyl)pyrrolidin-3-yl)nicotinamide Using 2',3',4',5'-tetrahydro-[1,1'-biphenyl]-3-carboxylic acid, the title compound was obtained as described for the Example 342. MS (ESI, m/z): 471.24 [M+H]$^+$

Example 476

(R)-2-amino-5-(1-methyl-1H-pyrazol-4-yl)-N-(1-(3'-(4-methylpiperazin-1-yl)-[1,1'-biphenyl]-3-carbonyl)pyrrolidin-3-yl)nicotinamide Using 3'-(4-methylpiperazin-1-yl)-[1,1'-biphenyl]-3-carboxylic acid, the title compound was obtained as described for the Example 342. MS (ESI, m/z): 565.30 [M+H]$^+$

Example 477

(R)-2-amino-5-(1-methyl-1H-pyrazol-4-yl)-N-(1-(3'-(piperidin-1-yl)-[1,1'-biphenyl]-3-carbonyl)pyrrolidin-3-yl)nicotinamide Using 3'-(piperidin-1-yl)-[1,1'-biphenyl]-3-carboxylic acid, the title compound was obtained as described for the Example 342. MS (ESI, m/z): 550.29 [M+H]$^+$

Example 478

(R)-2-amino-N-(1-(2'-chloro-[1,1'-biphenyl]-3-carbonyl)pyrrolidin-3-yl)-5-(1-methyl-1H-pyrazol-4-yl)nicotinamide Using 2'-chloro-[1,1'-biphenyl]-3-carboxylic acid, the title compound was obtained as described for the Example 342. MS (ESI, m/z): 501.17 [M+H]$^+$

Example 479

(R)-2-amino-N-(1-(3'-chloro-[1,1'-biphenyl]-3-carbonyl)pyrrolidin-3-yl)-5-(1-methyl-1H-pyrazol-4-yl)nicotinamide Using 3'-chloro-[1,1'-biphenyl]-3-carboxylic acid, the title compound was obtained as described for the Example 342. MS (ESI, m/z): 501.17 [M+H]$^+$

Example 480

(R)-2-amino-5-(1-methyl-1H-pyrazol-4-yl)-N-(1-(3-(2-(piperazin-1-yl)pyridin-4-yl)benzoyl)pyrrolidin-3-yl)nicotinamide Using 3-(2-(4-(tert-butoxycarbonyl)piperazin-1-yl)pyridin-4-yl)benzoic acid, the title compound was obtained as described for the Example 342. MS (ESI, m/z): 552.28 [M+H]$^+$

Example 481

(R)-2-amino-5-(1-methyl-1H-pyrazol-4-yl)-N-(1-(3'-(methylsulfonamido)-[1,1'-biphenyl]-3-carbonyl)pyrrolidin-3-yl)nicotinamide Using 3'-(methylsulfonamido)-[1,1'-biphenyl]-3-carboxylic acid, the title compound was obtained as described for the Example 342. MS (ESI, m/z): 560.20 [M+H]$^+$

Example 482

(R)-2-amino-5-(1-methyl-1H-pyrazol-4-yl)-N-(1-(6-methyl-[1,1'-biphenyl]-3-carbonyl)pyrrolidin-3-yl)nicotinamide Using 6-methyl-[1,1'-biphenyl]-3-carboxylic acid, the title compound was obtained as described for the Example 342. MS (ESI, m/z): 481.23 [M+H]$^+$

Example 483

(R)-2-amino-N-(1-(2'-chloro-6-methyl-[1,1'-biphenyl]-3-carbonyl)pyrrolidin-3-yl)-5-(1-methyl-1H-pyrazol-4-yl)nicotinamide Using 2'-chloro-6-methyl-[1,1'-biphenyl]-3-carboxylic acid, the title compound was obtained as described for the Example 342. MS (ESI, m/z): 515.19 [M+H]$^+$

Example 484

(R)-2-amino-N-(1-(3'-chloro-6-methyl-[1,1'-biphenyl]-3-carbonyl)pyrrolidin-3-yl)-5-(1-methyl-1H-pyrazol-4-yl)nicotinamide Using 3'-chloro-6-methyl-[1,1'-biphenyl]-3-carboxylic acid, the title compound was obtained as described for the Example 342. MS (ESI, m/z): 515.19 [M+H]$^+$

Example 485

(R)-2-amino-N-(1-(2-amino-5-methyl-[1,1'-biphenyl]-3-carbonyl)pyrrolidin-3-yl)-5-(1-methyl-1H-pyrazol-4-yl)nicotinamide Using 2-amino-5-methyl-[1,1'-biphenyl]-3-carboxylic acid, the title compound was obtained as described for the Example 342. MS (ESI, m/z): 496.24 [M+H]$^+$

Example 486

(R)-2-amino-N-(1-(4-amino-[1,1'-biphenyl]-3-carbonyl)pyrrolidin-3-yl)-5-(1-methyl-1H-pyrazol-4-yl)nicotinamide Using 4-amino-[1,1'-biphenyl]-3-carboxylic acid, the title compound was obtained as described for the Example 342. MS (ESI, m/z): 482.22 [M+H]$^+$

Example 487

(R)-2-amino-N-(1-(4-(furan-3-yl)benzoyl)pyrrolidin-3-yl)-5-(1-methyl-1H-pyrazol-4-yl)nicotinamide Using 4-(furan-3-yl)benzoic acid, the title compound was obtained as described for the Example 342. MS (ESI, m/z): 457.19 [M+H]$^+$

Example 488

(R)-2-amino-N-(1-(4-(1,3-dimethyl-1H-pyrazol-4-yl)benzoyl)pyrrolidin-3-yl)-5-(1-methyl-1H-pyrazol-4-yl)nicotinamide Using 4-(1,3-dimethyl-1H-pyrazol-4-yl)benzoic acid, the title compound was obtained as described for the Example 342. MS (ESI, m/z): 485.23 [M+H]$^+$

Example 489

(R)-2-amino-5-(1-methyl-1H-pyrazol-4-yl)-N-(1-(4-(pyridin-4-yl)benzoyl)pyrrolidin-3-yl)nicotinamide Using 4-(pyridin-4-yl)benzoic acid, the title compound was obtained as described for the Example 342. MS (ESI, m/z): 468.21 [M+H]$^+$

Example 490

(R)-2-amino-N-(1-(4-(benzo[b]thiophen-2-yl)benzoyl)pyrrolidin-3-yl)-5-(1-methyl-1H-pyrazol-4-yl)nicotinamide Using 4-(benzo[b]thiophen-2-yl)benzoic acid, the title compound was obtained as described for the Example 342. MS (ESI, m/z): 523.18 [M+H]$^+$

Example 491

(R)-2-amino-5-(1-methyl-1H-pyrazol-4-yl)-N-(1-(4-(2-(piperazin-1-yl)pyridin-4-yl)benzoyl)pyrrolidin-3-yl)nicotinamide Using 4-(2-(4-(tert-butoxycarbonyl)piperazin-1-yl)pyridin-4-yl)benzoic acid, the title compound was obtained as described for the Example 342. MS (ESI, m/z): 552.28 [M+H]$^+$

Example 492

(R)-2-amino-5-(1-methyl-1H-pyrazol-4-yl)-N-(1-(4'-morpholino-[1,1'-biphenyl]-4-carbonyl)pyrrolidin-3-yl)nicotinamide Using 4'-morpholino-[1,1'-biphenyl]-4-carboxylic acid, the title compound was obtained as described for the Example 342. MS (ESI, m/z): 552.26 [M+H]$^+$

Example 493

(R)-2-amino-5-(1-methyl-1H-pyrazol-4-yl)-N-(1-(4'-(morpholine-4-carbonyl)-[1,1'-biphenyl]-4-carbonyl)pyrrolidin-3-yl)nicotinamide Using 4'-(morpholine-4-carbonyl)-[1,1'-biphenyl]-4-carboxylic acid, the title compound was obtained as described for the Example 342. MS (ESI, m/z): 580.26 [M+H]$^+$

Example 494

(R)-2-amino-5-(1-methyl-1H-pyrazol-4-yl)-N-(1-(2',3',4',5'-tetrahydro-[1,1'-biphenyl]-4-carbonyl)pyrrolidin-3-yl)nicotinamide Using 2',3',4',5'-tetrahydro-[1,1'-biphenyl]-4-carboxylic acid, the title compound was obtained as described for the Example 342. MS (ESI, m/z): 471.24 [M+H]$^+$

Example 495

(R)-2-amino-N-(1-(3-(2,3-dioxoindolin-6-yl)benzoyl)pyrrolidin-3-yl)-5-(1-methyl-1H-pyrazol-4-yl)nicotinamide Using 3-(2,3-dioxoindolin-6-yl)benzoic acid, the title compound was obtained as described for the Example 342. MS (ESI, m/z): 536.20 [M+H]$^+$

Example 496

(R)-2-amino-N-(1-(2,3-dihydro-1H-indene-2-carbonyl)pyrrolidin-3-yl)-5-(1-methyl-1H-pyrazol-4-yl)nicotinamide Using 2,3-dihydro-1H-indene-2-carboxylic acid, the title compound was obtained as described for the Example 342. MS (ESI, m/z): 431.21 [M+H]$^+$

Example 497

(R)-2-amino-N-(1-(3-methyl-1H-indene-2-carbonyl)pyrrolidin-3-yl)-5-(1-methyl-1H-pyrazol-4-yl)nicotinamide Using 3-methyl-1H-indene-2-carboxylic acid, the title compound was obtained as described for the Example 342. MS (ESI, m/z): 443.21 [M+H]$^+$

Example 498

(R)-2-amino-N-(1-(5-chlorobenzo[d]oxazole-2-carbonyl)pyrrolidin-3-yl)-5-(1-methyl-1H-pyrazol-4-yl)nicotinamide Using 5-chlorobenzo[d]oxazole-2-carboxylic acid, the title compound was obtained as described for the Example 342. MS (ESI, m/z): 466.13 [M+H]$^+$

Example 499

(R)-2-amino-N-(1-(1-methyl-1H-indazole-3-carbonyl)pyrrolidin-3-yl)-5-(1-methyl-1H-pyrazol-4-yl)nicotinamide Using 1-methyl-1H-indazole-3-carboxylic acid, the title compound was obtained as described for the Example 342. MS (ESI, m/z): 445.20 [M+H]$^+$

Example 500

(R)-2-amino-5-(1-methyl-1H-pyrazol-4-yl)-N-(1-(5-methyl-3-phenylisoxazole-4-carbonyl)pyrrolidin-3-yl)nicotinamide Using 5-hydroxy-3-phenylisoxazole-4-carboxylic acid, the title compound was obtained as described for the Example 342. MS (ESI, m/z): 472.20 [M+H]$^+$

Example 501

(R)-2-amino-N-(1-(dibenzo[b,d]furan-4-carbonyl)pyrrolidin-3-yl)-5-(1-methyl-1H-pyrazol-4-yl)nicotinamide Using dibenzo[b,d]furan-4-carboxylic acid, the title compound was obtained as described for the Example 342. MS (ESI, m/z): 481.19 [M+H]$^+$

Example 502

(R)—N-(1-(1H-indole-5-carbonyl)pyrrolidin-3-yl)-2-amino-5-(1-methyl-1H-pyrazol-4-yl)nicotinamide Using 1-(tert-butoxycarbonyl)-1H-indole-5-carboxylic acid, the title compound was obtained as described for the Example 342. MS (ESI, m/z): 430.19 [M+H]$^+$

Example 503

(R)-2-amino-5-(1-methyl-1H-pyrazol-4-yl)-N-(1-(1,2,3,4-tetrahydrocyclopenta[b]indole-7-carbonyl)pyrrolidin-3-yl)nicotinamide Using 4-(tert-butoxycarbonyl)-1,2,3,4-tetrahydrocyclopenta[b]indole-7-carboxylic acid, the title compound was obtained as described for the Example 342. MS (ESI, m/z): 470.22 [M+H]$^+$

Example 504

(R)—N-(1-(1H-indole-4-carbonyl)pyrrolidin-3-yl)-2-amino-5-(1-methyl-1H-pyrazol-4-yl)nicotinamide Using 1-(tert-butoxycarbonyl)-1H-indole-4-carboxylic acid, the title compound was obtained as described for the Example 342. MS (ESI, m/z): 430.19 [M+H]$^+$

Example 505

(R)-2-amino-N-(1-(4'-(4-aminophenoxy)-[1,1'-biphenyl]-4-carbonyl)pyrrolidin-3-yl)-5-(1-methyl-1H-pyrazol-4-yl)nicotinamide Using 4'-(4-aminophenoxy)-[1,1'-biphenyl]-4-carboxylic acid, the title compound was obtained as described for the Example 342. MS (ESI, m/z): 574.25 [M+H]$^+$

Example 506

(R)-2-amino-5-(1-methyl-1H-pyrazol-4-yl)-N-(1-(4-(1-methyl-1H-pyrazol-4-yl)benzoyl)pyrrolidin-3-yl)nicotinamide Using 4-(1-methyl-1H-pyrazol-4-yl)benzoic acid, the title compound was obtained as described for the Example 342. MS (ESI, m/z): 471.22 [M+H]$^+$

Example 507

(R)-2-amino-5-(1-methyl-1H-pyrazol-4-yl)-N-(1-(4-(1,3,5-trimethyl-1H-pyrazol-4-yl)benzoyl)pyrrolidin-3-yl)nicotinamide Using 4-(1,3,5-trimethyl-1H-pyrazol-4-yl)benzoic acid, the title compound was obtained as described for the Example 342. MS (ESI, m/z): 499.25 [M+H]$^+$

Example 508

(R)-2-amino-N-(1-(4-(1-cyclopentyl-1H-pyrazol-4-yl)benzoyl)pyrrolidin-3-yl)-5-(1-methyl-1H-pyrazol-4-yl)nicotinamide Using 4-(1-cyclopentyl-1H-pyrazol-4-yl)benzoic acid, the title compound was obtained as described for the Example 342. MS (ESI, m/z): 525.26 [M+H]$^+$

Example 509

(R)-2-amino-5-(1-methyl-1H-pyrazol-4-yl)-N-(1-(4-(1-(tetrahydro-2H-pyran-4-yl)-1H-pyrazol-4-yl)benzoyl)pyrrolidin-3-yl)nicotinamide Using 4-(1-(tetrahydro-2H-pyran-4-yl)-1H-pyrazol-4-yl)benzoic acid, the title compound was obtained as described for the Example 342. MS (ESI, m/z): 541.26 [M+H]$^+$

Example 510

(R)-2-amino-5-(1-methyl-1H-pyrazol-4-yl)-N-(1-(4-(1-(piperidin-4-yl)-1H-pyrazol-4-yl)benzoyl)pyrrolidin-3-yl)nicotinamide Using 4-(1-(1-(tert-butoxycarbonyl)piperidin-4-yl)-1H-pyrazol-4-yl)benzoic acid, the title compound was obtained as described for the Example 342. MS (ESI, m/z): 540.28 [M+H]$^+$

Example 511 tert-butyl (R)-4-(4-(4-(3-(2-amino-5-(1-methyl-1H-pyrazol-4-yl)nicotinamido)pyrrolidine-1-carbonyl)phenyl)-1H-pyrazol-1-yl)piperidine-1-carboxylate Using 4-(1-(1-(tert-butoxycarbonyl)piperidin-4-yl)-1H-pyrazol-4-yl)benzoic acid, the title compound was obtained as described for the Example 342. MS (ESI, m/z): 640.33 [M+H]$^+$

Example 512

(R)-2-amino-5-(1-methyl-1H-pyrazol-4-yl)-N-(1-(5-phenylbenzofuran-2-carbonyl)pyrrolidin-3-yl)nicotinamide Using 5-phenylbenzofuran-2-carboxylic acid, the title compound was obtained as described for the Example 342. MS (ESI, m/z): 507.21 [M+H]$^+$

Example 513

(R)—N-(1-(1-acetyl-1H-indole-5-carbonyl)pyrrolidin-3-yl)-2-amino-5-(1-methyl-1H-pyrazol-4-yl)nicotinamide Using 1-acetyl-1H-indole-5-carboxylic acid, the title compound was obtained as described for the Example 342. MS (ESI, m/z): 472.20 [M+H]$^+$

Example 514

(R)—N-(1-(1-acetyl-1H-indole-4-carbonyl)pyrrolidin-3-yl)-2-amino-5-(1-methyl-1H-pyrazol-4-yl)nicotinamide Using 1-acetyl-1H-indole-4-carboxylic acid, the title compound was obtained as described for the Example 342. MS (ESI, m/z): 472.20 [M+H]$^+$

Example 515

(R)-2-amino-N-(1-(3-hydroxybenzoyl)pyrrolidin-3-yl)-5-(1-methyl-1H-pyrazol-4-yl)nicotinamide Using 3-hydroxybenzoic acid, the title compound was obtained as described for the Example 342. MS (ESI, m/z): 407.18 [M+H]$^+$

Example 516

(R)-2-amino-5-(1-methyl-1H-pyrazol-4-yl)-N-(1-(1-phenyl-3-(trifluoromethyl)-1H-pyrazole-4-carbonyl)pyrrolidin-3-yl)nicotinamide Using 1-phenyl-3-(trifluoromethyl)-1H-pyrazole-4-carboxylic acid, the title compound was obtained as described for the Example 342. MS (ESI, m/z): 525.19 [M+H]$^+$

Example 517

(R)-2-amino-N-(1-(4-(1,5-dimethyl-1H-pyrazol-4-yl)benzoyl)pyrrolidin-3-yl)-5-(1-methyl-1H-pyrazol-4-yl)nicotinamide Using 4-(1,5-dimethyl-1H-pyrazol-4-yl)benzoic acid, the title compound was obtained as described for the Example 342. MS (ESI, m/z): 485.23 [M+H]$^+$

Example 518

(R)-2-amino-N-(1-(4-(3,5-dimethyl-1H-pyrazol-4-yl)benzoyl)pyrrolidin-3-yl)-5-(1-methyl-1H-pyrazol-4-yl)nicotinamide Using 4-(3,5-dimethyl-1H-pyrazol-4-yl)benzoic acid, the title compound was obtained as described for the Example 342. MS (ESI, m/z): 485.23 [M+H]$^+$

Example 519

(R)-2-amino-N-(1-(4-(3,5-dimethyl-1-phenyl-1H-pyrazol-4-yl)benzoyl)pyrrolidin-3-yl)-5-(1-methyl-1H-pyrazol-4-yl)nicotinamide Using 4-(3,5-dimethyl-1-phenyl-1H-pyrazol-4-yl)benzoic acid, the title compound was obtained as described for the Example 342. MS (ESI, m/z): 561.26 [M+H]$^+$

Example 520

(R)-2-amino-N-(1-(4-(1-(4-aminophenyl)-3,5-dimethyl-1H-pyrazol-4-yl)benzoyl)pyrrolidin-3-yl)-5-(1-methyl-1H-pyrazol-4-yl)nicotinamide Using 4-(1-(4-aminophenyl)-3,5-dimethyl-1H-pyrazol-4-yl)benzoic acid, the title compound was obtained as described for the Example 342. MS (ESI, m/z): 576.28 [M+H]$^+$

Example 521

(R)-2-amino-N-(1-(4-(1,3-dimethyl-5-(trifluoromethyl)-1H-pyrazol-4-yl)benzoyl)pyrrolidin-3-yl)-5-(1-methyl-1H-pyrazol-4-yl)nicotinamide Using 4-(1,3-dimethyl-5-(trifluoromethyl)-1H-pyrazol-4-yl)benzoic acid, the title compound was obtained as described for the Example 342. MS (ESI, m/z): 553.22 [M+H]$^+$

Example 522

(R)-2-amino-N-(1-(4-(4-bromo-3,5-dimethylthiophen-2-yl)benzoyl)pyrrolidin-3-yl)-5-(1-methyl-1H-pyrazol-4-yl)nicotinamide Using 4-(4-bromo-3,5-dimethylthiophen-2-yl)benzoic acid, the title compound was obtained as described for the Example 342. MS (ESI, m/z): 579.11 [M+H]$^+$

Example 523

(R)-2-amino-5-(1-methyl-1H-pyrazol-4-yl)-N-(1-(4-(4-methylthiophen-3-yl)benzoyl)pyrrolidin-3-yl)nicotinamide Using 4-(4-methylthiophen-3-yl)benzoic acid, the title compound was obtained as described for the Example 342. MS (ESI, m/z): 487.18 [M+H]$^+$

Example 524

(R)-2-amino-N-(1-(4-(3-methoxythiophen-2-yl)benzoyl)pyrrolidin-3-yl)-5-(1-methyl-1H-pyrazol-4-yl)nicotinamide Using 4-(3-methoxythiophen-2-yl)benzoic acid, the title compound was obtained as described for the Example 342. MS (ESI, m/z): 503.18 [M+H]$^+$

Example 525

(R)-2-amino-5-(1-methyl-1H-pyrazol-4-yl)-N-(1-(4-(4-methylthiophen-2-yl)benzoyl)pyrrolidin-3-yl)nicotinamide Using 4-(4-methylthiophen-2-yl)benzoic acid, the title compound was obtained as described for the Example 342. MS (ESI, m/z): 487.18 [M+H]$^+$

Example 526

(R)-2-amino-5-(1-methyl-1H-pyrazol-4-yl)-N-(1-(4-(5-methylthiophen-2-yl)benzoyl)pyrrolidin-3-yl)nicotinamide Using 4-(5-methylthiophen-2-yl)benzoic acid, the title compound was obtained as described for the Example 342. MS (ESI, m/z): 487.18 [M+H]$^+$

Example 527

(R)-2-amino-5-(1-methyl-1H-pyrazol-4-yl)-N-(1-(4'-phenoxy-[1,1'-biphenyl]-4-carbonyl)pyrrolidin-3-yl)nicotinamide Using 4'-phenoxy-[1,1'-biphenyl]-4-carboxylic acid, the title compound was obtained as described for the Example 342. MS (ESI, m/z): 559.24 [M+H]$^+$

Example 528

(R)-2-amino-N-(1-(4'-(4-methoxyphenoxy)-[1,1'-biphenyl]-4-carbonyl)pyrrolidin-3-yl)-5-(1-methyl-1H-pyrazol-4-yl)nicotinamide Using 4'-(4-methoxyphenoxy)-[1,1'-biphenyl]-4-carboxylic acid, the title compound was obtained as described for the Example 342. MS (ESI, m/z): 589.25 [M+H]$^+$

Example 529

(R)-2-amino-N-(1-(4'-(4-(dimethylamino)phenoxy)-[1,1'-biphenyl]-4-carbonyl)pyrrolidin-3-yl)-5-(1-methyl-1H-pyrazol-4-yl)nicotinamide Using 4'-(4-(dimethylamino)phenoxy)-[1,1'-biphenyl]-4-carboxylic acid, the title compound was obtained as described for the Example 342. MS (ESI, m/z): 602.28 [M+H]$^+$

Example 530

(R)-2-amino-N-(1-(4'-(3-aminophenoxy)-[1,1'-biphenyl]-4-carbonyl)pyrrolidin-3-yl)-5-(1-methyl-1H-pyrazol-4-yl)nicotinamide Using 4'-(3-aminophenoxy)-[1,1'-biphenyl]-4-carboxylic acid, the title compound was obtained as described for the Example 342. MS (ESI, m/z): 574.25 [M+H]$^+$

Example 531

(R)-2-amino-5-(1-methyl-1H-pyrazol-4-yl)-N-(1-(4'-(piperidin-4-yloxy)-[1,1'-biphenyl]-4-carbonyl)pyrrolidin-3-yl)nicotinamide Using 4'-((1-(tert-butoxycarbonyl)piperidin-4-yl)oxy)-[1,1'-biphenyl]-4-carboxylic acid, the title compound was obtained as described for the Example 342. MS (ESI, m/z): 566.28 [M+H]$^+$

Example 532

2-amino-5-(1-methyl-1H-pyrazol-4-yl)-N-((3R)-1-(4'-(pyrrolidin-3-yloxy)-[1,1'-biphenyl]-4-carbonyl)pyrrolidin-3-yl)nicotinamide Using 4'-((1-(tert-butoxycarbonyl)pyrrolidin-3-yl)oxy)-[1,1'-biphenyl]-4-carboxylic acid, the title compound was obtained as described for the Example 342. MS (ESI, m/z): 552.26 [M+H]$^+$

Example 533

(R)-2-amino-N-(1-(4'-(4-aminophenoxy)-2'-fluoro-[1,1'-biphenyl]-4-carbonyl)pyrrolidin-3-yl)-5-(1-methyl-1H-pyrazol-4-yl)nicotinamide Using 4'-(4-aminophenoxy)-2'-fluoro-[1,1'-biphenyl]-4-carboxylic acid, the title compound was obtained as described for the Example 342. MS (ESI, m/z): 592.24 [M+H]$^+$

Example 534

(R)-2-amino-N-(1-(4-(5-chlorothiophen-2-yl)benzoyl)pyrrolidin-3-yl)-5-(1-methyl-1H-pyrazol-4-yl)nicotinamide Using 4-(5-chlorothiophen-2-yl)benzoic acid, the title compound was obtained as described for the Example 342. MS (ESI, m/z): 507.13 [M+H]$^+$

Example 535

(R)-2-amino-N-(1-(3-hydroxy-4-(5-methylthiophen-2-yl)benzoyl)pyrrolidin-3-yl)-5-(1-methyl-1H-pyrazol-4-yl)nicotinamide Using 3-hydroxy-4-(5-methylthiophen-2-yl)benzoic acid, the title compound was obtained as described for the Example 342. MS (ESI, m/z): 503.18 [M+H]$^+$

Example 536

(R)-2-amino-5-(1-methyl-1H-pyrazol-4-yl)-N-(1-(3-methyl-4-(5-methylthiophen-2-yl)benzoyl)pyrrolidin-3-yl)nicotinamide Using 3-methyl-4-(5-methylthiophen-2-yl)benzoic acid, the title compound was obtained as described for the Example 342. MS (ESI, m/z): 501.20 [M+H]$^+$

Example 537

(R)-2-amino-N-(1-(4-(5-cyanothiophen-2-yl)benzoyl)pyrrolidin-3-yl)-5-(1-methyl-1H-pyrazol-4-yl)nicotinamide Using 4-(5-cyanothiophen-2-yl)benzoic acid, the title compound was obtained as described for the Example 342. MS (ESI, m/z): 498.16 [M+H]$^+$

Example 538

(R)—N-(1-(4-(5-acetylthiophen-2-yl)benzoyl)pyrrolidin-3-yl)-2-amino-5-(1-methyl-1H-pyrazol-4-yl)nicotinamide Using 4-(5-acetylthiophen-2-yl)benzoic acid, the title compound was obtained as described for the Example 342. MS (ESI, m/z): 515.18 [M+H]$^+$

Example 539

(R)-2-amino-N-(1-(4-(3,5-dimethylisoxazol-4-yl)benzoyl)pyrrolidin-3-yl)-5-(1-methyl-1H-pyrazol-4-yl)nicotinamide Using 4-(3,5-dimethylisoxazol-4-yl)benzoic acid, the title compound was obtained as described for the Example 342. MS (ESI, m/z): 486.22 [M+H]$^+$

Example 540

(R)-2-amino-N-(1-(4-(3-amino-5-methylisoxazol-4-yl)benzoyl)pyrrolidin-3-yl)-5-(1-methyl-1H-pyrazol-4-yl)nicotinamide Using 4-(3-amino-5-methylisoxazol-4-yl)benzoic acid, the title compound was obtained as described for the Example 342. MS (ESI, m/z): 487.21 [M+H]$^+$

Example 541

2-amino-5-(1-methyl-1H-pyrazol-4-yl)-N—((R)-1-(4'-(((S)-pyrrolidin-3-yl)oxy)-[1,1'-biphenyl]-4-carbonyl)pyrrolidin-3-yl)nicotinamide Using (S)-4'-((1-(tert-butoxycarbonyl)pyrrolidin-3-yl)oxy)-[1,1'-biphenyl]-4-carboxylic acid, the title compound was obtained as described for the Example 342. MS (ESI, m/z): 552.26 [M+H]$^+$

Example 542

2-amino-N-((3R)-1-(4-(5-(1-hydroxyethyl)thiophen-2-yl)benzoyl)pyrrolidin-3-yl)-5-(1-methyl-1H-pyrazol-4-yl)nicotinamide Using 4-(5-(1-hydroxyethyl)thiophen-2-yl)benzoic acid, the title compound was obtained as described for the Example 342. MS (ESI, m/z): 517.19 [M+H]$^+$

Example 543

(R)-2-amino-5-(1-methyl-1H-pyrazol-4-yl)-N-(1-(4-(5-methylthiazol-2-yl)benzoyl)pyrrolidin-3-yl)nicotinamide Using 4-(5-methylthiazol-2-yl)benzoic acid, the title compound was obtained as described for the Example 342. MS (ESI, m/z): 488.18 [M+H]$^+$

Example 544

(R)-2-amino-5-(1-methyl-1H-pyrazol-4-yl)-N-(1-(4-(4-methylthiazol-2-yl)benzoyl)pyrrolidin-3-yl)nicotinamide Using 4-(4-methylthiazol-2-yl)benzoic acid, the title compound was obtained as described for the Example 342. MS (ESI, m/z): 488.18 [M+H]$^+$

Example 545

(R)—N-(1-(1H-benzo[d]imidazole-2-carbonyl)pyrrolidin-3-yl)-2-amino-5-(1-methyl-1H-pyrazol-4-yl)nicotinamide Using 1H-benzo[d]imidazole-2-carboxylic acid, the title compound was obtained as described for the Example 342. MS (ESI, m/z): 431.2 [M+H]$^+$

Example 546

(R)-2-amino-5-(1-methyl-1H-pyrazol-4-yl)-N-(1-(2-oxo-2-phenylacetyl)pyrrolidin-3-yl)nicotinamide Using 2-oxo-2-phenylacetic acid, the title compound was obtained as described for the Example 342. MS (ESI, m/z): 419.2 [M+H]±

Example 547

(R)-2-amino-N-(1-(4'-((4-aminopiperidin-1-yl)methyl)-[1,1'-biphenyl]-4-carbonyl)pyrrolidin-3-yl)-5-(1-methyl-1H-pyrazol-4-yl)nicotinamide Using Example 381 and 1-(tert-butoxycarbonyl)azetidin-3-yl)amine and trifluoroacetic acid, the title compound was obtained as described in general method F. MS (ESI, m/z): 579.1 [M+H]$^+$

Example 548

2-amino-N-((3R)-1-(4'-((methyl((1-methylpiperidin-3-yl)methyl)amino)methyl)-[1,1'-biphenyl]-4-carbonyl)pyrrolidin-3-yl)-5-(1-methyl-1H-pyrazol-4-yl)nicotinamide Using Example 381 and N-methyl-1-(1-methylpiperidin-3-yl)methanamine, the title compound was obtained as described in general method F. MS (ESI, m/z): 605.1 [M+H]$^+$

Example 549

(R)-2-amino-5-(1-methyl-1H-pyrazol-4-yl)-N-(1-(4'-(((1-methylpiperidin-4-yl)amino)methyl)-[1,1'-biphenyl]-4-carbonyl)pyrrolidin-3-yl)nicotinamide Using Example 381 and 1-methylpiperidin-4-amine, the title compound was obtained as described in general method F. MS (ESI, m/z): 593.1 [M+H]$^+$

Example 646

(R)-2-amino-5-(1-methyl-1H-pyrazol-4-yl)-N-(1-(2'-methyl-[1,1'-biphenyl]-4-carbonyl)pyrrolidin-3-yl)nicotinamide Using o-tolylboronic acid, the title compound was obtained as described in general method G. $^1$H NMR (600 MHz, METHANOL-d$_4$) δ ppm 2.10-2.22 (m, 1H) 2.24 (d, J=6.46 Hz, 3H) 2.29-2.45 (m, 1H) 3.60 (dd, J=11.15, 5.28 Hz, 0.5H) 3.66-3.74 (m, 1H) 3.75-3.83 (m, 1H) 3.84-3.91 (m, 0.5H) 3.94 (d, J=3.52 Hz, 3H) 3.97-4.06 (m, 1H) 4.58 (br t, J=5.87 Hz, 0.5H) 4.67-4.74 (m, 0.5H) 7.16-7.20 (m, 1H) 7.20-7.29 (m, 3H) 7.40 (t, J=8.80 Hz, 2 H) 7.63 (dd, J=14.97, 7.92 Hz, 2H) 7.91 (d, J=17.02 Hz, 1H) 8.06 (d, J=15.26 Hz, 1H) 8.24 (dd, J=18.19, 1.76 Hz, 1H) 8.62-8.75 (m, 1H); MS (ESI, m/z): 481.2 [M+H]$^+$

Example 647

(R)-2-amino-N-(1-(5'-chloro-2'-methyl-[1,1'-biphenyl]-4-carbonyl)pyrrolidin-3-yl)-5-(1-methyl-1H-pyrazol-4-yl)nicotinamide Using (5-chloro-2-methylphenyl)boronic acid, the title compound was obtained as described in general method G. $^1$H NMR (600 MHz, METHANOL-d$_4$) δ ppm 2.14-2.24 (br dd, J=12.33, 6.46 Hz, 1H) 2.21 (d, J=6.46 Hz, 3H) 2.29-2.46 (m, 1H) 3.59 (dd, J=11.15, 5.28 Hz, 0.5H) 3.66-3.73 (m, 1H) 3.73-3.83 (m, 1H) 3.83-3.92 (m, 0.5H) 3.95 (d, J=4.11 Hz, 3H) 3.96-4.05 (m, 1H) 4.58 (brt, J=6.16 Hz, 0.5H) 4.67-4.74 (m, 0.5H) 7.19 (d, J=9.98 Hz, 1H) 7.27 (d, J=5.87 Hz, 2H) 7.41 (t, J=8.34 Hz, 2H) 7.65 (dd, J=14.09, 8.22 Hz, 2H) 7.90 (d, J=17.02 Hz, 1H) 8.06 (d, J=15.26 Hz, 1H) 8.24 (dd, J=18.19, 1.76 Hz, 1H) 8.62-8.73 (m, 1H); MS (ESI, m/z): 515.2 [M+H]$^+$

Example 648

(R)-2-amino-N-(1-(3',5'-dimethyl-[1,1'-biphenyl]-4-carbonyl)pyrrolidin-3-yl)-5-(1-methyl-1H-pyrazol-4-yl)nicotinamide Using (3,5-dimethylphenyl)boronic acid, the title compound was obtained as described in general method G. $^1$H NMR (600 MHz, METHANOL-d₄) δ ppm 2.08-2.24 (m, 1H) 2.27-2.40 (br s, 1H) 2.35 (d, J=7.63 Hz, 6H) 3.58 (dd, J=11.15, 4.70 Hz, 0.5H) 3.64-3.72 (m, 1H) 3.72-3.81 (m, 1H) 3.82-3.90 (m, 0.5H) 3.94 (d, J=7.04 Hz, 3H) 3.95-4.04 (m, 1H) 4.54 (br t, J=5.87 Hz, 0.5H) 4.65-4.71 (m, 0.5H) 7.01 (br d, J=7.04 Hz, 1H) 7.22 (d, J=12.33 Hz, 2H) 7.60 (dd, J=16.14, 7.92 Hz, 2H) 7.63-7.68 (m, 2H) 7.85-7.93 (m, 1H) 8.00-8.07 (m, 1H) 8.17-8.24 (m, 1H) 8.58-8.71 (m, 1H); MS (ESI, m/z): 495.2 [M+H]⁺

Example 649

(R)-2-amino-N-(1-(3',4'-dimethyl-[1,1'-biphenyl]-4-carbonyl)pyrrolidin-3-yl)-5-(1-methyl-1H-pyrazol-4-yl)nicotinamide Using (3,4-dimethylphenyl)boronic acid, the title compound was obtained as described in general method G. ¹H NMR (600 MHz, METHANOL-d₄) δ ppm 2.08-2.23 (m, 1H) 2.29 (d, J=6.46 Hz, 3H) 2.31 (d, J=8.80 Hz, 3H) 2.28-2.39 (br dd, J=13.79, 6.75 Hz, 1H) 3.57 (dd, J=11.15, 5.28 Hz, 0.5H) 3.64-3.72 (m, 1H) 3.72-3.80 (m, 1H) 3.83-3.90 (m, 0.5 H) 3.94 (d, J=7.04 Hz, 3H) 3.95-4.03 (m, 1H) 4.50-4.57 (m, 0.5H) 4.65-4.71 (m, 0.5H) 7.19 (t, J=8.22 Hz, 1H) 7.34 (t, J=9.31 Hz, 1H) 7.38-7.41 (m, 1H) 7.60 (dd, J=16.43, 8.22 Hz, 2H) 7.63-7.69 (m, 2H) 7.86-7.93 (m, 1H) 8.00-8.07 (m, 1H) 8.18-8.24 (m, 1H) 8.58-8.69 (m, 1H); MS (ESI, m/z): 495.2 [M+H]⁺

Example 650

(R)-2-amino-N-(1-(4'-fluoro-2'-(trifluoromethyl)-[1,1'-biphenyl]-4-carbonyl)pyrrolidin-3-yl)-5-(1-methyl-1H-pyrazol-4-yl)nicotinamide Using (4-fluoro-2-(trifluoromethyl)phenyl)boronic acid, the title compound was obtained as described in general method G. ¹H NMR (600 MHz, METHANOL-d₄) δ ppm 2.10-2.24 (m, 1H) 2.30-2.46 (m, 1H) 3.58 (dd, J=11.15, 5.28 Hz, 0.5H) 3.65-3.73 (m, 1H) 3.74-3.81 (m, 1H) 3.83-3.92 (m, 0.5H) 3.95 (d, J=2.35 Hz, 3H) 3.96-4.06 (m, 1H) 4.59 (br t, J=5.87 Hz, 0.5H) 4.68-4.74 (m, 0.5H) 7.38-7.48 (m, 4H) 7.55-7.60 (m, 1H) 7.64 (dd, J=12.33, 8.22 Hz, 2H) 7.91 (d, J=15.26 Hz, 1H) 8.06 (d, J=14.09 Hz, 1H) 8.25 (dd, J=17.02, 1.76 Hz, 1H) 8.63-8.74 (m, 1H); MS (ESI, m/z): 553.2 [M+H]⁺

Example 651

(R)-2-amino-5-(1-methyl-1H-pyrazol-4-yl)-N-(1-(3'-(trifluoromethyl)-[1,1'-biphenyl]-4-carbonyl)pyrrolidin-3-yl)nicotinamide Using (3-(trifluoromethyl)phenyl)boronic acid, the title compound was obtained as described in general method G. ¹H NMR (600 MHz, METHANOL-d₄) δ ppm 2.10-2.26 (m, 1H) 2.30-2.46 (m, 1H) 3.58 (dd, J=10.86, 4.99 Hz, 0.5H) 3.65-3.74 (m, 1H) 3.75-3.83 (m, 1H) 3.83-3.92 (m, 0.5H) 3.93-3.97 (d, J=2.35 Hz, 3H) 3.97-4.06 (m, 1H) 4.57 (br t, J=5.87 Hz, 0.5H) 4.68-4.74 (m, 0.5H) 7.65-7.74 (m, 4H) 7.74-7.81 (m, 2H) 7.88-7.96 (m, 3H) 8.06 (d, J=18.19 Hz, 1H) 8.23 (s, 1H) 8.26 (s, 1H) 8.63-8.74 (m, 1H); MS (ESI, m/z): 535.2 [M+H]⁺

Example 652

(R)-2-amino-N-(1-(4'-chloro-2'-methyl-[1,1'-biphenyl]-4-carbonyl)pyrrolidin-3-yl)-5-(1-methyl-1H-pyrazol-4-yl)nicotinamide Using (4-chloro-2-methylphenyl)boronic acid, the title compound was obtained as described in general method G. ¹H NMR (600 MHz, METHANOL-d₄) δ ppm 2.10-2.22 (m, 1H) 2.24 (d, J=5.87 Hz, 3H) 2.30-2.47 (m, 1H) 3.58 (dd, J=11.15, 5.28 Hz, 0.5H) 3.66-3.73 (m, 1H) 3.74-3.83 (m, 1H) 3.84-3.91 (m, 0.5H) 3.95 (d, J=3.52 Hz, 3H) 3.96-4.05 (m, 1H) 4.55-4.61 (m, 0.5H) 4.68-4.73 (m, 0.5H) 7.18 (t, J=7.75 Hz, 1H) 7.22-7.27 (m, 1H) 7.32 (br d, J=3.52 Hz, 1H) 7.41 (t, J=8.51 Hz, 2H) 7.64 (dd, J=14.09, 8.22 Hz, 2H) 7.90 (d, J=16.43 Hz, 1H) 8.05 (d, J=15.26 Hz, 1H) 8.25 (dd, J=17.61, 1.76 Hz, 1H) 8.62-8.73 (m, 1H); MS (ESI, m/z): 515.2 [M+H]⁺

Example 653

(R)-2-amino-N-(1-(4'-fluoro-3'-methyl-[1,1'-biphenyl]-4-carbonyl)pyrrolidin-3-yl)-5-(1-methyl-1H-pyrazol-4-yl)nicotinamide Using (4-fluoro-3-methylphenyl)boronic acid, the title compound was obtained as described in general method G. ¹H NMR (600 MHz, METHANOL-d₄) δ ppm 2.09-2.24 (m, 1H) 2.31-2.43 (br d, J=7.04 Hz, 1H) 2.34 (br d, J=4.11 Hz, 3H) 3.58 (dd, J=11.15, 5.28 Hz, 0.5H) 3.66-3.73 (m, 1H) 3.73-3.81 (m, 1H) 3.83-3.92 (m, 0.5H) 3.95 (d, J=5.28 Hz, 3H) 3.96-4.05 (m, 1H) 4.53-4.62 (m, 0.5H) 4.67-4.75 (m, 0.5H) 7.12 (td, J=8.95, 5.58 Hz, 1H) 7.44-7.50 (m, 1H) 7.53 (br t, J=7.34 Hz, 1H) 7.60-7.66 (m, 2H) 7.66-7.72 (m, 2H) 7.91 (d, J=19.37 Hz, 1H) 8.06 (d, J=18.19 Hz, 1H) 8.20-8.28 (m, 1H) 8.61-8.76 (m, 1H); MS (ESI, m/z): 499.2 [M+H]⁺

Example 654

(R)—N-(1-(4-(1H-indol-5-yl)benzoyl)pyrrolidin-3-yl)-2-amino-5-(1-methyl-1H-pyrazol-4-yl)nicotinamide Using (1H-indol-5-yl)boronic acid, the title compound was obtained as described in general method G. ¹H NMR (600 MHz, METHANOL-d₄) δ ppm 2.09-2.23 (m, 1H) 2.28-2.43 (m, 1H) 3.61 (br dd, J=11.15, 5.28 Hz, 0.5H) 3.68-3.75 (m, 1H) 3.75-3.83 (m, 1H) 3.85-3.92 (m, 0.5H) 3.94 (d, J=7.63 Hz, 3H) 3.98-4.04 (m, 1H) 4.45-4.60 (m, 0.5H) 4.65-4.73 (m, 0.5H) 6.51 (dd, J=6.16, 3.23 Hz, 1H) 7.28 (br s, 1H) 7.38-7.43 (m, 1H) 7.43-7.49 (m, 1H) 7.62 (dd, J=16.14, 7.92 Hz, 2H) 7.71-7.77 (m, 2H) 7.83 (br d, J=8.80 Hz, 1H) 7.88-7.95 (m, 1H) 8.02-8.11 (m, 1H) 8.19-8.26 (m, 1H) 8.62-8.77 (n, 1H); MS (ESI, m/z): 506.2 [M+H]⁺

Example 655

(R)-2-amino-N-(1-(4-(indolin-5-yl)benzoyl)pyrrolidin-3-yl)-5-(1-methyl-1H-pyrazol-4-yl)nicotinamide Using indolin-5-ylboronic acid, the title compound was obtained as described in general method G. ¹H NMR (600 MHz, METHANOL-d₄) δ ppm 2.10-2.27 (m, 1H) 2.29-2.46 (m, 1H) 3.40-3.45 (m, 2H) 3.58 (br dd, J=11.15, 5.28 Hz, 0.5H) 3.67-3.74 (m, 1H) 3.75-3.82 (m, 1H) 3.84-3.90 (m, 1H) 3.92 (td, J=7.78, 3.23 Hz, 1.5H) 3.95 (d, J=5.28 Hz, 3H)

3.97-3.99 (m, 0.5H) 4.04 (br dd, J=12.91, 7.04 Hz, 0.5H) 4.54-4.61 (m, 0.5H) 4.69-4.75 (m, 0.5H) 7.57 (dd, J=8.22, 5.28 Hz, 1H) 7.62-7.78 (m, 5H) 7.81 (br d, J=7.63 Hz, 1H) 7.91 (d, J=17.61 Hz, 1H) 8.07 (d, J=15.85 Hz, 1H) 8.25 (dd, J=17.90, 2.05 Hz, 1H) 8.71 (dd, J=46.37, 1.76 Hz, 1H); MS (ESI, m/z): 508.2 [M+H]$^+$

Example 656

(R)-2-amino-5-(1-methyl-1H-pyrazol-4-yl)-N-(1-(3'-methyl-[1,1'-biphenyl]-4-carbonyl)pyrrolidin-3-yl)nicotinamide Using m-tolylboronic acid, the title compound was obtained as described in general method G. $^1$H NMR (600 MHz, METHANOL-d$_4$) δ ppm 2.09-2.26 (m, 1H) 2.32-2.45 (br dd, J=12.91, 6.46 Hz, 1H) 2.41 (d, J=6.46 Hz, 3H) 3.59 (br dd, J=11.15, 5.28 Hz, 0.5H) 3.65-3.73 (m, 1H) 3.74-3.82 (m, 1H) 3.85-3.91 (m, 0.5H) 3.95 (d, J=6.46 Hz, 3H) 3.96-4.05 (m, 1H) 4.51-4.63 (m, 0.5H) 4.66-4.74 (m, 0.5H) 7.20 (br t, J=6.46 Hz, 1H) 7.34 (q, J=7.63 Hz, 1H) 7.43 (t, J=8.42 Hz, 1H) 7.46 (d, J=9.82 Hz, 1H) 7.63 (dd, J=15.85, 8.22 Hz, 2H) 7.67-7.72 (m, 2H) 7.91 (d, J=19.96 Hz, 1H) 8.05 (d, J=19.96 Hz, 1H) 8.19-8.27 (m, 1H) 8.61-8.75 (m, 1H); MS (ESI, m/z): 481.2 [M+H]$^+$ Example 657

(R)-2-amino-N-(1-(3'-ethyl-[1,1'-biphenyl]-4-carbonyl)pyrrolidin-3-yl)-5-(1-methyl-1H-pyrazol-4-yl)nicotinamide Using (3-ethylphenyl)boronic acid, the title compound was obtained as described in general method G. $^1$H NMR (600 MHz, METHANOL-d$_4$) δ ppm 1.24-1.30 (m, 3H) 2.09-2.23 (m, 1H) 2.28-2.45 (m, 1H) 2.71 (quin, J=7.19 Hz, 2H) 3.58 (br dd, J=11.15, 5.28 Hz, 0.5H) 3.70 (br dd, J=12.33, 5.28 Hz, 1H) 3.74-3.81 (m, 1H) 3.84-3.91 (m, 0.5H) 3.95 (d, J=5.87 Hz, 3H) 3.96-4.04 (m, 1H) 4.52-4.59 (m, 0.5H) 4.67-4.73 (m, 0.5H) 7.23 (br t, J=6.16 Hz, 1H) 7.36 (q, J=7.04 Hz, 1H) 7.40-7.50 (m, 2H) 7.63 (dd, J=15.85, 8.22 Hz, 2H) 7.68-7.74 (m, 2H) 7.91 (d, J=19.96 Hz, 1H) 8.05 (d, J=19.37 Hz, 1H) 8.19-8.27 (m, 1H) 8.62-8.74 (m, 1H); MS (ESI, m/z): 495.2 [M+H]$^+$ Example 658

(R)-2-amino-N-(1-(3'-isopropyl-[1,1'-biphenyl]-4-carbonyl)pyrrolidin-3-yl)-5-(1-methyl-1H-pyrazol-4-yl)nicotinamide Using (3-isopropylphenyl)boronic acid, the title compound was obtained as described in general method G. $^1$H NMR (600 MHz, METHANOL-d$_4$) δ ppm 1.26-1.32 (m, 6H) 2.08-2.24 (m, 1H) 2.28-2.44 (m, 1H) 2.92-3.01 (m, 1H) 3.58 (dd, J=11.15, 5.28 Hz, 0.5H) 3.64-3.73 (m, 1H) 3.73-3.81 (m, 1H) 3.81-3.90 (m, 0.5H) 3.94 (d, J=5.87 Hz, 3H) 3.95-4.04 (m, 1H) 4.49-4.58 (m, 0.5H) 4.67-4.73 (m, 0.5H) 7.24-7.28 (m, 1H) 7.34-7.39 (m, 1H) 7.43 (t, J=8.10 Hz, 1H) 7.48 (d, J=9.11 Hz, 1H) 7.63 (dd, J=15.26, 8.22 Hz, 2H) 7.66-7.72 (m, 2H) 7.90 (d, J=19.96 Hz, 1H) 8.05 (d, J=19.37 Hz, 1H) 8.19-8.28 (m, 1H) 8.62-8.77 (m, 1H); MS (ESI, m/z): 509.3 [M+H]$^+$ Example 659

(R)-2-amino-N-(1-(3',4'-dimethoxy-[1,1'-biphenyl]-4-carbonyl)pyrrolidin-3-yl)-5-(1-methyl-1H-pyrazol-4-yl)nicotinamide Using (3,4-dimethoxyphenyl)boronic acid, the title compound was obtained as described in general method G. $^1$H NMR (600 MHz, METHANOL-d$_4$) δ ppm 2.07-2.23 (m, 1H) 2.27-2.43 (m, 1H) 3.58 (br dd, J=11.15, 5.28 Hz, 0.5H) 3.68 (br dd, J=12.62, 4.99 Hz, 1H) 3.72-3.81 (m, 1H) 3.86 (d, J=5.87 Hz, 3.5H) 3.89 (d, J=8.80 Hz, 3H) 3.94 (d, J=7.04 Hz, 3H) 3.95-4.03 (m, 1H) 4.49-4.57 (m, 0.5H) 4.65-4.71 (m, 0.5H) 6.98-7.06 (m, 1H) 7.16-7.23 (m, 2H) 7.60 (dd, J=16.14, 7.92 Hz, 2H) 7.67 (dd, J=12.91, 8.22 Hz, 2H) 7.85-7.94 (m, 1H) 7.99-8.08 (m, 1H) 8.17-8.25 (m, 1H) 8.60-8.73 (m, 1H); MS (ESI, m/z): 527.2 [M+H]$^+$ Example 660

(R)-2-amino-N-(1-(4'-(azetidin-1-ylsulfonyl)-[1,1'-biphenyl]-4-carbonyl)pyrrolidin-3-yl)-5-(1-methyl-1H-pyrazol-4-yl)nicotinamide Using (4-(azetidin-1-ylsulfonyl)phenyl)boronic acid, the title compound was obtained as described in general method G. $^1$H NMR (600 MHz, METHANOL-d$_4$) δ ppm 2.01-2.22 (m, 3H) 2.25-2.44 (m, 1H) 3.45-4.05 (m, 2H) 3.65-3.72 (m, 2H) 3.75-3.80 (m, 2H) 3.93 (s, 3H) 4.51-4.58 (m, 0.5H) 4.63-4.73 (m, 0.5H) 6.97 (d, J=8.80 Hz, 1H) 7.47 (dd, J=12.33, 8.22 Hz, 1H) 7.57-7.67 (m, 2H) 7.70 (dd, J=14.67, 8.22 Hz, 1H) 7.82 (br t, J=8.80 Hz, 1H) 7.87-7.99 (m, 3H) 7.99-8.09 (m, 1H) 8.19-8.28 (m, 1H) 8.61-8.74 (m, 1H); MS (ESI, m/z): 586.6 [M+H]$^+$ Example 661

(R)-2-amino-N-(1-(4'-chloro-3'-fluoro-[1,1'-biphenyl]-4-carbonyl)pyrrolidin-3-yl)-5-(1-methyl-1H-pyrazol-4-yl)nicotinamide Using (4-chloro-3-fluorophenyl)boronic acid, the title compound was obtained as described in general method G. $^1$H NMR (600 MHz, METHANOL-d$_4$) δ ppm 2.07-2.24 (m, 1H) 2.27-2.44 (m, 1H) 3.54 (dd, J=11.15, 5.28 Hz, 0.5H) 3.61-3.71 (m, 1H) 3.71-3.79 (m, 1H) 3.81-3.90 (m, 0.5H) 3.93 (d, J=5.28 Hz, 3H) 3.94-4.03 (m, 1H) 4.51-4.61 (m, 0.5H) 4.66-4.72 (m, 0.5H) 7.47 (td, J=7.92, 1.76 Hz, 1H) 7.51-7.59 (m, 2H) 7.65 (dd, J=14.67, 8.80 Hz, 2H) 7.69-7.76 (m, 2H) 7.89 (d, J=18.19 Hz, 1H) 8.04 (d, J=17.02 Hz, 1H) 8.16-8.27 (m, 1H) 8.61-8.74 (m, 1H); MS (ESI, m/z): 519.2 [M+H]$^+$ Example 662

(R)-2-amino-N-(1-(4'-amino-[1,1'-biphenyl]-4-carbonyl)pyrrolidin-3-yl)-5-(1-methyl-1H-pyrazol-4-yl)nicotinamide Using (4-aminophenyl)boronic acid, the title compound was obtained as described in general method G. $^1$H NMR (600 MHz, METHANOL-d$_4$) δ ppm 2.08-2.22 (m, 1H) 2.28-2.43 (m, 1H) 3.56 (dd, J=11.15, 4.70 Hz, 1H) 3.64-3.72 (m, 1H) 3.72-3.79 (m, 1H) 3.83-3.89 (m, 1H) 3.92-3.95 (m, 1H) 3.95-4.04 (m, 1H) 4.53-4.58 (m, 1H) 4.67-4.72 (m, 1H) 7.45-7.50 (m, 2H) 7.67 (dd, J=14.09, 8.22 Hz, 2H) 7.72-7.78 (m, 2H) 7.79-7.85 (m, 2H) 7.90 (d, J=17.61 Hz, 1H) 8.05 (d, J=16.43 Hz, 1H) 8.24 (dd, J=18.19, 2.35 Hz, 1H) 8.63-8.75 (m, 1H); MS (ESI, m/z): 482.2 [M+H]$^+$

Example 663

(R)-2-amino-N-(1-(3'-chloro-5'-fluoro-[1,1'-biphenyl]-4-carbonyl)pyrrolidin-3-yl)-5-(1-methyl-1H-pyrazol-4-yl)nicotinamide Using (3-chloro-5-fluorophenyl)boronic acid, the title compound was obtained as described in general method G. $^1$H NMR (600 MHz, METHANOL-d$_4$) δ ppm 2.08-2.22 (m, 1H) 2.27-2.42 (m, 1H) 3.54 (dd, J=11.15, 5.28 Hz, 0.5H) 3.63-3.71 (m, 1H) 3.71-3.79 (m, 1H) 3.82-3.89 (m, 0.5H) 3.93 (d, J=5.87 Hz, 3H) 3.94-4.04 (m, 1H) 4.51-4.58 (m, 0.5H) 4.65-4.72 (m, 0.5H) 7.22 (ddt, J=8.44, 4.18, 2.20, 2.20 Hz, 1H) 7.31-7.45 (m, 1H) 7.52 (d, J=8.22 Hz, 1H) 7.62-7.69 (m, 2H) 7.69-7.76 (m, 2H) 7.89 (d, J=18.19 Hz, 1H) 8.04 (d, J=17.61 Hz, 1H) 8.23 (dd, J=19.96, 2.35 Hz, 1H) 8.61-8.74 (m, 1H); MS (ESI, m/z): 519.2 [M+H]$^+$

Example 664

(R)-2-amino-N-(1-(3',5'-dichloro-4'-fluoro-[1,1'-biphenyl]-4-carbonyl)pyrrolidin-3-yl)-5-(1-methyl-1H-pyrazol-4-yl)nicotinamide Using (3,5-dichloro-4-fluorophenyl)boronic acid, the title compound was obtained as described in general method G. $^1$H NMR (600 MHz, METHANOL-d$_4$) δ ppm 2.07-2.23 (m, 1H) 2.27-2.42 (m, 1H) 3.54 (dd, J=11.15, 5.28 Hz, 0.5H) 3.63-3.70 (m, 1H) 3.71-3.78 (m, 1H) 3.82-3.88 (m, 0.5H) 3.93 (d, J=5.87 Hz, 3H) 3.94-4.04 (m, 1H) 4.51-4.59 (m, 0.5H) 4.65-4.71 (m, 0.5H) 7.62-7.76 (m, 6H) 7.89 (d, J=18.78 Hz, 1H) 8.04 (d, J=17.61 Hz, 1H) 8.23 (dd, J=19.37, 2.35 Hz, 1H) 8.60-8.71 (m, 1H); MS (ESI, m/z): 553.2 [M+H]$^+$

Example 665

(R)-2-amino-5-(1-methyl-1H-pyrazol-4-yl)-N-(1-(4'-(methylthio)-[1,1'-biphenyl]-4-carbonyl)pyrrolidin-3-yl)nicotinamide Using (4-(methylthio)phenyl)boronic acid, the title compound was obtained as described in general method G. $^1$H NMR (600 MHz, METHANOL-d$_4$) δ ppm 2.04-2.22 (m, 1H) 2.25-2.40 (m, 1H) 2.47-2.49 (d, J=4.11 Hz, 3H) 3.52 (dd, J=11.15, 5.87 Hz, 0.5H) 3.60-3.69 (m, 1H) 3.69-3.78 (m, 1H) 3.79-3.87 (m, 0.5H) 3.92 (d, J=3.52 Hz, 3H) 3.93-4.04 (m, 1H) 4.49-4.56 (m, 0.5H) 7.30 (dd, J=8.22, 5.87 Hz, 2H) 7.48-7.54 (m, 2H) 7.54-7.58 (m, 2H) 7.58-7.64 (m, 2H) 7.79 (d, J=15.85 Hz, 1H) 7.91 (d, J=12.33 Hz, 1H) 8.13 (dd, J=16.73, 2.05 Hz, 1H) 8.54-8.65 (m, 1H); MS (ESI, m/z): 513.2 [M+H]$^+$

Example 666

(R)-2-amino-N-(1-(4'-(ethylthio)-[1,1'-biphenyl]-4-carbonyl)pyrrolidin-3-yl)-5-(1-methyl-1H-pyrazol-4-yl)nicotinamide Using (4-(ethylthio)phenyl)boronic acid, the title compound was obtained as described in general method G. $^1$H NMR (600 MHz, METHANOL-d$_4$) δ ppm 1.30-1.33 (m, 3H) 2.04-2.22 (m, 1H) 2.25-2.41 (m, 1H) 2.96 (qd, J=7.34, 3.81 Hz, 2H) 3.52 (dd, J=11.15, 5.87 Hz, 0.5H) 3.61-3.69 (m, 1H) 3.71-3.78 (m, 1H) 3.82 (br dd, J=7.63, 5.87 Hz, 0.5H) 3.92 (d, J=4.11 Hz, 3H) 3.93-4.04 (m, 1H) 4.53 (br t, J=6.46 Hz, 0.5H) 7.35 (dd, J=8.51, 6.16 Hz, 2H) 7.49-7.54 (m, 2H) 7.57 (t, J=8.51 Hz, 2H) 7.59-7.66 (m, 2H) 7.79 (d, J=15.85 Hz, 1H) 7.91 (d, J=13.50 Hz, 1H) 8.14 (dd, J=16.43, 1.76 Hz, 1H) 8.50-8.61 (m, 1H); MS (ESI, m/z): 527.3 [M+H]$^+$

Example 667

(R)-2-amino-N-(1-(2'-chloro-5'-fluoro-[1,1'-biphenyl]-4-carbonyl)pyrrolidin-3-yl)-5-(1-methyl-1H-pyrazol-4-yl)nicotinamide Using (2-chloro-5-fluorophenyl)boronic acid, the title compound was obtained as described in general method G. $^1$H NMR (600 MHz, METHANOL-d$_4$) δ ppm 2.09-2.22 (m, 1H) 2.29-2.44 (m, 1H) 3.56 (dd, J=11.15, 5.28 Hz, 0.5H) 3.66-3.73 (m, 1H) 3.73-3.80 (m, 1H) 3.83-3.89 (m, 0.5H) 3.91-3.95 (d, J=4.70 Hz, 3H) 3.95-4.04 (m, 1H) 4.54-4.60 (m, 0.5H) 4.67-4.73 (m, 0.5H) 7.12-7.21 (m, 2H) 7.47-7.57 (m, 3H) 7.66 (dd, J=12.33, 8.22 Hz, 2H) 7.90 (d, J=17.02 Hz, 1H) 8.05 (d, J=15.26 Hz, 1H) 8.24 (dd, J=18.19, 1.76 Hz, 1H) 8.62-8.75 (m, 1H); MS (ESI, m/z): 519.2 [M+H]$^+$

Example 668

(R)-2-amino-N-(1-(3,5-dihydroxy-2-naphthoyl)pyrrolidin-3-yl)-5-(1-methyl-1H-pyrazol-4-yl)nicotinamide Using 3,5-dihydroxy-2-naphthoic acid, the title compound was obtained as described in general method G. $^1$H NMR (600 MHz, METHANOL-d$_4$) δ ppm 2.06-2.21 (m, 1H) 2.26-2.43 (m, 1H) 3.43-3.48 (m, 0.5H) 3.51-3.57 (m, 1H) 3.57-3.65 (m, 1H) 3.71 (br dd, J=12.91, 4.70 Hz, 0.5H) 3.76-3.81 (m, 0.5H) 3.93 (d, J=8.22 Hz, 3H) 4.02 (dd, J=12.91, 7.04 Hz, 0.5H) 4.51-4.56 (m, 0.5H) 4.65-4.70 (m, 0.5H) 6.76 (t, J=8.22 Hz, 1H) 7.09 (dt, J=11.30, 7.85 Hz, 1H) 7.19-7.26 (m, 1H) 7.50-7.58 (m, 1H) 7.66 (d, J=19.96 Hz, 1H) 7.85-7.93 (m, 1H) 7.98-8.05 (m, 1H) 8.14-8.24 (m, 1H) 8.58-8.70 (m, 1H); MS (ESI, m/z): 519.2 [M+H]$^+$

Example 669

(R)-2-amino-N-(1-(5-bromo-1-naphthoyl)pyrrolidin-3-yl)-5-(1-methyl-1H-pyrazol-4-yl)nicotinamide Using 5-bromo-1-naphthoic acid, the title compound was obtained as described in general method G. $^1$H NMR (600 MHz, METHANOL-d$_4$) δ ppm 2.00-2.08 (m, 0.5H) 2.15-2.31 (m, 1H) 2.40-2.49 (m, 0.5H) 3.18 (br dd, J=14.97, 7.34 Hz, 0.5H) 3.23-3.28 (m, 0.5H) 3.32-3.38 (m, 0.5H) 3.48-3.56 (m, 0.5H) 3.78 (dd, J=12.91, 5.28 Hz, 0.5H) 3.81-3.89 (m, 0.5H) 3.93 (d, J=9.39 Hz, 3H) 4.02 (br d, J=5.87 Hz, 0.5H) 4.15 (dd, J=12.91, 7.04 Hz, 0.5H) 4.46 (t, J=6.16 Hz, 0.5H) 4.66-4.72 (m, 0.5H) 7.31-7.45 (m, 1H) 7.59 (dd, J=18.78, 7.04 Hz, 1H) 7.63-7.71 (m, 1H) 7.78-7.92 (m, 3H) 8.02 (d, J=19.95 Hz, 1H) 8.16-8.25 (m, 1H) 8.26-8.36 (m, 1H) 8.55-8.68 (m, 1H); MS (ESI, m/z): 519.2, 521.2 [M+H]$^+$

Example 670

N-(1-([1,1'-biphenyl]-3-carbonyl)azetidin-3-yl)-2-amino-5-(1-methyl-1H-pyrazol-4-yl)nicotinamide Using tert-butyl 3-aminoazetidine-1-carboxylate and [1,1'-biphenyl]-3-carboxylic acid, the title compound was obtained as described in general method G. ¹H NMR (600 MHz, METHANOL-d₄) δ ppm 3.92 (s, 3H) 4.25 (br dd, J=10.86, 4.99 Hz, 1H) 4.43 (br dd, J=9.39, 5.28 Hz, 1H) 4.53-4.59 (m, 1H) 4.76 (br t, J=8.51 Hz, 1H) 4.85 (tt, J=7.92, 5.28 Hz, 1H) 7.34-7.38 (m, 1H) 7.45 (t, J=7.53 Hz, 2H) 7.52-7.56 (m, 1H) 7.62 (d, J=7.57 Hz, 3H) 7.75-7.79 (m, 1H) 7.87 (t, J=1.76 Hz, 1H) 7.88 (s, 1H) 8.02 (s, 1H) 8.23 (d, J=2.35 Hz, 1H) 8.71 (d, J=2.35 Hz, 1H); MS (ESI, m/z): 453.2 [M+H]⁺

Example 671

N-(1-([1,1'-biphenyl]-4-carbonyl)-3-(hydroxymethyl)pyrrolidin-3-yl)-2-amino-5-(1-methyl-1H-pyrazol-4-yl)nicotinamide Using tert-butyl 3-amino-3-(hydroxymethyl)pyrrolidine-1-carboxylate and [1,1'-biphenyl]-4-carboxylic acid, the title compound was obtained as described in general method G. ¹H NMR (600 MHz, METHANOL-d₄) δ ppm 2.28-2.50 (m, 2H) 3.67-3.86 (m, 4H) 3.88-4.10 (m, 2H) 3.93 (d, J=4.70 Hz, 3H) 7.33-7.41 (m, 1H) 7.45 (td, J=7.78, 2.05 Hz, 2H) 7.57-7.68 (m, 4H) 7.71 (d, J=8.22 Hz, 2H) 7.90 (d, J=17.61 Hz, 1H) 8.04 (d, J=16.43 Hz, 1H) 8.23 (d, J=14.97, 2.05 Hz, 1H) 8.60-8.75 (m, 1H); MS (ESI, m/z): 497.3 [M+H]⁺

Example 672

N-(1-([1,1'-biphenyl]-3-carbonyl)-3-(hydroxymethyl)pyrrolidin-3-yl)-2-amino-5-(1-methyl-1H-pyrazol-4-yl)nicotinamide Using tert-butyl 3-amino-3-(hydroxymethyl)pyrrolidine-1-carboxylate and [1,1'-biphenyl]-3-carboxylic acid, the title compound was obtained as described in general method G. ¹H NMR (600 MHz, METHANOL-d₄) δ ppm 2.26-2.49 (m, 2H) 3.64-3.90 (m, 4H) 3.90-3.94 (m, 3.5H) 4.02 (dd, J=11.74, 3.52 Hz, 1H) 4.10 (d, J=12.91 Hz, 0.5H) 7.31-7.39 (m, 1H) 7.43 (t, J=7.63 Hz, 2H) 7.47-7.55 (m, 2H) 7.61 (d, J=8.22 Hz, 2H) 7.70-7.77 (m, 2H) 7.89 (d, J=18.19 Hz, 1H) 8.03 (d, J=15.85 Hz, 1H) 8.20 (dd, J=18.78, 2.35 Hz, 1H) 8.60-8.76 (m, 1H); MS (ESI, m/z): 497.3 [M+H]⁺

Example 673

(R)-2-amino-N-(1-(2'-chloro-3'-fluoro-[1,1'-biphenyl]-4-carbonyl)pyrrolidin-3-yl)-5-(1-methyl-1H-pyrazol-4-yl)nicotinamide Using (2-chloro-3-fluorophenyl)boronic acid, the title compound was obtained as described in general method G. ¹H NMR (600 MHz, METHANOL-d₄) δ ppm 2.09-2.22 (m, 1H) 2.29-2.44 (m, 1H) 3.56 (dd, J=11.15, 5.28 Hz, 0.5H) 3.67-3.73 (m, 1H) 3.74-3.80 (m, 1H) 3.83-3.89 (m, 0.5H) 3.94 (d, J=4.70 Hz, 3H) 3.96-4.04 (m, 1H) 4.55-4.60 (m, 0.5H) 4.68-4.73 (m, 0.5H) 7.20-7.24 (m, 1H) 7.28 (t, J=8.73 Hz, 1H) 7.40 (tt, J=7.92, 4.70 Hz, 1H) 7.54 (t, J=7.55 Hz, 1H) 7.66 (dd, J=12.62, 7.92 Hz, 2H) 7.90 (d, J=16.43 Hz, 1H) 8.05 (d, J=15.85 Hz, 1H) 8.24 (dd, J=18.19, 1.76 Hz, 1H) 8.69 (dd, J=44.02, 2.35 Hz, 1H) MS (ESI, m/z): 519.2 [M+H]⁺

Example 674

N-((3S,4S)-1-([1,1'-biphenyl]-4-carbonyl)-4-((3-ethyl-4-methylbenzyl)oxy)pyrrolidin-3-yl)-2-amino-5-(1-methyl-1H-pyrazol-4-yl)nicotinamide Using tert-butyl (3S,4S)-3-amino-4-((3-ethyl-4-methylbenzyl)oxy)pyrrolidine-1-carboxylate and [1,1'-biphenyl]-4-carboxylic acid, the title compound was obtained as described in general method G. ¹H NMR (600 MHz, METHANOL-d₄) δ ppm 1.10 (t, J=7.63 Hz, 2H) 1.17 (t, J=7.63 Hz, 1H) 2.18 (s, 2H) 2.25 (s, 1H) 2.53 (q, J=7.63 Hz, 1.2H) 2.61 (q, J=7.63 Hz, 0.8H) 3.53 (br d, J=12.33 Hz, 0.5H) 3.58-3.65 (m, 0.5H) 3.73 (dd, J=13.21, 2.64 Hz, 0.5H) 3.78 (br d, J=12.91 Hz, 0.5H) 3.83 (br dd, J=12.03, 4.40 Hz, 0.5H) 3.92 (d, J=9.98 Hz, 3H) 4.06-4.13 (m, 0.5H) 4.15 (br d, J=1.76 Hz, 1H) 4.24-4.28 (m, 0.5H) 4.52 (d, J=11.74 Hz, 0.5H) 4.61-4.65 (m, 1H) 4.65-4.72 (m, 1H) 7.01 (s, 1H) 7.04-7.20 (m, 2H) 7.37 (t, J=7.56 Hz, 1H) 7.43-7.47 (m, 2H) 7.58-7.67 (m, 3H) 7.67-7.72 (m, 2H) 7.83-7.91 (m, 1H) 7.97-8.04 (m, 1H) 8.05-8.10 (m, 1H) 8.19-8.26 (m, 1H) 8.49-8.66 (m, 1H); MS (ESI, m/z): 615.3 [M+H]⁺

Example 675

N-((3S,4S)-1-([1,1'-biphenyl]-3-carbonyl)-4-((3-ethyl-4-methylbenzyl)oxy)pyrrolidin-3-yl)-2-amino-5-(1-methyl-1H-pyrazol-4-yl)nicotinamide Using tert-butyl (3S,4S)-3-amino-4-((3-ethyl-4-methylbenzyl)oxy)pyrrolidine-1-carboxylate and [1,1'-biphenyl]-3-carboxylic acid, the title compound was obtained as described in general method G. MS (ESI, m/z): 615.3 [M+H]⁺

Example 676

(R)-2-amino-N-(1-(4'-(cyanomethyl)-[1,1'-biphenyl]-4-carbonyl)pyrrolidin-3-yl)-5-(1-methyl-1H-pyrazol-4-yl)nicotinamide Using (4-(cyanomethyl)phenyl)boronic acid, the title compound was obtained as described in general method G. ¹H NMR (600 MHz, METHANOL-d₄) δ ppm 2.07-2.23 (m, 1H) 2.26-2.42 (m, 1H) 3.55 (dd, J=11.44, 4.99 Hz, 0.5H) 3.64-3.70 (m, 1H) 3.72-3.77 (m, 1H) 3.81-3.89 (m, 0.5H) 3.90-3.95 (m, 5H) 3.95-4.04 (m, 1H) 4.49-4.57 (m, 0.5H) 4.64-4.72 (m, 0.5H) 4.80-4.90 (m, 1H) 6.76 (d, J=8.17 Hz, 1H) 7.13 (d, J=7.93 Hz, 1H) 7.45 (dd, J=7.63, 6.46 Hz, 2H) 7.63 (t, J=7.92 Hz, 1H) 7.65-7.74 (m, 3H) 7.89 (d, J=19.96 Hz, 1H) 8.04 (d, J=18.19 Hz, 1H) 8.22 (dd, J=21.72, 1.76 Hz, 1H) 8.67 (dd, J=46.95, 1.76 Hz, 1H); MS (ESI, m/z): 506.2 [M+H]⁺

Example 677

(R,E)-3-(4'-(3-(2-amino-5-(1-methyl-1H-pyrazol-4-yl)nicotinamido)pyrrolidine-1-carbonyl)-[1,1'-biphenyl]-4-yl)acrylic acid Using (E)-3-(4-boronophenyl)acrylic acid, the title compound was obtained as described in general method G. ¹H NMR (600 MHz, METHANOL-d₄) δ ppm 2.07-2.21 (m, 1H) 2.25-2.42 (m, 1H) 3.55 (dd, J=11.15, 5.28 Hz, 0.5H) 3.63-3.70 (m, 1H) 3.71-3.79 (m, 1H) 3.80-3.88 (m, 0.5H) 3.92 (d, J=7.04 Hz, 3H) 3.94-4.05 (m, 1H) 4.53 (br t, J=5.87 Hz, 0.5H) 4.64-4.71 (m, 0.5H) 6.50 (dd, J=16.14, 7.34 Hz, 1H) 7.55-7.78 (m, 9H) 7.88 (d, J=21.13 Hz, 1H) 8.02 (d, J=21.13 Hz, 1H) 8.20 (dd, J=24.06, 2.35 Hz, 1H) 8.65 (dd, J=6404.39, 47.54 Hz, 1H); MS (ESI, m/z): 537.3 [M+H]$^+$ Example 678

(R)-3-(4'-(3-(2-amino-5-(1-methyl-1H-pyrazol-4-yl)nicotinamido)pyrrolidine-1-carbonyl)-[1,1'-biphenyl]-4-yl)propanoic acid Using 3-(4-boronophenyl)propanoic acid, the title compound was obtained as described in general method G. $^1$H NMR (600 MHz, METHANOL-d$_4$) δ ppm 2.06-2.22 (m, 1H) 2.26-2.44 (m, 1H) 2.63 (td, J=7.63, 3.52 Hz, 2H) 2.95 (td, J=7.63, 3.52 Hz, 2H) 3.56 (br dd, J=11.15, 4.70 Hz, 0.5H) 3.65-3.72 (m, 1H) 3.76 (br dd, J=11.44, 7.34 Hz, 1H) 3.81-3.90 (m, 0.5H) 3.94 (d, J=5.87 Hz, 3H) 3.95-4.03 (m, 1H) 4.51-4.58 (m, 0.5H) 4.66-4.72 (m, 0.5H) 7.33 (dd, J=7.92, 4.99 Hz, 2H) 7.57 (t, J=7.34 Hz, 2H) 7.62 (dd, J=15.26, 8.22 Hz, 2H) 7.69 (t, J=8.80 Hz, 2H) 7.91 (d, J=18.78 Hz, 1H) 8.04 (d, J=18.19 Hz, 1H) 8.23 (dd, J=21.13, 1.76 Hz, 1H) 8.66 (dd, J=48.71, 2.35 Hz, 1H); MS (ESI, m/z): 539.3 [M+H]$^+$ Example 679

(R)-2-amino-5-(1-methyl-1H-pyrazol-4-yl)-N-(1-(4'-(4-oxopiperidine-1-carbonyl)-[1,1'-biphenyl]-4-carbonyl)pyrrolidin-3-yl)nicotinamide Using (4-(4-oxopiperidine-1-carbonyl)phenyl)boronic acid, the title compound was obtained as described in general method G. $^1$H NMR (600 MHz, METHANOL-d$_4$) δ ppm 1.73 (br s, 2H) 1.84 (br s, 2H) 2.08-2.24 (m, 1H) 2.28-2.43 (m, 1H) 3.47 (br s, 2H) 3.56 (br d, J=11.15 Hz, 0.5H) 3.68 (br d, J=11.74 Hz, 1H) 3.75 (br s, 3H) 3.86 (br s, 0.5H) 3.93 (br s, 3H) 3.96-4.06 (m, 1H) 4.55 (br s, 0.5H) 4.69 (br s, 0.5H) 7.50 (br s, 2H) 7.59-7.70 (m, 2H) 7.74 (br s, 4H) 7.89 (br d, J=19.37 Hz, 1H) 8.04 (br d, J=17.61 Hz, 1H) 8.17-8.26 (m, 1H) 8.59-8.73 (m, 1H); MS (ESI, m/z): 592.2 [M+H]$^+$ Example 680

(R)-2-amino-N-(1-(4'-carbamoyl-3'-fluoro-[1,1'-biphenyl]-4-carbonyl)pyrrolidin-3-yl)-5-(1-methyl-1H-pyrazol-4-yl)nicotinamide Using (4-carbamoyl-3-fluorophenyl)boronic acid, the title compound was obtained as described in general method G.; MS (ESI, m/z): 528.2 [M+H]$^+$ Example 681

(R,E)-2-amino-5-(1-methyl-1H-pyrazol-4-yl)-N-(1-(4-(3-oxobut-1-en-1-yl)benzoyl)pyrrolidin-3-yl)nicotinamide Using (E)-4-(3-oxobut-1-en-1-yl)benzoic acid, the title compound was obtained as described in general method G. $^1$H NMR (600 MHz, METHANOL-d$_4$) δ ppm 2.07-2.23 (m, 1H) 2.29-2.40 (m, 1H) 2.38 (s, 3H) 3.50 (br dd, J=11.15, 5.28 Hz, 0.5H) 3.60-3.69 (m, 1H) 3.69-3.76 (m, 1H) 3.78-3.87 (m, 0.5H) 3.89-4.01 (m, 1H) 3.93 (d, J=4.70 Hz, 3H) 4.50-4.56 (m, 0.5H) 4.64-4.73 (m, 0.5H) 6.81-6.88 (m, 1H) 7.59 (dd, J=14.38, 8.51 Hz, 2H) 7.65 (dd, J=16.43, 7.63 Hz, 1H) 7.70-7.76 (m, 2H) 7.87-7.92 (m, 1H) 8.04 (d, J=16.43 Hz, 1H) 8.23 (dd, J=18.78, 2.35 Hz, 1H) 8.60-8.74 (m, 1H); MS (ESI, m/z): 649.2 [M+H]$^+$ Example 682

2-amino-N-((3S,4R)-1-(2'-chloro-4'-fluoro-[1,1'-biphenyl]-4-carbonyl)-4-fluoropyrrolidin-3-yl)-5-(1-methyl-1H-pyrazol-4-yl)nicotinamide Using tert-butyl (3S,4R)-3-amino-4-fluoropyrrolidine-1-carboxylate and (2-chloro-4-fluorophenyl)boronic acid, the title compound was obtained as described in general method G. $^1$H NMR (600 MHz, METHANOL-d$_4$) δ ppm 3.72-3.87 (m, 2H) 3.93 (d, J=11.15 Hz, 3H) 3.96-4.18 (m, 2H) 4.72-4.83 (m, 0.5H) 4.85-4.93 (br d, J=8.80 Hz, 0.5H) 5.20-5.44 (m, 1H) 7.15-7.22 (m, 1H) 7.30-7.38 (m, 1H) 7.42 (td, J=8.80, 5.87 Hz, 1H) 7.53 (dd, J=8.22, 2.35 Hz, 2H) 7.62-7.73 (m, 2H) 7.89 (d, J=18.19 Hz, 1H) 8.04 (d, J=17.61 Hz, 1H) 8.26 (dd, J=17.61, 2.35 Hz, 1H) 8.64-8.75 (m, 1H); MS (ESI, m/z): 537.1 [M+H]$^+$ Example 683 methyl (2R,4R)-1-([1,1'-biphenyl]-4-carbonyl)-4-(2-amino-5-(1-methyl-1H-pyrazol-4-yl)nicotinamido)pyrrolidine-2-carboxylate Using 1-(tert-butyl) 2-methyl (2R,4R)-4-aminopyrrolidine-1,2-dicarboxylate and [1,1'-biphenyl]-4-carboxylic acid, the title compound was obtained as described in general method G. $^1$H NMR (600 MHz, METHANOL-d$_4$) δ ppm 2.16-2.23 (m, 1H) 2.78 (td, J=6.60, 2.05 Hz, 1H) 3.73 (dd, J=10.86, 6.75 Hz, 1H) 3.81 (s, 3H) 3.93 (s, 3H) 4.05 (dd, J=10.56, 6.46 Hz, 1H) 4.54-4.62 (m, 1H) 4.75 (dd, J=8.22, 7.04 Hz, 1H) 7.34-7.39 (m, 1H) 7.42-7.48 (m, 2H) 7.63 (d, J=7.42 Hz, 2H) 7.66-7.75 (m, 4H) 7.91 (s, 1H) 8.04 (s, 1H) 8.22 (d, J=1.76 Hz, 1H) 8.61 (d, J=2.35 Hz, 1H); MS (ESI, m/z): 525.2 [M+H]$^+$ Example 684

Methyl (2R,4R)-1-([1,1'-biphenyl]-3-carbonyl)-4-(2-amino-5-(1-methyl-1H-pyrazol-4-yl)nicotinamido)pyrrolidine-2-carboxylate Using 1-(tert-butyl) 2-methyl (2R,4R)-4-aminopyrrolidine-1,2-dicarboxylate and [1,1'-biphenyl]-3-carboxylic acid, the title compound was obtained as described in general method G. $^1$H NMR (600 MHz, METHANOL-d$_4$) δ ppm 2.15-2.25 (m, 1H) 2.71-2.81 (m, 1H) 3.69-3.78 (m, 1H) 3.82 (s, 3H) 3.92 (s, 3H) 3.96-4.04 (m, 1H) 4.54-4.63 (m, 1H) 4.75 (br t, J=7.04 Hz, 1H) 7.35 (br d, J=7.63 Hz, 1H) 7.42 (br t, J=7.04 Hz, 2H) 7.54 (br d, J=9.39 Hz, 2H) 7.59 (br s, 2H) 7.73 (br s, 1H) 7.75-7.83 (m, 1H) 7.87 (br s, 1H) 8.00 (br s, 1H) 8.18 (br s, 1H) 8.59 (br s, 1H); MS (ESI, m/z): 525.2 [M+H]$^+$ Example 685 methyl (2S,4S)-1-([1,1'-biphenyl]-4-carbonyl)-4-(2-amino-5-(1-methyl-1H-pyrazol-4-yl)nicotinamido)pyrrolidine-2-carboxylate Using 1-(tert-butyl) 2-methyl (2R,4S)-4-aminopyrrolidine-1,2-dicarboxylate and [1,1'-biphenyl]-4-carboxylic acid, the title compound was obtained as described in general method G. $^1$H NMR (600 MHz, METHANOL-d$_4$) δ ppm 2.16-2.24 (m, 1H) 2.75-2.83 (m, 1H) 3.74 (dd, J=11.15, 6.46 Hz, 1H) 3.81 (s, 3H) 3.94 (s, 3H) 4.06 (dd, J=10.86, 6.16 Hz, 1H) 4.57-4.63 (m, 1H) 4.76 (dd, J=8.80, 7.04 Hz, 1H) 7.34-7.39 (m, 1H) 7.45 (t, J=7.92 Hz, 2H) 7.63-7.67 (m, 2H) 7.67-7.76 (m, 4H) 7.92 (s, 1H) 8.05 (s, 1H) 8.23 (d, J=2.35 Hz, 1H) 8.63 (d, J=2.35 Hz, 1H); MS (ESI, m/z): 525.2 [M+H]$^+$ Example 686 methyl (2S,4S)-1-([1,1'-biphenyl]-3-carbonyl)-4-(2-amino-5-(1-methyl-1H-pyrazol-4-yl)nicotinamido)pyrrolidine-2-carboxylate Using 1-(tert-butyl) 2-methyl (2R,4S)-4-aminopyrrolidine-1,2-dicarboxylate and [1,1'-biphenyl]-3-carboxylic acid, the title compound was obtained as described in general method G. $^1$H NMR (600 MHz, METHANOL-d$_4$) δ ppm 2.15-2.25 (m, 1H) 2.75-2.83 (m, 1H) 3.73 (dd, J=11.15, 6.46 Hz, 1H) 3.82 (s, 3H) 3.93 (s, 3H) 4.02 (dd, J=10.86, 6.16 Hz, 1H) 4.59 (t, J=6.75 Hz, 1H) 4.77 (dd, J=8.80, 6.46 Hz, 1H) 7.33-7.39 (m, 1H) 7.41-7.47 (m, 2H) 7.50-7.59 (m, 2H) 7.61-7.64 (m, 2H) 7.76 (dt, J=7.04, 1.76 Hz, 1H) 7.79-7.85 (m, 1H) 7.91 (s, 1H) 8.02-8.06 (m, 1H) 8.22 (d, J=2.35 Hz, 1H) 8.61 (d, J=1.76 Hz, 1H); MS (ESI, m/z): 525.2 [M+H]$^+$ Example 687 ethyl 1-([1,1'-biphenyl]-4-carbonyl)-4-(2-amino-5-(1-methyl-1H-pyrazol-4-yl)nicotinamido)pyrrolidine-3-carboxylate Using 1-(tert-butyl) 3-ethyl 4-aminopyrrolidine-1,3-dicarboxylate and [1,1'-biphenyl]-4-carboxylic acid, the title compound was obtained as described in general method G. $^1$H NMR (600 MHz, METHANOL-d$_4$) δ ppm 1.20 (t, J=7.04 Hz, 1.5H) 1.27 (t, J=7.04 Hz, 1.5H) 3.38 (br d, J=7.63 Hz, 1H) 3.61-3.73 (m, 1H) 3.92-3.96 (m, 3H) 3.92-4.02 (m, 1H) 4.05-4.14 (m, 2H) 4.15-4.18 (m, 1H) 4.19-4.26 (m, 1H) 4.82 (br d, J=7.04 Hz, 0.5H) 4.93-4.98 (m, 0.5H) 7.35-7.41 (m, 1H) 7.43-7.48 (m, 2H) 7.65 (dd, J=11.44, 8.51 Hz, 4H) 7.73 (dd, J=12.03, 8.51 Hz, 2H) 7.86-7.95 (m, 1H) 8.01-8.08 (m, 1H) 8.21-8.30 (m, 1H) 8.59-8.72 (m, 1H); MS (ESI, m/z): 539.2 [M+H]$^+$ Example 688 ethyl 1-([1,1'-biphenyl]-3-carbonyl)-4-(2-amino-5-(1-methyl-1H-pyrazol-4-yl)nicotinamido)pyrrolidine-3-carboxylate Using 1-(tert-butyl) 3-ethyl 4-aminopyrrolidine-1,3-dicarboxylate and [1,1'-biphenyl]-3-carboxylic acid, the title compound was obtained as described in general method G. MS (ESI, m/z): 539.2 [M+H]$^+$ Example 689 methyl (2R,4R)-4-(2-amino-5-(1-methyl-1H-pyrazol-4-yl)nicotinamido)-1-(2'-chloro-4'-fluoro-[1,1'-biphenyl]-4-carbonyl)pyrrolidine-2-carboxylate Using 1-(tert-butyl) 2-methyl (2R,4R)-4-aminopyrrolidine-1,2-dicarboxylate and (2-chloro-4-fluorophenyl)boronic acid, the title compound was obtained as described in general method G. $^1$H NMR (600 MHz, METHANOL-d$_4$) δ ppm 2.16-2.25 (m, 1H) 2.75-2.85 (m, 1H) 3.74 (dd, J=11.15, 6.46 Hz, 1H) 3.80-3.85 (s, 3H) 3.94 (s, 3H) 4.06 (dd, J=10.56, 6.46 Hz, 1H) 4.61 (t, J=6.75 Hz, 1H) 4.74-4.79 (m, 1H) 7.17 (td, J=8.36, 2.64 Hz, 1H) 7.34 (dd, J=8.80, 2.35 Hz, 1H) 7.41 (dd, J=8.51, 6.16 Hz, 1H) 7.52 (d, J=8.22 Hz, 2H) 7.67-7.72 (m, 2H) 7.92 (s, 1H) 8.05 (s, 1H) 8.23 (d, J=1.76 Hz, 1H) 8.62 (d, J=2.35 Hz, 1H); MS (ESI, m/z): 577.2 [M+H]$^+$ Example 690 ethyl 4-(2-amino-5-(1-methyl-1H-pyrazol-4-yl)nicotinamido)-1-(2'-chloro-4'-fluoro-[1,1'-biphenyl]-4-carbonyl)pyrrolidine-3-carboxylate Using 1-(tert-butyl) 3-ethyl 4-aminopyrrolidine-1,3-dicarboxylate and (2-chloro-4-fluorophenyl)boronic acid, the title compound was obtained as described in general method G. MS (ESI, m/z): 591.1 [M+H]$^+$ Example 691

(R)-2-amino-N-(1-(2'-chloro-5'-fluoro-3-methyl-[1,1'-biphenyl]-4-carbonyl)pyrrolidin-3-yl)-5-(1-methyl-1H-pyrazol-4-yl)nicotinamide Using 4-bromo-2-methylbenzoic acid and (2-chloro-5-fluorophenyl)boronic acid, the title compound was obtained as described in general method G. $^1$H NMR (600 MHz, METHANOL-d$_4$) δ ppm 2.07-2.21 (m, 1H) 2.30-2.45 (m, 1H) 2.36 (d, J=16.43 Hz, 3H) 3.36-3.44 (m, 0.5H) 3.45-3.52 (m, 0.5H) 3.64-3.70 (m, 1H) 3.72-3.78 (m, 0.5H) 3.87-3.92 (m, 0.5H) 3.94 (d, J=5.87 Hz, 3H) 4.05 (dd, J=12.91, 7.04 Hz, 1H) 4.56 (t, J=6.46 Hz, 0.5H) 4.66-4.72 (m, 0.5H) 7.08-7.20 (m, 2H) 7.27-7.42 (m, 3H) 7.51 (dt, J=8.80, 5.28 Hz, 1H) 7.90 (d, J=14.67 Hz, 1H) 8.05 (d, J=13.50 Hz, 1H) 8.25 (dd, J=13.50, 2.35 Hz, 1H) 8.62-8.74 (m, 1H); MS (ESI, m/z): 533.1 [M+H]$^+$ Example 692

(R)-2-amino-N-(1-(2'-chloro-5'-fluoro-2-methyl-[1,1'-biphenyl]-4-carbonyl)pyrrolidin-3-yl)-5-(1-methyl-1H-pyrazol-4-yl)nicotinamide Using 4-bromo-3-methylbenzoic acid and (2-chloro-5-fluorophenyl)boronic acid, the title compound was obtained as described in general method G. $^1$H NMR (600 MHz, METHANOL-d$_4$) δ ppm 2.08-2.21 (m, 4H) 2.28-2.44 (m, 1H) 3.55 (dd, J=11.15, 5.28 Hz, 0.5H) 3.65-3.72 (m, 1H) 3.72-3.80 (m, 1H) 3.81-3.90 (m, 0.5H) 3.91-3.95 (m, 3H) 3.95-4.04 (m, 1H) 4.54-4.60 (m, 0.5H) 4.66-4.74 (m, 0.5H) 7.04 (ddd, J=8.80, 7.04, 2.93 Hz, 1H) 7.17 (tt, J=8.51, 3.23 Hz, 1H) 7.19-7.25 (m, 1H) 7.42-7.55 (m, 3H) 7.91 (d, J=15.26 Hz, 1H) 8.05 (d, J=14.09 Hz, 1H) 8.24 (dd, J=16.43, 1.76 Hz, 1H) 8.63-8.77 (m, 1H); MS (ESI, m/z): 533.1 [M+H]$^+$ Example 693

(R)-2-amino-N-(1-(2',3-dichloro-5'-fluoro-[1,1'-biphenyl]-4-carbonyl)pyrrolidin-3-yl)-5-(1-methyl-1H-pyrazol-4-yl)nicotinamide Using 4-bromo-2-chlorobenzoic acid and (2-chloro-5-fluorophenyl)boronic acid, the title compound was obtained as described in general method G. $^1$H NMR (600 MHz, METHANOL-d₄) δ ppm 2.10-2.22 (m, 1H) 2.32-2.47 (m, 1H) 3.33-3.38 (m, 0.5H) 3.42-3.48 (m, 0.5H) 3.49-3.56 (m, 0.5H) 3.65-3.72 (m, 1H) 3.72-3.80 (m, 0.5H) 3.69-3.92 (m, 0.5H) 3.94 (d, J=5.28 Hz, 3H) 4.04 (dd, J=12.62, 6.75 Hz, 0.5H) 4.55-4.61 (m, 0.5H) 4.65-4.71 (m, 0.5H) 7.14-7.24 (m, 2H) 7.47-7.51 (m, 2H) 7.54 (dt, J=8.80, 5.28 Hz, 1H) 7.59 (d, J=17.02 Hz, 1H) 7.89 (d, J=12.33 Hz, 1H) 8.04 (d, J=10.56 Hz, 1H) 8.24 (dd, J=12.03, 2.05 Hz, 1H) 8.63-8.71 (m, 1H); MS (ESI, m/z): 553.1 [M+H]⁺

Example 694

(R)-2-amino-N-(1-(2',3-dichloro-4'-fluoro-[1,1'-biphenyl]-4-carbonyl)pyrrolidin-3-yl)-5-(1-methyl-1H-pyrazol-4-yl)nicotinamide Using 4-bromo-2-chlorobenzoic acid and (2-chloro-4-fluorophenyl)boronic acid, the title compound was obtained as described in general method G. ¹H NMR (600 MHz, METHANOL-d₄) δ ppm 2.10-2.22 (m, 1H) 2.32-2.47 (m, 1H) 3.35 (br dd, J=10.86, 4.99 Hz, 0.5H) 3.42-3.56 (m, 1H) 3.66-3.73 (m, 1H) 3.73-3.79 (m, 0.5H) 3.89-3.93 (m, 0.5H) 3.94 (d, J=4.70 Hz, 3H) 4.04 (dd, J=12.91, 7.04 Hz, 0.5H) 4.57 (br t, J=6.16 Hz, 0.5H) 4.65-4.72 (m, 0.5H) 7.19 (tdd, 1H) 7.37 (ddd, J=8.51, 5.58, 2.35 Hz, 1H) 7.40-7.45 (m, 1H) 7.45-7.52 (m, 2H) 7.56 (d, J=17.02 Hz, 1H) 7.90 (d, J=12.33 Hz, 1H) 8.04 (d, J=10.56 Hz, 1H) 8.24 (dd, J=12.03, 2.05 Hz, 1H) 8.62-8.71 (m, 1H); MS (ESI, m/z): 553.1 [M+H]⁺

Example 695

(R)-2-amino-N-(1-(1-methyl-1H-indole-2-carbonyl)pyrrolidin-3-yl)-5-(1-methyl-1H-pyrazol-4-yl)nicotinamide Using 1-methyl-1H-indole-2-carboxylic acid, the title compound was obtained as described in general method G. ¹H NMR (600 MHz, METHANOL-d₄) δ ppm 2.07-2.21 (m, 1H) 2.35 (br s, 1H) 3.67 (br d, J=12.91 Hz, 0.5H) 3.71-3.77 (m, 1H) 3.81 (m, 4.5H) 3.90 (br s, 3H) 4.01 (br s, 0.5H) 4.11 (br s, 0.5H) 4.46-4.58 (m, 0.5H) 4.64 (br s, 0.5H) 6.75-6.88 (m, 1H) 7.06 (br d, J=7.04 Hz, 1H) 7.23 (br s, 1H) 7.28-7.41 (m, 1H) 7.55 (br t, J=9.10 Hz, 1H) 7.84 (br d, J=19.96 Hz, 1H) 7.98 (br d, J=19.96 Hz, 1H) 8.06-8.17 (m, 1H) 8.50-8.66 (m, 1H); MS (ESI, m/z): 444.2 [M+H]⁺

Example 696

(R)-2-amino-N-(1-(5-fluoro-1H-indole-2-carbonyl)pyrrolidin-3-yl)-5-(1-methyl-1H-pyrazol-4-yl)nicotinamide Using 5-fluoro-1H-indole-2-carboxylic acid, the title compound was obtained as described in general method G. ¹H NMR (600 MHz, METHANOL-d₄) δ ppm 2.09-2.26 (m, 1H) 2.27-2.44 (m, 1H) 3.72 (br d, J=11.74 Hz, 1H) 3.83 (br d, J=5.28 Hz, 3.5H) 3.87-3.98 (m, 1.5H) 4.03 (br d, J=7.04 Hz, 0.5H) 4.20 (br s, 0.5H) 4.54-4.67 (m, 1H) 6.85 (br d, J=14.09 Hz, 1H) 6.94 (dt, J=18.05, 8.88 Hz, 1H) 7.18 (br s, 1H) 7.26-7.38 (m, 1H) 7.79 (br d, J=8.80 Hz, 1H) 7.90 (br d, J=10.56 Hz, 1H) 8.05-8.11 (m, 1H) 8.59 (br s, 1H); MS (ESI, m/z): 448.1 [M+H]⁺

Example 697

(R)—N-(1-(1H-indole-2-carbonyl)pyrrolidin-3-yl)-2-amino-5-(1-methyl-1H-pyrazol-4-yl)nicotinamide Using 1H-indole-2-carboxylic acid, the title compound was obtained as described in general method G. ¹H NMR (600 MHz, METHANOL-d₄) δ ppm 2.12-2.30 (m, 1H) 2.31-2.47 (m, 1H) 3.78 (br s, 1H) 3.89 (br s, 3.5H) 3.93-4.08 (m, 1.5H) 4.11 (br s, 0.5H) 4.30 (br s, 0.5H) 4.63-4.74 (m, 1H) 7.01 (br s, 1H) 7.02-7.10 (m, 2H) 7.21 (br d, J=7.04 Hz, 1H) 7.39-7.46 (m, 1H) 7.56-7.64 (m, 1H) 7.85 (br s, 1H) 7.91-8.05 (m, 1H) 8.18 (br s, 1H) 8.64 (br d, J=11.74 Hz, 1H); MS (ESI, m/z): 430.1 [M+H]⁺

Example 698

(R)-2-amino-N-(1-(2,3-dimethyl-1H-indole-6-carbonyl)pyrrolidin-3-yl)-5-(1-methyl-1H-pyrazol-4-yl)nicotinamide Using 2,3-dimethyl-1H-indole-6-carboxylic acid, the title compound was obtained as described in general method G. ¹H NMR (600 MHz, METHANOL-d₄) δ ppm 2.06-2.17 (m, 1H) 2.17 (br d, J=8.80 Hz, 3H) 2.24-2.40 (m, 1H) 2.33 (br d, J=9.39 Hz, 3H) 3.55-3.64 (m, 0.5H) 3.65-3.83 (m, 2.5H) 3.91 (br s, 3H) 3.96 (br d, J=8.80 Hz, 1H) 4.45-4.69 (m, 1H) 7.05-7.20 (m, 1H) 7.30-7.46 (m, 2H) 7.79-7.90 (m, 1H) 7.92-8.02 (m, 1H) 8.03-8.22 (m, 1H) 8.48-8.68 (m, 1H); MS (ESI, m/z): 458.2 [M+H]⁺

Example 699

(R)—N-(1-(1,8-naphthyridine-2-carbonyl)pyrrolidin-3-yl)-2-amino-5-(1-methyl-1H-pyrazol-4-yl)nicotinamide Using 1,8-naphthyridine-2-carboxylic acid, the title compound was obtained as described in general method G. ¹H NMR (600 MHz, METHANOL-d₄) δ ppm 2.17-2.24 (m, 1H) 2.29-2.43 (m, 1H) 3.78-3.89 (m, 1H) 3.92 (d, J=6.46 Hz, 3H) 3.90-3.99 (m, 1H) 4.02-4.13 (m, 1H) 4.19 (br d, J=11.74 Hz, 0.5H) 4.28 (dd, J=12.03, 6.16 Hz, 0.5H) 4.62-4.68 (m, 0.5H) 4.69-4.74 (m, 0.5H) 7.84-7.87 (m, 0.5H) 7.87-7.93 (m, 1H) 7.96 (s, 0.5H) 8.02-8.08 (m, 1H) 8.10 (t, J=8.80 Hz, 1H) 8.23 (dd, J=19.07, 2.05 Hz, 1H) 8.64-8.70 (m, 1.5H) 8.72 (ddd, J=8.07, 6.02, 1.76 Hz, 1H) 8.75 (d, J=2.35 Hz, 0.5H) 9.22 (ddd, J=10.86, 4.40, 1.76 Hz, 1H); MS (ESI, m/z): 443.2 [M+H]⁺

Example 700

(R)—N-(1-(1,6-naphthyridine-2-carbonyl)pyrrolidin-3-yl)-2-amino-5-(1-methyl-1H-pyrazol-4-yl)nicotinamide Using 1,6-naphthyridine-2-carboxylic acid, the title compound was obtained as described in general method G. ¹H NMR (600 MHz, METHANOL-d₄) δ ppm 2.16-2.26 (m, 1H) 2.38 (td, J=13.06, 6.16 Hz, 1H) 3.77-3.89 (m, 1H) 3.92 (d, J=5.87 Hz, 3.5H) 3.93-4.00 (m, 1H) 4.05-4.12 (m, 1H) 4.25 (dd, J=12.03, 6.16 Hz, 0.5H) 4.61-4.67 (m, 0.5H) 4.68-4.73 (m, 0.5H) 7.85-7.92 (m, 1H) 8.04 (d, J=18.78 Hz, 1H) 8.18 (dd, J=8.51, 6.75 Hz, 1H) 8.22 (dd, J=18.19, 2.35 Hz, 1H) 8.32 (dd, J=9.39, 6.46 Hz, 1H) 8.64-8.74 (m, 1H) 8.82-8.85 (m, 1H) 8.87 (d, J=8.95 Hz, 1H) 9.70 (d, J=8.22 Hz, 1H); MS (ESI, m/z): 443.2 [M+H]⁺

Example 701

(R)-2-amino-N-(1-(1-ethyl-1H-indole-2-carbonyl)pyrrolidin-3-yl)-5-(1-methyl-1H-pyrazol-4-yl)nicotinamide Using 1-ethyl-1H-indole-2-carboxylic acid, the title compound was obtained as described in general method G. ¹H NMR (600 MHz, METHANOL-d$_4$) δ ppm 1.31 (dt, J=18.49, 7.19 Hz, 3H) 2.08-2.25 (m, 1H) 2.28-2.47 (m, 1H) 3.68 (br dd, J=12.91, 4.11 Hz, 0.5H) 3.72-3.79 (m, 1H) 3.80-3.95 (m, 1.5H) 3.93 (s, 3H) 4.01-4.15 (m, 1H) 4.30-4.44 (m, 2H) 4.47-4.61 (m, 0.5H) 4.64-4.73 (m, 0.5H) 6.77-6.89 (m, 1H) 7.02-7.14 (m, 1H) 7.25 (q, J=6.85 Hz, 1H) 7.43 (br t, J=9.10 Hz, 1H) 7.59 (br t, J=6.75 Hz, 1H) 7.88 (br d, J=16.43 Hz, 1 H) 8.02 (br d, J=15.26 Hz, 1H) 8.20 (br d, J=17.02 Hz, 1H) 8.58-8.72 (m, 1H); MS (ESI, m/z): 458.2 [M+H]$^+$ Example 702

(R)-2-amino-N-(1-(1-benzyl-1H-indole-2-carbonyl)pyrrolidin-3-yl)-5-(1-methyl-1H-pyrazol-4-yl)nicotinamide Using 1-benzyl-1H-indole-2-carboxylic acid, the title compound was obtained as described in general method G. MS (ESI, m/z): 520.2 [M+H]$^+$ Example 703

(R)-2-amino-N-(1-(7-chloro-1-methyl-4-(trifluoromethyl)-1H-indole-2-carbonyl)pyrrolidin-3-yl)-5-(1-methyl-1H-pyrazol-4-yl)nicotinamide Using 7-chloro-1-methyl-4-(trifluoromethyl)-1H-indole-2-carboxylic acid, the title compound was obtained as described in general method G. $^1$H NMR (600 MHz, METHANOL-d$_4$) δ ppm 2.11-2.25 (m, 1H) 2.29-2.46 (m, 1H) 3.63 (dd, J=11.44, 5.58 Hz, 0.5H) 3.68-3.84 (m, 2H) 3.85-3.90 (m, 0.5H) 3.92 (d, J=6.46 Hz, 3H) 3.97-4.12 (m, 1H) 4.17 (d, J=8.22 Hz, 3H) 4.53-4.61 (m, 0.5H) 4.66-4.73 (m, 0.5H) 6.85-6.94 (m, 1H) 7.33 (d, J=8.75 Hz, 2H) 7.87 (d, J=18.19 Hz, 1H) 8.02 (d, J=17.02 Hz, 1H) 8.14-8.23 (m, 1H) 8.59-8.68 (m, 1H); MS (ESI, m/z): 546.1 [M+H]$^+$ Example 704

(R)-2-amino-N-(1-(7-chloro-4-(trifluoromethyl)-1H-indole-2-carbonyl)pyrrolidin-3-yl)-5-(1-methyl-1H-pyrazol-4-yl)nicotinamide Using 7-chloro-4-(trifluoromethyl)-1H-indole-2-carboxylic acid, the title compound was obtained as described in general method G. $^1$H NMR (600 MHz, METHANOL-d$_4$) δ ppm 2.19 (br s, 1H) 2.35-2.47 (m, 1H) 3.75-3.84 (m, 1H) 3.86-3.95 (m, 1H) 3.90 (s, 3H) 4.04 (br dd, J=12.62, 6.75 Hz, 1H) 4.08 (br s, 0.5H) 4.28 (br dd, J=11.15, 6.46 Hz, 0.5H) 4.65-4.73 (m, 1H) 7.04-7.13 (m, 1H) 7.39 (d, J=7.04 Hz, 2H) 7.86 (d, J=11.15 Hz, 1H) 8.00 (d, J=10.56 Hz, 1H) 8.20 (dd, J=12.91, 1.76 Hz, 1H) 8.65 (dd, J=18.78, 1.76 Hz, 1H); MS (ESI, m/z): 532.1 [M+H]$^+$ Example 705

2-amino-5-(1-methyl-1H-pyrazol-4-yl)-N—((R)-1-((1S,2S)-2-phenylcyclopropane-1-carbonyl)pyrrolidin-3-yl)nicotinamide Using (1S,2S)-2-phenylcyclopropane-1-carboxylic acid, the title compound was obtained as described in general method G. MS (ESI, m/z): 431.2 [M+H]$^+$ Example 706

(R)-2-amino-N-(1-(6-hydroxy-2-naphthoyl)pyrrolidin-3-yl)-5-(1-methyl-1H-pyrazol-4-yl)nicotinamide Using 6-hydroxy-2-naphthoic acid, the title compound was obtained as described in general method G. $^1$H NMR (600 MHz, METHANOL-d$_4$) δ ppm 2.05-2.22 (m, 1H) 2.24-2.46 (m, 1H) 3.59 (dd, J=11.15, 4.70 Hz, 0.5H) 3.70 (br dd, J=12.62, 4.99 Hz, 1H) 3.72-3.83 (m, 1H) 3.87-3.90 (m, 0.5H) 3.92 (d, J=8.80 Hz, 3H) 3.95-4.06 (m, 1H) 4.49-4.55 (m, 0.5H) 4.64-4.71 (m, 0.5H) 7.05-7.16 (m, 2H) 7.46-7.55 (m, 1H) 7.67 (dd, J=18.19, 8.80 Hz, 1H) 7.71-7.80 (m, 1H) 7.82-7.90 (m, 1H) 7.90-7.97 (m, 1H) 7.97-8.05 (m, 1H) 8.12-8.26 (m, 1H) 8.55-8.73 (n, 1H); MS (ESI, m/z): 457.2 [M+H]$^+$ Example 707

(R)-2-amino-N-(1-(3-(4-fluorophenyl)-2,4-dioxo-1,2,3,4-tetrahydropyrimidine-5-carbonyl)pyrrolidin-3-yl)-5-(1-methyl-1H-pyrazol-4-yl)nicotinamide Using 3-(4-fluorophenyl)-2,4-dioxo-1,2,3,4-tetrahydropyrimidine-5-carboxylic acid, the title compound was obtained as described in general method G. $^1$H NMR (600 MHz, METHANOL-d$_4$) δ ppm 2.11 (br dd, J=13.21, 4.99 Hz, 1H) 2.23-2.38 (m, 1H) 3.58-3.66 (m, 1.5H) 3.69-3.76 (m, 1H) 3.79 (dt, J=12.47, 7.85 Hz, 1H) 3.83-3.88 (m, 0.5H) 3.89 (d, J=1.76 Hz, 3H) 4.53-4.65 (m, 1H) 7.08 (br t, J=8.22 Hz, 1H) 7.21 (br t, J=8.22 Hz, 1H) 7.24 (br s, 1H) 7.30 (dd, J=8.80, 4.70 Hz, 1H) 7.74 (s, 0.5H) 7.82 (d, J=6.46 Hz, 1H) 7.85 (d, J=9.98 Hz, 1H) 7.98 (s, 0.5H) 8.20 (dd, J=17.90, 2.05 Hz, 1H) 8.55-8.63 (m, 1H); MS (ESI, m/z): 519.2 [M+H]$^+$ Example 708

(R)-2-amino-N-(1-(5-bromobenzo[b]thiophene-2-carbonyl)pyrrolidin-3-yl)-5-(1-methyl-1H-pyrazol-4-yl)nicotinamide Using 5-bromobenzo[b]thiophene-2-carboxylic acid, the title compound was obtained as described in general method G. $^1$H NMR (600 MHz, METHANOL-d$_4$) δ ppm 2.17-2.29 (m, 1H) 2.36-2.49 (m, 1H) 3.75 (br dd, J=12.91, 4.11 Hz, 0.5H) 3.77-3.83 (m, 0.5H) 3.86-3.93 (m, 1H) 3.94 (s, 3H) 4.01-4.08 (m, 0.5H) 4.08-4.15 (m, 0.5H) 4.31 (br dd, J=10.86, 6.16 Hz, 1H) 4.67-4.74 (m, 1H) 7.52-7.57 (m, 1H) 7.78-7.84 (m, 2H) 7.87 (d, J=9.39 Hz, 1H) 8.00 (d, J=8.22 Hz, 1H) 8.06 (s, 1H) 8.22 (br d, J=7.04 Hz, 1H) 8.70 (d, J=22.30 Hz, 1H); MS (ESI, m/z): 525.0/527.0 [M+H]$^+$ Example 709

(R)-2-amino-5-(1-methyl-1H-pyrazol-4-yl)-N-(1-(1-(piperidin-4-ylmethyl)-1H-indole-5-carbonyl)pyrrolidin-3-yl)nicotinamide Using 1-((1-(tert-butoxycarbonyl)piperidin-4-yl)methyl)-1H-indole-5-carboxylic acid and trifluoroacetic acid, the title compound was obtained as described in general method G. MS (ESI, m/z): 527.3 [M+H]$^+$

Example 710

(R)—N-(1-(1H-indole-3-carbonyl)pyrrolidin-3-yl)-2-amino-5-(1-methyl-1H-pyrazol-4-yl)nicotinamide Using 1H-indole-3-carboxylic acid, the title compound was obtained as described in general method G. MS (ESI, m/z): 430.2 [M+H]$^+$

Example 711

(R)-2-amino-5-(1-methyl-1H-pyrazol-4-yl)-N-(1-(4'-(morpholinomethyl)-[1,1'-biphenyl]-4-carbonyl)pyrrolidin-3-yl)nicotinamide Using (4-(morpholinomethyl)phenyl)boronic acid, the title compound was obtained as described in general method G. $^1$H NMR (600 MHz, METHANOL-d$_4$) δ ppm 2.04-2.20 (m, 1H) 2.23-2.39 (m, 1H) 2.47 (br s, 4H) 2.80-2.83 (m, 2H) 3.50-3.54 (m, 0.5H) 3.55 (d, J=5.28 Hz, 1H) 3.62-3.66 (m, 2H) 3.66-3.70 (m, 2H) 3.70-3.76 (m, 1H) 3.81-3.87 (m, 0.5H) 3.90 (d, J=5.28 Hz, 3H) 3.94 (br s, 0.5H) 3.99 (dd, J=12.91, 7.04 Hz, 0.5H) 4.47-4.53 (m, 0.5H) 4.62-4.69 (m, 0.5H) 7.43 (t, J=7.92 Hz, 2H) 7.55-7.66 (m, 4H) 7.67-7.73 (m, 2H) 7.79 (d, J=18.19 Hz, 1H) 7.90 (d, J=17.02 Hz, 1H) 8.09 (dd, J=45.78, 2.35 Hz, 1H) 8.25 (dd, J=18.78, 2.35 Hz, 1H); MS (ESI, m/z): 566.3 [M+H]$^+$

Example 712

(R)-2-amino-5-(1-methyl-1H-pyrazol-4-yl)-N-(1-(3'-(1-methyl-1H-tetrazol-5-yl)-[1,1'-biphenyl]-4-carbonyl)pyrrolidin-3-yl)nicotinamide Using (3-(1-methyl-1H-tetrazol-5-yl)phenyl)boronic acid, the title compound was obtained as described in general method G. $^1$H NMR (600 MHz, METHANOL-d$_4$) δ ppm 2.08-2.24 (m, 1H) 2.27-2.43 (m, 1H) 3.53-3.59 (m, 0.5H) 3.65-3.80 (m, 2H) 3.84-3.91 (m, 0.5H) 3.93 (d, J=7.04 Hz, 3H) 3.95-4.05 (m, 1H) 4.43 (d, J=3.52 Hz, 3H) 4.51-4.57 (m, 0.5H) 4.66-4.74 (m, 0.5H) 7.62 (td, J=7.63, 5.28 Hz, 1H) 7.69 (dd, J=15.85, 8.22 Hz, 2H) 7.75-7.82 (m, 3H) 7.86 (d, J=19.96 Hz, 1H) 7.99 (d, J=19.96 Hz, 1H) 8.08-8.13 (m, 1H) 8.21-8.28 (m, 1H) 8.38 (dt, J=6217.70, 6.80 Hz, 1H) 8.44 (dd, J=54.00, 2.35 Hz, 1H); MS (ESI, m/z): 549.2 [M+H]$^+$

Example 713

(R)—N-(1-(3'-(1H-tetrazol-5-yl)-[1,1'-biphenyl]-4-carbonyl)pyrrolidin-3-yl)-2-amino-5-(1-methyl-1H-pyrazol-4-yl)nicotinamide Using (3-(1H-tetrazol-5-yl)phenyl)boronic acid, the title compound was obtained as described in general method G. $^1$H NMR (600 MHz, METHANOL-d$_4$) δ ppm 2.06-2.20 (m, 1H) 2.28 (br d, J=7.04 Hz, 1H) 3.53-3.59 (m, 0.5H) 3.63-3.71 (m, 1H) 3.71-3.80 (m, 1H) 3.84 (br s, 0.5H) 3.90 (d, J=7.04 Hz, 3H) 3.92-4.05 (m, 1H) 4.49-4.56 (m, 0.5H) 4.68 (br d, J=5.87 Hz, 0.5H) 7.56 (td, J=7.78, 4.99 Hz, 1H) 7.61-7.74 (m, 3H) 7.74-7.85 (m, 3H) 7.90 (d, J=19.37 Hz, 1H) 8.03-8.06 (m, 1H) 8.12 (dd, J=46.95, 2.35 Hz, 1H) 8.26 (br dd, J=19.66, 2.05 Hz, 1H) 8.36 (br d, J=5.87 Hz, 1H); MS (ESI, m/z): 535.2 [M+H]$^+$

Example 714

(R)-2-amino-N-(1-(3'-(5-methyl-1,2,4-oxadiazol-3-yl)-[1,1'-biphenyl]-4-carbonyl)pyrrolidin-3-yl)-5-(1-methyl-1H-pyrazol-4-yl)nicotinamide Using (3-(5-methyl-1,2,4-oxadiazol-3-yl)phenyl)boronic acid, the title compound was obtained as described in general method G. $^1$H NMR (600 MHz, METHANOL-d$_4$) δ ppm 2.06-2.20 (m, 1H) 2.26-2.41 (m, 1H) 2.66 (d, J=3.52 Hz, 3H) 3.55 (br dd, J=11.15, 5.28 Hz, 0.5H) 3.63-3.71 (m, 1H) 3.72-3.80 (m, 1H) 3.81-3.89 (m, 0.5H) 3.91 (d, J=5.87 Hz, 3H) 3.92-4.04 (m, 1H) 4.51 (br t, J=5.87 Hz, 0.5H) 4.65-4.71 (m, 0.5H) 7.59-7.64 (m, 1H) 7.68 (dd, J=17.61, 8.22 Hz, 2H) 7.74-7.82 (m, 3H) 7.82-7.86 (m, 1H) 7.91 (d, J=16.43 Hz, 1H) 8.04 (dd, J=7.04, 5.87 Hz, 1H) 8.10 (dd, J=45.78, 2.35 Hz, 1H) 8.26 (br d, J=18.78 Hz, 1H) 8.31 (br d, J=5.87 Hz, 1H); MS (ESI, m/z): 549.2 [M+H]$^+$

Example 715

(R)-2-amino-N-(1-(2'-chloro-4'-fluoro-2-methyl-[1,1'-biphenyl]-4-carbonyl)pyrrolidin-3-yl)-5-(1-methyl-1H-pyrazol-4-yl)nicotinamide Using 4-bromo-3-methylbenzoic acid and (2-chloro-4-fluorophenyl)boronic acid, the title compound was obtained as described in general method G. $^1$H NMR (600 MHz, METHANOL-d$_4$) δ ppm 2.09-2.21 (m, 1H) 2.14 (d, J=7.63 Hz, 3H) 2.31-2.45 (m, 1H) 3.57 (br dd, J=11.15, 4.70 Hz, 0.5H) 3.67-3.73 (m, 1H) 3.75-3.82 (m, 1H) 3.84-3.90 (m, 0.5H) 3.96 (d, J=2.35 Hz, 3H) 3.97-4.07 (m, 1H) 4.55-4.62 (m, 0.5H) 4.68-4.75 (m, 0.5H) 7.14-7.20 (m, 1H) 7.21 (t, J=7.92 Hz, 1H) 7.25-7.31 (m, 1H) 7.34-7.38 (m, 1H) 7.45 (br dd, J=13.79, 7.92 Hz, 1H) 7.50 (br d, J=11.74 Hz, 1H) 7.92 (d, J=15.26 Hz, 1H) 8.07 (d, J=13.50 Hz, 1H) 8.26 (d, J=15.85 Hz, 1H) 8.73 (dd, J=39.32, 2.35 Hz, 1H); MS (ESI, m/z): 533.2 [M+H]$^+$

Example 716

(R)-2-amino-N-(1-(2-chloro-4-fluorobenzoyl)pyrrolidin-3-yl)-5-(1-methyl-1H-pyrazol-4-yl)nicotinamide Using 2-chloro-4-fluorobenzoic acid, the title compound was obtained as described in general method G. MS (ESI, m/z): 443.1 [M+H]$^+$

Example 717

(R)-2-amino-5-(1-methyl-1H-pyrazol-4-yl)-N-(1-(3-(1-(phenylsulfonyl)-1H-pyrazol-4-yl)benzoyl)pyrrolidin-3-yl)nicotinamide Using 3-bromobenzoic acid and (1-(phenylsulfonyl)-1H-pyrazol-4-yl)boronic acid, the title compound was obtained as described in general method G. MS (ESI, m/z): 597.2 [M+H]$^+$

Example 718

(R)-2-amino-N-(1-(4-(2-chlorophenoxy)benzoyl)pyrrolidin-3-yl)-5-(1-methyl-1H-pyrazol-4-yl)nicotinamide Using 4-(2-chlorophenoxy)benzoic acid, the title compound was obtained as described in general method G. $^1$H NMR (600 MHz, METHANOL-$d_4$) δ ppm 2.06-2.22 (m, 1H) 2.26-2.41 (m, 1H) 3.54 (dd, J=11.15, 5.28 Hz, 0.5H) 3.61-3.70 (m, 1H) 3.70-3.77 (m, 1H) 3.77-3.85 (m, 0.5H) 3.93 (s, 3H) 3.94-4.02 (m, 1H) 4.51-4.56 (m, 0.5H) 4.65-4.70 (m, 0.5H) 6.93 (t, J=8.51 Hz, 2H) 7.14 (t, J=6.46 Hz, 1H) 7.23 (t, J=7.81 Hz, 1H) 7.30-7.41 (m, 1H) 7.49-7.54 (m, 1H) 7.57 (dd, J=13.79, 8.51 Hz, 2H) 7.89 (d, J=14.09 Hz, 1H) 8.04 (d, J=12.91 Hz, 1H) 8.23 (dd, J=14.97, 2.05 Hz, 1H) 8.61-8.75 (m, 1H); MS (ESI, m/z): 517.2 [M+H]$^+$

Example 719

(R)-2-amino-N-(1-(4-(2-chloro-4-fluorophenoxy)benzoyl)pyrrolidin-3-yl)-5-(1-methyl-1H-pyrazol-4-yl)nicotinamide Using 4-(2-chloro-4-fluorophenoxy)benzoic acid, the title compound was obtained as described in general method G. $^1$H NMR (600 MHz, METHANOL-$d_4$) δ ppm 2.06-2.19 (m, 1H) 2.26-2.40 (m, 1H) 3.53 (br dd, J=11.44, 4.99 Hz, 0.5H) 3.62-3.69 (m, 1H) 3.69-3.77 (m, 1H) 3.78-3.88 (m, 0.5H) 3.94 (s, 3H) 3.95-4.01 (m, 1H) 4.51-4.56 (m, 0.5H) 4.65-4.70 (m, 0.5H) 6.94 (t, J=7.85 Hz, 2H) 7.12-7.18 (m, 1H) 7.18-7.24 (m, 1H) 7.35-7.43 (m, 1H) 7.57 (dd, J=12.91, 8.80 Hz, 2H) 7.90 (d, J=14.09 Hz, 1H) 8.04 (d, J=12.91 Hz, 1H) 8.24 (dd, J=14.38, 2.05 Hz, 1H) 8.60-8.72 (m, 1H); MS (ESI, m/z): 535.2 [M+H]$^+$

Example 720

(R)-2-amino-N-(1-(6-(benzyl(1-methylpiperidin-4-yl)amino)-2-naphthoyl)pyrrolidin-3-yl)-5-(1-methyl-1H-pyrazol-4-yl)nicotinamide Using 6-(benzyl(1-methylpiperidin-4-yl)amino)-2-naphthoic acid, the title compound was obtained as described in general method G. $^1$H NMR (600 MHz, METHANOL-$d_4$) δ ppm 1.20 (br t, J=6.16 Hz, 3H) 1.51 (s, 6H) 1.58 (s, 6H) 2.04-2.15 (m, 2.5H) 2.19 (br d, J=12.91 Hz, 2.5H) 2.28-2.44 (m, 1H) 2.86 (s, 3H) 3.53-3.63 (m, 2.5H) 3.71 (br dd, J=12.62, 4.99 Hz, 1H) 3.74-3.83 (m, 1H) 3.88 (br d, J=6.46 Hz, 0.5H) 3.93 (br d, J=5.28 Hz, 3H) 3.96-4.08 (m, 1H) 4.39 (br t, J=11.44 Hz, 1H) 4.51-4.59 (m, 0.5H) 4.67-4.74 (m, 0.5H) 7.40 (br s, 1H) 7.45 (br s, 1H) 7.55-7.62 (m, 1H) 7.82 (br t, J=8.22 Hz, 1H) 7.89 (d, J=22.89 Hz, 1H) 7.93 (br t, J=7.92 Hz, 1H) 8.00 (br d, J=15.85 Hz, 1H) 8.04 (d, J=20.54 Hz, 1H) 8.22 (d, J=24.65 Hz, 1H) 8.66 (d, J=56.34 Hz, 1H); MS (ESI, m/z): 643.3 [M+H]$^+$

Example 721

(R)-2-amino-N-(1-(6-(ethyl(1,2,2,6,6-pentamethylpiperidin-4-yl)amino)-2-naphthoyl)pyrrolidin-3-yl)-5-(1-methyl-1H-pyrazol-4-yl)nicotinamide Using 6-(ethyl(1,2,2,6,6-pentamethylpiperidin-4-yl)amino)-2-naphthoic acid, the title compound was obtained as described in general method G. $^1$H NMR (600 MHz, METHANOL-$d_4$) δ ppm 1.96 (br d, J=13.50 Hz, 0.5H) 2.11 (br s, 0.5H) 2.20 (br s, 2H) 2.30 (br s, 0.5H) 2.33-2.49 (m, 2.5H) 3.04 (br s, 2H) 3.08 (br s, 1H) 3.43-3.58 (m, 2H) 3.59-3.92 (m, 6H) 3.94 (br s, 3H) 4.03 (br s, 1H) 4.54 (br s, 0.5H) 4.60-4.68 (m, 2H) 4.68-4.74 (m, 0.5H) 6.91 (br s, 1H) 6.98-7.11 (m, 1H) 7.50 (br s, 1H) 7.52-7.61 (m, 4H) 7.62-7.68 (m, 1H) 7.71 (br s, 1H) 7.85-7.97 (m, 2H) 8.04 (br d, J=18.78 Hz, 1H) 8.18-8.29 (m, 1H) 8.59-8.74 (m, 1H) MS (ESI, m/z): 637.4 [M+H]$^+$

Example 722

(R)-2-amino-5-(1-methyl-1H-pyrazol-4-yl)-N-(1-(6-((1,2,2,6,6-pentamethylpiperidin-4-yl)amino)-2-naphthoyl)pyrrolidin-3-yl)nicotinamide Using 6-((1,2,2,6,6-pentamethylpiperidin-4-yl)amino)-2-naphthoic acid, the title compound was obtained as described in general method G. $^1$H NMR (600 MHz, METHANOL-$d_4$) δ ppm 1.50 (s, 6H) 1.61 (s, 6H) 1.74 (br t, J=12.91 Hz, 2H) 2.07-2.23 (m, 1H) 2.29 (br d, J=6.46 Hz, 0.5H) 2.35 (br d, J=13.50 Hz, 2H) 2.37-2.46 (m, 0.5H) 2.87 (s, 3H) 3.58-3.63 (m, 0.5H) 3.67-3.83 (m, 2H) 3.84-3.90 (m, 0.5H) 3.93 (br s, 3H) 3.97-4.09 (m, 2H) 4.50-4.57 (m, 0.5H) 4.65-4.73 (m, 0.5H) 6.87-6.96 (m, 1H) 7.04 (br d, J=6.46 Hz, 1H) 7.49 (br dd, J=12.62, 9.10 Hz, 1H) 7.60-7.74 (m, 2H) 7.86 (br s, 1H) 7.90 (br d, J=5.28 Hz, 1H) 8.03 (br d, J=19.96 Hz, 1H) 8.23 (d, J=27.00 Hz, 1H) 8.70 (d, J=55.17 Hz, 1H) MS (ESI, m/z): 609.4 [M+H]$^+$

Example 723

(R)-2-amino-N-(1-(6-(ethyl(1-methylpiperidin-4-yl)amino)-2-naphthoyl)pyrrolidin-3-yl)-5-(1-methyl-1H-pyrazol-4-yl)nicotinamide Using 6-(ethyl(1-methylpiperidin-4-yl)amino)-2-naphthoic acid, the title compound was obtained as described in general method G. $^1$H NMR (400 MHz, METHANOL-$d_4$) δ ppm 1.34-1.49 (m, 3H) 1.97 (br d, J=5.48 Hz, 2H) 2.09 (br s, 1H) 2.32 (br d, J=12.91 Hz, 2.5H) 2.36-2.47 (m, 0.5H) 3.12 (s, 3H) 3.42-3.68 (m, 6H) 3.70-3.90 (m, 3H) 3.95 (s, 3H) 4.04 (br dd, J=11.93, 6.46 Hz, 1H) 4.56 (br d, J=5.48 Hz, 0.5H) 4.71 (br s, 0.5H) 6.90 (br s, 1H) 7.05 (br d, J=9.39 Hz, 1H) 7.51 (br t, J=7.43 Hz, 1H) 7.64 (br s, 1H) 7.70 (br d, J=5.87 Hz, 1H) 7.89 (s, 1H) 7.92 (br d, J=5.09 Hz, 1H) 8.05 (br d, J=13.30 Hz, 1H) 8.24 (br d, J=16.04 Hz, 1H) 8.60-8.76 (n, 1H); MS (ESI, m/z): 581.3 [M+H]$^+$

Example 724

(R)-2-amino-N-(1-(4'-hydroxy-3',5'-dimethyl-[1,1'-biphenyl]-4-carbonyl)pyrrolidin-3-yl)-5-(1-methyl-1H-pyrazol-4-yl)nicotinamide Using 2,6-dimethyl-4-(4,4,5,5-tetramethyl-1,3,2-dioxaborolan-2-yl)phenol, the title compound was obtained as described in general method G. $^1$H NMR (600 MHz, METHANOL-$d_4$) δ ppm 2.05-2.20 (m, 1H) 2.27 (s, 3H) 2.28 (s, 3H) 2.28-2.41 (m, 1H) 3.56 (br dd, J=11.44, 5.58 Hz, 0.5H) 3.67 (td, J=12.33, 5.87 Hz, 1H) 3.71-3.80 (m, 1H) 3.83-3.89 (m, 0.5H) 3.92 (d, J=5.28 Hz, 3H) 3.94-4.03 (m, 1H) 4.49-4.54 (m, 0.5H) 4.65-4.71 (m, 0.5H) 7.24 (d, J=5.28 Hz, 2H) 7.55-7.61 (m, 2H) 7.61-7.66 (m, 2H) 7.81 (d, J=17.02 Hz, 1H) 7.92 (d, J=15.85 Hz, 1H) 8.13 (dd, J=45.78, 2.35 Hz, 1H) 8.27 (br d, J=17.61 Hz, 1H); MS (ESI, m/z): 511.2 [M+H]$^+$

Example 725

(R)-2-amino-N-(1-(4'-methoxy-3',5'-dimethyl-[1,1'-biphenyl]-4-carbonyl)pyrrolidin-3-yl)-5-(1-methyl-1H-pyrazol-4-yl)nicotinamide Using 2-(4-methoxy-3,5-dimethylphenyl)-4,4,5,5-tetramethyl-1,3,2-dioxaborolane, the title compound was obtained as described in general method G. $^1$H NMR (600 MHz, METHANOL-$d_4$) δ ppm 2.08-2.24 (m, 1H) 2.30-2.42 (m, 1H) 2.33 (s, 3H) 2.34 (s, 3H) 3.57 (br dd, J=11.15, 5.28 Hz, 0.5H) 3.67-3.74 (m, 1H) 3.75 (d, J=3.52 Hz, 3H) 3.76-3.80 (m, 1H) 3.83-3.91 (m, 0.5H) 3.95 (d, J=5.28 Hz, 3H) 3.96-4.04 (m, 1H) 4.52-4.58 (m, 0.5H) 4.68-4.74 (m, 0.5H) 7.31 (d, J=5.87 Hz, 2H) 7.58-7.64 (m, 2H) 7.64-7.69 (m, 2H) 7.90 (d, J=18.78 Hz, 1H) 8.03 (d, J=18.19 Hz, 1H) 8.25 (dd, J=19.66, 2.05 Hz, 1H) 8.53-8.66 (m, 1H); MS (ESI, m/z): 525.2 [M+H]$^+$

Example 726

(R)-2-amino-N-(1-(4'-cyano-[1,1'-biphenyl]-4-carbonyl)pyrrolidin-3-yl)-5-(1-methyl-1H-pyrazol-4-yl)nicotinamide Using (4-cyanophenyl)boronic acid, the title compound was obtained as described in general method G. $^1$H NMR (600 MHz, METHANOL-$d_4$) δ ppm 2.08-2.24 (m, 1H) 2.28-2.43 (m, 1H) 3.54 (dd, J=11.15, 5.28 Hz, 0.5H) 3.63-3.70 (m, 1H) 3.72-3.79 (m, 1H) 3.86 (dt, J=12.03, 7.48 Hz, 0.5H) 3.93 (d, J=5.28 Hz, 3H) 4.04 (br s, 1H) 4.50-4.62 (m, 0.5H) 4.63-4.72 (m, 0.5H) 6.87 (d, J=8.80 Hz, 0.5H) 7.52 (d, J=8.80 Hz, 0.5H) 7.63-7.73 (m, 2H) 7.75-7.86 (m, 5H) 7.89 (d, J=18.78 Hz, 1H) 8.04 (d, J=17.02 Hz, 1H) 8.23 (dd, J=20.54, 2.35 Hz, 1H) 8.67 (dd, J=46.37, 2.35 Hz, 1H); MS (ESI, m/z): 492.2 [M+H]$^+$

Example 727

(R)-2-amino-N-(1-(3'-(aminomethyl)-[1,1'-biphenyl]-4-carbonyl)pyrrolidin-3-yl)-5-(1-methyl-1H-pyrazol-4-yl)nicotinamide Using (3-(aminomethyl)phenyl)boronic acid, the title compound was obtained as described in general method G. $^1$H NMR (600 MHz, METHANOL-$d_4$) δ ppm 2.08-2.22 (m, 1H) 2.29-2.43 (m, 1H) 3.56 (br dd, J=11.15, 5.28 Hz, 0.5H) 3.68 (td, J=13.50, 5.87 Hz, 1H) 3.73-3.81 (m, 1H) 3.83-3.90 (m, 0.5H) 3.94 (d, J=5.28 Hz, 3H) 3.95-4.05 (m, 1H) 4.19 (d, J=3.52 Hz, 2H) 4.53-4.57 (m, 0.5H) 4.67-4.74 (m, 0.5H) 7.48 (br d, J=7.63 Hz, 1H) 7.56 (td, J=7.63, 5.28 Hz, 1H) 7.67 (dd, J=13.50, 8.22 Hz, 2H) 7.70-7.81 (m, 4H) 7.89 (d, J=19.37 Hz, 1H) 8.04 (d, J=17.02 Hz, 1H) 8.24 (dd, J=17.31, 2.05 Hz, 1H) 8.63 (dd, J=54.00, 2.35 Hz, 1H); MS (ESI, m/z): 496.2 [M+H]$^+$

Example 728

(R)-2-amino-N-(1-(3-amino-[1,1'-biphenyl]-4-carbonyl)pyrrolidin-3-yl)-5-(1-methyl-1H-pyrazol-4-yl)nicotinamide Using 2-amino-4-bromobenzoic acid, the title compound was obtained as described in general method G. $^1$H NMR (400 MHz, METHANOL-$d_4$) δ ppm 2.18 (br d, J=11.35 Hz, 1H) 2.28-2.46 (m, 1H) 3.59 (br s, 0.5H) 3.63-3.74 (m, 1H) 3.78 (br s, 1H) 3.81-3.91 (m, 0.5H) 3.94 (s, 3H) 3.97-4.13 (m, 1H) 4.56 (br s, 0.5H) 4.70 (br s, 0.5H) 7.30-7.42 (m, 3H) 7.42-7.57 (m, 3H) 7.62 (br d, J=7.04 Hz, 2H) 7.90 (br d, J=7.04 Hz, 1H) 8.05 (br d, J=8.22 Hz, 1H) 8.24 (br d, J=7.83 Hz, 1H) 8.69 (d, J=26.22 Hz, 1H); MS (ESI, m/z): 482.2 [M+H]$^+$

Example 729

(R)-2-amino-5-(1-methyl-1H-pyrazol-4-yl)-N-(1-(4'-((4-methylpiperazin-1-yl)methyl)-[1,1'-biphenyl]-3-carbonyl)pyrrolidin-3-yl)nicotinamide Using 3-bromobenzoic acid and 1-methyl-4-(4-(4,4,5,5-tetramethyl-1,3,2-dioxaborolan-2-yl)benzyl)piperazine, the title compound was obtained as described in general method G. MS (ESI, m/z): 579.3 [M+H]$^+$

Example 730

(R,E)-N-(1-(3-([1,1'-biphenyl]-4-yl)acryloyl)pyrrolidin-3-yl)-2-amino-5-(1-methyl-1H-pyrazol-4-yl)nicotinamide Using (E)-3-(4-bromophenyl)acrylic acid and phenylboronic acid, the title compound was obtained as described in general method G. $^1$H NMR (400 MHz, METHANOL-$d_4$) δ ppm 2.24 (br s, 1H) 2.43 (br s, 1H) 3.46 (br d, J=9.39 Hz, 0.5H) 3.65 (br s, 1H) 3.79 (br s, 1H) 3.93 (s, 3.5H) 4.16 (br s, 0.5H) 4.65 (br s, 0.5H) 4.71 (br s, 0.5H) 7.04 (br s, 1H) 7.35 (br s, 1H) 7.44 (br d, J=5.87 Hz, 2H) 7.51-7.59 (m, 1H) 7.60-7.81 (m, 6H) 7.90 (s, 1H) 8.04 (s, 1H) 8.24 (s, 1H) 8.69 (br s, 1H); MS (ESI, m/z): 493.2 [M+H]$^+$

Example 731

(R)-2-amino-5-(1-methyl-1H-pyrazol-4-yl)-N-(1-(4-phenoxybenzoyl)pyrrolidin-3-yl)nicotinamide Using 4-phenoxybenzoic acid, the title compound was obtained as described in general method G. $^1$H NMR (400 MHz, METHANOL-$d_4$) δ ppm 2.14 (ddd, J=19.07, 12.81, 6.46 Hz, 1H) 2.23-2.43 (m, 1H) 3.56 (br dd, J=10.96, 5.09 Hz, 0.5H) 3.62-3.71 (m, 1H) 3.71-3.87 (m, 1.5H) 3.94 (s, 3H) 3.95-4.03 (m, 1H) 4.50-4.58 (m, 0.5H) 4.64-4.73 (m, 0.5H) 6.97-7.07 (m, 4H) 7.18 (brt, J=7.63 Hz, 1H) 7.34-7.47 (m, 2H) 7.57 (t, J=9.19 Hz, 2H) 7.90 (d, J=9.00 Hz, 1H) 8.05 (d, J=7.83 Hz, 1H) 8.24 (dd, J=9.39, 1.96 Hz, 1H) 8.66 (dd, J=28.17, 1.96 Hz, 1H); MS (ESI, m/z): 483.22 [M+H]$^+$

Example 732

2-amino-N-((3S,4S)-1-(4-bromobenzoyl)-4-hydroxypyrrolidin-3-yl)-5-(1-methyl-1H-pyrazol-4-yl)nicotinamide Using tert-butyl (3S,4S)-3-amino-4-hydroxypyrrolidine-1-carboxylate and 4-bromobenzoic acid, the title compound was obtained as described in general method G. MS (ESI, m/z): 485.1/487.1 [M+H]$^+$

Example 733

(R)-2-amino-N-(1-(3-bromobenzoyl)pyrrolidin-3-yl)-5-(1-methyl-1H-pyrazol-4-yl)nicotinamide Using 3-bromobenzoic acid, the title compound was obtained as described in general method G. $^1$H NMR (400

MHz, METHANOL-d$_4$) δ ppm 2.07-2.23 (m, 1H) 2.26-2.45 (m, 1H) 3.48 (br dd, J=10.96, 5.09 Hz, 0.5H) 3.58-3.66 (m, 1H) 3.66-3.77 (m, 1H) 3.79-3.92 (m, 1H) 3.95 (d, J=2.35 Hz, 3H) 3.96-4.03 (m, 0.5H) 4.51-4.59 (m, 0.5H) 4.65-4.73 (m, 0.5H) 7.40 (td, J=7.83, 5.48 Hz, 1H) 7.53 (br t, J=8.22 Hz, 1H) 7.66 (br t, J=6.46 Hz, 1H) 7.72 (br d, J=8.61 Hz, 1H) 7.91 (d, J=10.17 Hz, 1H) 8.06 (d, J=9.78 Hz, 1H) 8.25 (dd, J=10.96, 2.35 Hz, 1H) 8.67 (dd, J=28.17, 1.96 Hz, 1H); MS (ESI, m/z): 469.1/471.1 [M+H]$^+$ Example 738

(S)—N-((1-([1,1'-biphenyl]-4-carbonyl)pyrrolidin-3-yl)methyl)-2-amino-5-(1-methyl-1H-pyrazol-4-yl)nicotinamide Using [1,1'-biphenyl]-4-carboxylic acid and (R)-2-amino-5-(1-methyl-1H-pyrazol-4-yl)-N-(pyrrolidin-3-ylmethyl)nicotinamide, title compound was obtained as described for Example 342 in general method G. $^1$H NMR (600 MHz, METHANOL-d$_4$) δ ppm 1.88 (m, 2H) 2.01-2.10 (m, 1H) 2.15 (m, 1H) 3.22-3.36 (m, 1H) 3.44-3.60 (m, 1H) 3.60-3.78 (m, 2H) 3.82 (m, 3H) 3.93 (m, 1H) 7.30 (m, 1H) 7.32-7.49 (m, 2H) 7.46-7.55 (m, 2H) 7.69-7.77 (m, 2H) 7.77-7.86 (m, 2H) 7.87 (s, 1H) 8.17 (s, 1H) 8.29 (s, 1H) 8.58 (s, 1H); MS (ESI, m/z): 481.2 [M+H]$^+$ Example 739

(S)—N-((1-([1,1'-biphenyl]-3-carbonyl)pyrrolidin-3-yl)methyl)-2-amino-5-(1-methyl-1H-pyrazol-4-yl)nicotinamide Using [1,1'-biphenyl]-3-carboxylic acid and (R)-2-amino-5-(1-methyl-1H-pyrazol-4-yl)-N-(pyrrolidin-3-ylmethyl)nicotinamide, title compound was obtained as described for Example 342 in general method G. $^1$H NMR (600 MHz, METHANOL-d$_4$) δ ppm 1.75-1.92 (m, 1H) 2.07-2.26 (m, 1H) 2.57-2.69 (m, 1H) 3.37-3.54 (m, 3H) 3.54-3.68 (m, 2H) 3.76-3.90 (m, 1H) 3.92 (d, J=17.02 Hz, 3H) 7.31-7.41 (m, 1H) 7.41-7.55 (m, 4H) 7.57-7.72 (m, 4H) 7.78 (m, 0.5H) 7.86 (m, 0.5H) 7.90 (s, 0.5H) 7.95 (s, 0.5H) 8.10 (m, 0.5H) 8.19 (m, 0.5H) 8.48 (d, J=1.76 Hz, 0.5H) 8.64 (d, J=2.35 Hz, 0.5H); MS (ESI, m/z): 481.2 [M+H]$^+$ Example 740

(R)—N-((1-([1,1'-biphenyl]-4-carbonyl)pyrrolidin-3-yl)methyl)-2-amino-5-(1-methyl-1H-pyrazol-4-yl)nicotinamide Using [1,1'-biphenyl]-4-carboxylic acid and (S)-2-amino-5-(1-methyl-1H-pyrazol-4-yl)-N-(pyrrolidin-3-ylmethyl)nicotinamide, title compound was obtained as described for Example 342 in general method G. $^1$H NMR (600 MHz, METHANOL-d$_4$) δ ppm 1.87 (m, 2H) 2.00-2.19 (m, 1H) 2.14 (m, 1H) 3.21-3.35 (m, 1H) 3.44-3.60 (m, 1H) 3.60-3.78 (m, 2H) 3.81 (m, 3H) 3.92 (m, 1H) 7.30 (m, 1H) 7.31-7.48 (m, 2H) 7.46-7.55 (m, 2H) 7.69-7.77 (m, 2H) 7.78-7.86 (m, 2H) 7.86 (s, 1H) 8.15 (s, 1H) 8.28 (s, 1H) 8.57 (s, 1H); MS (ESI, m/z): 481.2 [M+H]$^+$ Example 741

(R)—N-((1-([1,1'-biphenyl]-3-carbonyl)pyrrolidin-3-yl)methyl)-2-amino-5-(1-methyl-1H-pyrazol-4-yl)nicotinamide Using [1,1'-biphenyl]-3-carboxylic acid and (S)-2-amino-5-(1-methyl-1H-pyrazol-4-yl)-N-(pyrrolidin-3-ylmethyl)nicotinamide, title compound was obtained as described for Example 342 in general method G. $^1$H NMR (600 MHz, METHANOL-d$_4$) δ ppm 1.76-1.93 (m, 1H) 2.08-2.27 (m, 1H) 2.57-2.70 (m, 1H) 3.38-3.56 (m, 3H) 3.57-3.69 (m, 2H) 3.76-3.91 (m, 1H) 3.92 (d, J=17.02 Hz, 3H) 7.32-7.42 (m, 1H) 7.42-7.55 (m, 4H) 7.56-7.74 (m, 4H) 7.79 (m, 0.5H) 7.86 (m, 0.5H) 7.91 (s, 0.5H) 7.95 (s, 0.5H) 8.11 (m, 0.5H) 8.19 (m, 0.5H) 8.49 (d, J=1.76 Hz, 0.5H) 8.65 (d, J=2.35 Hz, 0.5H); MS (ESI, m/z): 481.2 [M+H]$^+$ Example 742

N-((3S,4S)-1-([1,1'-biphenyl]-4-carbonyl)-4-hydroxypyrrolidin-3-yl)-2-amino-5-(1-methyl-1H-pyrazol-4-yl)nicotinamide Using tert-butyl (3S,4S)-3-amino-4-hydroxypyrrolidine-1-carboxylate, the title compound was obtained as described in general method G. MS (ESI, m/z): 483.2 [M+H]$^+$ Example 743

N-((3R,4S)-1-([1,1'-biphenyl]-4-carbonyl)-4-hydroxypyrrolidin-3-yl)-2-amino-5-(1-methyl-1H-pyrazol-4-yl)nicotinamide Using tert-butyl (3R,4S)-3-amino-4-hydroxypyrrolidine-1-carboxylate, the title compound was obtained as described in general method G.; MS (ESI, m/z): 483.2 [M+H]$^+$ Example 744

(R)—N-(1-([1,1'-biphenyl]-4-carbonyl)pyrrolidin-3-yl)-3-amino-6-(1-methyl-1H-pyrazol-4-yl)pyrazine-2-carboxamide Using 3-amino-6-bromopyrazine-2-carboxylic acid, the title compound was obtained as described in general method G.; MS (ESI, m/z): 468.2 [M+H]$^+$ Example 745

(R)-3-amino-N-(1-(2'-chloro-4'-fluoro-[1,1'-biphenyl]-4-carbonyl)pyrrolidin-3-yl)-6-(1-methyl-1H-pyrazol-4-yl)pyrazine-2-carboxamide Using 3-amino-6-bromopyrazine-2-carboxylic acid and 2-chloro-4-fluorobenzeneboronic acid, the title compound was obtained as described in general method G. MS (ESI, m/z): 520.2 [M+H]$^+$ Example 746

2-amino-5-(1-methyl-1H-pyrazol-4-yl)-N-((3R)-1-(3'-(pyrrolidin-3-yloxy)-[1,1'-biphenyl]-4-carbonyl)pyrrolidin-3-yl)nicotinamide Using tert-butyl 3-(3-(4,4,5,5-tetramethyl-1,3,2-dioxaborolan-2-yl)phenoxy)pyrrolidine-1-carboxylate, the title compound was obtained as described in general method G and following deprotection with trifluoroacetic acid. MS (ESI, m/z): 552.3 [M+H]$^+$

Example 747

(R)-2-amino-N-(1-(4'-(hydroxymethyl)-[1,1'-biphenyl]-4-carbonyl)pyrrolidin-3-yl)-5-(l-methyl-1H-pyrazol-4-yl)nicotinamide Using (4-(hydroxymethyl)phenyl)boronic acid, the title compound was obtained as described in general method G. $^1$H NMR (400 MHz, METHANOL-$d_4$) δ ppm 2.05-2.26 (m, 1H) 2.27-2.48 (m, 1H) 3.58 (br dd, J=10.96, 5.09 Hz, 0.5H) 3.65-3.81 (m, 2H) 3.83-3.90 (m, 0.5H) 3.95 (d, J=3.52 Hz, 3H) 3.98-4.07 (m, 1H) 4.53-4.60 (m, 0.5H) 4.66 (s, 2H) 4.70 (br d, J=5.48 Hz, 0.5H) 7.46 (br d, J=5.87 Hz, 2H) 7.61-7.70 (m, 3H) 7.70-7.80 (m, 3H) 7.91 (d, J=12.52 Hz, 1H) 8.05 (d, J=11.74 Hz, 1H) 8.25 (dd, J=13.30, 1.96 Hz, 1H) 8.66 (dd, J=32.08, 1.57 Hz, 1H); MS (ESI, m/z): 497.2 [M+H]$^+$

Example 748

(R)-2-amino-N-(1-(3'-(hydroxymethyl)-[1,1'-biphenyl]-4-carbonyl)pyrrolidin-3-yl)-5-(l-methyl-1H-pyrazol-4-yl)nicotinamide Using (3-(hydroxymethyl)phenyl)boronic acid, the title compound was obtained as described in general method G. $^1$H NMR (400 MHz, METHANOL-$d_4$) δ ppm 2.06-2.26 (m, 1H) 2.27-2.48 (m, 1H) 3.58 (br dd, J=10.96, 5.09 Hz, 0.5H) 3.66-3.84 (m, 2H) 3.84-3.92 (m, 0.5H) 3.96 (d, J=3.52 Hz, 3H) 3.98-4.09 (m, 1H) 4.53-4.63 (m, 0.5H) 4.69 (d, J=2.35 Hz, 3H) 4.71-4.76 (m, 0.5H) 7.36-7.42 (m, 1H) 7.42-7.50 (m, 1H) 7.51-7.61 (m, 1H) 7.62-7.72 (m, 3H) 7.72-7.81 (m, 2H) 7.91 (d, J=12.52 Hz, 1H) 8.06 (d, J=11.35 Hz, 1H) 8.25 (dd, J=13.50, 2.15 Hz, 1H) 8.66 (dd, J=32.48, 1.96 Hz, 1H); MS (ESI, m/z): 497.2 [M+H]$^+$

Example 749

(R)-2-amino-N-(1-(4-(6-hydroxypyridin-3-yl)benzoyl)pyrrolidin-3-yl)-5-(1-methyl-1H-pyrazol-4-yl)nicotinamide Using (6-hydroxypyridin-3-yl)boronic acid, the title compound was obtained as described in general method G. $^1$H NMR (400 MHz, METHANOL-$d_4$) δ ppm 2.06-2.25 (m, 1H) 2.26-2.46 (m, 1H) 3.55 (br dd, J=11.54, 5.28 Hz, 0.5H) 3.64-3.81 (m, 2H) 3.82-3.92 (m, 0.5H) 3.95 (d, J=2.74 Hz, 3H) 4.01 (td, J=12.33, 7.04 Hz, 1H) 4.51-4.60 (m, 0.5H) 4.70 (br d, J=6.65 Hz, 0.5H) 6.67 (dd, J=9.59, 2.93 Hz, 1H) 7.65 (d, J=7.83 Hz, 4H) 7.76-7.81 (m, 1H) 7.91 (d, J=11.74 Hz, 1H) 7.96-8.02 (m, 1H) 8.06 (d, J=10.56 Hz, 1H) 8.25 (dd, J=11.54, 2.15 Hz, 1H) 8.66 (dd, J=31.69, 1.57 Hz, 1H); MS (ESI, m/z): 484.2 [M+H]$^+$

Example 750

(R)-2-amino-5-(1-methyl-1H-pyrazol-4-yl)-N-(1-(4-(naphthalen-2-yl)benzoyl)pyrrolidin-3-yl)nicotinamide Using naphthalen-2-ylboronic acid, the title compound was obtained as described in general method G. $^1$H NMR (400 MHz, METHANOL-$d_4$) δ ppm 2.07-2.24 (m, 1H) 2.25-2.46 (m, 1H) 3.55-3.61 (m, 0.5H) 3.63-3.83 (m, 2H) 3.84-3.92 (m, 0.5H) 3.92-3.95 (m, 3H) 3.95-4.09 (m, 1H) 4.51-4.58 (m, 0.5H) 4.67-4.73 (m, 0.5H) 7.52 (br dd, J=6.85, 3.33 Hz, 2 H) 7.70 (dd, J=11.74, 8.22 Hz, 2H) 7.82 (br d, J=11.74 Hz, 2H) 7.85-7.93 (m, 3H) 7.93-8.00 (m, 2H) 8.09 (d, J=2.35 Hz, 1H) 8.17 (br d, J=2.35 Hz, 2H) 8.28 (dd, J=12.52, 1.96 Hz, 1H); MS (ESI, m/z): 517.2 [M+H]$^+$

Example 751

(R)—N-(1-(4-(1H-indol-6-yl)benzoyl)pyrrolidin-3-yl)-2-amino-5-(1-methyl-1H-pyrazol-4-yl)nicotinamide Using (1H-indol-6-yl)boronic acid, the title compound was obtained as described in general method G. $^1$H NMR (600 MHz, METHANOL-$d_4$) δ ppm 2.06-2.23 (m, 1H) 2.24-2.45 (m, 1H) 3.59 (br dd, J=11.15, 4.70 Hz, 0.5H) 3.64-3.82 (m, 2H) 3.83-3.90 (m, 0.5H) 3.94 (d, J=7.04 Hz, 3H) 3.97-4.06 (m, 1H) 4.49-4.59 (m, 0.5H) 4.65-4.74 (m, 0.5H) 6.46 (br s, 1H) 7.28 (br s, 1H) 7.32 (br t, J=7.04 Hz, 1H) 7.57-7.69 (m, 4H) 7.75 (br t, J=7.92 Hz, 2H) 7.89 (br d, J=19.96 Hz, 1H) 8.00-8.07 (m, 1H) 8.23 (br d, J=19.37 Hz, 1H) 8.64 (dd, J=50.47, 1.17 Hz, 1H); MS (ESI, m/z): 506.2 [M+H]$^+$

Example 752

(R)-2-amino-5-(1-methyl-1H-pyrazol-4-yl)-N-(1-(4-(4-methyl-3,4-dihydro-2H-benzo[b][1,4]oxazin-7-yl)benzoyl)pyrrolidin-3-yl)nicotinamide Using (4-methyl-3,4-dihydro-2H-benzo[b][1,4]oxazin-7-yl)boronic acid, the title compound was obtained as described in general method G. $^1$H NMR (400 MHz, METHANOL-$d_4$) δ ppm 2.06-2.25 (m, 1H) 2.27-2.47 (m, 1H) 2.94 (s, 3H) 3.61 (br s, 0.5H) 3.75 (br d, J=18.78 Hz, 2H) 3.89 (br s, 0.5H) 3.96 (d, J=3.13 Hz, 3H) 3.99 (br s, 1H) 4.31 (br s, 2H) 4.56 (br s, 0.5H) 4.72 (br s, 0.5H) 6.73-6.84 (m, 1H) 7.04 (s, 1H) 7.16 (br d, J=6.65 Hz, 1H) 7.55-7.71 (m, 4H) 7.90 (br d, J=12.52 Hz, 1H) 8.03 (br d, J=11.74 Hz, 1H) 8.27 (br d, J=13.30 Hz, 1H) 8.46-8.61 (m, 1H); MS (ESI, m/z): 538.3 [M+H]$^+$

Example 753

(R)-2-amino-5-(1-methyl-1H-pyrazol-4-yl)-N-(1-(4-(1,2,3,6-tetrahydropyridin-4-yl)benzoyl)pyrrolidin-3-yl)nicotinamide Using (1,2,3,6-tetrahydropyridin-4-yl)boronic acid, the title compound was obtained as described in general method G. $^1$H NMR (600 MHz, METHANOL-$d_4$) δ ppm 2.02-2.18 (m, 1H) 2.22-2.40 (m, 1H) 2.77-2.83 (m, 2H) 3.43-3.47 (m, 2H) 3.62 (br dd, J=12.91, 4.70 Hz, 0.5H) 3.65-3.76 (m, 2H) 3.77-3.86 (m, 2H) 3.86-3.90 (m, 0.5H) 3.91 (d, J=3.52 Hz, 3H) 3.98 (br dd, J=12.62, 6.75 Hz, 1H) 4.47-4.52 (m, 0.5H) 4.62-4.69 (m, 0.5H) 6.23 (br dd, J=4.70, 2.93 Hz, 1H) 7.53-7.58 (m, 4H) 7.84 (d, J=19.96 Hz, 1H) 7.98 (d, J=18.19 Hz, 1H) 8.23 (br dd, J=13.50, 1.76 Hz, 1H) 8.38-8.42 (m, 1H) 8.51 (dd, J=66.32, 1.17 Hz, 1H); MS (ESI, m/z): 472.2 [M+H]$^+$

Example 754

(R)-2-amino-N-(1-(4-(1-methyl-1,2,3,6-tetrahydropyridin-4-yl)benzoyl)pyrrolidin-3-yl)-5-(1-methyl-1H-pyrazol-4-yl)nicotinamide Using (1-methyl-1,2,3,6-tetrahydropyridin-4-yl)boronic acid, the title compound was obtained as described in general method G. $^1$H NMR (600 MHz, METHANOL-$d_4$) δ ppm 2.02-2.19 (m, 1H) 2.22-2.39 (m, 1H) 2.87 (br s, 2H) 2.98 (d, J=4.11 Hz, 3H) 3.41-3.50 (m, 0.5H) 3.56-3.65 (m, 2H) 3.65-3.75 (m, 2H) 3.76-3.86 (m, 2H) 3.87 (br d, J=6.46 Hz, 0.5H) 3.91 (d, J=3.52 Hz, 3H) 3.98 (br dd, J=12.91, 7.04 Hz, 1H) 4.43-4.54 (m, 0.5H) 4.61-4.70 (m, 0.5H) 6.21 (dt, J=3.67, 1.98 Hz, 1H) 7.50-7.61 (m, 4H) 7.85 (d, J=18.78 Hz, 1H) 7.99 (d, J=17.02 Hz, 1H) 8.23 (dd, J=13.79, 2.05 Hz, 1H) 8.52 (dd, J=60.45, 2.35 Hz, 1H); MS (ESI, m/z): 486.3 $[M+H]^+$

Example 755

(R)-2-amino-5-(1-methyl-1H-pyrazol-4-yl)-N-(1-(4'-(1,2,3,6-tetrahydropyridin-4-yl)-[1,1'-biphenyl]-4-carbonyl)pyrrolidin-3-yl)nicotinamide Using (4-(1,2,3,6-tetrahydropyridin-4-yl)phenyl)boronic acid, the title compound was obtained as described in general method G. $^1$H NMR (600 MHz, METHANOL-d$_4$) δ ppm 2.01-2.22 (m, 1H) 2.25-2.48 (m, 1H) 2.83 (br s, 0.5H) 3.43-3.50 (m, 0.5H) 3.51-3.58 (m, 0.5H) 3.60-3.79 (m, 4H) 3.81-3.87 (m, 1H) 3.89-3.94 (m, 3H) 3.94-4.05 (m, 1H) 4.49-4.59 (m, 0.5H) 4.68 (br d, J=7.04 Hz, 0.5H) 6.23 (br s, 1H) 7.36 (br s, 1H) 7.53-7.66 (m, 6H) 7.77-7.87 (m, 1H) 7.87-7.96 (m, 1H) 8.00-8.07 (m, 1H) 8.17-8.29 (m, 1H) 8.46-8.63 (m, 1H) 8.77 (br s, 1H); MS (ESI, m/z): 548.3 $[M+H]^+$

Example 756

(R)-2-amino-N-(1-(4-(1-methyl-1H-indol-5-yl)benzoyl)pyrrolidin-3-yl)-5-(1-methyl-1H-pyrazol-4-yl)nicotinamide Using (1-methyl-1H-indol-5-yl)boronic acid, the title compound was obtained as described in general method G. $^1$H NMR (600 MHz, METHANOL-d$_4$) δ ppm 2.02-2.20 (m, 1H) 2.24-2.45 (m, 1H) 3.57 (br dd, J=10.86, 4.99 Hz, 0.5H) 3.61-3.79 (m, 4H) 3.81 (d, J=2.93 Hz, 3H) 3.82-3.89 (m, 0.5H) 3.92 (d, J=6.46 Hz, 3H) 3.95-4.04 (m, 1H) 4.49-4.57 (m, 0.5H) 4.64-4.73 (m, 0.5H) 6.47 (t, J=3.52 Hz, 1H) 7.17 (t, J=2.93 Hz, 1H) 7.40-7.50 (m, 2H) 7.61 (dd, J=14.67, 8.80 Hz, 2H) 7.73 (t, J=7.92 Hz, 2H) 7.81 (br d, J=4.70 Hz, 1H) 7.88 (d, J=19.37 Hz, 1H) 8.02 (d, J=18.78 Hz, 1H) 8.22 (dd, J=21.13, 2.35 Hz, 1H) 8.60 (dd, J=51.06, 1.76 Hz, 1H); MS (ESI, m/z): 520.2 $[M+H]^+$

Example 757

(R)-2-amino-N-(1-(4-(1-methyl-1H-indazol-5-yl)benzoyl)pyrrolidin-3-yl)-5-(1-methyl-1H-pyrazol-4-yl)nicotinamide Using (1-methyl-1H-indazol-5-yl)boronic acid, the title compound was obtained as described in general method G. $^1$H NMR (600 MHz, METHANOL-d$_4$) δ ppm 2.04-2.21 (m, 1H) 2.26-2.44 (m, 1H) 3.56 (br dd, J=11.15, 4.70 Hz, 0.5H) 3.63-3.79 (m, 2H) 3.81-3.87 (m, 0.5H) 3.92 (d, J=6.46 Hz, 3H) 3.95-4.04 (m, 1H) 4.07 (d, J=2.93 Hz, 3H) 4.53 (br d, J=6.46 Hz, 0.5H) 4.68 (br d, J=6.46 Hz, 0.5H) 7.60-7.68 (m, 3H) 7.72-7.79 (m, 3H) 7.88 (d, J=19.37 Hz, 1H) 7.99-8.08 (m, 3H) 8.22 (d, J=19.96, 2.35 Hz, 1H) 8.60 (dd, J=50.47, 1.76 Hz, 1H); MS (ESI, m/z): 521.2 $[M+H]^+$

Example 758

(R)-2-amino-5-(1-methyl-1H-pyrazol-4-yl)-N-(1-(4-(1-(2-(pyrrolidin-1-yl)ethyl)-1H-pyrazol-4-yl)benzoyl)pyrrolidin-3-yl)nicotinamide Using (1-(2-(pyrrolidin-1-yl)ethyl)-1H-pyrazol-4-yl)boronic acid, the title compound was obtained as described in general method G. $^1$H NMR (600 MHz, METHANOL-d$_4$) δ ppm 1.99-2.22 (m, 5H) 2.24-2.43 (m, 1H) 3.54 (br dd, J=11.15, 5.28 Hz, 0.5H) 3.60-3.80 (m, 8H) 3.82-3.89 (m, 0.5H) 3.93 (d, J=4.11 Hz, 3H) 4.00 (dd, J=12.91, 7.04 Hz, 1H) 4.48-4.55 (m, 0.5H) 4.60 (q, J=5.28 Hz, 2H) 4.68 (t, J=5.87 Hz, 0.5H) 7.58 (br dd, J=16.73, 7.92 Hz, 2H) 7.63-7.70 (m, 2H) 7.86 (d, J=19.37 Hz, 1H) 7.96-8.03 (m, 2H) 8.17 (d, J=7.04 Hz, 1H) 8.25 (br d, J=14.09 Hz, 1H) 8.44 (dd, J=61.04, 1.17 Hz, 1H); MS (ESI, m/z): 554.3 $[M+H]^+$

Example 759

(R)—N-(1-(4-(1H-indazol-5-yl)benzoyl)pyrrolidin-3-yl)-2-amino-5-(1-methyl-1H-pyrazol-4-yl)nicotinamide Using (1H-indazol-5-yl)boronic acid, the title compound was obtained as described in general method G. $^1$H NMR (600 MHz, METHANOL-d$_4$) δ ppm 2.05-2.22 (m, 1H) 2.25-2.44 (m, 1H) 3.57 (br dd, J=11.15, 5.28 Hz, 0.5H) 3.63-3.72 (m, 1H) 3.72-3.80 (m, 1H) 3.82-3.89 (m, 0.5H) 3.92 (d, J=7.63 Hz, 3H) 3.94-4.05 (m, 1H) 4.53 (dt, J=11.59, 5.65 Hz, 0.5H) 4.68 (dt, J=11.74, 5.87 Hz, 0.5H) 7.58-7.67 (m, 3H) 7.67-7.72 (m, 1H) 7.72-7.78 (m, 2H) 7.83-7.90 (m, 1H) 7.96-8.05 (m, 2H) 8.09 (d, J=5.87 Hz, 1H) 8.21 (br ddd, J=21.13, 19.96, 1.17 Hz, 1H) 8.58 (dd, J=49.89, 1.76 Hz, 1H); MS (ESI, m/z): 507.2 $[M+H]^+$

Example 760

(R)—N-(1-(4-(1H-indazol-6-yl)benzoyl)pyrrolidin-3-yl)-2-amino-5-(1-methyl-1H-pyrazol-4-yl)nicotinamide Using (1H-indazol-6-yl)boronic acid, the title compound was obtained as described in general method G. $^1$H NMR (600 MHz, METHANOL-d$_4$) δ ppm 2.06-2.22 (m, 1H) 2.26-2.44 (m, 1H) 3.57 (br dd, J=11.15, 5.28 Hz, 0.5H) 3.65-3.72 (m, 1H) 3.72-3.80 (m, 1H) 3.83-3.90 (m, 0.5H) 3.92 (d, J=7.04 Hz, 3H) 3.95-4.05 (m, 1H) 4.54 (dt, J=11.59, 5.65 Hz, 0.5H) 4.69 (dt, J=12.18, 5.94 Hz, 0.5H) 7.44 (t, J=7.92 Hz, 1H) 7.66 (dd, J=14.67, 8.22 Hz, 2H) 7.74-7.81 (m, 3H) 7.82-7.91 (m, 2H) 8.01 (d, J=19.96 Hz, 1H) 8.06 (d, J=3.52 Hz, 1H) 8.23 (dd, J=20.54, 1.17 Hz, 1H) 8.56 (dd, J=51.06, 1.17 Hz, 1H); MS (ESI, m/z): 507.2 $[M+H]^+$

Example 840

(R)-2-amino-N-(1-(4-hydroxybenzoyl)pyrrolidin-3-yl)-5-(1-methyl-1H-pyrazol-4-yl)nicotinamide Using 4-hydroxybenzoic acid, the title compound was obtained as described in general method G. MS (ESI, m/z): 407.2 $[M+H]^+$

Example 841

(R)-2-amino-N-(1-(4-formylbenzoyl)pyrrolidin-3-yl)-5-(1-methyl-1H-pyrazol-4-yl)nicotinamide Using 4-formylbenzoic acid, the title compound was obtained as described in general method G. MS (ESI, m/z): 419.2 [M+H]$^+$

Example 842 methyl (R)-6-(3-(2-amino-5-(1-methyl-1H-pyrazol-4-yl)nicotinamido)pyrrolidine-1-carbonyl)-2-naphthoate Using 6-(methoxycarbonyl)-2-naphthoic acid, the title compound was obtained as described in general method G. MS (ESI, m/z): 499.22 [M+H]$^+$

Example 847 tert-butyl (R)-4-(4-(3-(2-amino-5-(1-methyl-1H-pyrazol-4-yl)nicotinamido)pyrrolidine-1-carbonyl)phenyl)-3,6-dihydropyridine-1 (2H)-carboxylate The title compound was obtained as described in general method G.

General Method H

Example 550

(R)-2-amino-5-(1-methyl-1H-pyrazol-4-yl)-N-(1-(4'-(piperidin-4-ylmethoxy)-[1,1'-biphenyl]-4-carbonyl)pyrrolidin-3-yl)nicotinamide A mixture of Example 380 (20 mg, 0.04 mmol), tert-butyl 4-(chloromethyl)piperidine-1-carboxylate (19 mg, 0.08 mmol) and K$_2$CO$_3$ (14 mg, 0.1 mmol) in 1 mL of acetone was heated at 60° C. for 12 h, cooled to room temperature, and extracted with ethyl acetate, dried over anhydrous MgSO$_4$ and concentrated under vacuum. The crude residue was dissolved in 0.5 mL of dichloromethane/trifluoroacetic acid (4/1) and stirred at room temperature for 3 h. After concentration in vacuo, the crude residue was purified by preparative HPLC to afford 10 mg of the title compound. $^1$H NMR (400 MHz, METHANOL-d$_4$) δ ppm 1.56-1.71 (m, 2H) 2.11 (br d, J=12.91 Hz, 2H) 2.10-2.20 (m, 1H) 2.28-2.46 (m, 1H) 3.01-3.11 (m, 2H) 3.46 (br d, J=12.91 Hz, 2H) 3.58 (br dd, J=11.35, 4.70 Hz, 0.5H) 3.63-3.72 (m, 1H) 3.72-3.82 (m, 1H) 3.82-3.91 (m, 0.5H) 3.95 (d, J=3.52 Hz, 3H) 3.96 (d, J=1.96 Hz, 2H) 3.98-4.05 (m, 1H) 4.52-4.60 (m, 0.5H) 4.64-4.75 (m, 0.5H) 7.03 (dd, J=9.00, 2.74 Hz, 2H) 7.55-7.65 (m, 4H) 7.65-7.72 (m, 2H) 7.91 (d, J=11.74 Hz, 1H) 8.06 (d, J=10.96 Hz, 1H) 8.25 (dd, J=12.72, 2.15 Hz, 1H) 8.62-8.75 (m, 1H); MS (ESI, m/z): 580.2 [M+H]$^+$

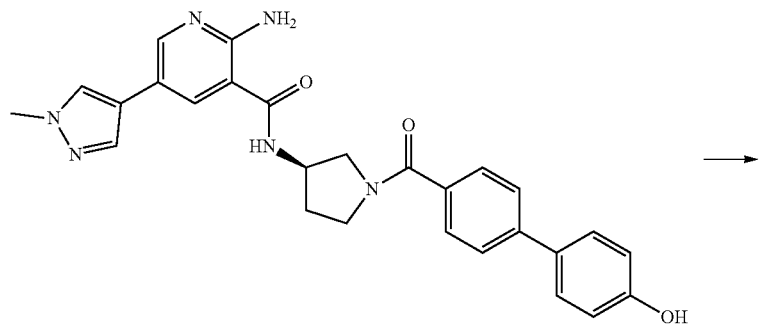

Example 380

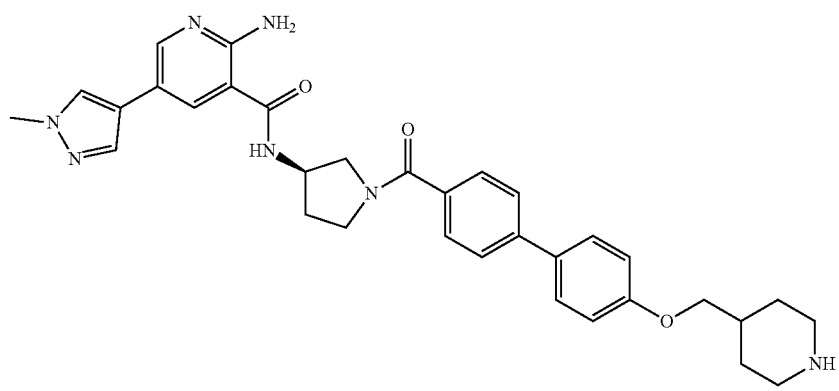

Example 550

Example 551

(R)-2-amino-N-(1-(4'-(3-(dimethylamino)propoxy)-[1,1'-biphenyl]-4-carbonyl)pyrrolidin-3-yl)-5-(1-methyl-1H-pyrazol-4-yl)nicotinamide Using 3-diethylaminopropyl chloride-hydrochloride, the title compound was obtained as described in general method H. $^1$H NMR (400 MHz, METHANOL-$d_4$) δ ppm 2.08-2.21 (m, 1H) 2.21-2.29 (m, 2H) 2.40 (br s, 1H) 2.96 (s, 6H) 3.35-3.42 (m, 2H) 3.57 (br dd, J=11.15, 5.28 Hz, 0.5H) 3.62-3.82 (m, 2H) 3.82-3.90 (m, 0.5H) 3.95 (d, J=3.13 Hz, 3H) 3.97-4.06 (m, 1H) 4.13-4.20 (m, 2H) 4.53-4.60 (m, 0.5H) 4.72 (br d, J=6.26 Hz, 0.5H) 7.06 (dd, J=8.80, 2.93 Hz, 2H) 7.63 (dt, J=8.41, 4.01 Hz, 4H) 7.66-7.75 (m, 2H) 7.91 (d, J=12.13 Hz, 1H) 8.06 (d, J=10.96 Hz, 1H) 8.25 (dd, J=12.72, 2.15 Hz, 1H) 8.62-8.75 (m, 1H); MS (ESI, m/z): 568.2 [M+H]$^+$

Example 552

(R)-2-amino-5-(1-methyl-1H-pyrazol-4-yl)-N-(1-(4'-((1-methylpiperidin-4-yl)methoxy)-[1,1'-biphenyl]-4-carbonyl)pyrrolidin-3-yl)nicotinamide Using 4-(chloromethyl)-1-methylpiperidine hydrochloride, the title compound was obtained as described in general method H. $^1$H NMR (400 MHz, METHANOL-$d_4$) δ ppm 1.61-1.76 (m, 2H) 2.08-2.24 (m, 3H) 2.26-2.44 (m, 1H) 2.89 (s, 3H) 3.06 (brt, J=12.13 Hz, 2H) 3.58 (br d, J=11.35 Hz, 2.5H) 3.63-3.81 (m, 2H) 3.86 (br d, J=11.35 Hz, 0.5H) 3.95 (d, J=3.13 Hz, 3H) 3.97 (br d, J=1.96 Hz, 2H) 3.99-4.07 (m, 1H) 4.52-4.60 (m, 0.5H) 4.67-4.75 (m, 0.5H) 7.03 (dd, J=9.00, 2.74 Hz, 2H) 7.53-7.65 (m, 4H) 7.65-7.73 (m, 2H) 7.91 (d, J=12.13 Hz, 1H) 8.06 (d, J=10.96 Hz, 1H) 8.25 (dd, J=12.72, 2.15 Hz, 1H) 8.63-8.78 (m, 1H); MS (ESI, m/z): 594.2 [M+H]$^+$

Example 761

(R)-2-amino-5-(1-methyl-1H-pyrazol-4-yl)-N-(1-(6-(piperidin-4-ylmethoxy)-2-naphthoyl)pyrrolidin-3-yl)nicotinamide Using Example 706, the title compound was obtained as described in general method H. $^1$H NMR (600 MHz, METHANOL-$d_4$) δ ppm 1.61-1.72 (m, 2H) 2.07-2.15 (m, 2.5H) 2.20 (dt, J=13.50, 6.75 Hz, 1.5H) 2.25-2.44 (m, 1H) 3.06 (br t, J=12.91 Hz, 2H) 3.42-3.51 (m, 2H) 3.60 (br dd, J=11.15, 5.28 Hz, 0.5H) 3.71 (br dd, J=12.91, 4.11 Hz, 1H) 3.74-3.83 (m, 1H) 3.87-3.91 (m, 0.5H) 3.93 (d, J=7.04 Hz, 3H) 3.99-4.04 (m, 1H) 4.01-4.09 (m, 2H) 4.49-4.57 (m, 0.5H) 4.66-4.73 (m, 0.5H) 7.16-7.22 (m, 1H) 7.28 (dd, J=9.39, 2.35 Hz, 1H) 7.52-7.63 (m, 1H) 7.82 (ddd, J=12.91, 9.39, 2.93 Hz, 1H) 7.86-7.92 (m, 1H) 7.95-8.01 (m, 1H) 8.01-8.09 (m, 1H) 8.16-8.27 (m, 1H) 8.59-8.74 (m, 1H); MS (ESI, m/z): 554.3 [M+H]$^+$

Example 762

((R)-2-amino-N-(1-(6-(2-(dimethylamino)ethoxy)-2-naphthoyl)pyrrolidin-3-yl)-5-(1-methyl-1H-pyrazol-4-yl)nicotinamide Using Example 706 and 2-chloro-N,N-dimethylethan-1-amine, the title compound was obtained as described in general method H. $^1$H NMR (600 MHz, METHANOL-$d_4$) δ ppm 2.08-2.24 (m, 1H) 2.26-2.45 (m, 1H) 3.01 (d, J=2.93 Hz, 6H) 3.59 (dd, J=11.15, 5.28 Hz, 0.5H) 3.64-3.69 (m, 2H) 3.69-3.73 (m, 1H) 3.75-3.83 (m, 1H) 3.87-3.91 (m, 0.5H) 3.93 (d, J=6.46 Hz, 3H) 3.96-4.11 (m, 1H) 4.49 (q, J=4.70 Hz, 2H) 4.52-4.56 (m, 0.5H) 4.67-4.75 (m, 0.5H) 7.30 (ddd, J=8.80, 6.46, 2.35 Hz, 1H) 7.40 (dd, J=7.63, 2.35 Hz, 1H) 7.62 (ddd, J=15.41, 8.36, 1.47 Hz, 1H) 7.83-7.94 (m, 3H) 8.02 (s, 1H) 8.04-8.07 (m, 1H) 8.18-8.28 (m, 1H) 8.59-8.78 (m, 1H); MS (ESI, m/z): 528.3 [M+H]$^+$

Example 763

2-amino-5-(1-methyl-1H-pyrazol-4-yl)-N-((3R)-1-(6-((1-methylpyrrolidin-3-yl)methoxy)-2-naphthoyl)pyrrolidin-3-yl)nicotinamide Using Example 706 and 3-(chloromethyl)-1-methylpyrrolidine, the title compound was obtained as described in general method H. $^1$H NMR (600 MHz, METHANOL-$d_4$) δ ppm 1.98-2.15 (m, 1H) 2.19 (br dd, J=13.79, 6.75 Hz, 1H) 2.31 (br dd, J=12.91, 6.46 Hz, 1H) 2.37-2.50 (m, 1H) 2.99 (br d, J=12.91 Hz, 3H) 3.04-3.15 (m, 1H) 3.15-3.28 (m, 1H) 3.34-3.42 (m, 1H) 3.59 (br dd, J=11.44, 4.99 Hz, 0.5H) 3.68-3.75 (m, 1H) 3.75-3.83 (m, 1H) 3.87-3.93 (m, 0.5H) 3.94 (d, J=6.46 Hz, 3H) 3.99-4.08 (m, 1H) 4.09-4.19 (m, 1H) 4.19-4.29 (m, 1H) 4.52-4.58 (m, 0.5H) 4.69-4.74 (m, 0.5H) 7.22-7.29 (m, 1H) 7.34 (dd, J=5.87, 2.35 Hz, 1H) 7.58-7.64 (m, 1H) 7.83-7.87 (m, 1H) 7.88 (s, 1H) 7.98-8.09 (m, 2H) 8.19-8.31 (m, 1H) 8.60-8.76 (m, 1H); MS (ESI, m/z): 554.3 [M+H]$^+$

Example 764

2-amino-5-(1-methyl-1H-pyrazol-4-yl)-N-((3R)-1-(6-(2-(1-methylpyrrolidin-2-yl)ethoxy)-2-naphthoyl)pyrrolidin-3-yl)nicotinamide Using Example 706 and 2-(2-chloroethyl)-1-methylpyrrolidine hydrochloride, the title compound was obtained as described in general method H. $^1$H NMR (600 MHz, METHANOL-$d_4$) δ ppm 1.93 (br d, J=9.98 Hz, 1H) 2.06-2.22 (m, 4H) 2.24-2.33 (m, 1H) 2.41 (dt, J=13.50, 6.75 Hz, 1H) 2.47 (br dd, J=8.22, 4.70 Hz, 1H) 2.93-2.97 (m, 3H) 2.99 (d, J=2.35 Hz, 2H) 3.16-3.23 (m, 1H) 3.41-3.46 (m, 0.5H) 3.53-3.62 (m, 1H) 3.68-3.75 (m, 2H) 3.76-3.83 (m, 1H) 3.85-3.91 (m, 0.5H) 3.94 (d, J=6.46 Hz, 3H) 3.99-4.08 (m, 1H) 4.23-4.35 (m, 1H) 4.52-4.58 (m, 0.5H) 4.69-4.74 (m, 0.5H) 7.21-7.27 (m, 1H) 7.34 (br d, J=2.93 Hz, 1H) 7.55-7.64 (m, 1H) 7.81-7.88 (m, 2H) 7.88 (s, 1H) 7.99-8.09 (m, 2H) 8.19-8.28 (m, 1H) 8.72 (d, J=2.35 Hz, 1H); MS (ESI, m/z): 568.3 [M+H]$^+$

Example 765

(R)-2-amino-5-(1-methyl-1H-pyrazol-4-yl)-N-(1-(6-(2-(pyrrolidin-1-yl)ethoxy)-2-naphthoyl)pyrrolidin-3-yl)nicotinamide Using Example 706 and 1-(2-chloroethyl)pyrrolidine hydrochloride, the title compound was obtained as described in general method H. $^1$H NMR (600 MHz, METHANOL-$d_4$) δ ppm 2.03-2.15 (m, 3H) 2.17-2.25 (m, 2H) 2.27-2.44 (m, 1H) 3.22-3.28 (m, 2H) 3.59 (br dd, J=11.44, 4.99 Hz, 0.5H) 3.68-3.84 (m, 6H) 3.87-3.93 (m, 0.5H) 3.94 (d, J=6.46 Hz, 3H) 3.98-4.06 (m, 1H) 4.45-4.51 (m, 2H) 4.51-4.57 (m, 0.5H) 4.67-4.75 (m, 0.5H) 7.31 (ddd, J=8.66, 5.72, 2.64 Hz, 1H) 7.40 (dd, J=7.04, 2.35 Hz, 1H) 7.63 (ddd, J=12.91, 8.51, 1.47 Hz, 1H) 7.82-7.96 (m, 3H) 7.98-8.12 (m, 2H) 8.19-8.28 (m, 1H) 8.61-8.77 (m, 1H); MS (ESI, m/z): 554.3 [M+H]$^+$

Example 766

(R)-2-amino-N-(1-(6-(3-(dimethylamino)propoxy)-2-naphthoyl)pyrrolidin-3-yl)-5-(1-methyl-1H-pyrazol-4-yl)nicotinamide Using Example 706 and 3-chloro-N,N-dimethylpropan-1-amine hydrochloride, the title compound was obtained as described in general method H. $^1$H NMR (600 MHz, METHANOL-d$_4$) δ ppm 2.07-2.23 (m, 1H) 2.25-2.34 (m, 2H) 2.25-2.45 (m, 1H) 2.95 (d, J=2.35 Hz, 6H) 3.37-3.43 (m, 2H) 3.59 (dd, J=11.15, 5.28 Hz, 0.5H) 3.66-3.75 (m, 1H) 3.79 (td, J=7.34, 2.93 Hz, 1H) 3.84-3.91 (m, 0.5H) 3.94 (d, J=7.04 Hz, 3H) 3.98-4.06 (m, 1H) 4.24 (q, J=5.87 Hz, 2H) 4.51-4.57 (m, 0.5H) 4.67-4.74 (m, 0.5H) 7.23 (ddd, J=8.80, 6.16, 2.64 Hz, 1H) 7.32 (dd, J=7.63, 2.35 Hz, 1H) 7.60 (ddd, J=14.67, 8.51, 1.47 Hz, 1H) 7.80-7.87 (m, 2H) 7.87-7.93 (m, 1H) 7.99-8.09 (m, 2H) 8.18-8.27 (m, 1H) 8.60-8.78 (m, 1H); MS (ESI, m/z): 542.3 [M+H]$^+$

Example 767

(R)-2-amino-5-(1-methyl-1H-pyrazol-4-yl)-N-(1-(6-((1-methylpiperidin-4-yl)methoxy)-2-naphthoyl)pyrrolidin-3-yl)nicotinamide Using Example 706 and 4-(bromomethyl)-1-methylpiperidine hydrochloride, the title compound was obtained as described in general method H. MS (ESI, m/z): 568.3 [M+H]$^+$

Example 768

(R)-2-amino-5-(1-methyl-1H-pyrazol-4-yl)-N-(1-(6-(piperidin-4-yloxy)-2-naphthoyl)pyrrolidin-3-yl)nicotinamide Using Example 706 and tert-butyl 4-bromopiperidine-1-carboxylate, the title compound was obtained as described in general method H. $^1$H NMR (600 MHz, METHANOL-d$_4$) δ ppm 2.06-2.28 (m, 5H) 2.28-2.46 (m, 1H) 3.23-3.29 (m, 2H) 3.40-3.48 (m, 2H) 3.59 (br dd, J=11.15, 5.28 Hz, 0.5H) 3.71 (br dd, J=12.62, 4.99 Hz, 1H) 3.75-3.83 (m, 1H) 3.86-3.90 (m, 0.5H) 3.94 (d, J=6.46 Hz, 3H) 3.96-4.08 (m, 1H) 4.51-4.57 (m, 0.5H) 4.68-4.73 (m, 0.5H) 7.26 (ddd, J=8.66, 6.02, 2.35 Hz, 1H) 7.40 (dd, J=6.75, 2.05 Hz, 1H) 7.55-7.65 (m, 1H) 7.81-7.95 (m, 3H) 7.99-8.10 (m, 2H) 8.18-8.28 (m, 1H) 8.60-8.76 (m, 1H); MS (ESI, m/z): 540.3 [M+H]$^+$

Example 769

(R)-2-amino-5-(1-methyl-1H-pyrazol-4-yl)-N-(1-(4-((4-nitrobenzyl)oxy)benzoyl)pyrrolidin-3-yl)nicotinamide Using Example 840 and 4-nitrobenzyl bromide, the title compound was obtained as described in general method H. $^1$H NMR (600 MHz, METHANOL-d$_4$) δ ppm 2.05-2.19 (m, 1H) 2.24-2.40 (m, 1H) 3.54 (br dd, J=11.44, 4.99 Hz, 0.5H) 3.60-3.69 (m, 1H) 3.69-3.77 (m, 1H) 3.78-3.87 (m, 0.5H) 3.93 (d, J=1.76 Hz, 3H) 3.94-4.02 (m, 1H) 4.48-4.54 (m, 0.5H) 4.62-4.71 (m, 0.5H) 5.28 (d, J=5.28 Hz, 2H) 7.08 (dd, J=9.98, 8.80 Hz, 2H) 7.55 (dd, J=16.43, 8.80 Hz, 2H) 7.68 (t, J=7.63 Hz, 2H) 7.89 (d, J=17.02 Hz, 1H) 8.04 (d, J=15.26 Hz, 1H) 8.20-8.28 (m, 3H) 8.60-8.73 (m, 1H); MS (ESI, m/z): 542.2 [M+H]$^+$

Example 770

(R)-2-amino-5-(1-methyl-1H-pyrazol-4-yl)-N-(1-(4-((3-nitrobenzyl)oxy)benzoyl)pyrrolidin-3-yl)nicotinamide Using Example 840 and 3-nitrobenzyl bromide, the title compound was obtained as described in general method H. $^1$H NMR (600 MHz, METHANOL-d$_4$) δ ppm 2.05-2.21 (m, 1H) 2.24-2.40 (m, 1H) 3.54 (br dd, J=11.15, 5.28 Hz, 0.5H) 3.61-3.69 (m, 1H) 3.69-3.77 (m, 1H) 3.77-3.86 (m, 0.5H) 3.89-3.99 (m, 1H) 3.92-3.94 (m, 3H) 4.47-4.55 (m, 0.5H) 4.62-4.71 (m, 0.5H) 5.27 (d, J=5.28 Hz, 2H) 7.09 (t, J=9.39 Hz, 2H) 7.56 (dd, J=16.14, 8.51 Hz, 2H) 7.63 (td, J=7.92, 4.11 Hz, 1H) 7.85 (t, J=6.35 Hz, 1H) 7.87-7.91 (m, 1H) 8.04 (d, J=15.85 Hz, 1H) 8.13-8.20 (m, 1H) 8.23 (dd, J=17.02, 1.76 Hz, 1H) 8.32 (br d, J=8.80 Hz, 1H) 8.59-8.74 (m, 1H); MS (ESI, m/z): 542.2 [M+H]$^+$

Example 771

(R)-2-amino-N-(1-(2'-chloro-4'-fluoro-[1,1'-biphenyl]-4-carbonyl)pyrrolidin-3-yl)-5-(2-(piperidin-4-ylmethoxy)phenyl)nicotinamide Using Example 778 and tert-butyl 4-(bromomethyl)piperidine-1-carboxylate, the title compound was obtained as described in general method H. $^1$H NMR (600 MHz, METHANOL-d$_4$) δ ppm 1.50-1.61 (m, 2H) 1.93-2.00 (m, 2H) 2.05-2.21 (m, 2H) 2.27-2.42 (m, 1H) 2.94-3.05 (m, 2H) 3.37-3.45 (m, 2H) 3.55 (dd, J=11.15, 4.70 Hz, 0.5H) 3.62-3.70 (m, 1H) 3.70-3.77 (m, 1H) 3.78-3.86 (m, 0.5H) 3.93-4.02 (m, 3H) 4.53-4.59 (m, 0.5H) 4.68-4.74 (m, 0.5H) 7.08-7.20 (m, 3H) 7.34 (dt, J=8.66, 2.71 Hz, 1H) 7.38-7.44 (m, 2H) 7.45-7.54 (m, 3H) 7.62 (t, J=7.90 Hz, 2H) 8.29 (d, J=1.76 Hz, 1H) 8.57-8.69 (m, 1H); MS (ESI, m/z): 656.2 [M+H]$^+$

Example 772

2-amino-N—((R)-1-(2'-chloro-4'-fluoro-[1,1'-biphenyl]-4-carbonyl)pyrrolidin-3-yl)-5-(2-((1-methylpyrrolidin-3-yl)methoxy)phenyl)nicotinamide Using Example 778 and 3-(chloromethyl)-1-methylpyrrolidine hydrochloride, the title compound was obtained as described in general method H. MS (ESI, m/z): 628.2 [M+H]$^+$

Example 773

2-amino-N—((R)-1-(2'-chloro-4'-fluoro-[1,1'-biphenyl]-4-carbonyl)pyrrolidin-3-yl)-5-(2-(2-(1-methylpyrrolidin-2-yl)ethoxy)phenyl)nicotinamide Using Example 778 and 2-(2-chloroethyl)-1-methylpyrrolidine hydrochloride, the title compound was obtained as described in general method H. MS (ESI, m/z): 642.3 [M+H]$^+$

Example 848

(R)—N-(1-(4'-(3-(dimethylamino)propoxy)-[1,1'-biphenyl]-4-carbonyl)pyrrolidin-3-yl)-2-((3-(dimethylamino)propyl)amino)-5-(1-methyl-1H-pyrazol-4-yl)nicotinamide The title compound was obtained as described in general method H.

General Method I

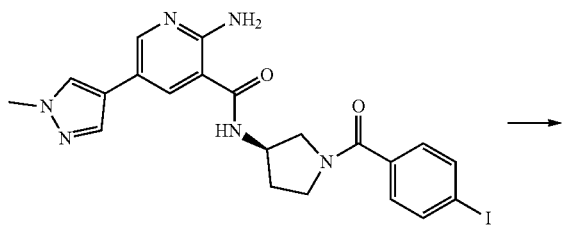

Example 400

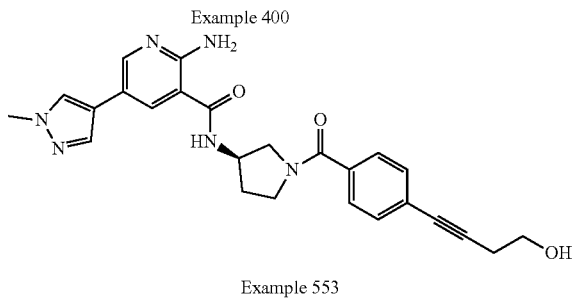

Example 553

Example 553

(R)-2-amino-N-(1-(4-(4-hydroxybut-1-yn-1-yl)benzoyl)pyrrolidin-3-yl)-5-(1-methyl-1H-pyrazol-4-yl)nicotinamide A mixture of Example 400 (30 mg, 0.06 mmol), Pd(PPh$_3$)$_2$Cl$_2$ (2 mg, 5 mol %) and CuI (1 mg, 10 mol %) in 0.6 mL of N,N-dimethylformamide/triethylamine (5/1) was degassed with nitrogen, and but-3-yn-1-ol (9 μl, 0.12 mmol) was added. The mixture was heated at 100° C. for 12 h. After cooling, the mixture was partitioned between ethyl acetate and water. The organic layer was separated and washed with water, brine dried over MgSO$_4$ and concentrated in vacuo. After concentration under vacuum, the crude residue was purified by preparative HPLC to afford 15 mg of the title compound. $^1$H NMR (400 MHz, METHANOL-d$_4$) δ ppm 2.03-2.23 (m, 1H) 2.23-2.43 (m, 1H) 2.63 (td, J=6.65, 2.74 Hz, 2H) 3.47-3.54 (m, 0.5H) 3.59-3.70 (m, 1H) 3.73 (td, J=6.65, 2.35 Hz, 2H) 3.78-3.86 (m, 1H) 3.86-3.92 (m, 0.5H) 3.94 (d, J=1.96 Hz, 3H) 3.98 (dd, J=13.11, 6.85 Hz, 1H) 4.49-4.59 (m, 0.5H) 4.63-4.71 (m, 0.5H) 7.42-7.60 (m, 4H) 7.90 (d, J=10.56 Hz, 1H) 8.05 (d, J=9.39 Hz, 1H) 8.24 (dd, J=10.96, 1.96 Hz, 1H) 8.60-8.72 (m, 1H); MS (ESI, m/z): 459.2 [M+H]$^+$

Example 554

(R)-2-amino-N-(1-(4-(5-hydroxypent-1-yn-1-yl)benzoyl)pyrrolidin-3-yl)-5-(1-methyl-1H-pyrazol-4-yl)nicotinamide Using pent-4-yn-1-ol, the title compound was obtained as described in general method I. $^1$H NMR (400 MHz, METHANOL-d$_4$) δ ppm 1.77-1.85 (m, 2H) 2.01-2.22 (m, 1H) 2.26-2.47 (m, 1H) 2.52 (td, J=7.24, 2.74 Hz, 2H) 3.46-3.53 (m, 0.5H) 3.63-3.76 (m, 1H) 3.69 (td, J=6.26, 2.35 Hz, 2H) 3.79-3.86 (m, 1H) 3.86-3.93 (m, 0.5H) 3.95 (d, J=1.96 Hz, 3H) 3.96-4.05 (m, 1H) 4.50-4.58 (m, 0.5H) 4.63-4.73 (m, 0.5H) 7.37-7.58 (m, 4H) 7.90 (d, J=10.56 Hz, 1H) 8.05 (d, J=9.78 Hz, 1H) 8.24 (dd, J=11.35, 1.96 Hz, 1H) 8.61-8.71 (m, 1H); MS (ESI, m/z): 473.2 [M+H]$^+$ General Method J

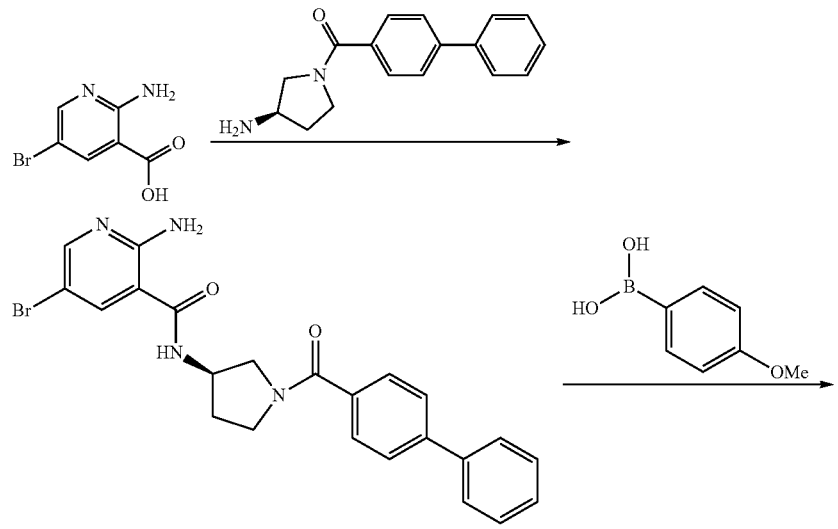

Intermediate 4

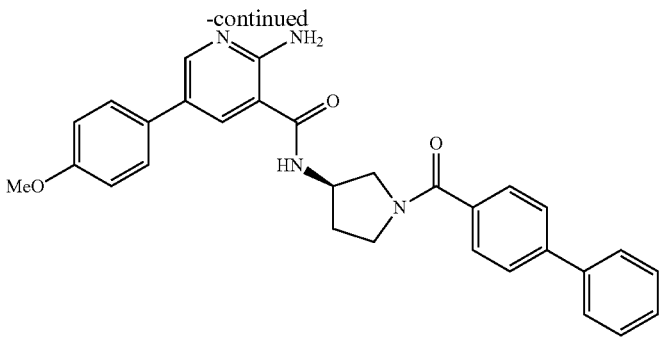

Example 555

Intermediate 4

To a mixture of 2-amino-5-bromonicotinic acid (1.0 g, 4.58 mmol) and triethylamine (0.958 mL, 6.87 mmol) in 12 mL of N,N-dimethylformamide was added 1-[bis(dimethylamino)methylene]-1H-1,2,3-triazolo[4,5-b]pyridinium 3-oxid hexafluorophosphate (1.7 g, 4.58 mmol) followed by (R)-[1,1'-biphenyl]-4-yl(3-aminopyrrolidin-1-yl)methanone (0.853 g, 4.58 mmol). The mixture was stirred at room temperature for 1 h and then saturated sodium bicarbonate solution was added. The mixture was extracted with ethyl acetate, washed with brine, dried over MgSO$_4$, and concentrated in vacuo. The crude product was purified through silica gel column chromatography (0 to 60% ethyl acetate/hexanes for 30 min) to give an off-white solid. To a mixture of product in dichloromethane (12 mL) was added trifluoroacetic acid (3 mL) and stirred at room temperature for overnight. After removing volatiles, the crude product was diluted with diethyl ether and the precipitate was collected by filtration and dried to afford 1.3 g of the title compound. MS (ESI, m/z): 465.1/467.1 [M+H]$^+$

Example 555

(R)—N-(1-([1,1'-biphenyl]-4-carbonyl)pyrrolidin-3-yl)-2-amino-5-(4-methoxyphenyl)nicotinamide To a mixture of Intermediate 4 (4.48 g, 20.6 mmol) and 4-methoxybenzeneboronic acid (5.5 g, 26.8 mmol) in 100 mL of 1,4-dioxane/water (3/1) was added K$_2$CO$_3$ (8.5 g, 61.9 mmol) followed by Pd(PPh$_3$)$_4$ (1.19 g, 1.03 mmol). The reaction mixture was heated at 100° C. for 3 h, cooled to room temperature, and extracted with ethyl acetate, dried over anhydrous MgSO$_4$ and concentrated under vacuum. The crude residue was purified by preparative HPLC to afford 10 mg of the title compound. $^1$H NMR (400 MHz, METHANOL-d$_4$) δ ppm 2.06-2.22 (m, 1H) 2.24-2.43 (m, 1H) 3.48-3.80 (m, 3H) 3.84 (s, 3H) 3.89-4.07 (m, 1H) 4.49 (br d, J=5.48 Hz, 0.5H) 4.52-4.61 (m, 0.5H) 7.06 (dd, J=8.41, 5.67 Hz, 2H) 7.34-7.41 (m, 1H) 7.46 (br t, J=6.46 Hz, 2H) 7.57-7.68 (m, 6H) 7.68-7.78 (m, 2H) 8.20-8.27 (m, 1H) 8.68-8.80 (m, 1H); MS (ESI, m/z): 493.2 [M+H]$^+$

Example 556

(R)—N-(1-([1,1'-biphenyl]-4-carbonyl)pyrrolidin-3-yl)-2-amino-5-(4-(4-methylpiperazin-1-yl)phenyl)nicotinamide Using (4-(4-methylpiperazin-1-yl)phenyl)boronic acid, the title compound was obtained as described in general method J. $^1$H NMR (400 MHz, METHANOL-d$_4$) δ ppm 2.06-2.25 (m, 1H) 2.26-2.48 (m, 1H) 2.98 (s, 3H) 3.00-3.18 (m, 2H) 3.30-3.81 (m, 2H) 3.55-3.80 (m, 4H) 3.80-3.91 (m, 1H) 3.91-4.06 (m, 3H) 4.52-4.63 (m, 0.5H) 4.67-4.75 (m, 0.5H) 7.15 (dd, J=8.61, 5.48 Hz, 2H) 7.33-7.41 (m, 1H) 7.41-7.50 (m, 2H) 7.56-7.68 (m, 6H) 7.68-7.76 (m, 2H) 8.24 (dd, J=13.69, 1.96 Hz, 1H) 8.67-8.80 (m, 1H); MS (ESI, m/z): 561.2 [M+H]$^+$

Example 557

(R)—N-(1-([1,1'-biphenyl]-4-carbonyl)pyrrolidin-3-yl)-2-amino-5-(4-morpholinophenyl)nicotinamide Using (4-morpholinophenyl)boronic acid, the title compound was obtained as described in general method J. $^1$H NMR (400 MHz, METHANOL-d$_4$) δ ppm 2.09-2.25 (m, 1H) 2.28-2.45 (m, 1H) 3.19-3.25 (m, 4H) 3.58 (br dd, J=11.54, 4.89 Hz, 0.5H) 3.64-3.80 (m, 2.5H) 3.83-3.89 (m, 4H) 3.91-4.06 (m, 1H) 4.57 (br d, J=5.87 Hz, 0.5H) 4.72 (br d, J=5.48 Hz, 0.5H) 7.10 (br dd, J=8.61, 5.48 Hz, 2H) 7.34-7.41 (m, 1H) 7.46 (br t, J=6.85 Hz, 2H) 7.57-7.69 (m, 6H) 7.69-7.75 (m, 2H) 8.23 (dd, J=13.69, 1.96 Hz, 1H) 8.68-8.81 (m, 1H); MS (ESI, m/z): 548.2 [M+H]$^+$

Example 558

(R)—N-(1-([1,1'-biphenyl]-4-carbonyl)pyrrolidin-3-yl)-6-amino-[3,3'-bipyridine]-5-carboxamide Using pyridine-3-boronic acid, the title compound was obtained as described in general method J. $^1$H NMR (400 MHz, METHANOL-d$_4$) δ ppm 2.08-2.25 (m, 1H) 2.28-2.47 (m, 1H) 3.58 (br dd, J=11.35, 5.09 Hz, 0.5H) 3.69 (br d, J=8.61 Hz, 1H) 3.74-3.82 (m, 1H) 3.86 (br dd, J=11.93, 6.46 Hz, 0.5H) 3.92-4.08 (m, 1H) 4.51-4.64 (m, 0.5H) 4.67-4.76 (m, 0.5H) 7.34-7.41 (m, 1H) 7.45 (td, J=7.43, 3.13 Hz, 2H) 7.60-7.67 (m, 4H) 7.67-7.75 (m, 2H) 7.97-8.05 (m, 1H) 8.36 (br dd, J=14.67, 6.85 Hz, 1H) 8.53 (dd, J=14.87, 1.96 Hz, 1H) 8.66-8.75 (m, 1H) 8.81 (br s, 1H) 9.14 (br d, J=12.91 Hz, 1H); MS (ESI, m/z): 464.2 [M+H]$^+$

Example 559

(R)—N-(1-([1,1,1'-biphenyl]-4-carbonyl)pyrrolidin-3-yl)-6-amino-6'-morpholino-[333'-bipyridine]-5-carboxamide Using (6-morpholinopyridin-3-yl)boronic acid, the title compound was obtained as described in general method J.

¹H NMR (400 MHz, METHANOL-d₄) δ ppm 2.07-2.25 (m, 1H) 2.29-2.47 (m, 1H) 3.52-3.60 (m, 0.5H) 3.64 (br d, J=4.30 Hz, 4H) 3.67-3.81 (m, 2.5H) 3.81-3.89 (m, 4H) 3.95-4.06 (m, 1H) 4.54-4.59 (m, 0.5H) 4.72 (br d, J=4.70 Hz, 0.5H) 7.19 (br dd, J=8.61, 5.87 Hz, 1H) 7.29-7.42 (m, 1H) 7.42-7.50 (m, 2H) 7.55-7.69 (m, 4H) 7.69-7.76 (m, 2H) 8.06-8.15 (m, 1H) 8.32 (br d, J=14.09 Hz, 1H) 8.38 (br d, J=15.26 Hz, 1H) 8.58-8.71 (m, 1H); MS (ESI, m/z): 549.2 [M+H]⁺

Example 560

(R)—N-(1-([1,1'-biphenyl]-4-carbonyl)pyrrolidin-3-yl)-6-amino-6'-fluoro-[3,3'-bipyridine]-5-carboxamide Using (6-fluoropyridin-3-yl)boronic acid, the title compound was obtained as described in general method J. ¹H NMR (600 MHz, METHANOL-d₄) δ ppm 2.07-2.23 (m, 1H) 2.27-2.45 (m, 1H) 3.56 (dd, J=11.15, 4.70 Hz, 0.5H) 3.64-3.72 (m, 1H) 3.72-3.80 (m, 1H) 3.80-3.90 (m, 0.5H) 3.92-4.06 (m, 1H) 4.52-4.62 (m, 0.5H) 4.65-4.74 (m, 0.5H) 7.21 (td, J=8.95, 2.64 Hz, 1H) 7.30-7.40 (m, 1H) 7.44 (td, J=7.63, 4.11 Hz, 2H) 7.59-7.67 (m, 4H) 7.70 (t, J=8.51 Hz, 2H) 8.19-8.32 (m, 1H) 8.33-8.42 (m, 1H) 8.48-8.57 (m, 1H) 8.68-8.81 (m, 1H); MS (ESI, m/z): 482.2 [M+H]⁺

Example 561 tert-butyl (R)-4-(4-(5-((1-([1,1'-biphenyl]-4-carbonyl)pyrrolidin-3-yl)carbamoyl)-6-aminopyridin-3-yl)-1H-pyrazol-1-yl)piperidine-1-carboxylate Using (1-(1-(tert-butoxycarbonyl)piperidin-4-yl)-1H-pyrazol-4-yl)boronic acid, the title compound was obtained as described in general method J. MS (ESI, m/z): 636.2 [M+H]⁺

Example 562

(R)—N-(1-([1,1'-biphenyl]-4-carbonyl)pyrrolidin-3-yl)-2-amino-5-(1-(piperidin-4-yl)-1H-pyrazol-4-yl)nicotinamide Following deprotection of example 561 with trifluoroacetic acid, the title compound was obtained. ¹H NMR (400 MHz, METHANOL-d₄) δ ppm 2.08-2.25 (m, 1H) 2.25-2.51 (m, 5H) 3.19-3.27 (m, 2H) 3.52-3.63 (m, 2.5H) 3.69 (br dd, J=12.91, 5.09 Hz, 1H) 3.74-3.82 (m, 1H) 3.82-3.91 (m, 0.5H) 3.92-4.06 (m, 1H) 4.52-4.65 (m, 1.5H) 4.66-4.75 (m, 0.5H) 7.33-7.41 (m, 1H) 7.45 (td, J=7.53, 3.33 Hz, 2H) 7.61-7.68 (m, 4H) 7.68-7.75 (m, 2H) 7.98 (d, J=12.13 Hz, 1H) 8.20 (d, J=11.35 Hz, 1H) 8.26 (dd, J=13.69, 1.96 Hz, 1H) 8.64-8.77 (m, 1H); MS (ESI, m/z): 536.2 [M+H]⁺

Example 563

(R)—N-(1-([1,1'-biphenyl]-4-carbonyl)pyrrolidin-3-yl)-2-amino-5-(1-(1-methylpiperidin-4-yl)-1H-pyrazol-4-yl)nicotinamide Using (1-(1-methylpiperidin-4-yl)-1H-pyrazol-4-yl)boronic acid, the title compound was obtained as described in general method J. MS (ESI, m/z): 550.2 [M+H]⁺

Example 564

(R)—N-(1-([1,1'-biphenyl]-4-carbonyl)pyrrolidin-3-yl)-2-amino-5-(4-(2-(piperazin-1-yl)propan-2-yl)phenyl)nicotinamide Using 1-(2-(4-(4,4,5,5-tetramethyl-1,3,2-dioxaborolan-2-yl)phenyl)propan-2-yl)piperazine, the title compound was obtained as described in general method J. MS (ESI, m/z): 589.2 [M+H]⁺

Example 565

(R)—N-(1-([1,1'-biphenyl]-4-carbonyl)pyrrolidin-3-yl)-2-amino-5-(4-(2-(4-(2-hydroxyethyl)piperazin-1-yl)propan-2-yl)phenyl)nicotinamide Using 2-(4-(2-(4-(4,4,5,5-tetramethyl-1,3,2-dioxaborolan-2-yl)phenyl)propan-2-yl)piperazin-1-yl)ethan-1-ol, the title compound was obtained as described in general method J. ¹H NMR (400 MHz, METHANOL-d₄) δ ppm 2.08-2.24 (m, 1H) 2.32 (br s, 1H) 2.96 (br s, 2H) 3.24 (br d, J=5.87 Hz, 4H) 3.33-3.43 (m, 4H) 3.59 (br d, J=11.74 Hz, 0.5H) 3.65-3.81 (m, 2H) 3.85 (br s, 2.5H) 3.91-4.07 (m, 1H) 4.58 (br s, 0.5H) 4.72 (br s, 0.5H) 7.31-7.41 (m, 1H) 7.41-7.51 (m, 2H) 7.59-7.80 (m, 10H) 8.32 (br d, J=14.09 Hz, 1H) 8.82 (s, 1H); MS (ESI, m/z): 633.2 [M+H]⁺

Example 567

(R)—N-(1-([1,1'-biphenyl]-4-carbonyl)pyrrolidin-3-yl)-2-amino-5-(4-((4-methylpiperazin-1-yl)methyl)phenyl)nicotinamide Using 1-methyl-4-(4-(4,4,5,5-tetramethyl-1,3,2-dioxaborolan-2-yl)benzyl)piperazine, the title compound was obtained as described in general method J. ¹H NMR (400 MHz, METHANOL-d₄) δ ppm 2.08-2.25 (m, 1H) 2.26-2.44 (m, 1H) 2.92 (s, 3H) 3.04-3.17 (m, 4H) 3.39-3.51 (m, 4H) 3.58 (br dd, J=11.54, 5.28 Hz, 0.5H) 3.70 (br dd, J=12.72, 5.28 Hz, 1H) 3.73-3.80 (m, 1H) 3.83 (br d, J=7.43 Hz, 0.5H) 3.95-4.07 (m, 1H) 4.02 (s, 2H) 4.53-4.61 (m, 0.5H) 4.66-4.76 (m, 0.5H) 7.34-7.40 (m, 1H) 7.42-7.49 (m, 2H) 7.50-7.85 (m, 10H) 8.30-8.38 (m, 1H) 8.73-8.85 (m, 1H); MS (ESI, m/z): 575.2 [M+H]⁺

Example 568

(R)—N-(1-([1,1'-biphenyl]-4-carbonyl)pyrrolidin-3-yl)-2-amino-5-(4-(hydroxymethyl)phenyl)nicotinamide Using (4-(hydroxymethyl)phenyl)boronic acid, the title compound was obtained as described in general method J. MS (ESI, m/z): 493.2 [M+H]⁺

Example 569

(R)—N-(1-([1,1'-biphenyl]-4-carbonyl)pyrrolidin-3-yl)-2-amino-5-(4-(morpholinomethyl)phenyl)nicotinamide Using (4-(morpholinomethyl)phenyl)boronic acid, the title compound was obtained as described in general method J. MS (ESI, m/z): 562.2 [M+H]⁺

Example 570

(R)-2-amino-N-(1-(2'-chloro-[1,1'-biphenyl]-4-carbonyl)pyrrolidin-3-yl)-5-(4-(4-methylpiperazin-1-yl)phenyl)nicotinamide Using (R)-(3-aminopyrrolidin-1-yl)(2'-chloro-[1,1'-biphenyl]-4-yl)methanone and (4-(4-methylpiperazin-1-yl)phenyl)boronic acid, the title compound was obtained as described in general method J. MS (ESI, m/z): 596.2 [M+H]$^+$

Example 571

(R)-2-amino-N-(1-(2'-chloro-[1,1'-biphenyl]-4-carbonyl)pyrrolidin-3-yl)-5-(4-morpholinophenyl)nicotinamide Using (R)-(3-aminopyrrolidin-1-yl)(2'-chloro-[1,1'-biphenyl]-4-yl)methanone and (4-morpholinophenyl)boronic acid, the title compound was obtained as described in general method J. $^1$H NMR (600 MHz, METHANOL-d$_4$) δ ppm 2.07-2.24 (m, 1H) 2.28-2.43 (m, 1H) 3.28-3.30 (m, 4H) 3.58 (dd, J=11.15, 5.28 Hz, 0.5H) 3.64-3.72 (m, 1H) 3.72-3.79 (m, 1H) 3.81-3.85 (m, 4H) 3.85-3.89 (m, 0.5H) 3.92-4.03 (m, 1H) 4.52-4.64 (m, 0.5H) 4.64-4.74 (m, 0.5H) 7.08 (dd, J=8.80, 7.04 Hz, 2H) 7.32-7.40 (m, 3H) 7.48-7.53 (m, 3H) 7.57 (d, J=8.80 Hz, 1H) 7.60 (d, J=8.80 Hz, 1H) 7.63 (dd, J=9.98, 8.22 Hz, 2H) 8.22 (dd, J=18.78, 1.76 Hz, 1H) 8.68-8.79 (m, 1H); MS (ESI, m/z): 583.2 [M+H]$^+$

Example 572

(R)-2-amino-N-(1-(2'-chloro-[1,1'-biphenyl]-4-carbonyl)pyrrolidin-3-yl)-5-(4-((4-methylpiperazin-1-yl)methyl)phenyl)nicotinamide Using (R)-(3-aminopyrrolidin-1-yl)(2'-chloro-[1,1'-biphenyl]-4-yl)methanone and 1-methyl-4-(4-(4,4,5,5-tetramethyl-1,3,2-dioxaborolan-2-yl)benzyl)piperazine, the title compound was obtained as described in general method J. MS (ESI, m/z): 610.2 [M+H]$^+$

Example 573

(R)-2-amino-N-(1-(2'-chloro-[1,1'-biphenyl]-4-carbonyl)pyrrolidin-3-yl)-5-(1-(2-methoxyethyl)-1H-pyrazol-4-yl)nicotinamide Using (R)-(3-aminopyrrolidin-1-yl)(2'-chloro-[1,1'-biphenyl]-4-yl)methanone and (1-(2-methoxyethyl)-1H-pyrazol-4-yl)boronic acid, the title compound was obtained as described in general method J. $^1$H NMR (400 MHz, METHANOL-d$_4$) δ ppm 2.17 (ddd, J=19.56, 12.91, 6.65 Hz, 1H) 2.29-2.47 (m, 1H) 3.33 (s, 3H) 3.58 (br dd, J=11.35, 5.09 Hz, 0.5H) 3.68-3.82 (m, 4H) 3.82-3.91 (m, 0.5H) 4.01 (td, J=12.72, 6.65 Hz, 1H) 4.33-4.41 (m, 2H) 4.55-4.62 (m, 0.5H) 4.71 (t, J=6.46 Hz, 0.5H) 7.31-7.44 (m, 3H) 7.50-7.59 (m, 3H) 7.65 (br t, J=8.41 Hz, 2H) 7.94 (d, J=10.96 Hz, 1H) 8.11 (d, J=10.96 Hz, 1H) 8.26 (dd, J=12.52, 1.96 Hz, 1H) 8.65-8.76 (m, 1H); MS (ESI, m/z): 546.2 [M+H]$^+$

Example 574

(R)-2-amino-5-(4-(azetidin-1-ylsulfonyl)phenyl)-N-(1-(2'-chloro-[1,1'-biphenyl]-4-carbonyl)pyrrolidin-3-yl)nicotinamide Using (R)-(3-aminopyrrolidin-1-yl)(2'-chloro-[1,1'-biphenyl]-4-yl)methanone and (4-(azetidin-1-ylsulfonyl)phenyl)boronic acid, the title compound was obtained as described in general method J. $^1$H NMR (400 MHz, METHANOL-d$_4$) δ ppm 2.04-2.11 (m, 2H) 2.11-2.24 (m, 1H) 2.28-2.46 (m, 1H) 3.60 (br dd, J=10.96, 5.09 Hz, 0.5H) 3.67-3.74 (m, 1H) 3.78 (t, J=7.63 Hz, 4H) 3.81-3.92 (m, 1.5H) 4.01 (td, J=13.11, 6.65 Hz, 1H) 4.55-4.66 (m, 0.5H) 4.68-4.75 (m, 0.5H) 7.34-7.43 (m, 3H) 7.44-7.58 (m, 3H) 7.64 (t, J=8.22 Hz, 2H) 7.92-8.05 (m, 4H) 8.47 (dd, J=12.72, 2.15 Hz, 1H) 8.73-8.85 (m, 1H); MS (ESI, m/z): 617.2 [M+H]$^+$

Example 575

(R)-2-amino-N-(1-(2'-chloro-[1,1'-biphenyl]-4-carbonyl)pyrrolidin-3-yl)-5-(4-sulfamoylphenyl)nicotinamide Using (R)-(3-aminopyrrolidin-1-yl)(2'-chloro-[1,1'-biphenyl]-4-yl)methanone and (4-sulfamoylphenyl)boronic acid, the title compound was obtained as described in general method J. $^1$H NMR (400 MHz, METHANOL-d$_4$) δ ppm 2.08-2.26 (m, 1H) 2.27-2.49 (m, 1H) 3.59 (dd, J=10.96, 5.09 Hz, 0.5H) 3.66-3.74 (m, 1H) 3.74-3.81 (m, 1H) 3.81-3.92 (m, 0.5H) 3.96-4.13 (m, 1H) 4.54-4.62 (m, 0.5H) 4.69-4.75 (m, 0.5H) 7.26-7.42 (m, 3H) 7.44-7.57 (m, 3H) 7.58-7.72 (m, 2H) 7.86 (br d, J=8.61 Hz, 1H) 7.88-7.95 (m, 1H) 8.02 (dd, J=8.41, 4.89 Hz, 2H) 8.42 (dd, J=12.72, 2.15 Hz, 1H) 8.72-8.85 (m, 1H); MS (ESI, m/z): 577.2 [M+H]$^+$

Example 576

(R)-2-amino-N-(1-(2'-chloro-[1,1'-biphenyl]-4-carbonyl)pyrrolidin-3-yl)-5-(4-(methylsulfonamido)phenyl)nicotinamide Using (R)-(3-aminopyrrolidin-1-yl)(2'-chloro-[1,1'-biphenyl]-4-yl)methanone and (4-(methylsulfonamido)phenyl)boronic acid, the title compound was obtained as described in general method J. $^1$H NMR (400 MHz, METHANOL-d$_4$) δ ppm 2.08-2.25 (m, 1H) 2.29-2.48 (m, 1H) 3.00 (s, 3H) 3.59 (br dd, J=11.15, 5.28 Hz, 0.5H) 3.65-3.80 (m, 2H) 3.80-3.92 (m, 0.5H) 3.93-4.07 (m, 1H) 4.55-4.62 (m, 0.5H) 4.71 (d, J=5.87 Hz, 0.5H) 7.35-7.45 (m, 4H) 7.50-7.61 (m, 4H) 7.61-7.74 (m, 4H) 8.30 (dd, J=12.52, 2.35 Hz, 1H) 8.69-8.81 (m, 1H); MS (ESI, m/z): 591.2 [M+H]$^+$

Example 577

(R)-2-amino-5-(1-(tert-butyl)-1H-pyrazol-4-yl)-N-(1-(2'-chloro-[1,1'-biphenyl]-4-carbonyl)pyrrolidin-3-yl)nicotinamide Using (R)-(3-aminopyrrolidin-1-yl)(2'-chloro-[1,1'-biphenyl]-4-yl)methanone and (1-(tert-butyl)-1H-pyrazol-4-yl)boronic acid pinacole ester, the title compound was obtained as described in general method J. MS (ESI, m/z): 544.2 [M+H]$^+$

Example 578

(R)-4-(6-amino-5-((1-(2'-chloro-[1,1'-biphenyl]-4-carbonyl)pyrrolidin-3-yl)carbamoyl)pyridin-3-yl)benzoic acid Using (R)-(3-aminopyrrolidin-1-yl)(2'-chloro-[1,1'-biphenyl]-4-yl)methanone and 4-carboxybenzeneboronic acid, the title compound was obtained as described in general method J. MS (ESI, m/z): 542.2 [M+H]+

Example 579

(R)-2-amino-N-(1-(2'-chloro-4'-fluoro-[1,1'-biphenyl]-4-carbonyl)pyrrolidin-3-yl)nicotinamide Using (R)-(3-aminopyrrolidin-1-yl)(2'-chloro-4'-fluoro-[111'-biphenyl]-4-yl)methanone and 2-aminonicotinic acid, the title compound was obtained as described for Intermediate 4 in general method J. $^1$H NMR (600 MHz, METHANOL-d$_4$) δ ppm 2.05-2.22 (m, 1H) 2.26-2.42 (m, 1H) 3.53 (dd, J=11.15, 4.70 Hz, 0.5H) 3.61-3.71 (m, 1H) 3.71-3.78 (m, 1H) 3.79-3.88 (m, 0.5H) 3.89-4.03 (m, 1H) 4.48-4.61 (m, 0.5H) 4.61-4.77 (m, 0.5H) 6.95-7.03 (m, 1H) 7.14-7.22 (m, 1H) 7.32-7.38 (m, 1H) 7.41 (dt, J=8.66, 5.94 Hz, 1H) 7.51 (t, J=7.95 Hz, 2H) 7.63 (dd, J=12.33, 8.22 Hz, 2H) 8.03 (ddd, J=17.61, 6.16, 1.47 Hz, 1H) 8.36-8.50 (m, 1H); MS (ESI, m/z): 439.2 [M+H]+

Example 580

(R)-2-amino-5-bromo-N-(1-(2'-chloro-4'-fluoro-[1,1'-biphenyl]-4-carbonyl)pyrrolidin-3-yl)nicotinamide Using (R)-(3-aminopyrrolidin-1-yl)(2'-chloro-4'-fluoro-[111'-biphenyl]-4-yl)methanone, the title compound was obtained as described for Intermediate 4 in general method J. $^1$H NMR (400 MHz, METHANOL-d$_4$) δ ppm 2.06-2.18 (m, 1H) 2.26-2.42 (m, 1H) 3.54 (br dd, J=11.15, 4.89 Hz, 0.5H) 3.66 (br dd, J=12.72, 4.89 Hz, 1H) 3.71-3.79 (m, 1H) 3.83 (br s, 0.5H) 3.87-4.03 (m, 1H) 4.47-4.59 (m, 0.5H) 4.60-4.73 (m, 0.5H) 7.18 (tt, J=8.41, 2.93 Hz, 1H) 7.33 (dt, J=8.80, 2.84 Hz, 1H) 7.41 (dt, J=8.41, 5.77 Hz, 1H) 7.50 (dd, J=7.83, 5.87 Hz, 2H) 7.63 (br t, J=8.41 Hz, 2H) 8.18-8.24 (m, 1H) 8.46-8.57 (m, 1H); MS (ESI, m/z): 517.2/519.2 [M+H]+

Example 581

(R)-6-amino-N-(1-(2'-chloro-4'-fluoro-[1,1'-biphenyl]-4-carbonyl)pyrrolidin-3-yl)-2'-(piperazin-1-yl)-[3,4'-bipyridine]-5-carboxamide Using (R)-(3-aminopyrrolidin-1-yl)(2'-chloro-4'-fluoro-[1,1'-biphenyl]-4-yl)methanone and (2-(piperazin-1-yl)pyridin-4-yl)boronic acid, the title compound was obtained as described in general method J. $^1$H NMR (600 MHz, METHANOL-d$_4$) δ ppm 2.09-2.25 (m, 1H) 2.28-2.44 (m, 1H) 3.39-3.44 (m, 4H) 3.58 (dd, J=11.15, 5.87 Hz, 0.5H) 3.64-3.72 (m, 1H) 3.72-3.80 (m, 1H) 3.83-3.89 (m, 0.5H) 3.94-4.05 (m, 5H) 4.55-4.61 (m, 0.5H) 4.68-4.75 (m, 0.5H) 7.14-7.20 (m, 1H) 7.29-7.36 (m, 2H) 7.40 (dt, J=8.51, 6.31 Hz, 1H) 7.47-7.52 (m, 3H) 7.62 (br d, J=8.22 Hz, 1H) 7.64 (br d, J=8.22 Hz, 1H) 8.19 (t, J=6.46 Hz, 1H) 8.60 (dd, J=17.61, 2.35 Hz, 1H) 8.73-8.86 (m, 1H); MS (ESI, m/z): 601.2 [M+H]+

Example 582

(R)-6'-acetamido-6-amino-N-(1-(2'-chloro-4'-fluoro-[1,1'-biphenyl]-4-carbonyl)pyrrolidin-3-yl)-[3,3'-bipyridine]-5-carboxamide Using (R)-(3-aminopyrrolidin-1-yl)(2'-chloro-4'-fluoro-[1,1'-biphenyl]-4-yl)methanone and (6-acetamidopyridin-3-yl)boronic acid, the title compound was obtained as described in general method J. $^1$H NMR (600 MHz, METHANOL-d$_4$) δ ppm 2.08-2.20 (m, 1H) 2.21 (s, 3H) 2.27-2.43 (m, 1H) 3.57 (br dd, J=11.15, 4.70 Hz, 0.5H) 3.63-3.72 (m, 1H) 3.72-3.80 (m, 1H) 3.80-3.88 (m, 0.5H) 3.95-4.04 (m, 1H) 4.55-4.61 (m, 0.5H) 4.65-4.74 (m, 0.5H) 7.13-7.20 (m, 1H) 7.34 (dt, J=8.80, 3.23 Hz, 1H) 7.40 (dt, J=8.66, 6.24 Hz, 2H) 7.45-7.52 (m, 2H) 7.62 (br d, J=8.22 Hz, 1H) 7.64 (br d, J=8.22 Hz, 1H) 8.10 (br t, J=8.22 Hz, 1H) 8.20 (br ddd, J=19.96, 8.80, 2.35 Hz, 1H) 8.37 (dd, J=19.07, 2.05 Hz, 1H) 8.62 (dd, J=19.37, 2.35 Hz, 1H) 8.71-8.82 (m, 1H); MS (ESI, m/z): 574.2 [M+H]+

Example 583

(R)-5',6-diamino-N-(1-(2'-chloro-4'-fluoro-[1,1'-biphenyl]-4-carbonyl)pyrrolidin-3-yl)-[3,3'-bipyridine]-5-carboxamide Using (R)-(3-aminopyrrolidin-1-yl)(2'-chloro-4'-fluoro-[1,1'-biphenyl]-4-yl)methanone and (5-aminopyridin-3-yl)boronic acid, the title compound was obtained as described in general method J. $^1$H NMR (600 MHz, METHANOL-d$_4$) δ ppm 2.06-2.24 (m, 1H) 2.29-2.44 (m, 1H) 3.56 (dd, J=11.15, 4.70 Hz, 0.5H) 3.63-3.72 (m, 1H) 3.72-3.81 (m, 1H) 3.81-3.89 (m, 0.5H) 3.95-4.05 (m, 1H) 4.51-4.63 (m, 0.5H) 4.64-4.78 (m, 0.5H) 7.11-7.22 (m, 1H) 7.34 (dt, J=6.75, 4.26 Hz, 1H) 7.41 (ddd, J=8.95, 5.72, 3.52 Hz, 1H) 7.50 (dd, J=8.22, 5.87 Hz, 2H) 7.60-7.67 (m, 2H) 7.84-7.91 (m, 1H) 7.99 (dd, J=5.28, 2.35 Hz, 1H) 8.26 (dd, J=18.78, 1.17 Hz, 1H) 8.44 (dd, J=17.90, 2.05 Hz, 1H) 8.47-8.57 (m, 1H); MS (ESI, m/z): 531.2 [M+H]+

Example 584

(R)-6-amino-N-(1-(2'-chloro-4'-fluoro-[1,1'-biphenyl]-4-carbonyl)pyrrolidin-3-yl)-6'-morpholino-[3,3'-bipyridine]-5-carboxamide Using (R)-(3-aminopyrrolidin-1-yl)(2'-chloro-4'-fluoro-[1,1'-biphenyl]-4-yl)methanone and (6-morpholinopyridin-3-yl)boronic acid, the title compound was obtained as described in general method J. $^1$H NMR (600 MHz, METHANOL-d$_4$) δ ppm 2.06-2.25 (m, 1H) 2.28-2.46 (m, 1H) 3.57 (dd, J=11.15, 5.28 Hz, 0.5H) 3.65-3.73 (m, 5H) 3.73-3.79 (m, 1H) 3.81-3.89 (m, 4.5H) 3.91-4.04 (m, 1H) 4.50-4.64 (m, 0.5H) 4.67-4.73 (m, 0.5H) 7.10-7.20 (m, 1H) 7.30-7.36 (m, 1H) 7.36-7.45 (m, 2H) 7.46-7.53 (m, 2H) 7.57-7.68 (m, 2H) 8.22-8.28 (m, 1H) 8.33-8.35 (m, 1H) 8.37 (d, J=2.35 Hz, 1H) 8.64-8.79 (m, 1H); MS (ESI, m/z): 602.2 [M+H]+

Example 585

(R)-2-amino-N-(1-(2'-chloro-4'-fluoro-[1,1'-biphenyl]-4-carbonyl)pyrrolidin-3-yl)-5-(4-(4-methylpiperazin-1-yl)phenyl)nicotinamide Using (R)-(3-aminopyrrolidin-1-yl)(2'-chloro-4'-fluoro-[1,1'-biphenyl]-4-yl)methanone and (4-(4-methylpiperazin-1-yl)phenyl)boronic acid, the title compound was obtained as described in general method J. $^1$H NMR (600 MHz, METHANOL-d$_4$) δ ppm 2.08-2.24 (m, 1H) 2.28-2.44 (m, 1H) 2.97 (s, 3H) 3.09 (br t, J=12.62 Hz, 2H) 3.19-3.28 (m, 2H) 3.57 (br dd, J=11.15, 5.28 Hz, 0.5H) 3.60-3.66 (m, 2H) 3.66-3.72 (m, 1H) 3.72-3.78 (m, 1H) 3.81-3.90 (m, 0.5H) 3.90-4.05 (m, 3H) 4.45-4.64 (m, 0.5H) 4.64-4.79 (m, 0.5H)

7.12-7.22 (m, 3H) 7.27-7.37 (m, 1H) 7.41 (dt, J=8.51, 5.72 Hz, 1H) 7.50 (dd, J=7.92, 6.75 Hz, 2H) 7.56-7.67 (m, 4H) 8.24 (dd, J=17.90, 2.05 Hz, 1H) 8.66-8.78 (m, 1H); MS (ESI, m/z): 614.2 [M+H]$^+$

Example 586

(R)-2-amino-N-(1-(2'-chloro-4'-fluoro-[1,1'-biphenyl]-4-carbonyl)pyrrolidin-3-yl)-5-(1-(pyridin-3-ylmethyl)-1H-pyrazol-4-yl)nicotinamide Using (R)-(3-aminopyrrolidin-1-yl)(2'-chloro-4'-fluoro-[1,1'-biphenyl]-4-yl)methanone and 3-((4-(4,4,5,5-tetramethyl-1,3,2-dioxaborolan-2-yl)-1H-pyrazol-1-yl)methyl) pyridine, the title compound was obtained as described in general method J. $^1$H NMR (600 MHz, METHANOL-d$_4$) δ ppm 2.08-2.23 (m, 1H) 2.28-2.43 (m, 1H) 3.56 (dd, J=11.15, 5.28 Hz, 0.5H) 3.64-3.72 (m, 1H) 3.72-3.80 (m, 1H) 3.82-3.88 (m, 0.5H) 3.94-4.05 (m, 1H) 4.54-4.60 (m, 0.5H) 4.67-4.73 (m, 0.5H) 5.64 (d, J=4.70 Hz, 2H) 7.14-7.20 (m, 1H) 7.34 (ddd, J=8.80, 4.70, 2.35 Hz, 1H) 7.40 (dt, J=8.66, 5.94 Hz, 1H) 7.50 (t, J=7.92 Hz, 2H) 7.60-7.66 (m, 2H) 7.98 (dd, J=7.92, 6.16 Hz, 1H) 8.02 (d, J=16.43 Hz, 1H) 8.27 (dd, J=17.61, 2.35 Hz, 1H) 8.30 (d, J=13.50 Hz, 1H) 8.36-8.42 (m, 1H) 8.65-8.76 (m, 1H) 8.79 (d, J=4.70 Hz, 2H); MS (ESI, m/z): 597.2 [M+H]$^+$ Example 587

(R)-6'-amino-5'-((1-(2'-chloro-4'-fluoro-[1,1'-biphenyl]-4-carbonyl)pyrrolidin-3-yl)carbamoyl)-[3,3'-bipyridine]-5-carboxylic acid Using (R)-(3-aminopyrrolidin-1-yl)(2'-chloro-4'-fluoro-[1,1'-biphenyl]-4-yl)methanone and 5-(carboxypyridin-3-yl) boronic acid, the title compound was obtained as described in general method J. $^1$H NMR (600 MHz, METHANOL-d$_4$) δ ppm 2.05-2.23 (m, 1H) 2.27-2.46 (m, 1H) 3.57 (dd, J=11.15, 5.28 Hz, 0.5H) 3.63-3.72 (m, 1H) 3.72-3.80 (m, 1H) 3.83-3.89 (m, 0.5H) 3.95-4.04 (m, 1H) 4.54-4.61 (m, 0.5H) 4.67-4.73 (m, 0.5H) 7.16 (tdd, J=8.29, 8.29, 5.43, 2.64 Hz, 1H) 7.33 (ddd, J=8.66, 6.02, 2.35 Hz, 1H) 7.36-7.44 (m, 1H) 7.46-7.53 (m, 2H) 7.59-7.69 (m, 3H) 8.45 (dd, J=18, 1.76 Hz, 1H) 8.72 (td, J=24, 2.05 Hz, 1H), 8.74 (dd, J=48, 1.76 Hz, 1H) 9.6 (dd, J=18, 2.35 Hz, 1H) 9.14 (dd, J=4.70, 1.76 Hz, 1H); MS (ESI, m/z): 560.2 [M+H]$^+$ Example 774

(R)-6-amino-N-(1-(2'-chloro-4'-fluoro-[1,1'-biphenyl]-4-carbonyl)pyrrolidin-3-yl)-6'-fluoro-[3,3'-bipyridine]-5-carboxamide Using (R)-(3-aminopyrrolidin-1-yl)(2'-chloro-4'-fluoro-[1,1'-biphenyl]-4-yl)methanone and (6-fluoropyridin-3-yl) boronic acid, the title compound was obtained as described in general method J. MS (ESI, m/z): 534.1 [M+H]$^+$ Example 775

(R)-2-amino-N-(1-(2'-chloro-4'-fluoro-[1,1'-biphenyl]-4-carbonyl)pyrrolidin-3-yl)-5-phenylnicotinamide Using (R)-(3-aminopyrrolidin-1-yl)(2'-chloro-4'-fluoro-[1,1'-biphenyl]-4-yl)methanone and phenylboronic acid, the title compound was obtained as described in general method J. $^1$H NMR (600 MHz, METHANOL-d$_4$) δ ppm 2.08-2.24 (m, 1H) 2.27-2.43 (m, 1H) 3.57 (dd, J=11.15, 5.28 Hz, 0.5H) 3.64-3.71 (m, 1H) 3.71-3.80 (m, 1H) 3.80-3.88 (m, 0.5H) 3.94-4.04 (m, 1H) 4.53-4.60 (m, 0.5H) 4.67-4.73 (m, 0.5H) 7.14-7.20 (m, 1H) 7.32-7.36 (m, 1H) 7.37-7.46 (m, 2H) 7.47-7.53 (m, 4H) 7.60-7.71 (m, 4H) 8.30 (dd, J=18.78, 2.35 Hz, 1H) 8.66-8.78 (m, 1H); MS (ESI, m/z): 515.1 [M+H]$^+$ Example 776

(R)-2-amino-5-(2-carbamoylphenyl)-N-(1-(2'-chloro-4'-fluoro-[1,1'-biphenyl]-4-carbonyl)pyrrolidin-3-yl)nicotinamide Using (R)-(3-aminopyrrolidin-1-yl)(2'-chloro-4'-fluoro-[1,1'-biphenyl]-4-yl)methanone and (2-carbamoylphenyl) boronic acid, the title compound was obtained as described in general method J. $^1$H NMR (600 MHz, METHANOL-d$_4$) δ ppm 2.04-2.18 (m, 1H) 2.24-2.39 (m, 1H) 3.53 (dd, J=11.15, 5.28 Hz, 0.5H) 3.65 (br dd, J=12.62, 4.40 Hz, 1H) 3.68-3.76 (m, 1H) 3.76-3.86 (m, 0.5H) 3.91-4.01 (m, 1H) 4.51-4.57 (m, 0.5H) 4.64-4.71 (m, 0.5H) 7.16 (tt, J=8.44, 2.42 Hz, 1H) 7.33 (dt, J=8.51, 2.79 Hz, 1H) 7.40 (ddd, J=8.66, 6.02, 2.93 Hz, 1H) 7.46-7.56 (m, 4H) 7.58-7.64 (m, 3H) 7.65-7.70 (m, 1H) 8.01 (dd, J=16.73, 2.05 Hz, 1H) 7.98-8.01 (m, 1H) 8.44-8.56 (m, 1H); MS (ESI, m/z): 558.2 [M+H]$^+$ Example 777

(R)-2-(6-amino-5-((1-(2'-chloro-4'-fluoro-[1,1'-biphenyl]-4-carbonyl)pyrrolidin-3-yl)carbamoyl)pyridin-3-yl)benzoic acid Using (R)-(3-aminopyrrolidin-1-yl)(2'-chloro-4'-fluoro-[1,1'-biphenyl]-4-yl)methanone and 2-boronobenzoic acid, the title compound was obtained as described in general method J. $^1$H NMR (600 MHz, METHANOL-d$_4$) δ ppm 2.01-2.16 (m, 1H) 2.24-2.39 (m, 1H) 3.51 (dd, J=11.15, 4.70 Hz, 0.5H) 3.58-3.67 (m, 1H) 3.67-3.75 (m, 1H) 3.75-3.83 (m, 0.5H) 3.90-4.00 (m, 1H) 4.51-4.57 (m, 0.5H) 4.65-4.71 (m, 0.5H) 7.14-7.20 (m, 1H) 7.34 (dd, J=8.80, 1.76 Hz, 1H) 7.39-7.47 (m, 2H) 7.49 (dd, J=8.22, 2.93 Hz, 2H) 7.55-7.64 (m, 3H) 7.64-7.72 (m, 1H) 8.00 (dd, J=19.96, 2.35 Hz, 1H) 8.10-8.14 (m, 1H) 8.42-8.54 (m, 1H); MS (ESI, m/z): 559.2 [M+H]$^+$ Example 778

(R)-2-amino-N-(1-(2'-chloro-4'-fluoro-[1,1'-biphenyl]-4-carbonyl)pyrrolidin-3-yl)-5-(2-hydroxyphenyl)nicotinamide Using (R)-(3-aminopyrrolidin-1-yl)(2'-chloro-4'-fluoro-[1,1'-biphenyl]-4-yl)methanone and (2-hydroxyphenyl)boronic acid, the title compound was obtained as described in general method J. $^1$H NMR (600 MHz, METHANOL-d$_4$) δ ppm 2.06-2.22 (m, 1H) 2.26-2.41 (m, 1H) 3.54 (dd, J=11.44, 4.99 Hz, 0.5H) 3.61-3.69 (m, 1H) 3.69-3.76 (m, 1H) 3.79-3.88 (m, 0.5H) 3.91-4.01 (m, 1H) 4.52-4.58 (m, 0.5H) 4.66-4.72 (m, 0.5H) 6.92-6.99 (m, 2H) 7.14-7.19 (m, 1H) 7.22-7.27 (m, 1H) 7.31-7.36 (m, 1H) 7.38-7.46 (m, 2H) 7.47-7.51 (m, 2H) 7.62 (t, J=8.72 Hz, 2H) 8.27-8.36 (m, 1H) 8.65-8.77 (m, 1H); MS (ESI, m/z): 531.1 [M+H]$^+$

Example 779

(R)-3-amino-6-(2-aminophenyl)-N-(1-(2'-chloro-4'-fluoro-[1,1'-biphenyl]-4-carbonyl)pyrrolidin-3-yl)pyrazine-2-carboxamide Using 3-amino-6-bromopyrazine-2-carboxylic acid and (2-aminophenyl)boronic acid, the title compound was obtained as described in general method J. $^1$H NMR (600 MHz, METHANOL-$d_4$) δ ppm 2.02-2.20 (m, 1H) 2.22-2.39 (m, 1H) 3.42 (br d, J=9.98 Hz, 0.5H) 3.53-3.61 (m, 1.5H) 3.68 (br d, J=5.28 Hz, 0.5H) 3.79 (br d, J=6.46 Hz, 1H) 3.97 (br dd, J=12.62, 7.34 Hz, 0.5H) 4.46-4.52 (m, 0.5H) 4.66-4.71 (m, 0.5H) 6.94-7.03 (m, 2H) 7.05-7.20 (m, 1H) 7.23 (br dd, J=15.55, 7.92 Hz, 2H) 7.27-7.34 (m, 1H) 7.37 (dd, J=18.49, 7.92 Hz, 2H) 7.42-7.59 (m, 3H) 7.71-7.79 (m, 1H); MS (ESI, m/z): 531.1 [M+H]$^+$

Example 780

(R)-6-amino-N-(1-(2'-chloro-4'-fluoro-[1,1'-fluoro-1-biphenyl]-4-carbonyl)pyrrolidin-3-yl)-2'-(4-methylpiperazin-1-yl)-[3,4'-bipyridine]-5-carboxamide Using (R)-(3-aminopyrrolidin-1-yl)(2'-chloro-4'-fluoro-[1,1'-biphenyl]-4-yl)methanone and (2-(4-methylpiperazin-1-yl)pyridin-4-yl)boronic acid, the title compound was obtained as described in general method J. $^1$H NMR (600 MHz, METHANOL-$d_4$) δ ppm 2.08-2.21 (m, 1H) 2.30-2.43 (m, 1H) 2.97 (s, 3H) 3.56 (br dd, J=11.15, 5.28 Hz, 0.5H) 3.66-3.73 (m, 1H) 3.75 (br dd, J=11.15, 7.04 Hz, 1H) 3.85 (br s, 0.5H) 3.96-4.05 (m, 1H) 4.55-4.59 (m, 0.5H) 4.72 (br s, 0.5H) 7.15-7.22 (m, 2H) 7.29 (br d, J=17.02 Hz, 1H) 7.33-7.37 (m, 1H) 7.41 (ddd, J=8.80, 5.87, 3.52 Hz, 1H) 7.50 (t, J=7.63 Hz, 2H) 7.63 (dd, J=12.33, 8.22 Hz, 2H) 8.24 (t, J=5.90 Hz, 1H) 8.50 (dd, J=17.31, 2.05 Hz, 1H) 8.67 (dd, J=48.71, 2.35 Hz, 1H); MS (ESI, m/z): 614.2 [M+H]$^+$

Example 781

(R)-2-amino-N-(1-(2'-chloro-4'-fluoro-[1,1'-biphenyl]-4-carbonyl)pyrrolidin-3-yl)-5-(3-chloro-4-(morpholine-4-carbonyl)phenyl)nicotinamide Using (R)-(3-aminopyrrolidin-1-yl)(2'-chloro-4'-fluoro-[1,1'-biphenyl]-4-yl)methanone and (3-chloro-4-(morpholine-4-carbonyl)phenyl)boronic acid, the title compound was obtained as described in general method J. $^1$H NMR (600 MHz, METHANOL-$d_4$) δ ppm 2.09-2.22 (m, 1H) 2.28-2.44 (m, 1H) 3.24-3.34 (m, 2H) 3.54-3.64 (m, 2H) 3.64-3.72 (m, 3H) 3.72-3.90 (m, 7H) 3.96-4.04 (m, 1H) 4.55-4.61 (m, 0.5H) 4.68-4.73 (m, 0.5H) 7.14-7.20 (m, 1H) 7.34 (ddd, J=8.66, 4.55, 2.64 Hz, 1H) 7.38-7.43 (m, 1H) 7.47-7.51 (m, 2H) 7.63 (dd, J=13.50, 8.22 Hz, 2H) 7.67-7.77 (m, 1.5H) 7.81 (d, J=1.17 Hz, 0.5H) 7.90 (d, J=22.89 Hz, 1H) 8.40 (dd, J=20.54, 2.35 Hz, 1H) 8.79 (dd, J=44.60, 2.35 Hz, 1H); MS (ESI, m/z): 662.2 [M+H]$^+$

Example 782

(R)-2-amino-N-(1-(2'-chloro-4'-fluoro-[1,1'-biphenyl]-4-carbonyl)pyrrolidin-3-yl)-5-(4-morpholinophenyl)nicotinamide Using (R)-(3-aminopyrrolidin-1-yl)(2'-chloro-4'-fluoro-[1,1'-biphenyl]-4-yl)methanone and (4-morpholinophenyl)boronic acid, the title compound was obtained as described in general method J. $^1$H NMR (600 MHz, METHANOL-$d_4$) δ ppm 2.09-2.24 (m, 1H) 2.28-2.42 (m, 1H) 3.19-3.23 (m, 4H) 3.57 (dd, J=11.15, 5.28 Hz, 0.5H) 3.65-3.72 (m, 1H) 3.72-3.78 (m, 1H) 3.82-3.84 (m, 4H) 3.84-3.87 (m, 0.5H) 3.94-4.02 (m, 1H) 4.54-4.59 (m, 0.5H) 4.67-4.72 (m, 0.5H) 7.06-7.11 (m, 2H) 7.17 (tdd, 1H) 7.32-7.36 (m, 1H) 7.40 (dt, J=8.36, 6.09 Hz, 1H) 7.49 (dd, J=8.22, 6.46 Hz, 2H) 7.55-7.65 (m, 4H) 8.22 (dd, J=18.49, 2.05 Hz, 1H) 8.72 (dd, J=41.67, 1.76 Hz, 1H); MS (ESI, m/z): 600.1 [M+H]$^+$

Example 783

(R)—N-(1-([1,1'-biphenyl]-4-carbonyl)pyrrolidin-3-yl)-2-amino-5-(4-(2-(4-((2-nitrophenyl)sulfonyl)piperazin-1-yl)propan-2-yl)phenyl)nicotinamide Using 1-((2-nitrophenyl)sulfonyl)-4-(2-(4-(4,4,5,5-tetramethyl-1,3,2-dioxaborolan-2-yl)phenyl)propan-2-yl)piperazine, the title compound was obtained as described in general method J. MS (ESI, m/z): 774.3 [M+H]$^+$

Example 784

2-amino-N—((R)-1-(2'-chloro-4'-fluoro-[1,'-biphenyl]-4-carbonyl)pyrrolidin-3-yl)-5-(2-(((r,4R)-4-hydroxycyclohexyl)carbamoyl)phenyl)nicotinamide Using Example 777 and (1r,4r)-4-aminocyclohexan-1-ol, the title compound was obtained as described in general method J. $^1$H NMR (600 MHz, METHANOL-$d_4$) δ ppm 1.22-1.35 (m, 2H) 1.35-1.49 (m, 1H) 1.54-1.68 (m, 1H) 1.85 (br s, 1H) 1.87-2.02 (m, 2H) 2.03-2.19 (m, 2H) 2.24-2.42 (m, 1H) 3.52 (br dd, J=11.15, 5.28 Hz, 1H) 3.63-3.84 (m, 3H) 3.91-4.02 (m, 1H) 4.53-4.58 (m, 0.5H) 4.65-4.70 (m, 0.5H) 4.82-4.92 (m, 1H) 7.13-7.20 (m, 1H) 7.31-7.37 (m, 1H) 7.37-7.43 (m, 1H) 7.46-7.73 (m, 8H) 7.95-8.03 (m, 1H) 8.40-8.50 (m, 1H); MS (ESI, m/z): 656.2 [M+H]$^+$

Example 845

(R)-2-amino-N-(1-(2'-chloro-4'-fluoro-[1,1'-biphenyl]-4-carbonyl)pyrrolidin-3-yl)-5-(2-formylphenyl)nicotinamide Using (R)-(3-aminopyrrolidin-1-yl)(2'-chloro-4'-fluoro-[1,1'-biphenyl]-4-yl)methanone and (2-formylphenyl)boronic acid, the title compound was obtained as described in general method J. MS (ESI, m/z): 543.2 [M+H]$^+$ General Method K

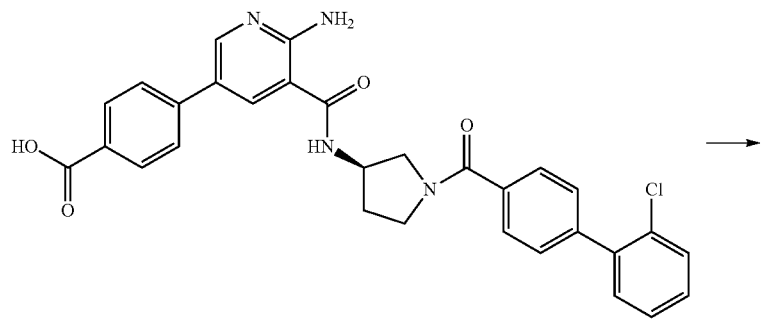

Example 578

Example 588

Example 588

(R)-2-amino-N-(1-(2'-chloro-[1,1'-biphenyl]-4-carbonyl)pyrrolidin-3-yl)-5-(4-(4-methylpiperazine-1-carbonyl)phenyl)nicotinamide To a mixture of Example 578 (10 mg, 0.02 mmol) and triethylamine (8 µl, 0.06 mmol) in 0.5 mL of N,N-dimethylformamide was added 1-[bis(dimethylamino)methylene]-1H-1,2,3-triazolo[4,5-b]pyridinium 3-oxid hexafluorophosphate (7 g, 0.02 mmol) followed by 1-methylpiperazine (2 µl, 0.02 mmol). The mixture was stirred at room temperature for 1 h and then saturated sodium bicarbonate solution was added. The mixture was extracted with ethyl acetate, washed with brine, dried over $MgSO_4$, and concentrated in vacuo. After removing volatiles, the crude product was diluted with diethyl ether and the precipitate was collected by filtration and dried to afford 5 mg of the title compound. $^1$H NMR (400 MHz, METHANOL-$d_4$) δ ppm 2.10-2.26 (m, 1H) 2.28-2.46 (m, 1H) 2.95 (s, 3H) 3.60 (br dd, J=10.96, 5.09 Hz, 0.5H) 3.71 (br dd, J=12.72, 4.89 Hz, 1H) 3.79 (br d, J=10.17 Hz, 1H) 3.85 (br s, 0.5H) 3.92-4.08 (m, 1H) 4.59 (t, J=5.87 Hz, 0.5H) 4.72 (t, J=5.48 Hz, 0.5H) 7.33-7.41 (m, 3H) 7.48-7.56 (m, 3H) 7.60-7.73 (m, 4H) 7.82 (br d, J=8.61 Hz, 1H) 7.84-7.88 (m, 1H) 8.35-8.44 (m, 1H) 8.76-8.88 (m, 1H); MS (ESI, m/z): 624.1 [M+H]$^+$

Example 589

(R)-2-amino-N-(1-(2'-chloro-[1,1'-biphenyl]-4-carbonyl)pyrrolidin-3-yl)-5-(4-(4-(2-hydroxyethyl)piperazine-1-carbonyl)phenyl)nicotinamide Using 1-(2-hydroxyethyl)piperazine, the title compound was obtained as described in general method K. $^1$H NMR (400 MHz, METHANOL-$d_4$) δ ppm 2.06-2.26 (m, 1H) 2.27-2.50 (m, 1H) 3.34 (br d, J=5.09 Hz, 4H) 3.60 (br dd, J=11.35, 5.09 Hz, 0.5H) 3.71 (br dd, J=12.13, 4.70 Hz, 1H) 3.79 (br d, J=9.78 Hz, 1H) 3.85 (br s, 0.5H) 3.88-3.94 (m, 2H) 3.95-4.06 (m, 1H) 4.57-4.62 (m, 0.5H) 4.72 (t, J=5.87 Hz, 0.5H) 7.38 (s, 3H) 7.52 (br dd, J=8.22, 3.13 Hz, 3H) 7.60-7.71 (m, 4H) 7.82 (br d, J=7.83 Hz, 1H) 7.85 (br d, J=8.22 Hz, 1H) 8.39 (dd, J=12.33, 2.15 Hz, 1H) 8.75-8.86 (m, 1H); MS (ESI, m/z): 654.2 [M+H]$^+$

Example 590

(R)-2-amino-N-(1-(2'-chloro-[1,1'-biphenyl]-4-carbonyl)pyrrolidin-3-yl)-5-(4-(morpholine-4-carbonyl)phenyl)nicotinamide Using morpholine, the title compound was obtained as described in general method K. $^1$H NMR (400 MHz, METHANOL-$d_4$) δ ppm 2.09-2.26 (m, 1H) 2.26-2.51 (m, 1H) 3.43-3.56 (m, 2H) 3.56-3.62 (m, 0.5H) 3.66 (br d, J=11.74 Hz, 2H) 3.68-3.83 (m, 6H) 3.84 (br d, J=7.83 Hz, 0.5H) 4.01 (br d, J=6.65 Hz, 1H) 4.56-4.64 (m, 0.5H) 4.69-4.75 (m, 0.5H) 7.35-7.43 (m, 3H) 7.49-7.55 (m, 3H) 7.58 (dd, J=8.22, 5.09 Hz, 2H) 7.64 (t, J=7.63 Hz, 2H) 7.79 (s, 1H) 7.80 (s, 1H) 7.83 (br d, J=8.61 Hz, 1H) 8.38 (dd, J=13.11, 2.15 Hz, 1H); MS (ESI, m/z): 611.2 [M+H]$^+$

Example 591

(R)-2-amino-N-(1-(2'-chloro-[1,1'-biphenyl]-4-carbonyl)pyrrolidin-3-yl)-5-(4-((1-methylpiperidin-4-yl)carbamoyl)phenyl)nicotinamide Using 4-amino-1-methylpiperidine, the title compound was obtained as described in general method K. $^1$H NMR (400 MHz, METHANOL-d$_4$) δ ppm 1.87-1.98 (m, 2H) 2.11-2.20 (m, 1H) 2.25 (br d, J=15.26 Hz, 2H) 2.29-2.45 (m, 1H) 2.89 (s, 3H) 3.13-3.22 (m, 2H) 3.60 (br d, J=11.35 Hz, 2H) 3.71 (br dd, J=13.11, 4.11 Hz, 1H) 3.74-3.81 (m, 1H) 3.90 (brs, 1H) 3.96-4.06 (m, 1H) 4.13-4.23 (m, 1H) 4.57-4.63 (m, 0.5H) 4.68-4.76 (n, 0.5H) 7.31-7.41 (m, 3H) 7.44-7.54 (m, 3H) 7.64 (t, J=7.63 Hz, 2H) 7.80 (br d, J=8.22 Hz, 1H) 7.84 (br d, J=8.22 Hz, 1H) 7.94-8.02 (m, 2H) 8.40 (dd, J=12.52, 2.35 Hz, 1H) 8.76-8.87 (m, 1H); MS (ESI, m/z): 638.2 [M+H]$^+$ Example 592

(R)-2-amino-N-(1-(2'-chloro-[1,1'-biphenyl]-4-carbonyl)pyrrolidin-3-yl)-5-(4-((4-methylcyclohexyl)carbamoyl)phenyl)nicotinamide Using 4-methylcyclohexan-1-amine, the title compound was obtained as described in general method K. $^1$H NMR (400 MHz, METHANOL-d$_4$) δ ppm 1.01 (d, J=6.65 Hz, 3H) 1.10 (br d, J=14.87 Hz, 1H) 1.35-1.52 (m, 2H) 1.60-1.74 (m, 3H) 1.74-1.86 (m, 2H) 1.96 (br d, J=9.78 Hz, 1H) 2.10-2.24 (m, 1H) 2.28-2.46 (m, 1H) 3.59 (br dd, J=11.15, 5.28 Hz, 0.5H) 3.71 (br dd, J=12.52, 4.70 Hz, 1H) 3.74-3.82 (m, 1H) 3.82-3.92 (m, 1H) 3.97-4.07 (m, 1.5H) 4.56-4.66 (m, 0.5H) 4.66-4.78 (m, 0.5H) 7.34-7.43 (m, 3H) 7.46-7.57 (m, 3H) 7.59-7.68 (m, 2H) 7.76-7.85 (m, 2H) 7.92-7.98 (m, 2H) 8.40 (dd, J=12.72, 1.76 Hz, 1H) 8.77-8.89 (m, 1H); MS (ESI, m/z): 637.2 [M+H]$^+$ Example 593

(R)-2-amino-N-(1-(2'-chloro-[1,1'-biphenyl]-4-carbonyl)pyrrolidin-3-yl)-5-(4-((tetrahydro-2H-pyran-4-yl)carbamoyl)phenyl)nicotinamide Using tetrahydro-2H-pyran-4-amine, the title compound was obtained as described in general method K. $^1$H NMR (600 MHz, METHANOL-d$_4$) δ ppm 1.68 (qd, J=12.13, 4.11 Hz, 2H) 1.90 (dt, J=12.47, 1.98 Hz, 2H) 2.06-2.25 (m, 1H) 2.29-2.44 (m, 1H) 3.52 (td, J=11.74, 1.76 Hz, 2H) 3.58 (dd, J=11.15, 5.28 Hz, 0.5H) 3.64-3.72 (m, 1H) 3.72-3.80 (m, 1H) 3.82-3.89 (m, 0.5H) 3.98 (br dd, J=11.44, 5.58 Hz, 2H) 4.00-4.04 (m, 1H) 4.12 (tt, J=11.22, 4.33 Hz, 1H) 4.55-4.62 (m, 0.5H) 4.68-4.74 (m, 0.5H) 7.32-7.40 (m, 3H) 7.45-7.54 (m, 3H) 7.63 (d, J=10.56, 8.22 Hz, 2H) 7.76-7.83 (m, 2H) 7.96 (t, J=8.22 Hz, 2H) 8.39 (dd, J=19.07, 2.05 Hz, 1H) 8.72-8.84 (m, 1H); MS (ESI, m/z): 625.2 [M+H]$^+$ Example 594

2-amino-N—((R)-1-(2'-chloro-[1,1'-biphenyl]-4-carbonyl)pyrrolidin-3-yl)-5-(4-(((1-methylpyrrolidin-3-yl)methyl)carbamoyl)phenyl)nicotinamide Using (1-methylpyrrolidin-3-yl)methanamine, the title compound was obtained as described in general method K. $^1$H NMR (600 MHz, METHANOL-d$_4$) δ ppm 1.80-1.87 (m, 0.5H) 1.98-2.06 (m, 0.5H) 2.09-2.25 (m, 1.5H) 2.29-2.43 (m, 1.5H) 2.71-2.78 (m, 0.5H) 2.88-2.92 (m, 0.5H) 2.94 (br d, J=11.15 Hz, 3H) 3.09-3.20 (m, 1H) 3.48-3.55 (m, 2H) 3.58 (br dd, J=11.15, 5.28 Hz, 0.5H) 3.64-3.73 (m, 2H) 3.73-3.80 (m, 2H) 3.82-3.89 (m, 1H) 3.96-4.05 (m, 1H) 4.35-4.38 (m, 0.5H) 4.55-4.61 (m, 0.5H) 4.68-4.75 (m, 0.5H) 7.32-7.41 (m, 3H) 7.48-7.55 (m, 3H) 7.62 (br d, J=8.22 Hz, 1H) 7.63-7.67 (m, 1H) 7.80 (d, J=8.22 Hz, 1H) 7.83 (br d, J=8.80 Hz, 1H) 7.96 (t, J=7.63 Hz, 2H) 8.40 (dd, J=18.19, 2.35 Hz, 1H) 8.64-8.75 (m, 1H); MS (ESI, m/z): 638.2 [M+H]$^+$ Example 595

(R)-2-amino-N-(1-(2'-chloro-[1,1'-biphenyl]-4-carbonyl)pyrrolidin-3-yl)-5-(4-((3-(2-oxopyrrolidin-1-yl)propyl)carbamoyl)phenyl)nicotinamide Using 1-(3-aminopropyl)pyrrolidin-2-one, the title compound was obtained as described in general method K. MS (ESI, m/z): 666.2 [M+H]$^+$ Example 785

(R)-2-amino-5-(1-methyl-1H-pyrazol-4-yl)-N-(1-(6-(4-methylpiperazine-1-carbonyl)-2-naphthoyl)pyrrolidin-3-yl)nicotinamide Using Example 843, the title compound was obtained as described in general method K. $^1$H NMR (600 MHz, METHANOL-d$_4$) δ ppm 2.09-2.26 (m, 1H) 2.29-2.45 (m, 1H) 2.95 (d, J=2.93 Hz, 3H) 3.16-3.27 (m, 2H) 3.56 (br dd, J=11.15, 4.70 Hz, 0.5H) 3.67-3.83 (m, 2H) 3.88-3.93 (m, 0.5H) 3.94 (d, J=7.04 Hz, 3H) 3.95-4.01 (m, 0.5H) 4.06 (br dd, J=12.91, 6.46 Hz, 0.5H) 4.53-4.58 (m, 0.5H) 4.70-4.75 (m, 0.5H) 7.61-7.66 (m, 1H) 7.73 (ddd, J=11.74, 8.80, 1.76 Hz, 1H) 7.87-7.94 (m, 1H) 8.02-8.12 (m, 4H) 8.16 (d, J=13.50 Hz, 1H) 8.21-8.29 (m, 1H) 8.61-8.75 (m, 1H); MS (ESI, m/z): 567.3 [M+H]$^+$ Example 786

(R)-2-amino-N-(1-(6-(4-(2-hydroxyethyl)piperazine-1-carbonyl)-2-naphthoyl)pyrrolidin-3-yl)-5-(1-methyl-1H-pyrazol-4-yl)nicotinamide Using Example 843 and 1-(2-hydroxyethyl)piperazine, the title compound was obtained as described in general method K. $^1$H NMR (600 MHz, METHANOL-d$_4$) δ ppm 2.10-2.26 (m, 1H) 2.30-2.47 (m, 1H) 3.20-3.30 (m, 2H) 3.33-3.37 (m, 2H) 3.57 (br dd, J=11.15, 5.28 Hz, 0.5H) 3.66-3.85 (m, 3H) 3.92 (br d, J=3.52 Hz, 2.5H) 3.95 (d, J=7.04 Hz, 3H) 3.96-4.00 (m, 0.5H) 4.07 (br dd, J=12.91, 7.04 Hz, 0.5H) 4.54-4.59 (m, 0.5H) 4.71-4.76 (m, 0.5H) 7.65 (ddd, J=8.51, 7.04, 1.47 Hz, 1H) 7.73 (ddd, J=14.09, 8.51, 1.47 Hz, 1H) 7.87-7.98 (m, 1H) 8.02-8.11 (m, 4H) 8.13-8.19 (m, 1H) 8.20-8.29 (m, 1H) 8.63-8.79 (m, 1H); MS (ESI, m/z): 597.3 [M+H]$^+$ Example 787

(R)-2-amino-N-(1-(4'-(4-(dimethylcarbamoyl)phenoxy)-[1,1'-biphenyl]-4-carbonyl)pyrrolidin-3-yl)-5-(1-methyl-1H-pyrazol-4-yl)nicotinamide Using Example 812 and dimethylamine, the title compound was obtained as described in general method K. $^1$H NMR (600 MHz, METHANOL-d$_4$) δ ppm 2.09-2.23 (m, 1H) 2.28-2.44 (m, 1H) 3.05 (br s, 3H) 3.10 (br s, 3H) 3.58 (br dd, J=11.15, 5.28 Hz, 0.5H) 3.64-3.73 (m, 1H) 3.73-3.82 (m, 1H) 3.87 (br d, J=6.46 Hz, 0.5H) 3.94 (d, J=5.87 Hz, 3H) 3.96-4.05 (m, 1H) 4.53-4.59 (m, 0.5H) 4.66-4.72 (m, 0.5H) 7.08 (dd, J=8.51, 4.99 Hz, 2H) 7.13 (t, J=7.92 Hz, 2H) 7.46 (dd, J=8.51, 3.23 Hz, 2H) 7.58-7.75 (m, 6H) 7.90 (d, J=19.37 Hz, 1H) 8.05 (d, J=18.19 Hz, 1H) 8.19-8.27 (m, 1H) 8.62-8.74 (m, 1H) MS (ESI, m/z): 630.3 [M+H]+

Example 788

(R)-2-amino-N-(1-(4'-(4-carbamoylphenoxy)-[1,1'-biphenyl]-4-carbonyl)pyrrolidin-3-yl)-5-(1-methyl-1H-pyrazol-4-yl)nicotinamide Using Example 812 and ammonium acetate, the title compound was obtained as described in general method K. MS (ESI, m/z): 602.2 [M+H]+

Example 789

(R,E)-2-amino-N-(1-(4'-(3-(dimethylamino)-3-oxo-prop-1-en-1-yl)-[1,1'-biphenyl]-4-carbonyl)pyrrolidin-3-yl)-5-(1-methyl-H-pyrazol-4-yl)nicotinamide Using Example 677 and dimethylamine, the title compound was obtained as described in general method K. MS (ESI, m/z): 564.3 [M+H]+

General Method L

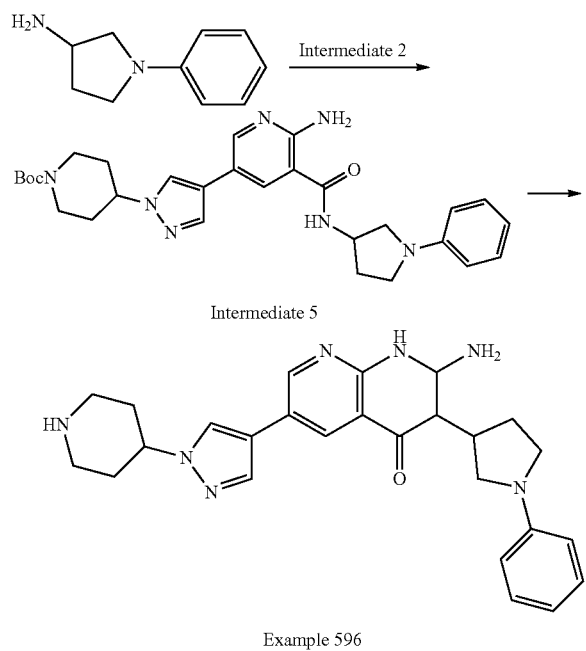

Example 596

Example 596

3-(1-phenylpyrrolidin-3-yl)-6-(1-(piperidin-4-yl)-1H-pyrazol-4-yl)-2,3-dihydropyrido[2,3-d]pyrimidin-4(1H)-one To a solution of Intermediate 2 (116 mg, 0.3 mmol) and triethylamine (0.05 mL, 0.36 mmol) in 2 mL of N,N-dimethylformamide was added 1-[bis(dimethylamino)methylene]-1H-1,2,3-triazolo[4,5-b]pyridinium 3-oxid hexafluorophosphate (137 mg, 0.36 mmol) followed by 1-phenylpyrrolidin-3-amine (53 mg, 0.33 mmol). The mixture was stirred at room temperature for 1 h and then saturated sodium bicarbonate solution was added. The mixture was extracted with ethyl acetate, washed with brine, dried over MgSO4, and concentrated in vacuo. A solution of Intermediate 5 (133 mg, 0.25 mmol) and 0.5 mL of N,N-dimethylformamide dimethyl acetal (DMFDMA) in 1 mL of N,N-dimethylformamide was heated at 120° C. for 3 h. The mixture was extracted with ethyl acetate and saturated aqueous NaHCO3 solution, dried over MgSO4, and concentrated in vacuo. A solution of the crude product and NaBH4 (20 mg, 0.5 mmol) in 2 mL of methanol was refluxed for 3 h. The mixture was extracted with ethyl acetate and saturated aqueous NaHCO3 solution, dried over MgSO4, and concentrated in vacuo. The residue in solution of 0.3 mL of trifluoroacetic acid and 1 mL of dichloromethane was stirred for 1 h. The mixture was evaporated to remove volatiles and purified by preparative HPLC to afford 40 mg of the title compound. MS (ESI, m/z): 444.24 [M+H]+

Example 597

(R)-3-(1-phenylpyrrolidin-3-yl)-6-(1-(piperidin-4-yl)-1H-pyrazol-4-yl)-2,3-dihydropyrido[2,3-d]pyrimidin-4(1H)-one Using (R)-1-phenylpyrrolidin-3-amine, the title compound was obtained as described in general method L. MS (ESI, m/z): 444.24 [M+H]+

General Method M

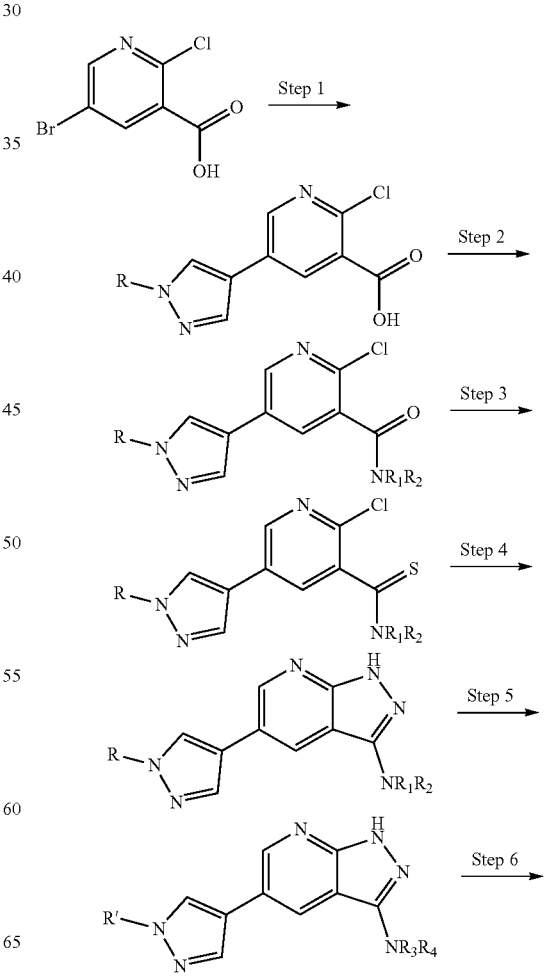

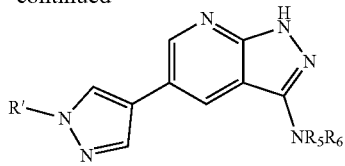

Step 1

2-chloro-5-(1-methyl-1H-pyrazol-4-yl)nicotinic acid

To a mixture of 5-bromo-2-chloronicotinic acid (5.57 g, 23.7 mmol) and 1-methylpyrazole-4-boronic acid pinacol ester (6.4 g, 30.8 mmol) in 100 mL of 1,4-dioxane/water (3/1) was added $K_2CO_3$ (6.5 g, 47.4 mmol) followed by $Pd(PPh_3)_4$ (1.9 g, 1.66 mmol). The reaction mixture was heated at 100° C. for 3 h, cooled to room temperature, and partitioned between water and ethyl acetate. Water layer was separated and adjusted to pH value around 4. The precipitate was collected by filtration, washed with water, and dried to afford 5.2 g of the title compound. The crude product was used for the next step without further purification. MS (ESI, m/z): 238.0 $[M+H]^+$

Step 2

To a mixture of 2-chloro-5-(1-methyl-1H-pyrazol-4-yl) nicotinic acid (1.0 mmol) and triethylamine (1.2 mmol) in 3 mL of N,N-dimethylformamide was added 1-[bis(dimethylamino)methylene]-1H-1,2,3-triazolo[4,5-b]pyridinium 3-oxid hexafluorophosphate (1.2 mmol) followed by amine (1.0 mmol). The mixture was stirred at room temperature for 1 h and then saturated sodium bicarbonate solution was added. The mixture was extracted with ethyl acetate, washed with brine, dried over $MgSO_4$, and concentrated in vacuo. The crude product was used for the next step without further purification.

Step 3

To a solution of amide coupled product from Step 2 (0.8 mmol) in 5 mL of tetrahydrofuran was added Lawessons's reagent (0.9 mmol). The mixture was stirred at between 40° C.—reflux, (50° C. for the exemplified reaction) for 1 h, and then saturated sodium bicarbonate solution was added. The mixture was extracted with ethyl acetate, washed with brine, dried over $MgSO_4$, and concentrated in vacuo. The crude product was used for the next step without further purification.

Step 4

To a solution of thioamide product from step 3 (0.8 mmol) in dimethyl sulfoxide (3 mL) was added hydrazine-monohydrate (6.4 mmol). The mixture was stirred at between 80-120° C. (80° C. for the exemplified reaction) for 6 h and then saturated sodium bicarbonate solution was added. The mixture was extracted with ethyl acetate, washed with brine, dried over $MgSO_4$, and concentrated in vacuo. The crude product was used for the next step without further purification.

Step 5

To a solution of pyrazolopyridine product from step 4 (0.5 mmol) in dichloromethane (2 mL) was added 0.5 mL of trifluoroacetic acid. The mixture was stirred at room temperature for 1 h. The mixture was extracted with UCT SPE CUBCX cartridge. The extract was concentrated in vacuo and the crude product was used for the next step without further purification.

Step 6

To a mixture of carboxylic acid (0.1 mmol) and triethylamine (0.12 mmol) in 1 mL of N,N-dimethylformamide was added 1-[bis(dimethylamino)methylene]-1H-1,2,3-triazolo[4,5-b]pyridinium 3-oxid hexafluorophosphate (0.12 mmol) followed by Boc-deprotected amine (from step 5, 0.1 mmol). The mixture was stirred at room temperature for 1 h and extracted with UCT SPE CUBCX cartridge. The extract was concentrated in vacuo and the crude product was purified by preparative HPLC to afford a corresponding compound.

Example 598

N-benzyl-5-(1-(piperidin-4-yl)-1H-pyrazol-4-yl)-1H-pyrazolo[3,4-b]pyridin-3-amine Using benzylamine and 1-(1-boc-piperidin-4-yl)-pyrazol-4-yl)boronic acid pinacol ester in place of 1-methylpyrazole-4-boronic acid pinacol ester, the title compound was obtained as described in general method M. MS (ESI, m/z): 374.20 $[M+H]^+$

Example 599

(R)—N-(1-benzylpyrrolidin-3-yl)-5-(1-(piperidin-4-yl)-1H-pyrazol-4-yl)-1H-pyrazolo[3,4-b]pyridin-3-amine Using (R)-1-benzylpyrrolidin-3-amine and 1-(1-boc-piperidin-4-yl)-pyrazol-4-yl)boronic acid pinacol ester, in place of 1-methylpyrazole-4-boronic acid pinacol ester, the title compound was obtained as described in general method M. MS (ESI, m/z): 443.26 $[M+H]^+$

Example 600

N-phenethyl-5-(1-(piperidin-4-yl)-1H-pyrazol-4-yl)-1H-pyrazolo[3,4-b]pyridin-3-amine Using 2-phenylethan-1- and 1-(1-boc-piperidin-4-yl)-pyrazol-4-yl)boronic acid pinacol ester, the title compound was obtained as described in general method M. MS (ESI, m/z): 388.22 $[M+H]^+$

Example 601

N-((1S,2S)-2-(benzyloxy)cyclopentyl)-5-(1-(piperidin-4-yl)-1H-pyrazol-4-yl)-1H-pyrazolo[3,4-b]pyridin-3-amine Using (1S,2S)-2-(benzyloxy)cyclopentan-1-amine and 1-(1-boc-piperidin-4-yl)-pyrazol-4-yl)boronic acid pinacol ester, the title compound was obtained as described in general method M. MS (ESI, m/z): 458.26 $[M+H]^+$

Example 602

N-((1R,2R)-2-(benzyloxy)cyclopentyl)-5-(1-methyl-1H-pyrazol-4-yl)-1H-pyrazolo[3,4-b]pyridin-3-amine Using (1R,2R)-2-(benzyloxy)cyclopentan-1-amine, the title compound was obtained as described in general method M. MS (ESI, m/z): 389.20 [M+H]$^+$

Example 603

N-((1R,2S)-2-(benzyloxy)cyclopentyl)-5-(1-methyl-1H-pyrazol-4-yl)-1H-pyrazolo[3,4-b]pyridin-3-amine Using (1R,2S)-2-(benzyloxy)cyclopentan-1-amine, the title compound was obtained as described in general method M. MS (ESI, m/z): 389.20 [M+H]$^+$

Example 604

N-((1R,2R)-2-(benzyloxy)cyclohexyl)-5-(1-methyl-1H-pyrazol-4-yl)-1H-pyrazolo[3,4-b]pyridin-3-amine Using (1R,2R)-2-(benzyloxy)cyclohexan-1-amine, the title compound was obtained as described in general method M. MS (ESI, m/z): 403.22 [M+H]$^+$

Example 605

N-((3R,4S)-4-(benzyloxy)tetrahydrofuran-3-yl)-5-(1-methyl-1H-pyrazol-4-yl)-1H-pyrazolo[3,4-b]pyridin-3-amine Using (3R,4S)-4-(benzyloxy)tetrahydrofuran-3-amine, the title compound was obtained as described in general method M. MS (ESI, m/z): 391.18 [M+H]$^+$

Example 606

N-(3-(benzyloxy)cyclohexyl)-5-(1-methyl-1H-pyrazol-4-yl)-1H-pyrazolo[3,4-b]pyridin-3-amine Using 3-(benzyloxy)cyclohexan-1-amine, the title compound was obtained as described in general method M. MS (ESI, m/z): 403.22 [M+H]$^+$

Example 608

N-(3-(benzyloxy)cyclopentyl)-5-(1-methyl-1H-pyrazol-4-yl)-1H-pyrazolo[3,4-b]pyridin-3-amine Using 3-(benzyloxy)cyclopentan-1-amine, the title compound was obtained as described in general method M. MS (ESI, m/z): 389.20 [M+H]$^+$

Example 609

N-((1S,2S)-2-((benzyloxy)methyl)cyclopentyl)-5-(1-methyl-1H-pyrazol-4-yl)-1H-pyrazolo[3,4-b]pyridin-3-amine Using (1S,2S)-2-((benzyloxy)methyl)cyclopentan-1-amine, the title compound was obtained as described in general method M. MS (ESI, m/z): 403.22 [M+H]$^+$

Example 610

N-((3R,4S)-4-((benzyloxy)methyl)pyrrolidin-3-yl)-5-(1-methyl-1H-pyrazol-4-yl)-1H-pyrazolo[3,4-b]pyridin-3-amine Using tert-butyl (3R,4S)-3-amino-4-((benzyloxy)methyl)pyrrolidine-1-carboxylate, the title compound was obtained as described in general method M. MS (ESI m/z): 404.21 [M+H]$^+$

Example 611

N-((3S,4S)-4-(benzyloxy)pyrrolidin-3-yl)-5-(1-methyl-1H-pyrazol-4-yl)-1H-pyrazolo[3,4-b]pyridin-3-amine Using tert-butyl (3S,4S)-3-amino-4-(benzyloxy)pyrrolidine-1-carboxylate, the title compound was obtained as described in general method M. MS (ESI, m/z): 390.20 [M+H]$^+$

Example 612

N-((3R,4R)-4-(benzyloxy)pyrrolidin-3-yl)-5-(1-methyl-1H-pyrazol-4-yl)-1H-pyrazolo[3,4-b]pyridin-3-amine Using 1-methylpyrazole-4-boronic acid pinacol ester and tert-butyl (3R,4R)-3-amino-4-(benzyloxy)pyrrolidine-1-carboxylate, the title compound was obtained as described in general method M. MS (ESI, m/z): 390.20 [M+H]$^+$

Example 613

N-((1S,2S)-2-(benzyloxy)cyclopentyl)-5-(1-methyl-1H-pyrazol-4-yl)-1H-pyrazolo[3,4-b]pyridin-3-amine Using (1S,2S)-2-(benzyloxy)cyclopentan-1-amine, the title compound was obtained as described in general method M. MS (ESI, m/z): 389.20 [M+H]$^+$

Example 614

N-((3R,4R)-4-((3-ethyl-4-methylbenzyl)oxy)pyrrolidin-3-yl)-5-(1-methyl-1H-pyrazol-4-yl)-1H-pyrazolo[3,4-b]pyridin-3-amine Using tert-butyl (3R,4R)-3-amino-4-((3-ethyl-4-methylbenzyl)oxy)pyrrolidine-1-carboxylate, the title compound was obtained as described in general method M. MS (ESI, m/z): 432.24 [M+H]$^+$

Example 615

(R)-(3-((5-(1-methyl-1H-pyrazol-4-yl)-1H-pyrazolo[3,4-b]pyridin-3-yl)amino)pyrrolidin-1-yl)(4-(5-methylthiophen-2-yl)phenyl)methanone Using 4-(5-methylthiophen-2-yl)benzoic acid, the title compound was obtained as described in general method M. MS (ESI, m/z): 484.18 [M+H]$^+$

Example 616

(R)-[1,1'-biphenyl]-4-yl(3-((5-(1-methyl-1H-pyrazol-4-yl)-1H-pyrazolo[3,4-b]pyridin-3-yl)amino)pyrrolidin-1-yl)methanone Using [1,1'-biphenyl]-4-carboxylic acid, the title compound was obtained as described in general method M. MS (ESI, m/z): 464.21 [M+H]$^+$

Example 617

(R)-(2'-chloro-[1,1'-biphenyl]-4-yl)(3-((5-(1-methyl-1H-pyrazol-4-yl)-1H-pyrazolo[3,4-b]pyridin-3-yl)amino)pyrrolidin-1-yl)methanone Using 2'-chloro-[1,1'-biphenyl]-4-carboxylic acid, the title compound was obtained as described in general method M. MS (ESI, m/z): 498.17 [M+H]$^+$

Example 618

(R)-(4-bromophenyl)(3-((5-(1-methyl-1H-pyrazol-4-yl)-1H-pyrazolo[3,4-b]pyridin-3-yl)amino)pyrrolidin-1-yl)methanone Using 4-bromobenzoic acid, the title compound was obtained as described in general method M. MS (ESI, m/z): 466.09 [M+H]$^+$

Example 619

(R)-(3-((5-(1-methyl-1H-pyrazol-4-yl)-1H-pyrazolo[3,4-b]pyridin-3-yl)amino)pyrrolidin-1-yl)(4'-phenoxy-[1,1'-biphenyl]-4-yl)methanone Using 4'-phenoxy-[1,1'-biphenyl]-4-carboxylic acid, the title compound was obtained as described in general method M. MS (ESI, m/z): 556.24 [M+H]$^+$

Example 620

(R)-(4'-(4-aminophenoxy)-[1,1'-biphenyl]-4-yl)(3-((5-(1-methyl-1H-pyrazol-4-yl)-1H-pyrazolo[3,4-b]pyridin-3-yl)amino)pyrrolidin-1-yl)methanone Using 4'-(4-aminophenoxy)-[1,1'-biphenyl]-4-carboxylic acid, the title compound was obtained as described in general method M. MS (ESI, m/z): 571.25 [M+H]$^+$

Example 790

(R)-(3-((5-(1-methyl-1H-pyrazol-4-yl)-1H-pyrazolo[3,4-b]pyridin-3-yl)amino)pyrrolidin-1-yl)(4-(1,2,3,4-tetrahydroquinolin-6-yl)phenyl)methanone Using 4-(1,2,3,4-tetrahydroquinolin-6-yl)benzoic acid, the title compound was obtained as described in general method M. MS (ESI, m/z): 519.3 [M+H]$^+$

Example 791

(R)-(3-((5-(1-methyl-1H-pyrazol-4-yl)-1H-pyrazolo[3,4-b]pyridin-3-yl)amino)pyrrolidin-1-yl)(4-phenoxyphenyl)methanone Using 4-phenoxybenzoic acid, the title compound was obtained as described in general method M. MS (ESI, m/z): 480.2 [M+H]$^+$

Example 792

(R)-(3-((5-(1-methyl-1H-pyrazol-4-yl)-1H-pyrazolo[3,4-b]pyridin-3-yl)amino)pyrrolidin-1-yl)(4'-(piperidin-4-yloxy)-[1,1'-biphenyl]-4-yl)methanone Using 4'-((1-(tert-butoxycarbonyl)piperidin-4-yl)oxy)-[1,1'-biphenyl]-4-carboxylic acid, the title compound was obtained as described in general method M. MS (ESI, m/z): 563.3 [M+H]$^+$

Example 793

(R)-(3-((5-(1-methyl-1H-pyrazol-4-yl)-1H-pyrazolo[3,4-b]pyridin-3-yl)amino)pyrrolidin-1-yl)(4'-(morpholinomethyl)-[1,1'-biphenyl]-4-yl)methanone Using 4'-(morpholinomethyl)-[1,1'-biphenyl]-4-carboxylic acid, the title compound was obtained as described in general method M. MS (ESI, m/z): 563.3 [M+H]$^+$

Example 794

(R)-(3-((5-(1-methyl-1H-pyrazol-4-yl)-1H-pyrazolo[3,4-b]pyridin-3-yl)amino)pyrrolidin-1-yl)(4'-((4-methylpiperazin-1-yl)methyl)-[1,1'-biphenyl]-4-yl)methanone Using 4'-((4-methylpiperazin-1-yl)methyl)-[1,1'-biphenyl]-4-carboxylic acid, the title compound was obtained as described in general method M. MS (ESI, m/z): 576.3 [M+H]$^+$

General Method O

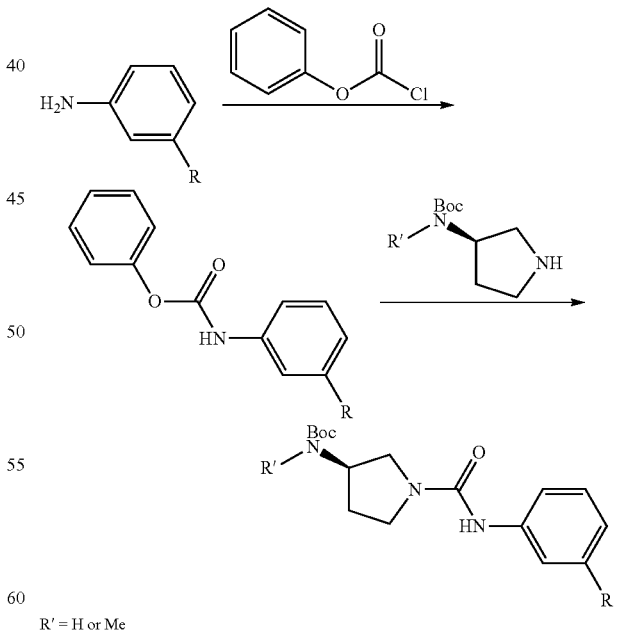

R' = H or Me

To the aniline (0.5 mmol) and triethylamine (0.105 mL, 0.75 mmol) in 1.5 mL of 1,4-dioxane was added phenyl chloroformate (0.078 g, 0.5 mmol). The mixture was stirred at room temperature for 1 h and then concentrated in vacuo.

To a mixture of the crude carbamate and triethylamine (0.105 mL, 0.75 mmol) in 1.5 mL of N,N-dimethylformamide was added tert-butyl (R)-pyrrolidin-3-ylcarbamate (0.093 g, 0.5 mmol). The reaction mixture was heated at 100° C. for 3 h, cooled to room temperature. The mixture was extracted with ethyl acetate, washed with brine, dried over MgSO$_4$, and concentrated in vacuo. To a mixture of crude urea in dichloromethane (2 mL) was added trifluoroacetic acid (0.5 mL) and stirred at room temperature for overnight. The mixture was extracted with UCT SPE CUBCX cartridge. The extract was concentrated in vacuo and the crude product was used for the next step without further purification.

General Method P

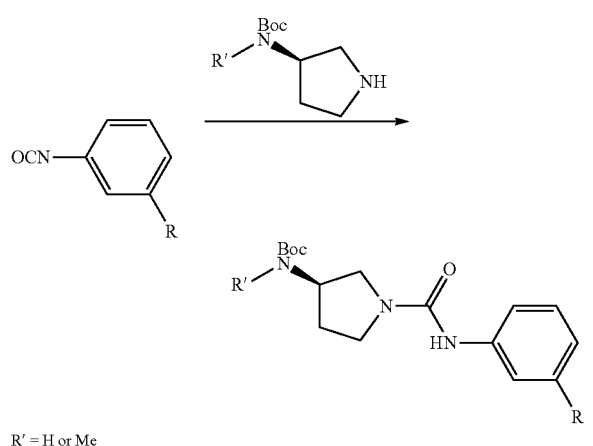

R' = H or Me

To a mixture of isocyanate (0.5 mmol) and triethylamine (0.105 mL, 0.75 mmol) in 1.5 mL of N,N-dimethylformamide was added tert-butyl (R)-pyrrolidin-3-ylcarbamate (0.093 g, 0.5 mmol). The reaction mixture was stirred at room temperature for 3 h, cooled to room temperature. The mixture was extracted with ethyl acetate, washed with brine, dried over MgSO$_4$, and concentrated in vacuo. To a mixture of crude urea in dichloromethane (2 mL) was added trifluoroacetic acid (0.5 mL). The mixture was allowed to stir overnight and extracted with UCT SPE CUBCX cartridge. The extract was concentrated in vacuo and the crude product was used for the next step without further purification General Method Q

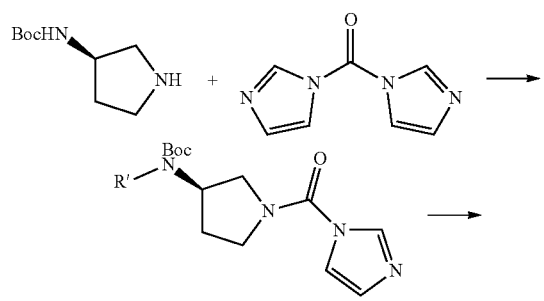

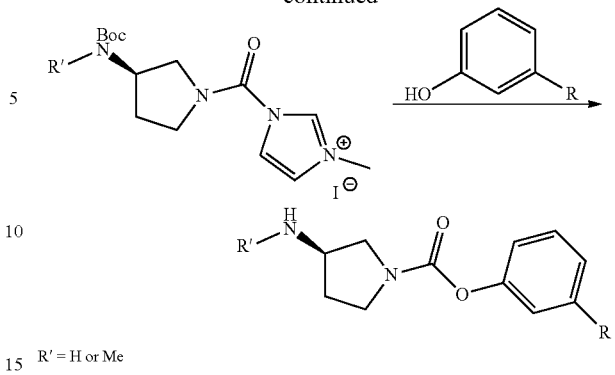

R' = H or Me

To a suspension of N,N'-carbonyldiimidazole (CDI, 60.0 mmol) in tetrahydrofuran (100 mL) was added tert-butyl (R)-pyrrolidin-3-ylcarbamate (55.0 mmol). The mixture was refluxed for 16 h. Removal of solvent under vacuum gave a viscous oil, which was dissolved in CH$_2$Cl$_2$ (100 mL) and washed with water (2×100 mL). The organic layer was dried over anhydrous MgSO$_4$, filtered and concentrated in vacuo to yield the carbamoylimidazole.

To a solution of carbamoylimidazole (8.00 mmol) in acetonitrile (15 mL) was added methyl iodide (32.0 mmol). The mixture was stirred at rt for 24 h. The solvent was removed under vacuum to yield the carbamoylimidazolium salt.

To a solution of carbamoylimidazolium salt (1.00 mmol) in acetonitrile (6 mL) was added the phenol (1.00 mmol) and triethylamine (1.00 mmol). The reaction was refluxed overnight. The solvent was removed under vacuum and the residue was dissolved in CH$_2$Cl$_2$ (15 mL) and 0.1 M HCl (15 mL) was added. The aqueous layer was extracted with CH$_2$Cl$_2$ (3×15 mL). The combined organic layers were washed with water (20 mL) and brine (20 mL). The organic layer was dried (MgSO$_4$), filtered and concentrated in vacuo to yield carbamate.

Alternatively, to a solution of carbamoylimidazolium salt (2.00 mmol) and alcohol (2.00 mmol) in tetrahydrofuran/N,N-dimethylformamide (2:1, 12 mL) was added portionwise NaH (2.20 mmol, 80% in mineral oil). The solution was stirred at rt for 1 day. H$_2$O (10 mL) and Et$_2$O (20 mL) were added, and the organic layer was washed with H$_2$O (2×10 mL). The organic layer was dried (MgSO$_4$), filtered and concentrated in vacuo. The oil was purified by flash column chromatography (CH$_2$Cl$_2$) to yield carbamate.

To a mixture of crude carbamate in dichloromethane (12 mL) was added trifluoroacetic acid (3 mL) and stirred at room temperature for overnight. The mixture was extracted with UCT SPE CUBCX cartridge. The extract was concentrated in vacuo and the crude product was used for the next step without further purification.

General Method R

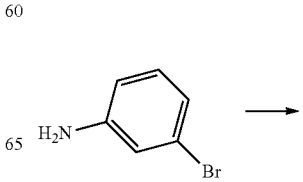

255
-continued

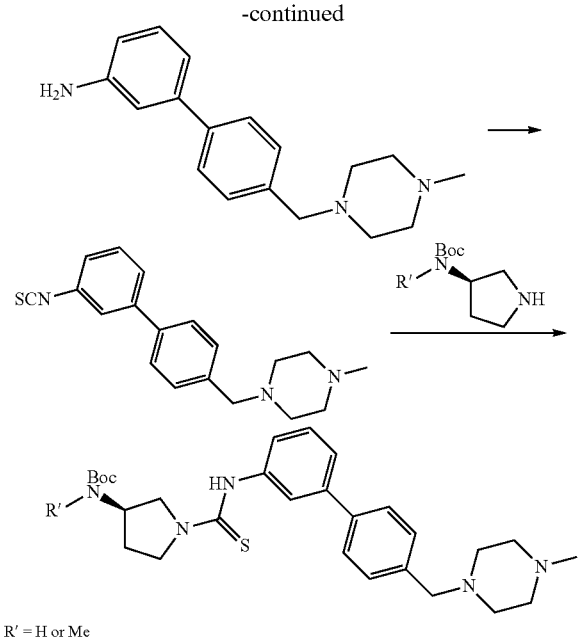

R' = H or Me

To a mixture of 3-bromoaniline (0.172 g, 1 mmol) and (4-((4-methylpiperazin-1-yl)methyl)phenyl)boronic acid pinacol ester (0.474 g, 1.5 mmol) in 3 mL of 1,4-dioxane/water (3/1) was added K$_2$CO$_3$ (0.276 g, 2 mmol) followed by Pd(PPh$_3$)$_4$ (0.05 mmol). The reaction mixture was heated at 100° C. for 3 h, cooled to room temperature. The mixture was extracted with UCT SPE CUBCX cartridge. The extract was concentrated in vacuo and the crude product was used for the next step without further purification.

To a mixture of the crude aniline in dichloromethane (5 mL) was added triethylamine (0.210 mL, 1.5 mmol) followed by di-2-pyridyl thionocarbonate (0.255 mg, 1.1 mmol). The reaction mixture was stirred room temperature for 3 h and to the reaction mixture was added tert-butyl (R)-pyrrolidin-3-ylcarbamate (0.186 mg, 1.0 mmol). The mixture was allowed to stir overnight and extracted with UCT SPE CUBCX cartridge. The extract was concentrated in vacuo and the crude product was used for the next step without further purification.

To a mixture of crude product in dichloromethane (2 mL) was added trifluoroacetic acid (0.5 mL) and stirred at room temperature for overnight. The mixture was extracted with UCT SPE CUBCX cartridge. The extract was concentrated in vacuo and the crude product was used for the next step without further purification.

General Method S

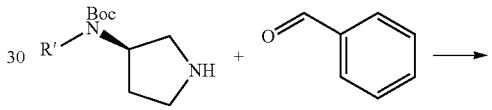

R' = H or Me

256

To a suspension of tert-butyl (R)-pyrrolidin-3-ylcarbamate (0.186 mg, 1.0 mmol), 4-bromotoluene (0.171 mg, 1 mmol), 2,2'-BIS(DIPHENYLPHOSPHINO)-1,1'-BINAPHTHYL (60 mg, 10 mol %) and sodium tert-butoxide (190 mg, 2.0 mmol) in 1,4-dioxane was added palladium(II) acetate (20 mg, 10 mol %) under nitrogen atmosphere. The mixture was heated at reflux and allowed to stir overnight. After being cooled to ambient temperature, the mixture was extracted with ethyl acetate, washed with brine, dried over MgSO$_4$, and concentrated in vacuo. To a mixture of crude compound in dichloromethane (3 mL) was added trifluoroacetic acid (0.5 mL). The mixture was allowed to stir overnight and extracted with UCT SPE CUBCX cartridge. The extract was concentrated in vacuo and the crude product was used for the next step without further purification.

General Method T

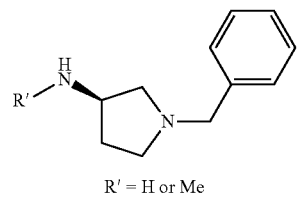

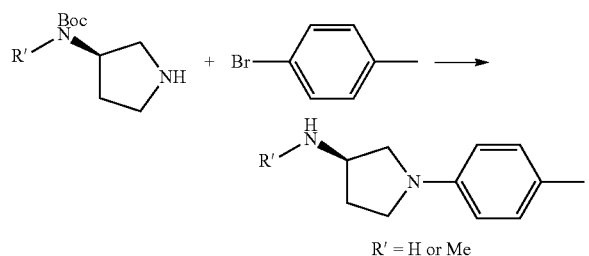

R' = H or Me

To a mixture of tert-butyl (R)-pyrrolidin-3-ylcarbamate (50 mg, 0.27 mmol) in 1,2-dichloroethane (1.5 mL) was added benzaldehyde (0.055 mL, 0.54 mmol) followed by NaBH(OAc)$_3$ (171 mg, 0.81 mmol). The mixture was stirred at room temperature for 4 h and then water was added. The mixture was extracted with ethyl acetate, washed with brine, dried over MgSO$_4$, and concentrated in vacuo. To a mixture of crude compound in dichloromethane (3 mL) was added trifluoroacetic acid (0.5 mL). The mixture was allowed to stir overnight and extracted with UCT SPE CUBCX cartridge. The extract was concentrated in vacuo and the crude product was used for the next step without further purification.

General Method U

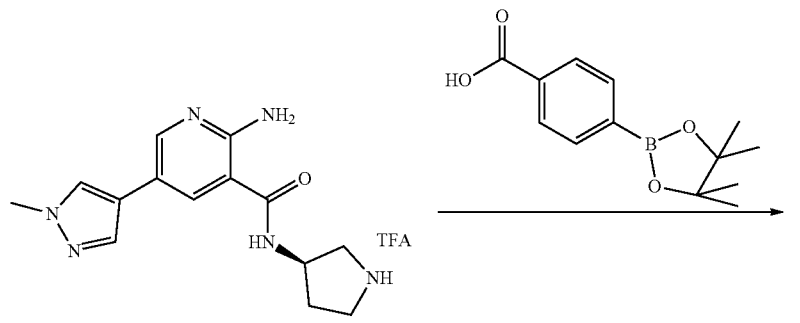

Intermediate 3

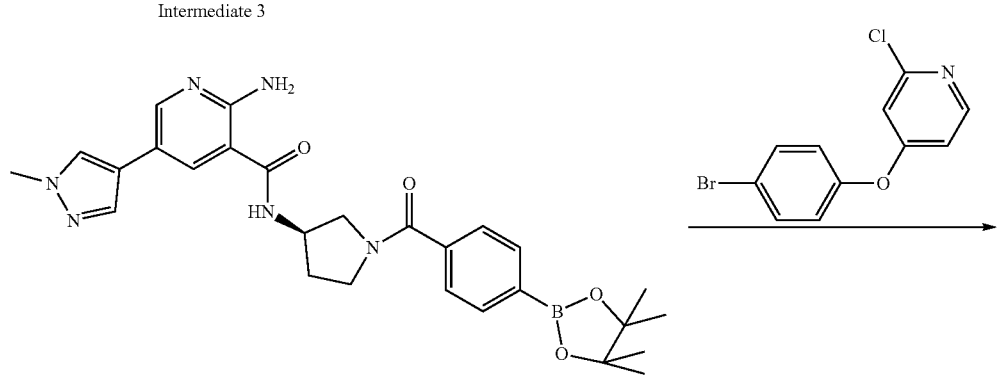

Intermediate 6

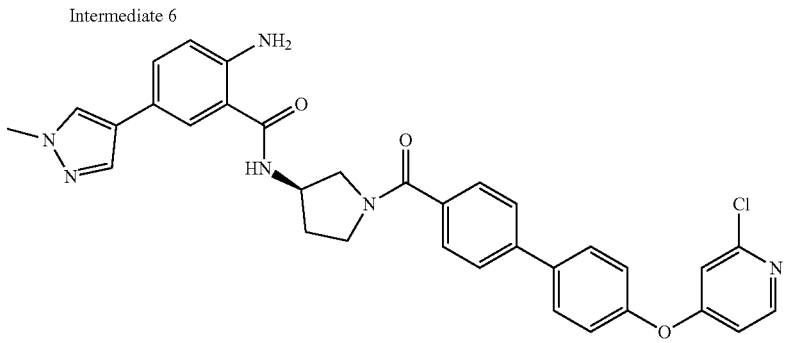

Example 795

Intermediate 6

(R)-2-amino-5-(1-methyl-1H-pyrazol-4-yl)-N-(1-(4-(4,4,5,5-tetramethyl-1,3,2-dioxaborolan-2-yl)benzoyl)pyrrolidin-3-yl)nicotinamide To a mixture of 4-(4,4,5,5-tetramethyl-1,3,2-dioxaborolan-2-yl)benzoic acid (0.65 g, 2.61 mmol) and triethylamine (1.09 mL, 7.83 mmol) in N,N-dimethylformamide (13 mL) was added 1-[bis(dimethylamino)methylene]-1H-1,2,3-triazolo[4,5-b]pyridinium 3-oxid hexafluorophosphate (1.0 g, 2.61 mmol) followed by Intermediate 3 (1.0 g, 2.61 mmol). The mixture was stirred at room temperature for 1 hr and then saturated sodium bicarbonate solution was added. The mixture was extracted with ethyl acetate, washed with brine, dried over MgSO$_4$, and concentrated in vacuo. The crude product was purified through silica gel column chromatography (5% methanol/CH$_2$Cl$_2$) to give 1.0 g off-white solid. $^1$H NMR (600 MHz, METHANOL-d$_4$) δ ppm 1.35 (s, 6H) 1.36 (s, 6H) 2.04-2.21 (m, 1H) 2.24-2.41 (m, 1H) 3.48 (td, J=10.56, 5.28 Hz, 0.5H) 3.56-3.75 (m, 2H) 3.79-3.90 (m, 1H) 3.93 (d, J=5.28 Hz, 3H) 3.99 (dd, J=12.91, 7.04 Hz, 0.5H) 4.47-4.54 (m, 0.5H) 4.65-4.71 (m, 0.5H) 7.47-7.56 (m, 2H) 7.79-7.86 (m, 2H) 7.96 (d, J=15.85 Hz, 1H) 8.24 (br d, J=4.11 Hz, 1H) 8.25-8.34 (m, 1H) 8.41 (dd, J=8.22, 1.17 Hz, 0.5H) 8.71 (d, J=3.52 Hz, 0.5H). MS (ESI, m/z): 517.3 [M+H]$^+$

Example 795

(R)-2-amino-N-(1-(4'-((2-chloropyridin-4-yl)oxy)-[1,1'-biphenyl]-4-carbonyl)pyrrolidin-3-yl)-5-(1-methyl-1H-pyrazol-4-yl)nicotinamide To a mixture of Intermediate 6 (30 mg, 0.058 mmol) and 4-(4-bromophenoxy)-2-chloropyridine (17 mg, 0.058 mmol) in 0.4 mL of 1,4-dioxane/water (3/1) was added K$_2$CO$_3$ (24 mg, 0.17 mmol) followed by Pd(PPh$_3$)$_4$ (3.4 mg, 0.003 mmol). The reaction mixture was heated at 100° C. for 3 hrs, cooled to room temperature, and extracted with ethyl acetate, dried over anhydrous MgSO₄ and concentrated under vacuum. The crude residue was purified by preparative HPLC to afford 20 mg of the title compound. ¹H NMR (600 MHz, METHANOL-d₄) δ ppm 2.09-2.25 (m, 1H) 2.29-2.45 (m, 1H) 3.57 (br d, J=11.15 Hz, 0.5H) 3.69 (br d, J=10.56 Hz, 1H) 3.77 (br s, 1H) 3.86 (br s, 0.5H) 3.94 (br s, 3H) 3.96-4.07 (m, 1H) 4.56 (br s, 0.5H) 4.66-4.75 (m, 0.5H) 6.96 (br s, 1H) 6.98 (s, 1H) 7.26 (br s, 2H) 7.59-7.70 (m, 2H) 7.71-7.81 (m, 4H) 7.89 (br d, J=18.19 Hz, 1H) 8.04 (br d, J=17.02 Hz, 1H) 8.18-8.26 (m, 2H) 8.60-8.73 (m, 1H); MS (ESI, m/z): 594.2 [M+H]⁺

Example 796

(R)-2-amino-N-(1-(4'-(4-aminophenoxy)-2'-chloro-[1,1'-biphenyl]-4-carbonyl)pyrrolidin-3-yl)-5-(1-methyl-1H-pyrazol-4-yl)nicotinamide Using 4-(4-bromo-3-chlorophenoxy)aniline, the title compound was obtained as described in general method U. ¹H NMR (600 MHz, METHANOL-d₄) δ ppm 2.11-2.26 (m, 1H) 2.29-2.46 (m, 1H) 3.59 (dd, J=11.15, 5.28 Hz, 0.5H) 3.66-3.74 (m, 1H) 3.74-3.83 (m, 1H) 3.84-3.91 (m, 0.5H) 3.94 (d, J=4.70 Hz, 3H) 3.96-4.06 (m, 1H) 4.58 (br t, J=5.87 Hz, 0.5H) 4.68-4.74 (m, 0.5H) 7.07 (ddd, J=8.36, 6.31, 2.35 Hz, 1H) 7.18 (dd, J=5.87, 2.35 Hz, 1H) 7.20-7.27 (m, 2H) 7.42 (t, J=8.22 Hz, 1H) 7.45 (dd, J=9.10, 2.64 Hz, 2H) 7.53 (t, J=8.51 Hz, 2H) 7.65 (dd, J=14.67, 8.22 Hz, 2H) 7.91 (d, J=16.43 Hz, 1H) 8.06 (d, J=15.26 Hz, 1H) 8.24 (dd, J=18.78, 1.76 Hz, 1H) 8.64-8.75 (m, 1H); MS (ESI, m/z): 608.2 [M+H]⁺

Example 797

(R)-2-amino-N-(1-(4'-(3-aminophenoxy)-2'-chloro-[1,1'-biphenyl]-4-carbonyl)pyrrolidin-3-yl)-5-(1-methyl-1H-pyrazol-4-yl)nicotinamide Using 3-(4-bromo-3-chlorophenoxy)aniline, the title compound was obtained as described in general method U. ¹H NMR (600 MHz, METHANOL-d₄) δ ppm 2.11-2.25 (m, 1H) 2.31-2.46 (m, 1H) 3.60 (br dd, J=11.15, 5.28 Hz, 0.5H) 3.71 (br dd, J=13.21, 4.99 Hz, 1H) 3.76-3.84 (m, 1H) 3.86-3.92 (m, 0.5H) 3.96 (d, J=4.11 Hz, 3H) 3.98-4.07 (m, 1H) 4.57-4.62 (m, 0.5H) 4.70-4.76 (m, 0.5H) 7.03-7.07 (m, 1H) 7.09-7.17 (m, 3H) 7.23 (dd, J=4.11, 2.35 Hz, 1H) 7.43-7.47 (m, 1H) 7.49-7.58 (m, 3H) 7.67 (dd, J=12.03, 7.92 Hz, 2H) 7.92 (d, J=17.02 Hz, 1H) 8.07 (d, J=14.67 Hz, 1H) 8.26 (dd, J=17.61, 1.76 Hz, 1H) 8.65-8.76 (m, 1H); MS (ESI, m/z): 608.2 [M+H]⁺

Example 798

(R)-2-amino-5-(1-methyl-1H-pyrazol-4-yl)-N-(1-(4'-(pyridin-4-yloxy)-[1,1'-biphenyl]-4-carbonyl)pyrrolidin-3-yl)nicotinamide Using 4-(4-bromophenoxy)pyridine, the title compound was obtained as described in general method U. MS (ESI, m/z): 560.2 [M+H]⁺

Example 799

(R)—N-(1-(4'-((1H-indol-5-yl)amino)-[1,1'-biphenyl]-4-carbonyl)pyrrolidin-3-yl)-2-amino-5-(1-methyl-1H-pyrazol-4-yl)nicotinamide Using N-(4-bromophenyl)-1H-indol-5-amine, the title compound was obtained as described in general method U. MS (ESI, m/z): 597.3 [M+H]⁺

Example 800

(R)-2-amino-N-(1-(4'-(4-hydroxyphenoxy)-[1,1'-biphenyl]-4-carbonyl)pyrrolidin-3-yl)-5-(1-methyl-1H-pyrazol-4-yl)nicotinamide Using 4-(4-bromophenoxy)phenol, the title compound was obtained as described in general method U. MS (ESI, m/z): 642.3 [M+H]⁺

Example 801

(R)-2-amino-N-(1-(4'-(2-aminopropan-2-yl)-[1,1'-biphenyl]-4-carbonyl)pyrrolidin-3-yl)-5-(1-methyl-1H-pyrazol-4-yl)nicotinamide Using 2-(4-bromophenyl)propan-2-amine, the title compound was obtained as described in general method U. ¹H NMR (600 MHz, METHANOL-d₄) δ ppm 1.76 (d, J=3.52 Hz, 6H) 2.05-2.24 (m, 1H) 2.25-2.44 (m, 1H) 3.56 (br dd, J=11.15, 5.28 Hz, 0.5H) 3.64-3.72 (m, 1H) 3.72-3.82 (m, 1H) 3.82-3.88 (m, 0.5H) 3.93 (d, J=4.70 Hz, 3H) 3.94-4.06 (m, 1H) 4.52-4.58 (m, 0.5H) 4.66-4.72 (m, 0.5H) 6.81 (br t, J=8.80 Hz, 2H) 7.40-7.54 (m, 2H) 7.59-7.68 (m, 2H) 7.71-7.80 (m, 2H) 7.89 (d, J=18.78 Hz, 1H) 8.05 (d, J=17.02 Hz, 1H) 8.22 (dd, J=19.96, 1.76 Hz, 1H) 8.67 (dd, J=46.37, 1.76 Hz, 1H); MS (ESI, m/z): 524.4 [M+H]⁺

Example 802

(R)-2-amino-5-(1-methyl-1H-pyrazol-4-yl)-N-(1-(4'-(pyridin-3-yloxy)-[1,1'-biphenyl]-4-carbonyl)pyrrolidin-3-yl)nicotinamide Using 3-(4-bromophenoxy)pyridine, the title compound was obtained as described in general method U. MS (ESI, m/z): 560.2 [M+H]⁺

Example 803

(R)-2-amino-N-(1-(4'-(methyl(4-nitrophenyl)amino)-[1,1'-biphenyl]-4-carbonyl)pyrrolidin-3-yl)-5-(1-methyl-1H-pyrazol-4-yl)nicotinamide Using 4-bromo-N-methyl-N-(4-nitrophenyl)aniline, the title compound was obtained as described in general method U. MS (ESI, m/z): 617.3 [M+H]⁺

Example 804

(R)-2-amino-N-(1-(4'-((2-fluoro-4-nitrophenyl)(methyl)amino)-[1,1'-biphenyl]-4-carbonyl)pyrrolidin-3-yl)-5-(1-methyl-1H-pyrazol-4-yl)nicotinamide Using N-(4-bromophenyl)-2-fluoro-N-methyl-4-nitroaniline, the title compound was obtained as described in general method U. ¹H NMR (400 MHz, METHANOL-d₄) δ ppm 2.06-2.24 (m, 1H) 2.26-2.48 (m, 1H) 3.46 (d, J=2.35 Hz, 3H) 3.58 (br dd, J=10.96, 5.09 Hz, 0.5H) 3.63-3.73 (m, 1H) 3.76 (br dd, J=11.15, 7.24 Hz, 1H) 3.86 (br d, J=7.43 Hz, 0.5H) 3.94 (d, J=3.91 Hz, 3H) 3.96-4.08 (m, 1H) 4.51-4.61 (m, 0.5H) 4.65-4.73 (m, 0.5H) 7.12 (br dd, J=8.41, 4.50 Hz, 2H) 7.37 (td, J=8.61, 2.35 Hz, 1H) 7.54-7.66 (m, 4H) 7.66-7.75 (m, 2H) 7.90 (d, J=13.30 Hz, 1H) 7.98 (br d, J=12.13 Hz, 1H) 8.01-8.12 (m, 2H) 8.23 (dd, J=14.87, 1.96 Hz, 1H) 8.61-8.74 (m, 1H); MS (ESI, m/z): 635.3 [M+H]$^+$ Example 805

(R)-2-amino-N-(1-(4'-(methyl(2-methyl-4-nitrophenyl)amino)-[1,1'-biphenyl]-4-carbonyl)pyrrolidin-3-yl)-5-(1-methyl-1H-pyrazol-4-yl)nicotinamide Using N-(4-bromophenyl)-N,2-dimethyl-4-nitroaniline, the title compound was obtained as described in general method U. $^1$H NMR (400 MHz, METHANOL-d$_4$) δ ppm 2.10-2.20 (br s, 1H) 2.16 (d, J=3.13 Hz, 3H) 2.35-2.40 (m, 1H) 3.36 (d, J=3.52 Hz, 3H) 3.52-3.61 (m, 0.5H) 3.62-3.70 (m, 1H) 3.75 (br t, J=7.04 Hz, 1H) 3.80-3.88 (m, 0.5H) 3.88-3.95 (m, 3H) 3.95-4.02 (m, 1H) 4.52 (br s, 0.5H) 4.67 (br s, 0.5H) 6.77 (dd, J=8.41, 5.67 Hz, 2H) 7.38 (dd, J=8.61, 3.91 Hz, 1H) 7.51-7.71 (m, 6H) 7.86 (d, J=13.69 Hz, 1H) 8.00 (d, J=12.91 Hz, 1 H) 8.07-8.17 (m, 2H) 8.23 (dd, J=14.48, 1.56 Hz, 1H) 8.44 (s, 1H); MS (ESI, m/z): 631.3 [M+H]$^+$ Example 806

(R)-2-amino-N-(1-(4'-((2-chloro-4-nitrophenyl)(methyl)amino)-[1,1'-biphenyl]-4-carbonyl)pyrrolidin-3-yl)-5-(1-methyl-1H-pyrazol-4-yl)nicotinamide Using N-(4-bromophenyl)-2-chloro-N-methyl-4-nitroaniline, the title compound was obtained as described in general method U. $^1$H NMR (400 MHz, METHANOL-d$_4$) δ ppm 2.06-2.23 (m, 1H) 2.25-2.44 (m, 1H) 3.39 (d, J=3.52 Hz, 3H) 3.57 (br dd, J=11.35, 5.09 Hz, 0.5H) 3.67 (br dd, J=13.50, 4.89 Hz, 1H) 3.76 (br t, J=6.85 Hz, 1H) 3.81-3.89 (m, 0.5H) 3.92-3.96 (m, 3H) 3.96-4.03 (m, 1H) 4.50-4.58 (m, 0.5H) 4.65-4.71 (m, 0.5H) 6.88 (dd, J=8.41, 6.06 Hz, 2H) 7.50-7.73 (m, 7H) 7.89 (d, J=14.09 Hz, 1H) 8.04 (d, J=13.30 Hz, 1H) 8.14-8.29 (m, 2H) 8.33 (t, J=2.35 Hz, 1H) 8.59-8.75 (m, 1H); MS (ESI, m/z): 651.2 [M+H]$^+$ Example 807

(R)-2-amino-5-(1-methyl-1H-pyrazol-4-yl)-N-(1-(4'-(piperidin-4-ylmethyl)-[1,1'-biphenyl]-4-carbonyl)pyrrolidin-3-yl)nicotinamide Using 4-(4-bromobenzyl)piperidine, the title compound was obtained as described in general method U. MS (ESI, m/z): 564.3 [M+H]$^+$ Example 808

(R)-2-amino-N-(1-(3'-chloro-4'-(4-hydroxyphenoxy)-[1,1'-biphenyl]-4-carbonyl)pyrrolidin-3-yl)-5-(1-methyl-1H-pyrazol-4-yl)nicotinamide Using 4-(4-bromo-2-chlorophenoxy)phenol, the title compound was obtained as described in general method U. $^1$H NMR (600 MHz, METHANOL-d$_4$) δ ppm 2.07-2.21 (m, 1H) 2.28-2.43 (m, 1H) 3.55 (br dd, J=11.15, 5.28 Hz, 0.5H) 3.64-3.71 (m, 1H) 3.71-3.79 (m, 1H) 3.82-3.90 (m, 0.5H) 3.93 (d, J=5.28 Hz, 3H) 3.95-4.04 (m, 1H) 4.52-4.57 (m, 0.5H) 4.66-4.72 (m, 0.5H) 6.80 (br d, J=7.63 Hz, 2H) 6.84-6.94 (m, 3H) 7.47-7.52 (m, 1H) 7.62 (dd, J=14.09, 8.22 Hz, 2H) 7.65-7.71 (m, 2H) 7.75 (dd, J=7.63, 2.35 Hz, 1H) 7.89 (d, J=18.19 Hz, 1H) 8.03 (d, J=17.02 Hz, 1H) 8.22 (dd, J=19.37, 1.76 Hz, 1H) 8.59-8.73 (m, 1H); MS (ESI, m/z): 609.2 [M+H]$^+$ Example 809

(R)-2-amino-5-(1-methyl-1H-pyrazol-4-yl)-N-(1-(4'-((1-methylpiperidin-4-yl)oxy)-[1,1'-biphenyl]-4-carbonyl)pyrrolidin-3-yl)nicotinamide Using 4-(4-bromophenoxy)-1-methylpiperidine, the title compound was obtained as described in general method U. $^1$H NMR (600 MHz, METHANOL-d$_4$) δ ppm 1.89 (br d, J=10.56 Hz, 1H) 2.06-2.21 (m, 2H) 2.22-2.36 (m, 2H) 2.36-2.42 (m, 1H) 2.90 (s, 3H) 3.18 (br t, J=12.91 Hz, 1H) 3.31-3.45 (m, 2.5H) 3.56 (br dd, J=11.15, 5.28 Hz, 0.5H) 3.61 (br d, J=12.33 Hz, 0.5H) 3.67 (br dd, J=13.21, 4.40 Hz, 1H) 3.72-3.81 (m, 1H) 3.81-3.89 (m, 0.5H) 3.93 (d, J=4.70 Hz, 3H) 3.94-4.02 (m, 1H) 4.51-4.58 (m, 0.5H) 4.59-4.66 (m, 0.5H) 4.66-4.72 (m, 0.5H) 4.79-4.85 (m, 0.5H) 7.03-7.14 (m, 2H) 7.56-7.70 (m, 6H) 7.89 (d, J=18.19 Hz, 1H) 8.04 (d, J=16.43 Hz, 1H) 8.22 (dd, J=19.37, 1.76 Hz, 1H) 8.62-8.72 (m, 1H); MS (ESI, m/z): 580.3 [M+H]$^+$ Example 810

(R)-2-amino-N-(1-(4'-((4-aminocyclohexyl)oxy)-[1,1'-biphenyl]-4-carbonyl)pyrrolidin-3-yl)-5-(1-methyl-1H-pyrazol-4-yl)nicotinamide Using tert-butyl (4-(4-bromophenoxy)cyclohexyl)carbamate and trifluoroacetic acid, the title compound was obtained as described in general method U. $^1$H NMR (600 MHz, METHANOL-d$_4$) δ ppm 1.74 (br d, J=14.09 Hz, 2H) 1.80-1.89 (m, 4H) 2.07-2.22 (m, 3H) 2.28-2.43 (m, 1H) 3.17-3.25 (m, 1H) 3.57 (br dd, J=11.15, 5.28 Hz, 0.5H) 3.62-3.72 (m, 1H) 3.72-3.80 (m, 1H) 3.80-3.89 (m, 0.5H) 3.94 (d, J=4.70 Hz, 3H) 3.95-4.03 (m, 1H) 4.52-4.58 (m, 0.5H) 4.65-4.75 (m, 1.5H) 7.05 (dd, J=8.51, 4.40 Hz, 2H) 7.56-7.69 (m, 6H) 7.90 (d, J=18.19 Hz, 1H) 8.05 (d, J=16.43 Hz, 1H) 8.24 (dd, J=18.78, 1.76 Hz, 1H) 8.61-8.73 (m, 1H); MS (ESI, m/z): 580.3 [M+H]$^+$ Example 811

(R)-2-amino-N-(1-(4'-(4-formylphenoxy)-[1,1'-biphenyl]-4-carbonyl)pyrrolidin-3-yl)-5-(1-methyl-1H-pyrazol-4-yl)nicotinamide Using 4-(4-bromophenoxy)benzaldehyde, the title compound was obtained as described in general method U. $^1$H NMR (600 MHz, METHANOL-d$_4$) δ ppm 2.08-2.24 (m, 1H) 2.28-2.43 (m, 1H) 3.56 (br dd, J=11.15, 4.70 Hz, 0.5H) 3.63-3.72 (m, 1H) 3.76 (br dd, J=10.86, 7.34 Hz, 1H) 3.82-3.90 (m, 10.5H) 3.93 (d, J=5.28 Hz, 3H) 3.95-4.03 (m, 1H) 4.52-4.57 (m, 0.5H) 4.66-4.72 (m, 0.5H) 7.02 (dd, J=8.80, 3.52 Hz, 2H) 7.07 (dd, J=8.80, 5.28 Hz, 2H) 7.43 (dd, J=8.22, 1.76 Hz, 2H) 7.59-7.76 (m, 6H) 7.89 (d, J=18.78 Hz, 1H) 8.04 (d, J=18.19 Hz, 1H) 8.14-8.26 (m, 1H) 8.60-8.74 (m, 1H); MS (ESI, m/z): 587.2 [M+H]$^+$

Example 812

(R)-4-((4'-(3-(2-amino-5-(1-methyl-1H-pyrazol-4-yl)nicotinamido)pyrrolidine-1-carbonyl)-[1,1'-biphenyl]-4-yl)oxy)benzoic acid Using 4-(4-bromophenoxy)benzoic acid, the title compound was obtained as described in general method U. MS (ESI, m/z): 603.2 [M+H]$^+$

Example 813

(R)-2-amino-N-(1-(4'-((6-aminopyridin-3-yl)oxy)-[1,1'-biphenyl]-4-carbonyl)pyrrolidin-3-yl)-5-(1-methyl-1H-pyrazol-4-yl)nicotinamide Using 5-(4-bromophenoxy)pyridin-2-amine, the title compound was obtained as described in general method U. MS (ESI, m/z): 575.2 [M+H]$^+$

Example 814

(R)—N-(1-(4'-((2H-tetrazol-5-yl)oxy)-[1,1'-biphenyl]-4-carbonyl)pyrrolidin-3-yl)-2-amino-5-(1-methyl-1H-pyrazol-4-yl)nicotinamide Using 5-(4-bromophenoxy)-2H-tetrazole, the title compound was obtained as described in general method U. MS (ESI, m/z): 551.2 [M+H]$^+$

Example 815

(R)-2-amino-N-(1-(4'-((4-aminophenyl)amino)-[1,1'-biphenyl]-4-carbonyl)pyrrolidin-3-yl)-5-(1-methyl-1H-pyrazol-4-yl)nicotinamide Using N-(4-bromophenyl)benzene-1,4-diamine, the title compound was obtained as described in general method U. MS (ESI, m/z): 573.3 [M+H]$^+$

Example 844

(R)-2-amino-N-(1-(2'-chloro-4'-(4-formylphenoxy)-[1,1'-biphenyl]-4-carbonyl)pyrrolidin-3-yl)-5-(1-methyl-1H-pyrazol-4-yl)nicotinamide Using 4-(4-bromo-3-chlorophenoxy)benzaldehyde, the title compound was obtained as described in general method U. MS (ESI, m/z): 621.2 [M+H]$^+$

General Method V

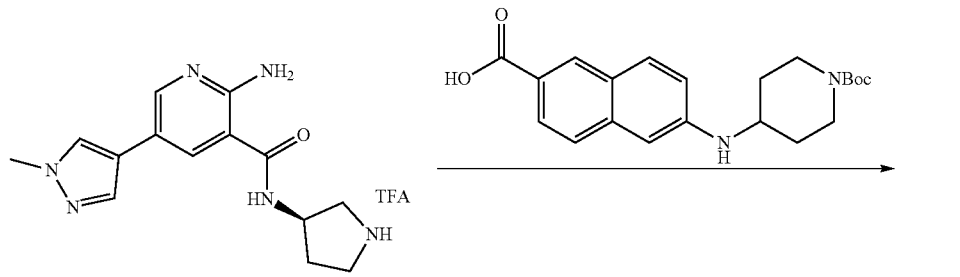

Intermediate 3

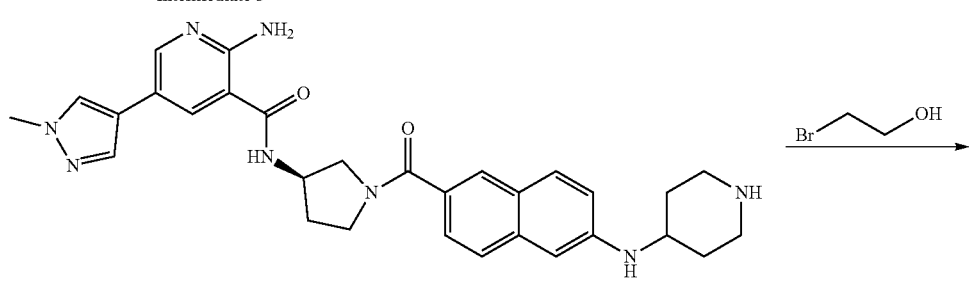

Example 816

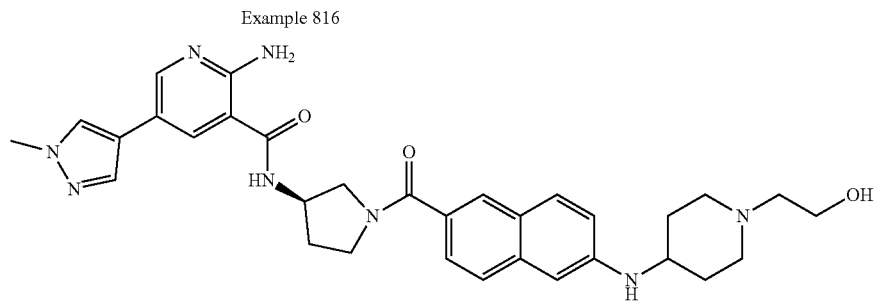

Example 817

Example 816

(R)-2-amino-5-(1-methyl-1H-pyrazol-4-yl)-N-(1-(6-(piperidin-4-ylamino)-2-naphthoyl)pyrrolidin-3-yl)nicotinamide To a mixture of 6-((1-(tert-butoxycarbonyl)piperidin-4-yl)amino)-2-naphthoic acid (80 mg, 0.208 mmol) and triethylamine (0.087 mL, 0.624 mmol) in N,N-dimethylformamide (1 mL) was added 1-[bis(dimethylamino)methylene]-1H-1,2,3-triazolo[4,5-b]pyridinium 3-oxid hexafluorophosphate (79 mg, 0.028 mmol) followed by Intermediate 3 (67 mg, 0.028 mmol). The mixture was stirred at room temperature for 1 hr and then saturated sodium bicarbonate solution was added. The mixture was extracted with ethyl acetate, washed with brine, dried over $MgSO_4$, and concentrated in vacuo. The crude product was purified through silica gel column chromatography (trieithylamine/methanol/$CH_2Cl_2$ 0.5/4.5/95) to give 0.1 g off-white solid. The isolated compound was dissolved in of 4:1 dichloromethane/trifluoroacetic acid (1 mL) and stirred at rt for 2 hrs. After concentration under vacuum, the crude residue was purified by preparative HPLC to afford 80 mg of the title compound. $^1$H NMR (600 MHz, METHANOL-$d_4$) δ ppm 1.68-1.82 (m, 2H) 2.07-2.24 (m, 1H) 2.30 (br d, J=13.50 Hz, 2H) 2.29-2.40 (m, 1H) 3.19 (br t, J=12.03 Hz, 2H) 3.47 (br d, J=12.91 Hz, 2H) 3.62 (br dd, J=10.86, 4.99 Hz, 0.5H) 3.69 (br dd, J=12.91, 4.70 Hz, 0.5H) 3.73-3.90 (m, 3H) 3.94 (d, J=5.87 Hz, 3H) 4.02 (dd, J=12.03, 6.75 Hz, 1H) 4.50-4.57 (m, 0.5H) 4.67-4.74 (m, 0.5H) 6.91 (br d, J=6.46 Hz, 1H) 6.97-7.09 (m, 1H) 7.49 (br dd, J=14.67, 8.80 Hz, 1H) 7.59-7.71 (m, 2H) 7.84-7.94 (m, 2H) 8.00-8.08 (m, 1H) 8.24 (s, 1H) 8.59-8.73 (m, 1H); MS (ESI, m/z): 539.3 [M+H]$^+$

Example 817

(R)-2-amino-N-(1-(6-((1-(2-hydroxyethyl)piperidin-4-yl)amino)-2-naphthoyl)pyrrolidin-3-yl)-5-(1-methyl-1H-pyrazol-4-yl)nicotinamide To a mixture of Example 816 (30 mg, 0.056 mmol) and potassium carbonate (15 mg, 0.111 mmol) in methanol (0.5 mL) was added 2-bromoethanol (5.90 μl, 0.084 mmol). The mixture was stirred at 50° C. for 4 hr and then saturated sodium bicarbonate solution was added. The mixture was extracted with ethyl acetate, washed with brine, dried over $MgSO_4$, and concentrated in vacuo. After concentration under vacuum, the crude residue was purified by preparative HPLC to afford 20 mg of the title compound. $^1$H NMR (600 MHz, METHANOL-$d_4$) δ ppm 1.69-1.88 (m, 2H) 2.09 (br dd, J=12.03, 6.16 Hz, 1H) 2.19 (dt, J=13.35, 6.53 Hz, 1H) 2.27 (dt, J=13.06, 6.68 Hz, 1H) 2.32-2.42 (m, 1H) 3.13-3.23 (m, 2H) 3.23-3.28 (m, 2H) 3.34-3.54 (m, 2H) 3.62 (br dd, J=11.15, 5.28 Hz, 0.5H) 3.67-3.88 (m, 3.5H) 3.89 (brd, J=4.70 Hz, 2H) 3.92 (d, J=6.46 Hz, 3H) 3.95-4.05 (m, 1H) 4.46-4.55 (m, 0.5H) 4.63-4.71 (m, 0.5H) 6.90 (br d, J=12.33 Hz, 1H) 7.03 (q, J=9.39 Hz, 1H) 7.41-7.52 (m, 1H) 7.58-7.70 (m, 2H) 7.84 (d, J=8.22 Hz, 1H) 7.89 (d, J=9.98 Hz, 1H) 7.98-8.07 (m, 1H) 8.13-8.25 (m, 1H) 8.57-8.73 (m, 1H); MS (ESI, m/z): 583.3 [M+H]$^+$

Example 818

(R)-2-amino-N-(1-(6-(methyl(piperidin-4-yl)amino)-2-naphthoyl)pyrrolidin-3-yl)-5-(1-methyl-1H-pyrazol-4-yl)nicotinamide Using 6-((1-(tert-butoxycarbonyl)piperidin-4-yl)(methyl)amino)-2-naphthoic acid, the title compound was obtained as described in general method V. MS (ESI, m/z): 553.3 [M+H]$^+$

Example 819

(R)-2-amino-N-(1-(4'-((1-(2-hydroxyethyl)piperidin-4-yl)methyl)-[1,1'-biphenyl]-4-carbonyl)pyrrolidin-3-yl)-5-(1-methyl-1H-pyrazol-4-yl)nicotinamide Using Example 807, the title compound was obtained as described in general method V. MS (ESI, m/z): 608.3 [M+H]$^+$

Example 820

(R)-2-amino-N-(1-(6-((1-(2-hydroxyethyl)piperidin-4-yl)(methyl)amino)-2-naphthoyl)pyrrolidin-3-yl)-5-(1-methyl-1H-pyrazol-4-yl)nicotinamide Using Example 818, the title compound was obtained as described in general method V. $^1$H NMR (600 MHz, METHANOL-$d_4$) δ ppm 2.03 (br d, J=11.15 Hz, 2H) 2.06-2.23 (m, 3H) 2.26-2.43 (m, 1H) 2.98 (br d, J=7.63 Hz, 3H) 3.21 (br t, J=12.62 Hz, 2H) 3.25 (br s, 2H) 3.61 (br dd, J=11.15, 5.28 Hz, 0.5H) 3.68-3.84 (m, 4H) 3.86-3.91 (m, 2.5H) 3.93 (d, J=7.04 Hz, 3H) 4.01 (td, J=13.21, 6.46 Hz, 1H) 4.16-4.30 (m, 1H) 4.49-4.57 (m, 0.5H) 4.65-4.73 (m, 0.5H) 7.23 (br d, J=14.67 Hz, 1H) 7.42 (br t, J=9.10 Hz, 1H) 7.49-7.57 (m, 1H) 7.74 (br dd, J=14.97, 8.51 Hz, 1H) 7.79-7.85 (m, 1H) 7.86-7.91 (m, 1H) 7.91-7.98 (m, 1H) 8.00-8.08 (m, 1H) 8.16-8.27 (m, 1H) 8.59-8.75 (m, 1H); MS (ESI, m/z): 597.3 [M+H]$^+$

Example 821

(R)-2-amino-N-(1-(6-((1-(2-hydroxyethyl)piperidin-4-yl)oxy)-2-naphthoyl)pyrrolidin-3-yl)-5-(1-methyl-1H-pyrazol-4-yl)nicotinamide Using Example 768, the title compound was obtained as described in general method V. $^1$H NMR (600 MHz, METHANOL-$d_4$) δ ppm 1.97-2.14 (m, 1H) 2.17-2.26 (m, 2H) 2.26-2.35 (m, 2H) 2.37-2.50 (m, 1H) 3.27 (br d, J=5.28 Hz, 1H) 3.32 (d, J=3.52 Hz, 2H) 3.37-3.44 (m, 1H) 3.55 (br d, J=10.56 Hz, 1H) 3.59 (br dd, J=10.56, 4.70 Hz, 0.5H) 3.68-3.84 (m, 3H) 3.86-3.92 (m, 2.5H) 3.94 (d, J=6.46 Hz, 3H) 3.98-4.08 (m, 1H) 4.51-4.57 (m, 0.5H) 4.67-4.74 (m, 0.5H) 4.80 (br d, J=4.70 Hz, 0.5H) 4.97-5.02 (m, 0.5H) 7.21-7.34 (m, 1H) 7.41 (br d, J=4.70 Hz, 1H) 7.58-7.64 (m, 1H) 7.85 (br t, J=9.10 Hz, 1H) 7.87-7.95 (m, 2H) 8.00-8.08 (m, 2H) 8.03-8.03 (m, 1H) 8.24 (dd, J=27.58, 2.35 Hz, 1H) 8.67 (dd, J=59.28, 2.35 Hz, 1H); MS (ESI, m/z): 584.3 [M+H]$^+$ General Method W

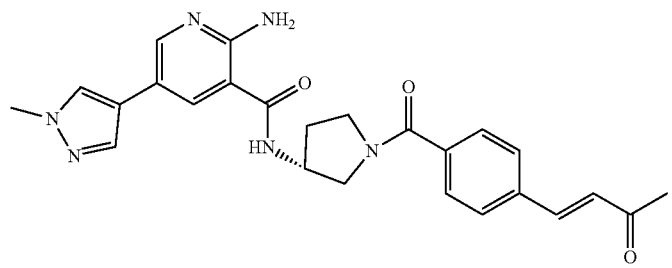

Example 681

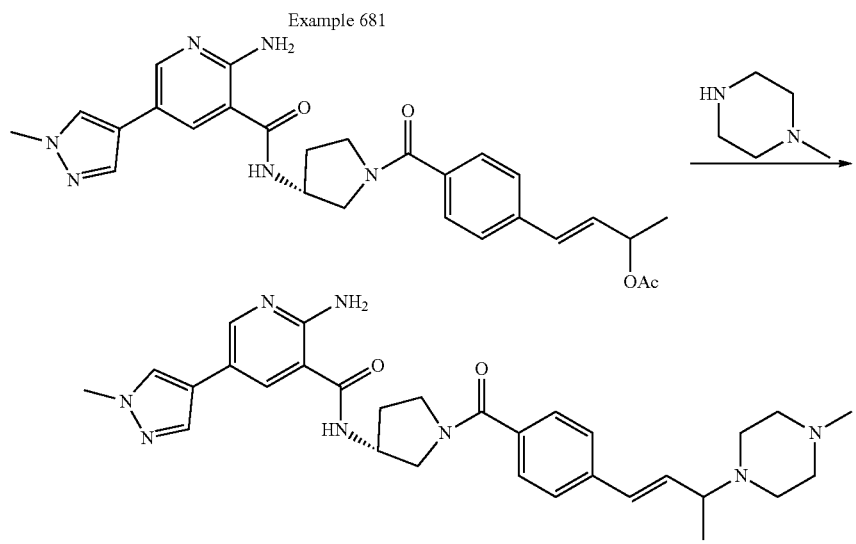

Example 822

Intermediate 7

(E)-4-(4-((R)-3-(2-amino-5-(1-methyl-1H-pyrazol-4-yl)nicotinamido)pyrrolidine-1-carbonyl)phenyl)but-3-en-2-yl acetate To an oven dried round bottom flask equipped with magnetic stir bar was added Example 681 (1.0 equiv.) and a 1:3 mixture of tetrahydrofuran and methanol, (0.65 M) and then the mixture was cooled to 0° C. Sodium borohydride (NaBH$_4$), (2.0 equiv.) was added portionwise and the reaction mixture was allowed to warm to room temperature and stirred for 2 hours. The reaction was monitored by TLC. After the complete consumption of the starting material the reaction mixture was quenched with saturated NH$_4$Cl and the solvent volume was reduced under vacuum. The residue left behind was extracted with ethyl acetate (3×30 mL). The organic layer was separated and dried over MgSO$_4$. The solvent was evaporated to yield the allylic alcohol which was used without further purification. To an oven dried round bottom flask equipped with magnetic stir bar was added allylic alcohol (1.0 equiv.), tetrahydrofuran (1.35 M), acetic anhydride (1.2 equiv.), 4-dimethylamino pyridine (DMAP), (0.005 equiv.), and triethylamine (1.8 equiv.). The reaction mixture was stirred at 0° C. for 1 hour and then warmed to room temperature and stirred for 14 hours. The reaction was monitored by TLC. After the complete consumption of the starting material the solvent was removed under vacuum. The residual oil was diluted with ethyl acetate. The organic layer was then washed with water and brine and then dried over MgSO$_4$ to obtain the desired Intermediate 6 which was used without further which was used without further purification. MS (ESI, m z): 503.2 [M+H]b purification. MS (ESI, m/z): 503.2 [M+H]$^+$

Example 822

2-amino-5-(1-methyl-1H-pyrazol-4-yl)-N-((3R)-1-(4-((E)-3-(4-methylpiperazin-yl) but-1 en-1-yl)benzoyl)pyrrolidin-3-yl)nicotinamide To an oven dried round bottom flask equipped with magnetic stir bar was added Intermediate 7 (20 mg, 0.04 mmol), dichloromethane (CH$_2$Cl$_2$), (0.3 mL), tetrakis(triphenylphosphine)palladium(0), (Pd(PPh$_3$)$_4$), (1 mg, 0.03 equiv.) and 1-methylpiperazine (0.05 mL, 005 mmol) under an Argon atmosphere. The reaction mixture was then heated to 40° C. for 16 hours. The reaction was monitored by TLC. After the complete consumption of the starting material the reaction mixture was quenched with NH$_4$OH. The organic layer was then separated, dried over MgSO$_4$ and concentrated to obtain the crude product. The crude residue was purified by preparative HPLC to afford 20 mg of the title compound. $^1$H NMR (600 MHz, CHLOROFORM-d) δ ppm 1.54-1.62 (m, 3H) 2.00-2.06 (m, 0.5H) 2.15-2.22 (m, 0.5H) 2.28-2.44 (m, 1H) 2.92 (d, J=4.11 Hz, 3H) 3.39-3.47 (m, 1H) 3.54-3.66 (m, 1H) 3.69 (s, 8H) 3.71-3.81 (m, 2H) 3.91 (br dd, J=13.21, 7.34 Hz, 0.5H) 3.95 (d, J=1.17 Hz, 3H) 4.01-4.12 (m, 0.5H) 4.62 (br s, 0.5H) 4.65-4.75 (m, 0.5H) 6.20-6.30 (m, 1H) 6.68-6.80 (m, 1H) 7.19-7.27 (m, 1H)

7.32-7.38 (m, 1H) 7.44-7.52 (m, 2H) 7.66-7.73 (m, 1H) 7.76 (s, 1H) 7.85-7.89 (m, 0.5H) 8.04 (d, J=1.76 Hz, 0.5H) 8.37-8.41 (m, 0.5H) 8.58 (s, 0.5H); MS (ESI, m/z): 543.3 [M+H]+

Example 823

2-amino-N-((3R)-1-(4-((E)-3-(4-(2-hydroxyethyl)piperazin-1-yl)but-1-en-1-yl)benzoyl)pyrrolidin-3-yl)-5-(1-methyl-1H-pyrazol-4-yl)nicotinamide Using 2-(piperazin-1-yl)ethan-1-ol, the title compound was obtained as described in general method W. $^1$H NMR (600 MHz, CHLOROFORM-d) δ ppm 1.48-1.61 (m, 3H) 1.94-2.18 (m, 1H) 2.19-2.37 (m, 1H) 3.20-3.30 (m, 4H) 3.34-3.41 (m, 1H) 3.48-3.55 (m, 1H) 3.56-3.64 (m, 4H) 3.64-3.79 (m, 5H) 3.84-3.89 (m, 2H) 3.90 (d, J=2.35 Hz, 3H) 3.93-4.06 (m, 1H) 4.55 (br dd, J=9.39, 4.70 Hz, 0.5H) 4.60-4.70 (m, 0.5H) 6.15-6.24 (m, 1H) 6.66-6.76 (m, 1H) 7.20-7.30 (m, 1H) 7.33 (dd, J=8.22, 5.87 Hz, 1H) 7.38-7.50 (m, 2H) 7.66 (dd, J=11.44, 3.23 Hz, 1H) 7.72 (d, J=2.35 Hz, 1H) 7.87 (dd, J=7.04, 1.76 Hz, 0.5H) 8.00 (d, J=2.35 Hz, 0.5H) 8.37 (s, 0.5H) 8.54 (s, 0.5H); MS (ESI, m/z): 573.3 [M+H]+

General Method X

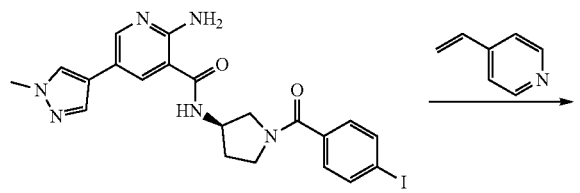

Example 400

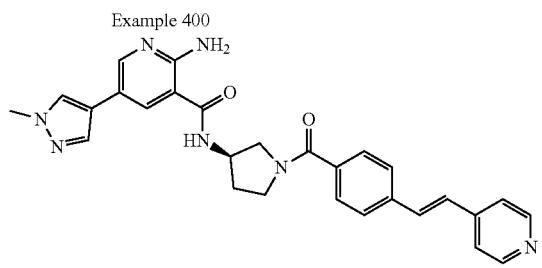

Example 824

Example 824

(R,E)-2-amino-5-(1-methyl-1H-pyrazol-4-yl)-N-(1-(4-(2-(pyridin-4-yl)vinyl)benzoyl)pyrrolidin-3-yl)nicotinamide A mixture of Example 400 (30 mg, 0.06 mmol), Pd(PPh$_3$)$_2$Cl$_2$ (2 mg, 5 mol %) and triethylamine (24 µL, 0.17 mmol) in N,N-dimethylformamide (0.5 mL) was degassed with nitrogen and 4-vinylpyridine (9 mg, 0.09 mmol) were added. The mixture was heated at 100° C. for 12 hrs. After cooling, the mixture was partitioned between ethyl acetate and water. The organic layer was separated and washed with water, brine dried over MgSO$_4$ and concentrated in vacuo. After concentration under vacuum, the crude residue was purified by preparative HPLC to afford 15 mg of the title compound. $^1$H NMR (600 MHz, METHANOL-d$_4$) δ ppm 2.09-2.24 (m, 1H) 2.28-2.47 (m, 1H) 3.53 (dd, J=11.15, 5.28 Hz, 0.5H) 3.61-3.71 (m, 1H) 3.71-3.78 (m, 1H) 3.81-3.89 (m, 0.5H) 3.94 (d, J=5.28 Hz, 3H) 3.91-3.95 (m, 0.5H) 4.02 (dd, J=12.91, 7.04 Hz, 0.5H) 4.52-4.58 (m, 0.5H) 4.67-4.72 (m, 0.5H) 7.53 (dd, J=16.43, 7.04 Hz, 1H) 7.65 (dd, J=14.09, 8.22 Hz, 2H) 7.84 (t, J=8.51 Hz, 2H) 7.90 (d, J=17.61 Hz, 1H) 7.95 (dd, J=16.43, 7.04 Hz, 1H) 8.05 (d, J=15.26 Hz, 1H) 8.19-8.30 (m, 3H) 8.64 (d, J=1.76 Hz, 0.5H) 8.72 (d, J=2.35 Hz, 0.5H) 8.72-8.77 (m, 2H); MS (ESI, m/z): 494.2 [M+H]+

Example 825

(R,E)-2-amino-5-(1-methyl-1H-pyrazol-4-yl)-N-(1-(4-(2-(pyridin-2-yl)vinyl)benzoyl)pyrrolidin-3-yl)nicotinamide Using 2-vinylpyridine, the title compound was obtained as described in general method X. $^1$H NMR (600 MHz, METHANOL-d$_4$) δ ppm 2.09-2.24 (m, 1H) 2.27-2.44 (m, 1H) 3.53 (dd, J=11.15, 5.28 Hz, 0.5H) 3.61-3.70 (m, 1H) 3.70-3.79 (m, 1H) 3.81-3.89 (m, 0.5H) 3.91-3.96 (m, 0.5H) 3.94 (d, J=4.70 Hz, 3H) 4.01 (dd, J=12.91, 6.46 Hz, 0.5H) 4.52-4.58 (m, 0.5H) 4.66-4.72 (m, 0.5H) 7.47 (dd, J=16.43, 5.87 Hz, 1H) 7.66 (dd, J=15.26, 8.22 Hz, 2H) 7.82 (t, J=8.80 Hz, 2H) 7.84-7.93 (m, 2H) 7.96 (dd, J=16.43, 7.63 Hz, 1H) 8.05 (d, J=15.85 Hz, 1H) 8.24 (dd, J=17.90, 2.05 Hz, 1H) 8.35-8.40 (m, 1H) 8.49-8.56 (m, 1H) 8.64 (d, J=1.76 Hz, 0.5H) 8.70-8.79 (n, 1.5H); MS (ESI, m/z): 494.2 [M+H]+

Example 826

(R,E)-2-amino-5-(1-methyl-1H-pyrazol-4-yl)-N-(1-(4-(2-phenylprop-1-en-1-yl)benzoyl)pyrrolidin-3-yl)nicotinamide Using prop-1-en-2-ylbenzene, the title compound was obtained as described in general method X. $^1$H NMR (600 MHz, METHANOL-d$_4$) δ ppm 2.08-2.21 (m, 1H) 2.27 (dd, J=5.87, 1.17 Hz, 3H) 2.29-2.43 (m, 1H) 3.56 (br dd, J=11.15, 5.28 Hz, 0.5H) 3.65-3.72 (m, 1H) 3.72-3.79 (m, 1H) 3.82-3.88 (m, 0.5H) 3.90-4.04 (m, 1H) 3.94 (d, J=4.7 Hz, 3H) 4.52-4.57 (m, 0.5H) 4.66-4.73 (m, 0.5H) 6.85 (br d, J=6.46 Hz, 1H) 7.25-7.31 (m, 1H) 7.35 (td, J=7.63, 2.93 Hz, 2H) 7.43-7.50 (m, 2H) 7.53 (dd, J=7.04, 5.28 Hz, 2H) 7.58 (dd, J=14.67, 8.22 Hz, 2H) 7.85-7.96 (m, 1H) 8.00-8.09 (m, 1H) 8.19-8.27 (m, 1H) 8.62-8.77 (m, 1H); MS (ESI, m/z): 507.2 [M+H]+

Example 827

(R,E)-2-amino-5-(1-methyl-1H-pyrazol-4-yl)-N-(1-(4-(2-(piperidin-4-yl)vinyl)benzoyl)pyrrolidin-3-yl)nicotinamide Using tert-butyl 4-vinylpiperidine-1-carboxylate and trifluoroacetic acid, the title compound was obtained as described in general method X. $^1$H NMR (600 MHz, METHANOL-d$_4$) δ ppm 1.31-1.40 (m, 1H) 1.67 (br d, J=13.50 Hz, 1H) 1.77 (br d, J=12.91 Hz, 1H) 2.04-2.22 (m, 2H) 2.28 (br dd, J=12.03, 6.75 Hz, 0.5H) 2.36 (dt, J=13.06, 6.68 Hz, 1H) 2.50-2.58 (m, 0.5H) 2.84 (br d, J=9.98 Hz, 1H)

3.01-3.11 (m, 1H) 3.39-3.47 (m, 1H) 3.52 (br dd, J=11.15, 5.28 Hz, 0.5H) 3.61-3.68 (m, 1H) 3.68-3.77 (m, 1H) 3.78-3.86 (m, 0.5H) 3.89-4.01 (m, 1H) 3.93 (d, J=3.52 Hz, 3H) 4.09 (br d, J=11.15 Hz, 1H) 4.50-4.55 (m, 0.5H) 4.64-4.71 (m, 0.5H) 6.28-6.36 (m, 1H) 6.43-6.57 (m, 1H) 7.42-7.58 (m, 4H) 7.89 (d, J=17.02 Hz, 1H) 8.05 (d, J=14.09 Hz, 1H) 8.18-8.28 (m, 1H) 8.61-8.74 (m, 1H); MS (ESI, m/z): 500.3 [M+H]$^+$

Example 828 methyl (R,E)-3-(4-(3-(2-amino-5-(1-methyl-1H-pyrazol-4-yl)nicotinamido)pyrrolidine-1-carbonyl)phenyl)acrylate Using methyl acrylate, the title compound was obtained as described in general method X. $^1$H NMR (600 MHz, METHANOL-d$_4$) δ ppm 2.07-2.20 (m, 1H) 2.26-2.41 (m, 1H) 3.50 (br dd, J=11.15, 5.28 Hz, 0.5H) 3.60-3.75 (m, 2H) 3.78 (d, J=4.11 Hz, 3H) 3.81-3.88 (m, 0.5H) 3.90 (dd, J=11.15, 6.46 Hz, 0.5H) 3.94 (d, J=4.11 Hz, 3H) 3.99 (br dd, J=12.91, 6.46 Hz, 0.5H) 4.49-4.57 (m, 0.5H) 4.64-4.72 (m, 0.5H) 6.60 (dd, J=16.14, 7.34 Hz, 1H) 7.58 (dd, J=15.26, 8.22 Hz, 1H) 7.63-7.76 (m, 4H) 7.85-7.93 (m, 1H) 8.00-8.08 (m, 1H) 8.17-8.28 (m, 1H) 8.59-8.75 (m, 1H); MS (ESI, m/z): 475.2 [M+H]$^+$ General Method Y

Example 829

(R)-2-amino-5-(1-methyl-1H-pyrazol-4-yl)-N-(1-(4-(3-nitrophenoxy)benzoyl)pyrrolidin-3-yl)nicotinamide To a stirred slurry of 1-fluoro-3-nitrobenzene (52 mg, 0.37 mmol) and Example 840 (0.1 g, 0.25 mmol) in N,N-dimethylformamide (1.5 mL) was added K$_2$CO$_3$ (68 mg, 0.49 mmol). The mixture was heated to 90° C. overnight. After cooling, the mixture was partitioned between ethyl acetate and water. The organic layer was separated and washed with water, brine dried over MgSO$_4$ and concentrated in vacuo. After concentration under vacuum, the crude residue was purified by preparative HPLC to afford 80 mg of the title compound. $^1$H NMR (600 MHz, METHANOL-d$_4$) δ ppm 2.08-2.22 (m, 1H) 2.28-2.43 (m, 1H) 3.53-3.58 (m, 0.5H) 3.64-3.71 (m, 1H) 3.71-3.80 (m, 0.5H) 3.81-3.87 (m, 0.5H) 3.93 (d, J=1.76 Hz, 3H) 3.95-4.02 (m, 1H) 4.52-4.58 (m, 0.5H) 4.66-4.71 (m, 0.5H) 7.15 (t, J=8.80 Hz, 2H) 7.46 (br d, J=8.22 Hz, 1H) 7.60-7.71 (m, 3H) 7.78-7.85 (m, 1H) 7.89 (d, J=14.67 Hz, 1H) 8.00-8.03 (m, 1H) 8.04 (d, J=12.91 Hz, 1H) 8.24 (dd, J=14.67, 2.35 Hz, 1H) 8.61-8.74 (m, 1H); MS (ESI, m/z): 528.2 [M+H]$^+$

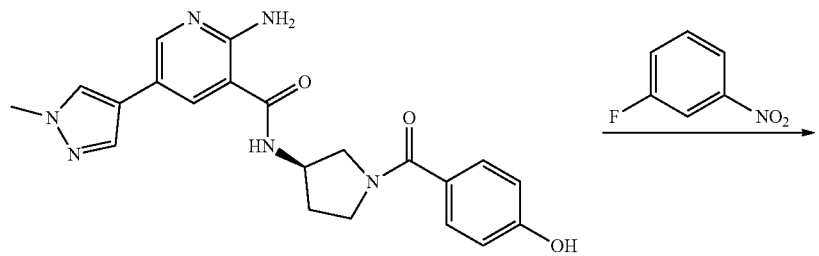

Example 840

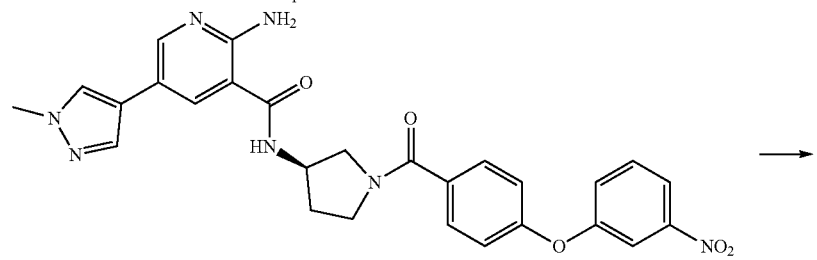

Example 829

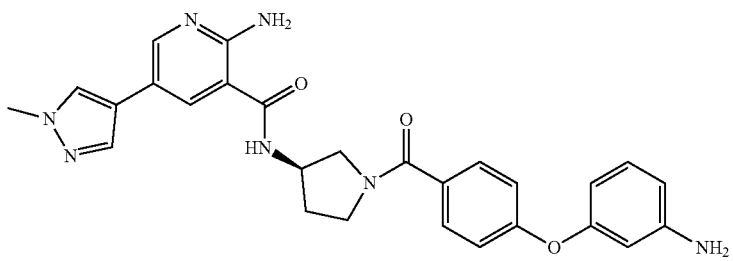

Example 830

Example 830

(R)-2-amino-N-(1-(4-(3-aminophenoxy)benzoyl)pyrrolidin-3-yl)-5-(1-methyl-1H-pyrazol-4-yl)nicotinamide To a stirred solution of Example 829 (22 mg, 0.042 mmol) in AcOH (0.3 mL) at 0° C. was added zinc powder (27 mg, 0.42 mmol). The mixture was stirred at rt for 2 h. The reaction mixture was filtered and filtrate was concentrated in vacuo. After concentration under vacuum, the crude residue was purified by preparative HPLC to afford 15 mg of the title compound. $^1$H NMR (600 MHz, METHANOL-$d_4$) δ ppm 2.08-2.22 (m, 1H) 2.25-2.41 (m, 1H) 3.56 (dd, J=11.15, 5.28 Hz, 0.5H) 3.62-3.69 (m, 1H) 3.70-3.78 (m, 1H) 3.79-3.87 (m, 0.5H) 3.92 (d, J=1.76 Hz, 3H) 3.93-4.03 (m, 1H) 4.50-4.57 (m, 0.5H) 4.63-4.71 (m, 0.5H) 7.05 (dt, J=4.70, 2.35 Hz, 1H) 7.06-7.13 (m, 3H) 7.13-7.17 (m, 1H) 7.51 (td, J=8.22, 5.28 Hz, 1H) 7.59-7.62 (m, 1H) 7.63 (d, J=7.88 Hz, 1H) 7.88 (d, J=12.91 Hz, 1H) 8.04 (d, J=11.15 Hz, 1H) 8.23 (dd, J=12.33, 1.76 Hz, 1H) 8.62-8.75 (m, 1H); MS (ESI, m/z): 498.2 [M+H]$^+$

Example 831

(R)-2-amino-5-(1-methyl-1H-pyrazol-4-yl)-N-(1-(4-(4-nitrophenoxy)benzoyl)pyrrolidin-3-yl)nicotinamide Using 1-fluoro-4-nitrobenzene, the title compound was obtained as described in general method Y. MS (ESI, m/z): 528.2 [M+H]$^+$

Example 832

(R)-2-amino-N-(1-(4-(4-aminophenoxy)benzoyl)pyrrolidin-3-yl)-5-(1-methyl-1H-pyrazol-4-yl)nicotinamide Using Example 831, the title compound was obtained as described in general method Y. $^1$H NMR (600 MHz, METHANOL-$d_4$) δ ppm 2.06-2.23 (m, 1H) 2.26-2.41 (m, 1H) 3.55 (dd, J=11.15, 5.28 Hz, 0.5H) 3.61-3.70 (m, 1H) 3.70-3.78 (m, 1H) 3.78-3.88 (m, 0.5H) 3.93 (s, 3H) 3.94-4.02 (m, 1H) 4.50-4.57 (m, 0.5H) 4.64-4.72 (m, 0.5H) 7.08 (t, J=8.51 Hz, 2H) 7.14-7.24 (m, 2H) 7.42 (d, J=7.60 Hz, 2H) 7.60 (d, J=7.71 Hz, 1H) 7.62 (d, J=8.43 Hz, 1H) 7.89 (d, J=12.91 Hz, 1H) 8.05 (d, J=11.15 Hz, 1H) 8.23 (dd, J=12.33, 2.35 Hz, 1H) 8.62-8.74 (m, 1H); MS (ESI, m/z): 498.2 [M+H]$^+$

Example 833

(R)-2-amino-N-(1-(6-(4-aminophenoxy)-2-naphthoyl)pyrrolidin-3-yl)-5-(1-methyl-1H-pyrazol-4-yl)nicotinamide Using Example 706 and 1-fluoro-4-nitrobenzene, the title compound was obtained as described in general method Y. $^1$H NMR (600 MHz, METHANOL-$d_4$) δ ppm 2.08-2.26 (m, 1H) 2.28-2.47 (m, 1H) 3.59 (br d, J=10.56 Hz, 0.5H) 3.72 (br d, J=11.15 Hz, 1H) 3.80 (br s, 1H) 3.89 (br s, 0.5H) 3.94 (br s, 3H) 3.98-4.11 (m, 1H) 4.56 (br s, 0.5H) 4.69-4.76 (m, 0.5H) 7.17-7.28 (m, 2H) 7.34 (br s, 1H) 7.43 (br s, 2H) 7.64 (br t, J=9.68 Hz, 1H) 7.85 (br s, 1H) 7.87-7.97 (m, 1H) 7.99-8.08 (m, 2H) 8.11 (br d, J=12.91 Hz, 1H) 8.20-8.30 (m, 1H) 8.61-8.78 (m, 1H); MS (ESI, m/z): 548.2 [M+H]$^+$

Example 834

(R)-2-amino-N-(1-(4'-((2-chloro-4-nitrophenyl)(methyl)amino)-[1,1'-biphenyl]-4-carbonyl)pyrrolidin-3-yl)-5-(1-methyl-1H-pyrazol-4-yl)nicotinamide Using Example 803, the title compound was obtained as described in general method Y $^1$H NMR (400 MHz, METHANOL-$d_4$) δ ppm 2.08-2.25 (m, 1H) 2.25-2.46 (m, 1H) 3.36 (d, J=2.74 Hz, 3H) 3.59 (br dd, J=10.96, 5.09 Hz, 0.5H) 3.69 (br dd, J=12.72, 4.89 Hz, 1H) 3.72-3.82 (m, 1H) 3.86 (br dd, J=13.11, 7.24 Hz, 0.5H) 3.94 (d, J=3.13 Hz, 3H) 3.96-4.10 (m, 1H) 4.50-4.61 (m, 0.5H) 4.62-4.73 (m, 0.5H) 7.04-7.14 (m, 2H) 7.19 (dd, J=8.41, 4.50 Hz, 2H) 7.26 (br d, J=8.22 Hz, 2H) 7.59-7.75 (m, 5H) 7.90 (d, J=12.13 Hz, 1H) 8.05 (d, J=10.96 Hz, 1H) 8.23 (dd, J=13.30, 1.96 Hz, 1H) 8.61-8.74 (m, 1H); MS (ESI, m/z): 651.2 [M+H]$^+$

Example 835

(R)-2-amino-N-(1-(4'-((4-amino-2-fluorophenyl)(methyl)amino)-[1,1'-biphenyl]-4-carbonyl)pyrrolidin-3-yl)-5-(1-methyl-1H-pyrazol-4-yl)nicotinamide Using Example 804, the title compound was obtained as described in general method Y $^1$H NMR (400 MHz, METHANOL-$d_4$) δ ppm 2.06-2.24 (m, 1H) 2.25-2.45 (m, 1H) 3.57 (br dd, J=11.15, 4.89 Hz, 0.5H) 3.64-3.72 (m, 1H) 3.72-3.81 (m, 1H) 3.84 (br s, 0.5H) 3.88-3.96 (m, 3H) 3.96-4.05 (m, 1H) 4.48-4.58 (m, 0.5H) 4.63-4.72 (m, 0.5H) 6.82 (br s, 2H) 7.08-7.19 (m, 2H) 7.37 (br d, J=5.09 Hz, 1H) 7.47-7.75 (m, 6H) 7.89 (d, J=12.91 Hz, 1H) 8.04 (d, J=12.13 Hz, 1H) 8.22 (dd, J=14.09, 1.96 Hz, 1H) 8.59-8.73 (m, 1H); MS (ESI, m/z): 605.3 [M+H]$^+$

Example 836

(R)-2-amino-N-(1-(4'-((4-amino-2-methylphenyl)(methyl)amino)-[1,1'-biphenyl]-4-carbonyl)pyrrolidin-3-yl)-5-(1-methyl-1H-pyrazol-4-yl)nicotinamide Using Example 805, the title compound was obtained as described in general method Y $^1$H NMR (400 MHz, METHANOL-$d_4$) δ ppm 1.97-2.15 (m, 1H) 2.19 (s, 3H) 2.23-2.46 (m, 1H) 3.28 (br s, 3H) 3.58 (br dd, J=11.35, 5.09 Hz, 0.5H) 3.63-3.72 (m, 1H) 3.72-3.80 (m, 1H) 3.84 (br dd, J=13.50, 6.85 Hz, 0.5H) 3.92-3.96 (br s, 3H) 3.96-4.10 (m, 1H) 4.51-4.58 (m, 0.5H) 4.64-4.73 (m, 0.5H) 6.62 (br dd, J=8.61, 3.52 Hz, 2H) 7.27-7.43 (m, 3H) 7.45-7.75 (m, 6H) 7.89 (d, J=12.13 Hz, 1H) 8.05 (d, J=11.74 Hz, 1H) 8.23 (br d, J=13.69 Hz, 1H) 8.60-8.74 (n, 1H); MS (ESI, m/z): 601.3 [M+H]$^+$

Example 837

(R)-2-amino-N-(1-(4'-((4-amino-2-chlorophenyl)(methyl)amino)-[1,1'-biphenyl]-4-carbonyl)pyrrolidin-3-yl)-5-(1-methyl-1H-pyrazol-4-yl)nicotinamide Using Example 806, the title compound was obtained as described in general method Y $^1$H NMR (400 MHz, METHANOL-$d_4$) δ ppm 2.06-2.23 (m, 1H) 2.23-2.45 (m, 1H) 3.26 (br s, 3H) 3.57 (br dd, J=11.35, 5.48 Hz, 0.5H) 3.64-3.72 (m, 1H) 3.72-3.80 (m, 1H) 3.80-3.89 (m, 0.5H)

3.93 (d, J=3.52 Hz, 3H) 3.95-4.03 (m, 1H) 4.48-4.58 (m, 0.5H) 4.64-4.72 (m, 0.5H) 6.58-6.71 (m, 2H) 7.14 (br d, J=7.83 Hz, 1H) 7.24-7.39 (m, 2H) 7.48 (brt, J=7.43 Hz, 2H) 7.54-7.73 (m, 4H) 7.89 (br d, J=13.30 Hz, 1H) 8.04 (br d, J=12.91 Hz, 1H) 8.22 (br d, J=14.87 Hz, 1H) 8.60-8.74 (m, 1H); MS (ESI, m/z): 621.2 [M+H]+

Example 838

(R)-2-amino-N-(1-(4-((3-aminobenzyl)oxy)benzoyl) pyrrolidin-3-yl)-5-(1-methyl-1H-pyrazol-4-yl)nicotinamide Using Example 770, the title compound was obtained as described in general method Y $^1$H NMR (600 MHz, METHANOL-$d_4$) δ ppm 2.05-2.21 (m, 1H) 2.25-2.41 (m, 1H) 3.55 (br dd, J=11.15, 5.28 Hz, 0.5H) 3.62-3.69 (m, 1H) 3.69-3.77 (m, 1H) 3.79-3.83 (m, 0.5H) 3.88-4.00 (m, 1H) 3.93 (s, 3H) 4.49-4.54 (m, 0.5H) 4.64-4.71 (m, 0.5H) 5.22 (d, J=5.87 Hz, 2H) 7.07 (br t, J=8.51 Hz, 2H) 7.35 (br d, J=4.11 Hz, 1H) 7.51 (br s, 1H) 7.52-7.61 (m, 4H) 7.89 (d, J=14.09 Hz, 1H) 8.05 (d, J=12.33 Hz, 1H) 8.23 (dd, J=13.79, 2.05 Hz, 1H) 8.61-8.73 (m, 1H); MS (ESI, m/z): 512.2 [M+H]+

General Method Z

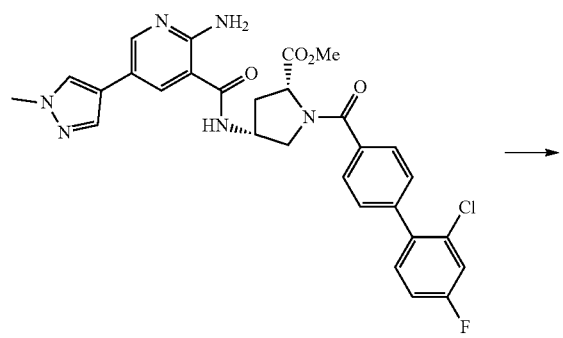

Example 689

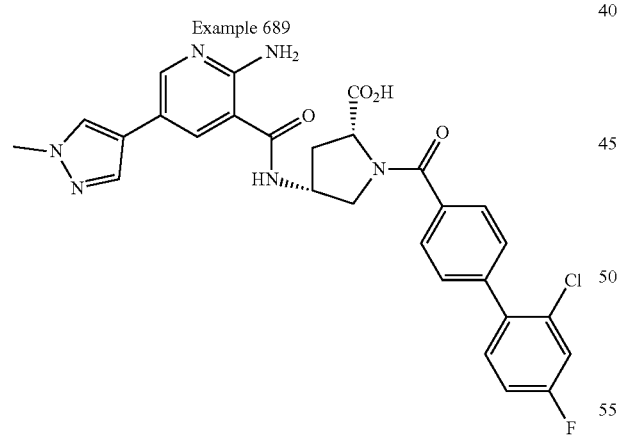

Example 839

Example 839

(2R,4R)-4-(2-amino-5-(1-methyl-1H-pyrazol-4-yl) nicotinamido)-1-(2'-chloro-4'-fluoro-[1,1'-biphenyl]-4-carbonyl)pyrrolidine-2-carboxylic acid A mixture of Example 689 (30 mg, 0.05 mmol) in 0.5 mL of 2N NaOH/tetrahydrofuran/methanol (2/2/1) was stirred at rt for 6 hrs. The mixture was neutralized with 2N HCl and partitioned between ethyl acetate and water. The organic layer was separated and washed with water, brine dried over MgSO$_4$ and concentrated in vacuo. After concentration under vacuum, the crude residue was purified by preparative HPLC to afford 20 mg of the title compound. $^1$H NMR (600 MHz, METHANOL-$d_4$) δ ppm 2.26 (dt, J=13.06, 6.68 Hz, 1H) 2.80 (ddd, J=13.06, 8.66, 6.46 Hz, 1H) 3.73 (dd, J=10.86, 6.16 Hz, 1H) 3.94 (s, 3H) 4.04 (dd, J=10.86, 6.16 Hz, 1H) 4.60 (t, J=6.46 Hz, 1H) 4.75 (dd, J=8.80, 6.46 Hz, 1H) 7.17 (td, J=8.51, 2.35 Hz, 1H) 7.35 (dd, J=8.80, 2.93 Hz, 1H) 7.41 (dd, J=8.51, 6.16 Hz, 1H) 7.52 (d, J=8.80 Hz, 2H) 7.70 (d, J=8.22 Hz, 2H) 7.91 (s, 1H) 8.05 (s, 1H) 8.21-8.28 (m, 1H) 8.51-8.65 (m, 1H); MS (ESI, m/z): 563.1 [M+H]+

Example 843

(R)-6-(3-(2-amino-5-(1-methyl-1H-pyrazol-4-yl) nicotinamido)pyrrolidine-1-carbonyl)-2-naphthoic acid Using Example 842, the title compound was obtained as described in general method Z. MS (ESI, m/z): 485.2 [M+H]+

General Method AA

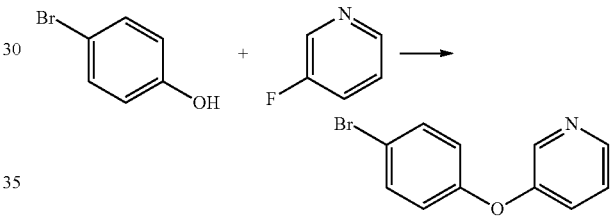

4-Bromophenol (0.5 mmol) and K$_2$CO$_3$ (1.5 mmol) were added to 3-fluoropyridine (0.5 mmol) in N,N-dimethylformamide (2 mL). The mixture was stirred at 100° C., and after the end of the process the reaction mixture was cooled to room temperature. The mixture was extracted with ethyl acetate, washed with brine, dried over MgSO$_4$, and concentrated in vacuo. The crude product was purified by flash column chromatography (ethyl acetate/hexanes) to yield product.

General Method AB

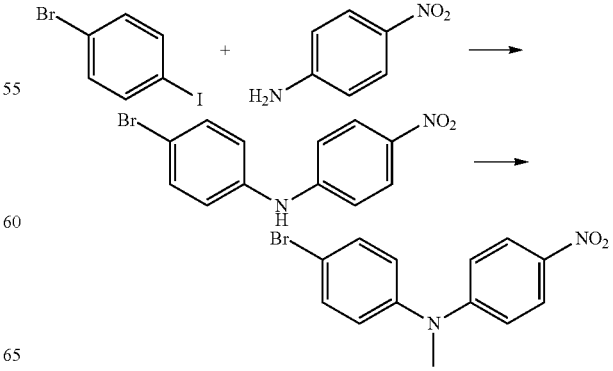

A mixture of 1-bromo-4-iodobenzene (0.5 mmol), 4-nitroaniline (0.5 mmol), $Cs_2CO_3$ (1.5 mmol), $Pd(OAc)_2$ (3 mol %) and 2,2'-bis(diphenylphosphino)-1,1'-binaphthyl (4.5 mol %) in toluene was heated to reflux for 6 h. After the completion of the reaction, the solvent was removed under reduced pressure, and the residue was extracted with ethyl acetate/water. The collected organic layer was dried over $MgSO_4$ overnight and then filtered to remove $MgSO_4$. After removing the solvent from the filtrate, the residue was purified by silica gel column chromatography (ethyl acetate/hexanes). MeI (1 mmol) was added to 4-bromo-N-(4-nitrophenyl)aniline (0.5 mmol) and $K_2CO_3$ (1.5 mmol) in N,N-dimethylformamide (2 mL). The mixture was stirred at 100° C., and after the end of the process the reaction mixture was cooled to room temperature. The mixture was extracted with ethyl acetate, washed with brine, dried over $MgSO_4$, and concentrated in vacuo. The crude product was purified by flash column chromatography (ethyl acetate/hexanes) to yield product.

General Method AC

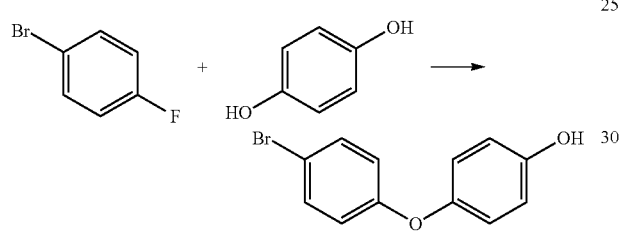

To a mixture of hydroquinone (2 mmol), KOtBu (2 mmol) and 18-crown-6 ether (2 mmol) in dimethyl sulfoxide (2 mL) was added 1-bromo-4-fluorobenzene (0.5 mmol). The mixture was stirred at 100° C. for 24 hr and then water was added. The mixture was extracted with ethyl acetate, washed with brine, dried over $MgSO_4$, and concentrated in vacuo. The crude product was purified by flash column chromatography (ethyl acetate/hexanes) to yield product.

General Method AD

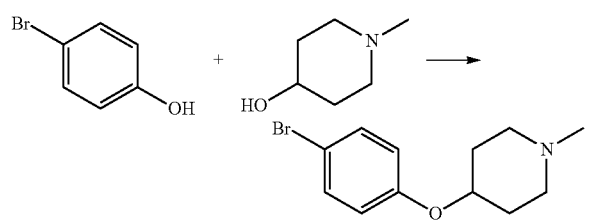

A mixture of 4-bromophenol (0.5 mmol), diisopropyl azodicarboxylate (0.65 mmol) and triphenylphosphine (0.65 mmol) in tetrahydrofuran (2.5 mL) was added 1-methylpiperidin-4-ol (0.6 mmol). The mixture was stirred at rt for 4 hr and then water was added. The mixture was extracted with ethyl acetate, washed with brine, dried over $MgSO_4$, and concentrated in vacuo. The crude product was purified by flash column chromatography (ethyl acetate/hexanes) to yield product.

General Method AE

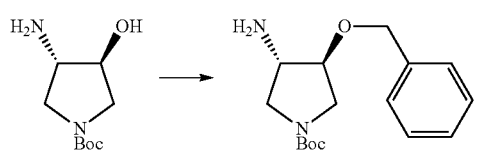 [SMILES: CC(C)(C)OC(=O)N1C[C@H](N)[C@@H](O)C1 ; CC(C)(C)OC(=O)N1C[C@H](OCc2ccccc2)[C@@H](N)C1]

To a mixture of tert-butyl (3S,4S)-3-amino-4-hydroxy-pyrrolidine-1-carboxylate (1 mol) in tetrahydrofuran (30 mL) was added KOtBu (1M in tetrahydrofuran, 4 mol). The mixture was stirred for 30 min at 50° C. To a stirred mixture was added benzyl bromide (1.1 mol) and stirred for 2 hrs at 50° C. The mixture was extracted with ethyl acetate, washed with brine, dried over $MgSO_4$, and concentrated in vacuo. The crude product was used for the next step without further purification.

General Method AF

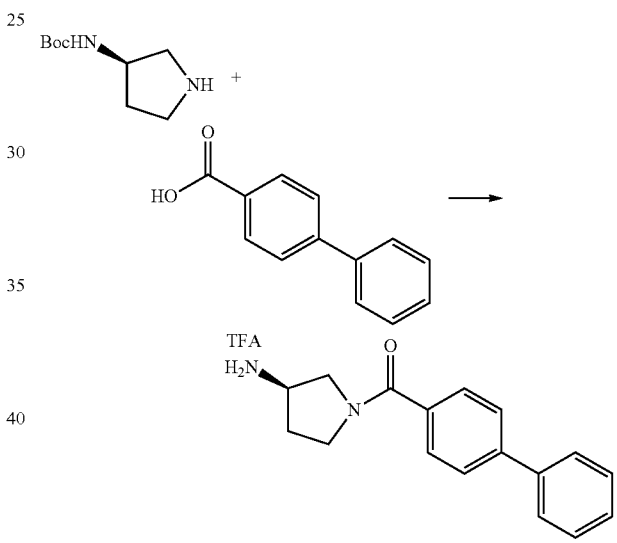

To a mixture of [1,1'-biphenyl]-4-carboxylic acid (1 mol), 1-[bis(dimethylamino)methylene]-1H-1,2,3-triazolo[4,5-b]pyridinium 3-oxid hexafluorophosphate (1.1 mol) and triethylamine (3 mol) in N,N-dimethylformamide (30 mL) was added tert-butyl (R)-pyrrolidin-3-ylcarbamate (1 mol). The mixture was stirred for 2 hrs at room temperature. The crude product was purified through silicagel column chromatography (5% methanol/$CH_2Cl_2$) to give an off-white solid. To a mixture of product in dichloromethane (12 mL) was added trifluoroacetic acid (3 mL) and stirred at room temperature for overnight. After removing volatiles, the crude product was used for the next step without further purification.

The following compounds were obtained by methods disclosed herein and/or by methods known to one skilled in the art.

Example 849

(R)-2-amino-N-(1-(2,4'-dimethyl-[1,1'-biphenyl]-4-carbonyl)pyrrolidin-3-yl)-5-(1-methyl-1H-pyrazol-4-yl)nicotinamide

Example 850

(R)-2-amino-N-(1-(4'-(ethylthio)-2-methyl-[1,1'-biphenyl]-4-carbonyl)pyrrolidin-3-yl)-5-(1-methyl-1H-pyrazol-4-yl)nicotinamide

Example 851

(R)-2-amino-5-(1-methyl-1H-pyrazol-4-yl)-N-(1-(3-methyl-4-(4-methylthiophen-2-yl)benzoyl)pyrrolidin-3-yl)nicotinamide

Example 852

(R)—N-(1-(4-(1H-indol-6-yl)-3-methylbenzoyl)pyrrolidin-3-yl)-2-amino-5-(1-methyl-1H-pyrazol-4-yl)nicotinamide

Example 853

(R)—N-(1-(4-(1H-indol-5-yl)-3-methylbenzoyl)pyrrolidin-3-yl)-2-amino-5-(1-methyl-1H-pyrazol-4-yl)nicotinamide

Example 854

(R)-2-amino-5-(1-methyl-1H-pyrazol-4-yl)-N-(1-(3-methyl-4-(1-methyl-1H-indol-5-yl)benzoyl)pyrrolidin-3-yl)nicotinamide

Example 855

(R)-2-amino-N-(1-(2',4'-difluoro-2-methyl-[1,1'-biphenyl]-4-carbonyl)pyrrolidin-3-yl)-5-(1-methyl-1H-pyrazol-4-yl)nicotinamide

Example 856

(R)-2-amino-N-(1-(2',3'-difluoro-2-methyl-[1,1'-biphenyl]-4-carbonyl)pyrrolidin-3-yl)-5-(1-methyl-1H-pyrazol-4-yl)nicotinamide

Example 857

(R)-2-amino-N-(1-(2'-chloro-3'-fluoro-2-methyl-[1,1'-biphenyl]-4-carbonyl)pyrrolidin-3-yl)-5-(1-methyl-1H-pyrazol-4-yl)nicotinamide

Example 858

(R)-2-amino-N-(1-(2',3'-dichloro-2-methyl-[1,1'-biphenyl]-4-carbonyl)pyrrolidin-3-yl)-5-(1-methyl-1H-pyrazol-4-yl)nicotinamide

Example 859

(R)-2-amino-5-(1-methyl-1H-pyrazol-4-yl)-N-(1-(2,3',5'-trimethyl-[1,1'-biphenyl]-4-carbonyl)pyrrolidin-3-yl)nicotinamide

Example 860

(R)-2-amino-5-(1-methyl-1H-pyrazol-4-yl)-N-(1-(2,3',4'-trimethyl-[1,1'-biphenyl]-4-carbonyl)pyrrolidin-3-yl)nicotinamide

Example 861

(R)-2-amino-N-(1-(2,3'-dimethyl-[1,1'-biphenyl]-4-carbonyl)pyrrolidin-3-yl)-5-(1-methyl-1H-pyrazol-4-yl)nicotinamide

Determination of Biological Activity

Biochemical Assay

Abbreviations: ATP for adenosine triphosphate; EDTA for ethylenediaminetetraacetic acid; DMEM for Dulbecco's Modified Eagle's Medium; FBS for fetal bovine serum; $GI_{50}$ for half-maximal growth inhibitory concentration; GT for glutamate-tyrosine; HEPES for (4-(2-hydroxyethyl)-1-piperazineethanesulfonic acid); HTRF for homogeneous time-resolved fluorescence; $IC_{50}$ for half maximal inhibitory concentration; RPMI for Roswell Park Memorial Institute; and SAR for structure-activity relationship.

TR-FRET Kinase Activity Biochemical Assay

For the SAR (structure-activity relationship) and compound screening, LanthaScreen™ TR-FRET (Time-Resolved fluorescence energy transfer) assay was employed using the phospho-tyrosine specific Terbium (Tb)-labeled antibody with a fluorescein labeled poly-GT (glutamate-tyrosine) as a substrate. Upon excitation at 340 nm by UV, the energy from Tb donor of the antibody is transferred to the fluorescein of the phosphorylated poly GT substrate, and fluorescein emits light at 520 nm. The ratio between the intensity of primary emission at 495 nm and that of secondary emission at 520 nm was used to quantify the level of kinase activity. The recombinant proteins of human c-MER and AXL catalytic domains, Fluorescein-labeled poly-GT substrate, Tb-labeled anti-phosphorylated tyrosine antibodies, the kinase assay buffer, and 0.5M EDTA solution were purchased (Life technologies, USA). The TR-FRET assays were carried out in the white low volume 384-well plate (Corning, USA). To measure the compound mediated inhibition of kinase activity, the recombinant kinases were pre-incubated with test compounds for 20 minutes prior to the addition of 200 nM fluorescein labeled poly-GT substrates and 10 uM ATP, and then the reaction was carried out for 1 hour at room temperature. 10 mM EDTA was added to terminate the enzyme reaction, and the level of phosphorylation of poly-GT substrate was determined following 30 min incubation with 2 nM Tb-labeled antibody. The fluorescence intensity was measured with Envision™ plate reader (PerkinElmer, USA).

TABLE 2

TR-FRET Kinase Activity Biochemical Assay

| Example | $IC_{50}{}^a$ |
|---------|---------------|
| 1 | ++ |
| 9 | +++ |
| 10 | +++ |
| 11 | +++ |
| 13 | + |
| 15 | +++ |
| 20 | + |
| 24 | ++ |
| 35 | ++ |
| 37 | +++ |
| 39 | +++ |
| 49 | ++ |
| 70 | + |
| 79 | + |
| 82 | +++ |
| 95 | ++ |

TABLE 2-continued

TR-FRET Kinase Activity Biochemical Assay

| Example | IC$_{50}$$^a$ |
|---|---|
| 108 | + |
| 113 | ++ |
| 117 | +++ |
| 118 | ++ |
| 120 | + |
| 121 | ++ |
| 123 | + |
| 126 | + |
| 127 | + |
| 128 | ++ |
| 134 | + |
| 138 | + |
| 148 | +++ |
| 149 | ++ |
| 167 | ++ |
| 215 | + |
| 217 | ++ |
| 221 | + |
| 222 | ++ |
| 223 | ++ |
| 234 | ++ |
| 235 | ++ |
| 236 | ++ |
| 238 | + |
| 240 | ++ |
| 247 | ++ |
| 248 | ++ |
| 249 | ++ |
| 252 | + |
| 253 | + |
| 263 | +++ |
| 266 | +++ |
| 269 | +++ |
| 272 | ++ |
| 273 | + |
| 276 | ++ |
| 277 | ++ |
| 283 | ++ |
| 285 | ++ |
| 286 | ++ |
| 291 | +++ |
| 292 | ++++ |
| 294 | +++ |
| 295 | +++ |
| 296 | +++ |
| 297 | ++ |
| 300 | ++ |
| 301 | ++ |
| 302 | +++ |
| 303 | +++ |
| 304 | ++ |
| 305 | ++ |
| 309 | +++ |
| 317 | +++ |
| 326 | ++ |
| 330 | +++ |
| 331 | +++ |
| 332 | +++ |
| 333 | +++ |
| 334 | ++ |
| 335 | ++ |
| 336 | ++ |
| 338 | +++ |
| 339 | ++ |
| 340 | ++ |
| 341 | +++ |
| 344 | + |
| 346 | + |
| 347 | + |
| 348 | + |
| 355 | +++ |
| 356 | ++ |
| 364 | +++ |
| 369 | ++++ |
| 374 | + |
| 379 | +++ |

TABLE 2-continued

TR-FRET Kinase Activity Biochemical Assay

| Example | IC$_{50}$$^a$ |
|---|---|
| 382 | +++ |
| 398 | ++ |
| 409 | + |
| 411 | ++ |
| 413 | + |
| 417 | ++ |
| 421 | + |
| 423 | + |
| 431 | ++ |
| 453 | + |
| 457 | + |
| 468 | + |
| 475 | + |
| 477 | + |
| 486 | ++ |
| 487 | ++ |
| 489 | ++ |
| 494 | +++ |
| 495 | + |
| 496 | + |
| 498 | + |
| 499 | ++ |
| 500 | + |
| 501 | + |
| 502 | + |
| 503 | + |
| 511 | ++ |
| 513 | ++ |
| 514 | + |
| 516 | + |
| 518 | ++ |
| 520 | ++ |
| 521 | ++ |
| 524 | +++ |
| 529 | +++ |
| 530 | +++ |
| 531 | +++ |
| 532 | ++ |
| 533 | +++ |
| 536 | +++ |
| 537 | +++ |
| 539 | ++ |
| 541 | +++ |
| 542 | ++ |
| 549 | ++ |
| 550 | +++ |
| 551 | +++ |
| 555 | ++ |
| 557 | +++ |
| 561 | +++ |
| 564 | ++++ |
| 569 | +++ |
| 570 | ++++ |
| 571 | +++ |
| 572 | ++++ |
| 579 | +++ |
| 583 | ++++ |
| 594 | ++++ |
| 595 | +++ |
| 615 | +++ |
| 616 | ++ |
| 617 | +++ |
| 620 | ++ |
| 626 | + |
| 633 | ++ |
| 660 | ++ |
| 665 | ++ |
| 666 | ++ |
| 670 | + |
| 671 | +++ |
| 672 | + |
| 677 | +++ |
| 678 | ++ |
| 681 | + |
| 687 | + |
| 689 | + |

TABLE 2-continued

TR-FRET Kinase Activity Biochemical Assay

| Example | IC$_{50}$$^a$ |
|---|---|
| 690 | + |
| 717 | + |
| 732 | + |
| 742 | ++ |
| 743 | + |
| 745 | +++ |
| 780 | ++++ |
| 782 | +++ |
| 790 | +++ |
| 791 | ++ |
| 792 | ++++ |
| 793 | ++ |
| 801 | ++ |
| 815 | +++ |
| 822 | ++++ |
| 848 | ++ |

$^a$++++ for IC$_{50}$ < 10; +++ for 10 ≤ IC$_{50}$ < 100; ++ for 100 ≤ IC$_{50}$ < 1000; + for IC$_{50}$ ≥ 1000 nM.

HTRF Kinase Activity Biochemical Assay

For the SAR (structure-activity relationship) and compound screening, HTRF (Homogeneous Time Resolved Fluorescence) kinase activity assay was employed for all MER, AXL and TYRO3 kinases using Cisbio HTRF® KinEASE™-TK kit (Cisbio, USA). The kit includes biotin-labeled TK substrate, streptavidin-XL665, Eu3+-cryptate-labeled TK antibody and HTRF® Detection buffer. There are two main steps in the kinase assay: kinase reaction and detection of phosphorylated substrate. The reaction was carried out in white low volume 384-well plate (Corning, USA) with 25 nL compound in dimethyl sulfoxide in each well. To measure the compound mediated inhibition of kinase activity, 2.5 uL the recombinant kinases were pre-incubated with test compounds for 30 minutes in the kinase reaction buffer (20 mM HEPES pH7.4, 2 mM MnCl$_2$, 10 mM MgCl$_2$, 100 uM Na$_3$VO$_4$, 0.0075% Triton X 100, 0.005% BSA and 1 mM DTT) prior to the addition of 2.5 uL of 1 uM biotin-labeled TK substrates and 10 uM ATP. Then the reaction was stopped after 1 hour incubation at room temperature by adding 5 uL of HTRF® Detection buffer which also contains 0.375 nM Eu3+-cryptate-labeled TK antibody and 0.062 uM streptavidin-XL665 (SA-XL665) to allow for detection of the phosphorylated peptide product. After 1h incubation at room temperature, the fluorescence intensity was measured with Envision™ plate reader (PerkinElmer, USA). Upon excitation at 340 nm by UV, the energy from Eu3+ donor of the antibody is transferred to the FRET acceptor XL665, and XL655 emits light at 665 nm. The level of kinase activity was quantified by the HTRF ratio that calculated from the intensity of emission at 665 nm and emission at 620 nm (fluorescence intensity @ 665 nm/fluorescence intensity @ 620 nm×10,000). The recombinant protein of human MER (528-end) was purchased from Carnabio, Japan. The recombinant human AXL (473-end) and TYRO3 (455-end) were purchased from SignalChem, Canada.

TABLE 3

HTRF Kinase Activity Biochemical Assay

| Example | IC$_{50}$$^a$ |
|---|---|
| 2 | + |
| 3 | + |
| 4 | + |
| 5 | + |
| 6 | + |
| 7 | + |
| 8 | + |
| 12 | + |
| 14 | + |
| 16 | + |
| 17 | +++ |
| 18 | + |
| 19 | + |
| 21 | + |
| 22 | + |
| 23 | ++ |
| 25 | + |
| 26 | + |
| 27 | + |
| 28 | + |
| 29 | + |
| 30 | ++ |
| 31 | + |
| 32 | + |
| 34 | ++ |
| 38 | +++ |
| 40 | + |
| 41 | + |
| 42 | + |
| 43 | + |
| 44 | + |
| 45 | + |
| 46 | + |
| 47 | + |
| 48 | + |
| 50 | ++ |
| 51 | ++ |
| 52 | + |
| 54 | + |
| 55 | + |
| 56 | ++ |
| 57 | + |
| 58 | + |
| 59 | + |
| 60 | + |
| 61 | + |
| 62 | + |
| 63 | + |
| 64 | + |
| 65 | + |
| 66 | + |
| 67 | ++ |
| 68 | + |
| 69 | ++ |
| 71 | + |
| 72 | + |
| 73 | + |
| 74 | + |
| 75 | + |
| 76 | + |
| 77 | + |
| 78 | + |
| 80 | + |
| 81 | ++ |
| 83 | ++ |
| 84 | + |
| 85 | + |
| 86 | + |
| 87 | + |
| 88 | + |
| 89 | + |
| 90 | + |
| 91 | + |
| 92 | + |
| 93 | ++ |
| 94 | + |
| 96 | ++ |
| 97 | + |
| 98 | + |

TABLE 3-continued

HTRF Kinase Activity Biochemical Assay

| Example | IC$_{50}$$^a$ |
|---|---|
| 99 | + |
| 100 | + |
| 101 | + |
| 102 | ++ |
| 103 | ++ |
| 104 | ++ |
| 105 | + |
| 106 | + |
| 107 | + |
| 109 | + |
| 110 | ++ |
| 111 | + |
| 112 | ++ |
| 114 | ++ |
| 115 | ++ |
| 116 | ++ |
| 119 | + |
| 125 | + |
| 129 | + |
| 130 | + |
| 133 | + |
| 135 | + |
| 136 | + |
| 137 | + |
| 139 | + |
| 146 | +++ |
| 147 | +++ |
| 150 | + |
| 152 | ++ |
| 153 | ++ |
| 154 | ++ |
| 156 | + |
| 157 | + |
| 158 | ++ |
| 159 | + |
| 160 | + |
| 162 | + |
| 163 | + |
| 166 | + |
| 168 | + |
| 169 | + |
| 170 | + |
| 205 | + |
| 207 | + |
| 208 | ++ |
| 209 | + |
| 210 | ++ |
| 211 | + |
| 212 | + |
| 213 | + |
| 214 | + |
| 216 | + |
| 218 | + |
| 219 | + |
| 220 | + |
| 224 | + |
| 225 | ++ |
| 226 | + |
| 227 | + |
| 228 | ++ |
| 229 | + |
| 230 | + |
| 231 | + |
| 232 | ++ |
| 233 | + |
| 237 | ++ |
| 243 | ++ |
| 244 | ++ |
| 245 | + |
| 246 | + |
| 250 | ++ |
| 254 | +++ |
| 255 | ++ |
| 256 | ++ |
| 257 | ++ |
| 258 | ++ |
| 259 | ++ |
| 260 | + |
| 261 | ++ |
| 262 | ++ |
| 264 | ++ |
| 265 | +++ |
| 267 | + |
| 268 | +++ |
| 270 | + |
| 271 | ++ |
| 274 | +++ |
| 275 | ++ |
| 278 | + |
| 279 | ++ |
| 280 | ++ |
| 284 | + |
| 287 | + |
| 288 | + |
| 289 | +++ |
| 290 | + |
| 293 | ++ |
| 298 | ++ |
| 299 | ++ |
| 306 | ++ |
| 307 | ++ |
| 308 | ++ |
| 310 | ++ |
| 311 | ++ |
| 312 | ++ |
| 313 | ++ |
| 314 | ++ |
| 315 | ++ |
| 316 | ++ |
| 318 | ++ |
| 319 | ++ |
| 320 | ++ |
| 321 | ++ |
| 322 | ++ |
| 323 | ++ |
| 324 | ++ |
| 325 | + |
| 327 | ++ |
| 328 | ++ |
| 329 | + |
| 337 | + |
| 342 | + |
| 343 | +++ |
| 345 | + |
| 349 | ++ |
| 350 | ++ |
| 351 | + |
| 352 | + |
| 353 | ++ |
| 354 | +++ |
| 357 | + |
| 358 | ++ |
| 359 | +++ |
| 360 | +++ |
| 361 | +++ |
| 362 | ++ |
| 363 | ++ |
| 365 | +++ |
| 366 | +++ |
| 367 | +++ |
| 368 | ++ |
| 370 | +++ |
| 371 | + |
| 372 | + |
| 373 | +++ |
| 375 | ++ |
| 376 | ++ |
| 377 | ++ |
| 378 | + |
| 380 | ++ |
| 381 | ++ |
| 383 | + |

TABLE 3-continued

HTRF Kinase Activity Biochemical Assay

| Example | IC$_{50}$$^a$ |
|---|---|
| 384 | +++ |
| 385 | +++ |
| 386 | ++ |
| 387 | ++ |
| 388 | ++ |
| 389 | ++ |
| 390 | + |
| 391 | + |
| 392 | ++ |
| 394 | ++ |
| 395 | ++ |
| 396 | + |
| 397 | ++ |
| 399 | ++ |
| 400 | + |
| 401 | + |
| 402 | + |
| 403 | + |
| 404 | + |
| 405 | ++ |
| 406 | ++ |
| 407 | + |
| 408 | + |
| 410 | ++ |
| 412 | + |
| 414 | + |
| 415 | + |
| 416 | + |
| 418 | + |
| 419 | + |
| 420 | + |
| 422 | + |
| 424 | + |
| 425 | + |
| 426 | + |
| 427 | ++ |
| 428 | + |
| 429 | ++ |
| 430 | + |
| 432 | + |
| 436 | + |
| 438 | + |
| 443 | + |
| 444 | + |
| 445 | + |
| 446 | + |
| 447 | + |
| 448 | + |
| 449 | + |
| 450 | + |
| 451 | + |
| 452 | + |
| 454 | + |
| 455 | + |
| 456 | + |
| 458 | + |
| 459 | + |
| 460 | + |
| 461 | + |
| 462 | + |
| 463 | + |
| 464 | + |
| 465 | + |
| 466 | ++ |
| 467 | + |
| 469 | + |
| 470 | + |
| 472 | + |
| 473 | + |
| 474 | + |
| 476 | + |
| 478 | + |
| 479 | + |
| 480 | + |
| 481 | + |
| 482 | + |

TABLE 3-continued

HTRF Kinase Activity Biochemical Assay

| Example | IC$_{50}$$^a$ |
|---|---|
| 483 | + |
| 484 | + |
| 485 | ++ |
| 488 | ++ |
| 490 | + |
| 491 | ++ |
| 492 | + |
| 493 | + |
| 497 | + |
| 504 | + |
| 505 | ++ |
| 506 | ++ |
| 507 | ++ |
| 508 | + |
| 509 | + |
| 510 | + |
| 512 | + |
| 515 | + |
| 517 | +++ |
| 519 | + |
| 522 | ++ |
| 523 | +++ |
| 525 | +++ |
| 526 | +++ |
| 527 | ++ |
| 528 | + |
| 534 | +++ |
| 535 | ++ |
| 538 | ++ |
| 540 | + |
| 543 | ++ |
| 544 | ++ |
| 545 | + |
| 546 | + |
| 547 | ++ |
| 548 | + |
| 552 | ++ |
| 553 | + |
| 554 | ++ |
| 556 | +++ |
| 558 | +++ |
| 559 | +++ |
| 560 | ++ |
| 562 | +++ |
| 563 | +++ |
| 565 | +++ |
| 567 | +++ |
| 568 | ++ |
| 573 | +++ |
| 574 | + |
| 575 | +++ |
| 576 | ++ |
| 577 | +++ |
| 580 | ++ |
| 581 | ++++ |
| 582 | ++ |
| 584 | +++ |
| 585 | ++++ |
| 586 | +++ |
| 587 | ++ |
| 588 | +++ |
| 589 | +++ |
| 590 | +++ |
| 591 | ++++ |
| 592 | + |
| 593 | +++ |
| 623 | + |
| 625 | + |
| 629 | + |
| 631 | + |
| 632 | ++ |
| 634 | ++++ |
| 635 | +++ |
| 636 | +++ |
| 640 | + |
| 641 | + |

TABLE 3-continued

HTRF Kinase Activity Biochemical Assay

| Example | IC$_{50}$$^a$ |
|---|---|
| 643 | ++ |
| 644 | +++ |
| 656 | +++ |
| 657 | +++ |
| 658 | ++ |
| 659 | ++ |
| 661 | +++ |
| 662 | + |
| 663 | +++ |
| 664 | ++ |
| 667 | +++ |
| 668 | + |
| 669 | + |
| 673 | +++ |
| 674 | + |
| 675 | + |
| 676 | ++ |
| 679 | + |
| 680 | ++ |
| 682 | + |
| 683 | ++ |
| 684 | + |
| 685 | + |
| 686 | + |
| 688 | + |
| 691 | + |
| 692 | +++ |
| 693 | + |
| 694 | + |
| 695 | + |
| 696 | + |
| 697 | + |
| 698 | ++ |
| 699 | + |
| 700 | + |
| 701 | + |
| 702 | + |
| 703 | + |
| 704 | + |
| 705 | + |
| 706 | ++ |
| 707 | + |
| 708 | ++ |
| 709 | ++ |
| 710 | + |
| 711 | + |
| 712 | +++ |
| 713 | ++ |
| 714 | +++ |
| 716 | + |
| 718 | +++ |
| 720 | ++ |
| 721 | +++ |
| 722 | + |
| 726 | ++ |
| 727 | +++ |
| 728 | ++ |
| 729 | + |
| 730 | ++ |
| 731 | ++ |
| 733 | + |
| 734 | + |
| 735 | + |
| 736 | + |
| 737 | + |
| 738 | + |
| 739 | + |
| 740 | + |
| 741 | + |
| 744 | ++ |
| 747 | ++ |
| 748 | +++ |
| 749 | + |
| 750 | +++ |
| 753 | + |
| 754 | + |
| 755 | + |
| 756 | ++ |
| 757 | ++ |
| 762 | ++ |
| 764 | ++ |
| 765 | ++ |
| 766 | ++ |
| 767 | ++ |
| 769 | ++ |
| 770 | ++ |
| 771 | ++ |
| 774 | +++ |
| 775 | ++ |
| 776 | + |
| 777 | + |
| 778 | ++ |
| 779 | ++ |
| 781 | +++ |
| 783 | ++ |
| 786 | + |
| 787 | +++ |
| 788 | +++ |
| 794 | +++ |
| 795 | +++ |
| 798 | +++ |
| 800 | +++ |
| 802 | ++ |
| 803 | ++ |
| 804 | ++ |
| 806 | + |
| 808 | +++ |
| 809 | +++ |
| 811 | +++ |
| 812 | +++ |
| 813 | ++ |
| 814 | ++ |
| 816 | ++ |
| 817 | ++ |
| 818 | +++ |
| 819 | +++ |
| 820 | +++ |
| 823 | +++ |
| 824 | ++ |
| 825 | ++ |
| 826 | + |
| 827 | + |
| 828 | + |
| 829 | + |
| 830 | ++ |
| 831 | ++ |
| 832 | + |
| 834 | ++ |
| 835 | ++ |
| 836 | ++ |
| 837 | ++ |
| 838 | ++ |
| 839 | + |

$^a$++++ for IC$_{50}$ < 10; +++ for 10 ≤ IC$_{50}$ < 100; ++ for 100 ≤ IC$_{50}$ < 1000; + for IC$_{50}$ ≥ 1000 nM.

In Cell MER Kinase Assay Using BaF3 Cellular System

CD8-MerTK is a chimeric fusion protein consisting of the extracellular and transmembrane domains of the human CD8u (amino acids 1 to 209) at its N-terminus and the kinase domain and intracellular parts of MerTK (amino acids 521-994) at its C-terminus. To establish an in cell kinase assay for MerTK kinase, the IL-3 dependent Ba/F3 cells of murine lymphoid origin was transfected with CD8-MerTK. The resulting Ba/F3-CDM line was then validated that Ba/F3-CDM cell proliferation is completely dependent on the activity of MerTK kinase activity when growing in the absence of IL-3. For a routine cellular assay, Ba/F3-CDM cells were seeded at 2,000 cells per well in 384-well cell culture plate containing DMEM/10% FBS culture media and incubated for 24 hours before addition of compounds pre-diluted in culture media. Following compound treatment, cells were further incubated for 48 hours and the proliferation was measured. To discriminate a Ba/F3 growth inhibition by a specific inhibition of MerTK kinase following compound treatment vs growth inhibition due to a non-specific unintended cytotoxicity of compounds, we routinely carried out control sets of Ba/F3 cells in parallel that grown in IL3-supplemented growth media. In the presence of IL-3, the proliferation of Ba/F3 is no longer dependent on the MerTK activity. Cell growth and proliferation was measured with Celltiter-Glo™ system (Promega, USA) according to the manufacturer's instruction. The half-maximal growth inhibitory concentration ($GI_{50}$) value was calculated with Prism6.0 software (GraphPad, USA).

TABLE 4

| In Cell MER Kinase Assay Data | |
|---|---|
| Example | $IC_{50}{}^a$ |
| 1 | + |
| 2 | + |
| 4 | + |
| 9 | + |
| 10 | + |
| 11 | + |
| 14 | + |
| 15 | + |
| 16 | + |
| 17 | + |
| 18 | + |
| 19 | + |
| 21 | + |
| 23 | + |
| 34 | + |
| 35 | + |
| 37 | ++ |
| 38 | + |
| 39 | + |
| 44 | + |
| 45 | + |
| 46 | + |
| 49 | + |
| 50 | + |
| 54 | + |
| 56 | + |
| 67 | + |
| 69 | + |
| 70 | + |
| 81 | + |
| 82 | + |
| 83 | + |
| 84 | + |
| 93 | + |
| 96 | + |
| 102 | +++ |
| 104 | + |
| 110 | ++ |
| 111 | + |
| 112 | + |
| 114 | + |
| 115 | + |
| 116 | + |
| 117 | + |
| 118 | + |
| 119 | + |
| 121 | + |
| 125 | + |
| 126 | + |
| 128 | + |
| 146 | + |
| 155 | + |
| 205 | + |
| 208 | + |
| 209 | + |
| 210 | ++ |

TABLE 4-continued

| In Cell MER Kinase Assay Data | |
|---|---|
| Example | $IC_{50}{}^a$ |
| 211 | + |
| 213 | + |
| 214 | + |
| 223 | + |
| 224 | + |
| 227 | + |
| 228 | + |
| 230 | + |
| 235 | +++ |
| 236 | +++ |
| 237 | ++ |
| 238 | + |
| 240 | + |
| 243 | + |
| 244 | + |
| 250 | + |
| 253 | + |
| 254 | + |
| 255 | + |
| 256 | + |
| 257 | + |
| 258 | + |
| 259 | + |
| 262 | + |
| 263 | + |
| 265 | + |
| 266 | + |
| 267 | + |
| 268 | + |
| 269 | + |
| 274 | + |
| 275 | + |
| 279 | + |
| 280 | + |
| 289 | + |
| 291 | ++ |
| 292 | +++ |
| 294 | + |
| 295 | ++ |
| 296 | + |
| 302 | + |
| 303 | ++ |
| 305 | + |
| 307 | + |
| 308 | + |
| 311 | + |
| 316 | + |
| 319 | + |
| 323 | + |
| 324 | + |
| 325 | + |
| 326 | + |
| 328 | + |
| 329 | + |
| 331 | + |
| 333 | + |
| 342 | + |
| 343 | ++ |
| 344 | + |
| 347 | + |
| 348 | + |
| 349 | + |
| 353 | + |
| 354 | + |
| 358 | + |
| 359 | ++ |
| 360 | ++ |
| 361 | ++ |
| 364 | + |
| 367 | +++ |
| 369 | ++ |
| 375 | + |
| 376 | + |
| 377 | + |
| 379 | + |
| 380 | + |

TABLE 4-continued

In Cell MER Kinase Assay Data

| Example | IC$_{50}$$^a$ |
|---|---|
| 382 | + |
| 383 | + |
| 384 | + |
| 385 | + |
| 386 | + |
| 387 | + |
| 388 | + |
| 389 | + |
| 390 | + |
| 391 | + |
| 392 | + |
| 394 | + |
| 395 | + |
| 399 | + |
| 400 | + |
| 402 | + |
| 403 | + |
| 405 | + |
| 406 | + |
| 410 | + |
| 421 | + |
| 422 | + |
| 425 | + |
| 427 | + |
| 429 | + |
| 430 | + |
| 431 | + |
| 434 | + |
| 438 | + |
| 441 | + |
| 487 | + |
| 488 | + |
| 494 | + |
| 507 | + |
| 516 | + |
| 517 | + |
| 522 | ++++ |
| 524 | +++ |
| 528 | ++ |
| 529 | + |
| 533 | +++ |
| 535 | + |
| 536 | +++ |
| 537 | + |
| 538 | + |
| 539 | + |
| 540 | + |
| 547 | + |
| 548 | + |
| 550 | + |
| 551 | + |
| 552 | + |
| 553 | + |
| 554 | + |
| 555 | + |
| 556 | +++ |
| 557 | +++ |
| 558 | ++ |
| 559 | +++ |
| 560 | + |
| 561 | + |
| 562 | + |
| 563 | + |
| 564 | + |
| 568 | + |
| 569 | + |
| 570 | +++ |
| 571 | ++ |
| 572 | +++ |
| 576 | + |
| 577 | +++ |
| 581 | ++ |
| 582 | + |
| 583 | + |
| 585 | +++ |
| 587 | + |
| 589 | + |
| 591 | + |
| 592 | + |
| 594 | + |
| 595 | + |
| 615 | + |
| 616 | + |
| 617 | ++ |
| 620 | ++ |
| 625 | + |
| 626 | + |
| 629 | + |
| 632 | + |
| 662 | + |
| 663 | +++ |
| 667 | +++ |
| 671 | ++ |
| 676 | + |
| 677 | + |
| 682 | + |
| 726 | + |
| 727 | + |
| 731 | + |
| 736 | + |
| 742 | + |
| 743 | + |
| 744 | ++ |
| 745 | ++ |
| 775 | + |
| 777 | + |
| 780 | +++ |
| 782 | ++ |
| 790 | + |
| 791 | + |
| 792 | +++ |
| 793 | + |
| 813 | + |
| 814 | + |
| 815 | +++ |
| 822 | + |

$^a$++++ for IC$_{50}$ < 100; +++ for 100 ≤ IC$_{50}$ < 500; ++ for 500 ≤ IC$_{50}$ < 1000; + for IC$_{50}$ ≥ 1000 nM.

In Cell TAM Kinase Assay Using BaF3 Cellular System

Three Ba/F3 cell lines (a murine IL-3 dependent pro-B cell line) expressing BCR fusions to the kinase domains of either MerTK (Ba/F3-MerTK), Axl (Ba/F3-Axl), or Tyro3 (Ba/F3-Tyro3) were purchased from Advanced Cellular Dynamics. The IL-3 independence of all 3 cell lines was confirmed. After thawing, the 3 Ba/F3 cell lines were split and maintained in cell culture media, which consisted of RPMI-1640-HEPES (Thermo-Cat #22400-089) with 1× Glutamax (Thermo-Cat #35050-061) and 10% FBS (Sigma-Cat #F4135 (500 ml), at a cell density range of 0.05× 10$^6$–1×10$^6$ cells/mL 4 days before used in the routine screen. Compound plates were prepared using Nunc™ white 384-well optical bottom plates (ThermoFisher, USA) with compound in 25 nL dimethyl sulfoxide in each well. For routine assays, each of the 3 Ba/F3 cell lines was seeded at 1,000 cells per well with 25 µL of cell culture media directly into 384-well compound plates and incubated for 72 hours. Cell proliferation was then measured by adding 25 µL of Cell Titer Glo 2.0 (Promega, USA). After incubating with Cell Titer Glo at room temperature for 30 mins, the luminescence intensity, which quantifies the cell viability, was measured using an Envision™ plate reader (PerkinElmer, USA). To discriminate a Ba/F3 growth inhibition by specific inhibition of each of the 3 kinases following compound treatment vs growth inhibition due to a non-specific cytotoxicity of compounds, control sets of Ba/F3-Tyro3 cells were routinely carried out in parallel that were grown in IL3-supplemented (0.1 µg/mL) growth media. In the presence of IL-3, the proliferation of the Ba/F3-Tyro3 cells is no longer dependent on the Tyro3 kinase activity.

TABLE 5

In Cell TAM Kinase Assay Data

| Example | IC$_{50}$$^a$ |
|---|---|
| 129 | +++ |
| 365 | + |
| 366 | +++ |
| 370 | + |
| 381 | + |
| 505 | + |
| 523 | ++ |
| 525 | +++ |
| 526 | + |
| 534 | + |
| 546 | + |
| 565 | + |
| 567 | + |
| 584 | + |
| 586 | ++ |
| 588 | + |
| 590 | + |
| 593 | + |
| 634 | ++ |
| 635 | +++ |
| 636 | +++ |
| 643 | + |
| 644 | +++ |
| 656 | ++++ |
| 657 | +++ |
| 658 | ++ |
| 659 | + |
| 661 | ++ |
| 673 | ++ |
| 679 | + |
| 695 | + |
| 696 | + |
| 697 | + |
| 698 | + |
| 699 | + |
| 700 | + |
| 701 | + |
| 702 | + |
| 703 | + |
| 704 | + |
| 706 | + |
| 707 | + |
| 708 | ++ |
| 709 | + |
| 710 | + |
| 711 | + |
| 712 | ++ |
| 713 | + |
| 714 | + |
| 718 | ++ |
| 720 | + |
| 721 | +++ |
| 722 | + |
| 734 | + |
| 735 | + |
| 737 | + |
| 740 | + |
| 741 | + |
| 747 | + |
| 748 | +++ |
| 749 | + |
| 750 | + |
| 753 | + |
| 754 | + |
| 755 | + |
| 756 | + |
| 757 | + |
| 761 | + |
| 762 | + |
| 764 | + |
| 765 | + |
| 766 | + |
| 767 | + |
| 769 | + |
| 770 | + |
| 771 | + |
| 774 | +++ |
| 776 | + |
| 778 | + |
| 779 | + |
| 781 | + |
| 786 | + |
| 787 | + |
| 788 | + |
| 794 | + |
| 795 | ++ |
| 798 | + |
| 800 | + |
| 802 | + |
| 803 | + |
| 804 | + |
| 806 | + |
| 808 | +++ |
| 809 | + |
| 811 | + |
| 812 | + |
| 816 | + |
| 817 | + |
| 818 | + |
| 819 | + |
| 820 | +++ |
| 823 | + |
| 829 | + |
| 830 | + |
| 831 | + |
| 832 | + |
| 834 | + |
| 835 | + |
| 836 | + |
| 837 | + |
| 838 | + |

$^a$++++ for IC$_{50}$ < 100; +++ for 100 ≤ IC$_{50}$ < 500; ++ for 500 ≤ IC$_{50}$ < 1000; + for IC$_{50}$ ≥ 1000 nM.

Based on the studies conducted and the results obtained so far, it is believed that the following compounds (numbered 1 to 383), including isomers, mixtures of isomer as well as pharmaceutically acceptable salts and solvates thereof, are particularly interesting.

It is understood that the foregoing detailed description and accompanying examples are merely illustrative and are not to be taken as limitations upon the scope of the present disclosure, which is defined by the appended claims and their equivalents. Various changes and modifications to the described embodiments will be apparent to those skilled in the art. Such changes and modifications, including without limitation those relating to the chemical structures, substituents, derivatives, intermediates, syntheses, formulations, or methods, or any combination of such changes and modifications of use of the present disclosure, may be made without departing from the spirit and scope thereof.

What is claimed is:

1. A compound of formula (II):

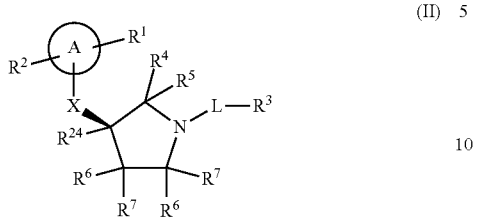

or a pharmaceutically acceptable salt thereof;
wherein:
Ring A is

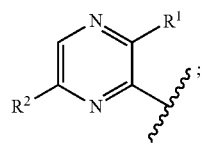

X is —C(=O)N(R$^8$)—, —N(R$^8$)—, or —O—;
L is C$_{1-3}$ alkyl, —C(=O)— —C(=O)O—, or —C(=O)N(R$^8$)—;
R$^1$ is NH$_2$;
R$^2$ is —Br, heteroaryl, or phenyl which phenyl or heteroaryl can optionally be substituted with one or more R$^{18}$;
R$^3$ is phenyl or biphenyl, which can optionally be substituted with one or more R$^9$;
R$^4$, R$^5$, R$^6$, and R$^7$ are each independently H;
R$^8$ is H, C$_{1-6}$ alkyl, C$_{1-3}$ alkylaryl, or C$_{1-3}$ alkylheteroaryl which C$_{1-6}$ alkyl, C$_{1-3}$ alkylaryl or C$_{1-3}$ alkylheteroaryl can optionally be substituted with one or more R$^9$;
R$^9$ is halogen, hydroxyl, —CN, —NO$_2$, —CHO, —COOH, —(C=O)H, C$_{1-6}$ alkyl, C$_{2-6}$ alkenyl, C$_{2-6}$ alkynyl, C$_{1-6}$ aminoalkyl, C$_{3-10}$ cycloalkyl, C$_{1-6}$ haloalkyl, C$_{1-4}$ hydroxyalkyl, C$_{1-6}$ alkoxy, cycloalkenyl, aryl, heterocycle, heteroaryl, —NR$^{10}$R$^{11}$, -J$^9$-NR$^{10}$R$^{11}$, -J$^9$-COOR$^8$, -J$^9$-alkyl, -J$^9$-C$_{3-10}$ cycloalkyl, -J$^9$-cycloalkenyl, -J$^9$-heterocycle, -J$^9$-heteroaryl, or -J$^9$-aryl which alkyl, C$_{1-6}$ alkoxy, C$_{3-10}$ cycloalkyl, heterocycle, heteroaryl, aryl, -J$^9$-alkyl, -J$^9$-C$_{3-10}$ cycloalky, -J$^9$-heterocycle, -J$^9$-heteroaryl, or -J$^9$-aryl, can be substituted with one or more R$^{16}$;
R$^{10}$ and R$^{11}$ each independently is H, C$_{1-6}$ alkyl, C$_{3-10}$ cycloalkyl or SO$_2$R$^8$;
R$^{16}$ is halogen, hydroxyl, —CN, —CHO, —NR$^{10}$R$^{11}$, —NO$_2$, C$_{1-6}$ alkyl, (=O), C$_{3-10}$ cycloalkyl, C$_{1-4}$ hydroxyalkyl, C$_{1-6}$ alkoxy, C$_{2-6}$ alkenyl, aryl, heterocycle, -J$^{16}$-alkyl, -J$^{16}$-aryl, -J$^{16}$-heterocycle, —(CH$_2$)$_l$—NR$^{10}$R$^{11}$, —(CH$_2$)$_l$—COOR$^8$, or —(CH$_2$)$_l$—C(=O)—NR$^{10}$R$^{11}$, which -J$^{16}$-heterocycle can be substituted with one or more R$^{17}$;
R$^{17}$ is C$_{1-6}$ alkyl, C$_{1-4}$ hydroxyalkyl, or C$_{1-4}$ aminoalkyl;
R$^{18}$ is halogen, hydroxyl, —CN, —NO$_2$, —CHO, —COOH, —(C=O)H, C$_{1-6}$ alkyl, C$_{2-6}$ alkenyl, C$_{2-6}$ alkynyl, C$_{1-6}$ aminoalkyl, C$_{3-10}$ cycloalkyl, C$_{1-6}$ haloalkyl, C$_{1-4}$ hydroxyalkyl, C$_{1-6}$ alkoxy, cycloalkenyl, aryl, heterocycle, heteroaryl, -J$^{19}$NR$^{10}$R$^{11}$, -J$^8$-NR$^{10}$R$^{11}$, -J$^{18}$-COOR$^8$, -J$^8$-alkyl, -J$^8$-C$_{3-10}$ cycloalkyl, -J$^{18}$-cycloalkenyl, -J$^{18}$-heterocycle, -J$^{18}$-heteroaryl, or -J$^{18}$-aryl which alkyl, C$_{1-6}$ alkoxy, C$_{3-10}$ cycloalkyl, heterocycle, heteroaryl, aryl, -J$^8$-alkyl, -J$^{18}$-C$_{3-10}$ cycloalky, -J$^{18}$-heterocycle, -J$^{18}$-heteroaryl, or -J$^{18}$-aryl, can be substituted with one or more R$^{19}$;
R$^{19}$ is halogen, hydroxyl, —CN, —CHO, —NR$^{10}$R$^{11}$, —NO$_2$, C$_{1-6}$ alkyl, (=O), C$_{3-10}$ cycloalkyl, C$_{1-4}$ hydroxyalkyl, C$_{1-6}$ alkoxy, C$_{2-6}$ alkenyl, aryl, heterocycle, -J$^{19}$-alkyl, -J$^{19}$-aryl, -J$^{19}$-heterocycle, —(CH$_2$)$_l$—NR$^{10}$R$^{11}$, —(CH$_2$)$_l$—COOR$^8$, or —(CH$_2$)$_l$—C(=O)—NR$^{10}$R$^{11}$, which -J$^{19}$-heterocycle can be substituted with one or more R$^{20}$;
R$^{20}$ is C$_{1-6}$ alkyl, C$_{1-4}$ hydroxyalkyl, or C$_{1-4}$ aminoalkyl;
R$^{24}$ is H;
J$^9$ is C$_{1-3}$ alkyl, C$_{1-3}$ alkyl-O—, C$_{2-6}$ alkenyl, C$_{2-6}$ alkynyl, C$_{3-10}$ cycloalkyl, —(CH$_2$)$_l$—C(=O)—(CH$_2$)$_m$—, —(CH$_2$)$_l$—CH=CH—C(=O)—(CH$_2$)$_m$—, —C(=O)O—, —(CH$_2$)$_l$—C(=O)NH—(CH$_2$)$_m$—, —(CH$_2$)—NHC(=O)—(CH$_2$)$_m$—, —(CR$^{10}$R$^{11}$)$_l$—NR$^8$—(CR$^{10}$R$^{11}$)$_m$, —NH—C(=O)—CR$^{10}$R$^{11}$—NH—C(=O)—, —NHC(=O)—, —O—, —O(C=O)—, —S—, —S(=O)—, —SO$_2$—, or —NHSO$_2$;
J$^{16}$ is C$_{1-3}$ alkyl, C$_{1-3}$ alkyl-O—, C$_{2-6}$ alkenyl, C$_{2-6}$ alkynyl, C$_{3-10}$ cycloalkyl, —(CH$_2$)$_l$—C(=O)—(CH$_2$)$_m$—, —(CH$_2$)$_l$—CH=CH—C(=O)—(CH$_2$)$_m$—, —C(=O)O—, —(CH$_2$)$_l$—C(=O)NH—(CH$_2$)$_m$—, —(CH$_2$)$_l$—NHC(=O)—(CH$_2$)$_m$—, —(CR$^{10}$R$^{11}$)$_l$—NR$^8$—(CR$^{10}$R$^{11}$)$_m$, —NH—C(=O)—CR$^{10}$R$^{11}$—NH—C(=O)—, —NHC(=O)—, —O—, —O(C=O)—, —S—, —S(=O)—, or —SO$_2$—;
J$^{18}$ is C$_{1-3}$ alkyl, C$_{1-3}$ alkyl-O—, C$_{2-6}$ alkenyl, C$_{2-6}$ alkynyl, C$_{3-10}$ cycloalkyl, —(CH$_2$)$_l$—C(=O)—(CH$_2$)$_m$, —(CH$_2$)$_l$—CH=CH—C(=O)—(CH$_2$)$_m$, —C(=O)—, —C(=O)O—, —(CH$_2$)$_l$—C(=O)NH—(CH$_2$)$_m$, —(CH$_2$)$_l$—NHC(=O)—(CH$_2$)$_m$, —(CR$^{10}$R$^{11}$)$_l$—NR$^8$—(CR$^{10}$R$^{11}$)$_m$, —NH—C(=O)—CR$^{10}$R$^{11}$—NH—C(=O)—, —NHC(=O)—, —O—, —O(C=O)—, —S—, —S(=O)—, —SO$_2$—, or —NHSO$_2$—;
J$^{19}$ is C$_{1-3}$ alkyl, C$_{1-3}$ alkyl-O—, C$_{2-6}$ alkenyl, C$_{2-6}$ alkynyl, C$_{3-10}$ cycloalkyl, —(CH$_2$)$_l$—C(=O)—(CH$_2$)$_m$, —(CH$_2$)$_l$—CH=CH—C(=O)—(CH$_2$)$_m$, —C(=O)O—, —(CH$_2$)$_l$—C(=O)NH—(CH$_2$)$_m$, —(CH$_2$)$_l$—NHC(=O)—(CH$_2$)$_m$—, —(CR$^{10}$R$^{11}$)$_l$—NR$^8$—(CR$^{10}$R$^{11}$)$_m$, —NH—C(=O)—CR$^{10}$R$^{11}$—NH—C(=O)—, —NHC(=O)—, —O—, —O(C=O)—, —S—, —S(=O)—, or —SO$_2$—;

and
l and m each independently is an integer of 0 to 3.

2. The compound of claim 1, a pharmaceutically acceptable salt thereof;
wherein
X is —C(=O)N(R$^8$)—.

3. The compound of claim 2, or a pharmaceutically acceptable salt thereof;
wherein R$^2$ is

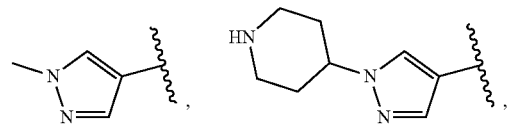

,

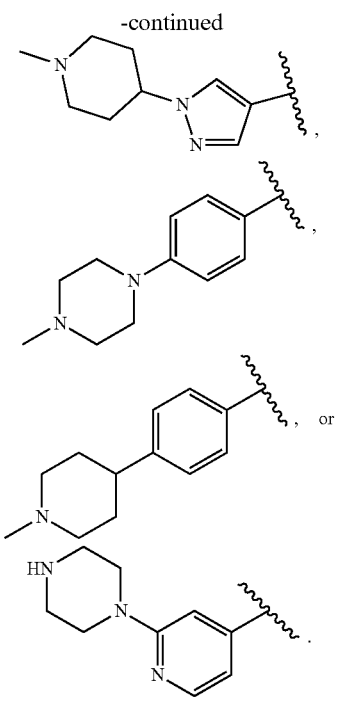

4. The compound of claim 3, or a pharmaceutically acceptable salt thereof;
wherein $R^9$ is halogen, $C_{1-6}$ alkyl, aryl, heterocycle, -$J^9$-heterocycle, or -$J^9$-aryl which alkyl, aryl, heterocycle, -$J^9$-heterocycle, or -$J^9$-aryl, can be substituted with one or more $R^{16}$; and
$R^{16}$ is —$NR^{10}R^{11}$, $C_{1-6}$ alkyl, $C_{1-4}$ hydroxyalkyl, or heterocycle.

5. The compound of claim 3, or a pharmaceutically acceptable salt thereof;
wherein
L is —C(=O)—; and
$R^3$ is biphenyl substituted with one, two, or three $R^9$; wherein $R^9$ is halogen.

6. The compound of claim 5 formula III:

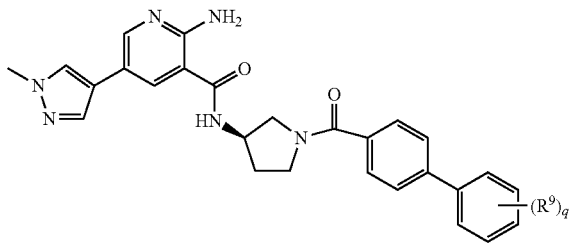

(III)

or a pharmaceutically acceptable salt thereof;
wherein $R^9$ is F or Cl; and
q is 1, 2, or 3.

7. The compound of claim 1, or a pharmaceutically acceptable salt thereof,
wherein
X is —C(=O)N($R^8$)—;
L is —C(=O)—;
$R^2$ is phenyl, pyridyl, or pyrazole, which phenyl, pyridyl, or pyrazole can optionally be substituted with one or more $R^{18}$;

$R^3$ is biphenyl which can optionally be substituted with one or more $R^9$;
$R^8$ is H;
$R^9$ is halogen, or -$J^9$-aryl which -$J^9$-aryl can be substituted with one or more $R^{16}$;
$R^{16}$ is —$(CH_2)_t$—$NR^{10}R^{11}$;
$R^{18}$ is $C_{1-6}$ alkyl, heterocycle, or -$J^{18}$-heterocycle, which heterocycle, or -$J^{18}$-heterocycle can be substituted with $R^{19}$;
$R^{19}$ is $C_{1-6}$ alkyl;
and
$J^9$ is —C(=O)NH—.

8. The compound of claim 7, or a pharmaceutically acceptable salt thereof;
wherein
$R^2$ is

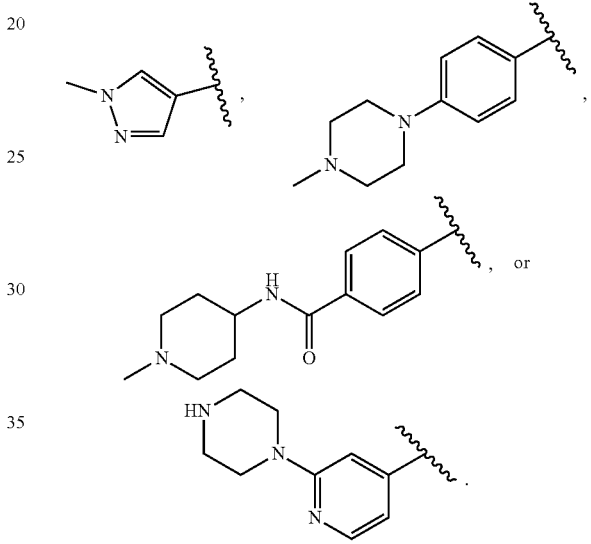

9. The compound of claim 1, or a pharmaceutically acceptable salt thereof;
wherein
$R^2$ is phenyl, pyridyl, or pyrazole which phenyl, pyridyl, or pyrazole an optionally be substituted with one or more $R^{18}$; and
$R^8$ is H, or $C_{1-6}$ alkyl.

10. The compound of claim 7, or a pharmaceutically acceptable salt thereof; wherein
$R^2$ is

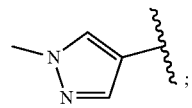 [SMILES: *c1cnn(C)c1];

and
$R^3$ is biphenyl substituted with 1-3 $R^9$; wherein $R^9$ is halogen.

11. The compound of claim 8, or a pharmaceutically acceptable salt thereof; wherein
$R^3$ is biphenyl substituted with 1-3 $R^9$; wherein $R^9$ is halogen.

12. The compound or pharmaceutically acceptable salt of claim 1, selected from:

(R)-2-amino-5-(1-methyl-1H-pyrazol-4-yl)-N-(1-(phenylcarbamoyl)pyrrolidin-3-yl)nicotinamide;
(R)-2-amino-N-(1-((3-fluorophenyl)carbamoyl)pyrrolidin-3-yl)-5-(1-methyl-1H-pyrazol-4-yl)nicotinamide;
(R)-2-amino-N-(1-((3,4-difluorophenyl)carbamoyl)pyrrolidin-3-yl)-5-(1-methyl-1H-pyrazol-4-yl)nicotinamide;
(R)-2-amino-N-(1-((3,5-dimethylphenyl)carbamoyl)pyrrolidin-3-yl)-5-(1-methyl-1H-pyrazol-4-yl)nicotinamide;
(R)-2-amino-N-(1-((3,5-bis(trifluoromethyl)phenyl)carbamoyl)pyrrolidin-3-yl)-5-(1-methyl-1H-pyrazol-4-yl)nicotinamide;
(R)-2-amino-5-(1-methyl-1H-pyrazol-4-yl)-N-(1-((4-(trifluoromethyl)phenyl)carbamoyl)pyrrolidin-3-yl)nicotinamide;
(R)-2-amino-N-(1-((4-cyanophenyl)carbamoyl)pyrrolidin-3-yl)-5-(1-methyl-1H-pyrazol-4-yl)nicotinamide;
(R)-2-amino-N-(1-((3,5-dichlorophenyl)carbamoyl)pyrrolidin-3-yl)-5-(4-(morpholine-4-carbonyl)phenyl)nicotinamide;
(R)-2-amino-N-(1-((3,5-dichlorophenyl)carbamoyl)pyrrolidin-3-yl)-5-(4-(hydroxymethyl)phenyl)nicotinamide;
(R)-2-amino-N-(1-((3,5-dichlorophenyl)carbamoyl)pyrrolidin-3-yl)-5-(1-(1-methylpiperidin-4-yl)-1H-pyrazol-4-yl)nicotinamide;
(R)-2-amino-N-(1-((3-chlorophenyl)carbamoyl)pyrrolidin-3-yl)-5-(1-methyl-1H-pyrazol-4-yl)nicotinamide;
(R)-2-amino-N-(1-((2,3-dichlorophenyl)carbamoyl)pyrrolidin-3-yl)-5-(1-methyl-1H-pyrazol-4-yl)nicotinamide;
(R)-2-amino-N-(1-((3-isopropoxyphenyl)carbamoyl)pyrrolidin-3-yl)-5-(1-methyl-1H-pyrazol-4-yl)nicotinamide;
(R)-2-amino-5-(1-methyl-1H-pyrazol-4-yl)-N-(1-((3-phenoxyphenyl)carbamoyl)pyrrolidin-3-yl)nicotinamide;
(R)-2-amino-5-(1-methyl-1H-pyrazol-4-yl)-N-(1-((2-phenoxyphenyl)carbamoyl)pyrrolidin-3-yl)nicotinamide;
(R)-2-amino-N-(1-((3-ethylphenyl)carbamoyl)pyrrolidin-3-yl)-5-(1-methyl-1H-pyrazol-4-yl)nicotinamide;
(R)-2-amino-N-(1-((2-ethylphenyl)carbamoyl)pyrrolidin-3-yl)-5-(1-methyl-1H-pyrazol-4-yl)nicotinamide;
(R)-2-amino-N-(1-((2-chlorophenyl)carbamoyl)pyrrolidin-3-yl)-5-(1-methyl-1H-pyrazol-4-yl)nicotinamide;
(R)—N-(1-([1,1'-biphenyl]-3-ylcarbamoyl)pyrrolidin-3-yl)-2-amino-5-(1-methyl-1H-pyrazol-4-yl)nicotinamide;
(R)-2-amino-N-(1-((3-bromophenyl)carbamoyl)pyrrolidin-3-yl)-5-(1-methyl-1H-pyrazol-4-yl)nicotinamide;
(R)-2-amino-N-(1-((4-bromophenyl)carbamoyl)pyrrolidin-3-yl)-5-(1-methyl-1H-pyrazol-4-yl)nicotinamide;
(R)-2-amino-5-(1-methyl-1H-pyrazol-4-yl)-N-(1-((3-(morpholinomethyl)phenyl)carbamoyl)pyrrolidin-3-yl)nicotinamide;
(S)-2-amino-5-(1-methyl-1H-pyrazol-4-yl)-N-(1-(phenylcarbamoyl)pyrrolidin-3-yl)nicotinamide;
(R)-2-amino-5-(1-methyl-1H-pyrazol-4-yl)-N-(1-((2,4,6-trichlorophenyl)carbamoyl)pyrrolidin-3-yl)nicotinamide;
(R)-2-amino-N-(1-((3,5-dichlorophenyl)carbamoyl)pyrrolidin-3-yl)-5-(1-methyl-1H-pyrazol-4-yl)nicotinamide;
(R)-2-amino-5-(1-methyl-1H-pyrazol-4-yl)-N-(1-((3,4,5-trimethoxyphenyl)carbamoyl)pyrrolidin-3-yl)nicotinamide;
(R)—N-(1-([1,1'-biphenyl]-2-ylcarbamoyl)pyrrolidin-3-yl)-2-amino-5-(1-methyl-) H-pyrazol-4-yl)nicotinamide;
(R)—N-(1-([1,1'-biphenyl]-3-ylcarbamoyl)pyrrolidin-3-yl)-2-amino-5-(4-((4-methylpiperazin-1-yl)methyl)phenyl)nicotinamide;
(R)—N-(1-([1,1'-biphenyl]-3-ylcarbamoyl)pyrrolidin-3-yl)-2-amino-5-(4-(morpholinomethyl)phenyl)nicotinamide;
(R)—N-(1-([1,1'-biphenyl]-3-ylcarbamoyl)pyrrolidin-3-yl)-2-amino-5-(4-((4-hydroxypiperidin-1-yl)methyl)phenyl)nicotinamide;
3-bromophenyl (R)-3-(2-amino-5-(1-methyl-1H-pyrazol-4-yl)nicotinamido)pyrrolidine--carboxylate;
phenyl (R)-3-(2-amino-5-(1-methyl-1H-pyrazol-4-yl)nicotinamido)pyrrolidine-1-carboxylate;
3-(piperidine-1-carbonyl)phenyl (R)-3-(2-amino-5-(1-methyl-1H-pyrazol-4-yl)nicotinamido)pyrrolidine-1-carboxylate;
3-isopropyl-5-methylphenyl (R)-3-(2-amino-5-(1-methyl-1H-pyrazol-4-yl)nicotinamido)pyrrolidine-1-carboxylate;
2-(benzyloxy)phenyl (R)-3-(2-amino-5-(1-methyl-1H-pyrazol-4-yl)nicotinamido)pyrrolidine-1-carboxylate;
3-(benzyloxy)phenyl (R)-3-(2-amino-5-(1-methyl-1H-pyrazol-4-yl)nicotinamido)pyrrolidine-1-carboxylate;
2,3-dichlorophenyl (R)-3-(2-amino-5-(1-methyl-1H-pyrazol-4-yl)nicotinamido)pyrrolidine-1-carboxylate;
2,5-dichlorophenyl (R)-3-(2-amino-5-(1-methyl-1H-pyrazol-4-yl)nicotinamido)pyrrolidine-1-carboxylate;
2-cyanophenyl (R)-3-(2-amino-5-(1-methyl-1H-pyrazol-4-yl)nicotinamido)pyrrolidine-1-carboxylate;
4-bromo-2-methoxyphenyl (R)-3-(2-amino-5-(1-methyl-1H-pyrazol-4-yl)nicotinamido)pyrrolidine-1-carboxylate;
3-(methoxycarbonyl)phenyl (R)-3-(2-amino-5-(1-methyl-1H-pyrazol-4-yl)nicotinamido)pyrrolidine-1-carboxylate;
5-methoxy-2-(methoxycarbonyl)phenyl (R)-3-(2-amino-5-(1-methyl-1H-pyrazol-4-yl)nicotinamido)pyrrolidine-1-carboxylate;
2-aminophenyl (R)-3-(2-amino-5-(1-methyl-1H-pyrazol-4-yl)nicotinamido)pyrrolidine-1-carboxylate;
2-(hydroxymethyl)phenyl (R)-3-(2-amino-5-(1-methyl-1H-pyrazol-4-yl)nicotinamido)pyrrolidine-1-carboxylate;
3-(ethylamino)-4-methylphenyl (R)-3-(2-amino-5-(1-methyl-1H-pyrazol-4-yl)nicotinamido)pyrrolidine-1-carboxylate;
4-chloro-2-cyclohexylphenyl (R)-3-(2-amino-5-(1-methyl-1H-pyrazol-4-yl)nicotinamido)pyrrolidine-1-carboxylate;
3-acetamidophenyl (R)-3-(2-amino-5-(1-methyl-1H-pyrazol-4-yl)nicotinamido)pyrrolidine-1-carboxylate;
4-(methylsulfonyl)phenyl (R)-3-(2-amino-5-(1-methyl-1H-pyrazol-4-yl)nicotinamido)pyrrolidine-1-carboxylate;
2-((dimethylamino)methyl)phenyl (R)-3-(2-amino-5-(1-methyl-1H-pyrazol-4-yl)nicotinamido)pyrrolidine-1-carboxylate;
[1,1'-biphenyl]-3-yl (R)-3-(2-amino-5-(4-(hydroxymethyl)phenyl)nicotinamido)pyrrolidine-1-carboxylate;

[1,1'-biphenyl]-3-yl (R)-3-(2-amino-5-(4-((4-methylpiperazin-1-yl)methyl)phenyl)nicotinamido)pyrrolidine-1-carboxylate;

[1,1'-biphenyl]-3-yl (R)-3-(2-amino-5-(4-(morpholine-4-carbonyl)phenyl)nicotinamido)pyrrolidine-1-carboxylate;

[1,1'-biphenyl]-3-yl (R)-3-(2-amino-5-(3,4-difluorophenyl)nicotinamido)pyrrolidine-1-carboxylate;

[1,1'-biphenyl]-3-yl(R)-3-(2-amino-5-bromonicotinamido)pyrrolidine-1-carboxylate;

4-chloro-3-methylphenyl (R)-3-(2-amino-5-(1-methyl-1H-pyrazol-4-yl)nicotinamido)pyrrolidine-1-carboxylate;

3-cyanophenyl (R)-3-(2-amino-5-(1-methyl-1H-pyrazol-4-yl)nicotinamido)pyrrolidine-1-carboxylate;

3,4-dichlorophenyl (R)-3-(2-amino-5-(1-methyl-1H-pyrazol-4-yl)nicotinamido)pyrrolidine-1-carboxylate;

4-amino-3-chlorophenyl (R)-3-(2-amino-5-(1-methyl-1H-pyrazol-4-yl)nicotinamido)pyrrolidine-1-carboxylate;

3,5-difluorophenyl (R)-3-(2-amino-5-(1-methyl-1H-pyrazol-4-yl)nicotinamido)pyrrolidine-1-carboxylate;

3,5-dimethylphenyl (R)-3-(2-amino-5-(1-methyl-1H-pyrazol-4-yl)nicotinamido)pyrrolidine-1-carboxylate;

2-(methoxycarbonyl)phenyl (R)-3-(2-amino-5-(1-methyl-1H-pyrazol-4-yl)nicotinamido)pyrrolidine-1-carboxylate;

4-ethylphenyl (R)-3-(2-amino-5-(1-methyl-1H-pyrazol-4-yl)nicotinamido)pyrrolidine-1-carboxylate;

3,4-dimethylphenyl (R)-3-(2-amino-5-(1-methyl-1H-pyrazol-4-yl)nicotinamido)pyrrolidine-1-carboxylate;

[1,1'-biphenyl]-3-yl (R)-3-(2-amino-5-(1-(1-methylpiperidin-4-yl)-1H-pyrazol-4-yl)nicotinamido)pyrrolidine-1-carboxylate;

2-hydroxyphenyl (R)-3-(2-amino-5-(1-methyl-1H-pyrazol-4-yl)nicotinamido)pyrrolidine-1-carboxylate;

2-amino-4-chlorophenyl (R)-3-(2-amino-5-(1-methyl-1H-pyrazol-4-yl)nicotinamido)pyrrolidine-1-carboxylate;

2-amino-5-nitrophenyl (R)-3-(2-amino-5-(1-methyl-1H-pyrazol-4-yl)nicotinamido)pyrrolidine-1-carboxylate;

3-hydroxyphenyl (R)-3-(2-amino-5-(1-methyl-1H-pyrazol-4-yl)nicotinamido)pyrrolidine-1-carboxylate;

4-phenoxyphenyl (R)-3-(2-amino-5-(1-methyl-1H-pyrazol-4-yl)nicotinamido)pyrrolidine-1-carboxylate;

3-phenoxyphenyl (R)-3-(2-amino-5-(1-methyl-1H-pyrazol-4-yl)nicotinamido)pyrrolidine-1-carboxylate;

4-(4-nitrophenoxy)phenyl (R)-3-(2-amino-5-(1-methyl-1H-pyrazol-4-yl)nicotinamido)pyrrolidine-1-carboxylate;

4-(4-aminophenoxy)phenyl (R)-3-(2-amino-5-(1-methyl-1H-pyrazol-4-yl)nicotinamido)pyrrolidine-1-carboxylate;

4-(4-((4-methylpiperazin-1-yl)methyl)phenoxy)phenyl (R)-3-(2-amino-5-(1-methyl-1H-pyrazol-4-yl)nicotinamido)pyrrolidine-1-carboxylate;

4-(4-(hydroxymethyl)phenoxy)phenyl (R)-3-(2-amino-5-(1-methyl-1H-pyrazol-4-yl)nicotinamido)pyrrolidine-1-carboxylate;

4-(4-((dimethylamino)methyl)phenoxy)phenyl (R)-3-(2-amino-5-(1-methyl-1H-pyrazol-4-yl)nicotinamido)pyrrolidine-1-carboxylate;

3,5-dichlorophenyl (R)-3-(2-amino-5-(1-methyl-1H-pyrazol-4-yl)nicotinamido)pyrrolidine-1-carboxylate;

[1,1'-biphenyl]-3-yl (R)-3-(2-amino-5-(1-methyl-1H-pyrazol-4-yl)nicotinamido)pyrrolidine-1-carboxylate;

phenyl (R)-3-(2-amino-5-(4-((4-methylpiperazin-1-yl)methyl)phenyl)nicotinamido)pyrrolidine-1-carboxylate;

phenyl (R)-3-(2-amino-5-(1-(1-methylpiperidin-4-yl)-1H-pyrazol-4-yl)nicotinamido)pyrrolidine-1-carboxylate;

[1,1'-biphenyl]-3-yl (R)-3-(2-amino-N-methyl-5-(1-methyl-1H-pyrazol-4-yl)nicotinamido)pyrrolidine-1-carboxylate;

(R)-2-amino-N-(1-benzylpyrrolidin-3-yl)-N-methyl-5-(1-methyl-H-pyrazol-4-yl)nicotinamide;

(R)-2-amino-N-(1-(2-chlorobenzyl)pyrrolidin-3-yl)-N-methyl-5-(1-methyl-1H-pyrazol-4-yl)nicotinamide;

(R)-2-amino-N-(1-((3,5-dichlorophenyl)carbamoyl)pyrrolidin-3-yl)-5-(1-(piperidin-4-yl)-1H-pyrazol-4-yl)nicotinamide;

[1,1'-biphenyl]-3-yl(R)-3-(2-amino-5-(1-(piperidin-4-yl)-1H-pyrazol-4-yl)nicotinamido)pyrrolidine-1-carboxylate;

2-amino-N-((3R)-1-(1-(2-chlorophenyl)ethyl)pyrrolidin-3-yl)-5-(1-(piperidin-4-yl)-1H-pyrazol-4-yl)nicotinamide;

2-amino-N-((3R)-1-(1-(3-chlorophenyl)ethyl)pyrrolidin-3-yl)-5-(1-(piperidin-4-yl)-1H-pyrazol-4-yl)nicotinamide;

2-amino-N-((3R)-1-(1-(3,4-dichlorophenyl)ethyl)pyrrolidin-3-yl)-5-(1-(piperidin-4-yl)-1H-pyrazol-4-yl)nicotinamide;

(R)-2-amino-N-(1-benzylpyrrolidin-3-yl)-5-(1-(piperidin-4-yl)-1H-pyrazol-4-yl)nicotinamide;

2-amino-N-(1-benzylpyrrolidin-3-yl)-5-(1-(piperidin-4-yl)-1H-pyrazol-4-yl)nicotinamide;

(R)-2-amino-N-(1-(4-fluorobenzyl)pyrrolidin-3-yl)-5-(1-(piperidin-4-yl)-1H-pyrazol-4-yl)nicotinamide;

(R)-2-amino-N-(1-(3-methoxybenzyl)pyrrolidin-3-yl)-5-(1-(piperidin-4-yl)-1H-pyrazol-4-yl)nicotinamide;

(R)-2-amino-N-(1-(2-chlorobenzyl)pyrrolidin-3-yl)-5-(1-(piperidin-4-yl)-1H-pyrazol-4-yl)nicotinamide;

(R)-2-amino-N-(1-(4-nitrobenzyl)pyrrolidin-3-yl)-5-(1-(piperidin-4-yl)-1H-pyrazol-4-yl)nicotinamide;

(R)-2-amino-5-(1-(piperidin-4-yl)-1H-pyrazol-4-yl)-N-(1-(2,4,5-trifluorobenzyl)pyrrolidin-3-yl)nicotinamide;

(R)-2-amino-N-(1-(3-chloro-4-fluorobenzyl)pyrrolidin-3-yl)-5-(1-(piperidin-4-yl)-1H-pyrazol-4-yl)nicotinamide;

(R)-2-amino-N-(1-(2,6-dichlorobenzyl)pyrrolidin-3-yl)-5-(1-(piperidin-4-yl)-1H-pyrazol-4-yl)nicotinamide;

(R)-2-amino-N-(1-(3,4-difluorobenzyl)pyrrolidin-3-yl)-5-(1-(piperidin-4-yl)-1H-pyrazol-4-yl)nicotinamide;

(R)-2-amino-N-(1-(3,4-dichlorobenzyl)pyrrolidin-3-yl)-5-(1-(piperidin-4-yl)-1H-pyrazol-4-yl)nicotinamide;

(R)-2-amino-5-(1-(piperidin-4-yl)-1H-pyrazol-4-yl)-N-(1-(2,3,6-trifluorobenzyl)pyrrolidin-3-yl)nicotinamide;

(R)-2-amino-N-(1-((2,4-dimethylthiazol-5-yl)methyl)pyrrolidin-3-yl)-5-(1-(piperidin-4-yl)-1H-pyrazol-4-yl)nicotinamide;

(R)-2-amino-N-(1-(2,3-dichlorobenzyl)pyrrolidin-3-yl)-5-(1-(piperidin-4-yl)-1H-pyrazol-4-yl)nicotinamide;

(R)-2-amino-N-(1-(2,4-dichlorobenzyl)pyrrolidin-3-yl)-5-(1-(piperidin-4-yl)-1H-pyrazol-4-yl)nicotinamide;

(R)-2-amino-N-(1-(2,5-dimethylbenzyl)pyrrolidin-3-yl)-5-(1-(piperidin-4-yl)-1H-pyrazol-4-yl)nicotinamide;

(R)-2-amino-N-(1-(2-methoxybenzyl)pyrrolidin-3-yl)-5-(1-(piperidin-4-yl)-1H-pyrazol-4-yl)nicotinamide;

(R)-2-amino-5-(1-(piperidin-4-yl)-1H-pyrazol-4-yl)-N-(1-(2-(trifluoromethyl)benzyl)pyrrolidin-3-yl)nicotinamide;

(R)-2-amino-N-(1-benzylpyrrolidin-3-yl)-5-(1-methyl-1H-pyrazol-4-yl)nicotinamide;
2-amino-N-(1-benzylpyrrolidin-3-yl)-5-(1-methyl-1H-pyrazol-4-yl)nicotinamide;
(S)-2-amino-N-(1-benzylpyrrolidin-3-yl)-5-(1-methyl-1H-pyrazol-4-yl)nicotinamide;
(R)-2-amino-N-(1-(2-chlorobenzyl)pyrrolidin-3-yl)-5-(1-methyl-1H-pyrazol-4-yl)nicotinamide;
(R)-2-amino-N-(1-(3-methoxybenzyl)pyrrolidin-3-yl)-5-(1-methyl-1H-pyrazol-4-yl)nicotinamide;
(R)-2-amino-N-(1-(4-chlorobenzyl)pyrrolidin-3-yl)-5-(1-methyl-1H-pyrazol-4-yl)nicotinamide;
(R)-2-amino-N-(1-(4-ethylbenzyl)pyrrolidin-3-yl)-5-(1-methyl-1H-pyrazol-4-yl)nicotinamide;
(R)-2-amino-N-(1-(4-isopropylbenzyl)pyrrolidin-3-yl)-5-(1-methyl-1H-pyrazol-4-yl)nicotinamide;
(R)-2-amino-N-(1-(3,4-dichlorobenzyl)pyrrolidin-3-yl)-5-(1-methyl-1H-pyrazol-4-yl)nicotinamide;
(R)-2-amino-N-(1-(3,4-dimethylbenzyl)pyrrolidin-3-yl)-5-(1-methyl-1H-pyrazol-4-yl)nicotinamide;
(R)-2-amino-N-(1-(3,5-dimethoxybenzyl)pyrrolidin-3-yl)-5-(1-methyl-1H-pyrazol-4-yl)nicotinamide;
(R)-2-amino-N-(1-(2,3-dimethoxybenzyl)pyrrolidin-3-yl)-5-(1-methyl-1H-pyrazol-4-yl)nicotinamide;
(R)-2-amino-N-(1-(2,5-dimethoxybenzyl)pyrrolidin-3-yl)-5-(1-methyl-1H-pyrazol-4-yl)nicotinamide;
(R)-2-amino-N-(1-(2-hydroxy-5-methoxybenzyl)pyrrolidin-3-yl)-5-(1-methyl-1H-pyrazol-4-yl)nicotinamide;
(R)-2-amino-N-(1-(2,4-dimethoxybenzyl)pyrrolidin-3-yl)-5-(1-methyl-1H-pyrazol-4-yl)nicotinamide;
(R)-2-amino-5-(1-methyl-1H-pyrazol-4-yl)-N-(1-(3-phenoxybenzyl)pyrrolidin-3-yl)nicotinamide;
(R)-2-amino-N-(1-(3-(benzyloxy)benzyl)pyrrolidin-3-yl)-5-(1-methyl-1H-pyrazol-4-yl)nicotinamide;
(R)-2-amino-N-(1-(3,5-dichloro-2-hydroxybenzyl)pyrrolidin-3-yl)-5-(1-methyl-1H-pyrazol-4-yl)nicotinamide;
(R)-2-amino-N-(1-(3,5-dichlorobenzyl)pyrrolidin-3-yl)-5-(1-methyl-1H-pyrazol-4-yl)nicotinamide;
(R)—N-(1-([1,1'-biphenyl]-2-ylmethyl)pyrrolidin-3-yl)-2-amino-5-(1-methyl-1H-pyrazol-4-yl)nicotinamide;
(R)—N-(1-([1,1'-biphenyl]-4-ylmethyl)pyrrolidin-3-yl)-2-amino-5-(1-methyl-1H-pyrazol-4-yl)nicotinamide;
(R)-2-amino-5-(1-methyl-1H-pyrazol-4-yl)-N-(1-(3-phenylpropyl)pyrrolidin-3-yl)nicotinamide;
(R)-2-amino-5-(1-methyl-1H-pyrazol-4-yl)-N-(1-phenethylpyrrolidin-3-yl)nicotinamide;
(R)-2-amino-N-(1-(3-bromobenzyl)pyrrolidin-3-yl)-5-(1-methyl-1H-pyrazol-4-yl)nicotinamide;
(R)-2-amino-N-(1-(2-bromobenzyl)pyrrolidin-3-yl)-5-(1-methyl-1H-pyrazol-4-yl)nicotinamide;
(R)-2-amino-N-(1-(3-bromo-4-fluorobenzyl)pyrrolidin-3-yl)-5-(1-methyl-1H-pyrazol-4-yl)nicotinamide;
(R)-2-amino-N-(1-(3-bromophenethyl)pyrrolidin-3-yl)-5-(1-methyl-1H-pyrazol-4-yl)nicotinamide;
(R)-2-amino-N-(1-(4-chlorobenzyl)pyrrolidin-3-yl)-5-(4-(morpholine-4-carbonyl)phenyl)nicotinamide;
(R)-2-amino-N-(1-(4-chlorobenzyl)pyrrolidin-3-yl)-5-(4-((4-methylpiperazin-1-yl)methyl)phenyl)nicotinamide;
(R)-2-amino-N-(1-(4-chlorobenzyl)pyrrolidin-3-yl)-5-(4-(hydroxymethyl)phenyl)nicotinamide;
(R)-2-amino-N-(1-(4-chlorobenzyl)pyrrolidin-3-yl)-5-(4-cyanophenyl)nicotinamide;
(R)-2-amino-N-(1-(4-chlorobenzyl)pyrrolidin-3-yl)-5-(quinolin-3-yl)nicotinamide;
(R)-5-(1-(1-acetylpiperidin-4-yl)-1H-pyrazol-4-yl)-2-amino-N-(1-benzylpyrrolidin-3-yl)nicotinamide;
(R)-2-amino-N-(1-benzylpyrrolidin-3-yl)-5-(1-(1-(methylsulfonyl)piperidin-4-yl)-1H-pyrazol-4-yl)nicotinamide;
(R)-2-amino-N-(1-benzylpyrrolidin-3-yl)-5-(1-(1-((3,4,5-trimethoxyphenyl)carbamoyl)piperidin-4-yl)-1H-pyrazol-4-yl)nicotinamide;
(R)-2-amino-N-(1-((3'-(hydroxymethyl)-[1,1'-biphenyl]-3-yl)methyl)pyrrolidin-3-yl)-5-(1-methyl-1H-pyrazol-4-yl)nicotinamide;
(R)-2-amino-N-(1-((4'-(hydroxymethyl)-[1,1'-biphenyl]-3-yl)methyl)pyrrolidin-3-yl)-5-(1-methyl-1H-pyrazol-4-yl)nicotinamide;
(R)-2-amino-5-(1-methyl-1H-pyrazol-4-yl)-N-(1-((3'-((4-methylpiperazin-1-yl)methyl)-[1,1'-biphenyl]-3-yl)methyl)pyrrolidin-3-yl)nicotinamide;
(R)-2-amino-5-(1-methyl-1H-pyrazol-4-yl)-N-(1-((4'-((4-methylpiperazin-1-yl)methyl)-[1,1'-biphenyl]-3-yl)methyl)pyrrolidin-3-yl)nicotinamide;
(R)-2-amino-N-(1-((3'-(hydroxymethyl)-[1,1'-biphenyl]-2-yl)methyl)pyrrolidin-3-yl)-5-(1-methyl-1H-pyrazol-4-yl)nicotinamide;
(R)-2-amino-N-(1-((4'-(hydroxymethyl)-[1,1'-biphenyl]-2-yl)methyl)pyrrolidin-3-yl)-5-(1-methyl-1H-pyrazol-4-yl)nicotinamide;
(R)-2-amino-N-(1-((6-fluoro-[1,1'-biphenyl]-3-yl)methyl)pyrrolidin-3-yl)-5-(1-methyl-1H-pyrazol-4-yl)nicotinamide;
(R)-2-amino-N-(1-((6-fluoro-3'-(hydroxymethyl)-[1,1'-biphenyl]-3-yl)methyl)pyrrolidin-3-yl)-5-(1-methyl-1H-pyrazol-4-yl)nicotinamide;
(R)-2-amino-N-(1-((6-fluoro-3'-((4-methylpiperazin-1-yl)methyl)-[1,1'-biphenyl]-3-yl)methyl)pyrrolidin-3-yl)-5-(1-methyl-1H-pyrazol-4-yl)nicotinamide;
(R)-2-amino-N-(1-(4-fluoro-3-(1,2,3,6-tetrahydropyridin-4-yl)benzyl)pyrrolidin-3-yl)-5-(1-methyl-1H-pyrazol-4-yl)nicotinamide;
(R)-2-amino-5-(1-methyl-1H-pyrazol-4-yl)-N-(1-(2-(4'-((4-methylpiperazin-1-yl)methyl)-[1,1'-biphenyl]-3-yl)ethyl)pyrrolidin-3-yl)nicotinamide;
(R)-2-amino-N-(1-((3'-(aminomethyl)-[1,1'-biphenyl]-3-yl)carbamoyl)pyrrolidin-3-yl)-5-(1-methyl-1H-pyrazol-4-yl)nicotinamide;
(R)-2-amino-N-(1-((4'-(aminomethyl)-[1,1'-biphenyl]-3-yl)carbamoyl)pyrrolidin-3-yl)-5-(1-methyl-1H-pyrazol-4-yl)nicotinamide;
(R)—N-(1-([1,1'-biphenyl]-3-ylcarbamoyl)pyrrolidin-3-yl)-2-amino-5-(4-(hydroxymethyl)phenyl)nicotinamide;
(R)-2-amino-N-(1-((3'-amino-[1,1'-biphenyl]-3-yl)carbamoyl)pyrrolidin-3-yl)-5-(1-methyl-1H-pyrazol-4-yl)nicotinamide;
(R)-2-amino-N-(1-((4'-amino-[1,1'-biphenyl]-3-yl)carbamoyl)pyrrolidin-3-yl)-5-(1-methyl-1H-pyrazol-4-yl)nicotinamide;
(R)-2-amino-N-(1-((4'-(hydroxymethyl)-[1,1'-biphenyl]-3-yl)carbamoyl)pyrrolidin-3-yl)-5-(1-methyl-1H-pyrazol-4-yl)nicotinamide;
(R)-2-amino-5-(1-methyl-1H-pyrazol-4-yl)-N-(1-((3-(1-(piperidin-4-yl)-1H-pyrazol-4-yl)phenyl)carbamoyl)pyrrolidin-3-yl)nicotinamide;
(R)-2-amino-5-(1-methyl-1H-pyrazol-4-yl)-N-(1-((3-(6-(piperazin-1-yl)pyridin-3-yl)phenyl)carbamoyl)pyrrolidin-3-yl)nicotinamide;
(R)-2-amino-5-(1-methyl-1H-pyrazol-4-yl)-N-(1-((4'-(methylamino)-[1,1'-biphenyl]-3-yl)carbamoyl)pyrrolidin-3-yl)nicotinamide;

(R)-2-amino-N-(1-((4'-(dimethylamino)-[1,1'-biphenyl]-3-yl)carbamoyl)pyrrolidin-3-yl)-5-(1-methyl-1H-pyrazol-4-yl)nicotinamide;
(R)-2-amino-N-(1-((3'-(hydroxymethyl)-[1,1'-biphenyl]-3-yl)carbamoyl)pyrrolidin-3-yl)-5-(1-methyl-1H-pyrazol-4-yl)nicotinamide;
(R)-2-amino-N-(1-((3'-((dimethylamino)methyl)-[1,1'-biphenyl]-3-yl)carbamoyl)pyrrolidin-3-yl)-5-(1-methyl-1H-pyrazol-4-yl)nicotinamide;
(R)-2-amino-N-(1-((4'-((dimethylamino)methyl)-[1,1'-biphenyl]-3-yl)carbamoyl)pyrrolidin-3-yl)-5-(1-methyl-1H-pyrazol-4-yl)nicotinamide;
(R)-2-amino-5-(1-methyl-1H-pyrazol-4-yl)-N-(1-((3'-((4-methylpiperazin-1-yl)methyl)-[1,1'-biphenyl]-3-yl)carbamoyl)pyrrolidin-3-yl)nicotinamide;
(R)-2-amino-5-(1-methyl-1H-pyrazol-4-yl)-N-(1-((4'-((4-methylpiperazin-1-yl)methyl)-[1,1'-biphenyl]-3-yl)carbamoyl)pyrrolidin-3-yl)nicotinamide;
(R)-2-amino-N-(1-((3'-(aminomethyl)-[1,1'-biphenyl]-4-yl)carbamoyl)pyrrolidin-3-yl)-5-(1-methyl-1H-pyrazol-4-yl)nicotinamide;
(R)-2-amino-N-(1-((4'-(aminomethyl)-[1,1'-biphenyl]-4-yl)carbamoyl)pyrrolidin-3-yl)-5-(1-methyl-1H-pyrazol-4-yl)nicotinamide;
(R)—N-(1-([1,1'-biphenyl]-4-ylcarbamoyl)pyrrolidin-3-yl)-2-amino-5-(1-methyl-1H-pyrazol-4-yl)nicotinamide;
(R)-2-amino-5-(1-methyl-1H-pyrazol-4-yl)-N-(1-((3'-((4-methylpiperazin-1-yl)methyl)-[1,1'-biphenyl]-4-yl)carbamoyl)pyrrolidin-3-yl)nicotinamide;
(R)-2-amino-5-(1-methyl-1H-pyrazol-4-yl)-N-(1-((4'-((4-methylpiperazin-1-yl)methyl)-[1,1'-biphenyl]-4-yl)carbamoyl)pyrrolidin-3-yl)nicotinamide;
4'-((4-methylpiperazin-1-yl)methyl)-[1,1'-biphenyl]-3-yl (R)-3-(2-amino-5-(1-methyl-1H-pyrazol-4-yl)nicotinamido)pyrrolidine-1-carboxylate;
(R)-3-(3'-((3-(2-amino-5-(1-methyl-1H-pyrazol-4-yl)nicotinamido)pyrrolidine-1-carbonyl)oxy)-[1,1'-biphenyl]-4-yl)propanoic acid;
3'-((2-cyanoethyl)carbamoyl)-[1,1'-biphenyl]-3-yl (R)-3-(2-amino-5-(1-methyl-1H-pyrazol-4-yl)nicotinamido)pyrrolidine-1-carboxylate;
(R)-3'-((3-(2-amino-5-(1-methyl-1H-pyrazol-4-yl)nicotinamido)pyrrolidine-1-carbonyl)oxy)-[1,1'-biphenyl]-4-carboxylic acid;
4'-hydroxy-[1,1'-biphenyl]-3-yl (R)-3-(2-amino-5-(1-methyl-1H-pyrazol-4-yl)nicotinamido)pyrrolidine-1-carboxylate;
4'-(hydroxymethyl)-[1,1'-biphenyl]-3-yl (R)-3-(2-amino-5-(1-methyl-1H-pyrazol-4-yl)nicotinamido)pyrrolidine-1-carboxylate;
4'-formyl-[1,1'-biphenyl]-3-yl (R)-3-(2-amino-5-(1-methyl-1H-pyrazol-4-yl)nicotinamido)pyrrolidine-1-carboxylate;
3'-formyl-[1,1'-biphenyl]-3-yl (R)-3-(2-amino-5-(1-methyl-1H-pyrazol-4-yl)nicotinamido)pyrrolidine-1-carboxylate;
3-(1-benzyl-1H-pyrazol-4-yl)phenyl (R)-3-(2-amino-5-(1-methyl-1H-pyrazol-4-yl)nicotinamido)pyrrolidine-1-carboxylate;
3-(1-(2-hydroxyethyl)-1H-pyrazol-4-yl)phenyl (R)-3-(2-amino-5-(1-methyl-1H-pyrazol-4-yl)nicotinamido)pyrrolidine-1-carboxylate;
3-(1-(piperidin-4-yl)-1H-pyrazol-4-yl)phenyl (R)-3-(2-amino-5-(1-methyl-1H-pyrazol-4-yl)nicotinamido)pyrrolidine-1-carboxylate;
3-(1-(2-(pyrrolidin-1-yl)ethyl)-1H-pyrazol-4-yl)phenyl (R)-3-(2-amino-5-(1-methyl-1H-pyrazol-4-yl)nicotinamido)pyrrolidine-1-carboxylate;
3-(1-(2-morpholinoethyl)-1H-pyrazol-4-yl)phenyl (R)-3-(2-amino-5-(1-methyl-1H-pyrazol-4-yl)nicotinamido)pyrrolidine-1-carboxylate;
3-(1-(2-(4-methylpiperazin-1-yl)ethyl)-1H-pyrazol-4-yl)phenyl (R)-3-(2-amino-5-(1-methyl-1H-pyrazol-4-yl)nicotinamido)pyrrolidine-1-carboxylate;
3-(isoquinolin-4-yl)phenyl (R)-3-(2-amino-5-(1-methyl-1H-pyrazol-4-yl)nicotinamido)pyrrolidine-1-carboxylate;
3-(2-(4-methylpiperazin-1-yl)pyridin-4-yl)phenyl (R)-3-(2-amino-5-(1-methyl-1H-pyrazol-4-yl)nicotinamido)pyrrolidine-1-carboxylate;
5-chloro-4'-(hydroxymethyl)-[1,1'-biphenyl]-3-yl (R)-3-(2-amino-5-(1-methyl-1H-pyrazol-4-yl)nicotinamido)pyrrolidine-1-carboxylate;
5-chloro-4'-((4-methylpiperazin-1-yl)methyl)-[1,1'-biphenyl]-3-yl (R)-3-(2-amino-5-(1-methyl-1H-pyrazol-4-yl)nicotinamido)pyrrolidine-1-carboxylate;
3-(piperidin-4-ylmethoxy)phenyl (R)-3-(2-amino-5-(1-methyl-1H-pyrazol-4-yl)nicotinamido)pyrrolidine-1-carboxylate;
3-(((1R,4R)-4-aminocyclohexyl)methoxy)phenyl (R)-3-(2-amino-5-(1-methyl-1H-pyrazol-4-yl)nicotinamido)pyrrolidine-1-carboxylate;
4'-((azetidin-3-ylamino)methyl)-[1,1'-biphenyl]-3-yl (R)-3-(2-amino-5-(1-methyl-1H-pyrazol-4-yl)nicotinamido)pyrrolidine-1-carboxylate;
4'-(((2-aminoethyl)amino)methyl)-[1,1'-biphenyl]-3-yl (R)-3-(2-amino-5-(1-methyl-1H-pyrazol-4-yl)nicotinamido)pyrrolidine-1-carboxylate;
4'-(((2-(dimethylamino)ethyl)amino)methyl)-[1,1'-biphenyl]-3-yl (R)-3-(2-amino-5-(1-methyl-1H-pyrazol-4-yl)nicotinamido)pyrrolidine-1-carboxylate;
4'-(((azetidin-3-ylmethyl)amino)methyl)-[1,1'-biphenyl]-3-yl (R)-3-(2-amino-5-(1-methyl-1H-pyrazol-4-yl)nicotinamido)pyrrolidine-1-carboxylate;
4'-((((R)-1-methylpyrrolidin-3-yl)amino)methyl)-[1,1'-biphenyl]-3-yl (R)-3-(2-amino-5-(1-methyl-1H-pyrazol-4-yl)nicotinamido)pyrrolidine-1-carboxylate;
4'-((3-(dimethylamino)pyrrolidin-1-yl)methyl)-[1,1'-biphenyl]-3-yl (3R)-3-(2-amino-5-(1-methyl-1H-pyrazol-4-yl)nicotinamido)pyrrolidine-1-carboxylate;
4'-(((((S)-pyrrolidin-2-yl)methyl)amino)methyl)-[1,1'-biphenyl]-3-yl (R)-3-(2-amino-5-(1-methyl-1H-pyrazol-4-yl)nicotinamido)pyrrolidine-1-carboxylate;
4'-((((R)-pyrrolidin-3-yl)amino)methyl)-[1,1'-biphenyl]-3-yl (R)-3-(2-amino-5-(1-methyl-1H-pyrazol-4-yl)nicotinamido)pyrrolidine-1-carboxylate;
4'-(((((R)-1-ethylpyrrolidin-2-yl)methyl)amino)methyl)-[1,1'-biphenyl]-3-yl (R)-3-(2-amino-5-(1-methyl-1H-pyrazol-4-yl)nicotinamido)pyrrolidine-1-carboxylate;
4'-((((S)-piperidin-3-yl)amino)methyl)-[1,1'-biphenyl]-3-yl (R)-3-(2-amino-5-(1-methyl-1H-pyrazol-4-yl)nicotinamido)pyrrolidine-1-carboxylate;
4'-(((R)-3-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate;
4'-((4-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate;
4'-(((1-methylpiperidin-4-yl)amino)methyl)-[1,1'-biphenyl]-3-yl (R)-3-(2-amino-5-(1-methyl-1H-pyrazol-4-yl)nicotinamido)pyrrolidine-1-carboxylate;

4'-((3-hydroxypiperidin-1-yl)methyl)-[1,1'-biphenyl]-3-yl (3R)-3-(2-amino-5-(1-methyl-1H-pyrazol-4-yl)nicotinamido)pyrrolidine-1-carboxylate;

4'-((3-(hydroxymethyl)piperidin-1-yl)methyl)-[1,1'-biphenyl]-3-yl (3R)-3-(2-amino-5-(1-methyl-1H-pyrazol-4-yl)nicotinamido)pyrrolidine-1-carboxylate;

4'-((4-(hydroxymethyl)piperidin-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-(((3aR,6aR)-1-methylhexahydropyrrolo[3,4-b]pyrrol-5(1H)-yl)methyl)-[1,1'-biphenyl]-3-yl (R)-3-(2-amino-5-(1-methyl-1H-pyrazol-4-yl)nicotinamido)pyrrolidine-1-carboxylate;

4'-((1,4-diazepan-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-(((R)-2-(hydroxymethyl)pyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-(((S)-2-carbamoylpyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate;

(R)-((3'-((3-(2-amino-5-(1-methyl-1H-pyrazol-4-yl)nicotinamido)pyrrolidine-1-carbonyl)oxy)-[1,1'-biphenyl]-4-yl)methyl)glycine;

4'-((((R)-1-hydroxypropan-2-yl)amino)methyl)-[1,1'-biphenyl]-3-yl (R)-3-(2-amino-5-(1-methyl-1H-pyrazol-4-yl)nicotinamido)pyrrolidine-1-carboxylate;

4'-(((3-hydroxypropyl)amino)methyl)-[1,1'-biphenyl]-3-yl (R)-3-(2-amino-5-(1-methyl-1H-pyrazol-4-yl)nicotinamido)pyrrolidine-1-carboxylate;

1-((3'-(((R)-3-(2-amino-5-(1-methyl-1H-pyrazol-4-yl)nicotinamido)pyrrolidine-1-carbonyl)oxy)-[1,1'-biphenyl]-4-yl)methyl)pyrrolidine-3-carboxylic acid;

4'-(((R)-3-aminopyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-(((S)-3-aminopyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-(((S)-3-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate;

4'-(pyrrolidin-1-ylmethyl)-[1,1'-biphenyl]-3-yl (R)-3-(2-amino-5-(1-methyl-1H-pyrazol-4-yl)nicotinamido)pyrrolidine-1-carboxylate;

4'-(piperidin-1-ylmethyl)-[1,1'-biphenyl]-3-yl (R)-3-(2-amino-5-(1-methyl-1H-pyrazol-4-yl)nicotinamido)pyrrolidine-1-carboxylate;

4'-(morpholinomethyl)-[1,1'-biphenyl]-3-yl (R)-3-(2-amino-5-(1-methyl-1H-pyrazol-4-yl)nicotinamido)pyrrolidine-1-carboxylate;

3'-(((R)-3-aminopyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate;

3'-(((S)-3-aminopyrrolidin-1-yl)methyl)-[1,1'-biphenyl]-3-yl (R)-3-(2-amino-5-(1-methyl-1H-pyrazol-4-yl)nicotinamido)pyrrolidine-1-carboxylate;

3'-(((R)-3-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate;

3'-(((S)-3-aminopiperidin-1-yl)methyl)-[1,1'-biphenyl]-3-yl (R)-3-(2-amino-5-(1-methyl-1H-pyrazol-4-yl)nicotinamido)pyrrolidine-1-carboxylate;

3'-((4-aminopiperidin-1-yl)methyl)-[1,1'-biphenyl]-3-yl (R)-3-(2-amino-5-(1-methyl-H-pyrazol-4-yl)nicotinamido)pyrrolidine-1-carboxylate;

3'-((1,4-diazepan-1-yl)methyl)-[1,1'-biphenyl]-3-yl (R)-3-(2-amino-5-(1-methyl-H-pyrazol-4-yl)nicotinamido)pyrrolidine-1-carboxylate;

(R)-2-amino-N-(1-(4-bromobenzoyl)pyrrolidin-3-yl)-5-(1-methyl-1H-pyrazol-4-yl)nicotinamide;

(R)—N-(1-([1,1'-biphenyl]-4-carbonyl)pyrrolidin-3-yl)-2-amino-5-(1-methyl-1H-pyrazol-4-yl)nicotinamide;

(S)—N-(1-([1,1'-biphenyl]-3-carbonyl)pyrrolidin-3-yl)-2-amino-5-(1-methyl-1H-pyrazol-4-yl)nicotinamide;

(S)—N-(1-([1,1'-biphenyl]-4-carbonyl)pyrrolidin-3-yl)-2-amino-5-(1-methyl-1H-pyrazol-4-yl)nicotinamide;

(R)-2-amino-N-(1-(2'-(hydroxymethyl)-[1,1'-biphenyl]-4-carbonyl)pyrrolidin-3-yl)-5-(1-methyl-1H-pyrazol-4-yl)nicotinamide;

(R)-2-amino-N-(1-(2'-isopropyl-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(2'-phenoxy-[1,1'-biphenyl]-4-carbonyl)pyrrolidin-3-yl)nicotinamide;

(R)—N-(1-([1,1':2',1''-terphenyl]-4-carbonyl)pyrrolidin-3-yl)-2-amino-5-(1-methyl-1H-pyrazol-4-yl)nicotinamide;

(R)-2-amino-N-(1-(2'-ethyl-[1,1'-biphenyl]-4-carbonyl)pyrrolidin-3-yl)-5-(1-methyl-1H-pyrazol-4-yl)nicotinamide;

(R)-2-amino-N-(1-(2'-methoxy-[1,1'-biphenyl]-4-carbonyl)pyrrolidin-3-yl)-5-(1-methyl-1H-pyrazol-4-yl)nicotinamide;

(R)-2-amino-N-(1-(2'-formyl-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(pyridin-3-yl)benzoyl)pyrrolidin-3-yl)nicotinamide;

(R)-2-amino-N-(1-(4-(6-fluoropyridin-3-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(thiophen-3-yl)benzoyl)pyrrolidin-3-yl)nicotinamide;

(R)-2-amino-N-(1-(2'-chloro-[1,1'-biphenyl]-4-carbonyl)pyrrolidin-3-yl)-5-(1-methyl-1H-pyrazol-4-yl)nicotinamide;

(R)-2-amino-N-(1-(3'-chloro-[1,1'-biphenyl]-4-carbonyl)pyrrolidin-3-yl)-5-(1-methyl-1H-pyrazol-4-yl)nicotinamide;

(R)-2-amino-N-(1-(2',4'-dichloro-[1,1'-biphenyl]-4-carbonyl)pyrrolidin-3-yl)-5-(1-methyl-1H-pyrazol-4-yl)nicotinamide;

(R)-2-amino-N-(1-(3',4'-dichloro-[1,1'-biphenyl]-4-carbonyl)pyrrolidin-3-yl)-5-(1-methyl-1H-pyrazol-4-yl)nicotinamide;

(R)-2-amino-N-(1-(3',5'-dichloro-[1,1'-biphenyl]-4-carbonyl)pyrrolidin-3-yl)-5-(1-methyl-1H-pyrazol-4-yl)nicotinamide;

(R)-2-amino-N-(1-(2',6'-difluoro-[1,1'-biphenyl]-4-carbonyl)pyrrolidin-3-yl)-5-(1-methyl-1H-pyrazol-4-yl)nicotinamide;

(R)-2-amino-N-(1-(2',4'-difluoro-[1,1'-biphenyl]-4-carbonyl)pyrrolidin-3-yl)-5-(1-methyl-1H-pyrazol-4-yl)nicotinamide;

(R)-2-amino-N-(1-(2'-chloro-4'-fluoro-[1,1'-biphenyl]-4-carbonyl)pyrrolidin-3-yl)-5-(1-methyl-1H-pyrazol-4-yl)nicotinamide;

(R)-2-amino-N-(1-(2',5'-dichloro-[1,1'-biphenyl]-4-carbonyl)pyrrolidin-3-yl)-5-(1-methyl-1H-pyrazol-4-yl)nicotinamide;

(R)-2-amino-N-(1-(2',6'-dichloro-[1,1'-biphenyl]-4-carbonyl)pyrrolidin-3-yl)-5-(1-methyl-1H-pyrazol-4-yl)nicotinamide;
(R)-2-amino-N-(1-(2',3'-dichloro-[1,1'-biphenyl]-4-carbonyl)pyrrolidin-3-yl)-5-(1-methyl-1H-pyrazol-4-yl)nicotinamide;
(R)-2-amino-N-(1-(2'-fluoro-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(4'-(trifluoromethyl)-[1,1'-biphenyl]-4-carbonyl)pyrrolidin-3-yl)nicotinamide;
(R)-2-amino-N-(1-(4'-(benzyloxy)-[1,1'-biphenyl]-4-carbonyl)pyrrolidin-3-yl)-5-(1-methyl-1H-pyrazol-4-yl)nicotinamide;
(R)-2-amino-N-(1-(2'-bromo-[1,1'-biphenyl]-4-carbonyl)pyrrolidin-3-yl)-5-(1-methyl-1H-pyrazol-4-yl)nicotinamide;
(R)-2-amino-N-(1-(2',4'-bis(trifluoromethyl)-[1,1'-biphenyl]-4-carbonyl)pyrrolidin-3-yl)-5-(1-methyl-1H-pyrazol-4-yl)nicotinamide;
(R)-2-amino-N-(1-(2'-hydroxy-[1,1'-biphenyl]-4-carbonyl)pyrrolidin-3-yl)-5-(1-methyl-1H-pyrazol-4-yl)nicotinamide;
(R)-2-amino-N-(1-(3'-amino-2'-methyl-[1,1'-biphenyl]-4-carbonyl)pyrrolidin-3-yl)-5-(1-methyl-1H-pyrazol-4-yl)nicotinamide;
(R)-2-amino-N-(1-(4'-chloro-[1,1'-biphenyl]-4-carbonyl)pyrrolidin-3-yl)-5-(1-methyl-1H-pyrazol-4-yl)nicotinamide;
(R)-2-amino-N-(1-(4'-(tert-butyl)-[1,1'-biphenyl]-4-carbonyl)pyrrolidin-3-yl)-5-(1-methyl-1H-pyrazol-4-yl)nicotinamide;
(R)-2-amino-N-(1-(4'-(dimethylamino)-[1,1'-biphenyl]-4-carbonyl)pyrrolidin-3-yl)-5-(1-methyl-1H-pyrazol-4-yl)nicotinamide;
(R)-2-amino-N-(1-(4'-hydroxy-[1,1'-biphenyl]-4-carbonyl)pyrrolidin-3-yl)-5-(1-methyl-1H-pyrazol-4-yl)nicotinamide;
(R)-2-amino-N-(1-(4'-formyl-[1,1'-biphenyl]-4-carbonyl)pyrrolidin-3-yl)-5-(1-methyl-1H-pyrazol-4-yl)nicotinamide;
(R)-2-amino-N-(1-(3'-formyl-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(4'-(4-methylpiperazin-1-yl)-[1,1'-biphenyl]-4-carbonyl)pyrrolidin-3-yl)nicotinamide;
(R)-2-amino-5-(1-methyl-1H-pyrazol-4-yl)-N-(1-(4'-(2-(piperazin-1-yl)propan-2-yl)-[1,1'-biphenyl]-4-carbonyl)pyrrolidin-3-yl)nicotinamide;
(R)-2-amino-5-(1-methyl-1H-pyrazol-4-yl)-N-(1-(4'-((4-methylpiperazin-1-yl)methyl)-[1,1'-biphenyl]-4-carbonyl)pyrrolidin-3-yl)nicotinamide;
(R)-2-amino-5-(1-methyl-1H-pyrazol-4-yl)-N-(1-(4'-(2-(4-methylpiperazin-1-yl)propan-2-yl)-[1,1'-biphenyl]-4-carbonyl)pyrrolidin-3-yl)nicotinamide;
(R)-2-amino-N-(1-(4'-(2-(4-(2-hydroxyethyl)piperazin-1-yl)propan-2-yl)-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(3'-((4-methylpiperazin-1-yl)methyl)-[1,1'-biphenyl]-4-carbonyl)pyrrolidin-3-yl)nicotinamide;
(R)-2-amino-N-(1-(3'-((4-(2-hydroxyethyl)piperazin-1-yl)methyl)-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(4'-((4-methylpiperazin-1-yl)methyl)-[1,1'-biphenyl]-3-carbonyl)pyrrolidin-3-yl)nicotinamide;
(R)-2-amino-5-(1-methyl-1H-pyrazol-4-yl)-N-(1-(3-methyl-4'-((4-methylpiperazin-1-yl)methyl)-[1,1'-biphenyl]-4-carbonyl)pyrrolidin-3-yl)nicotinamide;
(R)-2-amino-5-(1-methyl-1H-pyrazol-4-yl)-N-(1-(2-methyl-4'-((4-methylpiperazin-1-yl)methyl)-[1,1'-biphenyl]-4-carbonyl)pyrrolidin-3-yl)nicotinamide;
(R)-2-amino-N-(1-(3-amino-[1,1'-biphenyl]-4-carbonyl)pyrrolidin-3-yl)-5-(1-methyl-1H-pyrazol-4-yl)nicotinamide;
(R)-2-amino-N-(1-(2-chloro-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(2-methyl-[1,1'-biphenyl]-4-carbonyl)pyrrolidin-3-yl)nicotinamide;
(R)-2-amino-N-(1-(4-iodobenzoyl)pyrrolidin-3-yl)-5-(1-methyl-H-pyrazol-4-yl)nicotinamide;
(R)-2-amino-N-(1-(4-(benzyloxy)benzoyl)pyrrolidin-3-yl)-5-(1-methyl-1H-pyrazol-4-yl)nicotinamide;
2-amino-N-((3R)-1-(4-(cyclohex-2-en-1-yloxy)benzoyl)pyrrolidin-3-yl)-5-(1-methyl-1H-pyrazol-4-yl)nicotinamide;
(R)-2-amino-5-(1-methyl-1H-pyrazol-4-yl)-N-(1-(3-phenoxybenzoyl)pyrrolidin-3-yl)nicotinamide;
(R)-2-amino-N-(1-(4-(2-bromoethyl)benzoyl)pyrrolidin-3-yl)-5-(1-methyl-1H-pyrazol-4-yl)nicotinamide;
(R)-2-amino-N-(1-(4-(tert-butyl)benzoyl)pyrrolidin-3-yl)-5-(1-methyl-1H-pyrazol-4-yl)nicotinamide;
(R)-2-amino-N-(1-(3,4-dimethylbenzoyl)pyrrolidin-3-yl)-5-(1-methyl-1H-pyrazol-4-yl)nicotinamide;
(R)-2-amino-5-(1-methyl-1H-pyrazol-4-yl)-N-(1-(4-(4-methylpiperazin-1-yl)benzoyl)pyrrolidin-3-yl)nicotinamide;
(R)-2-amino-5-(1-methyl-1H-pyrazol-4-yl)-N-(1-(4-vinylbenzoyl)pyrrolidin-3-yl)nicotinamide;
(R)-2-amino-N-(1-(4-isopropylbenzoyl)pyrrolidin-3-yl)-5-(1-methyl-1H-pyrazol-4-yl)nicotinamide;
(R)-2-amino-N-(1-(4-cyanobenzoyl)pyrrolidin-3-yl)-5-(1-methyl-1H-pyrazol-4-yl)nicotinamide;
(R)-2-amino-5-(1-methyl-1H-pyrazol-4-yl)-N-(1-(4-(methylthio)benzoyl)pyrrolidin-3-yl)nicotinamide;
(R)-2-amino-N-(1-benzoylpyrrolidin-3-yl)-5-(1-methyl-1H-pyrazol-4-yl)nicotinamide;
(R)-2-amino-N-(1-(4-fluoro-2-methylbenzoyl)pyrrolidin-3-yl)-5-(1-methyl-1H-pyrazol-4-yl)nicotinamide;
(R)-2-amino-N-(1-(5-bromo-2-chlorobenzoyl)pyrrolidin-3-yl)-5-(1-methyl-1H-pyrazol-4-yl)nicotinamide;
(R)-2-amino-N-(1-(3,5-dichlorobenzoyl)pyrrolidin-3-yl)-5-(1-methyl-1H-pyrazol-4-yl)nicotinamide;
(R)-2-amino-5-(1-methyl-H-pyrazol-4-yl)-N-(1-(3-(4-((4-methylpiperazin-1-yl)methyl)phenoxy)benzoyl)pyrrolidin-3-yl)nicotinamide;
2-amino-N—((R)-1-(3-(4-(((R)-2-(hydroxymethyl)pyrrolidin-1l-yl)methyl)phenoxy)benzoyl)pyrrolidin-3-yl)-5-(1-methyl-1H-pyrazol-4-yl)nicotinamide;
(R)-2-amino-5-(1-methyl-1H-pyrazol-4-yl)-N-(1-(4-(4-((4-methylpiperazin-1-yl)methyl)phenoxy)benzoyl)pyrrolidin-3-yl)nicotinamide;
2-amino-N—((R)-1-(4-(4-(((R)-2-(hydroxymethyl)pyrrolidin-1-yl)methyl)phenoxy)benzoyl)pyrrolidin-3-yl)-5-(1-methyl-1H-pyrazol-4-yl)nicotinamide;
(R)—N-(1-([1,1'-biphenyl]-3-carbonyl)pyrrolidin-3-yl)-2-amino-5-(1-methyl-1H-pyrazol-4-yl)nicotinamide;

(R)-2-amino-5-(1-methyl-1H-pyrazol-4-yl)-N-(1-(3-(1-(piperidin-4-yl)-1H-pyrazol-4-yl)benzoyl)pyrrolidin-3-yl)nicotinamide;

(R)-2-amino-5-(1-methyl-1H-pyrazol-4-yl)-N-(1-(3'-(2-(4-methylpiperazin-1-yl)-2-oxoethyl)-[1,1'-biphenyl]-3-carbonyl)pyrrolidin-3-yl)nicotinamide;

(R)-2-amino-5-(1-methyl-1H-pyrazol-4-yl)-N-(1-(3'-(2-(4-methylpiperazin-1-yl)ethyl)-[1,1'-biphenyl]-3-carbonyl)pyrrolidin-3-yl)nicotinamide;

(R)-2-amino-5-(1-methyl-1H-pyrazol-4-yl)-N-(1-(4'-(2-(4-methylpiperazin-1-yl)-2-oxoethyl)-[1,1'-biphenyl]-3-carbonyl)pyrrolidin-3-yl)nicotinamide;

(R)-2-amino-5-(1-methyl-1H-pyrazol-4-yl)-N-(1-(4'-(2-(4-methylpiperazin-1-yl)ethyl)-[1,1'-biphenyl]-3-carbonyl)pyrrolidin-3-yl)nicotinamide;

(R)-3'-(3-(2-amino-5-(1-methyl-1H-pyrazol-4-yl)nicotinamido)pyrrolidine-1-carbonyl)-[1,1'-biphenyl]-3-carboxylic acid;

(R)-2-amino-N-(1-(3'-amino-[1,1'-biphenyl]-3-carbonyl)pyrrolidin-3-yl)-5-(1-methyl-1H-pyrazol-4-yl)nicotinamide;

(R)—N-(1-(3'-((1H-pyrazol-1-yl)methyl)-[1,1'-biphenyl]-3-carbonyl)pyrrolidin-3-yl)-2-amino-5-(1-methyl-1H-pyrazol-4-yl)nicotinamide;

(R)—N-(1-(3'-((1H-imidazol-1-yl)methyl)-[1,1'-biphenyl]-3-carbonyl)pyrrolidin-3-yl)-2-amino-5-(1-methyl-1H-pyrazol-4-yl)nicotinamide;

(R)-2-amino-5-(1-methyl-1H-pyrazol-4-yl)-N-(1-(3'-(morpholinomethyl)-[1,1'-biphenyl]-3-carbonyl)pyrrolidin-3-yl)nicotinamide;

2-amino-N—((R)-1-(3'-(((R)-2-(hydroxymethyl)pyrrolidin-1-yl)methyl)-[1,1'-biphenyl]-3-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(3'-(thiomorpholine-4-carbonyl)-[1,1'-biphenyl]-3-carbonyl)pyrrolidin-3-yl)nicotinamide;

(R)-2-amino-5-(1-methyl-1H-pyrazol-4-yl)-N-(1-(3'-(piperazine-1-carbonyl)-[1,1'-biphenyl]-3-carbonyl)pyrrolidin-3-yl)nicotinamide;

(R)-2-amino-5-(1-methyl-1H-pyrazol-4-yl)-N-(1-(4'-(piperazine-1-carbonyl)-[1,1'-biphenyl]-3-carbonyl)pyrrolidin-3-yl)nicotinamide;

(R)-2-amino-5-(1-methyl-1H-pyrazol-4-yl)-N-(1-(3'-(piperazine-1-carbonyl)-[1,1'-biphenyl]-4-carbonyl)pyrrolidin-3-yl)nicotinamide;

(R)-2-amino-5-(1-methyl-1H-pyrazol-4-yl)-N-(1-(4'-(piperazine-1-carbonyl)-[1,1'-biphenyl]-4-carbonyl)pyrrolidin-3-yl)nicotinamide;

(R)-2-amino-N-(1-(3-(furan-3-yl)benzoyl)pyrrolidin-3-yl)-5-(1-methyl-1H-pyrazol-4-yl)nicotinamide;

(R)-2-amino-N-(1-(3-(1,3-dimethyl-1H-pyrazol-4-yl)benzoyl)pyrrolidin-3-yl)-5-(1-methyl-1H-pyrazol-4-yl)nicotinamide;

(R)-2-amino-N-(1-(3-(1-cyclopentyl-1H-pyrazol-4-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(3-(1-(phenylsulfonyl)-1H-pyrazol-4-yl)benzoyl)pyrrolidin-3-yl)nicotinamide;

(R)-2-amino-5-(1-methyl-1H-pyrazol-4-yl)-N-(1-(3-(pyridin-3-yl)benzoyl)pyrrolidin-3-yl)nicotinamide;

(R)-2-amino-5-(1-methyl-1H-pyrazol-4-yl)-N-(1-(3-(pyridin-4-yl)benzoyl)pyrrolidin-3-yl)nicotinamide;

(R)-2-amino-N-(1-(3-(benzo[b]thiophen-2-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(2',3',4',5'-tetrahydro-[1,1'-biphenyl]-3-carbonyl)pyrrolidin-3-yl)nicotinamide;

(R)-2-amino-5-(1-methyl-1H-pyrazol-4-yl)-N-(1-(3'-(4-methylpiperazin-1-yl)-[1,1'-biphenyl]-3-carbonyl)pyrrolidin-3-yl)nicotinamide;

(R)-2-amino-5-(1-methyl-1H-pyrazol-4-yl)-N-(1-(3'-(piperidin-1-yl)-[1,1'-biphenyl]-3-carbonyl)pyrrolidin-3-yl)nicotinamide;

(R)-2-amino-N-(1-(2'-chloro-[1,1'-biphenyl]-3-carbonyl)pyrrolidin-3-yl)-5-(1-methyl-1H-pyrazol-4-yl)nicotinamide;

(R)-2-amino-N-(1-(3'-chloro-[1,1'-biphenyl]-3-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(3-(2-(piperazin-1-yl)pyridin-4-yl)benzoyl)pyrrolidin-3-yl)nicotinamide;

(R)-2-amino-5-(1-methyl-1H-pyrazol-4-yl)-N-(1-(3'-(methylsulfonamido)-[1,1'-biphenyl]-3-carbonyl)pyrrolidin-3-yl)nicotinamide;

(R)-2-amino-5-(1-methyl-1H-pyrazol-4-yl)-N-(1-(6-methyl-[1,1'-biphenyl]-3-carbonyl)pyrrolidin-3-yl)nicotinamide;

(R)-2-amino-N-(1-(2'-chloro-6-methyl-[1,1'-biphenyl]-3-carbonyl)pyrrolidin-3-yl)-5-(1-methyl-1H-pyrazol-4-yl)nicotinamide;

(R)-2-amino-N-(1-(3'-chloro-6-methyl-[1,1'-biphenyl]-3-carbonyl)pyrrolidin-3-yl)-5-(1-methyl-1H-pyrazol-4-yl)nicotinamide;

(R)-2-amino-N-(1-(2-amino-5-methyl-[1,1'-biphenyl]-3-carbonyl)pyrrolidin-3-yl)-5-(1-methyl-1H-pyrazol-4-yl)nicotinamide;

(R)-2-amino-N-(1-(4-amino-[1,1'-biphenyl]-3-carbonyl)pyrrolidin-3-yl)-5-(1-methyl-1H-pyrazol-4-yl)nicotinamide;

(R)-2-amino-N-(1-(4-(furan-3-yl)benzoyl)pyrrolidin-3-yl)-5-(1-methyl-1H-pyrazol-4-yl)nicotinamide;

(R)-2-amino-N-(1-(4-(1,3-dimethyl-1H-pyrazol-4-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(pyridin-4-yl)benzoyl)pyrrolidin-3-yl)nicotinamide;

(R)-2-amino-N-(1-(4-(benzo[b]thiophen-2-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(2-(piperazin-1-yl)pyridin-4-yl)benzoyl)pyrrolidin-3-yl)nicotinamide;

(R)-2-amino-5-(1-methyl-1H-pyrazol-4-yl)-N-(1-(4'-morpholino-[1,1'-biphenyl]-4-carbonyl)pyrrolidin-3-yl)nicotinamide;

(R)-2-amino-5-(1-methyl-1H-pyrazol-4-yl)-N-(1-(4'-(morpholine-4-carbonyl)-[1,1'-biphenyl]-4-carbonyl)pyrrolidin-3-yl)nicotinamide;

(R)-2-amino-5-(1-methyl-1H-pyrazol-4-yl)-N-(1-(2',3',4',5'-tetrahydro-[1,1'-biphenyl]-4-carbonyl)pyrrolidin-3-yl)nicotinamide;

(R)-2-amino-N-(1-(3-(2,3-dioxoindolin-6-yl)benzoyl)pyrrolidin-3-yl)-5-(1-methyl-1H-pyrazol-4-yl)nicotinamide;

(R)-2-amino-N-(1-(4'-(4-aminophenoxy)-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(1-methyl-1H-pyrazol-4-yl)benzoyl)pyrrolidin-3-yl)nicotinamide;

(R)-2-amino-5-(1-methyl-1H-pyrazol-4-yl)-N-(1-(4-(1,3,5-trimethyl-1H-pyrazol-4-yl)benzoyl)pyrrolidin-3-yl)nicotinamide;

(R)-2-amino-N-(1-(4-(1-cyclopentyl-1H-pyrazol-4-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(1-(tetrahydro-2H-pyran-4-yl)-1H-pyrazol-4-yl)benzoyl)pyrrolidin-3-yl)nicotinamide;

(R)-2-amino-5-(1-methyl-1H-pyrazol-4-yl)-N-(1-(4-(1-(piperidin-4-yl)-1H-pyrazol-4-yl)benzoyl)pyrrolidin-3-yl)nicotinamide;

(R)-2-amino-N-(1-(3-hydroxybenzoyl)pyrrolidin-3-yl)-5-(1-methyl-1H-pyrazol-4-yl)nicotinamide;

(R)-2-amino-N-(1-(4-(1,5-dimethyl-1H-pyrazol-4-yl)benzoyl)pyrrolidin-3-yl)-5-(1-methyl-1H-pyrazol-4-yl)nicotinamide;

(R)-2-amino-N-(1-(4-(3,5-dimethyl-1H-pyrazol-4-yl)benzoyl)pyrrolidin-3-yl)-5-(1-methyl-1H-pyrazol-4-yl)nicotinamide;

(R)-2-amino-N-(1-(4-(3,5-dimethyl-1-phenyl-1H-pyrazol-4-yl)benzoyl)pyrrolidin-3-yl)-5-(1-methyl-1H-pyrazol-4-yl)nicotinamide;

(R)-2-amino-N-(1-(4-(4-bromo-3,5-dimethylthiophen-2-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(4-methylthiophen-3-yl)benzoyl)pyrrolidin-3-yl)nicotinamide;

(R)-2-amino-N-(1-(4-(3-methoxythiophen-2-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(4-methylthiophen-2-yl)benzoyl)pyrrolidin-3-yl)nicotinamide;

(R)-2-amino-5-(1-methyl-1H-pyrazol-4-yl)-N-(1-(4-(5-methylthiophen-2-yl)benzoyl)pyrrolidin-3-yl)nicotinamide;

(R)-2-amino-5-(1-methyl-1H-pyrazol-4-yl)-N-(1-(4'-phenoxy-[1,1'-biphenyl]-4-carbonyl)pyrrolidin-3-yl)nicotinamide;

(R)-2-amino-N-(1-(4'-(4-methoxyphenoxy)-[1,1'-biphenyl]-4-carbonyl)pyrrolidin-3-yl)-5-(1-methyl-1H-pyrazol-4-yl)nicotinamide;

(R)-2-amino-N-(1-(4'-(4-(dimethylamino)phenoxy)-[1,1'-biphenyl]-4-carbonyl)pyrrolidin-3-yl)-5-(1-methyl-1H-pyrazol-4-yl)nicotinamide;

(R)-2-amino-N-(1-(4'-(3-aminophenoxy)-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-(piperidin-4-yloxy)-[1,1'-biphenyl]-4-carbonyl)pyrrolidin-3-yl)nicotinamide;

2-amino-5-(1-methyl-1H-pyrazol-4-yl)-N-((3R)-1-(4'-(pyrrolidin-3-yloxy)-[1,1'-biphenyl]-4-carbonyl)pyrrolidin-3-yl)nicotinamide;

(R)-2-amino-N-(1-(4'-(4-aminophenoxy)-2'-fluoro-[1,1'-biphenyl]-4-carbonyl)pyrrolidin-3-yl)-5-(1-methyl-1H-pyrazol-4-yl)nicotinamide;

(R)-2-amino-N-(1-(4-(5-chlorothiophen-2-yl)benzoyl)pyrrolidin-3-yl)-5-(1-methyl-1H-pyrazol-4-yl)nicotinamide;

(R)-2-amino-N-(1-(3-hydroxy-4-(5-methylthiophen-2-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(3-methyl-4-(5-methylthiophen-2-yl)benzoyl)pyrrolidin-3-yl)nicotinamide;

(R)-2-amino-N-(1-(4-(5-cyanothiophen-2-yl)benzoyl)pyrrolidin-3-yl)-5-(1-methyl-1H-pyrazol-4-yl)nicotinamide;

(R)—N-(1-(4-(5-acetylthiophen-2-yl)benzoyl)pyrrolidin-3-yl)-2-amino-5-(1-methyl-1H-pyrazol-4-yl)nicotinamide;

(R)-2-amino-N-(1-(4-(3,5-dimethylisoxazol-4-yl)benzoyl)pyrrolidin-3-yl)-5-(1-methyl-1H-pyrazol-4-yl)nicotinamide;

(R)-2-amino-N-(1-(4-(3-amino-5-methylisoxazol-4-yl)benzoyl)pyrrolidin-3-yl)-5-(1-methyl-1H-pyrazol-4-yl)nicotinamide;

2-amino-5-(1-methyl-1H-pyrazol-4-yl)-N—((R)-1-(4'-(((S)-pyrrolidin-3-yl)oxy)-[1,1'-biphenyl]-4-carbonyl)pyrrolidin-3-yl)nicotinamide;

2-amino-N-((3R)-1-(4-(5-(1-hydroxyethyl)thiophen-2-yl)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(5-methylthiazol-2-yl)benzoyl)pyrrolidin-3-yl)nicotinamide;

(R)-2-amino-5-(1-methyl-1H-pyrazol-4-yl)-N-(1-(4-(4-methylthiazol-2-yl)benzoyl)pyrrolidin-3-yl)nicotinamide;

(R)-2-amino-N-(1-(4'-((4-aminopiperidin-1-yl)methyl)-[1,1'-biphenyl]-4-carbonyl)pyrrolidin-3-yl)-5-(1-methyl-1H-pyrazol-4-yl)nicotinamide;

2-amino-N-((3R)-1-(4'-((methyl((1-methylpiperidin-3-yl)methyl)amino)methyl)-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-(((1-methylpiperidin-4-yl)amino)methyl)-[1,1'-biphenyl]-4-carbonyl)pyrrolidin-3-yl)nicotinamide;

(R)-2-amino-5-(1-methyl-1H-pyrazol-4-yl)-N-(1-(4'-(piperidin-4-ylmethoxy)-[1,1'-biphenyl]-4-carbonyl)pyrrolidin-3-yl)nicotinamide;

(R)-2-amino-N-(1-(4'-(3-(dimethylamino)propoxy)-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-((1-methylpiperidin-4-yl)methoxy)-[1,1'-biphenyl]-4-carbonyl)pyrrolidin-3-yl)nicotinamide;

(R)-2-amino-N-(1-(4-(4-hydroxybut-1-yn-1-yl)benzoyl)pyrrolidin-3-yl)-5-(1-methyl-1H-pyrazol-4-yl)nicotinamide;

(R)-2-amino-N-(1-(4-(5-hydroxypent-1-yn-1-yl)benzoyl)pyrrolidin-3-yl)-5-(1-methyl-1H-pyrazol-4-yl)nicotinamide;

(R)—N-(1-([1,1'-biphenyl]-4-carbonyl)pyrrolidin-3-yl)-2-amino-5-(4-methoxyphenyl)nicotinamide;

(R)—N-(1-([1,1'-biphenyl]-4-carbonyl)pyrrolidin-3-yl)-2-amino-5-(4-(4-methylpiperazin-1-yl)phenyl)nicotinamide;

(R)—N-(1-([1,1'-biphenyl]-4-carbonyl)pyrrolidin-3-yl)-2-amino-5-(4-morpholinophenyl)nicotinamide;

(R)—N-(1-([1,1'-biphenyl]-4-carbonyl)pyrrolidin-3-yl)-6-amino-[3,3'-bipyridine]-5-carboxamide;

(R)—N-(1-([1,1'-biphenyl]-4-carbonyl)pyrrolidin-3-yl)-6-amino-6'-morpholino-[3,3'-bipyridine]-5-carboxamide;

(R)—N-(1-([1,1'-biphenyl]-4-carbonyl)pyrrolidin-3-yl)-6-amino-6'-fluoro-[3,3'-bipyridine]-5-carboxamide;

tert-butyl (R)-4-(4-(5-((1-([1,1'-biphenyl]-4-carbonyl)pyrrolidin-3-yl)carbamoyl)-6-aminopyridin-3-yl)-1H-pyrazol-1-yl)piperidine-1-carboxylate;
(R)—N-(1-([1,1'-biphenyl]-4-carbonyl)pyrrolidin-3-yl)-2-amino-5-(1-(piperidin-4-yl)-1H-pyrazol-4-yl)nicotinamide;
(R)—N-(1-([1,1'-biphenyl]-4-carbonyl)pyrrolidin-3-yl)-2-amino-5-(1-(1-methylpiperidin-4-yl)-1H-pyrazol-4-yl)nicotinamide;
(R)—N-(1-([1,1'-biphenyl]-4-carbonyl)pyrrolidin-3-yl)-2-amino-5-(4-(2-(piperazin-1-yl)propan-2-yl)phenyl)nicotinamide;
(R)—N-(1-([1,1'-biphenyl]-4-carbonyl)pyrrolidin-3-yl)-2-amino-5-(4-(2-(4-(2-hydroxyethyl)piperazin-1-yl)propan-2-yl)phenyl)nicotinamide;
(R)—N-(1-([1,1'-biphenyl]-4-carbonyl)pyrrolidin-3-yl)-2-amino-5-(4-((4-methylpiperazin-1-yl)methyl)phenyl)nicotinamide;
(R)—N-(1-([1,1'-biphenyl]-4-carbonyl)pyrrolidin-3-yl)-2-amino-5-(4-(hydroxymethyl)phenyl)nicotinamide;
(R)—N-(1-([1,1'-biphenyl]-4-carbonyl)pyrrolidin-3-yl)-2-amino-5-(4-(morpholinomethyl)phenyl)nicotinamide;
(R)-2-amino-N-(1-(2'-chloro-[1,1'-biphenyl]-4-carbonyl)pyrrolidin-3-yl)-5-(4-(4-methylpiperazin-1-yl)phenyl)nicotinamide;
(R)-2-amino-N-(1-(2'-chloro-[1,1'-biphenyl]-4-carbonyl)pyrrolidin-3-yl)-5-(4-morpholinophenyl)nicotinamide;
(R)-2-amino-N-(1-(2'-chloro-[1,1'-biphenyl]-4-carbonyl)pyrrolidin-3-yl)-5-(4-((4-methylpiperazin-1-yl)methyl)phenyl)nicotinamide;
(R)-2-amino-N-(1-(2'-chloro-[1,1'-biphenyl]-4-carbonyl)pyrrolidin-3-yl)-5-(1-(2-methoxyethyl)-1H-pyrazol-4-yl)nicotinamide;
(R)-2-amino-5-(4-(azetidin-1-ylsulfonyl)phenyl)-N-(1-(2'-chloro-[1,1'-biphenyl]-4-carbonyl)pyrrolidin-3-yl)nicotinamide;
(R)-2-amino-N-(1-(2'-chloro-[1,1'-biphenyl]-4-carbonyl)pyrrolidin-3-yl)-5-(4-sulfamoylphenyl)nicotinamide;
(R)-2-amino-N-(1-(2'-chloro-[1,1'-biphenyl]-4-carbonyl)pyrrolidin-3-yl)-5-(4-(methylsulfonamido)phenyl)nicotinamide;
(R)-2-amino-5-(1-(tert-butyl)-1H-pyrazol-4-yl)-N-(1-(2'-chloro-[1,1'-biphenyl]-4-carbonyl)pyrrolidin-3-yl)nicotinamide;
(R)-4-(6-amino-5-((1-(2'-chloro-[1,1'-biphenyl]-4-carbonyl)pyrrolidin-3-yl)carbamoyl)pyridin-3-yl)benzoic acid;
(R)-2-amino-5-bromo-N-(1-(2'-chloro-4'-fluoro-[1,1'-biphenyl]-4-carbonyl)pyrrolidin-3-yl)nicotinamide;
(R)-6-amino-N-(1-(2'-chloro-4'-fluoro-[1,1'-biphenyl]-4-carbonyl)pyrrolidin-3-yl)-2'-(piperazin-1-yl)-[3,4'-bipyridine]-5-carboxamide;
(R)-6'-acetamido-6-amino-N-(1-(2'-chloro-4'-fluoro-[1,1'-biphenyl]-4-carbonyl)pyrrolidin-3-yl)-[3,3'-bipyridine]-5-carboxamide;
(R)-5',6-diamino-N-(1-(2'-chloro-4'-fluoro-[1,1'-biphenyl]-4-carbonyl)pyrrolidin-3-yl)-[3,3'-bipyridine]-5-carboxamide;
(R)-6-amino-N-(1-(2'-chloro-4'-fluoro-[1,1'-biphenyl]-4-carbonyl)pyrrolidin-3-yl)-6'-morpholino-[3,3'-bipyridine]-5-carboxamide;
(R)-2-amino-N-(1-(2'-chloro-4'-fluoro-[1,1'-biphenyl]-4-carbonyl)pyrrolidin-3-yl)-5-(4-(4-methylpiperazin-1-yl)phenyl)nicotinamide;
(R)-2-amino-N-(1-(2'-chloro-4'-fluoro-[1,1'-biphenyl]-4-carbonyl)pyrrolidin-3-yl)-5-(1-(pyridin-3-ylmethyl)-1H-pyrazol-4-yl)nicotinamide;
(R)-6'-amino-5'-((1-(2'-chloro-4'-fluoro-[1,1'-biphenyl]-4-carbonyl)pyrrolidin-3-yl)carbamoyl)-[3,3'-bipyridine]-5-carboxylic acid;
(R)-2-amino-N-(1-(2'-chloro-[1,1'-biphenyl]-4-carbonyl)pyrrolidin-3-yl)-5-(4-(4-methylpiperazine-1-carbonyl)phenyl)nicotinamide;
(R)-2-amino-N-(1-(2'-chloro-[1,1'-biphenyl]-4-carbonyl)pyrrolidin-3-yl)-5-(4-(4-(2-hydroxyethyl)piperazine-1-carbonyl)phenyl)nicotinamide;
(R)-2-amino-N-(1-(2'-chloro-[1,1'-biphenyl]-4-carbonyl)pyrrolidin-3-yl)-5-(4-(morpholine-4-carbonyl)phenyl)nicotinamide;
(R)-2-amino-N-(1-(2'-chloro-[1,1'-biphenyl]-4-carbonyl)pyrrolidin-3-yl)-5-(4-((1-methylpiperidin-4-yl)carbamoyl)phenyl)nicotinamide;
(R)-2-amino-N-(1-(2'-chloro-[1,1'-biphenyl]-4-carbonyl)pyrrolidin-3-yl)-5-(4-((4-methylcyclohexyl)carbamoyl)phenyl)nicotinamide;
(R)-2-amino-N-(1-(2'-chloro-[1,1'-biphenyl]-4-carbonyl)pyrrolidin-3-yl)-5-(4-((tetrahydro-2H-pyran-4-yl)carbamoyl)phenyl)nicotinamide;
2-amino-N—((R)-1-(2'-chloro-[1,1'-biphenyl]-4-carbonyl)pyrrolidin-3-yl)-5-(4-(((1-methylpyrrolidin-3-yl)methyl)carbamoyl)phenyl)nicotinamide;
(R)-2-amino-N-(1-(2'-chloro-[1,1'-biphenyl]-4-carbonyl)pyrrolidin-3-yl)-5-(4-((3-(2-oxopyrrolidin-1-yl)propyl)carbamoyl)phenyl)nicotinamide;
(R)-2-amino-N-(1-benzylpyrrolidin-3-yl)-N-methyl-5-(1-methyl-1H-pyrazol-4-yl)nicotinamide;
(R)-2-amino-N-(1-(2-chlorobenzyl)pyrrolidin-3-yl)-N-methyl-5-(1-methyl-1H-pyrazol-4-yl)nicotinamide;
(R)-2-amino-N-(1-(methyl(phenyl)carbamoyl)pyrrolidin-3-yl)-5-(1-methyl-1H-pyrazol-4-yl)nicotinamide;
(R)-2-amino-N-(1-(2-chlorobenzyl)pyrrolidin-3-yl)-5-(1-isobutyl-1H-pyrazol-4-yl)nicotinamide;
(R)-2-amino-N-(1-((6-fluoro-4'-((4-methylpiperazin-1-yl)methyl)-[1,1'-biphenyl]-3-yl)methyl)pyrrolidin-3-yl)-5-(1-methyl-H-pyrazol-4-yl)nicotinamide;
(R)-2-amino-N-(1-(4'-(4-(aminomethyl)phenoxy)-[1,1'-biphenyl]-4-carbonyl)pyrrolidin-3-yl)-5-(1-methyl-1H-pyrazol-4-yl)nicotinamide;
(R)-2-amino-N-(1-(4'-(4-(hydroxymethyl)phenoxy)-[1,1'-biphenyl]-4-carbonyl)pyrrolidin-3-yl)-5-(1-methyl-1H-pyrazol-4-yl)nicotinamide;
(R)-2-amino-N-(1-(4'-(4-((dimethylamino)methyl)phenoxy)-[1,1'-biphenyl]-4-carbonyl)pyrrolidin-3-yl)-5-(1-methyl-1H-pyrazol-4-yl)nicotinamide;
(R)-2-amino-N-(1-(4'-(4-(aminomethyl)phenoxy)-2'-chloro-[1,1'-biphenyl]-4-carbonyl)pyrrolidin-3-yl)-5-(1-methyl-1H-pyrazol-4-yl)nicotinamide;
(R)-2-amino-N-(1-(2'-chloro-4'-(4-((dimethylamino)methyl)phenoxy)-[1,1'-biphenyl]-4-carbonyl)pyrrolidin-3-yl)-5-(1-methyl-1H-pyrazol-4-yl)nicotinamide;
(R)-2-amino-N-(1-(2'-chloro-4'-(4-(hydroxymethyl)phenoxy)-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(4-((4-methylpiperazin-1-yl)methyl)benzoyl)pyrrolidin-3-yl)nicotinamide;
(R)-2-amino-N-(1-(4-((4-(2-hydroxyethyl)piperazin-1-yl)methyl)benzoyl)pyrrolidin-3-yl)-5-(1-methyl-1H-pyrazol-4-yl)nicotinamide;

2-amino-N—((R)-1-(2'-chloro-4'-fluoro-[1,1'-biphenyl]-4-carbonyl)pyrrolidin-3-yl)-5-(2-((((1r,4R)-4-hydroxycyclohexyl)amino)methyl)phenyl)nicotinamide;
(R)-2-amino-5-(1-methyl-1H-pyrazol-4-yl)-N-(1-(4'-((1-methylpiperidin-4-yl)methyl)-[1,1'-biphenyl]-4-carbonyl)pyrrolidin-3-yl)nicotinamide;
(R)-2-amino-5-(1-methyl-1H-pyrazol-4-yl)-N-(1-(2'-methyl-[1,1'-biphenyl]-4-carbonyl)pyrrolidin-3-yl)nicotinamide;
(R)-2-amino-N-(1-(5'-chloro-2'-methyl-[1,1'-biphenyl]-4-carbonyl)pyrrolidin-3-yl)-5-(1-methyl-1H-pyrazol-4-yl)nicotinamide;
(R)-2-amino-N-(1-(3',5'-dimethyl-[1,1'-biphenyl]-4-carbonyl)pyrrolidin-3-yl)-5-(1-methyl-1H-pyrazol-4-yl)nicotinamide;
(R)-2-amino-N-(1-(3',4'-dimethyl-[1,1'-biphenyl]-4-carbonyl)pyrrolidin-3-yl)-5-(1-methyl-1H-pyrazol-4-yl)nicotinamide;
(R)-2-amino-N-(1-(4'-fluoro-2'-(trifluoromethyl)-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(3'-(trifluoromethyl)-[1,1'-biphenyl]-4-carbonyl)pyrrolidin-3-yl)nicotinamide;
(R)-2-amino-N-(1-(4'-chloro-2'-methyl-[1,1'-biphenyl]-4-carbonyl)pyrrolidin-3-yl)-5-(1-methyl-1H-pyrazol-4-yl)nicotinamide;
(R)-2-amino-N-(1-(4'-fluoro-3'-methyl-[1,1'-biphenyl]-4-carbonyl)pyrrolidin-3-yl)-5-(1-methyl-1H-pyrazol-4-yl)nicotinamide;
(R)—N-(1-(4-(1H-indol-5-yl)benzoyl)pyrrolidin-3-yl)-2-amino-5-(1-methyl-1H-pyrazol-4-yl)nicotinamide;
(R)-2-amino-N-(1-(4-(indolin-5-yl)benzoyl)pyrrolidin-3-yl)-5-(1-methyl-1H-pyrazol-4-yl)nicotinamide;
(R)-2-amino-5-(1-methyl-1H-pyrazol-4-yl)-N-(1-(3'-methyl-[1,1'-biphenyl]-4-carbonyl)pyrrolidin-3-yl)nicotinamide;
(R)-2-amino-N-(1-(3'-ethyl-[1,1'-biphenyl]-4-carbonyl)pyrrolidin-3-yl)-5-(1-methyl-1H-pyrazol-4-yl)nicotinamide;
(R)-2-amino-N-(1-(3'-isopropyl-[1,1'-biphenyl]-4-carbonyl)pyrrolidin-3-yl)-5-(1-methyl-1H-pyrazol-4-yl)nicotinamide;
(R)-2-amino-N-(1-(3',4'-dimethoxy-[1,1'-biphenyl]-4-carbonyl)pyrrolidin-3-yl)-5-(1-methyl-1H-pyrazol-4-yl)nicotinamide;
(R)-2-amino-N-(1-(4'-(azetidin-1-ylsulfonyl)-[1,1'-biphenyl]-4-carbonyl)pyrrolidin-3-yl)-5-(1-methyl-1H-pyrazol-4-yl)nicotinamide;
(R)-2-amino-N-(1-(4'-chloro-3'-fluoro-[1,1'-biphenyl]-4-carbonyl)pyrrolidin-3-yl)-5-(1-methyl-1H-pyrazol-4-yl)nicotinamide;
(R)-2-amino-N-(1-(4'-amino-[1,1'-biphenyl]-4-carbonyl)pyrrolidin-3-yl)-5-(1-methyl-1H-pyrazol-4-yl)nicotinamide;
(R)-2-amino-N-(1-(3'-chloro-5'-fluoro-[1,1'-biphenyl]-4-carbonyl)pyrrolidin-3-yl)-5-(1-methyl-1H-pyrazol-4-yl)nicotinamide;
(R)-2-amino-N-(1-(3',5'-dichloro-4'-fluoro-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(4'-(methylthio)-[1,1'-biphenyl]-4-carbonyl)pyrrolidin-3-yl)nicotinamide;
(R)-2-amino-N-(1-(4'-(ethylthio)-[1,1'-biphenyl]-4-carbonyl)pyrrolidin-3-yl)-5-(1-methyl-1H-pyrazol-4-yl)nicotinamide;
(R)-2-amino-N-(1-(2'-chloro-5'-fluoro-[1,1'-biphenyl]-4-carbonyl)pyrrolidin-3-yl)-5-(1-methyl-1H-pyrazol-4-yl)nicotinamide;
(R)-2-amino-N-(1-(2'-chloro-3'-fluoro-[1, l'-biphenyl]-4-carbonyl)pyrrolidin-3-yl)-5-(1-methyl-1H-pyrazol-4-yl)nicotinamide;
(R)-2-amino-N-(1-(4'-(cyanomethyl)-[1,1'-biphenyl]-4-carbonyl)pyrrolidin-3-yl)-5-(1-methyl-1H-pyrazol-4-yl)nicotinamide;
(R,E)-3-(4'-(3-(2-amino-5-(1-methyl-1H-pyrazol-4-yl)nicotinamido)pyrrolidine-1-carbonyl)-[1,1'-biphenyl]-4-yl)acrylic acid;
(R)-3-(4'-(3-(2-amino-5-(1-methyl-1H-pyrazol-4-yl)nicotinamido)pyrrolidine-1-carbonyl)-[1,1'-biphenyl]-4-yl)propanoic acid;
(R)-2-amino-5-(1-methyl-1H-pyrazol-4-yl)-N-(1-(4'-(4-oxopiperidine-1-carbonyl)-[1,1'-biphenyl]-4-carbonyl)pyrrolidin-3-yl)nicotinamide;
(R)-2-amino-N-(1-(4'-carbamoyl-3'-fluoro-[1,1'-biphenyl]-4-carbonyl)pyrrolidin-3-yl)-5-(1-methyl-1H-pyrazol-4-yl)nicotinamide;
(R,E)-2-amino-5-(1-methyl-1H-pyrazol-4-yl)-N-(1-(4-(3-oxobut-1-en-1-yl)benzoyl)pyrrolidin-3-yl)nicotinamide;
(R)-2-amino-N-(1-(2'-chloro-5'-fluoro-3-methyl-[1,1'-biphenyl]-4-carbonyl)pyrrolidin-3-yl)-5-(1-methyl-1H-pyrazol-4-yl)nicotinamide;
(R)-2-amino-N-(1-(2'-chloro-5'-fluoro-2-methyl-[1,1'-biphenyl]-4-carbonyl)pyrrolidin-3-yl)-5-(1-methyl-1H-pyrazol-4-yl)nicotinamide;
(R)-2-amino-N-(1-(2',3-dichloro-5'-fluoro-[1,1'-biphenyl]-4-carbonyl)pyrrolidin-3-yl)-5-(1-methyl-1H-pyrazol-4-yl)nicotinamide;
(R)-2-amino-N-(1-(2',3-dichloro-4'-fluoro-[1,1'-biphenyl]-4-carbonyl)pyrrolidin-3-yl)-5-(1-methyl-1H-pyrazol-4-yl)nicotinamide;
(R)-2-amino-5-(1-methyl-1H-pyrazol-4-yl)-N-(1-(4'-(morpholinomethyl)-[1,1'-biphenyl]-4-carbonyl)pyrrolidin-3-yl)nicotinamide;
(R)-2-amino-5-(1-methyl-1H-pyrazol-4-yl)-N-(1-(3'-(1-methyl-1H-tetrazol-5-yl)-[1,1'-biphenyl]-4-carbonyl)pyrrolidin-3-yl)nicotinamide;
(R)—N-(1-(3'-(1H-tetrazol-5-yl)-[1,1'-biphenyl]-4-carbonyl)pyrrolidin-3-yl)-2-amino-5-(1-methyl-1H-pyrazol-4-yl)nicotinamide;
(R)-2-amino-N-(1-(3'-(5-methyl-1,2,4-oxadiazol-3-yl)-[1,1'-biphenyl]-4-carbonyl)pyrrolidin-3-yl)-5-(1-methyl-1H-pyrazol-4-yl)nicotinamide;
(R)-2-amino-N-(1-(2'-chloro-4'-fluoro-2-methyl-[1,1'-biphenyl]-4-carbonyl)pyrrolidin-3-yl)-5-(1-methyl-1H-pyrazol-4-yl)nicotinamide;
(R)-2-amino-N-(1-(2-chloro-4-fluorobenzoyl)pyrrolidin-3-yl)-5-(1-methyl-1H-pyrazol-4-yl)nicotinamide;
(R)-2-amino-5-(1-methyl-1H-pyrazol-4-yl)-N-(1-(3-(1-(phenylsulfonyl)-1H-pyrazol-4-yl)benzoyl)pyrrolidin-3-yl)nicotinamide;
(R)-2-amino-N-(1-(4-(2-chlorophenoxy)benzoyl)pyrrolidin-3-yl)-5-(1-methyl-1H-pyrazol-4-yl)nicotinamide;
(R)-2-amino-N-(1-(4-(2-chloro-4-fluorophenoxy)benzoyl)pyrrolidin-3-yl)-5-(1-methyl-1H-pyrazol-4-yl)nicotinamide;
(R)-2-amino-N-(1-(4'-hydroxy-3',5'-dimethyl-[1, l'-biphenyl]-4-carbonyl)pyrrolidin-3-yl)-5-(1-methyl-1H-pyrazol-4-yl)nicotinamide;
(R)-2-amino-N-(1-(4'-methoxy-3',5'-dimethyl-[1,1'-biphenyl]-4-carbonyl)pyrrolidin-3-yl)-5-(1-methyl-1H-pyrazol-4-yl)nicotinamide;

(R)-2-amino-N-(1-(4'-cyano-[1,1'-biphenyl]-4-carbonyl)
pyrrolidin-3-yl)-5-(1-methyl-1H-pyrazol-4-yl)nicoti-
namide;

(R)-2-amino-N-(1-(3'-(aminomethyl)-[1,1'-biphenyl]-4-
carbonyl)pyrrolidin-3-yl)-5-(1-methyl-1H-pyrazol-4-
yl)nicotinamide;

(R)-2-amino-N-(1-(3-amino-[1,1'-biphenyl]-4-carbonyl)
pyrrolidin-3-yl)-5-(1-methyl-1H-pyrazol-4-yl)nicoti-
namide;

(R)-2-amino-5-(1-methyl-1H-pyrazol-4-yl)-N-(1-(4'-((4-
methylpiperazin-1-yl)methyl)-[1,1'-biphenyl]-3-carbo-
nyl)pyrrolidin-3-yl)nicotinamide;

(R)-2-amino-5-(1-methyl-1H-pyrazol-4-yl)-N-(1-(4-phe-
noxybenzoyl)pyrrolidin-3-yl)nicotinamide;

(R)-2-amino-N-(1-(3-bromobenzoyl)pyrrolidin-3-yl)-5-
(1-methyl-1H-pyrazol-4-yl)nicotinamide;

2-amino-5-(1-methyl-1H-pyrazol-4-yl)-N-((3R)-1-(3'-
(pyrrolidin-3-yloxy)-[1,1'-biphenyl]-4-carbonyl)pyrro-
lidin-3-yl)nicotinamide;

(R)-2-amino-N-(1-(4'-(hydroxymethyl)-[1,1'-biphenyl]-
4-carbonyl)pyrrolidin-3-yl)-5-(1-methyl-1H-pyrazol-
4-yl)nicotinamide;

(R)-2-amino-N-(1-(3'-(hydroxymethyl)-[1,1'-biphenyl]-
4-carbonyl)pyrrolidin-3-yl)-5-(1-methyl-1H-pyrazol-
4-yl)nicotinamide;

(R)-2-amino-N-(1-(4-(6-hydroxypyridin-3-yl)benzoyl)
pyrrolidin-3-yl)-5-(1-methyl-1H-pyrazol-4-yl)nicoti-
namide;

(R)-2-amino-5-(1-methyl-1H-pyrazol-4-yl)-N-(1-(4-
(naphthalen-2-yl)benzoyl)pyrrolidin-3-yl)nicotina-
mide;

(R)—N-(1-(4-(1H-indol-6-yl)benzoyl)pyrrolidin-3-yl)-2-
amino-5-(1-methyl-1H-pyrazol-4-yl)nicotinamide;

(R)-2-amino-5-(1-methyl-1H-pyrazol-4-yl)-N-(1-(4-(4-
methyl-3,4-dihydro-2H-benzo[b][1,4]oxazin-7-yl)ben-
zoyl)pyrrolidin-3-yl)nicotinamide;

(R)-2-amino-5-(1-methyl-1H-pyrazol-4-yl)-N-(1-(4-(1,2,
3,6-tetrahydropyridin-4-yl)benzoyl)pyrrolidin-3-yl)
nicotinamide;

(R)-2-amino-N-(1-(4-(1-methyl-1,2,3,6-tetrahydropyri-
din-4-yl)benzoyl)pyrrolidin-3-yl)-5-(1-methyl-1H-
pyrazol-4-yl)nicotinamide;

(R)-2-amino-5-(1-methyl-1H-pyrazol-4-yl)-N-(1-(4'-(1,2,
3,6-tetrahydropyridin-4-yl)-[1,1'-biphenyl]-4-carbo-
nyl)pyrrolidin-3-yl)nicotinamide;

(R)-2-amino-N-(1-(4-(1-methyl-1H-indol-5-yl)benzoyl)
pyrrolidin-3-yl)-5-(1-methyl-1H-pyrazol-4-yl)nicoti-
namide;

(R)-2-amino-N-(1-(4-(1-methyl-1H-indazol-5-yl)ben-
zoyl)pyrrolidin-3-yl)-5-(1-methyl-1H-pyrazol-4-yl)
nicotinamide;

(R)-2-amino-5-(1-methyl-1H-pyrazol-4-yl)-N-(1-(4-(1-
(2-(pyrrolidin-1-yl)ethyl)-1H-pyrazol-4-yl)benzoyl)
pyrrolidin-3-yl)nicotinamide;

(R)—N-(1-(4-(1H-indazol-5-yl)benzoyl)pyrrolidin-3-yl)-
2-amino-5-(1-methyl-1H-pyrazol-4-yl)nicotinamide;

(R)—N-(1-(4-(1H-indazol-6-yl)benzoyl)pyrrolidin-3-yl)-
2-amino-5-(1-methyl-1H-pyrazol-4-yl)nicotinamide;

(R)-2-amino-5-(1-methyl-1H-pyrazol-4-yl)-N-(1-(4-((4-
nitrobenzyl)oxy)benzoyl)pyrrolidin-3-yl)nicotinamide;

(R)-2-amino-5-(1-methyl-1H-pyrazol-4-yl)-N-(1-(4-((3-
nitrobenzyl)oxy)benzoyl)pyrrolidin-3-yl)nicotinamide;

(R)-2-amino-N-(1-(2'-chloro-4'-fluoro-[1,1'-biphenyl]-4-
carbonyl)pyrrolidin-3-yl)-5-(2-(piperidin-4-yl-
methoxy)phenyl)nicotinamide;

2-amino-N—((R)-1-(2'-chloro-4'-fluoro-[1,1'-biphenyl]-
4-carbonyl)pyrrolidin-3-yl)-5-(2-((1-methylpyrrolidin-
3-yl)methoxy)phenyl)nicotinamide;

2-amino-N—((R)-1-(2'-chloro-4'-fluoro-[1,1'-biphenyl]-
4-carbonyl)pyrrolidin-3-yl)-5-(2-(2-(1-methylpyrroli-
din-2-yl)ethoxy)phenyl)nicotinamide;

(R)-6-amino-N-(1-(2'-chloro-4'-fluoro-[1,1'-biphenyl]-4-
carbonyl)pyrrolidin-3-yl)-6'-fluoro-[3,3'-bipyridine]-5-
carboxamide;

(R)-2-amino-N-(1-(2'-chloro-4'-fluoro-[1,1'-biphenyl]-4-
carbonyl)pyrrolidin-3-yl)-5-phenylnicotinamide;

(R)-2-amino-5-(2-carbamoylphenyl)-N-(1-(2'-chloro-4'-
fluoro-[1,1'-biphenyl]-4-carbonyl)pyrrolidin-3-yl)
nicotinamide;

(R)-2-(6-amino-5-((1-(2'-chloro-4'-fluoro-[1,1'-biphe-
nyl]-4-carbonyl)pyrrolidin-3-yl)carbamoyl)pyridin-3-
yl)benzoic acid;

(R)-2-amino-N-(1-(2'-chloro-4'-fluoro-[1,1'-biphenyl]-4-
carbonyl)pyrrolidin-3-yl)-5-(2-hydroxyphenyl)nicoti-
namide;

(R)-6-amino-N-(1-(2'-chloro-4'-fluoro-[1,1'-biphenyl]-4-
carbonyl)pyrrolidin-3-yl)-2'-(4-methylpiperazin-1-yl)-
[3,4'-bipyridine]-5-carboxamide;

(R)-2-amino-N-(1-(2'-chloro-4'-fluoro-[1,1'-biphenyl]-4-
carbonyl)pyrrolidin-3-yl)-5-(3-chloro-4-(morpholine-
4-carbonyl)phenyl)nicotinamide;

(R)-2-amino-N-(1-(2'-chloro-4'-fluoro-[1,1'-biphenyl]-4-
carbonyl)pyrrolidin-3-yl)-5-(4-morpholinophenyl)
nicotinamide;

2-amino-N—((R)-1-(2'-chloro-4'-fluoro-[1,1'-biphenyl]-
4-carbonyl)pyrrolidin-3-yl)-5-(2-(((1r,4R)-4-hydroxy-
cyclohexyl)carbamoyl)phenyl)nicotinamide;

(R)-2-amino-N-(1-(6'(4-(dimethylcarbamoyl)phenoxy)-
[1,1'-biphenyl]-4-carbonyl)pyrrolidin-3-yl)-5-(1-
methyl-1H-pyrazol-4-yl)nicotinamide;

(R)-2-amino-N-(1-(4'-(4-carbamoylphenoxy)-[1,1'-bi-
phenyl]-4-carbonyl)pyrrolidin-3-yl)-5-(1-methyl-1H-
pyrazol-4-yl)nicotinamide;

(R,E)-2-amino-N-(1-(4'-(3-(dimethylamino)-3-oxoprop-
1-en-1-yl)-[1,1'-biphenyl]-4-carbonyl)pyrrolidin-3-yl)-
5-(1-methyl-1H-pyrazol-4-yl)nicotinamide;

(R)-2-amino-N-(1-(4'-((2-chloropyridin-4-yl)oxy)-[1,1'-
biphenyl]-4-carbonyl)pyrrolidin-3-yl)-5-(1-methyl-
1H-pyrazol-4-yl)nicotinamide;

(R)-2-amino-N-(1-(4'-(4-aminophenoxy)-2'-chloro-[1,1'-
biphenyl]-4-carbonyl)pyrrolidin-3-yl)-5-(1-methyl-
1H-pyrazol-4-yl)nicotinamide;

(R)-2-amino-N-(1-(4'-(3-aminophenoxy)-2'-chloro-[1,1'-
biphenyl]-4-carbonyl)pyrrolidin-3-yl)-5-(1-methyl-
1H-pyrazol-4-yl)nicotinamide;

(R)-2-amino-5-(1-methyl-1H-pyrazol-4-yl)-N-(1-(4'-
(pyridin-4-yloxy)-[1,1'-biphenyl]-4-carbonyl)pyrroli-
din-3-yl)nicotinamide;

(R)—N-(1-(4'-((1H-indol-5-yl)amino)-[1,1'-biphenyl]-4-
carbonyl)pyrrolidin-3-yl)-2-amino-5-(1-methyl-1H-
pyrazol-4-yl)nicotinamide;

(R)-2-amino-N-(1-(4'-(4-hydroxyphenoxy)-[1,1'-biphe-
nyl]-4-carbonyl)pyrrolidin-3-yl)-5-(1-methyl-1H-pyra-
zol-4-yl)nicotinamide;

(R)-2-amino-N-(1-(4'-(2-aminopropan-2-yl)-[1,1'-biphe-
nyl]-4-carbonyl)pyrrolidin-3-yl)-5-(1-methyl-1H-pyra-
zol-4-yl)nicotinamide;

(R)-2-amino-5-(1-methyl-1H-pyrazol-4-yl)-N-(1-(4'-
(pyridin-3-yloxy)-[1,1'-biphenyl]-4-carbonyl)pyrroli-
din-3-yl)nicotinamide;

(R)-2-amino-N-(1-(4'-(methyl(4-nitrophenyl)amino)-[1,1'-biphenyl]-4-carbonyl)pyrrolidin-3-yl)-5-(1-methyl-1H-pyrazol-4-yl)nicotinamide;

(R)-2-amino-N-(1-(4'-((2-fluoro-4-nitrophenyl)(methyl)amino)-[1,1'-biphenyl]-4-carbonyl)pyrrolidin-3-yl)-5-(1-methyl-1H-pyrazol-4-yl)nicotinamide;

(R)-2-amino-N-(1-(4'-(methyl(2-methyl-4-nitrophenyl)amino)-[1,1'-biphenyl]-4-carbonyl)pyrrolidin-3-yl)-5-(1-methyl-1H-pyrazol-4-yl)nicotinamide;

(R)-2-amino-N-(1-(4'-((2-chloro-4-nitrophenyl)(methyl)amino)-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-(piperidin-4-ylmethyl)-[1,1'-biphenyl]-4-carbonyl)pyrrolidin-3-yl)nicotinamide;

(R)-2-amino-N-(1-(3'-chloro-4'-(4-hydroxyphenoxy)-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(4'-((1-methylpiperidin-4-yl)oxy)-[1,1'-biphenyl]-4-carbonyl)pyrrolidin-3-yl)nicotinamide;

(R)-2-amino-N-(1-(4'-((4-aminocyclohexyl)oxy)-[1,1'-biphenyl]-4-carbonyl)pyrrolidin-3-yl)-5-(1-methyl-1H-pyrazol-4-yl)nicotinamide;

(R)-2-amino-N-(1-(4'-(4-formylphenoxy)-[1,1'-biphenyl]-4-carbonyl)pyrrolidin-3-yl)-5-(1-methyl-1H-pyrazol-4-yl)nicotinamide;

(R)-4-((4'-(3-(2-amino-5-(1-methyl-1H-pyrazol-4-yl)nicotinamido)pyrrolidine-1-carbonyl)-[1,1'-biphenyl]-4-yl)oxy)benzoic acid;

(R)-2-amino-N-(1-(4'-((6-aminopyridin-3-yl)oxy)-[1,1'-biphenyl]-4-carbonyl)pyrrolidin-3-yl)-5-(1-methyl-1H-pyrazol-4-yl)nicotinamide;

(R)—N-(1-(4'-((2H-tetrazol-5-yl)oxy)-[1,1'-biphenyl]-4-carbonyl)pyrrolidin-3-yl)-2-amino-5-(1-methyl-1H-pyrazol-4-yl)nicotinamide;

(R)-2-amino-N-(1-(4'-((4-aminophenyl)amino)-[1,1'-biphenyl]-4-carbonyl)pyrrolidin-3-yl)-5-(1-methyl-1H-pyrazol-4-yl)nicotinamide;

(R)-2-amino-N-(1-(4'-((1-(2-hydroxyethyl)piperidin-4-yl)methyl)-[2'-biphenyl]-4-carbonyl)pyrrolidin-3-yl)-5-(1-methyl-1H-pyrazol-4-yl)nicotinamide;

2-amino-5-(1-methyl-H-pyrazol-4-yl)-N-((3R)-1-(4-((E)-3-(4-methylpiperazin-1-yl)but-1-en-1-yl)benzoyl)pyrrolidin-3-yl)nicotinamide;

2-amino-N-((3R)-1-(4-((E)-3-(4-(2-hydroxyethyl)piperazin-1-yl)but-1-en-1-yl)benzoyl)pyrrolidin-3-yl)-5-(1-methyl-1H-pyrazol-4-yl)nicotinamide;

(R,E)-2-amino-5-(1-methyl-1H-pyrazol-4-yl)-N-(1-(4-(2-(pyridin-4-yl)vinyl)benzoyl)pyrrolidin-3-yl)nicotinamide;

(R,E)-2-amino-5-(1-methyl-1H-pyrazol-4-yl)-N-(1-(4-(2-(pyridin-2-yl)vinyl)benzoyl) pyrrolidin-3-yl)nicotinamide;

(R,E)-2-amino-5-(1-methyl-H-pyrazol-4-yl)-N-(1-(4-(2-phenylprop-1-en-1-yl)benzoyl)pyrrolidin-3-yl)nicotinamide;

(R,E)-2-amino-5-(1-methyl-1H-pyrazol-4-yl)-N-(1-(4-(2-(piperidin-4-yl)vinyl)benzoyl)pyrrolidin-3-yl)nicotinamide;

methyl (R,E)-3-(4-(3-(2-amino-5-(1-methyl-H-pyrazol-4-yl)nicotinamido)pyrrolidine-1-carbonyl)phenyl)acrylate;

(R)-2-amino-5-(1-methyl-1H-pyrazol-4-yl)-N-(1-(4-(3-nitrophenoxy)benzoyl)pyrrolidin-3-yl)nicotinamide;

(R)-2-amino-N-(1-(4-(3-aminophenoxy)benzoyl)pyrrolidin-3-yl)-5-(1-methyl-1H-pyrazol-4-yl)nicotinamide;

(R)-2-amino-5-(1-methyl-1H-pyrazol-4-yl)-N-(1-(4-(4-nitrophenoxy)benzoyl)pyrrolidin-3-yl)nicotinamide;

(R)-2-amino-N-(1-(4-(4-aminophenoxy)benzoyl)pyrrolidin-3-yl)-5-(1-methyl-1H-pyrazol-4-yl)nicotinamide;

(R)-2-amino-N-(1-(6-(4-aminophenoxy)-2-naphthoyl)pyrrolidin-3-yl)-5-(1-methyl-1H-pyrazol-4-yl)nicotinamide;

(R)-2-amino-N-(1-(4'-((2-chloro-4-nitrophenyl)(methyl)amino)-[1,1'-biphenyl]-4-carbonyl)pyrrolidin-3-yl)-5-(1-methyl-1H-pyrazol-4-yl)nicotinamide;

(R)-2-amino-N-(1-(4'-((4-amino-2-fluorophenyl)(methyl)amino)-[1,1'-biphenyl]-4-carbonyl)pyrrolidin-3-yl)-5-(1-methyl-1H-pyrazol-4-yl)nicotinamide;

(R)-2-amino-N-(1-(4'-((4-amino-2-methylphenyl)(methyl)amino)-[1,1'-biphenyl]-4-carbonyl)pyrrolidin-3-yl)-5-(1-methyl-1H-pyrazol-4-yl)nicotinamide;

(R)-2-amino-N-(1-(4'-((4-amino-2-chlorophenyl)(methyl)amino)-[1,1'-biphenyl]-4-carbonyl)pyrrolidin-3-yl)-5-(1-methyl-1H-pyrazol-4-yl)nicotinamide;

(R)-2-amino-N-(1-(4-((3-aminobenzyl)oxy)benzoyl)pyrrolidin-3-yl)-5-(1-methyl-1H-pyrazol-4-yl)nicotinamide;

(R)-2-amino-N-(1-(4-hydroxybenzoyl)pyrrolidin-3-yl)-5-(1-methyl-1H-pyrazol-4-yl)nicotinamide;

(R)-2-amino-N-(1-(4-formylbenzoyl)pyrrolidin-3-yl)-5-(1-methyl-1H-pyrazol-4-yl)nicotinamide;

(R)-2-amino-N-(1-(2'-chloro-4'-(4-formylphenoxy)-[1,1'-biphenyl]-4-carbonyl)pyrrolidin-3-yl)-5-(1-methyl-1H-pyrazol-4-yl)nicotinamide;

(R)-2-amino-N-(1-(2'-chloro-4'-fluoro-[1,1'-biphenyl]-4-carbonyl)pyrrolidin-3-yl)-5-(2-formylphenyl)nicotinamide;

3-bromo-5-chlorophenyl (R)-3-(2-amino-5-(1-methyl-1H-pyrazol-4-yl)nicotinamido)pyrrolidine-1-carboxylate;

tert-butyl (R)-4-(4-(3-(2-amino-5-(1-methyl-1H-pyrazol-4-yl)nicotinamido)pyrrolidine-1-carbonyl)phenyl)-3,6-dihydropyridine-1(2H)-carboxylate;

(R)-2-amino-N-(1-(2,4'-dimethyl-[1,1'-biphenyl]-4-carbonyl)pyrrolidin-3-yl)-5-(1-methyl-1H-pyrazol-4-yl)nicotinamide;

(R)-2-amino-N-(1-(4'-(ethylthio)-2-methyl-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(3-methyl-4-(4-methylthiophen-2-yl)benzoyl)pyrrolidin-3-yl)nicotinamide;

(R)—N-(1-(4-(1H-indol-6-yl)-3-methylbenzoyl)pyrrolidin-3-yl)-2-amino-5-(1-methyl-1H-pyrazol-4-yl)nicotinamide;

(R)—N-(1-(4-(1H-indol-5-yl)-3-methylbenzoyl)pyrrolidin-3-yl)-2-amino-5-(1-methyl-1H-pyrazol-4-yl)nicotinamide;

(R)-2-amino-5-(1-methyl-1H-pyrazol-4-yl)-N-(1-(3-methyl-4-(1-methyl-1H-indol-5-yl)benzoyl)pyrrolidin-3-yl)nicotinamide;

(R)-2-amino-N-(1-(2',4'-difluoro-2-methyl-[1,1'-biphenyl]-4-carbonyl)pyrrolidin-3-yl)-5-(1-methyl-1H-pyrazol-4-yl)nicotinamide;

(R)-2-amino-N-(1-(2',3'-difluoro-2-methyl-[1,1'-biphenyl]-4-carbonyl)pyrrolidin-3-yl)-5-(1-methyl-1H-pyrazol-4-yl)nicotinamide;

(R)-2-amino-N-(1-(2'-chloro-3'-fluoro-2-methyl-[1,1'-biphenyl]-4-carbonyl)pyrrolidin-3-yl)-5-(1-methyl-1H-pyrazol-4-yl)nicotinamide;

(R)-2-amino-N-(1-(2',3'-dichloro-2-methyl-[1,1'-biphenyl]-4-carbonyl)pyrrolidin-3-yl)-5-(1-methyl-1H-pyrazol-4-yl)nicotinamide;

(R)-2-amino-5-(1-methyl-1H-pyrazol-4-yl)-N-(1-(2,3',5'-trimethyl-[1,1'-biphenyl]-4-carbonyl)pyrrolidin-3-yl)nicotinamide;

(R)-2-amino-5-(1-methyl-1H-pyrazol-4-yl)-N-(1-(2,3',4'-trimethyl-[1,1'-biphenyl]-4-carbonyl)pyrrolidin-3-yl)nicotinamide; and (R)-2-amino-N-(1-(2,3'-dimethyl-[1,1'-biphenyl]-4-carbonyl)pyrrolidin-3-yl)-5-(1-methyl-1H-pyrazol-4-yl)nicotinamide.

13. A pharmaceutical composition comprising a compound of claim 1, or a pharmaceutically acceptable salt thereof, and a pharmaceutically acceptable excipient.

14. A method of inhibiting Mer kinase, the method comprising administering an effective amount of a compound of claim 1, or pharmaceutically acceptable salt thereof, to a subject in need thereof, wherein the subject has cancer or an immune-related disease.

* * * * *

UNITED STATES PATENT AND TRADEMARK OFFICE
CERTIFICATE OF CORRECTION

PATENT NO. : 10,913,730 B2
APPLICATION NO. : 16/341005
DATED : February 9, 2021
INVENTOR(S) : Jin Kwan Kim et al.

Page 1 of 1

It is certified that error appears in the above-identified patent and that said Letters Patent is hereby corrected as shown below:

In the Claims

Column 297, Lines 20-25, Claim 1 delete " 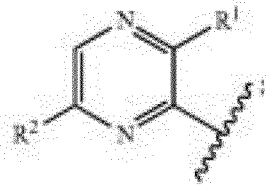 " and substitute therefor

--- 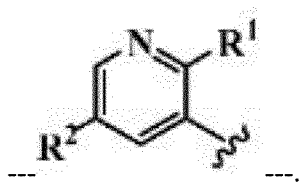 ---.

Signed and Sealed this
Third Day of October, 2023

Katherine Kelly Vidal
*Director of the United States Patent and Trademark Office*